United States Patent
Cheung et al.

(10) Patent No.: US 9,879,021 B2
(45) Date of Patent: Jan. 30, 2018

(54) COMPOUNDS AS REARRANGED DURING TRANSFECTION (RET) INHIBITORS

(71) Applicant: GlaxoSmithKline Intellectual Property Development Limited, Brentford, Middlesex (GB)

(72) Inventors: Mui Cheung, King of Prussia, PA (US); Michael P. Demartino, King of Prussia, PA (US); Hilary Schenck Eidam, King of Prussia, PA (US); Huiping Amy Guan, Shanghai (CN); Donghui Qin, King of Prussia, PA (US); Chengde Wu, Shanghai (CN); Zhen Gong, Shanghai (CN); Haiying Yang, Shanghai (CN); Haiyu Yu, Shanghai (CN); Zhiliu Zhang, Shanghai (CN)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/509,569

(22) PCT Filed: Sep. 10, 2015

(86) PCT No.: PCT/CN2015/089332
§ 371 (c)(1),
(2) Date: Mar. 8, 2017

(87) PCT Pub. No.: WO2016/037578
PCT Pub. Date: Mar. 17, 2016

(65) Prior Publication Data
US 2017/0298074 A1   Oct. 19, 2017

(30) Foreign Application Priority Data

Sep. 10, 2014   (WO) ................ PCT/CN2014/000834

(51) Int. Cl.
*C07D 491/048* (2006.01)
*C07D 471/04* (2006.01)
(Continued)

(52) U.S. Cl.
CPC ....... *C07D 491/048* (2013.01); *C07D 213/64* (2013.01); *C07D 213/69* (2013.01);
(Continued)

(58) Field of Classification Search
CPC .............. C07D 491/048; C07D 471/04; C07D 413/12; C07D 413/14; C07D 409/12; C07D 405/12; C07D 405/14; C07D 401/12; C07D 401/14; C07D 401/04; C07D 221/04; C07D 217/24; C07D 213/69; C07D 213/64
See application file for complete search history.

(56) References Cited

U.S. PATENT DOCUMENTS 7,034,049 B1   4/2006   Pevarello et al.
8,236,799 B2   8/2012   Hangauer
(Continued)

FOREIGN PATENT DOCUMENTS

CN   100360507 C   1/2008
WO   199932106 A1   7/1999
(Continued)

OTHER PUBLICATIONS

Gradler et al., Fragment-based discovery of focal adhesion kinase inhibitors. Bioorg Med Chem Lett. Oct. 1, 2013;23(19):5401-9.
(Continued)

*Primary Examiner* — Alexander R Pagano
*Assistant Examiner* — Ebenezer O Sackey
(74) *Attorney, Agent, or Firm* — Duke M. Fitch; Kathryn A. Lutomski; Edward R. Gimmi

(57) ABSTRACT

This invention relates to novel compounds which are inhibitors of the Rearranged during Transfection (RET) kinase, to pharmaceutical compositions containing them, to processes for their preparation, and to their use in therapy, alone or in combination, for the normalization of gastrointestinal sensitivity, motility and/or secretion and/or abdominal disorders or diseases and/or treatment related to diseases related to RET dysfunction or where modulation of RET activity may have therapeutic benefit including but not limited to all classifications of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer, adenocarcinoma, and any malignancy with increased RET kinase activity.

20 Claims, 40 Drawing Sheets

(51) Int. Cl.
*C07D 413/14* (2006.01)
*C07D 409/12* (2006.01)
*C07D 405/14* (2006.01)
*C07D 401/12* (2006.01)
*C07D 401/14* (2006.01)
*C07D 221/04* (2006.01)
*C07D 217/24* (2006.01)
*C07D 213/69* (2006.01)
*C07D 213/64* (2006.01)
*C07D 401/04* (2006.01)
*C07D 405/12* (2006.01)
*C07D 413/12* (2006.01)

(52) U.S. Cl.
CPC ......... *C07D 217/24* (2013.01); *C07D 221/04* (2013.01); *C07D 401/04* (2013.01); *C07D 401/12* (2013.01); *C07D 401/14* (2013.01); *C07D 405/12* (2013.01); *C07D 405/14* (2013.01); *C07D 409/12* (2013.01); *C07D 413/12* (2013.01); *C07D 413/14* (2013.01); *C07D 471/04* (2013.01); *C07B 2200/13* (2013.01)

(56) References Cited

U.S. PATENT DOCUMENTS

| | | |
|---|---|---|
| 8,937,071 B2 | 1/2015 | Eidam et al. |
| 9,035,063 B2 | 5/2015 | Eidam et al. |
| 9,382,238 B2 | 7/2016 | Eidam |
| 2007/0244120 A1 | 10/2007 | Dumas et al. |
| 2012/0046290 A1 | 2/2012 | Dumas et al. |
| 2013/0035326 A1 | 2/2013 | Abraham et al. |

FOREIGN PATENT DOCUMENTS

| | | |
|---|---|---|
| WO | 199932111 A1 | 7/1999 |
| WO | 200248114 A1 | 6/2002 |
| WO | 2003059903 A2 | 7/2003 |
| WO | 2003099771 A2 | 12/2003 |
| WO | 2004024694 A1 | 3/2004 |
| WO | 2005018624 A2 | 3/2005 |
| WO | 2008002676 A2 | 1/2008 |
| WO | 2008046802 A1 | 4/2008 |
| WO | 2008058341 A1 | 5/2008 |
| WO | 2011022473 A1 | 2/2011 |
| WO | 2012082817 A1 | 6/2012 |
| WO | 2014141187 A1 | 9/2014 |
| WO | 2016037578 A1 | 3/2016 |
| WO | 2016038552 A1 | 3/2016 |

OTHER PUBLICATIONS

Mologni, Development of RET kinase inhibitors for targeted cancer therapy. Curr Med Chem. 2011;18(2):162-75.

Shih et al., Pharmacophore modeling and virtual screening to identify potential RET kinase inhibitors. Bioorg Med Chem Lett. Aug. 1, 2011;21(15):4490-7.

Zuercher et al., Current review of small molecule Ret kinase inhibitors. Mini Rev Med Chem. Feb. 2010;10(2):138-46.

COMPOUNDS AS REARRANGED DURING TRANSFECTION (RET) INHIBITORS

This application is a §371 of International Application No. PCT/CN2015/089332, filed 10 Sep. 2015, which claims the priority of PCT/CN2014/000834, filed 10 Sep. 2014, which are incorporated herein in their entireties.

FIELD OF INVENTION

This invention relates to novel compounds which are inhibitors of the Rearranged during Transfection (RET) kinase, to pharmaceutical compositions containing them, to processes for their preparation, and to their use in therapy, alone or in combination, for the normalization of gastrointestinal sensitivity, motility and/or secretion and/or abdominal disorders or diseases and/or treatment related to diseases related to RET dysfunction or where modulation of RET activity may have therapeutic benefit including but not limited to all classifications of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma, and any malignancy with increased RET kinase activity.

BACKGROUND OF THE INVENTION

Irritable bowel syndrome (IBS) is a common illness affecting 10, 1, or 20% of individuals in developed countries and is characterized by abnormal bowel habits, bloating and visceral hypersensitivity (Camilleri, M., N. Engl. J. Med., 2012, 367:1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in a majority of IBS patients the sensitization of the peripheral nervous system results in visceral hypersensitivity or allodynia (Keszthelyi, D., Eur. J. Pain, 2012, 16:1444-1454).

While IBS does not directly alter life expectancy it has a considerable effect on a patient's quality of life. Moreover there is a significant financial cost for IBS associated healthcare and lost productivity due to worker absenteeism (Nellesen, D., et al., J. Manag. Care Pharm., 2013, 19:755-764). One of the most important symptoms that greatly affect an IBS patient's quality of life is visceral pain (Spiegel, B., et al., Am. J. Gastroenterol., 2008, 103:2536-2543). Molecular strategies that inhibit IBS associated visceral pain would greatly influence the IBS patient's quality of life and reduce associated costs.

Rearranged during transfection (RET) is a neuronal growth factor receptor tyrosine kinase that is activated upon binding one of four neurotrophic factors glial cell line-derived neurotrophic factor (GDNF), neurturin, artemin and persephin in combination with a co-receptor GDNF family receptor alpha-1, 2, 3, and 4 respectively (Plaza-Menacho, I., et al., Trends Genet., 2006, 22:627-636). RET is known to play an important role in the development and survival of afferent nociceptors in the skin and gut. RET kinase knockout mice lack enteric neurons and have other nervous system anomalies suggesting that a functional RET kinase protein product is required during development (Taraviras, S. et al., Development, 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., Transl. Res., 2013, 162:1-15).

Similarly, aberrant RET kinase activity is associated with multiple endocrine neoplasia (MEN 2A and 2B), familial medullary thyroid carcinoma (FMTC), papillary thyroid carcinoma (PTC) and Hirschsprung's disease (HSCR) (Borello, M., et al., Expert Opin. Ther. Targets, 2013, 17:403-419). MEN 2A is a cancer syndrome resulting from a mutation in the extracellular cysteine-rich domain of RET leading to dimerization via a disulfide bond which causes constitutive activation of the tyrosine kinase activity (Wells Jr, S., et al., J. Clin. Endocrinol. Metab., 2013, 98:3149-3164). Individuals with this mutation may develop medullary thyroid carcinoma (MTC), parathyroid hyperplasia, and pheochromocytoma. MEN 2B is caused by a Met918Thr mutation in RET which changes the tyrosine kinase specificity. MEN 2B is similar to MEN 2A, but lacks the parathyroid hyperplasia and also leads to development of numerous mucosal ganglia of the lips, tongue, and intestinal tract. Chromosomal rearrangements linking the promoter and NH2-terminal domains or unrelated gene(s) to the COOH-terminus of RET kinase resulting in constitutively activated chimeric forms of the receptor (RET/PTC) are thought to be tumor initiating events in PTC (Viglietto, G. et al., Oncogene, 1995, 11:1207-1210). PTC's encompass about 80% of all thyroid carcinomas. These data indicate that inhibition of RET may be an attractive therapeutic strategy for the treatment of pain associated with IBS and other gastrointestinal disorders and for the treatment of cancers with constitutive RET kinase activity.

SUMMARY OF THE INVENTION

The present invention relates to compounds according to Formula (I), or pharmaceutically acceptable salts thereof:

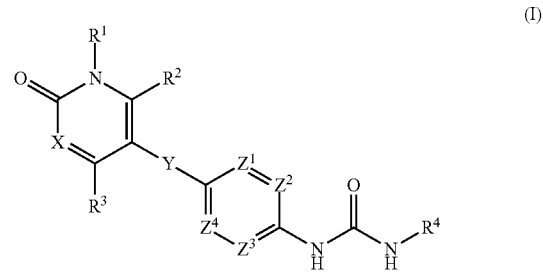

wherein:
X is N or $CR^5$;
Y is a bond or —O—;
$Z^1$, $Z^2$, $Z^3$, and $Z^4$ are each independently N, CH, or $CR^6$;

$R^1$ is hydrogen, $(C_1-C_6)$alkyl, halo$(C_1-C_6)$alkyl, or $(C_3-C_6)$cycloalkyl;

$R^2$ and $R^3$ are each independently selected from the group consisting of hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-; wherein said $(C_1-C_6)$alkyl, $(C_3-C_6)$cycloalkyl, $(C_1-C_6)$alkoxy, or $(C_3-C_6)$cycloalkoxy is optionally substituted by hydroxyl, $(C_1-C_6)$alkoxy, halo$(C_1-C_6)$alkoxy, or $(C_3-C_6)$cycloalkoxy;

$R^4$ is phenyl or 5- or 6-membered heteroaryl, each of which is optionally substituted by one, two, or three substituents independently selected from halogen, $(C_1-C_6)$alkyl, halo$(C_1-C_6)$alkyl, $(C_3-C_6)$cycloalkyl, cyano, phenyl, 5- or 6-membered heteroaryl, hydroxyl, —$OR^7$, —$CONR^8R^9$, —$SO_2R^7$, and —$SO_2NR^8R^9$; wherein said $(C_1-C_6)$alkyl is optionally substituted by cyano, hydroxyl, $(C_1-C_4)$alkoxy, halo$(C_1-C_4)$alkoxy, —$NR^8R^9$ or —$CONR^8R^9$; and wherein said 5- or 6-membered heteroaryl substituent is optionally substituted by halogen, $(C_1-C_4)$alkyl, or halo$(C_1-C_4)$alkyl;

$R^5$ is hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, or $((C_1-C_6)$alkyl)$((C_1-C_6)$alkyl)amino-; wherein said $(C_1-C_6)$alkyl, $(C_3-C_6)$cycloalkyl, $(C_1-C_6)$alkoxy, or $(C_3-C_6)$cycloalkoxy is optionally substituted by hydroxyl, $(C_1-C_6)$alkoxy, halo$(C_1-C_6)$alkoxy, or $(C_3-C_6)$cycloalkoxy;

or $R^3$ and $R^5$ taken together with the carbon atoms to which they are attached represent a 5- or 6-membered ring, optionally containing one, two, or three heteroatoms independently selected from nitrogen, oxygen, and sulfur, wherein said ring is optionally substituted by one or two substituents independently selected from halogen, $(C_1-C_4)$alkyl, halo$(C_1-C_4)$alkyl, $(C_3-C_6)$cycloalkyl, hydroxyl, $(C_1-C_4)$alkoxy, halo$(C_1-C_4)$alkoxy, $(C_3-C_6)$cycloalkoxy, amino, $((C_1-C_4)$alkyl)amino-, and $((C_1-C_4)$alkyl)$((C_1-C_4)$alkyl)amino-;

each $R^6$ is independently selected from the group consisting of halogen, $(C_1-C_6)$alkyl, halo$(C_1-C_6)$alkyl, $(C_3-C_6)$cycloalkyl, cyano, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-;

$R^7$ is $(C_1-C_6)$alkyl, halo$(C_1-C_6)$alkyl, $(C_3-C_6)$cycloalkyl, or 4- to 6-membered heterocycloalkyl; wherein said $(C_1-C_6)$alkyl is optionally substituted by cyano, hydroxyl, $(C_1-C_4)$alkoxy, halo$(C_1-C_4)$alkoxy, or —$NR^8R^9$; and wherein said $(C_3-C_6)$cycloalkyl is optionally substituted by one or two substituents independently selected from $(C_1-C_4)$alkyl, halo$(C_1-C_4)$alkyl, hydroxyl, hydroxy$(C_1-C_4)$alkyl, $(C_1-C_4)$alkoxy, and halo$(C_1-C_4)$alkoxy; and wherein said 4- to 6-membered heterocycloalkyl is optionally substituted by one or two substituents independently selected from $(C_1-C_4)$alkyl and halo$(C_1-C_4)$alkyl; and $R^8$ and $R^9$ are each independently selected from the group consisting of hydrogen, $(C_1-C_4)$alkyl, halo$(C_1-C_4)$alkyl, amino$(C_1-C_4)$alkyl-, $((C_1-C_4)$alkyl)amino$(C_1-C_4)$alkyl-, and $((C_1-C_4)$alkyl)$((C_1-C_4)$alkyl)amino$(C_1-C_4)$alkyl-;

or $R^8$ and $R^9$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, halo$(C_1-C_4)$alkyl, or hydroxy$(C_1-C_4)$alkyl;

provided that the compound is not 1-(4-(5-hydroxy-1-oxo-1,2-dihydroisoquinolin-4-yl)phenyl)-3-phenylurea, 1-(5-(tert-butyl)isoxazol-3-yl)-3-(4-((6-oxo-1,6-dihydropyridin-3-yl)oxy)phenyl)urea, 1-(4-chloro-3-(trifluoromethyl)phenyl)-3-(4-((6-oxo-1,6-dihydropyridin-3-yl)oxy)phenyl)urea, 1-(4-ethylphenyl)-3-(4-((6-oxo-1,6-dihydropyridin-3-yl)oxy)phenyl)urea, 1-(4-((6-oxo-1,6-dihydropyridin-3-yl)oxy)phenyl)-3-(p-tolyl)urea, 1-(4-((6-oxo-1,6-dihydropyridin-3-yl)oxy)phenyl)-3-(3-(trifluoromethyl)phenyl)urea, or 1-(4-(tert-butyl)phenyl)-3-(4-((6-oxo-1,6-dihydropyridin-3-yl)oxy)phenyl)urea.

This invention also relates to a pharmaceutical composition comprising a compound of Formula (I) and a pharmaceutically acceptable excipient.

This invention also relates to a method of treating irritable bowel syndrome comprising administering to a human in need thereof an effective amount of a compound of Formula (I) or a pharmaceutically acceptable salt thereof. This invention also relates to a method of treating cancer comprising administering to a human in need thereof an effective amount of a compound of Formula (I) or a pharmaceutically acceptable salt thereof.

This invention also relates to compounds of Formula (I) for use in therapy. This invention also relates to the use of a compound of Formula (I) or a pharmaceutically acceptable salt thereof for the treatment of irritable bowel syndrome. This invention also relates to the use of a compound of Formula (I) or a pharmaceutically acceptable salt thereof for the treatment of cancer.

This invention also relates to the use of a compound of Formula (I) or a pharmaceutically acceptable salt thereof in the preparation of a medicament for the treatment of diseases mediated by RET. This invention also relates to the use of a compound of Formula (I) or a pharmaceutically acceptable salt thereof in the manufacture of a medicament for the treatment of irritable bowel syndrome. This invention also relates to the use of a compound of Formula (I) or a pharmaceutically acceptable salt thereof in the manufacture of a medicament for the treatment of cancer.

DETAILED DESCRIPTION OF THE INVENTION

Figure 1:
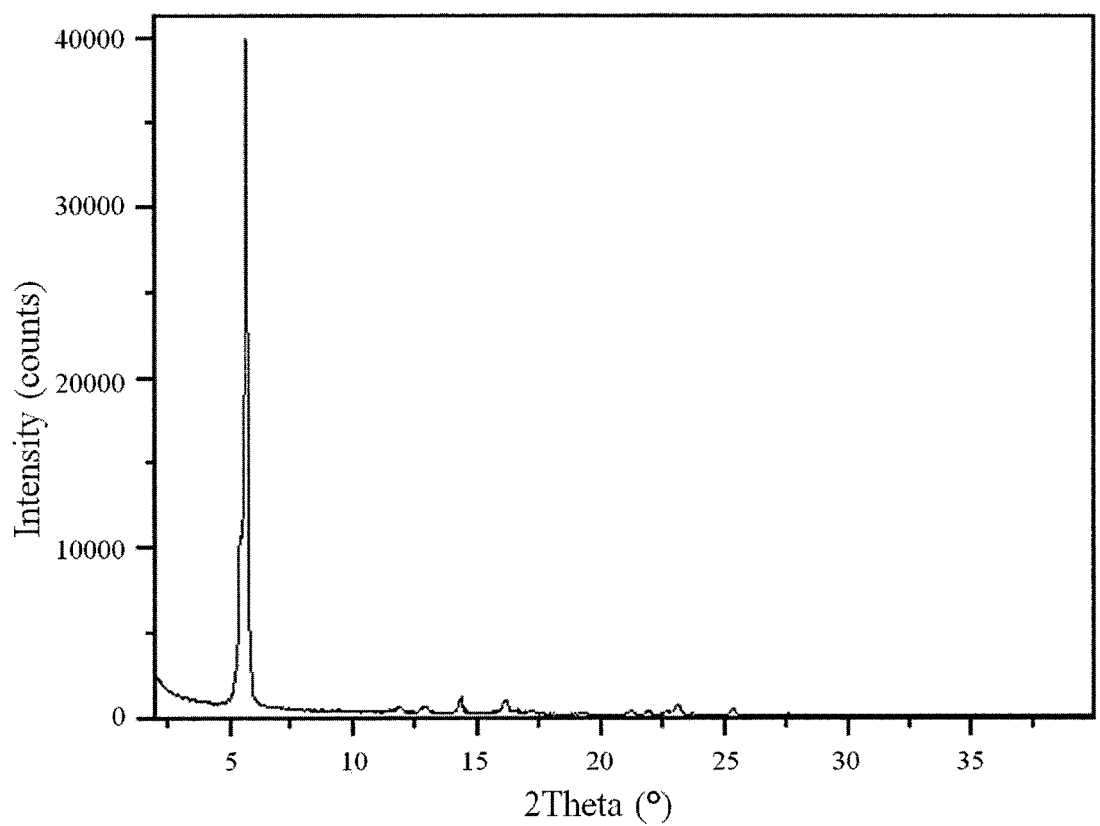
FIG. 1 shows an X-ray powder diffraction pattern of Compound A free base anhydrate.

This invention relates to compounds of the Formula (I) or pharmaceutically acceptable salts thereof as defined above. This invention further relates to compounds of the Formula (I) or pharmaceutically acceptable salts thereof wherein:

X is N or $CR^5$;

Y is a bond or —O—;

$Z^1$, $Z^2$, $Z^3$, and $Z^4$ are each independently N, CH, or $CR^6$;

$R^1$ is hydrogen, $(C_1-C_6)$alkyl, halo$(C_1-C_6)$alkyl, or $(C_3-C_6)$cycloalkyl;

$R^2$ and $R^3$ are each independently selected from the group consisting of hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-; wherein said $(C_1-C_6)$alkyl, $(C_3-C_6)$cycloalkyl, $(C_1-C_6)$alkoxy, or $(C_3-C_6)$cycloalkoxy is optionally substituted by hydroxyl, $(C_1-C_6)$alkoxy, halo$(C_1-C_6)$alkoxy, or $(C_3-C_6)$cycloalkoxy;

$R^4$ is phenyl or 5- or 6-membered heteroaryl, each of which is optionally substituted by one, two, or three substituents independently selected from halogen, $(C_1-C_6)$alkyl, halo$(C_1-C_6)$alkyl, $(C_3-C_6)$cycloalkyl, cyano, phenyl, 5- or 6-membered heteroaryl, hydroxyl, —$OR^7$, —$CONR^8R^9$, —$SO_2R^7$, and —$SO_2NR^8R^9$; wherein said $(C_1-C_6)$alkyl is optionally substituted by cyano, hydroxyl, $(C_1-C_4)$alkoxy, halo$(C_1-C_4)$alkoxy, —$NR^8R^9$ or —$CONR^8R^9$; and wherein said 5- or 6-membered heteroaryl substituent is optionally substituted by halogen, $(C_1-C_4)$alkyl, or halo$(C_1-C_4)$alkyl;

$R^5$ is hydrogen, halogen, $(C_1-C_6)$alkyl, halo$(C_1-C_6)$alkyl, $(C_3-C_6)$cycloalkyl, hydroxyl, $(C_1-C_6)$alkoxy, halo$(C_1-C_6)$alkoxy, $(C_3-C_6)$cycloalkoxy, amino, $((C_1-C_6)$alkyl)amino-, or $((C_1-C_6)$alkyl)$((C_1-C_6)$alkyl)amino-; wherein said $(C_1-C_6)$alkyl, $(C_3-C_6)$cycloalkyl, $(C_1-C_6)$alkoxy, or $(C_3-C_6)$cycloalkoxy is optionally substituted by hydroxyl, $(C_1-C_6)$alkoxy, halo$(C_1-C_6)$alkoxy, or $(C_3-C_6)$cycloalkoxy;

or $R^3$ and $R^5$ taken together with the carbon atoms to which they are attached represent a 5- or 6-membered ring, optionally containing one, two, or three heteroatoms independently selected from nitrogen, oxygen, and sulfur, wherein said ring is optionally substituted by one or two substituents independently selected from halogen, $(C_1-C_4)$alkyl, halo$(C_1-C_4)$alkyl, $(C_3-C_6)$cycloalkyl, hydroxyl, $(C_1-C_4)$alkoxy, halo$(C_1-C_4)$alkoxy, $(C_3-C_6)$cycloalkoxy, amino, $((C_1-C_4)$alkyl)amino-, and $((C_1-C_4)$alkyl)$((C_1-C_4)$alkyl)amino-;

each $R^6$ is independently selected from the group consisting of halogen, $(C_1-C_6)$alkyl, halo$(C_1-C_6)$alkyl, $(C_3-C_6)$cycloalkyl, cyano, hydroxyl, $(C_1-C_6)$alkoxy, halo$(C_1-C_6)$alkoxy, $(C_3-C_6)$cycloalkoxy, amino, $((C_1-C_6)$alkyl)amino-, and $((C_1-C_6)$alkyl)$((C_1-C_6)$alkyl)amino-;

$R^7$ is $(C_1-C_6)$alkyl, halo$(C_1-C_6)$alkyl, $(C_3-C_6)$cycloalkyl, or 4- to 6-membered heterocycloalkyl; wherein said $(C_1-C_6)$alkyl is optionally substituted by cyano, hydroxyl, $(C_1-C_4)$alkoxy, halo$(C_1-C_4)$alkoxy, or —$NR^8R^9$; and wherein said $(C_3-C_6)$cycloalkyl is optionally substituted by one or two substituents independently selected from $(C_1-C_4)$alkyl, halo$(C_1-C_4)$alkyl, hydroxyl, hydroxy$(C_1-C_4)$alkyl, $(C_1-C_4)$alkoxy, and halo$(C_1-C_4)$alkoxy; and wherein said 4- to 6-membered heterocycloalkyl is optionally substituted by one or two substituents independently selected from $(C_1-C_4)$alkyl and halo$(C_1-C_4)$alkyl; and $R^8$ and $R^9$ are each independently selected from the group consisting of hydrogen, $(C_1-C_4)$alkyl, and halo$(C_1-C_4)$alkyl;

or $R^8$ and $R^9$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, or halo$(C_1-C_4)$alkyl;

provided that the compound is not 1-(4-(5-hydroxy-1-oxo-1,2-dihydroisoquinolin-4-yl)phenyl)-3-phenylurea, 1-(5-(tert-butyl)isoxazol-3-yl)-3-(4-((6-oxo-1,6-dihydropyridin-3-yl)oxy)phenyl)urea, 1-(4-chloro-3-(trifluoromethyl)phenyl)-3-(4-((6-oxo-1,6-dihydropyridin-3-yl)oxy)phenyl)urea, 1-(4-ethylphenyl)-3-(4-((6-oxo-1,6-dihydropyridin-3-yl)oxy)phenyl)urea, 1-(4-((6-oxo-1,6-dihydropyridin-3-yl)oxy)phenyl)-3-(p-tolyl)urea, 1-(4-((6-oxo-1,6-dihydropyridin-3-yl)oxy)phenyl)-3-(3-(trifluoromethyl)phenyl)urea, or 1-(4-(tert-butyl)phenyl)-3-(4-((6-oxo-1,6-dihydropyridin-3-yl)oxy)phenyl)urea.

This invention also relates to compounds of Formula (II):

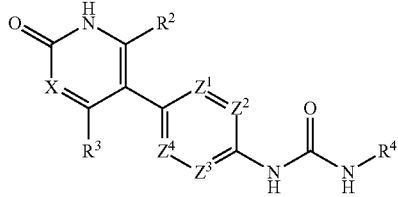

(II)

or pharmaceutically acceptable salts thereof, wherein X, $Z^1$, $Z^2$, $Z^3$, $Z^4$, $R^2$, $R^3$, and $R^4$ are defined according to Formula (I), provided that the compound is not 1-(4-(5-hydroxy-1-oxo-1,2-dihydroisoquinolin-4-yl)phenyl)-3-phenylurea.

This invention also relates to compounds of Formula (III):

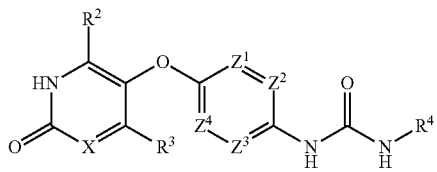

(III)

or pharmaceutically acceptable salts thereof, wherein X, $Z^1$, $Z^2$, $Z^3$, $Z^4$, $R^2$, $R^3$, and $R^4$ are defined according to Formula (I), provided that the compound is not 1-(5-(tert-butyl)isoxazol-3-yl)-3-(4-((6-oxo-1,6-dihydropyridin-3-yl)oxy)phenyl)urea, 1-(4-chloro-3-(trifluoromethyl)phenyl)-3-(4-((6-oxo-1,6-dihydropyridin-3-yl)oxy)phenyl)urea, 1-(4-ethylphenyl)-3-(4-((6-oxo-1,6-dihydropyridin-3-yl)oxy)phenyl)urea, 1-(4-((6-oxo-1,6-dihydropyridin-3-yl)oxy)phenyl)-3-(p-tolyl)urea, 1-(4-((6-oxo-1,6-dihydropyridin-3-yl)oxy)phenyl)-3-(3-(trifluoromethyl)phenyl)urea, or 1-(4-(tert-butyl)phenyl)-3-(4-((6-oxo-1,6-dihydropyridin-3-yl)oxy)phenyl)urea.

This invention also relates to compounds of Formula (IV):

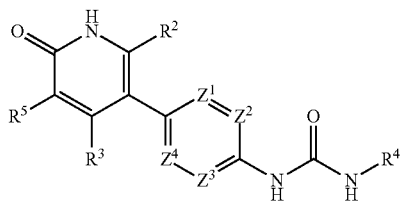

(IV)

or pharmaceutically acceptable salts thereof, wherein $Z^1$, $Z^2$, $Z^3$, $Z^4$, $R^2$, $R^3$, $R^4$, and $R^5$ are defined according to Formula (I), provided that the compound is not 1-(4-(5-hydroxy-1-oxo-1,2-dihydroisoquinolin-4-yl)phenyl)-3-phenylurea.

This invention also relates to compounds of Formula (V):

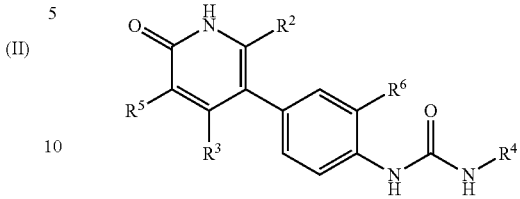

(V)

or pharmaceutically acceptable salts thereof, wherein $R^2$, $R^3$, $R^4$, $R^5$, and $R^6$ are defined according to Formula (I).

This invention also relates to compounds of Formula (VI):

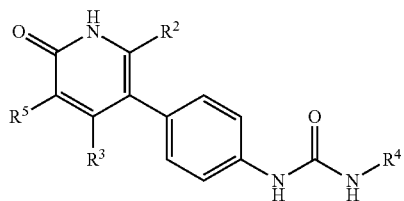

(VI)

or pharmaceutically acceptable salts thereof, wherein $R^2$, $R^3$, $R^4$, and $R^5$ are defined according to Formula (I), provided that the compound is not 1-(4-(5-hydroxy-1-oxo-1,2-dihydroisoquinolin-4-yl)phenyl)-3-phenylurea.

This invention also relates to compounds of Formula (VII):

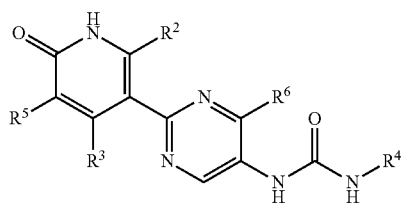

(VII)

or pharmaceutically acceptable salts thereof, wherein $R^2$, $R^3$, $R^4$, $R^5$, and $R^6$ are defined according to Formula (I).

This invention also relates to compounds of Formula (VIII):

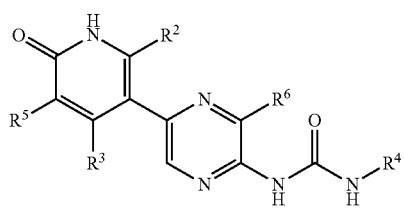

(VIII)

or pharmaceutically acceptable salts thereof, wherein $R^2$, $R^3$, $R^4$, $R^5$, and $R^6$ are defined according to Formula (I).

This invention also relates to compounds of Formula (IX):

(IX)

or pharmaceutically acceptable salts thereof, wherein $R^2$, $R^3$, $R^4$, $R^5$, and $R^6$ are defined according to Formula (I).

This invention also relates to compounds of Formula (X):

(X)

or pharmaceutically acceptable salts thereof, wherein $R^2$, $R^3$, $R^4$, $R^5$, and $R^6$ are defined according to Formula (I).

This invention also relates to compounds of Formula (XI):

(XI)

or pharmaceutically acceptable salts thereof, wherein X, $Z^1$, $Z^2$, $Z^3$, $Z^4$, $R^2$, and $R^3$ are defined according to Formula (I) and wherein:

A is N or $CR^{13}$;

$R^{10}$ is hydrogen, halogen, or $(C_1$-$C_4)$alkoxy;

$R^{11}$ is hydrogen, halogen, $(C_1$-$C_6)$alkyl, halo$(C_1$-$C_6)$alkyl, $(C_3$-$C_6)$cycloalkyl, cyano, 5- or 6-membered heteroaryl, hydroxyl, —$OR^7$, or —$CONR^8R^9$; wherein said $(C_1$-$C_6)$ alkyl is optionally substituted by cyano, hydroxyl, $(C_1$-$C_4)$ alkoxy, halo$(C_1$-$C_4)$alkoxy, or —$NR^8R^9$; and wherein said 5- or 6-membered heteroaryl is optionally substituted by halogen, $(C_1$-$C_4)$alkyl, or halo$(C_1$-$C_4)$alkyl;

$R^{12}$ is hydrogen, halogen, or halo$(C_1$-$C_4)$alkyl; and $R^{13}$ is hydrogen, halogen, halo$(C_1$-$C_4)$alkyl, or 5- or 6-membered heteroaryl, wherein said 5- or 6-membered heteroaryl is optionally substituted by halogen, $(C_1$-$C_4)$ alkyl, or halo$(C_1$-$C_4)$alkyl;

provided that the compound is not 1-(4-(5-hydroxy-1-oxo-1,2-dihydroisoquinolin-4-yl)phenyl)-3-phenylurea; and provided that when A is $CR^{13}$ at least one of $R^{10}$, $R^{11}$, $R^{12}$, and $R^{13}$ is hydrogen.

This invention also relates to compounds of Formula (XII):

(XII)

or pharmaceutically acceptable salts thereof, wherein $Z^1$, $Z^2$, $Z^3$, $Z^4$, $R^2$, $R^3$, and $R^5$ are defined according to Formula (I) and wherein:

A is N or $CR^{13}$;

$R^{10}$ is hydrogen, halogen, or $(C_1$-$C_4)$alkoxy;

$R^{11}$ is hydrogen, halogen, $(C_1$-$C_6)$alkyl, halo$(C_1$-$C_6)$alkyl, $(C_3$-$C_6)$cycloalkyl, cyano, 5- or 6-membered heteroaryl, hydroxyl, —$OR^7$, or —$CONR^8R^9$; wherein said $(C_1$-$C_6)$ alkyl is optionally substituted by cyano, hydroxyl, $(C_1$-$C_4)$ alkoxy, halo$(C_1$-$C_4)$alkoxy, or —$NR^8R^9$; and wherein said 5- or 6-membered heteroaryl is optionally substituted by halogen, $(C_1$-$C_4)$alkyl, or halo$(C_1$-$C_4)$alkyl;

$R^{12}$ is hydrogen, halogen, or halo$(C_1$-$C_4)$alkyl; and $R^{13}$ is hydrogen, halogen, halo$(C_1$-$C_4)$alkyl, or 5- or 6-membered heteroaryl, wherein said 5- or 6-membered heteroaryl is optionally substituted by halogen, $(C_1$-$C_4)$ alkyl, or halo$(C_1$-$C_4)$alkyl;

provided that the compound is not 1-(4-(5-hydroxy-1-oxo-1,2-dihydroisoquinolin-4-yl)phenyl)-3-phenylurea; and provided that when A is $CR^{13}$ at least one of $R^{10}$, $R^{11}$, $R^{12}$, and $R^{13}$ is hydrogen.

This invention also relates to compounds of Formula (XIII):

(XIII)

or pharmaceutically acceptable salts thereof, wherein $R^2$, $R^3$, $R^4$, $R^5$, and $R^6$ are defined according to Formula (I) and wherein:

A is N or $CR^{13}$;

$R^{10}$ is hydrogen, halogen, or $(C_1$-$C_4)$alkoxy;

$R^{11}$ is hydrogen, halogen, $(C_1$-$C_6)$alkyl, halo$(C_1$-$C_6)$alkyl, $(C_3$-$C_6)$cycloalkyl, cyano, 5- or 6-membered heteroaryl, hydroxyl, —$OR^7$, or —$CONR^8R^9$; wherein said $(C_1$-$C_6)$ alkyl is optionally substituted by cyano, hydroxyl, $(C_1$-$C_4)$ alkoxy, halo$(C_1$-$C_4)$alkoxy, or —$NR^8R^9$; and wherein said 5- or 6-membered heteroaryl is optionally substituted by halogen, $(C_1$-$C_4)$alkyl, or halo$(C_1$-$C_4)$alkyl;

$R^{12}$ is hydrogen, halogen, or halo$(C_1$-$C_4)$alkyl; and $R^{13}$ is hydrogen, halogen, halo$(C_1$-$C_4)$alkyl, or 5- or 6-membered heteroaryl, wherein said 5- or 6-membered heteroaryl is optionally substituted by halogen, $(C_1$-$C_4)$ alkyl, or halo$(C_1$-$C_4)$alkyl;

provided that when A is $CR^{13}$ at least one of $R^{10}$, $R^{11}$, $R^{12}$, and $R^{13}$ is hydrogen.

This invention also relates to compounds of Formula (XIV):

(XIV)

or pharmaceutically acceptable salts thereof, wherein $R^2$, $R^3$, $R^4$, $R^5$, and $R^6$ are defined according to Formula (I) and wherein:

A is N or $CR^{13}$;
$R^{10}$ is hydrogen, halogen, or $(C_1-C_4)$alkoxy;
$R^{11}$ is hydrogen, halogen, $(C_1-C_6)$alkyl, halo$(C_1-C_6)$alkyl, $(C_3-C_6)$cycloalkyl, cyano, 5- or 6-membered heteroaryl, hydroxyl, —$OR^7$, or —$CONR^8R^9$; wherein said $(C_1-C_6)$ alkyl is optionally substituted by cyano, hydroxyl, $(C_1-C_4)$ alkoxy, halo$(C_1-C_4)$alkoxy, or —$NR^8R^9$; and wherein said 5- or 6-membered heteroaryl is optionally substituted by halogen, $(C_1-C_4)$alkyl, or halo$(C_1-C_4)$alkyl;
$R^{12}$ is hydrogen, halogen, or halo$(C_1-C_4)$alkyl; and
$R^{13}$ is hydrogen, halogen, halo$(C_1-C_4)$alkyl, or 5- or 6-membered heteroaryl, wherein said 5- or 6-membered heteroaryl is optionally substituted by halogen, $(C_1-C_4)$ alkyl, or halo$(C_1-C_4)$alkyl;
provided that the compound is not 1-(4-(5-hydroxy-1-oxo-1,2-dihydroisoquinolin-4-yl)phenyl)-3-phenylurea;
and provided that when A is $CR^{13}$ at least one of $R^{10}$, $R^{11}$, $R^{12}$, and $R^{13}$ is hydrogen.

This invention also relates to compounds of Formula (XV):

(XV)

or pharmaceutically acceptable salts thereof, wherein $R^2$, $R^3$, $R^4$, $R^5$, and $R^6$ are defined according to Formula (I) and wherein:

A is N or $CR^{13}$;
$R^{10}$ is hydrogen, halogen, or $(C_1-C_4)$alkoxy;
$R^{11}$ is hydrogen, halogen, $(C_1-C_6)$alkyl, halo$(C_1-C_6)$alkyl, $(C_3-C_6)$cycloalkyl, cyano, 5- or 6-membered heteroaryl, hydroxyl, —$OR^7$, or —$CONR^8R^9$; wherein said $(C_1-C_6)$ alkyl is optionally substituted by cyano, hydroxyl, $(C_1-C_4)$ alkoxy, halo$(C_1-C_4)$alkoxy, or —$NR^8R^9$; and wherein said 5- or 6-membered heteroaryl is optionally substituted by halogen, $(C_1-C_4)$alkyl, or halo$(C_1-C_4)$alkyl;
$R^{12}$ is hydrogen, halogen, or halo$(C_1-C_4)$alkyl; and
$R^{13}$ is hydrogen, halogen, halo$(C_1-C_4)$alkyl, or 5- or 6-membered heteroaryl, wherein said 5- or 6-membered heteroaryl is optionally substituted by halogen, $(C_1-C_4)$ alkyl, or halo$(C_1-C_4)$alkyl;

provided that when A is $CR^{13}$ at least one of $R^{10}$, $R^{11}$, $R^{12}$, and $R^{13}$ is hydrogen.

This invention also relates to compounds of Formula (XVI):

(XVI)

or pharmaceutically acceptable salts thereof, wherein $R^2$, $R^3$, $R^4$, $R^5$, and $R^6$ are defined according to Formula (I) and wherein:

A is N or $CR^{13}$;
$R^{10}$ is hydrogen, halogen, or $(C_1-C_4)$alkoxy;
$R^{11}$ is hydrogen, halogen, $(C_1-C_6)$alkyl, halo$(C_1-C_6)$alkyl, $(C_3-C_6)$cycloalkyl, cyano, 5- or 6-membered heteroaryl, hydroxyl, —$OR^7$, or —$CONR^8R^9$; wherein said $(C_1-C_6)$ alkyl is optionally substituted by cyano, hydroxyl, $(C_1-C_4)$ alkoxy, halo$(C_1-C_4)$alkoxy, or —$NR^8R^9$; and wherein said 5- or 6-membered heteroaryl is optionally substituted by halogen, $(C_1-C_4)$alkyl, or halo$(C_1-C_4)$alkyl;
$R^{12}$ is hydrogen, halogen, or halo$(C_1-C_4)$alkyl; and
$R^{13}$ is hydrogen, halogen, halo$(C_1-C_4)$alkyl, or 5- or 6-membered heteroaryl, wherein said 5- or 6-membered heteroaryl is optionally substituted by halogen, $(C_1-C_4)$ alkyl, or halo$(C_1-C_4)$alkyl;
provided that when A is $CR^{13}$ at least one of $R^{10}$, $R^{11}$, $R^{12}$, and $R^{13}$ is hydrogen.

This invention also relates to compounds of Formula (XVII):

(XVII)

or pharmaceutically acceptable salts thereof, wherein $R^2$, $R^3$, $R^4$, $R^5$, and $R^6$ are defined according to Formula (I) and wherein:

A is N or $CR^{13}$;
$R^{10}$ is hydrogen, halogen, or $(C_1-C_4)$alkoxy;
$R^{11}$ is hydrogen, halogen, $(C_1-C_6)$alkyl, halo$(C_1-C_6)$alkyl, $(C_3-C_6)$cycloalkyl, cyano, 5- or 6-membered heteroaryl, hydroxyl, —$OR^7$, or —$CONR^8R^9$; wherein said $(C_1-C_6)$ alkyl is optionally substituted by cyano, hydroxyl, $(C_1-C_4)$ alkoxy, halo$(C_1-C_4)$alkoxy, or —$NR^8R^9$; and wherein said 5- or 6-membered heteroaryl is optionally substituted by halogen, $(C_1-C_4)$alkyl, or halo$(C_1-C_4)$alkyl;
$R^{12}$ is hydrogen, halogen, or halo$(C_1-C_4)$alkyl; and
$R^{13}$ is hydrogen, halogen, halo$(C_1-C_4)$alkyl, or 5- or 6-membered heteroaryl, wherein said 5- or 6-membered heteroaryl is optionally substituted by halogen, $(C_1-C_4)$ alkyl, or halo$(C_1-C_4)$alkyl;

provided that when A is CR$^{13}$ at least one of R$^{10}$, R$^{11}$, R$^{12}$, and R$^{13}$ is hydrogen.

This invention also relates to compounds of Formula (XVIII):

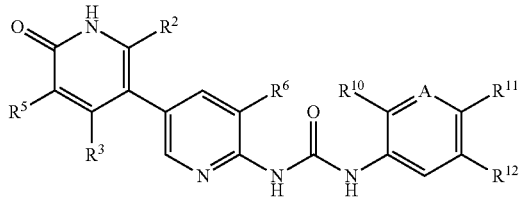

(XVIII)

or pharmaceutically acceptable salts thereof, wherein R$^2$, R$^3$, R$^4$, R$^5$, and R$^6$ are defined according to Formula (I) and wherein:

A is N or CR$^{13}$;

R$^{10}$ is hydrogen, halogen, or (C$_1$-C$_4$)alkoxy;

R$^{11}$ is hydrogen, halogen, (C$_1$-C$_6$)alkyl, halo(C$_1$-C$_6$)alkyl, (C$_3$-C$_6$)cycloalkyl, cyano, 5- or 6-membered heteroaryl, hydroxyl, —OR$^7$, or —CONR$^8$R$^9$; wherein said (C$_1$-C$_6$) alkyl is optionally substituted by cyano, hydroxyl, (C$_1$-C$_4$) alkoxy, halo(C$_1$-C$_4$)alkoxy, or —NR$^8$R$^9$; and wherein said 5- or 6-membered heteroaryl is optionally substituted by halogen, (C$_1$-C$_4$)alkyl, or halo(C$_1$-C$_4$)alkyl;

R$^{12}$ is hydrogen, halogen, or halo(C$_1$-C$_4$)alkyl; and

R$^{13}$ is hydrogen, halogen, halo(C$_1$-C$_4$)alkyl, or 5- or 6-membered heteroaryl, wherein said 5- or 6-membered heteroaryl is optionally substituted by halogen, (C$_1$-C$_4$) alkyl, or halo(C$_1$-C$_4$)alkyl;

provided that when A is CR$^{13}$ at least one of R$^{10}$, R$^{11}$, R$^{12}$, and R$^{13}$ is hydrogen.

This invention also relates to compounds of Formula (XIX):

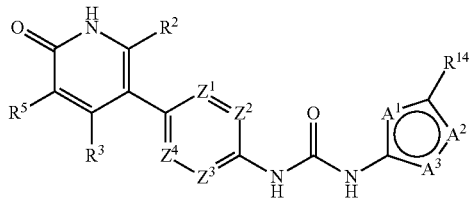

(XIX)

or pharmaceutically acceptable salts thereof, wherein Z$^1$, Z$^2$, Z$^3$, Z$^4$, R$^2$, R$^3$, and R$^5$ are defined according to Formula (I) and wherein:

One of A$^1$, A$^2$, and A$^3$ is selected from O, S, and NR$^{15}$ and the other two are each independently selected from N and CH;

R$^{14}$ is hydrogen, halogen, (C$_1$-C$_6$)alkyl, halo(C$_1$-C$_6$)alkyl, (C$_3$-C$_6$)cycloalkyl, cyano, hydroxyl, —OR$^7$, —CONR$^8$R$^9$, —SO$_2$R$^7$, and —SO$_2$NR$^8$R$^9$; wherein said (C$_1$-C$_6$)alkyl is optionally substituted by cyano, hydroxyl, (C$_1$-C$_4$)alkoxy, halo(C$_1$-C$_4$)alkoxy, or —NR$^8$R$^9$; and R$^{15}$ is hydrogen, (C$_1$-C$_6$)alkyl, halo(C$_1$-C$_6$)alkyl, (C$_3$-C$_6$) cycloalkyl, or phenyl.

In another embodiment, X is CR$^5$. In a specific embodiment, X is N.

In a specific embodiment, Y is a bond. In another specific embodiment, Y is —O—.

In another embodiment, Z$^1$, Z$^2$, Z$^3$, and Z$^4$ are each independently N, CH, or CR$^6$, wherein 0, 1, 2, or 3 of Z$^1$, Z$^2$, Z$^3$, and Z$^4$ are N and 0, 1, 2, or 3 of Z$^1$, Z$^2$, Z$^3$, and Z$^4$ are CR$^6$. In another embodiment, Z$^1$, Z$^2$, Z$^3$, and Z$^4$ are each independently N, CH, or CR$^6$, wherein 0, 1, or 2 of Z$^1$, Z$^2$, Z$^3$, and Z$^4$ are N and 0, 1, or 2 of Z$^1$, Z$^2$, Z$^3$, and Z$^4$ are CR$^6$. In another embodiment, Z$^1$, Z$^2$, Z$^3$, and Z$^4$ are each independently CH or CR$^6$. In a specific embodiment, Z$^1$, Z$^2$, Z$^3$, and Z$^4$ are each independently CH. In another embodiment, one of Z$^1$, Z$^2$, Z$^3$, and Z$^4$ is CR$^6$ and the other three are each independently CH. In another embodiment, Z$^2$ is CR$^6$ and Z$^1$, Z$^3$, and Z$^4$ are each independently CH. In another embodiment, Z$^1$ is CR$^6$ and Z$^2$, Z$^3$, and Z$^4$ are each independently CH. In another embodiment, two of Z$^1$, Z$^2$, Z$^3$, and Z$^4$ are each independently CR$^6$ and the other two are each independently CH. In another embodiment, Z$^1$ and Z$^2$ are each independently CR$^6$ and Z$^3$ and Z$^4$ are each independently CH. In another embodiment, Z$^2$ and Z$^3$ is each independently CR$^6$ and Z$^1$ and Z$^4$ are each independently CH.

In another embodiment, one of Z$^1$, Z$^2$, Z$^3$, and Z$^4$ is N and the other three are each independently CH or CR$^6$. In a specific embodiment, one of Z$^1$, Z$^2$, Z$^3$, and Z$^4$ is N and the other three are each independently CH. In another embodiment, Z$^1$ is N and Z$^2$, Z$^3$, and Z$^4$ are each independently CH or CR$^6$. In another embodiment, Z$^1$ is N, Z$^2$ is CR$^6$, and Z$^3$ and Z$^4$ are each independently CH. In another embodiment, Z$^2$ is N and Z$^1$, Z$^3$, and Z$^4$ are each independently CH or CR$^6$. In another embodiment, Z$^2$ is N, Z$^1$ is CR$^6$, and Z$^3$ and Z$^4$ are each independently CH. In another embodiment, two of Z$^1$, Z$^2$, Z$^3$, and Z$^4$ are N and the other two are each independently CH or CR$^6$. In another embodiment, two of Z$^1$, Z$^2$, Z$^3$, and Z$^4$ are N and the other two are each independently CH. In another embodiment, Z$^1$ and Z$^4$ are N and Z$^2$ and Z$^3$ are each independently CH or CR$^6$. In another embodiment, Z$^1$ and Z$^4$ are N and Z$^2$ and Z$^3$ are each independently CR$^6$. In another embodiment, Z$^1$ and Z$^4$ are N, Z$^2$ is CR$^6$, and Z$^3$ is CH. In another embodiment, Z$^1$ and Z$^3$ are N and Z$^2$ and Z$^4$ are each independently CH or CR$^6$. In another embodiment, Z$^1$ and Z$^3$ are N and Z$^2$ and Z$^4$ are each independently CR$^6$. In another embodiment, Z$^1$ and Z$^3$ are N, Z$^2$ is CR$^6$, and Z$^4$ is CH.

In another embodiment, R$^1$ is hydrogen or (C$_1$-C$_4$)alkyl. In a specific embodiment, R$^1$ is hydrogen, methyl, or ethyl. In a further specific embodiment, R$^1$ is hydrogen.

In another embodiment, R$^2$ is hydrogen, fluorine, chlorine, (C$_1$-C$_4$)alkyl, halo(C$_1$-C$_4$)alkyl, hydroxyl, (C$_1$-C$_4$) alkoxy, halo(C$_1$-C$_4$)alkoxy, (C$_3$-C$_6$)cycloalkoxy, amino, ((C$_1$-C$_6$)alkyl)amino-, or ((C$_1$-C$_6$)alkyl)((C$_1$-C$_6$)alkyl) amino-. In another embodiment, R$^2$ is hydrogen, (C$_1$-C$_4$) alkyl, or (C$_1$-C$_4$)alkoxy. In a specific embodiment, R$^2$ is hydrogen, methyl, ethyl, methoxy, or ethoxy. In a further specific embodiment, R$^2$ is hydrogen.

In another embodiment, R$^3$ is hydrogen, fluorine, chlorine, (C$_1$-C$_4$)alkyl, halo(C$_1$-C$_4$)alkyl, hydroxyl, (C$_1$-C$_4$) alkoxy, halo(C$_1$-C$_4$)alkoxy, (C$_3$-C$_6$)cycloalkoxy, amino, ((C$_1$-C$_6$)alkyl)amino-, or ((C$_1$-C$_6$)alkyl)((C$_1$-C$_6$)alkyl) amino-. In another embodiment, R$^3$ is hydrogen, hydroxyl, (C$_1$-C$_4$)alkoxy, or (C$_3$-C$_6$)cycloalkoxy. In a specific embodiment, R$^3$ is hydrogen, fluorine, methyl, hydroxyl, methoxy, difluoromethoxy, ethoxy, n-propyloxy, isopropyloxy, 3-fluoropropyloxy, cyclopropyloxy, or methylamino-. In another embodiment, R$^3$ is hydrogen or (C$_1$-C$_4$)alkoxy. In another specific embodiment, R$^3$ is hydrogen or ethoxy. In a further specific embodiment, R$^3$ is ethoxy. In another further specific embodiment, R$^3$ is hydrogen.

In another embodiment, $R^4$ is phenyl which is optionally substituted by one, two, or three substituents independently selected from halogen, $(C_1-C_6)$alkyl, halo$(C_1-C_6)$alkyl, $(C_3-C_6)$cycloalkyl, cyano, phenyl, 5- or 6-membered heteroaryl, hydroxyl, —$OR^7$, —$CONR^8R^9$, —$SO_2R^7$, and —$SO_2NR^8R^9$; wherein said $(C_1-C_6)$alkyl is optionally substituted by cyano, hydroxyl, $(C_1-C_4)$alkoxy, halo$(C_1-C_4)$alkoxy, —$NR^8R^9$ or —$CONR^8R^9$; and wherein said 5- or 6-membered heteroaryl substituent is optionally substituted by halogen, $(C_1-C_4)$alkyl, or halo$(C_1-C_4)$alkyl. In another embodiment, $R^4$ is phenyl which is optionally substituted by one, two, or three substituents independently selected from fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, (3-methyloxetan-3-yl)oxy-, and —$CONH_2$; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-. In another embodiment, $R^4$ is phenyl which is optionally substituted by one or two substituents independently selected from $(C_1-C_4)$alkyl, halo$(C_1-C_4)$alkyl, $(C_1-C_4)$alkoxy, and (3-methyloxetan-3-yl)oxy-; wherein said $(C_1-C_4)$alkyl is optionally substituted by cyano, hydroxyl, or dimethylamino-. In another embodiment, $R^4$ is phenyl which is optionally substituted by one or two substituents independently selected from $(C_1-C_4)$alkyl and halo$(C_1-C_4)$alkyl; wherein said $(C_1-C_4)$alkyl is optionally substituted by cyano, hydroxyl, or dimethylamino-.

In another embodiment, $R^4$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted by one, two, or three substituents independently selected from halogen, $(C_1-C_6)$alkyl, halo$(C_1-C_6)$alkyl, $(C_3-C_6)$cycloalkyl, cyano, phenyl, 5- or 6-membered heteroaryl, hydroxyl, —$OR^7$, —$CONR^8R^9$, —$SO_2R^7$, and —$SO_2NR^8R^9$; wherein said $(C_1-C_6)$alkyl is optionally substituted by cyano, hydroxyl, $(C_1-C_4)$alkoxy, halo$(C_1-C_4)$alkoxy, —$NR^8R^9$ or —$CONR^8R^9$; and wherein said 5- or 6-membered heteroaryl substituent is optionally substituted by halogen, $(C_1-C_4)$alkyl, or halo$(C_1-C_4)$alkyl. In another embodiment, $R^4$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted by one, two, or three substituents independently selected from fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, and —$CONH_2$; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-.

In another embodiment, $R^4$ is pyridinyl which is optionally substituted by one, two, or three substituents independently selected from fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, and —$CONH_2$; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-. In another embodiment, $R^4$ is pyridinyl which is optionally substituted by one or two substituents independently selected from $(C_1-C_4)$alkyl and halo$(C_1-C_4)$alkyl; wherein said $(C_1-C_4)$alkyl is optionally substituted by cyano, hydroxyl, or dimethylamino-.

In another embodiment, $R^4$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted by one or two substituents independently selected from $(C_1-C_4)$alkyl and halo$(C_1-C_4)$alkyl. In another embodiment, $R^4$ is isoxazolyl which is optionally substituted by $(C_1-C_4)$alkyl or halo$(C_1-C_4)$alkyl.

In another embodiment, $R^5$ is hydrogen, fluorine, chlorine, $(C_1-C_4)$alkyl, halo$(C_1-C_4)$alkyl, hydroxyl, $(C_1-C_4)$alkoxy, halo$(C_1-C_4)$alkoxy, $(C_3-C_6)$cycloalkoxy, amino, $((C_1-C_6)$alkyl)amino-, or $((C_1-C_6)$alkyl)$((C_1-C_6)$alkyl)amino-. In another embodiment, $R^5$ is hydrogen, hydroxyl, $(C_1-C_4)$alkoxy, or $(C_3-C_6)$cycloalkoxy. In a specific embodiment, $R^5$ is hydrogen, fluorine, methyl, hydroxyl, methoxy, difluoromethoxy, ethoxy, n-propyloxy, isopropyloxy, 3-fluoropropyloxy, cyclopropyloxy, or methylamino-. In another embodiment, $R^5$ is hydrogen or $(C_1-C_4)$alkoxy. In another specific embodiment, $R^5$ is hydrogen or ethoxy. In a further specific embodiment, $R^5$ is ethoxy. In another further specific embodiment, $R^5$ is hydrogen.

In another embodiment, $R^3$ and $R^5$ taken together with the carbon atoms to which they are attached represent a 5- or 6-membered ring, optionally containing one, two, or three heteroatoms independently selected from nitrogen, oxygen, and sulfur, wherein said ring is optionally substituted by one or two substituents independently selected from halogen, $(C_1-C_4)$alkyl, halo$(C_1-C_4)$alkyl, $(C_3-C_6)$cycloalkyl, hydroxyl, $(C_1-C_4)$alkoxy, halo$(C_1-C_4)$alkoxy, $(C_3-C_6)$cycloalkoxy, amino, $((C_1-C_4)$alkyl)amino-, and $((C_1-C_4)$alkyl)$((C_1-C_4)$alkyl)amino-. In another embodiment, $R^3$ and $R^5$ taken together with the carbon atoms to which they are attached represent a phenyl ring which is optionally substituted by one or two substituents independently selected from halogen, $(C_1-C_4)$alkyl, halo$(C_1-C_4)$alkyl, $(C_3-C_6)$cycloalkyl, hydroxyl, $(C_1-C_4)$alkoxy, halo$(C_1-C_4)$alkoxy, $(C_3-C_6)$cycloalkoxy, amino, $((C_1-C_4)$alkyl)amino-, and $((C_1-C_4)$alkyl)$((C_1-C_4)$alkyl)amino-. In a specific embodiment, $R^3$ and $R^5$ taken together with the carbon atoms to which they are attached represent a phenyl ring.

In another embodiment, $R^3$ and $R^5$ taken together with the carbon atoms to which they are attached represent pyridinyl, pyridazinyl, pyrazinyl, pyrimidinyl, or triazinyl, each of which is optionally substituted by halogen, $(C_1-C_4)$alkyl, halo$(C_1-C_4)$alkyl, $(C_3-C_6)$cycloalkyl, hydroxyl, $(C_1-C_4)$alkoxy, halo$(C_1-C_4)$alkoxy, $(C_3-C_6)$cycloalkoxy, amino, $((C_1-C_4)$alkyl)amino-, or $((C_1-C_4)$alkyl)$((C_1-C_4)$alkyl)amino-. In a specific embodiment, $R^3$ and $R^5$ taken together with the carbon atoms to which they are attached represent pyridinyl, pyridazinyl, pyrazinyl, pyrimidinyl, or triazinyl. In a further specific embodiment, $R^3$ and $R^5$ taken together with the carbon atoms to which they are attached represent pyridinyl.

In another embodiment, $R^3$ and $R^5$ taken together with the carbon atoms to which they are attached represent furanyl, dihydrofuranyl, thienyl, pyrrolyl, pyrrolinyl, imidazolyl, imidazolinyl, pyrazolyl, pyrazolinyl, triazolyl, oxazolyl, thiazolyl, isoxazolyl, isothiazolyl, oxadiazolyl, or thiadiazolyl, wherein said furanyl, dihydrofuranyl, thienyl, pyrrolyl, pyrrolinyl, imidazolyl, imidazolinyl, pyrazolyl, pyrazolinyl, triazolyl, oxazolyl, thiazolyl, isoxazolyl, or isothiazolyl is optionally substituted by halogen, $(C_1-C_4)$alkyl, halo$(C_1-C_4)$alkyl, $(C_3-C_6)$cycloalkyl, hydroxyl, $(C_1-C_4)$alkoxy, halo$(C_1-C_4)$alkoxy, $(C_3-C_6)$cycloalkoxy, amino, $((C_1-C_4)$alkyl)amino-, or $((C_1-C_4)$alkyl)$((C_1-C_4)$alkyl)amino-. In a specific embodiment, $R^3$ and $R^5$ taken together with the carbon atoms to which they are attached represent furanyl, dihydrofuranyl, thienyl, pyrrolyl, pyrrolinyl, imidazolyl, imidazolinyl, pyrazolyl, pyrazolinyl, triazolyl, oxazolyl, thiazolyl, isoxazolyl, isothiazolyl, oxadiazolyl, or thiadiazolyl. In another specific embodiment, $R^3$ and $R^5$ taken together with the carbon atoms to which they are attached represent furanyl, dihydrofuranyl, or pyrazolyl. In another specific embodiment, $R^3$ and $R^5$ taken together with the carbon atoms to which they are attached represent cyclopentenyl.

In another embodiment, each $R^6$ is independently selected from the group consisting of halogen, $(C_1-C_4)$alkyl, halo$(C_1-C_4)$alkyl, $(C_3-C_6)$cycloalkyl, cyano, hydroxyl, $(C_1-C_4)$alkoxy, halo$(C_1-C_4)$alkoxy, $(C_3-C_6)$cycloalkoxy, amino, $((C_1-C_4)$alkyl)amino-, and $((C_1-C_4)$alkyl)$((C_1-C_6)$alkyl)amino-. In a specific embodiment, each $R^6$ is independently selected from the group consisting of fluorine, chlorine, methyl, ethyl, difluoromethyl, cyclopropyl, methoxy, isopropoxy, and dimethylamino-. In a further specific embodiment, $R^6$ is fluorine. In another further specific embodiment, $R^6$ is methyl.

In another embodiment, $R^8$ and $R^9$ are each independently selected from the group consisting of hydrogen, $(C_1-C_4)$alkyl, halo$(C_1-C_4)$alkyl, amino$(C_1-C_4)$alkyl-, $((C_1-C_4)$alkyl)amino$(C_1-C_4)$alkyl-, and $((C_1-C_4)$alkyl)$((C_1-C_4)$alkyl)amino$(C_1-C_4)$alkyl-. In another embodiment, $R^8$ and $R^9$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, halo$(C_1-C_4)$alkyl, or hydroxy$(C_1-C_4)$alkyl.

In another embodiment, $R^8$ and $R^9$ are each independently selected from the group consisting of hydrogen, $(C_1-C_4)$alkyl, and halo$(C_1-C_4)$alkyl; or $R^8$ and $R^9$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, or halo$(C_1-C_4)$alkyl. In another embodiment, $R^8$ and $R^9$ are each independently selected from the group consisting of hydrogen, $(C_1-C_4)$alkyl, and halo$(C_1-C_4)$alkyl. In another embodiment, $R^8$ and $R^9$ taken together with the nitrogen to which they are attached represent a 5- or 6-membered saturated ring, optionally containing an additional heteroatom selected from oxygen, nitrogen, and sulfur, wherein said ring is optionally substituted by halogen, $(C_1-C_4)$alkyl, or halo$(C_1-C_4)$alkyl.

In another embodiment, A is $CR^{13}$ and $R^{13}$ is hydrogen, halogen, halo$(C_1-C_4)$alkyl, furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, wherein said furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl is optionally substituted by halogen, $(C_1-C_4)$alkyl, or halo$(C_1-C_4)$alkyl. In another embodiment, A is $CR^{13}$ and $R^{13}$ is hydrogen, fluorine, chlorine, or trifluoromethyl. In a specific embodiment, A is CH. In another specific embodiment, A is N.

In another embodiment, $R^{10}$ is hydrogen or halogen. In a specific embodiment, $R^{10}$ is hydrogen or fluorine. In a more specific embodiment, $R^{10}$ is hydrogen.

In another embodiment, $R^{11}$ is hydrogen, fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, (3-methyloxetan-3-yl)oxy-, or $-CONH_2$; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-. In another embodiment, $R^{11}$ is hydrogen, $(C_1-C_4)$alkoxy, or $(C_1-C_6)$alkyl; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-. In another embodiment, $R^{11}$ is $(C_1-C_4)$alkyl which is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-.

In another embodiment, $R^{12}$ is halo$(C_1-C_4)$alkyl. In a specific embodiment, $R^{12}$ is trifluoromethyl.

In another embodiment, $A^1$ is CH, $A^2$ is O, and $A^3$ is N; or $A^1$ is CH, $A^2$ is N, and $A^3$ is O; or $A^1$ is CH, $A^2$ is N, and $A^3$ is $NR^{15}$. In another embodiment, $A^1$ is CH, $A^2$ is O, and $A^3$ is N. In another embodiment, $A^1$ is CH, $A^2$ is N, and $A^3$ is O. In another embodiment, $A^1$ is CH, $A^2$ is N, and $A^3$ is $NR^{15}$.

In another embodiment, $R^{14}$ is hydrogen, halogen, $(C_1-C_4)$alkyl, halo$(C_1-C_4)$alkyl, or $(C_3-C_6)$cycloalkyl. In another embodiment, $R^{14}$ is $(C_1-C_4)$alkyl or halo$(C_1-C_4)$alkyl. In another embodiment, $R^{14}$ is halo$(C_1-C_4)$alkyl.

In another embodiment, $R^{15}$ is hydrogen, $(C_1-C_4)$alkyl, halo$(C_1-C_4)$alkyl, $(C_3-C_6)$cycloalkyl, or phenyl. In a specific embodiment, $R^{15}$ is hydrogen, methyl, ethyl, or phenyl.

In a particular embodiment, this invention relates to compounds of Formula (I) or pharmaceutically acceptable salts thereof wherein:

X is $CR^5$;

Y is a bond;

$Z^1$, $Z^3$, and $Z^4$ are each independently N, CH, or $CR^6$, wherein 0, 1, or 2 of $Z^1$, $Z^2$, $Z^3$, and $Z^4$ are N and 0, 1, or 2 of $Z^1$, $Z^2$, $Z^3$, and $Z^4$ are $CR^6$;

$R^1$ is hydrogen;

$R^2$ is hydrogen, $(C_1-C_4)$alkyl, or $(C_1-C_4)$alkoxy;

$R^3$ is hydrogen, hydroxyl, $(C_1-C_4)$alkoxy, or $(C_3-C_6)$cycloalkoxy;

$R^4$ is phenyl which is optionally substituted by one, two, or three substituents independently selected from fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, (3-methyloxetan-3-yl)oxy-, and $-CONH_2$; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-;

$R^5$ is hydrogen, hydroxyl, $(C_1-C_4)$alkoxy, or $(C_3-C_6)$cycloalkoxy; and each $R^6$ is independently selected from the group consisting of fluorine, chlorine, methyl, ethyl, difluoromethyl, cyclopropyl, methoxy, isopropoxy, and dimethylamino-.

In another particular embodiment, this invention relates to compounds of Formula (I) or pharmaceutically acceptable salts thereof wherein:

X is $CR^5$;

Y is a bond;

$Z^1$, $Z^2$, $Z^3$, and $Z^4$ are each independently N, CH, or $CR^6$, wherein 0, 1, or 2 of $Z^1$, $Z^2$, $Z^3$, and $Z^4$ are N and 0, 1, or 2 of $Z^1$, $Z^2$, $Z^3$, and $Z^4$ are $CR^6$;

$R^1$ is hydrogen;

$R^2$ is hydrogen, $(C_1-C_4)$alkyl, or $(C_1-C_4)$alkoxy;

$R^3$ is hydrogen, hydroxyl, $(C_1-C_4)$alkoxy, or $(C_3-C_6)$cycloalkoxy;

$R^4$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted by one or two substituents independently selected from $(C_1-C_4)$alkyl and halo$(C_1-C_4)$alkyl;

$R^5$ is hydrogen, hydroxyl, $(C_1-C_4)$alkoxy, or $(C_3-C_6)$cycloalkoxy; and each $R^6$ is independently selected from the group consisting of fluorine, chlorine, methyl, ethyl, difluoromethyl, cyclopropyl, methoxy, isopropoxy, and dimethylamino-.

In another particular embodiment, this invention relates to compounds of Formula (XII) or pharmaceutically acceptable salts thereof wherein:

$Z^1$, $Z^2$, $Z^3$, and $Z^4$ are each independently N, CH, or $CR^6$, wherein 0, 1, or 2 of $Z^1$, $Z^2$, $Z^3$, and $Z^4$ are N and 0, 1, or 2 of $Z^1$, $Z^2$, $Z^3$, and $Z^4$ are $CR^6$;

$R^2$ is hydrogen, $(C_1-C_4)$alkyl, or $(C_1-C_4)$alkoxy;

$R^3$ is hydrogen, hydroxyl, $(C_1-C_4)$alkoxy, or $(C_3-C_6)$cycloalkoxy;

$R^5$ is hydrogen, hydroxyl, $(C_1-C_4)$alkoxy, or $(C_3-C_6)$cycloalkoxy;

A is N or $CR^{13}$;

$R^{10}$ is hydrogen or halogen;

$R^{11}$ is hydrogen, fluorine, chlorine, $(C_1-C_6)$alkyl, halo$(C_1-C_4)$alkyl, cyano, $(C_1-C_4)$alkoxy, hydroxy$(C_2-C_4)$alkoxy-, $(C_1-C_4)$alkoxy$(C_2-C_4)$alkoxy-, amino$(C_2-C_4)$alkoxy-, $((C_1-C_4)$alkyl)amino$(C_2-C_4)$alkoxy-, $((C_1-C_4)$alkyl)$((C_1-C_4)$alkyl)amino$(C_2-C_4)$alkoxy-, (3-methyloxetan-3-yl)oxy-, or —$CONH_2$; wherein said $(C_1-C_6)$alkyl is optionally substituted by cyano, hydroxyl, $(C_1-C_4)$alkoxy, amino, $((C_1-C_4)$alkyl)amino-, or $((C_1-C_4)$alkyl)$((C_1-C_4)$alkyl)amino-;

$R^{12}$ is halo$(C_1-C_4)$alkyl; and $R^{13}$ is hydrogen, halogen, halo$(C_1-C_4)$alkyl, furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, wherein said furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl is optionally substituted by halogen, $(C_1-C_4)$alkyl, or halo$(C_1-C_4)$alkyl.

In another particular embodiment, this invention relates to compounds of Formula (XIX) or pharmaceutically acceptable salts thereof wherein:

$Z^1$, $Z^2$, $Z^3$, and $Z^4$ are each independently N, CH, or $CR^6$, wherein 0, 1, or 2 of $Z^1$, $Z^2$, $Z^3$, and $Z^4$ are N and 0, 1, or 2 of $Z^1$, $Z^2$, $Z^3$, and $Z^4$ are $CR^6$;

$R^2$ is hydrogen, $(C_1-C_4)$alkyl, or $(C_1-C_4)$alkoxy;

$R^3$ is hydrogen, hydroxyl, $(C_1-C_4)$alkoxy, or $(C_3-C_6)$cycloalkoxy;

$R^5$ is hydrogen, hydroxyl, $(C_1-C_4)$alkoxy, or $(C_3-C_6)$cycloalkoxy;

$A^1$ is CH, $A^2$ is O, and $A^3$ is N; or $A^1$ is CH, $A^2$ is N, and $A^3$ is O; or $A^1$ is CH, $A^2$ is N, and $A^3$ is $NR^{15}$;

$R^{14}$ is $(C_1-C_4)$alkyl or halo$(C_1-C_4)$alkyl; and $R^{15}$ is hydrogen, methyl, ethyl, or phenyl.

This invention also relates to compounds that are exemplified in the Experimental section.

Specific compounds of this invention include:

1-(2-fluoro-4-(7-oxo-6,7-dihydrofuro[2,3-c]pyridin-4-yl)phenyl)-3-(4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(3-(4-methyl-1H-imidazol-1-yl)-5-(trifluoromethyl)phenyl)urea;

1-(4-ethoxy-3-(trifluoromethyl)phenyl)-3-(2-fluoro-4-(1-oxo-2,5,6,7-tetrahydro-1H-cyclopenta[c]pyridin-4-yl)phenyl)urea;

1-(2-fluoro-4-(4-oxo-4,5-dihydro-1H-pyrazolo[4,3-c]pyridin-7-yl)phenyl)-3-(4-((3-methyloxetan-3-yl)oxy)-3-(trifluoromethyl)phenyl)urea;

1-(5'-ethoxy-6-methyl-6'-oxo-1',6'-dihydro-[2,3'-bipyridin]-5-yl)-3-(4-isopropoxy-3-(trifluoromethyl)phenyl)urea;

1-(3-(difluoromethyl)-4-isopropoxyphenyl)-3-(5'-ethoxy-6-methyl-6'-oxo-1',6'-dihydro-[2,3'-bipyridin]-5-yl)urea;

1-(2-fluoro-4-(5-methyl-6-oxo-1,6-dihydropyridin-3-yl)phenyl)-3-(4-((3-methyloxetan-3-yl)oxy)-3-(trifluoromethyl)phenyl)urea;

1-(5'-ethoxy-2-methyl-6'-oxo-1',6'-dihydro-[3,3'-bipyridin]-6-yl)-3-(4-isopropoxy-3-(trifluoromethyl)phenyl)urea;

1-(5'-ethoxy-5-methyl-6'-oxo-1',6'-dihydro-[3,3'-bipyridin]-6-yl)-3-(4-(3-hydroxy-2,2-dimethylpropyl)-3-(trifluoromethyl)phenyl)urea;

1-(2-(5-ethoxy-6-oxo-1,6-dihydropyridin-3-yl)-4-methylpyrimidin-5-yl)-3-(4-(1-hydroxyethyl)-3-(trifluoromethyl)phenyl)urea;

1-(4-(5-ethoxy-6-oxo-1,6-dihydropyridin-3-yl)-2-fluorophenyl)-3-(5-(1,1,1-trifluoro-2-methylpropan-2-yl)isoxazol-3-yl)urea;

1-(2-(4-ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea;

1-(2-(5-ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea;

1-(4-(2-cyano-2-methylpropyl)-3-(trifluoromethyl)phenyl)-3-(2-(5-ethoxy-6-oxo-1,6-dihydropyridin-3-yl)-4-methylpyrimidin-5-yl)urea;

1-(2-(5-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea;

1-(5-(5-ethoxy-6-oxo-1,6-dihydropyridin-3-yl)-3-methylpyrazin-2-yl)-3-(5-(1,1,1-trifluoro-2-methylpropan-2-yl)isoxazol-3-yl)urea;

1-(4-(6-oxo-1,6-dihydropyridin-3-yl)phenyl)-3-(4-(piperazin-1-ylmethyl)-3-(trifluoromethyl)phenyl)urea;

1-(4-(4-ethoxy-6-oxo-1,6-dihydropyridin-3-yl)-2-fluorophenyl)-3-(4-((3-methyloxetan-3-yl)oxy)-3-(trifluoromethyl)phenyl)urea;

1-(2-fluoro-4-(4-oxo-4,5-dihydrofuro[3,2-c]pyridin-7-yl)phenyl)-3-(4-((3-methyloxetan-3-yl)oxy)-3-(trifluoromethyl)phenyl)urea;

1-(4-(5-cyclopropoxy-6-oxo-1,6-dihydropyridin-3-yl)-2-fluorophenyl)-3-(4-((3-methyloxetan-3-yl)oxy)-3-(trifluoromethyl)phenyl)urea;

1-(4-(5-methoxy-6-oxo-1,6-dihydropyridin-3-yl)phenyl)-3-(4-((3-methyloxetan-3-yl)oxy)-3-(trifluoromethyl)phenyl)urea;

1-(2-fluoro-4-(4-oxo-2,3,4,5-tetrahydrofuro[3,2-c]pyridin-7-yl)phenyl)-3-(4-((3-methyloxetan-3-yl)oxy)-3-(trifluoromethyl)phenyl)urea;

1-(4-(2-cyanopropan-2-yl)-3-(trifluoromethyl)phenyl)-3-(2-(5-ethoxy-6-oxo-1,6-dihydropyridin-3-yl)-4-methylpyrimidin-5-yl)urea;

1-(4-(1-cyanoethyl)-3-(trifluoromethyl)phenyl)-3-(2-(4-ethoxy-6-oxo-1,6-dihydropyridin-3-yl)-4-methylpyrimidin-5-yl)urea;

1-(4-(1-cyanoethyl)-3-(trifluoromethyl)phenyl)-3-(2-(5-ethoxy-6-oxo-1,6-dihydropyridin-3-yl)-4-methylpyrimidin-5-yl)urea;

1-(4-(2-cyanopropan-2-yl)-3-(trifluoromethyl)phenyl)-3-(2-(4-ethoxy-6-oxo-1,6-dihydropyridin-3-yl)-4-methylpyrimidin-5-yl)urea;

1-(5'-ethoxy-6'-oxo-1',6'-dihydro-[3,3'-bipyridin]-6-yl)-3-(4-((3-methyloxetan-3-yl)oxy)-3-(trifluoromethyl)phenyl)urea;

1-(2-(4-ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea;

1-(2-(5-ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea;

1-(2-(difluoromethyl)-4-(5-ethoxy-6-oxo-1,6-dihydropyridin-3-yl)phenyl)-3-(4-((4-ethylpiperazin-1-yl)methyl)-3-(trifluoromethyl)phenyl)urea;

1-(4-((5-ethoxy-6-oxo-1,6-dihydropyridin-3-yl)oxy)phenyl)-3-(4-((4-ethylpiperazin-1-yl)methyl)-3-(trifluoromethyl)phenyl)urea;

1-(2-(5-ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea;

1-(2-(5-ethoxy-6-oxo-1,6-dihydropyridin-3-yl)-4,6-dimethylpyrimidin-5-yl)-3-(4-((4-ethylpiperazin-1-yl)methyl)-3-(trifluoromethyl)phenyl)urea;

1-(4-(4-ethoxy-2-oxo-1,2-dihydropyrimidin-5-yl)-2-fluorophenyl)-3-(4-((3-methyloxetan-3-yl)oxy)-3-(trifluoromethyl)phenyl)urea;

1-(4-(2-ethoxy-6-oxo-1,6-dihydropyridin-3-yl)-2-fluorophenyl)-3-(4-((3-methyloxetan-3-yl)oxy)-3-(trifluoromethyl)phenyl)urea;

1-(2-fluoro-4-(5-fluoro-6-oxo-1,6-dihydropyridin-3-yl)phenyl)-3-(4-((3-methyloxetan-3-yl)oxy)-3-(trifluoromethyl)phenyl)urea;

1-(2-fluoro-4-(4-fluoro-6-oxo-1,6-dihydropyridin-3-yl)phenyl)-3-(4-((3-methyloxetan-3-yl)oxy)-3-(trifluoromethyl)phenyl)urea;

1-(2-(4-ethoxy-6-oxo-1,6-dihydropyridin-3-yl)-4-methylpyrimidin-5-yl)-3-(3-(trifluoromethyl)phenyl)urea;

1-(6-(2-hydroxypropan-2-yl)-5-(trifluoromethyl)pyridin-3-yl)-3-(4-methyl-2-(7-oxo-6,7-dihydrofuro[2,3-c]pyridin-4-yl)pyrimidin-5-yl)urea;

1-(2-fluoro-4-(2-methyl-6-oxo-1,6-dihydropyridin-3-yl)phenyl)-3-(4-((3-methyloxetan-3-yl)oxy)-3-(trifluoromethyl)phenyl)urea;

1-(5-(5-ethoxy-6-oxo-1,6-dihydropyridin-3-yl)-3-methylpyrazin-2-yl)-3-(4-(3-hydroxy-2,2-dimethylpropyl)-3-(trifluoromethyl)phenyl)urea;

1-(2-(5-ethoxy-6-oxo-1,6-dihydropyridin-3-yl)-4-methylpyrimidin-5-yl)-3-(3-(trifluoromethyl)phenyl)urea;

1-(4-cyano-3-(trifluoromethyl)phenyl)-3-(2-(5-ethoxy-6-oxo-1,6-dihydropyridin-3-yl)-4-methylpyrimidin-5-yl)urea;

1-(4-cyano-3-(trifluoromethyl)phenyl)-3-(2-(4-ethoxy-6-oxo-1,6-dihydropyridin-3-yl)-4-methylpyrimidin-5-yl)urea;

1-(4-(5-ethoxy-6-oxo-1,6-dihydropyridin-3-yl)-2-fluorophenyl)-3-(4-(morpholinomethyl)-3-(trifluoromethyl)phenyl)urea;

1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea;

1-(2-(4-ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea;

1-(2-(5-ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea;

1-(4-((5-ethoxy-6-oxo-1,6-dihydropyridin-3-yl)oxy)phenyl)-3-(4-((3-methyloxetan-3-yl)oxy)-3-(trifluoromethyl)phenyl)urea;

1-(5'-ethoxy-6-methyl-6'-oxo-1',6'-dihydro-[2,3'-bipyridin]-5-yl)-3-(4-((3-methyloxetan-3-yl)oxy)-3-(trifluoromethyl)phenyl)urea;

1-(2-(4-ethoxy-6-oxo-1,6-dihydropyridin-3-yl)-4-methylpyrimidin-5-yl)-3-(4-(2-hydroxypropan-2-yl)-3-(trifluoromethyl)phenyl)urea;

1-(2-(4-ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea;

1-(2-(5-ethoxy-6-oxo-1,6-dihydropyridin-3-yl)-4,6-dimethylpyrimidin-5-yl)-3-(3-(4-methyl-1H-imidazol-1-yl)-5-(trifluoromethyl)phenyl)urea;

1-(4-chloro-3-(trifluoromethyl)phenyl)-3-(2-(4-ethoxy-6-oxo-1,6-dihydropyridin-3-yl)-4-methylpyrimidin-5-yl)urea;

1-(4-((dimethylamino)methyl)-3-(trifluoromethyl)phenyl)-3-(2-(4-ethoxy-6-oxo-1,6-dihydropyridin-3-yl)-4-methylpyrimidin-5-yl)urea;

1-(2-(5-ethoxy-6-oxo-1,6-dihydropyridin-3-yl)-4-ethylpyrimidin-5-yl)-3-(3-(4-methyl-1H-imidazol-1-yl)-5-(trifluoromethyl)phenyl)urea;

1-(2-(5-ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea;

1-(4-((dimethylamino)methyl)-3-(trifluoromethyl)phenyl)-3-(2-(5-ethoxy-6-oxo-1,6-dihydropyridin-3-yl)-4-methylpyrimidin-5-yl)urea;

1-(4-((dimethylamino)methyl)-3-(trifluoromethyl)phenyl)-3-(2-(5-ethoxy-6-oxo-1,6-dihydropyridin-3-yl)-4,6-dimethylpyrimidin-5-yl)urea;

1-(4-chloro-3-(trifluoromethyl)phenyl)-3-(2-(5-ethoxy-6-oxo-1,6-dihydropyridin-3-yl)-4-methylpyrimidin-5-yl)urea;

2-(4-(3-(2-(4-ethoxy-6-oxo-1,6-dihydropyridin-3-yl)-4-methylpyrimidin-5-yl)ureido)-2-(trifluoromethyl)phenyl)-2-methylpropanamide;

1-(5'-ethoxy-4-methyl-6'-oxo-1',6'-dihydro-[3,3'-bipyridin]-6-yl)-3-(4-((3-methyloxetan-3-yl)oxy)-3-(trifluoromethyl)phenyl)urea;

2-(4-(3-(2-(5-ethoxy-6-oxo-1,6-dihydropyridin-3-yl)-4-methylpyrimidin-5-yl)ureido)-2-(trifluoromethyl)phenyl)-2-methylpropanamide;

1-(4-(5-ethoxy-6-oxo-1,6-dihydropyridin-3-yl)-2-fluorophenyl)-3-(4-(3-hydroxy-2,2-dimethylpropyl)-3-(trifluoromethyl)phenyl)urea;

1-(4-((4-ethylpiperazin-1-yl)methyl)-3-(trifluoromethyl)phenyl)-3-(4-(6-oxo-1,6-dihydropyridin-3-yl)phenyl)urea;

1-(2-(5-ethoxy-6-oxo-1,6-dihydropyridin-3-yl)-4-methylpyrimidin-5-yl)-3-(4-(1-(hydroxymethyl)cyclopropyl)-3-(trifluoromethyl)phenyl)urea;

1-(2-(4-ethoxy-6-oxo-1,6-dihydropyridin-3-yl)-4-methylpyrimidin-5-yl)-3-(3-(5-methyl-1,3,4-oxadiazol-2-yl)-5-(trifluoromethyl)phenyl)urea;

1-(3-(tert-butyl)-1-phenyl-1H-pyrazol-5-yl)-3-(4-(6-oxo-1,6-dihydropyridin-3-yl)phenyl)urea;

1-(4-(5-ethoxy-6-oxo-1,6-dihydropyridin-3-yl)-2-fluorophenyl)-3-(4-((4-ethylpiperazin-1-yl)methyl)-3-(trifluoromethyl)phenyl)urea;

1-(4-(1-amino-2-methylpropan-2-yl)-3-(trifluoromethyl)phenyl)-3-(2-(5-ethoxy-6-oxo-1,6-dihydropyridin-3-yl)-4-methylpyrimidin-5-yl)urea;

1-(2-(5-ethoxy-6-oxo-1,6-dihydropyridin-3-yl)-4-methylpyrimidin-5-yl)-3-(4-(2-hydroxypropan-2-yl)-3-(trifluoromethyl)phenyl)urea;

1-(3-(1H-1,2,4-Triazol-1-yl)-5-(trifluoromethyl)phenyl)-3-(4-(5-ethoxy-6-oxo-1,6-dihydropyridin-3yl)-2-fluorophenyl)urea;

1-(4-(1-(dimethylamino)-2-methylpropan-2-yl)-3-(trifluoromethyl)phenyl)-3-(2-(5-ethoxy-6-oxo-1,6-dihydropyridin-3-yl)-4-methylpyrimidin-5-yl)urea;

1-(3-(2-(dimethylamino)ethoxy)-5-(trifluoromethyl)phenyl)-3-(2-(5-ethoxy-6-oxo-1,6-dihydropyridin-3-yl)-4-methylpyrimidin-5-yl)urea;

1-(2-fluoro-4-(1-oxo-1,2-dihydroisoquinolin-4-yl)phenyl)-3-(4-(2-hydroxypropan-2-yl)-3-(trifluoromethyl)phenyl)urea;

1-(4-((dimethylamino)methyl)-3-(trifluoromethyl)phenyl)-3-(4-(5-ethoxy-6-oxo-1,6-dihydropyridin-3-yl)-2-fluorophenyl)urea;

1-(4-(5-ethoxy-6-oxo-1,6-dihydropyridin-3-yl)-2-fluorophenyl)-3-(4-(1-(hydroxymethyl)cyclopropyl)-3-(trifluoromethyl)phenyl)urea;

1-(4-(5-ethoxy-6-oxo-1,6-dihydropyridin-3-yl)-2-fluorophenyl)-3-(2-fluoro-5-(trifluoromethyl)phenyl)urea;

1-(4-(tert-butoxy)-3-(trifluoromethyl)phenyl)-3-(4-(5-ethoxy-6-oxo-1,6-dihydropyridin-3-yl)phenyl)urea;

1-(4-ethoxy-3-(trifluoromethyl)phenyl)-3-(4-(5-ethoxy-6-oxo-1,6-dihydropyridin-3-yl)-2-fluorophenyl)urea;

1-(4-(2-cyano-2-methylpropyl)-3-(trifluoromethyl)phenyl)-3-(4-(5-ethoxy-6-oxo-1,6-dihydropyridin-3-yl)-2-fluorophenyl)urea;

1-(4-(5-ethoxy-6-oxo-1,6-dihydropyridin-3-yl)-2-fluorophenyl)-3-(4-isopropoxy-3-(trifluoromethyl)phenyl)urea;

1-(4-((2-cyanopropan-2-yl)oxy)-3-(trifluoromethyl)phenyl)-3-(4-(5-ethoxy-6-oxo-1,6-dihydropyridin-3-yl)-2-fluorophenyl)urea;

1-(4-(5-ethoxy-6-oxo-1,6-dihydropyridin-3-yl)-2-fluorophenyl)-3-(4-(3-hydroxy-1-methylcyclobutoxy)-3-(trifluoromethyl)phenyl)urea;

1-(4-(5-ethoxy-6-oxo-1,6-dihydropyridin-3-yl)-2-fluorophenyl)-3-(4-((1-isopropyl-3-methylpyrrolidin-3-yl)oxy)-3-(trifluoromethyl)phenyl)urea;

1-(4-((5-ethoxy-6-oxo-1,6-dihydropyridin-3-yl)oxy)phenyl)-3-(2-fluoro-5-(trifluoromethyl)phenyl)urea;

1-(6-chloro-5'-ethoxy-6'-oxo-1',6'-dihydro-[2,3'-bipyridin]-5-yl)-3-(4-((3-methyloxetan-3-yl)oxy)-3-(trifluoromethyl)phenyl)urea;

1-(2-(4-ethoxy-6-oxo-1,6-dihydropyridin-3-yl)-4-methylpyrimidin-5-yl)-3-(4-(1-(hydroxymethyl)cyclopropyl)-3-(trifluoromethyl)phenyl)urea;

1-(4-(5-ethoxy-6-oxo-1,6-dihydropyridin-3-yl)-2-fluorophenyl)-3-(6-(2-hydroxypropan-2-yl)-5-(trifluoromethyl)pyridin-3-yl)urea;

1-(4-(5-ethoxy-6-oxo-1,6-dihydropyridin-3-yl)-2,6-difluorophenyl)-3-(4-((3-methyloxetan-3-yl)oxy)-3-(trifluoromethyl)phenyl)urea;

N-(2-(dimethylamino)ethyl)-3-(3-(2-(5-ethoxy-6-oxo-1,6-dihydropyridin-3-yl)-4-methylpyrimidin-5-yl)ureido)-5-(trifluoromethyl)benzamide;

1-(4-(5-ethoxy-6-oxo-1,6-dihydropyridin-3-yl)-2-fluorophenyl)-3-(6-isopropoxy-5-(trifluoromethyl)pyridin-3-yl)urea;

1-(3-(difluoromethyl)-4-((3-methyloxetan-3-yl)oxy)phenyl)-3-(4-(5-ethoxy-6-oxo-1,6-dihydropyridin-3-yl)-2-fluorophenyl)urea;

1-(2-fluoro-4-(5-hydroxy-6-oxo-1,6-dihydropyridin-3-yl)phenyl)-3-(4-((3-methyloxetan-3-yl)oxy)-3-(trifluoromethyl)phenyl)urea;

1-(2-fluoro-4-(5-(methylamino)-6-oxo-1,6-dihydropyridin-3-yl)phenyl)-3-(4-((3-methyloxetan-3-yl)oxy)-3-(trifluoromethyl)phenyl)urea;

1-(2-(5-ethoxy-6-oxo-1,6-dihydropyridin-3-yl)-4-methylpyrimidin-5-yl)-3-(4-((3-methyloxetan-3-yl)oxy)-3-(trifluoromethyl)phenyl)urea;

1-(5'-ethoxy-4-methyl-6'-oxo-1',6'-dihydro-[2,3'-bipyridin]-5-yl)-3-(4-((3-methyloxetan-3-yl)oxy)-3-(trifluoromethyl)phenyl)urea;

1-(4-ethoxy-3-(trifluoromethyl)phenyl)-3-(2-fluoro-4-(4-oxo-4,5-dihydrofuro[3,2-c]pyridin-7-yl)phenyl)urea;

1-(2-(5-ethoxy-6-oxo-1,6-dihydropyridin-3-yl)-4-methylpyrimidin-5-yl)-3-(3-(2-morpholinoethoxy)-5-(trifluoromethyl)phenyl)urea;

1-(5'-methoxy-6-methyl-6'-oxo-1',6'-dihydro-[2,3'-bipyridin]-5-yl)-3-(4-((3-methyloxetan-3-yl)oxy)-3-(trifluoromethyl)phenyl)urea;

1-(6-((5-ethoxy-6-oxo-1,6-dihydropyridin-3-yl)oxy)pyridin-3-yl)-3-(4-((3-methyloxetan-3-yl)oxy)-3-(trifluoromethyl)phenyl)urea;

1-(5'-ethoxy-6-ethyl-6'-oxo-1',6'-dihydro-[2,3'-bipyridin]-5-yl)-3-(4-((3-methyloxetan-3-yl)oxy)-3-(trifluoromethyl)phenyl)urea;

1-(5'-ethoxy-5-fluoro-6'-oxo-1',6'-dihydro-[3,3'-bipyridin]-6-yl)-3-(4-((3-methyloxetan-3-yl)oxy)-3-(trifluoromethyl)phenyl)urea;

1-(6-cyclopropyl-5'-ethoxy-6'-oxo-1',6'-dihydro-[2,3'-bipyridin]-5-yl)-3-(4-((3-methyloxetan-3-yl)oxy)-3-(trifluoromethyl)phenyl)urea;

1-(5'-ethoxy-5-methyl-6'-oxo-1',6'-dihydro-[3,3'-bipyridin]-6-yl)-3-(4-((3-methyloxetan-3-yl)oxy)-3-(trifluoromethyl)phenyl)urea;

1-(5'-ethoxy-6'-oxo-1',6'-dihydro-[2,3'-bipyridin]-5-yl)-3-(4-((3-methyloxetan-3-yl)oxy)-3-(trifluoromethyl)phenyl)urea;

1-(4-fluoro-3-(trifluoromethyl)phenyl)-3-(2-fluoro-4-(5-(3-fluoropropoxy)-6-oxo-1,6-dihydropyridin-3-yl)phenyl)urea;

1-(5-(5-ethoxy-6-oxo-1,6-dihydropyridin-3-yl)-3-methylpyrazin-2-yl)-3-(4-((3-methyloxetan-3-yl)oxy)-3-(trifluoromethyl)phenyl)urea;

1-(4-(azetidin-1-ylmethyl)-3-(trifluoromethyl)phenyl)-3-(2-(5-ethoxy-6-oxo-1,6-dihydropyridin-3-yl)-4-methylpyrimidin-5-yl)urea;

1-(5'-ethoxy-6-methoxy-6'-oxo-1',6'-dihydro-[2,3'-bipyridin]-5-yl)-3-(4-((3-methyloxetan-3-yl)oxy)-3-(trifluoromethyl)phenyl)urea;

1-(2-(5-ethoxy-6-oxo-1,6-dihydropyridin-3-yl)-4-methylpyrimidin-5-yl)-3-(4-(pyrrolidin-1-ylmethyl)-3-(trifluoromethyl)phenyl)urea;

1-(6-(dimethylamino)-5'-ethoxy-6'-oxo-1',6'-dihydro-[2,3'-bipyridin]-5-yl)-3-(4-((3-methyloxetan-3-yl)oxy)-3-(trifluoromethyl)phenyl)urea;

1-(4-ethoxy-3-(trifluoromethyl)phenyl)-3-(4-(1-ethyl-6-oxo-1,6-dihydropyridin-3-yl)-2-fluorophenyl)urea;

1-(4-((dimethylamino)methyl)-3-(trifluoromethyl)phenyl)-3-(5-(5-ethoxy-6-oxo-1,6-dihydropyridin-3-yl)-3-methylpyrazin-2-yl)urea;

1-(5'-ethoxy-6-isopropoxy-6'-oxo-1',6'-dihydro-[2,3'-bipyridin]-5-yl)-3-(4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(4-(1-hydroxyethyl)-3-(trifluoromethyl)phenyl)urea;

1-(4-((1,3-dimethylazetidin-3-yl)oxy)-3-(trifluoromethyl)phenyl)-3-(4-(5-ethoxy-6-oxo-1,6-dihydropyridin-3-yl)-2-fluorophenyl)urea;

1-(4-(5-ethoxy-6-oxo-1,6-dihydropyridin-3-yl)-2-fluorophenyl)-3-(4-((1-hydroxy-2-methylpropan-2-yl)oxy)-3-(trifluoromethyl)phenyl)urea;

1-(4-(5-ethoxy-6-oxo-1,6-dihydropyridin-3-yl)-2,3-difluorophenyl)-3-(4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(4-(1-hydroxy-2-methylpropan-2-yl)-3-(trifluoromethyl)phenyl)urea;

1-(2-fluoro-4-(5-fluoropropoxy)-6-oxo-1,6-dihydropyridin-3-yl)phenyl)-3-(4-isopropoxy-3-(trifluoromethyl)phenyl)urea;

1-(4-(5-ethoxy-6-oxo-1,6-dihydropyridin-3-yl)-2-fluorophenyl)-3-(4-((1-hydroxypropan-2-yl)oxy)-3-(trifluoromethyl)phenyl)urea;

1-(4-(5-ethoxy-6-oxo-1,6-dihydropyridin-3-yl)-2-fluorophenyl)-3-(4-(1-(hydroxymethyl)cyclopropoxy)-3-(trifluoromethyl)phenyl)urea;

1-(3-(difluoromethyl)-4-((3-methyloxetan-3-yl)oxy)phenyl)-3-(4-(4-ethoxy-6-oxo-1,6-dihydropyridin-3-yl)-2-fluorophenyl)urea;

1-(4-(2,2-difluoro-3-hydroxypropyl)-3-(trifluoromethyl)phenyl)-3-(4-(5-ethoxy-6-oxo-1,6-dihydropyridin-3-yl)-2-fluorophenyl)urea;

1-(4-(4-(difluoromethoxy)-6-oxo-1,6-dihydropyridin-3-yl)-2-fluorophenyl)-3-(4-((3-methyloxetan-3-yl)oxy)-3-(trifluoromethyl)phenyl)urea;

1-(4-(1-cyanoethyl)-3-(trifluoromethyl)phenyl)-3-(4-(5-ethoxy-6-oxo-1,6-dihydropyridin-3-yl)-2-fluorophenyl)urea;

1-(4-(4-ethoxy-6-oxo-1,6-dihydropyridin-3-yl)-2-fluorophenyl)-3-(2-fluoro-5-(trifluoromethyl)phenyl)urea;

1-(4-(5-ethoxy-6-oxo-1,6-dihydropyridin-3-yl)-2-fluorophenyl)-3-(4-(2-hydroxypropan-2-yl)-3-(trifluoromethyl)phenyl)urea;

1-(4-(5-ethoxy-6-oxo-1,6-dihydropyridin-3-yl)-2-fluorophenyl)-3-(4-((3-methyloxetan-3-yl)oxy)-3-(trifluoromethyl)phenyl)urea;

1-(4-((3-methyloxetan-3-yl)oxy)-3-(trifluoromethyl)phenyl)-3-(4-(6-oxo-5-propoxy-1,6-dihydropyridin-3-yl)phenyl)urea;

1-(4-(5-ethoxy-6-oxo-1,6-dihydropyridin-3-yl)-2-fluorophenyl)-3-(4-(hydroxymethyl)-3-(trifluoromethyl)phenyl)urea;

1-(4-(5-ethoxy-6-oxo-1,6-dihydropyridin-3-yl)-3-fluorophenyl)-3-(4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(4-(1-(hydroxymethyl)cyclobutoxy)-3-(trifluoromethyl)phenyl)urea;

1-(4-(2-cyanopropan-2-yl)-3-(trifluoromethyl)phenyl)-3-(4-(5-ethoxy-6-oxo-1,6-dihydropyridin-3-yl)-2-fluorophenyl)urea;

1-(2-fluoro-4-(5-isopropoxy-6-oxo-1,6-dihydropyridin-3-yl)phenyl)-3-(4-((3-methyloxetan-3-yl)oxy)-3-(trifluoromethyl)phenyl)urea;

1-(2-methyl-4-(6-oxo-1,6-dihydropyridin-3-yl)phenyl)-3-(4-((3-methyloxetan-3-yl)oxy)-3-(trifluoromethyl)phenyl)urea;

1-(2-fluoro-4-(6-oxo-5-propoxy-1,6-dihydropyridin-3-yl)phenyl)-3-(4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(4-((1-fluoro-2-methylpropan-2-yl)oxy)-3-(trifluoromethyl)phenyl)urea;

1-(4-(5-ethoxy-6-oxo-1,6-dihydropyridin-3-yl)phenyl)-3-(4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(2-hydroxy-5-(trifluoromethyl)phenyl)urea;

1-(4-(5-ethoxy-6-oxo-1,6-dihydropyridin-3-yl)-2-fluorophenyl)-3-(4-((3-methyloxetan-3-yl)methyl)-3-(trifluoromethyl)phenyl)urea;

1-(4-(5-ethoxy-6-oxo-1,6-dihydropyridin-3-yl)-2-fluorophenyl)-3-(4-(2-hydroxyethoxy)-3-(trifluoromethyl)phenyl)urea;

1-(4-((1,3-dimethylpyrrolidin-3-yl)oxy)-3-(trifluoromethyl)phenyl)-3-(4-(5-ethoxy-6-oxo-1,6-dihydropyridin-3-yl)-2-fluorophenyl)urea;

1-(4-(5-ethoxy-6-oxo-1,6-dihydropyridin-3-yl)-2-fluorophenyl)-3-(4-(2-hydroxypropoxy)-3-(trifluoromethyl)phenyl)urea;

1-(4-(5-ethoxy-6-oxo-1,6-dihydropyridin-3-yl)-2-fluorophenyl)-3-(4-((1-methyl-1H-pyrazol-4-yl)methyl)-3-(trifluoromethyl)phenyl)urea;

1-(2-fluoro-4-(6-oxo-1,6-dihydropyridin-3-yl)phenyl)-3-(4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(6-((3-methyloxetan-3-yl)oxy)-5-(trifluoromethyl)pyridin-3-yl)urea;

1-(4-(5-ethoxy-6-oxo-1,6-dihydropyridin-3-yl)-2-fluorophenyl)-3-(4-(1-methylcyclobutoxy)-3-(trifluoromethyl)phenyl)urea;

1-(4-(5-ethoxy-6-oxo-1,6-dihydropyridin-3-yl)-2-fluorophenyl)-3-(4-((3-methyl-1,1-dioxidothietan-3-yl)oxy)-3-(trifluoromethyl)phenyl)urea;

1-(4-(5-ethoxy-6-oxo-1,6-dihydropyridin-3-yl)-2-fluorophenyl)-3-(4-(ethoxymethyl)-3-(trifluoromethyl)phenyl)urea;

1-(4-chloro-3-(trifluoromethyl)phenyl)-3-(4-(5-ethoxy-6-oxo-1,6-dihydropyridin-3-yl)-2-fluorophenyl)urea;

1-(2-ethoxy-4-fluoro-5-(trifluoromethyl)phenyl)-3-(4-(5-ethoxy-6-oxo-1,6-dihydropyridin-3-yl)-2-fluorophenyl)urea;

(S)-1-(4-(5-ethoxy-6-oxo-1,6-dihydropyridin-3-yl)-2-fluorophenyl)-3-(4-((3-fluoropyrrolidin-1-yl)methyl)-3-(trifluoromethyl)phenyl)urea;

1-(2-fluoro-4-(7-oxo-6,7-dihydrofuro[2,3-c]pyridin-4-yl)phenyl)-3-(2-fluoro-5-(trifluoromethyl)phenyl)urea;

1-(4-(5-ethoxy-6-oxo-1,6-dihydropyridin-3-yl)-2-fluorophenyl)-3-(4-fluoro-3-(trifluoromethyl)phenyl)urea;

1-(4-((3-methyloxetan-3-yl)oxy)-3-(trifluoromethyl)phenyl)-3-(4-(6-oxo-1,6-dihydropyridin-3-yl)phenyl)urea;

1-(4-cyano-3-(trifluoromethyl)phenyl)-3-(4-(5-ethoxy-6-oxo-1,6-dihydropyridin-3-yl)-2-fluorophenyl)urea;

1-(4-(5-ethoxy-6-oxo-1,6-dihydropyridin-3-yl)-2-fluorophenyl)-3-(4-((1-methoxy-2-methylpropan-2-yl)oxy)-3-(trifluoromethyl)phenyl)urea;

1-(3-(difluoromethyl)-4-isopropoxyphenyl)-3-(4-(5-ethoxy-6-oxo-1,6-dihydropyridin-3-yl)-3-fluorophenyl)urea;

1-(4-(3,3-difluorocyclobutoxy)-3-(trifluoromethyl)phenyl)-3-(4-(5-ethoxy-6-oxo-1,6-dihydropyridin-3-yl)-2-fluorophenyl)urea;

4-(3-(4-(5-ethoxy-6-oxo-1,6-dihydropyridin-3-yl)-2-fluorophenyl)ureido)-2-(trifluoromethyl)benzamide;

1-(4-isopropoxy-3-(trifluoromethyl)phenyl)-3-(4-(6-oxo-1,6-dihydropyridin-3-yl)phenyl)urea;

1-(4-(5-(difluoromethoxy)-6-oxo-1,6-dihydropyridin-3-yl)-2-fluorophenyl)-3-(4-(2-hydroxyethoxy)-3-(trifluoromethyl)phenyl)urea;

1-(4-(2-(dimethylamino)ethyl)-3-(trifluoromethyl)phenyl)-3-(4-(5-ethoxy-6-oxo-1,6-dihydropyridin-3-yl)-2-fluorophenyl)urea;

1-(4-(5-ethoxy-6-oxo-1,6-dihydropyridin-3-yl)-2-fluorophenyl)-3-(2-fluoro-4-((3-methyloxetan-3-yl)oxy)-3-(trifluoromethyl)phenyl)urea;

1-(4-(5-ethoxy-6-oxo-1,6-dihydropyridin-3-yl)-2-fluorophenyl)-3-(4-((3-methyltetrahydrofuran-3-yl)oxy)-3-(trifluoromethyl)phenyl)urea;

1-(2-fluoro-4-(4-methyl-6-oxo-1,6-dihydropyridin-3-yl)phenyl)-3-(4-((3-methyloxetan-3-yl)oxy)-3-(trifluoromethyl)phenyl)urea;

1-(3-(difluoromethyl)-4-((3-methyloxetan-3-yl)oxy)phenyl)-3-(4-(6-oxo-1,6-dihydropyridin-3-yl)phenyl)urea;

1-(3,4-dichlorophenyl)-3-(4-(5-ethoxy-6-oxo-1,6-dihydropyridin-3-yl)-2-fluorophenyl)urea;

1-(2-(5-ethoxy-6-oxo-1,6-dihydropyridin-3-yl)-4-methylpyrimidin-5-yl)-3-(2-fluoro-4-((4-(2-hydroxyethyl)piperazin-1-yl)methyl)-5-(trifluoromethyl)phenyl)urea;

1-(4-((4-ethylpiperazin-1-yl)methyl)-2-fluoro-5-(trifluoromethyl)phenyl)-3-(2-(5-(2-hydroxyethoxy)-6-oxo-1,6-dihydropyridin-3-yl)-4-methylpyrimidin-5-yl)urea;

1-(2-fluoro-4-((4-(2-hydroxyethyl)piperazin-1-yl)methyl)-5-(trifluoromethyl)phenyl)-3-(2-(5-(2-hydroxyethoxy)-6-oxo-1,6-dihydropyridin-3-yl)-4-methylpyrimidin-5-yl)urea;

N-(2-(dimethylamino)ethyl)-3-(3-(2-(5-ethoxy-6-oxo-1,6-dihydropyridin-3-yl)-4-methylpyrimidin-5-yl)ureido)-5-(trifluoromethyl)benzenesulfonamide;

1-(4-(1-aminoethyl)-3-(trifluoromethyl)phenyl)-3-(2-(5-ethoxy-6-oxo-1,6-dihydropyridin-3-yl)-4-methylpyrimidin-5-yl)urea;

1-(4-(1-(dimethylamino)ethyl)-3-(trifluoromethyl)phenyl)-3-(2-(5-ethoxy-6-oxo-1,6-dihydropyridin-3-yl)-4-methylpyrimidin-5-yl)urea;

1-(2-(5-ethoxy-6-oxo-1,6-dihydropyridin-3-yl)-4-methylpyrimidin-5-yl)-3-(4-(2-(pyrrolidin-1-yl)ethyl)-3-(trifluoromethyl)phenyl)urea;

1-(3-(2-(dimethylamino)ethoxy)-5-(trifluoromethyl)phenyl)-3-(2-(5-ethoxy-6-oxo-1,6-dihydropyridin-3-yl)pyrimidin-5-yl)urea;

1-(4-((dimethylamino)methyl)-3-(trifluoromethyl)phenyl)-3-(2-(5-ethoxy-6-oxo-1,6-dihydropyridin-3-yl)pyrimidin-5-yl)urea;

1-(2-(4-ethoxy-6-oxo-1,6-dihydropyridin-3-yl)pyrimidin-5-yl)-3-(5-(1,1,1-trifluoro-2-methylpropan-2-yl)isoxazol-3-yl)urea;

1-(2-(5-ethoxy-6-oxo-1,6-dihydropyridin-3-yl)pyrimidin-5-yl)-3-(5-(1,1,1-trifluoro-2-methylpropan-2-yl)isoxazol-3-yl)urea;

1-(4-((4-ethylpiperazin-1-yl)methyl)-2-fluoro-5-(trifluoromethyl)phenyl)-3-(2-(4-(2-methoxyethoxy)-6-oxo-1,6-dihydropyridin-3-yl)-4-methylpyrimidin-5-yl)urea;

1-(2-(5-ethoxy-6-oxo-1,6-dihydropyridin-3-yl)pyrimidin-5-yl)-3-(4-((4-ethylpiperazin-1-yl)methyl)-2-fluoro-5-(trifluoromethyl)phenyl)urea;

1-(2-fluoro-4-((4-methylpiperazin-1-yl)methyl)-5-(trifluoromethyl)-phenyl)-3-(2-(5-(2-methoxyethoxy)-6-oxo-1,6-dihydropyridin-3-yl)-4-methylpyrimidin-5-yl)urea;

1-(4-(2-amino-2-methylpropyl)-3-(trifluoromethyl)phenyl)-3-(2-(5-ethoxy-6-oxo -1,6-dihydropyridin-3-yl)-4-methylpyrimidin-5-yl)urea;

1-(4-(2-amino-2-methylpropyl)-3-(trifluoromethyl)phenyl)-3-(2-(4-ethoxy-6-oxo-1,6-dihydropyridin-3-yl)-4-methylpyrimidin-5-yl)urea;

N-(2-(dimethylamino)ethyl)-3-(3-(2-(4-(2-methoxyethoxy)-6-oxo-1,6-dihydropyridin-3-yl)-4-methylpyrimidin-5-yl)ureido)-5-(trifluoromethyl)benzamide;

1-(4-((dimethylamino)methyl)-2-fluoro-5-(trifluoromethyl)phenyl)-3-(2-(5-ethoxy-6-oxo-1,6-dihydropyridin-3-yl)pyrimidin-5-yl)urea;

N-(2-(dimethylamino)ethyl)-3-(3-(2-(5-ethoxy-6-oxo-1,6-dihydropyridin-3-yl)-pyrimidin-5-yl)ureido)-5-(trifluoromethyl)benzamide;

1-(4-((dimethylamino)methyl)-2-fluoro-5-(trifluoromethyl)phenyl)-3-(2-(5-ethoxy-6-oxo-1,6-dihydropyridin-3-yl)-4-methylpyrimidin-5-yl)urea; and 1-(2-(4-ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea;

or pharmaceutically acceptable salts thereof.

A person of ordinary skills in the art recognizes that compounds of the present invention may have alternative names when different naming software is used.

This invention also relates to compounds of Formulae (I)-(XIX) or any of the exemplified compounds, or pharmaceutically acceptable salts thereof, for use in therapy, in particular, for use in therapy wherein the subject is a human. In particular, for use in the treatment of diseases mediated by RET: irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, caner of the esophagus and gastroesophageal junction, biliary cancer and adenocarcinoma. In particular, this invention relates to compounds of Formulae (I)-(XIX) or any of the exemplified compounds, or pharmaceutically acceptable salts thereof, for use in the treatment of irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, cancer of the esophagus and gastroesophageal junction, biliary cancer and adenocarcinoma.

This invention also relates to compounds of Formulae (I)-(XIX) or any of the exemplified compounds, or pharmaceutically acceptable salts thereof, for use as a medicament.

In another embodiment, the invention relates to the use of compounds of the invention in the preparation of a medicament for the treatment of diseases mediated by RET. This invention also relates to compounds of Formulae (I)-(XIX) or any of the exemplified compounds, or pharmaceutically acceptable salts thereof, in the manufacture of a medicament for the treatment of irritable bowel syndrome. This invention also relates to compounds of Formulae (I)-(XIX) or any of the exemplified compounds, or pharmaceutically acceptable salts thereof, in the manufacture of a medicament for the treatment of cancer.

This invention also relates to the use of compounds of Formulae (I)-(XIX) or any of the exemplified compounds in therapy. The invention further includes the use of compounds of the invention as an active therapeutic substance, in particular in the treatment of diseases mediated by RET. This invention also relates to the use of compounds of Formulae (I)-(XIX) or any of the exemplified compounds for the treatment of irritable bowel syndrome. This invention also relates to the use of compounds of Formulae (I)-(XIX) or any of the exemplified compounds for the treatment of cancer.

Because of their potential use in medicine, the salts of the compounds of Formulae (I)-(XIX) are preferably pharmaceutically acceptable. Suitable pharmaceutically acceptable salts include those described by Berge, Bighley, and Monkhouse, *J. Pharm. Sci*. (1977) 66, pp 1-19. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as trifluoroacetate, while not in themselves pharmaceutically acceptable, may be useful in the preparation of salts useful as intermediates in obtaining the compounds of the invention and their pharmaceutically acceptable salts.

If a compound of the invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of the invention containing a carboxylic acid or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

As used herein, the term "a compound of Formulae (I)-(XIX)" or "the compound of Formulae (I)-(XIX)" refers to one or more compounds according to any one of Formulae (I)-(XIX). The compound of Formulae (I)-(XIX) may exist in solid or liquid form. In the solid state, it may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The present invention is further directed to certain crystalline forms of the free base and various salts of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea. Particular salt forms include the hydrochloric acid salt, ethanesulfonic acid salt, and sulfuric acid salt.

In some embodiments, a crystalline form of the anhydrous free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A free base anhydrate) is characterized by an X-ray powder diffraction (XRPD) pattern comprising at least nine diffraction angles, when measured using Cu $K_\alpha$ radiation, selected from a group consisting of about 2.2, 4.9, 5.5, 5.7, 11.8, 11.9, 12.8, 12.9, 13.1, 14.3, 16.1, 16.6, 17.1, 17.2, 21.2, 21.3, 21.9, 22.0, 22.7, 22.8, 23.1, 25.3, and 25.4 degrees 2θ. In another embodiment, Compound A free base anhydrate is characterized by an X-ray powder diffraction (XRPD) pattern comprising at least eight diffraction angles or at least seven diffraction angles or at least six diffraction angles or at least five diffraction angles or at least four diffraction angles, when measured using Cu $K_\alpha$ radiation, selected from a group consisting of about 2.2, 4.9, 5.5, 5.7, 11.8, 11.9, 12.8, 12.9, 13.1, 14.3, 16.1, 16.6, 17.1, 17.2, 21.2, 21.3, 21.9, 22.0, 22.7, 22.8, 23.1, 25.3, and 25.4 degrees 2θ. In another embodiment, Compound A free base anhydrate is characterized by an X-ray powder diffraction (XRPD) pattern comprising at least three diffraction angles, when measured using Cu $K_\alpha$ radiation, selected from a group consisting of about 2.2, 4.9, 5.5, 5.7, 11.8, 11.9, 12.8, 12.9, 13.1, 14.3, 16.1, 16.6, 17.1, 17.2, 21.2, 21.3, 21.9, 22.0, 22.7, 22.8, 23.1, 25.3, and 25.4 degrees 2θ.

In still another embodiment, Compound A free base anhydrate is characterized by an X-ray powder diffraction (XRPD) pattern comprising diffraction angles, when measured using Cu $K_\alpha$ radiation, of about 5.7, 11.9, 12.9, 14.3, 16.1, and 23.1 degrees 2θ. In yet another embodiment, Compound A free base anhydrate is characterized by an X-ray powder diffraction (XRPD) pattern substantially in accordance with FIG. 1.

In other embodiments, Compound A free base anhydrate is characterized by a Raman spectrum comprising at least nine peaks at positions selected from a group consisting of peaks at about 409, 442, 467, 585, 708, 743, 773, 790, 851, 904, 950, 1005, 1247, 1314, 1330, 1397, 1435, 1469, 1492, 1530, 1577, 1623, 1653, 1710, 2940 cm$^{-1}$. In another embodiment, Compound A free base anhydrate is characterized by a Raman spectrum comprising at least eight peaks or at least seven peaks or at least six peaks or at least five peaks or at least four three peaks at positions selected from a group consisting of peaks at about 409, 442, 467, 585, 708, 743, 773, 790, 851, 904, 950, 1005, 1247, 1314, 1330, 1397, 1435, 1469, 1492, 1530, 1577, 1623, 1653, 1710, 2940 cm$^{-1}$. In another embodiment, Compound A free base anhydrate is characterized by a Raman spectrum comprising at least three peaks at positions selected from a group consisting of peaks at about 409, 442, 467, 585, 708, 743, 773, 790, 851, 904, 950, 1005, 1247, 1314, 1330, 1397, 1435, 1469, 1492, 1530, 1577, 1623, 1653, 1710, 2940 cm$^{-1}$.

In still another embodiment, Compound A free base anhydrate is characterized by a Raman spectrum comprising peaks at about 1247, 1314, 1330, 1435, 1469, 1492, 1530, 1577, 1623, 1653, 1710, 2940 cm$^{-1}$. In yet another embodiment, Compound A free base anhydrate is characterized by a Raman spectrum substantially in accordance with FIG. 2.

Figure 3:
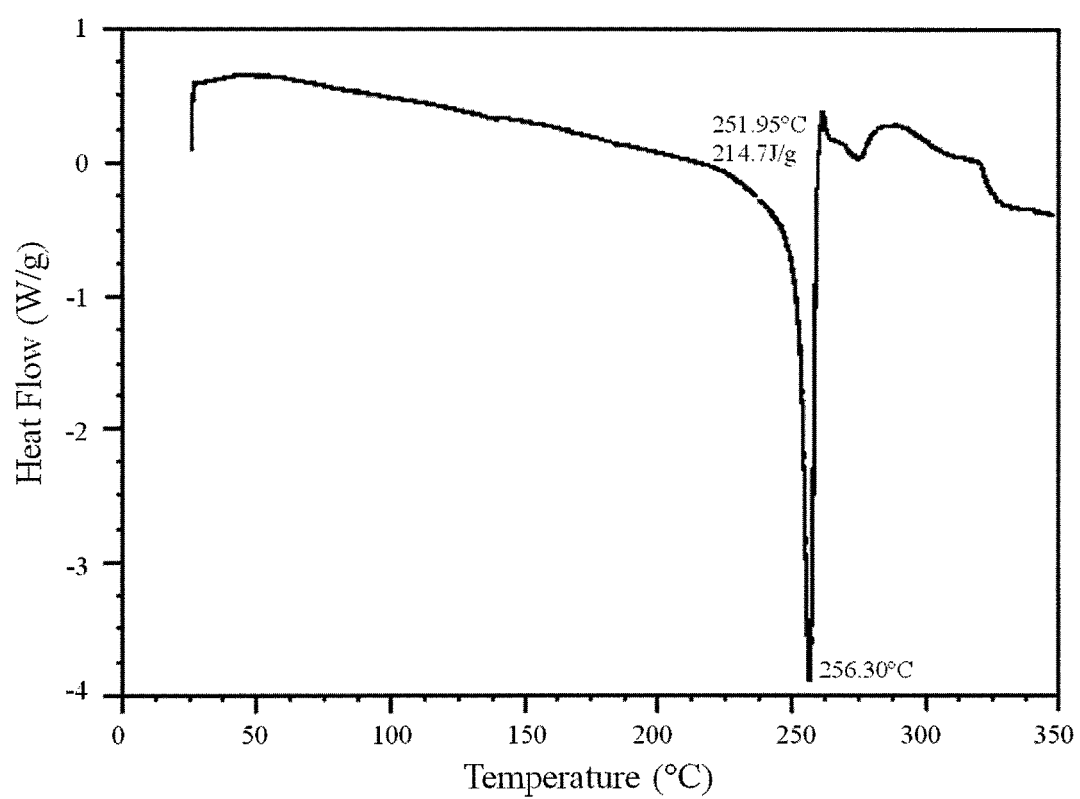
FIG. 3 shows a differential scanning calorimetry trace of Compound A free base anhydrate.
Figure 4:
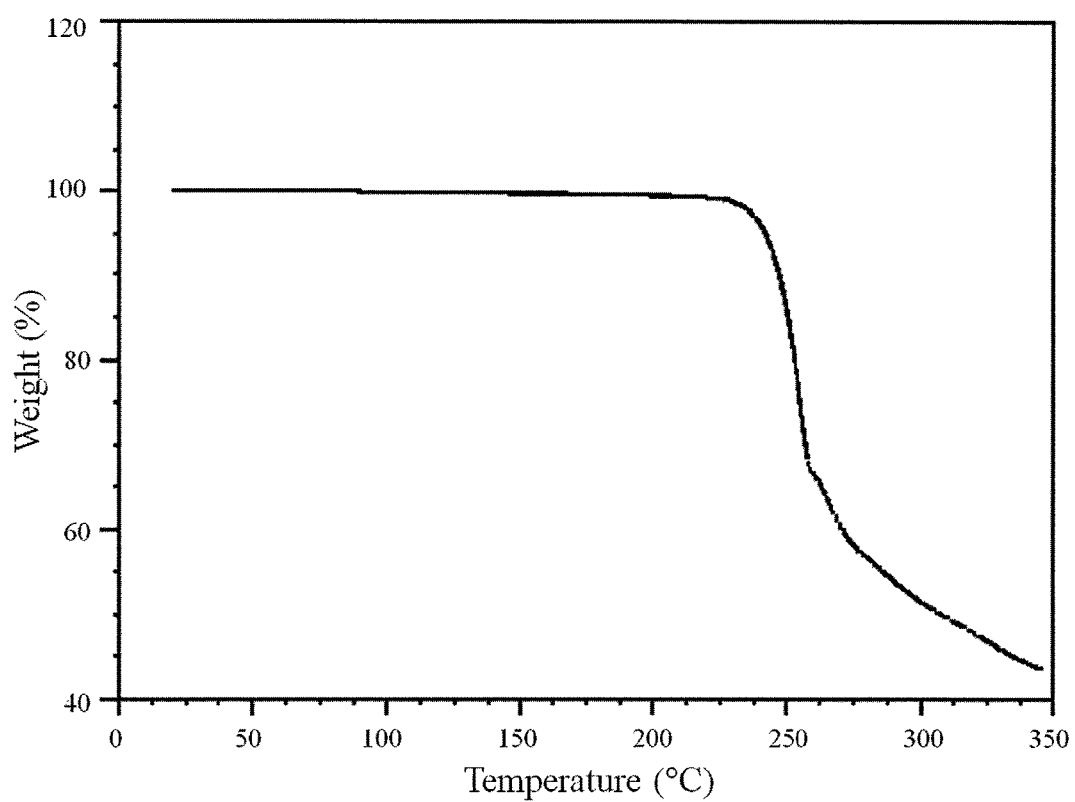
FIG. 4 shows a thermogravimetric analysis trace of Compound A free base anhydrate.

In further embodiments, Compound A free base anhydrate is characterized by a differential scanning calorimetry trace substantially in accordance with FIG. 3 and/or a thermogravimetric analysis trace substantially in accordance with FIG. 4.

In still further embodiments, as a person having ordinary skill in the art will understand, Compound A free base anhydrate is characterized by any combination of the analytical data characterizing the aforementioned embodiments. For example, in one embodiment, Compound A free base anhydrate is characterized by an X-ray powder diffraction (XRPD) pattern substantially in accordance with FIG. 1 and a Raman spectrum substantially in accordance with FIG. 2 and a differential scanning calorimetry trace substantially in accordance with FIG. 3 and a thermogravimetric analysis trace substantially in accordance with FIG. 4. In another embodiment, Compound A free base anhydrate is characterized by an X-ray powder diffraction (XRPD) pattern substantially in accordance with FIG. 1 and a Raman spectrum substantially in accordance with FIG. 2. In another embodiment, Compound A free base anhydrate is characterized by an X-ray powder diffraction (XRPD) pattern substantially in accordance with FIG. 1 and a differential scanning calorimetry trace substantially in accordance with FIG. 3. In another embodiment, Compound A free base anhydrate is characterized by an X-ray powder diffraction (XRPD) pattern substantially in accordance with FIG. 1 and a thermogravimetric analysis trace substantially in accordance with FIG. 4. In another embodiment, Compound A free base anhydrate is characterized by an X-ray powder diffraction (XRPD) pattern comprising diffraction angles, when measured using Cu $K_\alpha$ radiation, of about 5.7, 11.9, 12.9, 14.3, 16.1, and 23.1 degrees 2θ, and a Raman spectrum comprising peaks at about 1247, 1314, 1330, 1435, 1469, 1492, 1530, 1577, 1623, 1653, 1710, 2940 cm$^{-1}$. In another embodiment, Compound A free base anhydrate is characterized by an X-ray powder diffraction (XRPD) pattern comprising diffraction angles, when measured using Cu $K_\alpha$ radiation, of about 5.7, 11.9, 12.9, 14.3, 16.1, and 23.1 degrees 2θ, and a differential scanning calorimetry trace substantially in accordance with FIG. 3. In another embodiment, Compound A free base anhydrate is characterized by an X-ray powder diffraction (XRPD) pattern comprising diffraction angles, when measured using Cu $K_\alpha$ radiation, of about 5.7, 11.9, 12.9, 14.3, 16.1, and 23.1 degrees 2θ, and a thermogravimetric analysis trace substantially in accordance with FIG. 4.

An XRPD pattern will be understood to comprise a diffraction angle (expressed in degrees 2θ) of "about" a value specified herein when the XRPD pattern comprises a diffraction angle within ±0.3 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1, 5, 9, 13, 17, 21, 25, 29, 33, or 37 provided herein is an XRPD pattern that would be considered by one skilled in the art to represent a compound possessing the same crystal form as the compound that provided the XRPD pattern of FIG. 1, 5, 9, 13, 17, 21, 25, 29, 33, or 37. That is, the XRPD pattern may be identical to that of FIG. 1, 5, 9, 13, 17, 21, 25, 29, 33, or 37, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of the free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea, with FIG. 1 and, using expertise and knowledge in the art, readily determine whether the XRPD pattern of the sample is substantially in accordance with the XRPD pattern of Compound A free base anhydrate disclosed herein. If the XRPD pattern is substantially in accordance with FIG. 1, the sample form can be readily and accurately identified as having the same form as Compound A free base anhydrate disclosed herein.

A Raman spectrum will be understood to comprise a peak (expressed in cm$^{-1}$) of "about" a value specified herein when the Raman spectrum comprises a peak within ±5.0 cm$^{-1}$ of the specified value. Further, it is also well known and understood to those skilled in the art that the apparatus employed, humidity, temperature, orientation of the powder crystals, and other parameters involved in obtaining a Raman spectrum may cause some variability in the appearance, intensities, and positions of the peaks in the spectrum. A Raman spectrum that is "substantially in accordance" with that of FIG. 2, 6, 10, 14, 18, 22, 26, 30, 34, or 38 provided herein is a Raman spectrum that would be considered by one skilled in the art to represent a compound possessing the same crystal form as the compound that provided the Raman spectrum of FIG. 2, 6, 10, 14, 18, 22, 26, 30, 34, or 38. That is, the Raman spectrum may be identical to that of FIG. 2, 6, 10, 14, 18, 22, 26, 30, 34, or 38, or more likely it may be somewhat different. Such a Raman spectrum may not necessarily show each of the peaks of any one of the spectra presented herein, and/or may show a slight change in appearance, intensity, or a shift in position of said peaks resulting from differences in the conditions involved in obtaining the data. A person skilled in the art is capable of determining if a sample of a crystalline compound has the same form as, or a different form from, a form disclosed herein by comparison of their Raman spectra. For example, one skilled in the art can overlay a Raman spectrum of a sample of the free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea, with FIG. 2 and, using expertise and knowledge in the art, readily determine whether the Raman spectrum of the sample is substantially in accordance with the Raman spectrum of Compound A free base anhydrate disclosed herein.

The compounds of Formulae (I)-(XIX) or salts thereof may exist in stereoisomeric forms (e.g., it contains one or more asymmetric carbon atoms). The individual stereoisomers (enantiomers and diastereomers) and mixtures of these are included within the scope of the present invention. The scope of the present invention includes mixtures of stereoisomers as well as purified enantiomers or enantiomerically/diastereomerically enriched mixtures.

Likewise, it is understood that a compound or salt of Formulae (I)-(XIX) may exist in tautomeric forms other than that shown in the formula and these are also included within the scope of the present invention. For example, while the compounds of Formulae (I)-(XIX) are depicted as containing a pyridin-2-one moiety, the corresponding 2-hydroxypyridine tautomer is also included within the scope of the present invention. It is to be understood that the present invention includes all combinations and subsets of the particular groups defined hereinabove.

It will be appreciated by those skilled in the art that certain protected derivatives of compounds of Formulae (I)-(XIX), which may be made prior to or following a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention.

Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1. It will further be appreciated by those skilled in the art, that certain moieties, known to those skilled in the art as "pro-moieties", for example as described by H. Bundgaard in "Design of Prodrugs" may be placed on appropriate functionalities when such functionalities are present within compounds of the invention. Preferred "pro-moieties" for compounds of the invention include: ester, carbonate ester, hemi-ester, phosphate ester, nitro ester, sulfate ester, sulfoxide, amide, carbamate, azo-, phosphamide, glycoside, ether, acetal, and ketal derivatives of the compounds of Formulae (I)-(XIX).

Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound.

The subject invention also includes isotopically-labelled compounds, which are identical to those recited in Formulae (I)-(XIX), but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I, and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H or $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

Definitions

Terms are used within their accepted meanings. The following definitions are meant to clarify, but not limit, the terms defined.

As used herein, the term "alkyl" represents a saturated, straight, or branched hydrocarbon moiety. The term "($C_1$-$C_6$)alkyl" refers to an alkyl moiety containing from 1 to 6 carbon atoms. Exemplary alkyls include, but are not limited to methyl, ethyl, n-propyl, isopropyl, n-butyl, isobutyl, s-butyl, t-butyl, pentyl, and hexyl.

When the term "alkyl" is used in combination with other substituent groups, such as "halo($C_1$-$C_4$)alkyl" or "hydroxy ($C_1$-$C_4$)alkyl", the term "alkyl" is intended to encompass a divalent straight or branched-chain hydrocarbon radical, wherein the point of attachment is through the alkyl moiety. The term "halo($C_1$-$C_4$)alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo($C_1$-$C_4$) alkyl" groups useful in the present invention include, but are not limited to, —$CHF_2$ (difluoromethyl), —$CF_3$ (trifluoromethyl), —$CCl_3$ (trichloromethyl), 1,1-difluoroethyl, 2,2,2-trifluoroethyl, and hexafluoroisopropyl. Examples of "hydroxy($C_1$-$C_4$)alkyl" groups useful in the present invention include, but are not limited to, hydroxymethyl, hydroxyethyl, and hydroxyisopropyl.

"Alkoxy" refers to a group containing an alkyl radical, defined hereinabove, attached through an oxygen linking atom. The term "($C_1$-$C_4$)alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, isobutoxy, and t-butoxy.

When the term "alkoxy" is used in combination with other substituent groups, such as "halo($C_1$-$C_6$)alkoxy", "hydroxy ($C_2$-$C_4$)alkoxy", or "($C_1$-$C_4$)alkoxy($C_2$-$C_4$)alkoxy", the term "alkoxy" is intended to encompass a divalent straight or branched-chain hydrocarbon radical, wherein the point of attachment is to the alkyl moiety through an oxygen linking atom. The term "halo($C_1$-$C_6$)alkoxy" refers to a straight- or branched-chain hydrocarbon radical, having at least 1 and up to 6 carbon atoms with one or more halogen atoms, which may be the same or different, attached to one or more carbon atoms, which radical is attached through an oxygen linking atom. Exemplary "halo($C_1$-$C_6$)alkoxy" groups useful in the present invention include, but are not limited to, —$OCHF_2$ (difluoromethoxy), —$OCF_3$ (trifluoromethoxy), and —$OCH(CF_3)_2$ (hexafluoroisopropoxy). Examples of "hydroxy($C_2$-$C_4$)alkoxy" groups useful in the present invention include, but are not limited to, 2-hydroxyethoxy and 2-hydroxyisopropoxy. Examples of "($C_1$-$C_4$)alkoxy($C_2$-$C_4$)alkoxy" groups useful in the present invention include, but are not limited to, 2-methoxyethoxy, 2-ethoxyethoxy, 2-isopropoxyethoxy, 2-methoxyisopropoxy, and 2-ethoxyisopropoxy.

As used herein, the term "cycloalkyl" refers to a non-aromatic, saturated, cyclic hydrocarbon ring containing the specified number of carbon atoms. The term "($C_3$-$C_6$)cycloalkyl" refers to a non-aromatic cyclic hydrocarbon ring having from three to six ring carbon atoms. Exemplary "($C_3$-$C_6$)cycloalkyl" groups useful in the present invention include cyclopropyl, cyclobutyl, cyclopentyl, and cyclohexyl.

As used herein, the term "cycloalkyloxy-" refers to a group containing a cycloalkyl radical, defined hereinabove, attached through an oxygen linking atom. Exemplary "($C_3$-$C_8$)cycloalkyloxy-" groups useful in the present invention include cyclopropyloxy, cyclobutyloxy, cyclopentyloxy, cyclohexyloxy, cycloheptyloxy, and cyclooctyloxy.

As used herein, "4- to 6-membered heterocycloalkyl" represents a group or moiety comprising a non aromatic, monovalent monocyclic radical, which is saturated or partially unsaturated, containing 4, 5, or 6 ring atoms, which includes one or two heteroatoms selected independently from oxygen, sulfur, and nitrogen. Illustrative examples of 4- to 6-membered heterocycloalkyl groups useful in the present invention include, but are not limited to azetidinyl, oxetanyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, and 1,4-dithianyl.

As used herein, "5- or 6-membered heteroaryl" represents a group or moiety comprising an aromatic monovalent monocyclic radical, containing 5 or 6 ring atoms, including at least one carbon atom and 1 to 4 heteroatoms independently selected from nitrogen, oxygen, and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Illustrative examples of 5- or 6-membered heteroaryl groups useful in the present invention include, but are not limited to furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, and triazinyl.

The terms "halogen" and "halo" represent chloro, fluoro, bromo, or iodo substituents. "Hydroxy" or "hydroxyl" is intended to mean the radical —OH. As used herein, the term "cyano" refers to the group —CN.

As used herein, the term "optionally substituted" indicates that a group, such as alkyl, cycloalkyl, phenyl, or heteroaryl, may be unsubstituted, or the group may be substituted by one or more substituent(s) as defined. In the case where groups may be selected from a number of alternative groups the selected groups may be the same or different.

The term "independently" means that where more than one substituent is selected from a number of possible substituents, those substituents may be the same or different. The alternative definitions for the various groups and substituent groups of Formulae (I)-(XIX) provided throughout the specification are intended to particularly describe each compound species disclosed herein, individually, as well as groups of one or more compound species. The scope of this invention includes any combination of these group and substituent group definitions.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Pharmaceutical Compositions

The invention further provides a pharmaceutical composition (also referred to as pharmaceutical formulation) comprising a compound of Formulae (I)-(XIX) or a pharmaceutically acceptable salt thereof, and one or more excipients (also referred to as carriers and/or diluents in the pharmaceutical arts). The excipients are pharmaceutically acceptable in the sense of being compatible with the other ingredients of the formulation and not deleterious to the recipient thereof (i.e., the patient).

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In accordance with another aspect of the invention there is provided a process for the preparation of a pharmaceutical composition comprising mixing (or admixing) a compound of Formulae (I)-(XIX) or a pharmaceutically acceptable salt thereof, with at least one excipient.

Pharmaceutical compositions may be in unit dose form containing a predetermined amount of active ingredient per unit dose. Such a unit may contain a therapeutically effective dose of the compound of Formulae (I)-(XIX) or a pharmaceutically acceptable salt thereof, or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules, powders or granules, solutions or suspensions in aqueous or non-aqueous liquids, edible foams or whips, oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as a syrup, starch paste, acadia mucilage, or solutions of cellulosic or polymeric materials and forcing through a screen. As an alternative to granulating, the powder mixture can be run through a tablet machine, resulting in imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

In certain embodiments, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl) isoxazol-3-yl)urea. In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea wherein at least 10% by weight of the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea is present as Compound A free base anhydrate described herein. In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea wherein at least 20% by weight, or at least 30% by weight, or at least 40% by weight, or at least 50% by weight, or at least 60% by weight, or at least 70% by weight, or at least 80% by weight, or at least 90% by weight of the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea is present as Compound A free base anhydrate described herein. In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea wherein at least 95% by weight, or at least 96% by weight, or at least 97% by weight, or at least 98% by weight, or at least 99% by weight, or at least 99.5% by weight, or at least 99.8% by weight, or at least 99.9% by weight of the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea is present as Compound A free base anhydrate described herein.

In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl) isoxazol-3-yl)urea, wherein not more than 90% by weight of the free base is amorphous. In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea, wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the free base is amorphous. In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea, wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the free base is amorphous.

In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl) isoxazol-3-yl)urea wherein not more than 90% by weight of the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea is present in a form other than Compound A free base anhydrate described herein. In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl) isoxazol-3-yl)urea is present in a form other than Compound A free base anhydrate described herein. In another embodiment, this invention relates to a pharmaceutical composition comprising the free base of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the free base of 1-(2-(4-ethoxy-6-oxo-1, 6-dihydropyridin-3-yl)-4-methylpyrimidin-5-yl)-3-(5-(1,1, 1-trifluoro-2-methylpropan-2-yl)isoxazol-3-yl)urea is present in a form other than Compound A free base anhydrate described herein.

As used herein, the term "treatment" refers to alleviating the specified condition, eliminating or reducing one or more symptoms of the condition, slowing or eliminating the progression of the condition, and preventing or delaying the reoccurrence of the condition in a previously afflicted or diagnosed patient or subject.

The present invention provides a method of treatment in a mammal, especially a human, suffering from irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, inflammatory bowel disease, proliferative diseases such as non-small cell lung cancer, hepatocellular carcinoma, colorectal cancer, medullary thyroid cancer, follicular thyroid cancer, anaplastic thyroid cancer, papillary thyroid cancer, brain tumors, peritoneal cavity cancer, solid tumors, other lung cancer, head and neck cancer, gliomas, neuroblastomas, Von Hippel-Lindau Syndrome and kidney tumors, breast cancer, fallopian tube cancer, ovarian cancer, transitional cell cancer, prostate cancer, caner of the esophagus and gastroesophageal junction, biliary cancer and adenocarcinoma or a combination thereof. Such treatment comprises the step of administering a therapeutically effective amount of a compound of Formulae (I)-(XIX) or a pharmaceutically acceptable salt thereof, to said mammal, particularly a human. Treatment can also comprise the step of administering a therapeutically effective amount of a pharmaceutical composition containing a compound of Formulae (I)-(XIX) or a pharmaceutically acceptable salt thereof, to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formulae (I)-(XIX), as well as salts thereof, may be administered as the raw chemical. Additionally, the active ingredient may be presented as a pharmaceutical composition. While it is possible that, for use in therapy, a therapeutically effective amount of a compound of Formulae (I)-(XIX) or a pharmaceutically acceptable salt thereof, may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formulae (I)-(XIX) or a pharmaceutically acceptable salt thereof, will be given for the treatment in the range of about 0.1 to 100 mg/kg body weight of recipient (patient, mammal) per day and more usually in the range of 0.1 to 10 mg/kg body weight per day. Acceptable daily dosages may be from about 0.1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formulae (I)-(XIX) per se. Similar dosages should be appropriate for treatment of the other conditions referred herein for treatment. In general, determination of appropriate dosing can be readily arrived at by one skilled in medicine or the pharmacy art.

The compounds of the invention may be used alone or in combination with one or more other therapeutic agents. Accordingly the present invention provides a combination comprising a compound of Formulae (I)-(XIX) or a pharmaceutically acceptable salt thereof and one or more other therapeutic agents. Such combinations may be presented individually (wherein each active is in separate composition) or the actives are presented in a combined composition.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the RET inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein refers to either simultaneous administration or any manner of separate sequential administration of a RET inhibiting compound, as described herein, and a further active ingredient or ingredients, particularly those known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S.

Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical antineoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical antineoplastic agents useful in the present invention include, but are not limited to: alkylating agents, anti-metabolites, anti-tumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deacetylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb®) and erlotinib (TARCEVA®). Imatinib mesylate (GLEEVEC®) is one example of a PDGFR inhibitor. Examples of VEGFR inhibitors include pazopanib (Votrient®), ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem. Soc., 93:2325 (1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Int. Med., 111:273, 1989) and for the treatment of breast cancer (Holmes et al., J. Nat. Cancer Inst., 83:1797, 1991.). It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)-N-carboxy-3-phenylisoserine N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R-(R*,R*)-2,3-dihydroxybutanedioate (1:2)(salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTICDome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)-oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl,7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyrano side], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenialeukopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leukopenialeukopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H)pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leukopenialeukopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leukopenialeukopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leukopenialeukopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leukopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Compound Preparation

Generic Synthesis Schemes

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The synthesis of the compounds of the general Formula (I) and pharmaceutically acceptable derivatives and salts thereof may be accomplished as outlined below in Schemes 1-5 by those skilled in the art. In the following description, the groups are as defined above for compounds of Formula (I) unless otherwise indicated. Starting materials are commercially available or are made from commercially available starting materials using methods known to those skilled in the art.

Compounds of Formula (II) may be prepared as illustrated in Scheme 1. Appropriately substituted aryl bromide urea intermediate A can be coupled with boronate ester intermediate B under palladium coupling conditions, such as with $PdCl_2(dppf)$ and $Cs_2CO_3$, to yield intermediate C. Deprotection of the paramethoxybenzyl (PMB) or benzyl (Bn) moiety can accomplished in the presence of palladium on carbon under a $H_2$ atmosphere or under acidic conditions, such as with TFA or HCl, resulting in compounds of Formula (II).

Scheme 1

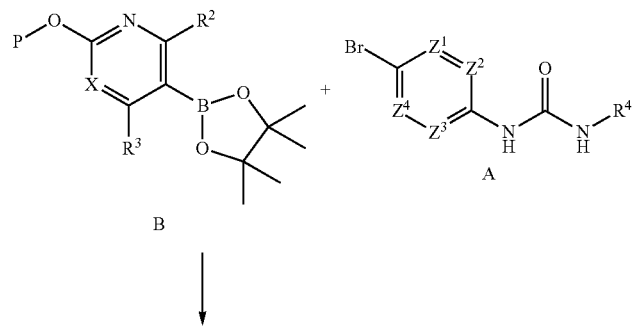

-continued

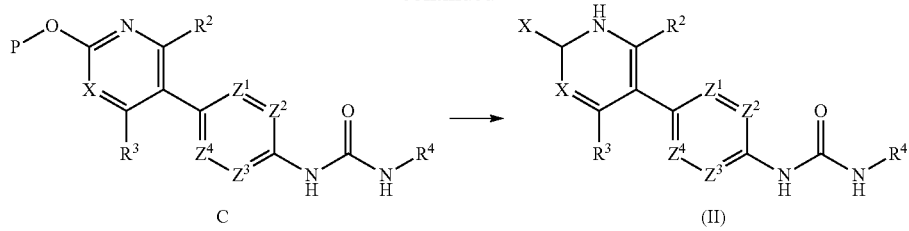

P = PMB or Bn

Intermediate C may also be prepared as illustrated in Scheme 2. Appropriately substituted pyridinyl (or pyrimidinyl) bromide intermediate D can be coupled with boronic acid (or boronate ester)urea intermediate E under palladium coupling conditions, such as with $PdCl_2(dppf)$ and $Cs_2CO_3$, to yield intermediate C. Conditions similar to those in scheme 1 can further transform intermediate C to compounds of Formula (II). Alternatively, compounds of Formula (II) can be prepared directly following the procedure of scheme 2 by using the unprotected variant of intermediate D.

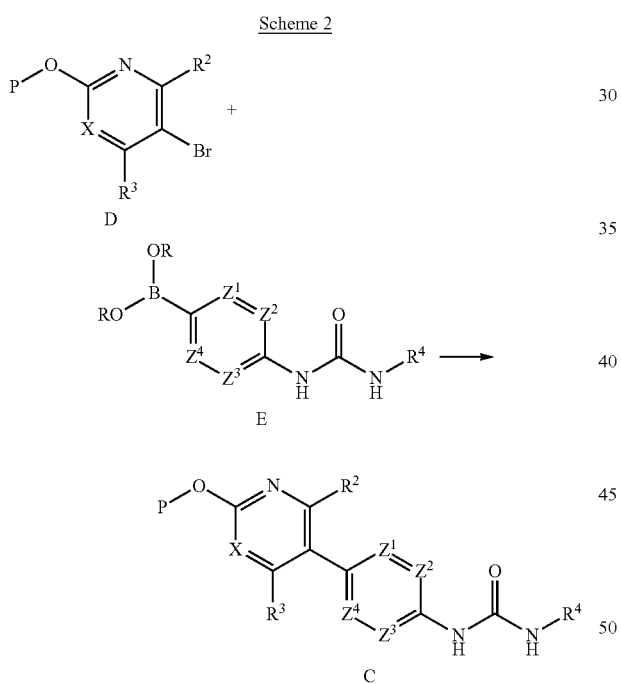

P = PMB or Bn

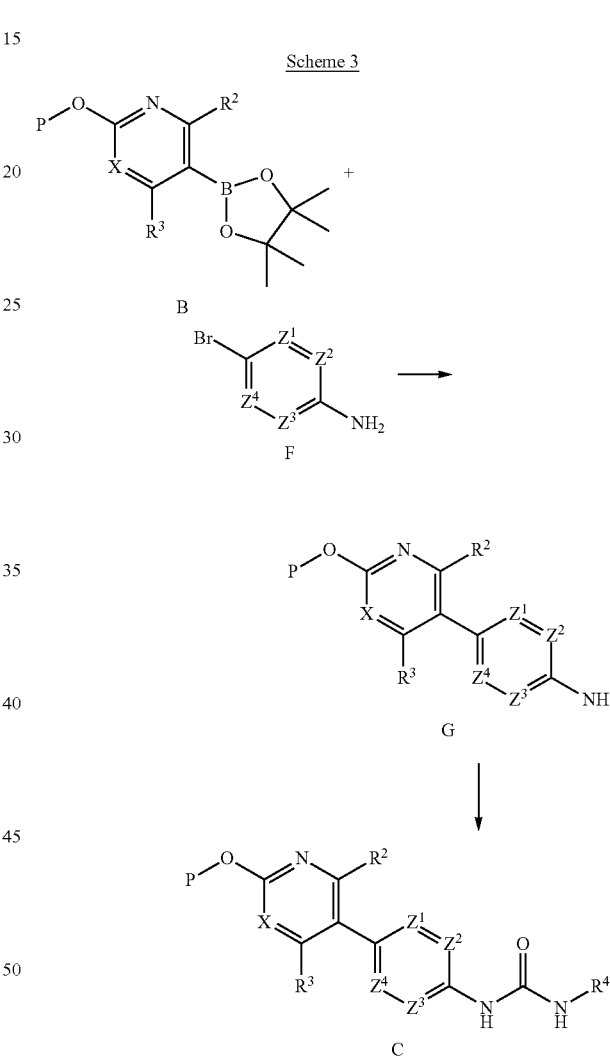

P = PMB or Bn

Intermediate C may also be prepared as illustrated in Scheme 3. Aryl bromide F can be coupled to boronate ester intermediate B under appropriate conditions, such as with $PdCl_2(dppf)$ and $Cs_2CO_3$, to yield intermediate G which can then be coupled with an appropriately substituted isocyanate to provide urea intermediate C. Alternatively, intermediate G can be converted to an isocyanate with an appropriate reagent, such as triphosgene, and then coupled with an appropriately substituted amine to provide urea intermediate C. Conditions similar to those in scheme 1 can further transform intermediate C to compounds of Formula (II).

Intermediate C may also be prepared as illustrated in Scheme 4. Appropriately substituted acid H can be converted to an isocyanate with an appropriate reagent, such as DPPA, and then coupled with an appropriately substituted amine to provide urea intermediate C. Conditions similar to those in scheme 1 can further transform intermediate C to compounds of Formula (II).

Scheme 4

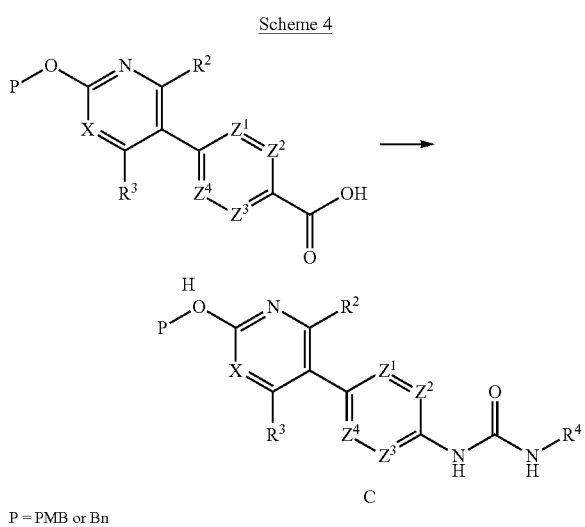

P = PMB or Bn

Compounds of Formula (III) may be prepared as illustrated in Scheme 5 . Appropriately substituted hydroxypyridine I can be coupled with nitro compound J to provide an ether which can then be reduced under appropriate conditions, such as with zinc in methanol, to afford aniline intermediate K. Intermediate K can be coupled with an appropriately substituted isocyanate, or converted to an isocyanate with an appropriate reagent, such as triphosgene, and then coupled with an appropriately substituted amine, to provide urea intermediate L. Deprotection of the paramethoxybenzyl (PMB) or benzyl (Bn) moiety can accomplished in the presence of palladium on carbon under a $H_2$ atmosphere or under acidic conditions, such as with TFA or HCl, resulting in compounds of Formula (III).

invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), dq (double quartet), m (multiplet), br (broad).

Flash column chromatography was performed on silica gel.

The naming programs used are ACDLABs 11.0 Namebatch, ACD IUPAC, or ChemBioDraw® Ultra.

Abbreviations
$Ac_2O$ acetic anhydride
AcOH acetic acid
$BH_3$.DMS borane dimethyl sulfide complex
$BH_3$.THF borane tetrahydrofuran complex
Bn benzyl
$Boc_2O$ di-tert-butyl dicarbonate
$CDCl_3$ chloroform-d
$CD_3OD$ methanol-$d_4$
$Cs_2CO_3$ cesium carbonate
DAST diethylaminosulfur trifluoride
DCM dichloromethane

Scheme 5

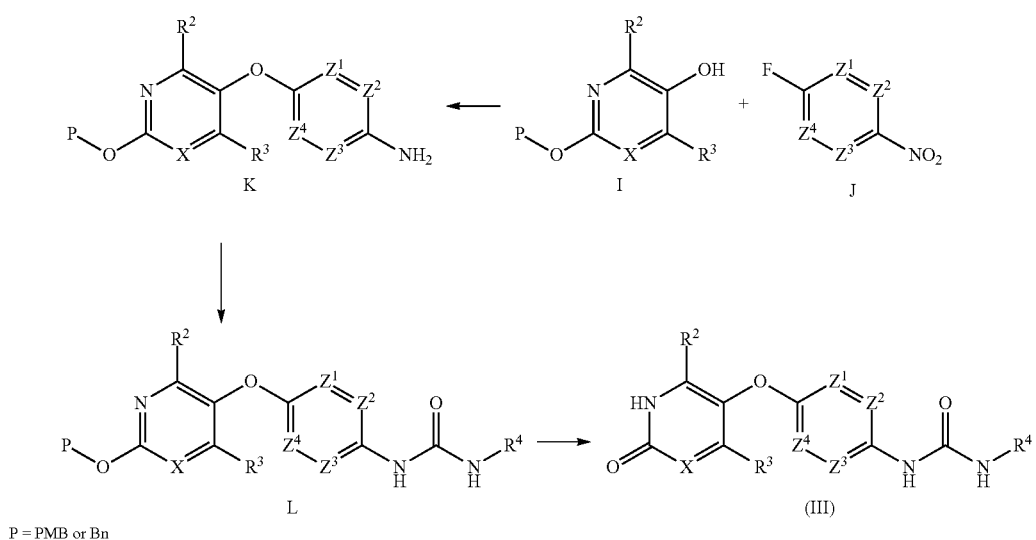

P = PMB or Bn

EXPERIMENTALS

The following examples illustrate the invention. These examples are not intended to limit the scope of the present DIBAl-H diisobutylaluminum hydride
DIEA diisopropylethylamine
DMAP 4-dimethylaminopyridine
DMF N,N-dimethylformamide DMSO-d₆ dimethylsulfoxide-d₆
DPPA diphenylphosphoryl azide
EA ethyl acetate
EDC 1-ethyl-3-(3-dimethylaminopropyl)carbodiimide
ES-LCMS electrospray liquid chromatography-mass spectrometry
EtI ethyl iodide
Et₃N triethylamine
EtOH ethanol
g gram(s)
h hour(s)
H₂ hydrogen gas
HATU O-(7-azabenzotriazol-1-yl)-N,N,N',N'-tetramethyluronium hexafluorophosphate
HBr hydrogen bromide
HCl hydrochloric acid
H₂O water
H₂O₂ hydrogen peroxide
HOBt hydroxybenzotriazole
HPLC high performance liquid chromatography
H₃PO₂ phosphinic acid
H₂SO₄ sulfuric acid
in vacuo under vacuum
K₂CO₃ potassium carbonate
KOAc potassium acetate
KOH potassium hydroxide
LAH lithium aluminium hydride
LCMS liquid chromatography-mass spectrometry
LiOH lithium hydroxide
LiOH.H₂O lithium hydroxide hydrate
m-CPBA meta-chloroperoxybenzoic acid
MeCN acetonitrile
MeI methyl iodide
MeMgBr methylmagnesium bromide
MeOH methanol
mg milligram(s)
MgSO₄ magnesium sulfate
min minute(s)
mL milliliter(s)
mmol millimole(s)
N₂ nitrogen gas
NaBH₄ sodium borohydride
NaBH(OAc)₃ sodium triacetoxyborohydride
Na₂CO₃ sodium carbonate
NaH sodium hydride
NaHCO₃ sodium bicarbonate
NaI sodium iodide
NaIO₄ sodium periodate
NaNO₂ sodium nitrite
NaOEt sodium ethoxide
NaOH sodium hydroxide
Na₂SO₄ sodium sulfate
NBS N-bromosuccinimide
n-BuLi n-butyl lithium
NH₄Cl ammonium chloride
(NH₄)HCO₃ ammonium bicarbonate
NH₄OAc ammonium acetate
NH₄OH ammonium hydroxide
NIS N-iodosuccinimide
NMR nuclear magnetic resonance
Pd/C palladium on carbon
PdCl₂(dppf) 1,1'-bis(diphenylphosphino)ferrocene]dichloropalladium(II)
PdCl₂(PPh₃)₂ bis(triphenylphosphine)palladium(II) dichloride
Pd₂(dba)₃ tris(dibenzylideneacetone)dipalladium(0)
PE petroleum ether PMB p-methoxybenzyl
POCl₃ phosphorus oxychloride
rt room temperature
SnCl₂.H₂O tin(II) chloride hydrate
SOCl₂ thionyl chloride
TBME tert-butyl methyl ether
TBS tert-butyldimethylsilyl
TBSCl tert-butyldimethylsilyl chloride
TFA trifluoroacetic acid
TFAA trifluoroacetic anhydride
THF tetrahydrofuran
TLC thin layer chromatography
Preparation of Intermediates Intermediate 1

3-Ethoxy-2-((4-methoxybenzyl)oxy)-5-(4,4,5,5-tetramethyl-1,3,2-dioxaborolan-2-yl)pyridine

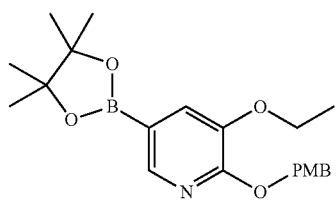

Step 1: 3-Bromo-5-ethoxypyridine

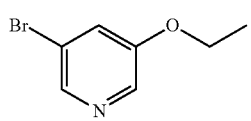

A solution of 5-bromopyridin-3-ol (70 g, 402 mmol), K₂CO₃ (111 g, 805 mmol) and EtI (69.0 g, 443 mmol) in DMF (700 mL) was stirred for 16 h at 25° C. Then the mixture was concentrated, diluted with water, extracted with DCM (2×200 mL), dried over Na₂SO₄ and concentrated to give 3-bromo-5-ethoxypyridine (53 g, 218 mmol, 54.2% yield): ¹H NMR (400 MHz, CD₃OD) δ 8.19-8.17 (m, 2H), 7.60-7.59 (m, 1H), 4.13-4.07 (m, 2H), 1.40 (t, J=7.0 Hz, 3H); ES-LCMS m/z 202 (M+H).

Step 2: 3-Bromo-5-ethoxypyridine 1-oxide

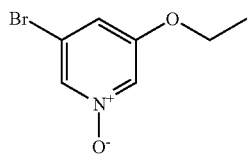

To a solution of 3-bromo-5-ethoxypyridine (53 g, 262 mmol) in DCM (200 mL) at 0° C. was slowly added m-CPBA (67.9 g, 393 mmol) over 30 min. After the resulting solution was stirred for 15 h, the mixture was washed with NaS₂O₃ solution and extracted with DCM (2×300 mL), dried over Na₂SO₄ and the organic phase was concentrated to give 3-bromo-5-ethoxypyridine 1-oxide (40 g, 165 mmol, 62.9% yield): $^1$H NMR (400 MHz, CD$_3$OD) δ 8.19-8.18 (m, 1H), 8.08-8.07 (m, 1H), 7.50-7.49 (m, 1H), 4.17-4.15 (d, J=8.8 Hz, 2H), 1.43 (t, J=7.0 Hz, 3H); ES-LCMS m/z 217 (M+H).

Step 3: 5-Bromo-2-chloro-3-ethoxypyridine

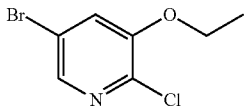

To a solution of 3-bromo-5-ethoxypyridine 1-oxide (40 g, 183 mmol) in DCM (200 mL) at 0° C. was slowly added POCl$_3$ (159 mL, 1701 mmol) over 30 min. Then the resulting solution was warmed to 45° C. for 15 h. The mixture was concentrated and extracted with DCM (2×200 mL), dried over Na$_2$SO$_4$ and concentrated to give 5-bromo-2-chloro-3-ethoxypyridine (30 g, 60.9 mmol, 33.2% yield): $^1$H NMR (400 MHz, CD$_3$OD) δ 8.00-7.99 (d, J=2.0 Hz, 1H), 7.65-7.64 (d, J=2.0 Hz, 1H), 4.17-4.12 (m, 2H), 1.44 (t, J=7.0 Hz, 2H); ES-LCMS m/z 235 (M+H).

Step 4:
5-Bromo-3-ethoxy-2-((4-methoxybenzyl)oxy)pyridine

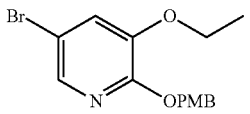

To a mixture of (4-methoxyphenyl)methanol (16.71 g, 121 mmol) in DMF (200 mL) was added NaH (3.96 g, 165 mmol) at 0° C. After the mixture was stirred for 30 min, 5-bromo-2-chloro-3-ethoxypyridine (26 g, 110 mmol) was added to above mixture and the mixture was stirred for 12 h at 80-90° C. The mixture was quenched by H$_2$O (20 mL), extracted with DCM (2×200 mL), dried over Na$_2$SO$_4$, filtered, concentrated, and purified by via column chromatography (10% EA/90% PE, 360 g silica column). All fractions found to contain product by TLC (EA/PE=5:1, R$_f$=0.5) were combined and concentrated to yield a white solid of 5-bromo-3-ethoxy-2-((4-methoxybenzyl)oxy)pyridine (36 g, 74.5 mmol, 67.8% yield): $^1$H NMR (400 MHz, CD$_3$OD) δ 7.71 (d, J=2.0 Hz, 1H), 7.36-7.31 (m, 3H), 6.89-6.87 (m, 2H), 5.27 (s, 2H), 4.05-4.00 (m, 2H) 3.77 (s, 3H), 2.37 (d, J=7.0 Hz, 3H); ES-LCMS m/z 338 (M+H).

Step 5: 3-Ethoxy-2-((4-methoxybenzyl)oxy)-5-(4,4,5,5-tetramethyl-1,3,2-dioxaborolan-2-yl)pyridine

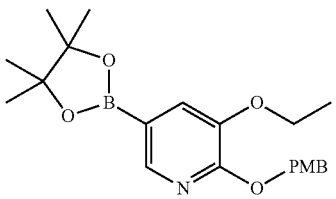

To a solution of 5-bromo-3-ethoxy-2-((4-methoxybenzyl)oxy)pyridine (10 g, 29.6 mmol), 4,4,4',4',5,5,5',5'-octamethyl-2,2'-bi(1,3,2-dioxaborolane) (8.26 g, 32.5 mmol) and KOAc (7.25 g, 73.9 mmol) in 1,4-dioxane (250 mL) stirred under N$_2$ at 20° C. was added PdCl$_2$(dppf) (1.082 g, 1.478 mmol) in one charge. The reaction mixture was stirred at 100° C. for 3 h. The mixture was filtered and the filtrate was concentrated in vacuo and then purified by silica column chromatography (PE/EA=10:1). All fractions found to contain product by TLC (PE/EA=10:1, R$_f$=0.6) were combined and concentrated to yield a white solid of 3-ethoxy-2-((4-methoxybenzyl)oxy)-5-(4,4,5,5-tetramethyl-1,3,2-dioxaborolan-2-yl)pyridine (9.2 g, 23.88 mmol, 81.0% yield): $^1$H NMR (400 MHz, CDCl$_3$) δ 8.10 (s, 1H), 7.42 (d, J=8.8 Hz, 2H), 7.33 (s, 1H), 6.88-6.85 (m, 2H), 5.45 (s, 2H), 4.11-4.06 (m, 2H), 3.78 (s, 3H), 1.43 (t, J=7.0 Hz, 3H), 1.33 (s, 12H); ES-LCMS m/z 386.0 (M+H).

Intermediate 2

4-(4-Ethyl-piperazin-1-ylmethyl)-3-trifluoromethyl-phenylamine

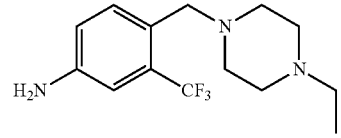 [SMILES: CCN1CCN(Cc2ccc(N)cc2C(F)(F)F)CC1]

Step 1: (4-Amino-2-trifluoromethyl-phenyl)-(4-ethyl-piperazin-1-yl)-methanone

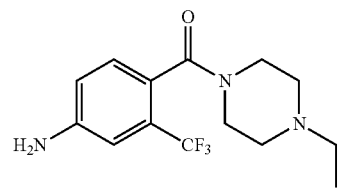 [SMILES: CCN1CCN(C(=O)c2ccc(N)cc2C(F)(F)F)CC1]

A mixture of 4-amino-2-trifluoromethyl-benzoic acid (15 g, 73.1 mmol), HOBT (14.56 g, 95 mmol), EDC (16.82 g, 88 mmol), Et$_3$N (20.38 mL, 146 mmol), 1-ethyl-piperazine (8.35 g, 73.1 mmol) in DCM (200 mL) was stirred at 25° C. for 2 h. To the mixture was added DCM (200 mL) and then washed with H$_2$O, 2 mol/L NaOH (2×150 mL) and brine. The organic layer was dried over Na$_2$SO$_4$ and concentrated to give a off white solid of (4-amino-2-trifluoromethyl-phenyl)-(4-ethyl-piperazin-1-yl)-methanone (20 g, 65.2 mmol, 89.0% yield): $^1$H NMR (400 MHz, CDCl$_3$) δ 7.07 (d, J=8.0 Hz, 1H), 6.92 (d, J=2.4 Hz, 1H), 6.79 (dd, J=2.0, 8.0 Hz, 1H), 3.99 (s, 2H), 3.84-3.76 (m, 2H), 3.25-3.23 (m, 2H), 2.50-2.39 (m, 4H), 2.33-2.31 (m, 2H), 1.08 (t, J=7.2 Hz, 3H); ES-LCMS m/z 302 (M+H).

Step 2: 4-(4-Ethyl-piperazin-1-ylmethyl)-3-trifluoromethyl-phenylamine

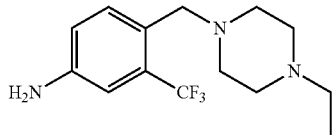 [SMILES: CCN1CCN(Cc2ccc(N)cc2C(F)(F)F)CC1]

To a mixture of (4-amino-2-trifluoromethyl-phenyl)-(4-ethyl-piperazin-1-yl)-methanone (20 g, 66.4 mmol) in THF (500 mL) was added BH$_3$.DMS (19.91 mL, 199 mmol) dropwise. Then the mixture was stirred at 80° C. for 4 h. The mixture was quenched by adding MeOH and then concentrated. The residue was purified by silica column chromatography on silica gel (PE:EA=2:1, R$_f$=0.35) to give a white solid of 4-(4-ethyl-piperazin-1-ylmethyl)-3-trifluoromethyl-phenylamine (14 g, 46.0 mmol, 69.4% yield): $^1$H NMR (400 MHz, CDCl$_3$) δ 7.48 (d, J=8.4 Hz, 1H), 6.91 (d, J=2.8 Hz, 1H), 6.79 (dd, J=2.4, 8.4 Hz, 1H), 3.76 (s, 2H), 3.53 (s, 2H), 2.45-2.39 (m, 8H), 1.08 (t, J=7.2 Hz, 3H); ES-LCMS m/z 288 (M+H).

Intermediate 3

4((3-Methyloxetan-3-yl)oxy)-3-(trifluoromethyl)aniline

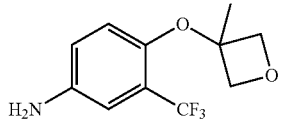

Step 1: 3-Methyloxetan-3-ol

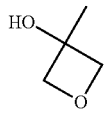

To a mixture of oxetan-3-one (8 g, 111 mmol) in THF (300 mL) cooled to 0° C. was added MeMgBr (74.0 mL, 222 mmol) dropwise. The mixture was stirred at 25° C. for 2 h. The mixture was quenched with NH$_4$Cl (aq). The precipitate was filtered and washed with DCM. The filtrate was concentrated to give a light yellow oil of 3-methyloxetan-3-ol (7.5 g, 85 mmol, 77% yield): $^1$H NMR (400 MHz, CDCl$_3$) δ 4.61 (d, J=6.4 Hz, 2H), 4.46 (d, J=7.2 Hz, 2H), 2.31 (s, 1H), 1.56 (s, 3H).

Step 2: 3-Methyl-3-(4-nitro-2-(trifluoromethyl)phenoxy)oxetane

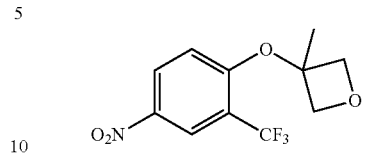

To a mixture of 1-fluoro-4-nitro-2-(trifluoromethyl)benzene (10 g, 47.8 mmol) and 3-methyloxetan-3-ol (3.51 mL, 47.8 mmol) in MeCN (100 mL) was added Cs$_2$CO$_3$ (46.7 g, 143 mmol). The mixture was stirred at 80° C. for 10 h. The mixture was filtered. The filtrate was concentrated, and the residue was purified by silica column chromatography (PE/EA=20:1). All fractions found to contain product by TLC (PE/EA=5:1, R$_f$=0.6) were combined and concentrated to yield a light yellow solid of 3-methyl-3-(4-nitro-2-(trifluoromethyl)phenoxy)oxetane (10 g, 35.8 mmol, 74.8% yield): $^1$H NMR (400 MHz, CDCl$_3$) δ 8.54 (d, J=2.8 Hz, 1H), 8.36 (dd, J=2.8, 9.2 Hz, 1H), 6.50 (d, J=9.2 Hz, 1H), 4.98 (d, J=6.8 Hz, 2H), 4.67 (d, J=7.6 Hz, 2H), 1.84 (s, 3H); ES-LCMS m/z 278 (M+H).

Step 3: 4-((3-Methyloxetan-3-yl)oxy)-3-(trifluoromethyl)aniline

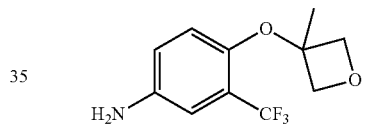

A reaction mixture of 3-methyl-3-(4-nitro-2-(trifluoromethyl)phenoxy)oxetane (10 g, 36.1 mmol) and Pd/C (0.384 g, 3.61 mmol; 10%) in MeOH (50 mL) was hydrogenated under H$_2$ atmosphere (50 psi) at 40° C. for 20 h. The mixture was concentrated to give a brown oil of 4-((3-methyloxetan-3-yl)oxy)-3-(trifluoromethyl)aniline (8.5 g, 34.1 mmol, 95% yield): $^1$H NMR (400 MHz, CDCl$_3$) δ 6.92 (d, J=2.8 Hz, 1H), 6.72 (dd, J=2.8, 8.8 Hz, 1H), 6.35 (d, J=8.4 Hz, 1H), 4.95 (d, J=6.4 Hz, 2H), 4.52 (d, J=7.2 Hz, 2H), 3.60 (s, 2H), 1.68 (s, 3H); ES-LCMS m/z 248 (M+H).

Intermediate 4

1-(2-Fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea

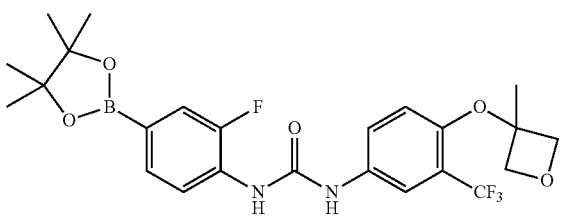 [SMILES: CC1(Oc2ccc(NC(=O)Nc3ccc(B4OC(C)(C)C(C)(C)O4)cc3F)cc2C(F)(F)F)COC1]

Step 1: 2-Fluoro-4-(4,4,5,5-tetramethyl-1,3,2-dioxaborolan-2-yl)aniline

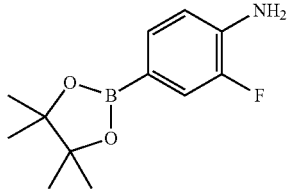 [SMILES: CC1(C)OB(c2ccc(N)c(F)c2)OC1(C)C]

To a solution of 4-bromo-2-fluoroaniline (40 g, 211 mmol), 4,4,4',4',5,5,5',5'-octamethyl-2,2'-bi(1,3,2-dioxaborolane) (64.1 g, 253 mmol) and KOAc (41.3 g, 421 mmol) in 1,4-dioxane (500 mL) stirred under $N_2$ at 20° C. was added $PdCl_2(dppf)$ (7.70 g, 10.53 mmol) in one charge. The reaction mixture was stirred at 100° C. for 3 h. The solution was concentrated in vacuo to give 2-fluoro-4-(4,4,5,5-tetramethyl-1,3,2-dioxaborolan-2-yl)aniline (44 g, 158 mmol, 74.9% yield): $^1$H NMR (400 MHz, $CDCl_3$) δ 7.46-7.40 (m, 2H), 6.75-6.71 (m, 1H), 1.30 (s, J=3.6 Hz, 12H); ES-LCMS m/z 238.1 (M+H).

Step 2: 2-(3-Fluoro-4-isocyanatophenyl)-4,4,5,5-tetramethyl-1,3,2-dioxaborolane

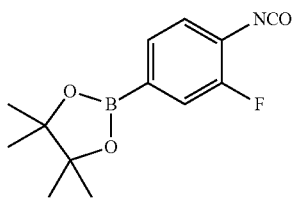

To a mixture of 2-fluoro-4-(4,4,5,5-tetramethyl-1,3,2-dioxaborolan-2-yl)aniline (500 mg, 2.109 mmol) in THF (10 mL) was added triphosgene (250 mg, 0.844 mmol). The mixture was stirred at 60° C. for 30 min. The residue was evaporated to give 2-(3-fluoro-4-isocyanatophenyl)-4,4,5,5-tetramethyl-1,3,2-dioxaborolane (500 mg, 1.616 mmol, 77% yield); ES-LCMS m/z 296.1 (M+MeOH+H).

Step 3: 1-(2-Fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea

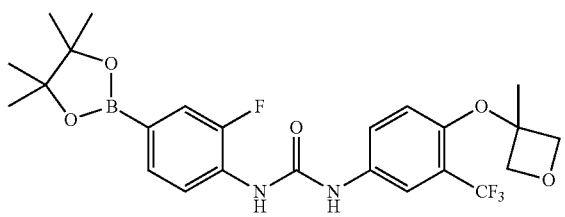 [SMILES: CC1(Oc2ccc(NC(=O)Nc3ccc(B4OC(C)(C)C(C)(C)O4)cc3F)cc2C(F)(F)F)COC1]

To a mixture of 2-(3-fluoro-4-isocyanatophenyl)-4,4,5,5-tetramethyl-1,3,2-dioxaborolane (500 mg, 1.901 mmol) in THF (10 mL) was added 4-((3-methyloxetan-3-yl)oxy)-3-(trifluoromethyl)aniline (517 mg, 2.091 mmol) and $Et_3N$ (0.530 mL, 3.80 mmol). The mixture was stirred at 60° C. for 1 h. The mixture was concentrated and purified by preparative TLC (PE/EA=3:1, $R_f$=0.6) to yield a light yellow solid of 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (500 mg, 0.980 mmol, 51.6% yield): $^1$H NMR (400 MHz, $CDCl_3$) δ 8.15 (t, J=8.0 Hz, 1H), 7.77-7.76 (d J=2.8 Hz, 1H), 7.55-7.52 (m, 1H), 7.49-7.47 (m, 1H), 7.42-7.38 (m, 1H), 6.62-6.60 (d, J=8.8 Hz, 1H), 4.91-4.89 (d, J=6.0 Hz, 2H), 4.63-4.61 (d, J=7.6 Hz, 2H), 1.71(s, 3H), 1.33 (s, 12H); ES-LCMS m/z 511.2 (M+H).

Intermediate 5: 2-(5-Ethoxy-6-((4-methoxybenzyl)oxy)pyridin-3-yl)-4-methylpyrimidine-5-carboxylic acid

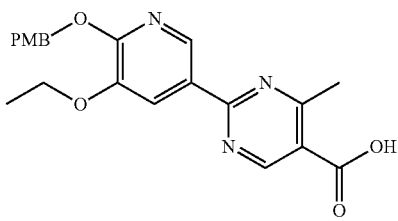

Step 1: Ethyl 6-methyl-2-oxo-1,2-dihydropyrimidine-5-carboxylate

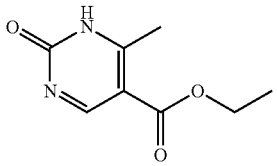

A solution of urea (50 g, 833 mmol), ethyl 3-oxobutanoate (119 g, 916 mmol) in triethoxymethane (136 g, 916 mmol) was stirred for 28 h while distilling off EtOH at 80° C. under $N_2$ atmosphere. Then the mixture was cooled to 20° C. and EtOH (800 mL) was added, NaOEt (85 g, 1249 mmol) in EtOH (500 mL) was added to above mixture and the mixture was stirred for 2 h at 80° C., the mixture was cooled to 20° C., followed by addition of water (400 mL), AcOH (60 mL) was added at 20-30° C., then the mixture was filtered, the solid was washed with water (200 mL) and then dried to give ethyl 6-methyl-2-oxo-1,2-dihydropyrimidine-5-carboxylate (70 g, 384 mmol, 46.2% yield). $^1$H NMR (400 MHz, DMSO-$d_6$) δ 8.81 (s, 1H), 4.31 (q, J=7.2 Hz, 2H), 2.64 (s, 3H), 1.35 (t, J=7.2 Hz, 3H); LCMS m/z 183.2 (M+H).

Step 2: Ethyl 2-chloro-4-methylpyrimidine-5-carboxylate

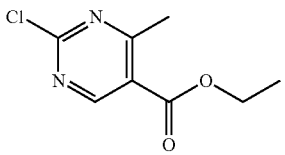

To a solution of ethyl 6-methyl-2-oxo-1,2-dihydropyrimidine-5-carboxylate (62 g, 340 mmol) stirred under N$_2$ at 20° C. was added POCl$_3$ (496 g, 3233 mmol) slowly. The reaction mixture was stirred at 80° C. for 12 h. Then the solution was concentrated and distributed between EA and saturated NaHCO$_3$ solution. The combined organic extract was washed with brine, dried over Na$_2$SO$_4$, filtered and concentrated. The residue was purified by silica column chromatography (PE/EA=10:1). All fractions found to contain product by TLC (PE/EA=10:1, R$_f$=0.7) were combined and concentrated to yield a yellow solid of ethyl 2-chloro-4-methylpyrimidine-5-carboxylate (9 g, 44.9 mmol, 13.18% yield): $^1$H NMR (400 MHz, CDCl$_3$) δ 9.01 (s, 1H), 4.41 (q, J=7.2 Hz, 2H), 2.82 (s, 3H), 1.41 (t, J=7.2 Hz, 3H).

Step 3: Ethyl 2-(5-ethoxy-6-((4-methoxybenzyl)oxy)pyridin-3-yl)-4-methylpyrimidine-5-carboxylate

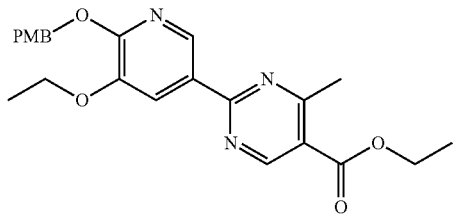

To a solution of 3-ethoxy-2-((4-methoxybenzyl)oxy)-5-(4,4,5,5-tetramethyl-1,3,2-dioxaborolan-2-yl)pyridine (6.34 g, 16.45 mmol), ethyl 2-chloro-4-methylpyrimidine-5-carboxylate (3 g, 14.95 mmol) and Cs$_2$CO$_3$ (9.74 g, 29.9 mmol) in 1,4-dioxane (20 mL) and water (6.67 mL) stirred under N$_2$ atmosphere at 20° C. was added PdCl$_2$(dppf) (0.547 g, 0.748 mmol) in one charge. The reaction vessel was heated at 110° C. for 2 h. Then the solution was concentrated and distributed between EA and water. The combined organic extract was washed with brine, dried over MgSO$_4$, filtered and concentrated. The residue was purified by silica column chromatography (PE/EA=10:1, 5:1). All fractions found to contain product by TLC (PE/EA=5:1, R$_f$=0.5) were combined and concentrated to yield a yellow solid of ethyl 2-(5-ethoxy-6-((4-methoxybenzyl)oxy)pyridin-3-yl)-4-methylpyrimidine-5-carboxylate (6 g, 14.17 mmol, 95% yield): $^1$H NMR (400 MHz, CDCl$_3$) δ 9.15 (s, 1H), 8.90 (s, 1H), 8.10 (m, 1H), 7.45 (d, J=8.8 Hz, 2H), 6.89 (d, J=8.8 Hz, 2H), 5.50 (s, 2H), 4.45-4.37 (m, 2H), 4.20-4.15 (m, 2H), 3.80 (s, 3H), 2.90-2.81 (m, 3H), 1.48 (t, J=6.8 Hz, 3H), 1.42 (t, J=7.2 Hz, 3H); LCMS m/z 424.1 (M+H).

Step 4: 2-(5-Ethoxy-6-((4-methoxybenzyl)oxy)pyridin-3-yl)-4-methylpyrimidine-5-carboxylic acid

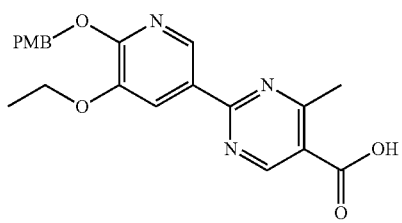

To a solution of ethyl 2-(5-ethoxy-6-((4-methoxybenzyl)oxy)pyridin-3-yl)-4-methylpyrimidine-5-carboxylate (6 g, 14.17 mmol) in THF (20 mL) stirred under N$_2$ at 20° C. was added LiOH.H$_2$O (11.34 mL, 28.3 mmol) in one charge. The reaction mixture was stirred at 60° C. for 12 h. Then the solution was concentrated and neutralized with conc. HCl to pH=7.0 with stirring. Solution was then filtered, and the filtrate cake was washed with water (10 mL). The filtrate cake was dried in vacuo to give an off white solid of 2-(5-ethoxy-6-((4-methoxybenzyl)oxy)pyridin-3-yl)-4-methylpyrimidine-5-carboxylic acid (4 g, 10.12 mmol, 71.4% yield): $^1$H NMR (400 MHz, CD$_3$OD) δ 8.89 (s, 1H), 8.73 (s, 1H), 8.12 (d, J=1.6 Hz, 1H), 7.40 (d, J=8.8 Hz, 2H), 6.91 (d, J=8.8 Hz, 2H), 5.39 (s, 2H), 4.16 (q, J=6.8 Hz, 2H), 3.78 (s, 3H), 2.76 (s, 3H), 1.43 (t, J=6.8 Hz, 3H); LCMS m/z 396.1 (M+H).

Intermediate 6: 2-(4-Ethoxy-6-((4-methoxybenzyl)oxy)pyridin-3-yl)-4-methylpyrimidine-5-carboxylic acid

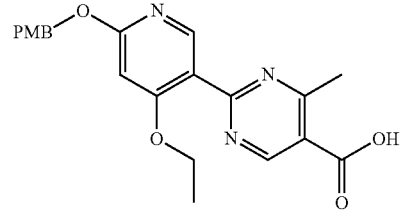

Step 1: 2-Chloro-4-ethoxypyridine

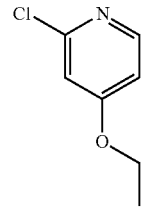

A mixture of 2-chloro-4-nitropyridine (170 g, 1070 mmol) in THF (2 L) was added NaOEt (109.45 g, 1610 mmol) slowly at 0° C. The mixture was stirred at 25° C. for 12 h. LCMS and TLC (PE/EA=5:1, R$_f$=0.6) showed the reaction was finished. The mixture was filtered, and most solvent of the filtrate was removed in vacuo. The residue was extracted with EA (800 mL×3), and the organic layer was washed with saturated NaCl solution (1 L), dried over Na$_2$SO$_4$ and concentrated to give 2-chloro-4-ethoxypyridine (157 g, 1.0 mol, 92% yield) as a solid: $^1$H NMR (400 MHz, CD$_3$OD) δ 8.15 (d, J=6.0 Hz, 1H), 6.99 (d, J=2.0 Hz, 1H), 6.91-6.89 (m, 1H), 4.16-4.14 (m, 2H), 1.41-1.38 (m, 3H); ES-LCMS m/z 158 (M+H).

Step 2: 5-Bromo-2-chloro-4-ethoxypyridine

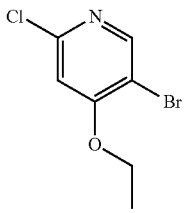

Solid 2-chloro-4-ethoxypyridine (100 g, 0.63 mol) was added to H₂SO₄ (500 mL) slowly. Then 1-bromopyrrolidine-2,5-dione (124.2 g, 0.70 mol) was added into above mixture at rt. The mixture was stirred at 80° C. for 3 h. TLC (PE/EA=10:1, $R_f$=0.5) showed the reaction was finished. The reaction mixture was poured into ice-water (2 L), and extracted with EA (1 L×3). The organic layer was washed with saturated Na₂CO₃ solution (1 L×2), dried over Na₂SO₄ and concentrated. The residue was purified on silica column chromatography (PE/EA=60:1-30:1). All fractions found to contain product by TLC (PE/EA=10:1, $R_f$=0.5) were combined and concentrated to yield 5-bromo-2-chloro-4-ethoxypyridine (60.9 g, 0.26 mol, 40% yield): ¹H NMR (400 MHz, CD₃OD) δ 8.31 (s, 1H), 7.14 (s, 1H), 4.32-4.10 (m, 2H), 1.58-1.35 (m, 3H); ES-LCMS m/z 237 (M+2).

Step 3: 5-Bromo-4-ethoxy-2-((4-methoxybenzyl)oxy)pyridine

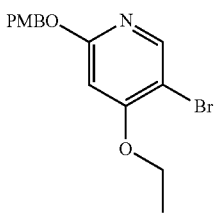

A mixture of 5-bromo-2-chloro-4-ethoxypyridine (75 g, 317.1 mmol) in toluene (500 mL) was added (4-methoxyphenyl)methanol (52.6 g, 380.6 mmol), KOH (35.6 g, 634.3 mmol) and 18-crown-6 (8.4 g, 31.2 mmol) at rt. The reaction mixture was stirred at 120° C. for 2 h. The mixture was portioned between 2-methoxy-2-methylpropane (500 mL) and brine (800 mL). The organic layer was concentrated. The residue was purified by column (PE/EA=10:1, $R_f$=0.5) to give 5-bromo-4-ethoxy-2-((4-methoxybenzyl)oxy)pyridine (72.2 g, 221 mmol, 70% yield): ¹H NMR (400 MHz, CD₃OD) δ 8.05 (s, 1H), 7.33 (d, J=8.8 Hz, 2H), 6.90-6.84 (m, 2H), 6.38 (s, 1H), 5.20 (s, 2H), 4.16-4.05 (m, 2H), 3.77 (s, 3H), 1.43 (q, J=6.8 Hz, 3H); ES-LCMS m/z 338 (M+2H).

Step 4: Ethyl 6-methyl-2-oxo-1,2-dihydropyrimidine-5-carboxylate

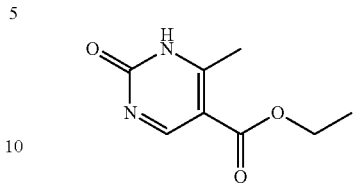

A solution of urea (50 g, 833 mmol), ethyl 3-oxobutanoate (119 g, 916 mmol) in triethoxymethane (136 g, 916 mmol) was stirred for 2 h while distilling off EtOH at 80° C. under N₂ atmosphere. Then the mixture was cooled to 20° C. and EtOH (800 mL) was added, NaOEt (85 g, 1249 mmol) in EtOH (500 mL) was added to above mixture and the mixture was stirred for 2 h at 80° C., the mixture was cooled to 20° C., followed by addition of water (1 L), AcOH (60 mL) was added at 20° C.-30° C., then the mixture was filtered, the solid was washed with water (200 mL), dried to give ethyl 6-methyl-2-oxo-1,2-dihydropyrimidine-5-carboxylate (70 g, 384 mmol, 46.2% yield): ¹H NMR (400 MHz, DMSO-d₆) δ 8.81 (s, 1H), 4.31 (q, J=7.2 Hz, 2H), 2.64 (s, 3H), 1.35 (t, J=7.1 Hz, 3H); LCMS m/z 183.1 (M+H).

Step 5: Ethyl 2-chloro-4-methylpyrimidine-5-carboxylate

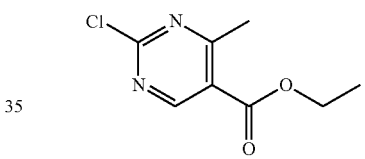

To a solution of ethyl 6-methyl-2-oxo-1,2-dihydropyrimidine-5-carboxylate (62 g, 340 mmol) and stirred under N₂ at 20° C. was added POCl₃ (496 g, 3233 mmol) slowly. The reaction mixture was stirred at 80° C. for 12 h. Then the solution was concentrated and distributed between EA and saturated NaHCO₃ solution. The combined organic extract was washed with brine, dried over Na₂SO₄, filtered and concentrated. The residue was purified by silica column chromatography (PE/EA=10:1). All fractions found to contain product by TLC (PE/EA=10:1, $R_f$=0.7) were combined and concentrated to yield a yellow solid of ethyl 2-chloro-4-methylpyrimidine-5-carboxylate (9 g, 44.9 mmol, 13.18% yield): ¹H NMR (400 MHz, CDCl₃) δ 9.01 (s, 1H), 4.41 (q, J=7.1 Hz, 2H), 2.82 (s, 3H), 1.41 (t, J=7.1 Hz, 3H); ES-LCMS m/z 201.1 (M+H).

Step 6: 4-Ethoxy-2-((4-methoxybenzyl)oxy)-5-(4,4,5,5-tetramethyl-1,3,2-dioxaborolan-2-yl)pyridine

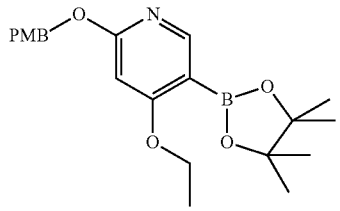

To a solution of 5-bromo-4-ethoxy-2-((4-methoxybenzyl)oxy)pyridine (5 g, 14.78 mmol) in THF (25 mL) stirred under N₂ at −70° C. was added n-BuLi (6.51 mL, 16.26 mmol) portionwise during 1 min. The reaction mixture was stirred at −70° C. for 1 h. Then to the solution was added 2-isopropoxy-4,4,5,5-tetramethyl-1,3,2-dioxaborolane (3.03 g, 16.26 mmol) in THF (1 mL) at −70° C. with stirring. The solution was stirred at −70° C. for 1 h. To the mixture was added saturated NH₄Cl solution. Then the solution was concentrated and distributed between EA and water. The combined organic extract was washed with brine, dried over Na₂SO₄, filtered and concentrated. The resulting 4-ethoxy-2-((4-methoxybenzyl)oxy)-5-(4,4,5,5-tetramethyl-1,3,2-dioxaborolan-2-yl)pyridine (4 g, 10.38 mmol, 70.2% yield). TLC (PE/EA=10:1, $R_f$=0.2): $^1$H NMR (400 MHz, CDCl₃) δ 8.29 (s, 1H), 7.37 (d, J=8.6 Hz, 2H), 6.89 (d, J=8.6 Hz, 2H), 6.13 (s, 1H), 5.30 (s, 2H), 4.00-3.97 (m, 2H), 3.80 (s, 3H), 1.40 (t, J=6.9 Hz, 3H), 1.33 (s, 12H); ES-LCMS m/z 386.1 (M+H).

Step 7: Ethyl 2-(4-ethoxy-6-((4-methoxybenzyl)oxy)pyridin-3-yl)-4-methylpyrimidine-5-carboxylate

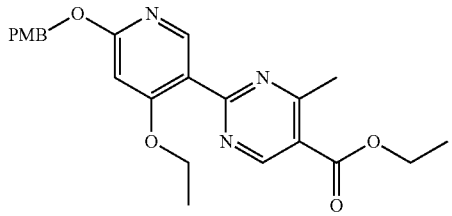

To a solution of 4-ethoxy-2-((4-methoxybenzyl)oxy)-5-(4,4,5,5-tetramethyl-1,3,2-dioxaborolan-2-yl)pyridine (4.99 g, 12.96 mmol), ethyl 2-chloro-4-methylpyrimidine-5-carboxylate (2 g, 9.97 mmol) and Cs₂CO₃ (6.50 g, 19.94 mmol) in 1,4-dioxane (15 mL) and water (5.00 mL) stirred under N₂ at 20° C. was added PdCl₂(dppf) (0.365 g, 0.498 mmol) in one charge. The reaction vessel was heated in 110° C. for 2 h. Then the solution was concentrated and distributed between EA and water. The combined organic extract was washed with brine, dried over MgSO₄, filtered and concentrated. The residue was purified by silica column chromatography (20% EA:80% PE, 60 g silica column). All fractions found to contain product by TLC (EA:PE=2:1, $R_f$=0.5) were combined and concentrated to yield a light yellow solid of ethyl 2-(4-ethoxy-6-((4-methoxybenzyl)oxy)pyridin-3-yl)-4-methylpyrimidine-5-carboxylate (3.5 g, 8.27 mmol, 83% yield): $^1$H NMR (400 MHz, CDCl₃) δ 9.20 (s, 1H), 8.59 (s, 1H), 7.40 (d, J=8.4 Hz, 2H), 6.90 (d, J=8.4 Hz, 2H), 6.32 (s, 1H), 5.36 (s, 2H), 4.45-4.39 (m, 2H), 4.13-4.05 (m, 2H), 3.81 (s, 3H), 2.87 (s, 3H), 1.44-1.36 (m, 6H); ES-LCMS m/z 424.0 (M+H).

Step 8: 2-(4-Ethoxy-6-((4-methoxybenzyl)oxy)pyridin-3-yl)-4-methylpyrimidine-5-carboxylic acid

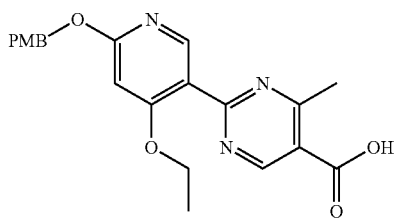

To a solution of ethyl 2-(4-ethoxy-6-((4-methoxybenzyl)oxy)pyridin-3-yl)-4-methylpyrimidine-5-carboxylate (3.5 g, 8.27 mmol) in THF (10 mL) stirred under N₂ at 20° C. was added and LiOH in H₂O (6.61 mL, 16.53 mmol) in one charge. The reaction mixture was heated to 50° C. for 12 h. Then the solution was concentrated and neutralized with conc. HCl to pH=7.0 with stirring. Then the solution was concentrated in vacuo to give 2-(4-ethoxy-6-((4-methoxybenzyl)oxy)pyridin-3-yl)-4-methylpyrimidine-5-carboxylic acid: $^1$H NMR (400 MHz, CD₃OD) δ 8.86 (s, 1H), 8.27 (s, 1H), 7.38 (d, J=8.6 Hz, 2H), 6.91 (d, J=8.6 Hz, 2H), 5.31 (s, 2H), 4.15-4.08 (m, 2H), 3.79 (s, 3H), 2.75 (s, 3H), 1.33 (t, J=6.9 Hz, 3H); LCMS m/z: 396.1 (M+H).

Intermediate 7

Ethyl 3-(4-amino-2-(trifluoromethyl)phenyl)-2,2-dimethylpropanoate

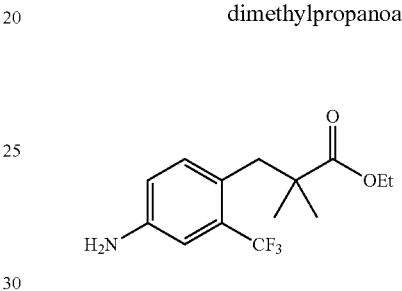

Step 1: Ethyl 2,2-dimethyl-3-(2-(trifluoromethyl)phenyl)propanoate

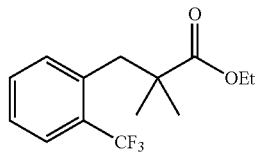 [SMILES: CCOC(=O)C(C)(C)Cc1ccccc1C(F)(F)F]

To a mixture of diisopropylamine (8.00 mL, 57.1 mmol) in THf (300 mL) cooled to 0° C. was added n-BuLi (24.60 mL, 61.5 mmol) dropwise. The mixture was stirred at 0° C. for 1 h. Then to the mixture cooled to −30° C. was added a solution of ethyl isobutyrate (6.12 g, 52.7 mmol) in THF (2 mL). The mixture was stirred at −30° C. for 1 h. To the mixture was added a solution of 1-(bromomethyl)-2-(trifluoromethyl)benzene (10.5 g, 43.9 mmol) in THF (5 mL) at −30° C. The whole mixture was stirred at −30° C. for 3 h and then stirred at 25° C. for 12 h. The mixture was quenched with NH₄Cl (aq) and extracted with EA. The organic layer was washed with brine, dried over MgSO₄, filtered and concentrated. The residue was purified on silica column chromatography (PE/EA=200:1). All fractions found to contain product by TLC (PE/EA=10:1, $R_f$=0.6) were combined and concentrated to yield a light yellow solid of ethyl 2,2-dimethyl-3-(2-(trifluoromethyl)phenyl)propanoate (10 g, 35.3 mmol, 80.0% yield): $^1$H NMR (400 MHz, CDCl₃) δ: 7.62 (d, J=8.0 Hz, 1H), 7.41 (t, J=7.6 Hz, 1H), 7.29 (t, J=7.6 Hz, 1H), 7.22 (d, J=8.0 Hz, 1H), 4.17 (q, J=7.2 Hz, 2H), 3.14 (s, 3H), 1.25 (t, J=7.2 Hz, 3H), 1.18 (s, 6H); ES-LCMS m/z 275 (M+H).

Step 1: 4-Ethoxypyridine 1-oxide

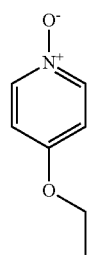

To a mixture of 4-nitropyridine 1-oxide (50 g, 357 mmol) in THF (500 mL) was added NaOEt (48.6 g, 714 mmol). The mixture was stirred at 25° C. for 16 h. The reaction residue was concentrated. The residue was purified by silica column chromatography (DCM/MeOH=25:1). All fractions found to contain product by TLC (DCM/MeOH=25:1, $R_f$=0.6) were combined and concentrated to yield a dark red solid of 4-ethoxypyridine 1-oxide (25 g, 162 mmol, 45.3% yield): $^1$H NMR (400 MHz, CD$_3$OD) δ 8.20-8.18 (m, 2H), 7.11-7.10 (m, 2H), 4.21-4.15 (m, 2H), 1.42 (t, J=7.2 Hz, 3H); ES-LCMS m/z 140.0 (M+H).

Step 2: 4-Ethoxypyridin-2-ol

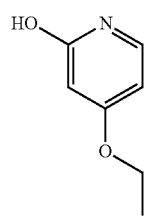

A mixture of 4-ethoxypyridine 1-oxide (5 g, 35.9 mmol) in Ac$_2$O (36.7 g, 359 mmol) was heated to reflux for 4 h. Then the solvent was removed in vacuo, and the residue was dissolved in MeOH (25 mL) and H$_2$O (25 mL) and stirred at 25° C. for 16 h. The mixture was concentrated. The residue was purified by silica column chromatography (DCM/MeOH=10:1). All fractions found to contain product by TLC (DCM/MeOH=10:1, $R_f$=0.6) were combined and concentrated to yield a dark yellow solid of 4-ethoxypyridin-2-ol (2.5 g, 16.17 mmol, 45.0% yield): $^1$H NMR (400 MHz, CD$_3$OD) δ 7.28 (d, J=7.6 Hz, 1H), 6.07 (d, J=3.2, 7.2 Hz, 1H), 5.86-7.85 (d, J=2.4 Hz, 1H), 4.06-4.01 (m, 2H), 1.38 (t, J=7.2 Hz, 3H); ES-LCMS m/z 140.0 (M+H).

Step 3: 4-Ethoxy-5-iodopyridin-2-ol

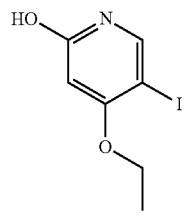

Step 2: Ethyl 2,2-dimethyl-3-(4-nitro-2-(trifluoromethyl)phenyl)propanoate

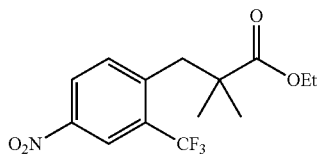

To a solution of ethyl 2,2-dimethyl-3-(2-(trifluoromethyl)phenyl)propanoate (10 g, 36.5 mmol) in H$_2$SO$_4$ (5 mL, 94 mmol) cooled to 0° C. was added potassium nitroperoxous acid (4.05 g, 40.1 mmol) in portions. The mixture was stirred at 0° C. for 30 min. The mixture was poured into ice-water and extracted with DCM. The organic layer was washed with brine, dried over Na$_2$SO$_4$ and concentrated to give a yellow solid of ethyl 2,2-dimethyl-3-(4-nitro-2-(trifluoromethyl)phenyl)propanoate (8.5 g, 24.54 mmol, 67.3% yield): $^1$H NMR (400 MHz, CDCl$_3$) δ: 8.59 (d, J=2.4 Hz, 1H), 8.47 (dd, J=2.4, 8.8 Hz, 1H), 7.82 (d, J=8.4 Hz, 1H), 5.97-5.83 (m, 2H); ES-LCMS m/z 320 (M+H).

Step 3: Ethyl 3-(4-amino-2-(trifluoromethyl)phenyl)-2,2-dimethylpropanoate

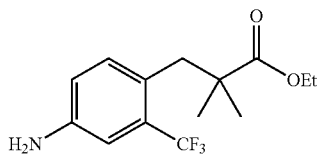 [SMILES: CCOC(=O)C(C)(C)Cc1ccc([N+](=O)[O-])cc1C(F)(F)F]

A reaction mixture of ethyl 2,2-dimethyl-3-(4-nitro-2-(trifluoromethyl)phenyl)propanoate (8.5 g, 26.6 mmol) and Pd/C (0.283 g, 2.66 mmol) in MeOH (50 mL) was hydrogenated using an H-cube (settings: 50° C., 50 psi, 24 h). The mixture was filtered and the filtrate was concentrated. The residue was purified on silica column chromatography (PE/EA=10:1). All fractions found to contain product by TLC (PE/EA=5:1, $R_f$=0.4) were combined and concentrated to yield a off white solid of ethyl 3-(4-amino-2-(trifluoromethyl)phenyl)-2,2-dimethylpropanoate (7 g, 22.42 mmol, 84.0% yield): $^1$H NMR (400 MHz, CDCl$_3$) δ: 6.98 (d, J=8.4 Hz, 1H), 6.91 (d, J=2.4 Hz, 1H), 6.71 (dd, J=2.4, 8.4 Hz, 1H), 4.15 (q, J=6.8 Hz, 2H), 3.00 (s, 2H), 1.25 (t, J=7.2 Hz, 3H), 1.14 (s, 6H); ES-LCMS m/z 290 (M+H).

Intermediate 8

2-(Benzyloxy)-4-ethoxy-5-iodopyridine

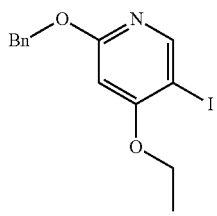 [SMILES: CCOc1cc(OCc2ccccc2)ncc1I]

To a mixture of 4-ethoxypyridin-2-ol (2.5 g, 17.97 mmol) in DMF (30 mL) was added NIS (4.04 g, 17.97 mmol). The mixture was stirred at 80° C. for 16 h. The mixture was concentrated and purified by preparative HPLC (MeCN/H₂O as eluants, acidic condition) to yield a yellow solid of 4-ethoxy-5-iodopyridin-2-ol (1.2 g, 4.30 mmol, 23.9% yield): ¹H NMR (400 MHz, CD₃OD) δ 7.70(s, 1H), 5.92 (s, 1H), 4.15-4.10 (m, 2H), 1.48 (t, J=6.8 Hz, 3H); ES-LCMS m/z 265.8 (M+H).

Step 4: 2-(Benzyloxy)-4-ethoxy-5-iodopyridine

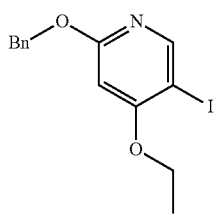 [SMILES: CCOc1cc(OCc2ccccc2)ncc1I]

To a mixture of 4-ethoxy-5-iodopyridin-2-ol (800 mg, 3.02 mmol) in THF (10 mL) was added (bromomethyl)benzene (619 mg, 3.62 mmol) and silver carbonate (1665 mg, 6.04 mmol). The mixture was stirred at 70° C. for 16 h. The reaction residue was filtered and the filtrate was concentrated. The mixture was diluted with H₂O and extracted with DCM. The combined organic extract was washed with brine, dried over MgSO₄, filtered and concentrated. The resulting 2-(benzyloxy)-4-ethoxy-5-iodopyridine (800 mg, 1.915 mmol, 63.4% yield): ¹H NMR (400 MHz, CDCl₃) δ 8.28 (s, 1H), 7.45-7.43 (m, 2H), 7.38-7.36 (m, 3H), 6.22 (s, 1H), 5.33 (s, 2H), 4.12-4.07 (m, 2H), 1.48 (t, J=6.8 Hz, 3H); ES-LCMS m/z 355.9 (M+H).

Intermediate 9

5-(1,1,1-Trifluoro-2-methylpropan-2-yl)isoxazol-3-amine

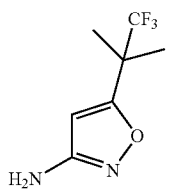

Step 1: 5,5,5-Trifluoro-4,4-dimethyl-3-oxopentanenitrile

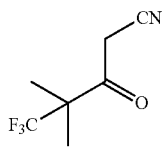

To a mixture of MeCN (3.32 mL, 97 mmol) in THF (300 mL) cooled to −78° C. was added n-BuLi (56.4 mL, 141 mmol). The mixture was stirred at −30° C. for 30 min. Then to the mixture was added methyl 3,3,3-trifluoro-2,2-dimethylpropanoate (15 g, 88 mmol) dropwise. The mixture was stirred at 25° C. for 10 h. The mixture was quenched with aqueous NH₄Cl and extracted with DCM/MeOH (10:1). The organic layer was dried over Na₂SO₄, filtered and concentrated. The residue was purified by silica column chromatography (PE/EA=10:1). All fractions found to contain product by TLC (PE/EA=5:1, R_f=0.6) were combined and concentrated to yield a light yellow solid of 5,5,5-trifluoro-4,4-dimethyl-3-oxopentanenitrile (5 g, 27.9 mmol, 31.7% yield): ¹H NMR (400 MHz, CDCl₃) δ: 3.75 (s, 2H), 1.41 (s, 6H).

Step 2: 5-(1,1,1-Trifluoro-2-methylpropan-2-yl)isoxazol-3-amine

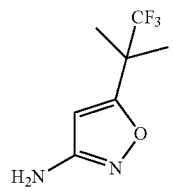

To a mixture of hydroxylamine hydrochloride (3.10 g, 44.7 mmol) in H₂O (25 mL) cooled to 0° C. was added NaHCO₃ (3.94 g, 46.9 mmol) to adjust to pH=7.5. Then to the mixture was added a solution of 5,5,5-trifluoro-4,4-dimethyl-3-oxopentanenitrile (4 g, 22.33 mmol) in MeOH (25 mL). The mixture was stirred at 65° C. for 15 h. After cooling, the mixture was acified with concentrated HCl to pH=1.0 and then refluxed for 2 h. After cooling, the mixture was neutralized by 4 M NaOH to pH=8.0. The mixture was extracted with DCM/MeOH (10:1). The organic layer was dried over Na₂SO₄, filtered and concentrated to yield a white solid of 5-(1,1,1-trifluoro-2-methylpropan-2-yl)isoxazol-3-amine (2 g, 9.06 mmol, 40.6% yield): ¹H NMR (400 MHz, CDCl₃) δ 5.78 (s, 1H), 3.93 (s., 2H), 1.51 (s, 6H); ES-LCMS m/z 195 (M+1).

Intermediate 10

3-(4-Methyl-1H-imidazol-1-yl)-5-(trifluoromethyl)aniline

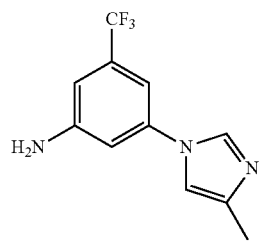 [SMILES: Cc1cn(-c2cc([N+](=O)[O-])cc(C(F)(F)F)c2)cn1]

Step 1: 4-Methyl-1-(3-nitro-5-(trifluoromethyl)phenyl)-1H-imidazole

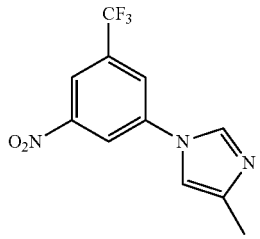

A suspension of 4-methyl-1H-imidazole (1.178 g, 14.35 mmol) in DMF (15 mL) was added to a solution of 1-fluoro-3-nitro-5-(trifluoromethyl)benzene (2 g, 9.56 mmol) in DMF (15 mL). $Cs_2CO_3$ (6.23 g, 19.13 mmol) was added and the mixture was stirred at 80° C. for 8 h. The mixture was cooled to rt and then the solution was concentrated and distributed between EA and saturated $NaHCO_3$ solution. The combined organic extract was washed with brine, dried over $MgSO_4$, filtered and concentrated. The residue was purified by silica column chromatography (PE/EA=5:1). All fractions found to contain product by TLC (PE/EA=1:1, $R_f$=0.5) were combined and concentrated to yield a light yellow solid of 4-methyl-1-(3-nitro-5-(trifluoromethyl)phenyl)-1H-imidazole (800 mg, 2.95 mmol, 30.8% yield): $^1$H NMR (400 MHz, $CD_3OD$) δ 8.61-8.78 (m, 1H), 8.44-8.51 (m, 1H), 8.31-8.39 (m, 2H), 7.55 (s, 1H), 2.27 (s, 3H); ES-LCMS m/z 272.0 (M+H).

Step 2: 3-(4-Methyl-1H-imidazol-1-yl)-5-(trifluoromethyl)aniline

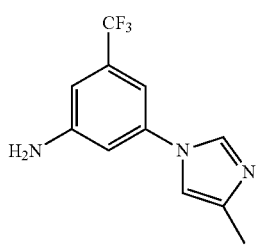

A suspension of 4-methyl-1-(3-nitro-5-(trifluoromethyl)phenyl)-1H-imidazole (800 mg, 2.95 mmol) in MeOH (15 mL) was added to a suspension of Pd/C (5.02 μL, 0.078 mmol) in MeOH (15 mL). The mixture was at 25° C. for 5 h under a $H_2$ atmosphere. Then the solution was concentrated and distributed between EA and saturated $NaHCO_3$ solution. The combined organic extract was washed with brine, dried over $MgSO_4$, filtered and concentrated. The residue was purified by preparative HPLC (MeCN/$H_2O$ as eluants, basic condition) to yield a white solid of 3-(4-methyl-1H-imidazol-1-yl)-5-(trifluoromethyl)aniline (321.83 mg, 1.334 mmol, 86.0% yield). TLC (PE/EA=1:1, $R_f$=0.3): 1H NMR (400 MHz, $CD_3OD$) δ 7.98 (s, 1H), 7.24 (s, 1H), 7.02-6.76 (m, 3H), 2.31-2.17 (m, 3H); ES-LCMS m/z 242.1 (M+H).

Intermediate 11

4-((3-Methyloxetan-3-yl)methyl)-3-(trifluoromethyl)aniline

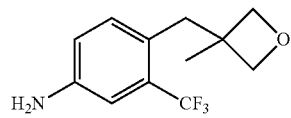

Step 1: Diethyl 2-methyl-2-(2-(trifluoromethyl)benzyl)malonate

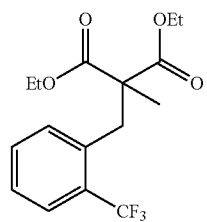 [SMILES: CCOC(=O)C(C)(Cc1ccccc1C(F)(F)F)C(=O)OCC]

To a solution of diethyl 2-methylmalonate (4.37 g, 25.1 mmol) in THF (100 mL) cooled to 0° C. was added NaH (1.506 g, 37.7 mmol). The mixture was stirred at 0° C. for 0.5 h. To the mixture was added 1-(bromomethyl)-2-(trifluoromethyl)benzene (5 g, 20.92 mmol) and the mixture was stirred at 25° C. for 10 h. TLC (PE/EA=10:1, $R_f$=0.6) showed the started material was disappeared. The mixture was quenched with $H_2O$ (50 mL) and extracted with EA (100 mL×2). The organic layer was washed with brine (100 mL), dried over $Na_2SO_4$ and concentrated. The residue was purified by silica column chromatography (PE/EA=50:1). All fractions found to contain product by TLC (PE/EA=10:1, $R_f$=0.6) were combined and concentrated to yield diethyl 2-methyl-2-(2-(trifluoromethyl)benzyl)malonate (4 g, 8.02 mmol, 38.3% yield): $^1$H NMR (400 MHz, $CDCl_3$) δ=7.62 (d, J=7.6 Hz, 1H), 7.41 (t, J=7.6 Hz, 1H), 7.34-7.27 (m, 1H), 7.27-7.21 (m, 1H), 4.26-4.14 (m, 4H), 3.53 (s, 2H), 1.30-1.21 (m, 9H); ES-LCMS m/z: 333.2 (M+H).

Step 2: Diethyl 2-methyl-2-(4-nitro-2-(trifluoromethyl)benzyl)malonate

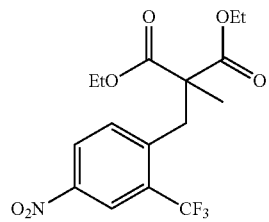 [SMILES: CCOC(=O)C(C)(Cc1ccc([N+](=O)[O-])cc1C(F)(F)F)C(=O)OCC]

To a solution of diethyl 2-methyl-2-(2-(trifluoromethyl)benzyl)malonate (4 g, 12.04 mmol) in $H_2SO_4$ (15 mL, 281 mmol) cooled to 0° C. was added potassium nitroperoxous acid (1.339 g, 13.24 mmol) in portions. The mixture was stirred at 0° C. for 5 min. The mixture was poured into ice-water (100 extracted with EA (100 mL×2). The organic layer was washed with saturated Na₂CO₃ (100 mL×2), dried over Na₂SO₄ and concentrated to give a yellow solid of diethyl 2-methyl-2-(4-nitro-2-(trifluoromethyl)benzyl)malonate (4.5 g, 10.00 mmol, 83% yield): ¹H NMR (400 MHz, CDCl₃) δ=8.50 (s, 1H), 8.27 (s, 1H), 7.57 (s, 1H), 4.19 (s, 4H), 3.58 (s, 2H), 1.31 (s, 3H), 1.22 (d, J=3.2 Hz, 6H); ES-LCMS m/z: 378.1 (M+H).

Step 3: Diethyl 2-(4-amino-2-(trifluoromethyl)benzyl)-2-methylmalonate

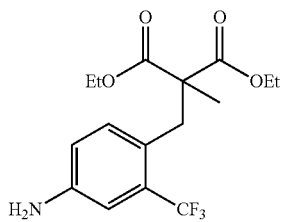 [SMILES: CCOC(=O)C(C)(Cc1ccc(N)cc1C(F)(F)F)C(=O)OCC]

A reaction mixture of diethyl 2-methyl-2-(4-nitro-2-(trifluoromethyl)benzyl)malonate (4.5 g, 11.93 mmol) and Pd/C (0.127 g, 1.193 mmol) in MeOH (200 mL) was stirred under H₂ atmosphere at 25° C. for 5 h. The mixture was filtered, and the filtrate was concentrated to give a brown oil of diethyl 2-(4-amino-2-(trifluoromethyl)benzyl)-2-methylmalonate (4.1 g, 9.67 mmol, 81% yield): ¹H NMR (400 MHz, CD₃OD) δ=7.03-6.93 (m, 2H), 6.79 (d, J=8.4 Hz, 1H), 4.21 (q, J=6.8 Hz, 4H), 3.36 (s, 2H), 1.26 (t, J=7.2 Hz, 6H), 1.20 (s, 3H); ES-LCMS m/z: 348.1 (M+H).

Step 4: Diethyl 2-(4-(bis(4-methoxybenzyl)amino)-2-(trifluoromethyl)benzyl)-2-methylmalonate

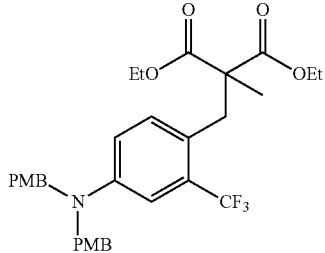

A mixture of diethyl 2-(4-amino-2-(trifluoromethyl)benzyl)-2-methylmalonate (4.1 g, 11.80 mmol), 1-(chloromethyl)-4-methoxybenzene (5.55 g, 35.4 mmol) and Cs₂CO₃ (26.9 g, 83 mmol) in DMF (50 mL) was stirred at 110° C. for 12 h. The mixture was concentrated. The residue was added to DCM (150 mL) and filtered. The filtrate was washed with brine (100 mL), dried over Na₂SO₄ and concentrated to give a yellow oil of diethyl 2-(4-(bis(4-methoxybenzyl)amino)-2-(trifluoromethyl)benzyl)-2-methylmalonate (3 g, 3.83 mmol, 32.4% yield): ¹H NMR (400 MHz, CD₃OD) δ=7.45-7.30 (m, 4H), 7.25 (d, J=1.6 Hz, 1H), 6.36 (s, 1H), 4.12 (q, J=6.8 Hz, 2H), 3.82 (s, 2H), 1.52 (s, 6H), 1.46 (t, J=6.8 Hz, 3H); ES-LCMS m/z: 588.1 (M+H).

Step 5: 2-(4-((4-Methoxybenzyl)amino)-2-(trifluoromethyl)benzyl)-2-methylpropane-1,3-diol

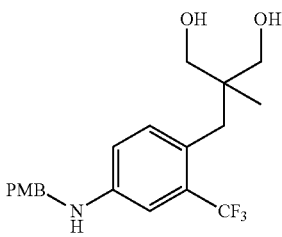

A mixture of diethyl 2-(4-(bis(4-methoxybenzyl)amino)-2-(trifluoromethyl)benzyl)-2-methylmalonate (4.3 g, 7.32 mmol) in THF (100 mL) cooled to 0° C. was added LAH (1.111 g, 29.3 mmol) in portions. The mixture was stirred at 25° C. for 10 h. The mixture was quenched with 15% NaOH (aq, 40 mL). The mixture was dried over Na₂SO₄. After filtered, the filtrate was concentrated. The residue was purified on silica column chromatography (PE/EA=5:1). All fractions found to contain product by TLC (PE/EA=2:1, R$_f$=0.35) were combined and concentrated to yield a yellow oil of 2-(4-((4-methoxybenzyl)amino)-2-(trifluoromethyl)benzyl)-2-methylpropane-1,3-diol (3 g, 6.45 mmol, 88% yield): ¹H NMR (400 MHz, CD₃OD) δ=7.27 (d, J=8.4 Hz, 2H), 7.20 (d, J=8.4 Hz, 1H), 6.89-6.83 (m, 3H), 6.73 (dd, J=2.4, 8.4 Hz, 1H), 4.23 (s, 2H), 3.80-3.72 (m, 4H), 3.34 (s, 1H), 2.67 (s, 2H), 0.63 (s, 3H); ES-LCMS m/z: 406.1 (M+Na).

Step 6: N-(4-Methoxybenzyl)-4-((3-methyloxetan-3-yl)methyl)-3-(trifluoromethyl)aniline

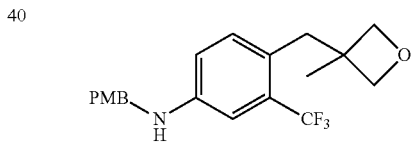

To a mixture of 2-(4-((4-methoxybenzyl)amino)-2-(trifluoromethyl)benzyl)-2-methylpropane-1,3-diol (3 g, 7.82 mmol) in THF (50 mL) cooled to 0° C. was added n-BuLi (4.69 mL, 11.74 mmol) and stirred for 0.5 h. Then to the mixture was added 4-methylbenzene-1-sulfonyl chloride (2.238 g, 11.74 mmol) and stirred at 25° C. for 1 h. Then to the mixture was added another n-BuLi (4.69 mL, 11.74 mmol) and stirred at 60° C. for 2 h and then at 25° C. for 10 h. The mixture was quenched with NH₄Cl (aq., 50 mL) and extracted with EA (100 mL×2). The organic layer was concentrated. The residue was purified on silica column chromatography (PE/EA=5:1). All fractions found to contain product by TLC (PE/EA=2:1, R$_f$=0.5) were combined and concentrated to yield a off white solid of N-(4-methoxybenzyl)-4((3-methyloxetan-3-yl)methyl)-3-(trifluoromethyl)aniline (1 g, 1.888 mmol, 24.13% yield): ¹H NMR (400 MHz, CDCl₃) δ=7.30-7.22 (m, 2H), 6.94-6.80 (m, 4H), 6.68 (d, J=8.4 Hz, 1H), 4.65 (d, J=5.6 Hz, 2H), 4.29 (d, J=5.2 Hz, 2H), 4.24 (s, 2H), 3.85-3.76 (m, 3H), 2.92 (s, 2H), 1.33 (s, 3H); ES-LCMS m/z 388.0 (M+Na).

Step 7: 4-((3-Methyloxetan-3-yl)methyl)-3-(trifluoromethyl)aniline

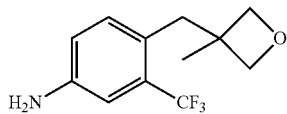

A mixture of N-(4-methoxybenzyl)-4-((3-methyloxetan-3-yl)methyl)-3-(trifluoromethyl)aniline (1 g, 2.74 mmol) in MeOH (50 mL) was added Pd/C (0.291 g, 2.74 mmol) under $N_2$. The mixture was stirred under a $H_2$ atmosphere (50 psi, 50° C., 2 h). The mixture was filtered and the filtrate was concentrated to yield a light yellow oil of 4-((3-methyloxetan-3-yl)methyl)-3-(trifluoromethyl)aniline (500 mg, 1.788 mmol, 65.3% yield): $^1$H NMR (400 MHz, CDCl$_3$) δ: 6.97 (s, 1H), 6.90 (d, J=8.4 Hz, 1H), 6.79 (d, J=7.6 Hz, 1H), 4.65 (d, J=5.2 Hz, 2H), 4.29 (d, J=5.2 Hz, 2H), 2.93 (s, 2H), 1.59 (s, 2H), 1.32 (s, 3H); ES-LCMS m/z 246.1 (M+H).

Intermediate 12

1-(5-Amino-3-(trifluoromethyl)pyridin-2-yl)ethanone

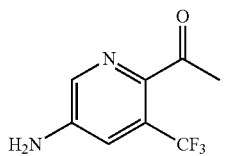

Step 1: 5-Nitro-3-(trifluoromethyl)pyridin-2-ol

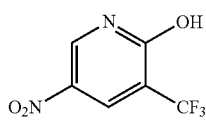 [SMILES: O=[N+]([O-])c1cnc(O)c(C(F)(F)F)c1]

To a mixture of 3-(trifluoromethyl)pyridin-2-ol (2 g, 12.26 mmol) was added nitric acid (1.644 mL, 36.8 mmol) and $H_2SO_4$ (12.03 g, 123 mmol) at 0° C. Then the mixture was stirred at 25° C. for 16 h. The mixture was then warmed to 60° C. for 5 h, cooled and added to 150 g of ice. The mixture was extracted with EA (2×100 mL) and washed with $H_2O$ (100 mL) to give the organic layer. The combined organic extract was washed with brine, dried over Na$_2$SO$_4$, concentrated to yield a brown solid of 5-nitro-3-(trifluoromethyl)pyridin-2-ol (2.2 g, 8.99 mmol, 73.3% yield): $^1$H NMR (400 MHz, CD$_3$OD) δ 8.91 (d, J=2.43 Hz, 1H), 9.42 (d, J=2.43 Hz, 1H); ES-LCMS m/z 209.0 (M+H).

Step 2: 2-Chloro-5-nitro-3-(trifluoromethyl)pyridine

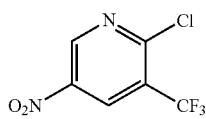

To a mixture of 5-nitro-3-(trifluoromethyl)pyridin-2-ol (2 g, 9.61 mmol) was added SOCl$_2$ (21.04 mL, 288 mmol) and DMF (0.074 mL, 0.961 mmol). Then the mixture was stirred at 80° C. for 16 h. The mixture was concentrated and extracted with EA (2×100 mL) and washed with $H_2O$ (100 mL) to give the organic layer. The combined organic extract was washed with brine, dried over Na$_2$SO$_4$, concentrated to yield a brown solid of 2-chloro-5-nitro-3-(trifluoromethyl)pyridine (2 g, 5.30 mmol, 55.1% yield): $^1$H NMR (400 MHz, CD$_3$OD) δ 8.91 (d, J=2.43 Hz, 1H), 9.42 (d, J=2.43 Hz, 1H).

Step 3: 6-Chloro-5-(trifluoromethyl)pyridin-3-amine

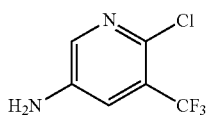

To a mixture of 2-chloro-5-nitro-3-(trifluoromethyl)pyridine (2 g, 8.83 mmol) in AcOH (10 mL) was added iron (2.465 g, 44.1 mmol) in one portion. The mixture was stirred at 80° C. for 15 min. The mixture was filtered and concentrated and then washed with aq. NaOH and extracted with EA. The residue was purified by silica column chromatography (PE/EA=5:1). All fractions found to contain product by TLC (PE/EA=8:1, R$_f$=0.6) were combined and concentrated to yield a yellow solid of 6-chloro-5-(trifluoromethyl)pyridin-3-amine (1 g, 4.58 mmol, 51.9% yield): $^1$H NMR (400 MHz, CD$_3$OD) δ 8.06 (s, 1H), 7.86 (d, J=8.60 Hz, 1H), 7.53 (d, J=8.60 Hz, 1H), 7.46-7.26 (m, 5H), 4.16-4.11 (m, 2H), 3.81 (s, 2H), 1.47 (t, J=6.62 Hz, 3H); ES-LCMS m/z 197.0 (M+H).

Step 4: 1-(5-Amino-3-(trifluoromethyl)pyridin-2-yl)ethanone

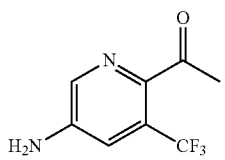

To a mixture of 6-chloro-5-(trifluoromethyl)pyridin-3-amine (200 mg, 1.018 mmol) in MeOH (3 mL) was added 6-chloro-5-(trifluoromethyl)pyridin-3-amine (200 mg, 1.018 mmol), NaHCO$_3$ (171 mg, 2.035 mmol) and PdCl$_2$(dppf) (74.5 mg, 0.102 mmol). The mixture was stirred under a N$_2$ atmosphere at 110° C. for 30 min under microwave. Then the reaction residue was filtered and the solid was washed by MeOH. Then 6M HCl was added to the solution, which was stirred a rt for 1 h and then concentrated. The residue was purified by preparative TLC (PE/EA=1:1, R$_f$=0.6) to yield a light yellow solid of 1-(5-amino-3-(trifluoromethyl)pyridin-2-yl)ethanone (120 mg, 0.500 mmol, 49.1% yield): $^1$H NMR (400 MHz, CD$_3$OD) δ 8.10 (d, J=2.43 Hz, 1H), 7.30 (d, J=2.43 Hz, 1H), 2.56 (s, 3H); ES-LCMS m/z 205.0 (M+H).

Intermediate 13

4-((Dimethylamino)methyl)-3-(trifluoromethyl)aniline

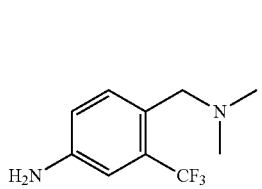

Step 1: N,N-Dimethyl-4-nitro-2-(trifluoromethyl)benzamide

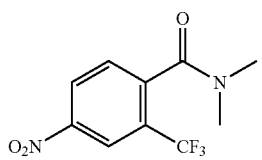

To a solution of 4-nitro-2-(trifluoromethyl)benzoic acid (10 g, 42.5 mmol), dimethylamine hydrochloride (4.51 g, 55.3 mmol) and $Et_3N$ (17.78 mL, 128 mmol) in DCM (150 mL) stirred under $N_2$ at 20° C. was added HATU (19.41 g, 51.0 mmol) in one charge. The reaction mixture was stirred at 20° C. for 2 h. Then the solution was distributed between DCM and saturated $NaHCO_3$ solution. The combined organic extract was washed with brine, dried over $MgSO_4$, filtered and concentrated to afford N,N-dimethyl-4-nitro-2-(trifluoromethyl)benzamide (10 g, 25.2 mmol, 59.2% yield). TLC (PE/EA=5:1, $R_f$ 0.6): $^1$H NMR (400 MHz, $CDCl_3$) δ 8.57 (d, J=1.8 Hz, 1H), 8.46 (dd, J=2.0, 8.4 Hz, 1H), 7.58 (d, J=8.4 Hz, 1H), 2.79 (s, 6H); ES-LCMS m/z 263.0 (M+H).

Step 2: 4-Amino-N,N-dimethyl-2-(trifluoromethyl)benzamide

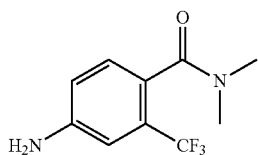 [SMILES: CN(C)C(=O)c1ccc([N+](=O)[O-])cc1C(F)(F)F]

To a solution of N,N-dimethyl-4-nitro-2-(trifluoromethyl)benzamide (10 g, 25.2 mmol) in MeOH (100 mL) stirred under $N_2$ at 20° C. was added Pd/C (1 g, 9.40 mmol) in one charge. The reaction mixture stirred under a $H_2$ atmosphere at 20° C. for 12 h. The mixture was filtered, and the filtrate was concentrated in vacuo to give 4-amino-N,N-dimethyl-2-(trifluoromethyl)benzamide (8.3 g, 23.59 mmol, 94.0% yield). TLC (DCM/MeOH=10:1, $R_f$=0.4): $^1$H NMR (400 MHz, $CDCl_3$) δ 7.07 (d, J=8.2 Hz, 1H), 6.90 (s, 1H), 6.79 (d, J=8.2 Hz, 1H), 3.95 (br. s., 2H), 3.08 (s, 3H), 2.80 (s, 3H); ES-LCMS m/z 233.0 (M+H).

Step 3: 4-((Dimethylamino)methyl)-3-(trifluoromethyl)aniline

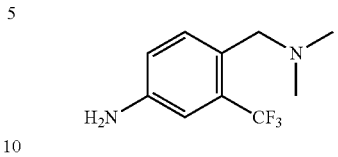

To a solution of 4-amino-N,N-dimethyl-2-(trifluoromethyl)benzamide (8.3 g, 23.59 mmol) in THF (100 mL) stirred under a $N_2$ atmosphere at 20° C. was added $BH_3$.DMS (11.20 mL, 118 mmol) dropwise. The reaction mixture was stirred at 80° C. for 2 h. To the solution was added MeOH, then concentrated in vacuo. The residue was purified by silica column chromatography (DCM/MeOH=30:1). All fractions found to contain product by TLC (DCM/MeOH=10:1, $R_f$=0.4) were combined and concentrated to yield light yellow oil of 4-((dimethylamino)methyl)-3-(trifluoromethyl)aniline (4 g, 18.33 mmol, 78.0% yield): $^1$H NMR (400 MHz, $CD_3OD$) δ 7.99 (d, J=8.0 Hz, 1H), 7.73 (s, 1H), 7.67 (d, 8.0 Hz, 1H), 4.57 (s, 2H), 2.96 (s, 6H); ES-LCMS m/z 219.2 (M+H).

Intermediate 14

2-(4-(4-Amino-5-fluoro-2-(trifluoromethyl)benzyl)piperazin-1-yl)ethyl acetate

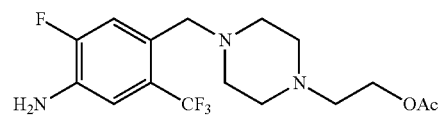 [SMILES: CC(=O)OCCN1CCN(Cc2cc(F)c(N)cc2C(F)(F)F)CC1]

Step 1: 4-Bromo-2-fluoro-5-(trifluoromethyl)aniline

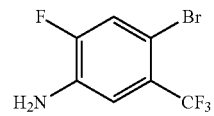

To a mixture of 2-fluoro-5-(trifluoromethyl)aniline (4 g, 22.33 mmol) in DMF (60 mL) was added NBS (4.77 g, 26.8 mmol), which was stirred at 20° C. for 2 hrs. The mixture was concentrated to give crude product, and distributed between ethyl acetate (50 mL×3) and saturated $NaHCO_3$ (30 mL×3) solution. The combined organic extract was washed with brine, dried over $Na_2SO_4$, filtered and concentrated, which was not purified to give 4-bromo-2-fluoro-5-(trifluoromethyl)aniline (4.8 g, 17.80 mmol, 80.0% yield) as a brown solid: $^1$H NMR (400 MHz, METHANOL-$d_4$) δ 7.35 (d, J=10.6 Hz, 1H), 7.20 (d, J=8.8 Hz, 1H); ES-LCMS m/z 259.0, 260.0 (M+H).

Step 2: Tert-butyl (4-bromo-2-fluoro-5-(trifluoromethyl)phenyl)carbamate

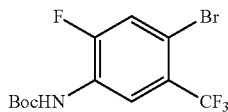

To a mixture of 4-bromo-2-fluoro-5-(trifluoromethyl)aniline (3 g, 11.13 mmol) in THF (30 mL) was added Boc$_2$O (3.88 mL, 16.69 mmol) and DMAP (2.039 g, 16.69 mmol). The mixture was stirred at 20° C. for 12 hr. The mixture was concentrated to give crude product, which was purified by column (PE/EtOAc=10:1, R$_f$=0.5) to give tert-butyl (4-bromo-2-fluoro-5-(trifluoromethyl)phenyl)carbamate (3.1 g, 7.53 mmol, 67.7% yield) as colorless oil: $^1$H NMR (400 MHz, METHANOL-d$_4$) δ 7.82 (dd, J=8.60, 4.63 Hz, 2 H), 1.42 (s, 9 H).

Step 3: Methyl 4-((tert-butoxycarbonyl)amino)-5-fluoro-2-(trifluoromethyl)benzoate

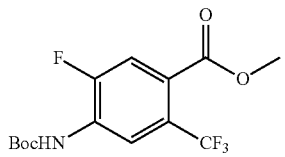

A mixture of tert-butyl (4-bromo-2-fluoro-5-(trifluoromethyl)phenyl)carbamate (4 g, 9.72 mmol) in MeOH (15 mL) was added PdCl$_2$(dppf) (0.711 g, 0.972 mmol) and Et$_3$N (2.71 mL, 19.43 mmol) under N$_2$ atmosphere. The mixture was stirred at 60° C. under CO atmosphere at 50 psi for 12 hr. TLC (PE/EtOAc=10:1, R$_f$=0.3) showed the reaction was finished. The mixture was concentrated to give crude product, which was purified by column (PE/EtOAc=10:1, R$_f$=0.3) to give methyl 4-((tert-butoxycarbonyl)amino)-5-fluoro-2-(trifluoromethyl)benzoate (2.8 g, 7.71 mmol, 79.0% yield) as colorless oil: $^1$H NMR (400 MHz, CHLOROFORM-d) δ 7.58 (d, J=11.0 Hz, 1H), 6.90 (br. s., 1H), 3.90 (s, 3H), 1.53 (s, 9H).

Step 4: Tert-butyl (2-fluoro-4-(hydroxymethyl)-5-(trifluoromethyl)phenyl)carbamate

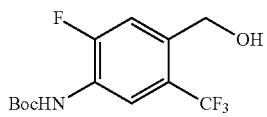

A mixture of methyl 4-((tert-butoxycarbonyl)amino)-5-fluoro-2-(trifluoromethyl)benzoate (2.8 g, 7.71 mmol) in DCM (50 mL) was added DIBAL-H (23.14 mL, 23.14 mmol) under N$_2$ atmosphere at −78° C. The mixture was stirred at −78° C. for 1 hr. The reaction was quenched by water (20 mL). The mixture was distributed between DCM (50 mL×3), washed with saturated brine (30 mL×3) solution. The combined organic extract was dried over Na$_2$SO$_4$, filtered and concentrated to give tert-butyl (2-fluoro-4-(hydroxymethyl)-5-(trifluoromethyl)phenyl)carbamate (2.4 g, 6.05 mmol, 78.0% yield) as color oil: $^1$H NMR (400 MHz, METHANOL-d$_4$) δ 8.36-8.16 (m, 1H), 7.49 (d, J=11.9 Hz, 1H), 4.72 (s, 2H), 1.53 (s, 9H).

Step 5: 4-((Tert-butoxycarbonyl)amino)-5-fluoro-2-(trifluoromethyl)benzyl methanesulfonate

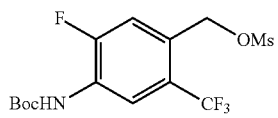

To a mixture of tert-butyl (2-fluoro-4-(hydroxymethyl)-5-(trifluoromethyl)phenyl)carbamate (2.4 g, 6.05 mmol) in DCM (30 mL) was added triethylamine (1.225 g, 12.11 mmol) and methanesulfonyl chloride (1.040 g, 9.08 mmol) at −78° C. The mixture was stirred at −78° C. for 0.5 hr. The mixture was extracted with DCM (40 mL×3), washed with saturated brine (30 mL×3) solution. The combined organic extract was dried over Na$_2$SO$_4$, filtered and concentrated to give crude 4-((tert-butoxycarbonyl)amino)-5-fluoro-2-(trifluoromethyl)benzyl methanesulfonate (2.5 g, 4.84 mmol, 80.0% yield) as a brown solid: $^1$H NMR (METHANOL-d$_4$, 400 MHz) δ 8.69 (d, J=7.5 Hz, 1H), 7.49 (d, J=11.9 Hz, 1H), 4.62 (s, 2H), 3.42 (s, 3H), 1.55 ppm (s, 9H).

Step 6: Tert-butyl (2-fluoro-4-((4-(2-hydroxyethyl)piperazin-1-yl)methyl)-5-trifluoromethyl)phenyl)carbamate

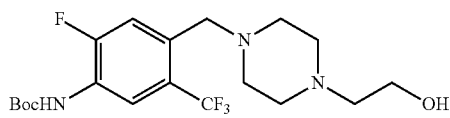 [SMILES: CC(C)(C)OC(=O)Nc1cc(C(F)(F)F)c(CN2CCN(CCO)CC2)cc1F]

A mixture of 4-((tert-butoxycarbonyl)amino)-5-fluoro-2-(trifluoromethyl)benzyl methanesulfonate (2.5 g, 4.84 mmol) in MeCN (50 mL) was added K$_2$CO$_3$ (2.007 g, 14.52 mmol) and 2-(piperazin-1-yl)ethanol (0.756 g, 5.81 mmol), which was stirred at 50° C. for 2 hrs. LCMS showed the reaction was finished. The mixture was concentrated to give crude product, and distributed between ethyl acetate (50 mL×3) and saturated NaHCO$_3$ (30 mL×3) solution. The combined organic extract was washed with brine, dried over Na$_2$SO$_4$, filtered and concentrated to give tert-butyl (2-fluoro-4-((4-(2-hydroxyethyl)piperazin-1-yl)methyl)-5-(trifluoromethyl)phenyl)carbamate (2.4 g, 4.56 mmol, 94.0% yield) as a brown solid: $^1$H NMR (400 MHz, METHANOL-d$_4$) δ 8.30-8.20 (m, 1H), 7.53 (s, 1H), 3.68 (t, J=6.2 Hz, 2H), 3.60 (s, 2H), 2.70-2.44 (m, 10H), 1.53 (s, 9H); ES-LCMS m/z 422.3 (M+H).

Step 7

2-(4-(4-((Tert-butoxycarbonyl)amino)-5-fluoro-2-(trifluoromethyl)benzyl)piperazin-1-yl)ethyl acetate

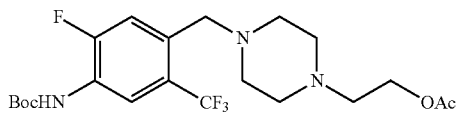 [SMILES: CC(=O)OCCN1CCN(Cc2cc(F)c(NC(=O)OC(C)(C)C)cc2C(F)(F)F)CC1]

To a mixture of tert-butyl (2-fluoro-4-((4-(2-hydroxyethyl)piperazin-1-yl)methyl)-5-(trifluoromethyl)phenyl)carbamate (2.4 g, 4.56 mmol) in DCM (50 mL) was added pyridine (1.802 g, 22.78 mmol), DMAP (0.557 g, 4.56 mmol) and acetic anhydride (2.326 g, 22.78 mmol). The mixture was stirred at 20° C. for 12 hrs. LCMS showed the reaction was finished. The mixture was concentrated to give crude product, and distributed between ethyl acetate (30 mL×3) and saturated NaHCO$_3$ (20 mL×3) solution. The combined organic extract was washed with brine, dried over Na$_2$SO$_4$, filtered and concentrated, which was purified by column (DCM:MeOH=20:1, R$_f$=0.5) to give 2-(4-(4-((tert-butoxycarbonyl)amino)-5-fluoro-2-(trifluoromethyl)benzyl)-piperazin-1-yl)ethyl acetate (2.4 g, 4.14 mmol, 91.0% yield) as brown oil: $^1$H NMR (400 MHz, METHANOL-d$_4$) δ 8.31-8.19 (m, 1H), 7.55 (d, J=11.9 Hz, 1H), 4.24 (t, J=5.5 Hz, 2H), 3.62 (s, 2H), 2.78-2.67 (m, 6H), 2.56 (br. s., 4H), 2.05 (s, 3H), 1.53 (s, 9H); ES-LCMS m/z 464.3 (M+H).

Step 8: 2-(4-(4-Amino-5-fluoro-2-(trifluoromethyl)benzyl)piperazin-1-yl)ethyl acetate

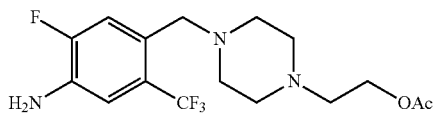

To a mixture of 2-(4-(4-((tert-butoxycarbonyl)amino)-5-fluoro-2-(trifluoro-methyl)benzyl)piperazin-1-yl)ethyl acetate (2.4 g, 4.30 mmol) in dichloromethane (DCM) (20 mL) was added hydrogen chloride, methanol (solvate) (10.75 mL, 4 N, 43.0 mmol), which was stirred at 20° C. for 1 hr. LCMS showed the reaction was finished. The mixture was concentrated to give crude product 2-(4-(4-amino-5-fluoro-2-(trifluoromethyl)-benzyl)piperazin-1-yl)ethyl acetate (1.8 g, 3.72 mmol, 86.0% yield) as a yellow solid: $^1$H NMR (400 MHz, METHANOL-d$_4$) δ 8.90 (d, J=5.3 Hz, 1H), 8.16-8.12 (m, 1H), 4.48-4.44 (m, 2H), 4.43-4.31 (m, 2H), 3.85-3.67 (m, 4H), 3.67-3.57 (m, 4H), 3.46 (br. s., 2H), 2.12 (d, J=1.3 Hz, 3H); ES-LCMS m/z 364.2 (M+H).

Intermediate 15

2-(5-(2-(Benzyloxy)ethoxy)-6-((4-methoxybenzyl)oxy)pyridin-3-yl)-4-methylpyrimidine-5-carboxylic acid

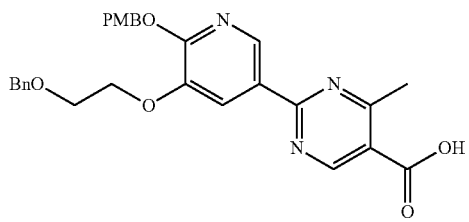

Step 1:
3-(2-(Benzyloxy)ethoxy)-5-bromo-2-chloropyridine

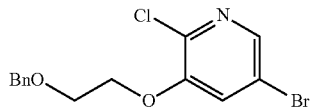 [SMILES: Clc1ncc(Br)cc1OCCOCc1ccccc1]

To a mixture of ((2-bromoethoxy)methyl)benzene (4.54 g, 21.11 mmol) in DMF (40 mL) was added 5-bromo-2-chloropyridin-3-ol (4 g, 19.19 mmol), which was stirred at 60° C. for 12 hrs. The mixture was diluted with water (50 mL). The mixture was extracted with EtOAc (50 mL×3) and concentrated to give crude product, which was purified by column (PE/EtOAc=10:1, R$_f$=0.5) to give 3-(2-(benzyloxy)ethoxy)-5-bromo-2-chloropyridine (6.5 g, 17.36 mmol, 90% yield) as a yellow solid: $^1$H NMR (400 MHz, METHANOL-d$_4$) δ 8.01 (s, 1H), 7.73 (s, 1H), 7.43-7.15 (m, 5H), 4.61 (s, 2H), 4.30-4.27 (m, 2H), 3.91-3.82 (m, 2H); ES-LCMS m/z 342.0,344.0 (M+H)

Step 2: 3-(2-(Benzyloxy)ethoxy)-5-bromo-2-((4-methoxybenzyl)oxy)pyridine

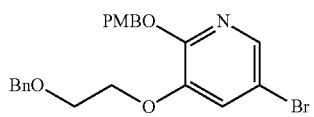

To a mixture of 3-(2-(benzyloxy)ethoxy)-5-bromo-2-chloropyridine (6 g, 17.5 mmol) in toluene (60 mL) was added potassium hydroxide (1.965 g, 35.0 mmol), (4-methoxyphenyl)methanol (2.90 g, 21.01 mmol) and 18-crown-6 (0.463 g, 1.751 mmol). The mixture was stirred at 120° C. for 2 hrs. The mixture was filtered and the filtrate was concentrated to give crude product, which was purified by column (PE/EtOAc=5:1, R$_f$=0.4) to give 3-(2-(benzyloxy)ethoxy)-5-bromo-2-((4-methoxybenzyl)oxy)pyridine (6.8 g, 14.16 mmol, 81% yield) as a yellow solid: $^1$H NMR (400 MHz, CHLOROFORM-d) δ 7.78 (d, J=1.8 Hz, 1H), 7.39 (d, J=8.4 Hz, 2H), 7.33-7.25 (m, 5H), 7.21 (d, J=1.8 Hz, 1H), 6.85 (d, J=8.8 Hz, 2H), 5.34 (s, 2H), 4.60 (s, 2H), 4.19-4.14 (m, 2H), 3.84-3.80 (m, 2H), 3.79 (s, 3H); ES-LCMS m/z 324.0,326.0 (M-PMB+H).

Step 3: 3-(2-(Benzyloxy)ethoxy)-2-((4-methoxybenzyl)oxy)-5-(4,4,5,5-tetramethyl-1,3,2-dioxaborolan-2-yl)pyridine

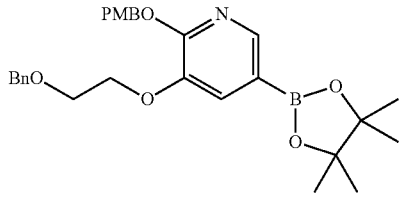

To a mixture of 3-(2-(benzyloxy)ethoxy)-5-bromo-2-((4-methoxybenzyl)oxy)pyridine (4 g, 9.00 mmol) in 1,4-dioxane (60 mL) was added 4,4,4',4',5,5,5',5'-octamethyl-2,2'-bi(1,3,2-dioxaborolane) (2.286 g, 9.00 mmol), PdCl$_2$(dppf) (0.329 g, 0.450 mmol) and potassium acetate (2.65 g, 27.0 mmol) under N$_2$ atmosphere, which was stirred at 110° C. for 3 hrs. The mixture was filtered and the filtrate was concentrated to give crude product, which was purified by column (PE/EtOAc=10:1, R$_f$=0.4) to give 3-(2-(benzyloxy)ethoxy)-2-((4-methoxybenzyl)oxy)-5-(4,4,5,5-tetramethyl-1,3,2-dioxaborolan-2-yl)pyridine (4.5 g, 8.21 mmol, 91% yield) as a yellow solid: $^1$H NMR (400 MHz, CHLOROFORM-d) δ 8.13 (s, 1H), 7.46-7.35 (m, 3H), 7.32-7.25 (m, 5H), 6.84 (d, J=8.8 Hz, 2H), 5.41 (s, 2H), 4.62 (s, 2H), 4.20 (t, J=4.9 Hz, 2H), 3.83 (t, J=4.9 Hz, 2H), 3.77 (s, 3H), 1.32 (s, 12H); ES-LCMS m/z 492.2 (M+H)

Step 4: Ethyl 2-(5-(2-(benzyloxy)ethoxy)-6-((4-methoxybenzyl)oxy)pyridin-3-yl)-4-methylpyrimidine-5-carboxylate

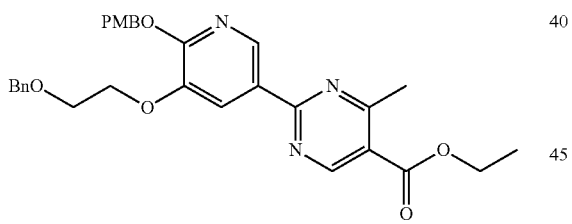

To a mixture of 3-(2-(benzyloxy)ethoxy)-2-((4-methoxybenzyl)oxy)-5-(4,4,5,5-tetramethyl-1,3,2-dioxaborolan-2-yl)pyridine (4.2 g, 8.55 mmol) in 1,4-dioxane (60 mL) and water (20 mL) was added ethyl 2-chloro-4-methylpyrimidine-5-carboxylate (1.715 g, 8.55 mmol), PdCl$_2$(dppf) (0.625 g, 0.855 mmol) and Cs$_2$CO$_3$ (5.57 g, 17.09 mmol) under N$_2$ atmosphere. The mixture was stirred at 120° C. for 2 hr, was filtered and the filtrate was concentrated to give crude product, which was purified by column (PE/EtOAc=3:1, R$_f$=0.4) to give ethyl 2-(5-(2-(benzyloxy)ethoxy)-6-((4-methoxybenzyl)-oxy)pyridin-3-yl)-4-methylpyrimidine-5-carboxylate (4.1 g, 6.77 mmol, 79% yield) as a brown solid: $^1$H NMR (400 MHz, CHLOROFORM-d) δ 9.09 (s, 1H), 8.86 (s, 1H), 8.11 (d, J=1.3 Hz, 1H), 7.39 (d, J=8.8 Hz, 2H), 7.23 (d, J=16.3 Hz, 5H), 6.81 (d, J=8.4 Hz, 2H), 5.42 (s, 2H), 4.59 (s, 2H), 4.39-4.26 (m, 2H), 4.26 (t, J=4.9 Hz, 2H), 3.83 (t, J=4.6 Hz, 2H), 3.73 (s, 3H), 2.79 (s, 3H), 1.36 (t, J=7.1 Hz, 3H); ES-LCMS m/z 530.2 (M+H).

Step 5: 2-(5-(2-(Benzyloxy)ethoxy)-6-((4-methoxybenzyl)oxy)pyridin-3-yl)-4-methylpyrimidine-5-carboxylic acid

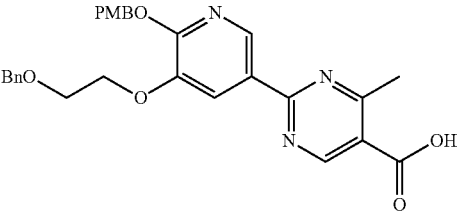

To a mixture of ethyl 2-(5-(2-(benzyloxy)ethoxy)-6-((4-methoxybenzyl)oxy)pyridin-3-yl)-4-methylpyrimidine-5-carboxylate (4 g, 7.55 mmol) in THF (20 mL) and water (20 mL) was added LiOH (0.543 g, 22.66 mmol). The mixture was stirred at 50° C. for 12 hr and then was treated with aq. HCl (2N) until pH=7 was achieved. The mixture was filtered and the filtrate was dried to give 2-(5-(2-(benzyloxy)ethoxy)-6-((4-methoxybenzyl)oxy)pyridin-3-yl)-4-methyl-pyrimidine-5-carboxylic acid (2.6 g, 4.44 mmol, 58.8% yield) as a yellow solid: $^1$H NMR (400 MHz, METHANOL-d$_4$) δ 8.89 (s, 1H), 8.77 (d, J=1.8 Hz, 1H), 8.20 (d, J=1.8 Hz, 1H), 7.42 (d, J=8.8 Hz, 2H), 7.35-7.12 (m, 5H), 6.88 (d, J=8.8 Hz, 2H), 5.41 (s, 2H), 4.61 (s, 2H), 4.34-4.25 (m, 2H), 3.90-3.82 (m, 2H), 3.77 (s, 3H), 2.77 (s, 3H): ES-LCMS m/z 502.2 (M+H).

Intermediate 16

3-Amino-N-(2-(dimethylamino)ethyl)-5-(trifluoromethyl)benzenesulfonamide

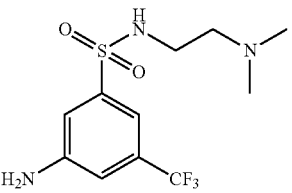

Step 1: 3-Nitro-5-(trifluoromethyl)benzene-1-sulfonyl chloride

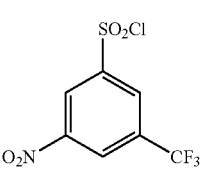 [SMILES: O=[N+]([O-])c1cc(C(F)(F)F)cc(S(=O)(=O)Cl)c1]

To a solution of 3-nitro-5-(trifluoromethyl)aniline (4.6 g, 22.32 mmol) in concentrated HCl (20 mL) and acetic acid (6 mL) stirred under N$_2$ atmosphere at −10° C. was added sodium nitrite (1.694 g, 24.55 mmol) in H$_2$O (3 mL) dropwise during 15 minutes. The reaction mixture was stirred for 45 minutes while the temperature was maintained between −10° C. and −5° C. While the diazotization was being completed, glacial acetic acid (60 mL) was placed in a 100 mL beaker and stirred magnetically. Sulfur dioxide was introduced by a bubbler tube with a fritted end immersed below the surface of the acetic acid until saturation is evident. Copper(I) chloride (0.552 g, 5.58 mmol) was added to the solution. The introduction of sulfur dioxide was continued until the yellow-green suspension becomes blue-green. Most of the solids dissolve during this time (15-20 min). The mixture was then placed in an ice bath and cooled with stirring. When the temperature approached 10° C., the diazotization reaction mixture was added in portions over a 10 minute period to the sulfur dioxide solution. Considerable foaming occurred after each addition and the temperature rose during the addition, but did not exceed 30° C. After all the diazonium salt mixture had been added, the mixture was poured into ice water. Then the solution was distributed between EtOAc (60 mL) and saturated NaHCO$_3$ (30 mL) solution. The combined organic layers were washed with brine (20 mL), dried over Na$_2$SO$_4$, filtered and concentrated to yield crude product of 3-nitro-5-(trifluoromethyl)benzene-1-sulfonyl chloride (4.42 g, 9.16 mmol, 41.0% yield) as a yellow oil. The crude product was detected by TLC (PE/EtOAc=10:1, R$_f$=0.5): $^1$H NMR (400 MHz, CDCl$_3$) δ 9.07 (s, 1H), 8.85 (s, 1H), 8.61 (s, 1H).

Step 2: N-(2-(dimethylamino)ethyl)-3-nitro-5-(trifluoromethyl)benzenesulfonamide

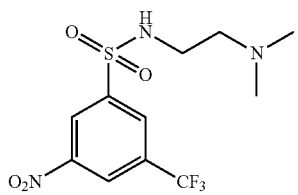

To a solution of 3-nitro-5-(trifluoromethyl)benzene-1-sulfonyl chloride (2 g, 6.91 mmol) in DCM (15 mL) stirred at 25° C. was added N,N-dimethylethane-1,2-diamine (0.913 g, 10.36 mmol) in one charge. The reaction mixture was stirred at 25° C. under N$_2$ atmosphere for 1 hour. LCMS analysis showed the starting material had disappeared, the solution was distributed between DCM (60 mL) and saturated NaHCO$_3$ (30 mL) solution. The combined organic extracts were washed with brine (20 mL), dried over Na$_2$SO$_4$, filtered and concentrated. The crude material was purified by silica column chromatography (DCM/MeOH=20:1 to 10:1). All fractions found to contain product by TLC (DCM/MeOH=10:1, R$_f$=0.4) were combined and concentrated to yield a yellow oil of N-(2-(dimethylamino)ethyl)-3-nitro-5-(trifluoromethyl)benzenesulfonamide (1.200 g, 3.41 mmol, 49.4% yield): $^1$H NMR (400 MHz, CDCl$_3$) δ 8.90 (s, 1H), 8.67 (s, 1H), 8.46 (s, 1H), 3.14-3.07 (m, 2H), 2.97(s, 1H), 2.45-2.39 (m, 2H), 2.15 (s, 6H); ES-LCMS m/z: 342.1 (M+H).

Step 3: 3-Amino-N-(2-(dimethylamino)ethyl)-5-(trifluoromethyl)benzenesulfonamide

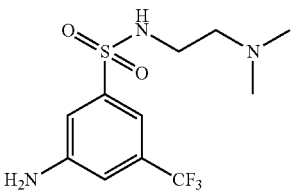 [SMILES: CN(C)CCNS(=O)(=O)c1cc([N+](=O)[O-])cc(C(F)(F)F)c1]

To a solution of N-(2-(dimethylamino)ethyl)-3-nitro-5-(trifluoromethyl)benzenesulfon-amide (1.2 g, 3.52 mmol) in methanol (20 mL) stirred under N$_2$ atmosphere was added Pd/C (10%, 0.374 g, 0.352 mmol) in one portion. Then the suspension was degassed under vacuum and purged with H$_2$ three times. The mixture was stirred at 25° C. under 15 psi of H$_2$ atmosphere for 12 hours. LCMS analysis showed the starting material disappeared. The reaction mixture was filtered through a pad of celite and the filter cake was washed with DCM (30 mL). The combined filtrates were concentrated to dryness to give crude product of 3-amino-N-(2-(dimethylamino)ethyl)-5-(trifluoromethyl)benzenesulfonamide (1 g, 3.08 mmol, 88.0% yield) as a yellow oil: $^1$H NMR (400 MHz, CDCl$_3$) δ 7.43 (s, 1H), 7.32 (s, 1H), 7.04 (s, 1H), 4.19 (br. s., 2H), 3.00 (t, J=5.8 Hz, 2H), 2.34 (t, J=5.8 Hz, 2H), 2.10 (s, 6H); ES-LCMS m/z: 312.1 (M+H).

Intermediate 17

Tert-butyl (1-(4-amino-2-(trifluoromethyl)phenyl)ethyl)carbamate

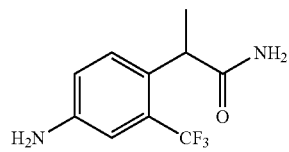

Step 1: 2-(4-Amino-2-(trifluoromethyl)phenyl)propanamide

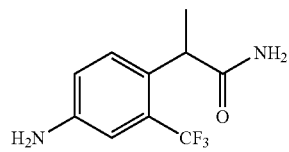

A mixture of 2-(4-amino-2-(trifluoromethyl)phenyl)propanenitrile (800 mg, 3.74 mmol) in sulfuric acid (8 mL, 150 mmol) was stirred at 60° C. for 2 hrs. The reaction mixture was added slowly to ice water (20 mL) and basified by excess solution of 50% NaOH. The mixture was extracted with EtOAc (50 mL×2). The combined organic extracts were washed with brine, dried over MgSO$_4$, filtered and concentrated to afford 2-(4-amino-2-(trifluoromethyl)phenyl)propanamide (700 mg, 2.86 mmol, 77.0% yield). TLC (PE/EtOAc=1:1, R$_f$=0.5). $^1$H NMR (400 MHz, CD$_3$OD) δ 7.39 (d, J=8.0 Hz, 1H), 6.99 (d, J=2.0 Hz, 1H), 6.89 (dd, J=2.4, 8.4 Hz, 1H), 3.90 (q, J=7.2Hz, 1H), 1.44 (d, J=7.2 Hz, 3H); ES-LCMS m/z 233.0 (M+H).

Step 2: 2-(4-(1,3-Dioxoisoindolin-2-yl)-2-(trifluoromethyl)phenyl)propanamide

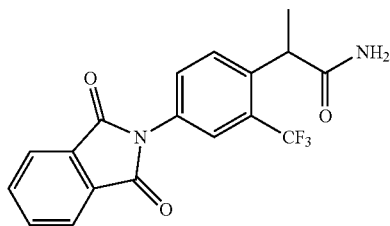 [SMILES: CC(C(N)=O)c1ccc(N2C(=O)c3ccccc3C2=O)cc1C(F)(F)F]

To a mixture of 2-(4-amino-2-(trifluoromethyl)phenyl)propanamide (700 mg, 3.01 mmol) in acetic acid (10 mL) was added isobenzofuran-1,3-dione (670 mg, 4.52 mmol). The mixture was stirred at 120° C. for 16 hrs. The mixture was concentrated, saturated NaHCO$_3$ solution (10 mL) was added and extracted with EtOAc (50 mL×2). The combined organic extracts were washed with brine, dried over Na$_2$SO$_4$, filtered and concentrated. The crude product was purified by silica column chromatography (PE/EtOAc=5:1-2:1). All fractions containing product by TLC (PE/EtOAc=2:1, R$_f$=0.5) were combined and concentrated to yield an off-white solid of 2-(4-(1,3-dioxoisoindolin-2-yl)-2-(trifluoromethyl)phenyl)propanamide (900 mg, 2.434 mmol, 81.0% yield): $^1$H NMR (400 MHz, CD$_3$OD) δ 8.03-7.96 (m, 2H), 7.95-7.88 (m, 3H), 7.86 (d, J=2.0 Hz, 1H), 7.78 (dd, J=1.6, 8.4 Hz, 1H), 4.16 (q, J=6.8 Hz, 1H), 1.58 (d, J=7.2 Hz, 3H); ES-LCMS m/z 363.0 (M+H).

Step 3: Tert-butyl (1-(4-(1,3-dioxoisoindolin-2-yl)-2-(trifluoromethyl)phenyl)ethyl)carbamate

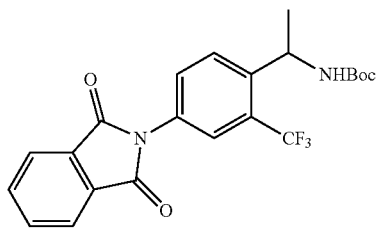 [SMILES: CC(NC(=O)OC(C)(C)C)c1ccc(N2C(=O)c3ccccc3C2=O)cc1C(F)(F)F]

To a mixture of 2-(4-(1,3-dioxoisoindolin-2-yl)-2-(trifluoromethyl)-phenyl)-propanamide (900 mg, 2.484 mmol) in tert-butanol (15 mL) was added [bis(trifluoroacetoxy)iodo]benzene (1602 mg, 3.73 mmol) portionwise. The mixture was stirred at 85° C. for 30 min. Pyridine (0.603 mL, 7.45 mmol) was added to the above mixture. The reaction mixture was stirred at 85° C. for 2 hrs and then was concentrated to give the crude product. The crude was purified by silica column chromatography (PE/EtOAc=5:1~2:1). All fractions found to contain product by TLC (PE/EtOAc=2:1, R$_f$=0.6) were combined and concentrated to yield a light yellow solid of tert-butyl (1-(4-(1,3-dioxoisoindolin-2-yl)-2-(trifluoromethyl)phenyl)ethyl)carbamate (660 mg, 1.291 mmol, 52.0% yield): $^1$H NMR (400 MHz, CD$_3$OD) δ 7.97 (dd, J=3.2, 5.6 Hz, 2H), 7.88 (dd, J=3.2, 5.6 Hz, 2H), 7.80-7.78 (m, 2H), 7.76-7.72 (m, 1H), 5.15-5.08 (m, 1H), 1.40 (s, 12H); ES-LCMS m/z 457.0 (M+Na)

Step 4: Tert-butyl (1-(4-amino-2-(trifluoromethyl)phenyl)ethyl)carbamate

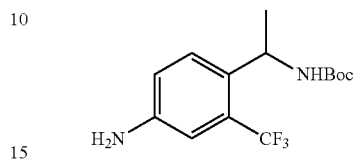

To a mixture of tert-butyl (1-(4-(1,3-dioxoisoindolin-2-yl)-2-(trifluoromethyl)phenyl)ethyl)carbamate (660 mg, 1.519 mmol) in ethanol (10 mL) was added hydrazine (0.281 mL, 7.60 mmol). The mixture was stirred at 80° C. for 3 hrs. Then the mixture was filtered and concentrated. The crude material was purified by preparative TLC (PE/EtOAc=1:1, R$_f$=0.6) to yield an off-white solid of tert-butyl (1-(4-amino-2-(trifluoromethyl)phenyl)-ethyl)carbamate (400 mg, 1.052 mmol, 69.2% yield): $^1$H NMR (400 MHz, CD$_3$OD) δ 7.31 (d, J=8.4 Hz, 1H), 6.93-6.92 (m, 1H), 6.88-6.86 (m, 1H), 5.00-4.99 (m, 1H), 1.39-1.29 (m, 12H) ES-LCMS m/z 327.1 (M+Na).

Intermediate 18

4-(2-(Pyrrolidin-1-yl)ethyl)-3-(trifluoromethyl)aniline

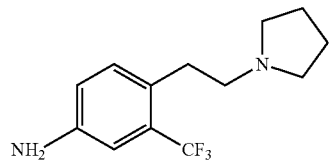 [SMILES: Nc1ccc(CCN2CCCC2)c(C(F)(F)F)c1]

Step 1: 2-(4-Nitro-2-(trifluoromethyl)phenyl)acetic acid

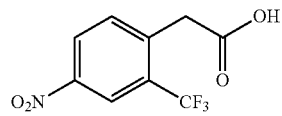

A solution of 2-(2-(trifluoromethyl)phenyl)acetonitrile (3 g, 16.20 mmol) in H$_2$SO$_4$ (15 mL) stirred at 0° C. in an ice bath was added potassium nitroperoxous acid (1.638 g, 16.20 mmol) slowly. Then the mixture was stirred at 0° C. for 1 hour. TLC (PE/EA=2:1, R$_f$=0.35) analysis showed the starting material disappeared, 15 g of ice was added and the mixture was heated to 110° C. for 15 hrs. TLC (PE/EA=1:1, R$_f$=0.25) analysis showed the starting material disappeared and desired product was observed. The reaction mixture was cooled to 20° C. and 20 mL of ice water was added dropwise and stirred for 30 minutes. The suspension was filtered through a pad of Celite and the filter cake was washed with water (10 mL×3), dried in vacuum to afford pure product 2-(4-nitro-2-(trifluoromethyl)phenyl)acetic acid (3.5 g, 13.35 mmol, 82.0% yield): $^1$H NMR (400 MHz, CD$_3$OD) δ 8.52 (d, J=2.0 Hz, 1H), 8.47-8.44 (m, 1H), 7.78 (d, J=8.4 Hz, 1H), 3.98 (s, 2H).

Step 2: 2-(4-Nitro-2-(trifluoromethyl)phenyl)-1-(pyrrolidin-1-yl)ethanone

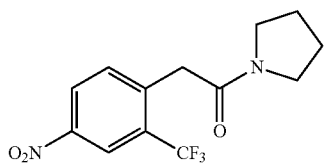

To a solution of 2-(4-nitro-2-(trifluoromethyl)phenyl)acetic acid (2.5 g, 10.03 mmol) in pyridine (20 mL) was added pyrrolidine (1.070 g, 15.05 mmol) in one portion, then 2,4,6-tripropyl-1,3,5,2,4,6-trioxatriphosphinane 2,4,6-trioxide (13 mL, 10.03 mmol) was added in dropwise. The mixture was stirred at 20° C. for 3 hours. LCMS analysis showed the starting material disappeared. 40 mL of ice water was added and the mixture was extracted with EtOAc (50 mL×2). The combined organic layers were washed with brine (30 mL), evaporated to dryness to give crude product, which was purified by silica column chromatography (DCM/MeOH=20:1 to 15:1) to afford pure product 2-(4-nitro-2-(trifluoromethyl)phenyl)-1-(pyrrolidin-1-yl)ethanone (2.189 g, 5.36 mmol, 53.4% yield) as a brown solid: $^1$H NMR (400 MHz, CD$_3$OD) δ 8.51 (d, J=2.2 Hz, 1H), 8.45-8.43 (m, 1H), 7.69 (d, J=8.4 Hz, 1H), 4.03 (s, 2H), 3.60 (t, J=6.8 Hz, 2H), 3.45 (t, J=7.0 Hz, 2H), 2.09-2.00 (m, 2H), 1.96-1.89 (m, 2H); ES-LCMS: m/z 303.1 (M+H).

Step 3: 2-(4-Amino-2-(trifluoromethyl)phenyl)-1-(pynolidin-1-yl)ethanone

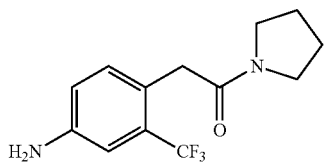 [SMILES: Nc1ccc(CC(=O)N2CCCC2)c(C(F)(F)F)c1]

To a solution of 2-(4-nitro-2-(trifluoromethyl)phenyl)-1-(pyrrolidin-1-yl)ethanone (2.19 g, 7.25 mmol) in methanol (15 mL) stirred under N$_2$ atmosphere was added Pd/C (10%, 0.077 g, 0.725 mmol) in one portion. Then the suspension was degassed under vacuum and purged with H$_2$ three times. The mixture was stirred under 15 psi of H$_2$ at 18° C. for 12 hours. LCMS analysis showed the starting material disappeared, the reaction mixture was filtered through a pad of Celite and the filter cake was washed with MeOH. The combined filtrates were concentrated to dryness to give crude product which was purified by silica column chromatography (PE/EA=3:1 to 1:1) to afford pure product 2-(4-amino-2-(trifluoromethyl)phenyl)-1-(pyrrolidin-1-yl)ethanone (1.44 g, 4.97 mmol, 68.6% yield) as a yellow solid: $^1$H NMR (400 MHz, CDCl$_3$) δ 7.17 (d, J=8.4 Hz, 1H), 6.94 (d, J=2.4 Hz, 1H), 6.80-6.77 (m, 1H), 3.80 (br. s., 2H), 3.69 (s, 2H), 3.51 (t, J=6.8 Hz, 2H), 3.41 (t, J=6.8 Hz, 2H), 1.99-1.91 (m, 2H), 1.90-1.81 (m, 2H); ES-LCMS: m/z 273.1 (M+H).

Step 4: 4-(2-(Pyrrolidin-1-yl)ethyl)-3-(trifluoromethyl)aniline

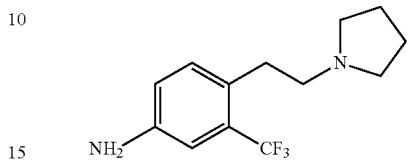

To a solution of 2-(4-amino-2-(trifluoromethyl)phenyl)-1-(pyrrolidin-1-yl)ethanone (1.44 g, 5.29 mmol) in tetrahydrofuran (THF) (15 mL) was added BH$_3$.DMS (3.01 mL, 31.7 mmol) in portions. Then the mixture was stirred at 18° C. for 12 hours. After LCMS analysis showed the starting material disappeared, the mixture was cooled to 0° C. in the ice bath. Then 2 mL of MeOH was added dropwise to quench the mixture. The solvent was removed in vacuo. The residue was dissolved in DCM (60 mL) and washed with H$_2$O (20 mL) and brine (20 mL). The organic layer was dried over Na$_2$SO$_4$, filtered and concentrated to yield a yellow solid of 4-(2-(pyrrolidin-1-yl)ethyl)-3-(trifluoromethyl)aniline (1.2 g, 4.04 mmol, 76.0% yield): $^1$H NMR (400 MHz, CDCl$_3$) δ 7.17 (d, J=8.2 Hz, 1H), 6.92 (d, J=2.0 Hz, 1H), 6.79 (dd, J=1.8, 8.2 Hz, 1H), 3.79 (br. s., 2H), 3.36-3.24 (m, 2H), 3.23-3.14 (m, 2H), 2.93-2.84 (m, 2H), 2.82-2.71 (m, 2H), 2.26-2.13 (m, 2H), 1.91 (t, J=7.2 Hz, 2H); ES-LCMS: m/z 271.0 (M+BH$_3$), 259.1 (M+H).

Intermediate 19

2-Chloropyrimidin-5-amine

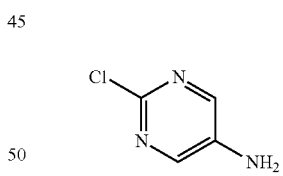

To a solution of 2-chloro-5-nitropyrimidine (5 g, 31.3 mmol) and zinc (20.49 g, 313 mmol) in Methanol (150 mL) was added ammonium chloride (16.77 g, 313 mmol) at 0° C. The resulting mixture was stirred at 25° C. for 16 hr. After LCMS analysis showed the starting material disappeared, the mixture was filtered. The filtrate was concentrated to give the crude product, which was purified by column chromatography (PE/EA=3/1 to 1/1). All fractions found to contain product by TLC (PE/EA=1/1, R$_f$=0.5) were combined and concentrated to yield a yellow solid of 2-chloropyrimidin-5-amine (1 g, 7.72 mmol, 24.63% yield): $^1$H NMR (400 MHz, METHANOL-d$_4$) δ 8.04 (s, 2H); ES-LCMS m/z 130.1 (M+H).

Intermediate 20

4-((4-Ethylpiperazin-1-yl)methyl)-2-fluoro-5-(trifluoromethyl)aniline

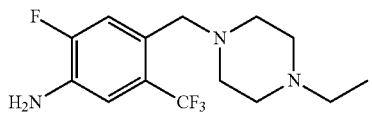

Step 1: 1-Ethyl-4-(5-fluoro-2-(trifluoromethyl)benzyl)piperazine

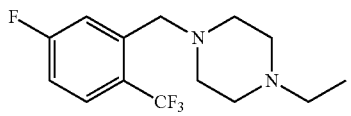 [SMILES: CCN1CCN(Cc2cc(F)ccc2C(F)(F)F)CC1]

A solution of 5-fluoro-2-(trifluoromethyl)benzaldehyde (2 g, 10.41 mmol) and 1-ethylpiperazine (1.783 g, 15.62 mmol) in DCM (60 mL) was stirred at 20° C. After 2 hrs, sodium triacetoxyborohydride (6.62 g, 31.2 mmol) was added. The resulting mixture was stirred at 20° C. overnight. After LCMS analysis showed the starting material disappeared, the mixture was dissolved in H₂O (30 mL) and adjusted to pH 8 with aq NaHCO₃. The organic layer was washed with brine and dried over Na₂SO₄. After filtration, the filtrate was concentrated to give the crude product, which was purified by column chromatography (DCM/MeOH=0 to 20:1) to yield a yellow oil of 1-ethyl-4-(5-fluoro-2-(trifluoromethyl)benzyl)piperazine (3 g, 8.74 mmol, 84% yield): $^1$H NMR (400 MHz, CD₃OD) δ7.77 (dd, J=8.8, 5.2 Hz, 1H), 7.63 (dd, J=10.0, 2.0 Hz, 1H), 7.21 (dt, J=8.4, 2.4 Hz, 1H), 3.80 (s, 2H), 3.24 (br. s., 4H), 3.13 (q, J=7.6 Hz, 2H), 2.77 (br. s., 4H), 1.34 (t, J=7.2 Hz, 3H); ES-LCMS m/z: 291.1 (M+H).

Step 2: 1-Ethyl-4-(5-fluoro-4-nitro-2-(trifluoromethyl)benzyl)piperazine

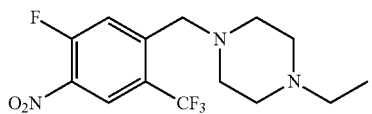 [SMILES: CCN1CCN(Cc2cc(F)c([N+](=O)[O-])cc2C(F)(F)F)CC1]

To a solution of 1-ethyl-4-(5-fluoro-2-(trifluoromethyl)benzyl)piperazine (3 g, 10.33 mmol) in sulfuric acid (6 ml, 113 mmol) was added nitric acid (0.716 g, 11.37 mmol). The resulting mixture was stirred at room temperature overnight. The mixture was stirred at 50° C. for 2 hrs. After TLC analysis (PE/EA=10:1) showed the starting material disappeared, the mixture was adjusted to pH 8 by aq NaOH and extracted by EA (50 mL×2). The organic layer was washed with H₂O (50 mL) and brine (50 mL), then dried over Na₂SO₄ and filtered. The filtrate was concentrated to give a yellow oil of 1-ethyl-4-(5-fluoro-4-nitro-2-(trifluoromethyl)benzyl)-piperazine (2.2 g, 6.56 mmol, 63.5% yield): $^1$H NMR (400 MHz, CD₃OD) δ8.39 (d, J=7.0 Hz, 1H), 7.92 (d, J=12.0 Hz, 1H), 3.75 (s, 2H), 2.60-2.47 (m, 10H), 1.14-1.10 (m, 3H); ES-LCMS m/z 336.1 (M+H)

Step 3: 4-((4-Ethylpiperazin-1-yl)methyl)-2-fluoro-5-(trifluoromethyl)aniline

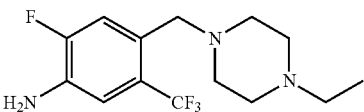

To a solution of 1-ethyl-4-(5-fluoro-4-nitro-2-(trifluoromethyl)benzyl)piperazine (2.2 g, 6.56 mmol) and zinc (4.29 g, 65.6 mmol) in methanol (100 mL) was added ammonium chloride (3.51 g, 65.6 mmol) by portions. The resulting mixture was stirred at 20° C. for 12 hrs. After LCMS analysis showed the starting material disappeared, the mixture was filtered. The filtrate was concentrated to give the crude product, which was purified by preparative HPLC (Mobile phase A: water with 0.05% NH₃.H₂O solution/ Mobile phase B: MeCN/Flow rate: 80 mL/min/Detection: UV 220 nm/254 nm/Column: Phenomenex Gemini C18 250*50 mm,10 um/Column temperature: RT/Gradient Profile Description: 40-70 (B %)) to yield a yellow solid of 4-((4-ethylpiperazin-1-yl)methyl)-2-fluoro-5-(trifluoromethyl)aniline (0.7 g, 2.265 mmol, 34.5% yield): $^1$H NMR (400 MHz, CD₃OD) δ7.31 (d, J=12.6 Hz, 1H), 7.10 (d, J=8.6 Hz, 1H), 3.51 (s, 2H), 2.74-2.15 (m, 10H), 1.10 (t, J=7.3 Hz, 3H); ES-LCMS m/z: 306.1 (M+H).

Intermediate 21

2-(6-((4-Methoxybenzyl)oxy)-4-(2-methoxyethoxy)pyridin-3-yl)-4-methylpyrimidine-5-carboxylic acid

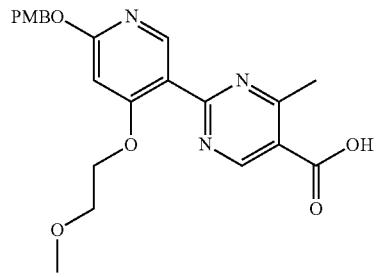

Step 1: 2-Chloro-4-(2-methoxyethoxy)pyridine

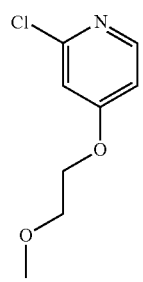

To a mixture of 2-methoxyethanol (5.62 g, 73.8 mmol) in THF (100 mL) cooled to 0° C. was added 60% NaH (2.95 g, 73.8 mmol) in portions followed by 2-chloro-4-nitropyridine (9 g, 56.8 mmol). The whole mixture was stirred at 25° C. for 10 hrs. The mixture was concentrated to give the residue, which was purified by silica column chromatography (PE/EtOAc=8:1~2:1). All fractions contained product by TLC (PE/EtOAc=5:1, $R_f$=0.5) were combined and concentrated to yield yellow oil of 2-chloro-4-(2-methoxyethoxy)pyridine (11 g, 55.7 mmol, 98.0% yield): $^1$H NMR (400 MHz, CDCl$_3$) δ 8.15 (d, J=4.6 Hz, 1H), 6.87-6.72 (m, 2H), 4.19-4.08 (m, 2H), 3.77-3.67 (m, 2H), 3.41 (s, 3H); LCMS (m/z) 188.1 (M+H).

Step 2:
5-Bromo-2-chloro-4-(2-methoxyethoxy)pyridine

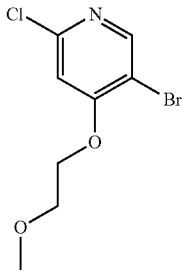

To a solution of 2-chloro-4-(2-methoxyethoxy)pyridine (11 g, 58.6 mmol) and H$_2$SO$_4$ (100 mL, 1876 mmol) was added NBS (11.48 g, 64.5 mmol). Then the mixture was stirred at 50° C. for 4 hrs. After cooling to room temperature, the mixture was poured into cold water (500 mL), neutralized with 2 mol/L NaOH to pH=7.5 . The mixture was extracted with EtOAc (200 mL×3). The organic layer was dried over Na$_2$SO$_4$, filtered, and concentrated. The crude product was purified by silica column chromatography (5% EtOAc:95% petroleum ether, 100 g silica column). All fractions containing product by TLC (EtOAc:Petroleum ether=1:5, $R_f$=0.6) were combined and concentrated to yield a yellow oil of 5-bromo-2-chloro-4-(2-methoxyethoxy)pyridine (6.9 g, 23.30 mmol, 39.7% yield): $^1$H NMR (400 MHz, CDCl$_3$) δ 8.31 (s, 1H), 6.83 (s, 1H), 4.27-4.18 (m, 2H), 3.83-3.76 (m, 2H), 3.45 (s, 3H); ES-LCMS m/z 266.0, 268.0 (M+H).

Step 3: 5-Bromo-2-((4-methoxybenzyl)oxy)-4-(2-methoxyethoxy)pyridine

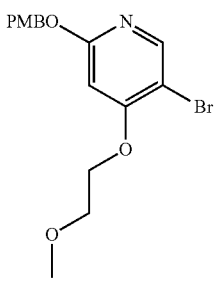

To a mixture of 5-bromo-2-chloro-4-(2-methoxyethoxy)pyridine (4.0 g, 15.01 mmol), 18-crown-6 (0.198 g, 0.750 mmol) and (4-methoxyphenyl)methanol (2.488 g, 18.01 mmol) in toluene (50 mL) was added KOH (2.53 g, 45.0 mmol). The whole mixture was stirred at 110° C. for 2 hrs. The mixture was filtered and concentrated to yield the crude product, which was purified by silica column chromatography (10% EtOAc:90% Petroleum ether, 50 g silica column). All fractions found to contain product by TLC (EtOAc:Petroleum ether=1:5, $R_f$=0.6) were combined and concentrated to yield 5-bromo-2-((4-methoxybenzyl)oxy)-4-(2-methoxyethoxy)pyridine (5.0 g, 12.22 mmol, 81.0% yield) as a white solid: $^1$H NMR (400 MHz, CDCl$_3$) δ 8.13 (s, 1H), 7.38 (d, J=8.8 Hz, 2H), 6.92 (d, J=8.4 Hz, 2H), 6.27 (s, 1H), 5.27 (s, 2H), 4.20-4.12 (m, 2H), 3.82 (s, 3H), 3.80 (d, J=4.4 Hz, 2H), 3.48 (s, 3H); ES-LCMS m/z: 368.1, 370.1 (M+H).

Step 4: 2-((4-Methoxybenzyl)oxy)-4-(2-methoxyethoxy)-5-(4,4,5,5-tetramethyl-1,3,2-dioxaborolan-2-yl)pyridine

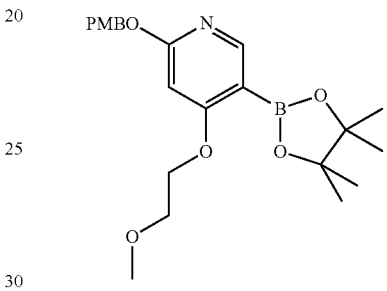

To a mixture of 5-bromo-2-((4-methoxybenzyl)oxy)-4-(2-methoxyethoxy)pyridine (2 g, 5.43 mmol) in THF (30 mL) was added BuLi (3.26 mL, 2.5 N, 8.15 mmol) at −78° C. slowly under nitrogen atmosphere; the mixture was stirred at −78° C. for 0.5 hr. Then 2-isopropoxy-4,4,5,5-tetramethyl-1,3,2-dioxaborolane (1.213 g, 6.52 mmol) was added to the mixture, and the reaction mixture was stirred at −78° C. for 1 hr. Then the mixture was concentrated give a residue, which was extracted with DCM (30 mL×2). The organic extracts were washed with brine (30 mL), dried over Na$_2$SO$_4$, filtered, and concentrated to yield a yellow solid of 2-((4-methoxybenzyl)oxy)-4-(2-methoxyethoxy)-5-(4,4,5,5-tetramethyl-1,3,2-dioxaborolan-2-yl)pyridine (2.5 g, 2.71 mmol, 49.9% yield): $^1$H NMR (400 MHz, CD$_3$OD) δ 7.34 (d, J=8.4 Hz, 3H), 6.92-6.88 (m, 3H), 5.25-5.22 (m, 2H), 4.14-4.10 (m, 2H), 3.77 (s, 3H), 3.48-3.43 (m, 2H), 3.41-3.38 (m, 3H), 1.35-1.29 (m, 12H); LCMS (m/z): 416.1 (M+H).

Step 5: Ethyl 2-(6-((4-methoxybenzyl)oxy)-4-(2-methoxyethoxy)pyridin-3-yl)-4-methylpyrimidine-5-carboxylate

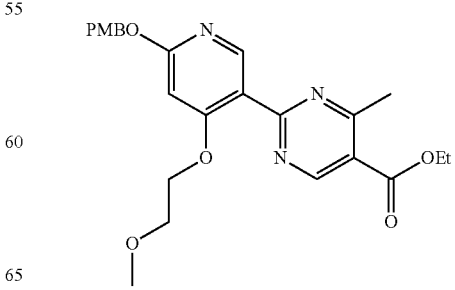

A suspension of 2-((4-methoxybenzyl)oxy)-4-(2-methoxyethoxy)-5-(4,4,5,5-tetramethyl-1,3,2-dioxaborolan-2-yl)pyridine (2 g, 4.82 mmol), PdCl$_2$(dppf) (0.176 g, 0.241 mmol), ethyl 2-chloro-4-methylpyrimidine-5-carboxylate (1.159 g, 5.78 mmol), K$_2$CO$_3$ (4.82 ml, 9.63 mmol) in 1,4-dioxane (20 mL) and water (5 mL) was stirred at 80° C. for 2 hrs under N$_2$ atmosphere. The mixture was concentrated to give the residue which was extracted with DCM (40 mL×2). The organic extract was washed with brine (40 mL), dried over Na$_2$SO$_4$, filtered and concentrated, and purified by silica column chromatography (10% EtOAc:90% Petroleum ether, 20 g silica column). All fractions found to contain product by TLC (EtOAc:Petroleum ether=1:5, R$_f$=0.5) were combined and concentrated to yield a white solid of ethyl 2-(6-((4-methoxybenzyl)oxy)-4-(2-methoxyethoxy)pyridin-3-yl)-4-methyl-pyrimidine-5-carboxylate (1.1 g, 1.941 mmol, 40.3% yield): $^1$H NMR (400 MHz, CD$_3$OD) δ 9.18-9.13 (m, 1H), 8.50-8.44 (m, 1H), 7.39 (d, J=8.4 Hz, 2H), 6.95-6.89 (m, 2H), 6.56-6.51 (m, 1H), 5.49 (s, 1H), 5.33 (s, 1H), 4.47-4.36 (m, 3H), 4.25-4.17 (m, 2H), 3.81-3.77 (m, 3H), 3.76-3.71 (m, 2H), 3.34 (s, 3H), 2.85 (s, 2H), 1.45-1.40 (m, 3H); LCMS (m/z) 454.1 (M+H).

Step 6: 2-(6-((4-Methoxybenzyl)oxy)-4-(2-methoxyethoxy)pyridin-3-yl)-4-methylpyrimidine-5-carboxylic acid

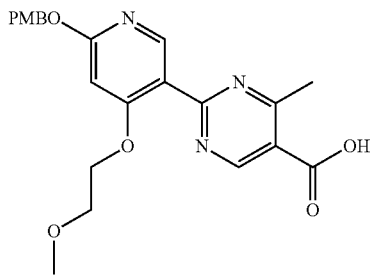

A suspension of ethyl 2-(6-((4-methoxybenzyl)oxy)-4-(2-methoxyethoxy)pyridin-3-yl)-4-methylpyrimidine-5-carboxylate (1.1 g, 2.426 mmol), lithium hydroxide, H$_2$O (0.305 g, 7.28 mmol) in THF (15 mL) and water (5 mL) was stirred at 60° C. for 12 hrs. The mixture was concentrated to give the residue. The crude product was purified by Prep. HPLC (Column: Phenomenex Gemini C18 250*50 10 u; Mobile phase: 0.05% ammonia-ACN; Gradient: B from 12 to 42 in 30 min; Flow rate: 90 mL/min; Wavelength: 220/254 nm) and lyophilized to yield white solid of 2-(6-((4-methoxybenzyl)oxy)-4-(2-methoxyethoxy)pyridin-3-yl)-4-methylpyrimidine-5-carboxylic acid (800 mg, 1.692 mmol, 69.8% yield): $^1$H NMR (400 MHz, CD$_3$OD) δ 8.93-8.86 (m, 1H), 8.35-8.27 (m, 1H), 7.39 (d, J=8.8 Hz, 2H), 6.94-6.85 (m, 2H), 6.51 (s, 1H), 5.32 (s, 2H), 4.23-4.18 (m, 2H), 3.81-3.77 (m, 3H), 3.72-3.68 (m, 2H), 3.31 (br. s., 3H), 2.78-2.74 (m, 3H); LCMS (m/z): 426.1 (M+H).

Intermediate 22

2-Fluoro-4-((4-methylpiperazin-1-yl)methyl)-5-(trifluoromethyl)aniline

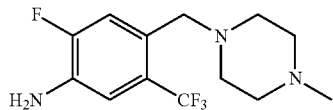 [SMILES: CN1CCN(Cc2cc(F)c([N+](=O)[O-])cc2C(F)(F)F)CC1]

Step 1: 1-(5-Fluoro-2-(trifluoromethyl)benzyl)-4-methylpiperazine

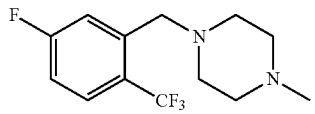

A solution of 5-fluoro-2-(trifluoromethyl)benzaldehyde (4 g, 20.82 mmol) and 1-methylpiperazine (3.13 g, 31.2 mmol) in DCM (150 mL) was stirred at 25° C. After 2 hours, sodium cyanoborohydride (3.93 g, 62.5 mmol) was added. The resulting mixture was stirred at 25° C. for 16 hours. LCMS analysis showed the starting material disappeared. The mixture was washed with H$_2$O (80 mL). The organic layer was washed with brine (50 mL) and dried over Na$_2$SO$_4$. After filtration, the filtrate was concentrated to give the crude product, which was purified by column chromatography (DCM to DCM/MeOH=20/1). All fractions found to contain product by TLC (DCM/MeOH=20/1, R$_f$=0.4) were combined and concentrated to yield a yellow oil of 1-(5-fluoro-2-(trifluoromethyl)benzyl)-4-methylpiperazine (2.41 g, 37% yield): $^1$H NMR (400 MHz, METHANOL-d4) d=7.73 (dd, J=8.4, 5.6 Hz, 1H), 7.60 (d, J=10.0 Hz, 1H), 7.17 (t, J=8.4 Hz, 1H), 3.70 (s, 2H), 2.55 (brs, 8H), 2.32 (s, 3H); ES-LCMS m/z: 277.2 (M+H).

Step 2: 1-(5-Fluoro-4-nitro-2-(trifluoromethyl)benzyl)-4-methylpiperazine

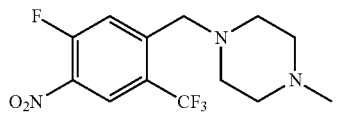

To a solution of 1-(5-fluoro-2-(trifluoromethyl)benzyl)-4-methylpiperazine (3 g, 10.86 mmol) in sulfuric acid (20 mL) was added nitric acid (0.728 mL, 16.29 mmol) dropwise. The resulting mixture was stirred at 60° C. for 16 hr. LCMS analysis showed the starting material disappeared. The mixture was poured into ice-water and adjusted to pH=8 by aq NaOH. The mixture was extracted by EA (50 mL×2). The organic layer was washed with brine (30 mL), dried over sodium sulfate, filtered and concentrated to yield a brown solid of 1-(5-fluoro-4-nitro-2-(trifluoromethyl)benzyl)-4-methylpiperazine (3.3 g, 9.76 mmol, 90% yield): $^1$H NMR (400 MHz, METHANOL-d$_4$) δ8.41 (d, J=7.2 Hz, 1H), 7.93 (d, J=12.0 Hz, 1H), 3.78 (s, 2H), 2.78 (brs, 4H), 2.62 (br. s., 4H), 2.48 (s, 3H); ES-LCMS m/z: 322.1 (M+H).

Step 3: 2-Fluoro-4-((4-methylpiperazin-1-yl)methyl)-5-(trifluoromethyl)aniline

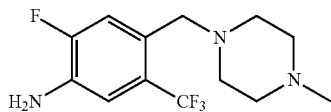

A solution of 1-(5-fluoro-4-nitro-2-(trifluoromethyl)benzyl)-4-methylpiperazine (3.3 g, 10.27 mmol) and 10% Pd/C (0.4 g, 0.376 mmol) in methanol (100 mL) was stirred at 25° C. for 2 hr under a H$_2$ atmosphere. LCMS analysis showed the starting material disappeared. The mixture was filtered. The filtrate was concentrated to give the crude product, which was purified by column chromatography (DCM/MeOH=50:1 to 20:1). All fractions found to contain product by TLC (DCM/MeOH=10:1, R$_f$=0.5) were combined and concentrated to yield a brown solid of 2-fluoro-4-((4-methylpiperazin-1-yl)methyl)-5-(trifluoromethyl)aniline (1.4 g, 4.09 mmol, 39.8% yield): $^1$H NMR (400 MHz, METHANOL-d4) δ7.31 (d, J=12.4 Hz, 1H), 7.10 (d, J=8.8 Hz, 1H), 3.51 (s, 2H), 2.53 (br. s., 8H), 2.32-2.29 (m, 3H); ES-LCMS m/z 292.1 (M+H).

Intermediate 23

2-((4-Methoxybenzyl)oxy)-3-(2-methoxyethoxy)-5-(4,4,5,5-tetra-methyl-1,3,2-dioxaborolan-2-yl)pyridine

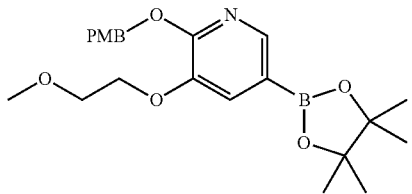

Step 1: 5-Bromo-2-chloropyridin-3-ol

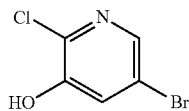

A mixture of 5-bromo-2-chloro-3-methoxypyridine (36 g, 162 mmol) in hydrobromic acid (200 mL, 3683 mmol) was stirred at 100° C. for 48 hrs. Then the mixture was concentrated, basified with saturated NaHCO$_3$ solution and extracted with EtOAc (600 mL×2). The combined organic extract was washed with brine, dried over Na$_2$SO$_4$, filtered and concentrated. The crude material was purified by silica column chromatography (PE/EtOAc=1:0~2:1). All fractions found to contain product by TLC (PE/EtOAc=2:1, R$_f$=0.6) were combined and concentrated to yield a light yellow oil of 5-bromo-2-chloropyridin-3-ol (21 g, 86 mmol, 52.9% yield): $^1$H NMR (400 MHz, METHANOL-d$_4$) δ7.96 (t, J=2.0 Hz, 1H), 7.47 (d, J=2.4 Hz, 1H); ES-LCMS m/z 208.0, 210.0 (M+H).

Step 2: 5-Bromo-2-chloro-3-(2-methoxyethoxy)pyridine

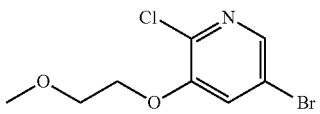

A solution of 5-bromo-2-chloropyridin-3-ol (5 g, 23.99 mmol), 1-bromo-2-methoxy-ethane (5.00 g, 36.0 mmol) and K$_2$CO$_3$ (6.63 g, 48.0 mmol) in DMF (15 mL) was stirred at 60° C. for 16 hrs under a N$_2$ atmosphere. LCMS analysis showed the starting material disappeared. The mixture was filtered and the filtrate was concentrated to give the crude product, which was purified by column chromatography (PE to PE/EA=5/1). All fractions found to contain product by TLC (PE/EA=5/1, R$_f$=0.5) were combined and concentrated to yield a white solid of 5-bromo-2-chloro-3-(2-methoxyethoxy)pyridine (5 g, 18.39 mmol, 77% yield): $^1$H NMR (400 MHz, CHLOROFORM-d) δ8.07 (s, 1H), 7.39-7.32 (m, 1H), 4.21-4.18 (m, 2H), 3.82-3.80 (m, 2H), 3.47 (d, J=3.2 Hz, 3H); ES-LCMS m/z 265.9, 267.9 (M+H).

Step 3: 5-Bromo-2-((4-methoxybenzyl)oxy)-3-(2-methoxyethoxy)pyridine

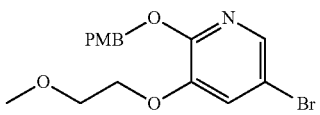

To a solution of 5-bromo-2-chloro-3-(2-methoxyethoxy) pyridine (5.3 g, 19.89 mmol) in DMF (50 mL) was added 60% NaH (1.193 g, 29.8 mmol) at 0° C. After 0.5 hr, (4-methoxyphenyl)methanol (3.30 g, 23.86 mmol) was added. The resulting mixture was stirred at 70° C. for 16 hr. The solvent was removed in vacuo. The residue was distributed between EA (60 mL) and water (40 mL), extracted with EtOAc (60 mL×2). The organic layer was washed with brine (40 mL), dried over sodium sulfate, filtered and concentrated to yield a crude product, which was purified by column chromatography (PE/EA=10:1 to 5:1). All fractions found to contain product by TLC (PE/EA=5:1, R$_f$=0.5) were combined and concentrated to yield a yellow solid of 5-bromo-2-((4-methoxybenzyl)oxy)-3-(2-methoxyethoxy) pyridine (4.3 g, 11.09 mmol, 55.8% yield): $^1$H NMR (400 MHz, METHANOL-d$_4$) δ7.76 (d, J=1.8 Hz, 1H), 7.41 (d, J=2.0 Hz, 1H), 7.37 (d, J=8.8 Hz, 2H), 6.89 (d, J=8.8 Hz, 2H), 5.29 (s, 2H), 4.14-4.12 (m, 2H), 3.78 (s, 3H), 3.74-3.71 (m, 2H), 3.38 (s, 3H); ES-LCMS m/z 368.0, 370.0 (M+H).

Step 4: 2-((4-Methoxybenzyl)oxy)-3-(2-methoxyethoxy)-5-(4,4,5,5-tetramethyl-1,3,2-dioxaborolan-2-yl)pyridine

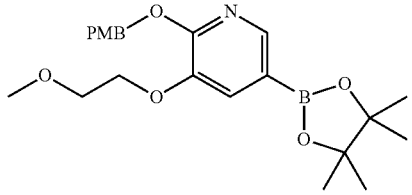

A solution of 5-bromo-2-((4-methoxybenzyl)oxy)-3-(2-methoxyethoxy)pyridine (3 g, 8.15 mmol), 4,4,4',4',5,5,5',5'-octamethyl-2,2'-bi(1,3,2-dioxaborolane) (2.276 g, 8.96 mmol), PdCl$_2$(dppf) (0.596 g, 0.815 mmol) and potassium acetate (1.599 g, 16.29 mmol) in 1,4-dioxane (100 mL) was stirred at 90° C. for 2 hr under a N$_2$ atmosphere. LCMS analysis showed the starting material disappeared. The mixture was filtered. The filtrate was concentrated to give the crude product, which was purified by column chromatography (PE/EA=10:1 to 5:1). All fractions found to contain product by TLC (PE/EA=5/1, R$_f$=0.45) were combined and concentrated to yield a pale yellow solid of 2-((4-methoxybenzyl)oxy)-3-(2-methoxyethoxy)-5-(4,4,5,5-tetramethyl-1,3,2-dioxaborolan-2-yl)pyridine (3.6 g, 7.80 mmol, 96% yield): $^1$H NMR (400 MHz, METHANOL-d$_4$) δ8.03 (s, 1H), 7.43 (s, 1H), 7.37 (d, J=8.4 Hz, 2H), 6.88 (d, J=8.4 Hz, 2H), 5.33 (s, 2H), 4.13-4.10 (m, 2H), 3.77 (s, 3H), 3.73-3.70 (m, 2H), 3.37 (s, 3H), 1.33 (s, 12H); ES-LCMS m/z 296.2 (M+H-PMB).

Intermediate 24

4-((Dimethylamino)methyl)-2-fluoro-5-(trifluoromethyl)aniline

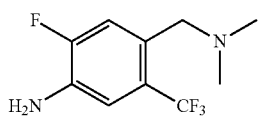

Step 1: 1-(5-Fluoro-2-(trifluoromethyl)phenyl)-N,N-dimethylmethanamine

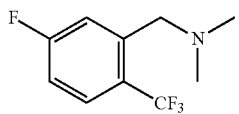

A mixture of 2-(bromomethyl)-4-fluoro-1-(trifluoromethyl)benzene (0.5 g, 1.945 mmol), dimethylamine hydrochloride (0.190 g, 2.334 mmol), Et$_3$N (0.597 mL, 4.28 mmol) in acetonitrile (20 mL) was stirred overnight. Then the mixture was concentrated to give a residue which was extracted with DCM (20 mL×2), dried over Na$_2$SO$_4$, and concentrated to give 1-(5-fluoro-2-(trifluoromethyl)-phenyl)-N,N-dimethylmethanamine (400 mg, 1.808 mmol, 93% yield): $^1$H NMR (400 MHz, CD$_3$OD) δ 7.71-7.75 (m, 1H), 7.55-7.58 (m, 1H), 7.15-7.19 (m, 1H), 3.62 (s, 2H), 2.29 (s, 6H); ES-LCMS m/z 222 (M+H).

Step 2: 1-(5-Fluoro-4-nitro-2-(trifluoromethyl)phenyl)-N,N-dimethylmethanamine

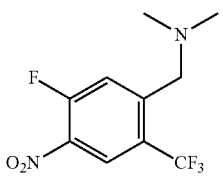

To a mixture of 1-(5-fluoro-2-(trifluoromethyl)phenyl)-N,N-dimethylmethanamine (100 mg, 0.452 mmol) in H$_2$SO$_4$ (24.10 µl, 0.452 mmol) was added nitric acid (28.5 mg, 0.452 mmol) at 0° C. dropwise. The mixture was stirred for 30 min, and then was poured into ice/water. The mixture was adjusted pH=9 with saturated NaHCO$_3$ solution, extracted with DCM (20 mL×2), dried over Na$_2$SO$_4$, and concentrated to give 1-(5-fluoro-4-nitro-2-(trifluoromethyl)phenyl)-N,N-dimethylmethanamine (100 mg, 0.376 mmol, 83% yield): $^1$H NMR (400 MHz, CD$_3$OD) δ 7.62-7.64 (m, 1H), 7.12-7.15 (m, 1H), 2.89 (s, 2H), 1.52 (s, 6H); ES-LCMS m/z 267 (M+H).

Step 3: 4-((Dimethylamino)methyl)-2-fluoro-5-(trifluoromethyl)aniline

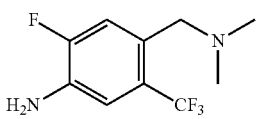

To a mixture of 1-(5-fluoro-4-nitro-2-(trifluoromethyl)phenyl)-N,N-dimethylmethanamine (4.6 g, 17.28 mmol) and zinc (11.30 g, 173 mmol) in methanol (50 mL) was added NH$_4$Cl (9.24 g, 173 mmol). The mixture was stirred for 12 hours at 15° C. The mixture was filtered and the filtrate was concentrated to give the residue which was distributed between DCM (100 mL) and H$_2$O (50 mL), extracted with DCM (100 mL×2). The organic extracts were washed with brine (50 mL), dried over Na$_2$SO$_4$, filtered and concentrated to yield 3.5 g of crude product. After purification by preparative HPLC (Instrument: DC/Column: Gemini C18 150*25 mm*10 ul/Mobile phase A: Water (Water+0.1% HCl)/Mobile phase B: Acetonitrile/Gradient: 43-63B %)/Flowrate: 25 ml/min/Run time: 15 min) to yield an off white solid 4-((dimethylamino)methyl)-2-fluoro-5-(trifluoromethyl)aniline dihydrochloride (560.65 mg, 1.814 mmol, 10.5% yield): $^1$H NMR (400 MHz, MeOD-d4) δ7.42 (d, J=11.6 Hz, 1H), 7.27 (d, J=8.4 Hz, 1H), 4.34 (s, 2H), 2.88 (s, 6H); ES-LCMS m/z 237.1 (M+H).

Intermediate 25

Tert-butyl (1-(4-amino-2-(trifluoromethyl)phenyl)-2-methyl-propan-2-yl)carbamate

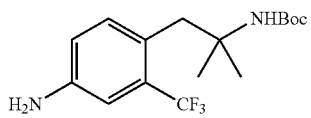

Step 1: Ethyl 2,2-dimethyl-3-(2-(trifluoromethyl)phenyl)propanoate

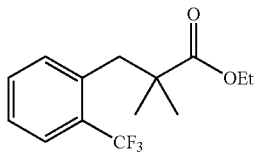 [SMILES: CCOC(=O)C(C)(C)Cc1ccccc1C(F)(F)F]

To a mixture of ethyl isobutyrate (37.9 g, 326 mmol) in THF (1 L) cooled to −30° C. was added LDA (188 mL, 377 mmol) dropwise. The mixture was stirred at −30° C. for 1 hr. To the mixture was added a solution of 1-(bromomethyl)-2-(trifluoromethyl)benzene (60 g, 251 mmol) in THF (150 mL) at −30° C. The whole mixture was stirred at −30° C. for 1 hour and then stirred at 25° C. for 1 hr. The mixture was quenched with NH$_4$Cl (aq, 200 mL). The mixture was added to H$_2$O (200 mL) and extracted with EtOAc (800 mL×3). The organic layer was washed with brine (800 mL), dried over Na$_2$SO$_4$, filtered and concentrated. The crude material was purified on silica column chromatography (PE/EtOAc=200:1). All fractions found to contain product by TLC (PE/EtOAc=10:1, R$_f$=0.6) were combined and concentrated to yield a light yellow solid of ethyl 2,2-dimethyl-3-(2-(trifluoromethyl)phenyl)propanoate (57.5 g, 83.2% yield): $^1$H NMR (400 MHz, CDCl$_3$) δ7.62 (d, J=7.9 Hz, 1H), 7.46-7.38 (m, 1H), 7.29 (t, J=7.6 Hz, 1H), 7.22 (d, J=7.7 Hz, 1H), 4.17 (q, J=7.1 Hz, 2H), 3.14 (s, 2H), 1.25 (t, J=7.2 Hz, 3H), 1.17 (s, 6H).

Step 2: Ethyl 2,2-dimethyl-3-(4-nitro-2-(trifluoromethyl)phenyl)propanoate

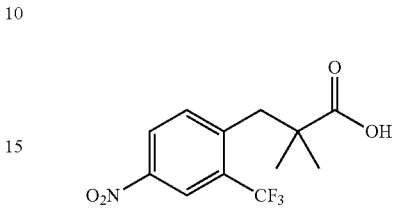

To a solution of ethyl 2,2-dimethyl-3-(2-(trifluoromethyl)phenyl)propanoate (115 g, 419.1 mmol) in H$_2$SO$_4$ (500 mL) cooled to 0° C. was added KNO$_3$ (44.4 g, 440.8 mmol) in portions. The mixture was stirred at 0° C. for 30 min. The mixture was poured into ice-water (1.5 L) and extracted with EtOAc (1 L×3). The combine organic layer was washed with saturated Na$_2$CO$_3$ solution (1 L×3), dried over Na$_2$SO$_4$ and concentrated to give a brown oil of ethyl 2,2-dimethyl-3-(4-nitro-2-(trifluoromethyl)phenyl)propanoate (120 g, 376.1 mmol, 89.5% yield): $^1$H NMR (400 MHz, CDCl$_3$) 8.53 (d, J=2.0 Hz, 1H), 8.29 (dd, J=2.0, 8.5 Hz, 1H), 7.49 (d, J=8.5 Hz, 1H), 4.20 (q, J=7.0 Hz, 2H), 3.25 (s, 2H), 1.27 (t, J=7.0 Hz, 3H), 1.24-1.17 (m, 6H); ES-LCMS m/z: 320 (M+H).

Step 3: 2,2-Dimethyl-3-(4-nitro-2-(trifluoromethyl)phenyl)propanoic acid

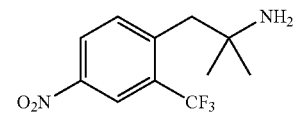

To a solution of ethyl 2,2-dimethyl-3-(4-nitro-2-(trifluoromethyl)phenyl)propanoate (20 g, 62.6 mmol) in THF (60 mL) was added NaOH (39.2 mL, 313 mmol). The mixture was stirred at 80° C. for 12 hrs. Then, THF was removed. The pH of the mixture was adjusted with concentrated HCl to pH=1-2. The mixture was extracted with DCM (30 mL×3). The organic phases were washed with water (20 mL×2) and brine (20 mL), dried over Na$_2$SO$_4$, filtered and concentrated. The crude material was purified by silica column chromatography (Silica gel=20 g) (from PE/EtOAc=10:1 to PE/EtOAc=1:1). All fractions found to contain product by TLC (PE/EtOAc=1:1, R$_f$=0.3) were combined and concentrated to yield a yellow solid of 2,2-dimethyl-3-(4-nitro-2-(trifluoromethyl)phenyl)propanoic acid (16.04 g, 52.3 mmol, 84% yield): $^1$H NMR (400 MHz, CDCl$_3$) δ 8.55 (d, J=2.2 Hz, 1H), 8.41-8.26 (m, 1H), 7.70-7.54 (m, 1H), 3.29 (s, 2H), 1.28 (s, 6H).

Step 4: 2-Methyl-1-(4-nitro-2-(trifluoromethyl)phenyl)propan-2-amine

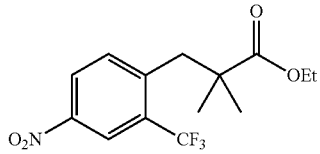 [SMILES: CCOC(=O)C(C)(C)Cc1ccc([N+](=O)[O-])cc1C(F)(F)F]

Et$_3$N (8.21 mL, 58.9 mmol) was added to a solution of 2,2-dimethyl-3-(4-nitro-2-(trifluoromethyl)phenyl)propanoic acid (16.04 g, 55.1 mmol) in toluene (160 mL). Diphenyl phosphorazidate (16.22 g, 58.9 mmol) was added at 0° C. and the mixture was stirred at 0° C. for 1 hr. The mixture was stirred at 20° C. for an additional 1 hour, and then the mixture was stirred at 100° C. for 3 hours. The solution was cooled and washed with water (3×50 mL), and the toluene phase was separated, dried over Na$_2$SO$_4$, and evaporated in vacuum. A mixture of 15% hydrochloric acid (36 mL) and acetic acid (36 mL) was added, and the resulting mixture was stirred at 20° C. 12 hours. The mixture was partitioned between EtOAc (30 mL) and water (40 mL). The aqueous layer was extracted with EtOAc (3×20 mL). The aqueous layer was then adjusted with 2N NaOH to pH=9 and extracted with EtOAc (3×30 mL). The combined organic phases were concentrated in vacuum to afford yellow oil of 2-methyl-1-(4-nitro-2-(trifluoromethyl)phenyl)propan-2-amine (8 g, 27.5 mmol, 49.9% yield): $^1$H NMR (400 MHz, CDCl$_3$) δ 8.55 (d, J=1.8 Hz, 1H), 8.33 (dd, J=1.8, 8.4 Hz, 1H), 8.03-7.86 (m, 1H), 3.00 (s, 2H), 1.18 (s, 6H); ES-LCMS m/z 263.4 (M+H).

Step 5: Tert-butyl (2-methyl-1-(4-nitro-2-(trifluoromethyl)-phenyl)-propan-2-yl)-carbamate

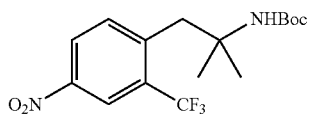

To a solution of 2-methyl-1-(4-nitro-2-(trifluoromethyl)phenyl)propan-2-amine (6 g, 22.88 mmol) in THF (60 mL) was added sodium hydroxide (22.88 mL, 45.8 mmol) and di-tert-butyl dicarbonate (5.99 g, 27.5 mmol). The mixture was stirred at 20° C. for 12 hours. Then the solution was distributed between ethyl acetate (20 mL) and water (40 mL). The aqueous phase was extracted with ethyl acetate (3×30 mL). The combined organic extracts were washed with brine (40 mL), dried over Na$_2$SO$_4$, filtered and concentrated to afford tert-butyl (2-methyl-1-(4-nitro-2-(trifluoromethyl)phenyl)propan-2-yl)carbamate (6.675 g, 16.12 mmol, 70.5% yield). TLC (PE/EtOAc=5:1, R$_f$=0.6): $^1$H NMR (400 MHz, CDCl$_3$) δ 8.54 (s, 1H), 8.39-8.25 (m, 1H), 7.58 (d, J=8.4 Hz, 1H), 3.40 (br. s., 2H), 1.51 (s, 9H), 1.25 (s, 6H); ES-LCMS m/z 307.3 (M-t-Bu+H).

Step 6: Tert-butyl (1-(4-amino-2-(trifluoromethyl)phenyl)-2-methylpropan-2-yl)carbamate

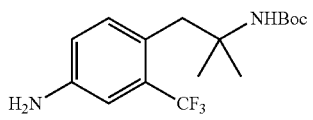 [SMILES: CC(C)(Cc1ccc([N+](=O)[O-])cc1C(F)(F)F)NC(=O)OC(C)(C)C]

To a suspension of tert-butyl (2-methyl-1-(4-nitro-2-(trifluoromethyl)-phenyl)propan-2-yl)carbamate (6.675 g, 18.42 mmol) in methanol (60 mL) was added palladium on carbon (10% in water, 0.196 g, 1.842 mmol). The mixture was hydrogenated under a H$_2$ atmosphere (15 Psi) at 20° C. for 5 hrs. Then the solution was filtered and concentrated to yield a yellow oil of tert-butyl (1-(4-amino-2-(trifluoromethyl)phenyl)-2-methylpropan-2-yl)carbamate (4.5 g, 8.53 mmol, 46.3% yield): TLC (PE/EA=1:1, R$_f$=0.4); $^1$H NMR (400 MHz, CD$_3$OD) δ 7.78 (s, 1H), 7.51 (d, J=7.9 Hz, 1H), 7.28 (d, J=8.4 Hz, 1H), 3.34 (s, 2H), 1.52 (s, 9H), 1.18 (br. s., 6H).

Intermediate 26

3-Amino-N-(2-(dimethylamino)ethyl)-5-(trifluoromethyl)benzamide

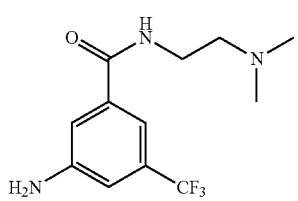 [SMILES: CN(C)CCNC(=O)c1cc([N+](=O)[O-])cc(C(F)(F)F)c1]

Step 1: 3-Nitro-5-(trifluoromethyl)benzoic acid

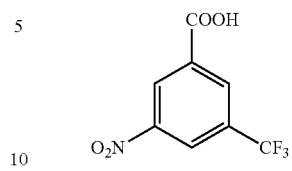

To a mixture of 3-(trifluoromethyl)benzoic acid (5 g, 26.3 mmol) in sulfuric acid (50 ml, 938 mmol) was added nitric acid (3.53 ml, 79 mmol). The mixture was stirred at 0° C. for 15 min and warmed to 90° C. over 1 hour. Then the mixture was added to ice water dropwise. The mixture was then filtered to give a white solid of 3-nitro-5-(trifluoromethyl)benzoic acid (5 g, 20.20 mmol, 77% yield): $^1$H NMR (400 MHz, METHANOL-d$_4$) δ 8.99 (s, 1H), 8.72 (s, 1H), 8.61 (s, 1H).

Step 2: N-(2-(dimethylamino)ethyl)-3-nitro-5-(trifluoromethyl)benzamide

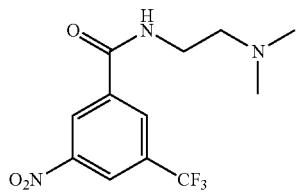 [SMILES: CN(C)CCNC(=O)c1cc(N)cc(C(F)(F)F)c1]

To a mixture of 3-nitro-5-(trifluoromethyl)benzoic acid (500 mg, 2.127 mmol) in DCM (20 mL) was added N$^1$,N$^1$-dimethylethane-1,2-diamine (0.112 mL, 2.339 mmol), HATU (970 mg, 2.55 mmol) and DIEA (0.557 mL, 3.19 mmol). The mixture was stirred at 25° C. for 16 hours. Then a saturated NaHCO$_3$ solution (20 mL) was added. The combined organic extract was washed with brine, dried over MgSO$_4$, filtered and concentrated to afford N-(2-(dimethylamino)ethyl)-3-nitro-5-(trifluoromethyl)-benzamide (400 mg, 1.114 mmol, 52.4% yield). TLC (DCM/MeOH=15:1, R$_f$0.4): $^1$H NMR (400 MHz, METHANOL-d$_4$) δ 8.98 (s, 1H), 8.67 (s, 1H), 8.59 (s, 1H), 3.57 (t, J=6.5 Hz, 2H), 2.60 (t, J=6.5 Hz, 2H), 2.34-2.29 (m, 6H); ES-LCMS m/z 306.1 (M+H).

Step 3: 3-Amino-N-(2-(dimethylamino)ethyl)-5-(trifluoromethyl)benzamide

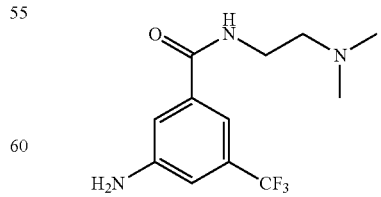

To a mixture of N-(2-(dimethylamino)ethyl)-3-nitro-5-(trifluoromethyl)benzamide (400 mg, 1.310 mmol) in methanol (20 mL) was added Pd/C (10%, 40 mg). The mixture was stirred at 25° C. for 16 hours under Hydrogen.

Then the mixture was filtered and concentrated to afford 3-amino-N-(2-(dimethylamino)ethyl)-5-(trifluoromethyl)benzamide (300 mg, 0.926 mmol, 70.7% yield). TLC (DCM/MeOH=10:1, $R_f$=0.2): $^1$H NMR (400 MHz, METHANOL-$d_4$) δ 7.28 (d, J=10.8 Hz, 2H), 7.03 (s, 1H), 3.50 (t, J=6.7 Hz, 2H), 2.55 (t, J=6.7 Hz, 2H), 2.30 (s, 6H); ES-LCMS m/z 276.1 (M+H).

Preparation Of Compounds Of The Invention

EXAMPLE 1

1-(2-Fluoro-4-(7-oxo-6,7-dihydrofuro[2,3-c]pyridin-4-yl)phenyl)-3-(4-((3-methyloxetan-3-yl)oxy)-3-(trifluoromethyl)phenyl)urea

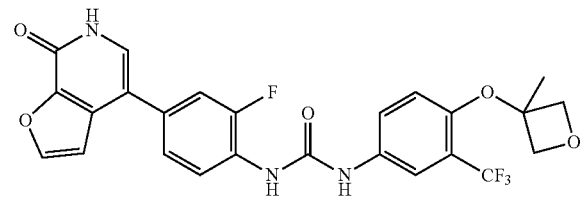 [SMILES: CC1(Oc2ccc(NC(=O)Nc3ccc(-c4c[nH]c(=O)c5occc45)cc3F)cc2C(F)(F)F)COC1]

Step 1: (3-Fluoro-4-(3-(4-((3-methyloxetan-3-yl)oxy)-3-(trifluoromethyl)phenyl)ureido)phenyl)boronic acid

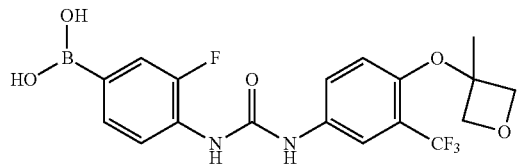 [SMILES: CC1(Oc2ccc(NC(=O)Nc3ccc(B(O)O)cc3F)cc2C(F)(F)F)COC1]

To a mixture of 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (6 g, 11.76 mmol), NH$_4$OAc (2.72 g, 35.3 mmol) in acetone (50 mL) and water (50 mL) was added NaIO$_4$ (7.54 g, 35.3 mmol). Then mixture was stirred at 25° C. for 12 h. Then the mixture was concentrated to give the residue, which was extracted with DCM (20 mL×2). The organic extract was washed with brine, dried over Na$_2$SO$_4$, filtered and concentrated to yield an off white solid of (3-fluoro-4-(3-(4-((3-methyloxetan-3-yl)oxy)-3-(trifluoromethyl)phenyl)ureido)phenyl)boronic acid (4.5 g, 9.32 mmol, 79% yield): $^1$H NMR (400 MHz, CDCl$_3$) δ 8.12-8.08 (m, 1H), 7.80 (s, 1H), 7.57-7.44 (br, 3H), 6.65-6.63 (d, J=8.8 Hz, 1H), 4.93-4.91 (d, J=6.4 Hz, 2H), 4.66-4.64 (d, J=7.6 Hz, 2H), 1.74(s, 3H); ES-LCMS m/z 429.1 (M+H).

Step 2: (E)-3-(Furan-3-yl)acrylic acid

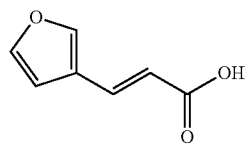

To a suspension of furan-3-carbaldehyde (2.3 g, 23.94 mmol) in pyridine (15 mL) was added malonic acid (2.74 g, 26.3 mmol). Piperidine (0.204 g, 2.394 mmol) was added and the mixture was stirred at 100° C. for 12 h. The mixture was then cooled to rt. Then the solution was poured into water (10 mL) and acidified with 6M HCl. The resulting solution was diluted with EA. The combined organic extract was washed with brine, dried over MgSO$_4$, filtered and concentrated. The resulting (E)-3-(furan-3-yl)acrylic acid (2.49 g, 18.03 mmol, 75% yield). TLC (PE/EA=5:1, $R_f$=0.6): $^1$H NMR (400 MHz, CD$_3$OD) δ 7.81 (s, 1H), 7.59 (s, 1H), 7.55-7.52 (d, J=12.8 Hz, 1H), 6.73 (s, 1H), 6.20-6.16 (d, J=15.6 Hz, 1H); ES-LCMS m/z 139.0 (M+H).

Step 3: (E)-3-(Furan-3-yl)acryloyl azide

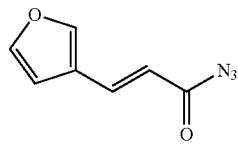 [SMILES: [N-]=[N+]=NC(=O)/C=C/c1ccoc1]

To a solution of (E)-3-(furan-3-yl)acrylic acid (2.49 g, 18.03 mmol) in THF (10 mL) was added Et$_3$N (2.189 g, 21.63 mmol). DPPA (5.46 g, 19.83 mmol) was added and the mixture was at 25° C. for 4 h. Then the solution was distributed between EA and saturated NaHCO$_3$ solution. The combined organic extract was washed with brine, dried over MgSO$_4$, filtered and concentrated. The residue was washed with MeOH, and filtered to give a light yellow solid of (E)-3-(furan-3-yl)acryloyl azide (3.46 g, 21.21 mmol, 118% yield): $^1$H NMR (400 MHz, CDCl$_3$) δ 8.76 (s, 1H), 7.46 (s, 1H), 4.16 (s, 3H); $^1$H NMR (400 MHz, CD$_3$Cl) δ 7.69 (s, 1H), 7.65-7.61 (d, J=16 Hz, 1H), 7.43 (s, 1H), 6.58 (s, 1H), 6.15-6.11 (d, J=16 Hz, 1H).

Step 4: Furo[2,3-c]pyridin-7(6H)-one

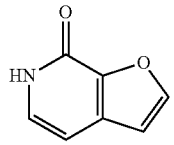

To a solution of (E)-3-(furan-3-yl)acryloyl azide (3.46 g, 21.21 mmol) in 1,2-dichlorobenzene (31.2 g, 212 mmol) was added I$_2$ (0.022 g, 0.085 mmol). The mixture was at 180° C. for 2 h. Then the solution was concentrated. The residue was purified by silica column chromatography (PE/EA=1:1). All fractions found to contain product by TLC (DCM/MeOH=10:1, $R_f$=0.5) were combined and concentrated to yield a light yellow solid of furo[2,3-c]pyridin-7(6H)-one (765 mg, 5.66 mmol, 26.7% yield): $^1$H NMR (400 MHz, CD$_3$OD) δ 7.96-7.95 (d, J=2.0 Hz, 1H), 7.20-7.18 (d, J=6.8 Hz, 1H), 6.84-6.83 (d, J=2.0 Hz, 1H), 6.70-6.68 (d, J=6.8 Hz, 1H); ES-LCMS m/z 241 (M+H).

Step 5: 4-bromofuro[2,3-c]pyridin-7(6H)-one

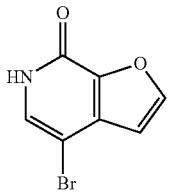

To a solution of furo[2,3-c]pyridin-7(6H)-one (20 mg, 0.148 mmol) in AcOH (5 mL) was added Br$_2$ (7.63 µL, 0.148 mmol). The mixture was at 25° C. for 2 h. Then the solution was concentrated and distributed between EA and saturated NaHCO$_3$ solution. The combined organic extract was washed with brine, dried over MgSO$_4$, filtered and concentrated. The resulting 4-bromofuro[2,3-c]pyridin-7(6H)-one (16 mg, 0.075 mmol, 50.5% yield). TLC (PE/EA=5:1, R$_f$=0.6): ES-LCMS m/z 214.9-215.9 (M+H).

Step 6: 1-(2-Fluoro-4-(7-oxo-6,7-dihydrofuro[2,3-c]pyridin-4-yl)phenyl)-3-(4-((3-methyloxetan-3-yl)oxy)-3-(trifluoromethyl)phenyl)urea

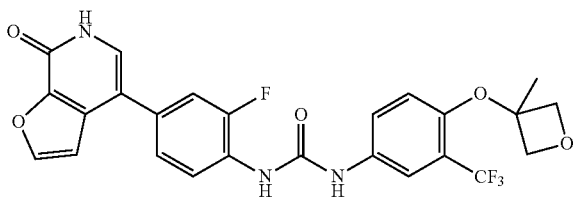 [SMILES: CC1(Oc2ccc(NC(=O)Nc3ccc(-c4c[nH]c(=O)c5occc45)cc3F)cc2C(F)(F)F)COC1]

A suspension of (3-fluoro-4-(3-(4-((3-methyloxetan-3-yl)oxy)-3-(trifluoromethyl)phenyl)ureido)phenyl)boronic acid (100 mg, 0.234 mmol) in 1,4-dioxane (1.8 mL) and water (0.600 mL) was added to a solution of 4-bromofuro[2,3-c]pyridin-7(6H)-one (50 mg, 0.234 mmol) in 1,4-dioxane (1.8 mL) and water (0.600 mL). PdCl$_2$(dppf) (17.09 mg, 0.023 mmol) and Cs$_2$CO$_3$ (190 mg, 0.584 mmol) were added and the mixture was stirred at 110° C. for 30 min under microwave. The mixture was then cooled to rt. Then the solution was concentrated and distributed between EA and saturated NaHCO$_3$ solution. The combined organic extract was washed with brine, dried over MgSO$_4$, filtered and concentrated. The residue was purified by preparative HPLC (MeCN/H$_2$O as eluants, acidic condition) to yield a yellow solid of 1-(2-fluoro-4-(7-oxo-6,7-dihydrofuro[2,3-c]pyridin-4-yl)phenyl)-3-(4-((3-methyloxetan-3-yl)oxy)-3-(trifluoromethyl)phenyl)urea (16.89 mg, 0.033 mmol, 13.97% yield): $^1$H NMR (400 MHz, CD$_3$OD) δ 8.22-8.20 (m, 1H), 8.06 (s, 1H), 7.80 (s, 1H), 7.56-7.53(m, 1H), 7.38-7.33 (m, 3H), 7.03 (s, 1H), 6.63-6.61 (d, J=8.8 Hz, 1H), 4.90-4.88 (d, J=7.2 Hz, 2H), 4.64-4.62 (d, J=7.6 Hz, 2H), 1.72 (s, 3H); ES-LCMS m/z 518.1 (M+H).

EXAMPLE 2

1-(4-(5-Ethoxy-6-oxo-1,6-dihydropyridin-3-yl)-2-fluorophenyl)-3-(3-(4-methyl-1H-imidazol-1-yl)-5-(trifluoromethyl)phenyl)urea

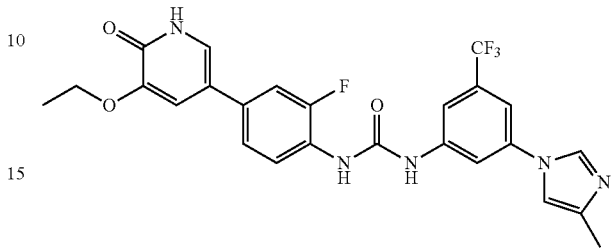

Step 1: 2-Fluoro-4-(4,4,5,5-tetramethyl-1,3,2-dioxaborolan-2-yl)aniline

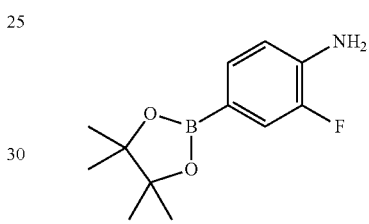

To a solution of 4-bromo-2-fluoroaniline (40 g, 211 mmol), 4,4,4',4',5,5,5',5'-octamethyl-2,2'-bi(1,3,2-dioxaborolane) (64.1 g, 253 mmol) and KOAc (41.3 g, 421 mmol) in 1,4-dioxane (500 mL) stirred under N$_2$ at 20° C. was added PdCl$_2$(dppf) (7.70 g, 10.53 mmol) in one charge. The reaction mixture was stirred at 100° C. for 3 h. The solution was concentrated in vacuo to give 2-fluoro-4-(4,4,5,5-tetramethyl-1,3,2-dioxaborolan-2-yl)aniline (44 g, 158 mmol, 74.9% yield): $^1$H NMR (400 MHz, CDCl$_3$) δ 7.46-7.40 (m, 2H), 6.75-6.71 (m, 1H), 1.30 (s, J=3.6 Hz, 12H); ES-LCMS m/z 238.1 (M+H).

Step 2: 4-(5-Ethoxy-6-((4-methoxybenzyl)oxy)pyridin-3-yl)-2-fluoroaniline

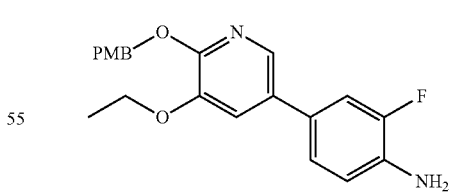

To a mixture of 5-bromo-3-ethoxy-2-((4-methoxybenzyl)oxy)pyridine (5 g, 14.78 mmol) in 1,4-dioxane (30 mL) and water (10.0 mL) was added 5-bromo-3-ethoxy-2-((4-methoxybenzyl)oxy)pyridine (5 g, 14.78 mmol), Cs$_2$CO$_3$ (9.63 g, 29.6 mmol) and PdCl$_2$(dppf) (1.082 g, 1.478 mmol). The mixture was stirred under N$_2$ at 110° C. for 16 h. Then the reaction residue was filtered and the filtrate was concentrated, which was purified by silica column chromatography (PE/EA=8/1). All fractions found to contain product by TLC (PE/EA=8/1, R$_f$=0.6) were combined and concentrated to yield a white solid of 4-(5-ethoxy-6-((4-methoxybenzyl)oxy)pyridin-3-yl)-2-fluoroaniline (4 g, 9.77 mmol, 66.1% yield): $^1$H NMR (400 MHz, CD$_3$OD) δ 7.83 (d, J=2.0 Hz, 1H), 7.40-7.37 (m, 2H), 7.34 (d, J=2.0 Hz, 1H), 7.24-7.20 (m, 1H), 7.17-7.14 (m, 1H), 6.92-6.89 (m, 3H), 5.33 (s, 2H), 4.15-4.09 (m, 2H), 3.78 (s, 3H), 1.40 (t, J=7.2 Hz, 3H); ES-LCMS m/z 369.1 (M+H).

Step 3: 3-Ethoxy-5-(3-fluoro-4-isocyanatophenyl)-2-((4-methoxybenzyl)oxy)pyridine

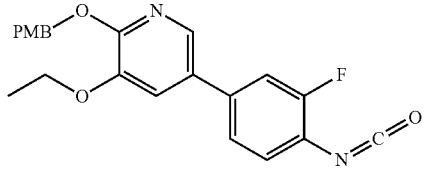

A suspension of 4-(5-ethoxy-6-((4-methoxybenzyl)oxy)pyridin-3-yl)-2-fluoroaniline (197 mg, 0.535 mmol) in THF (10 mL) was added to a solution of triphosgene (71.4 mg, 0.241 mmol) in THF (10 mL). The mixture was at 60° C. for 5 min. The mixture was then cooled to rt. Then the solution was concentrated. The resulting 3-ethoxy-5-(3-fluoro-4-isocyanatophenyl)-2-((4-methoxybenzyl)oxy)pyridine (200 mg, 0.507 mmol, 95% yield). TLC (PE/EA=5/1, R$_f$=0.5): ES-LCMS m/z 307.1 (M-87H).

Step 4: 1-(4-(5-Ethoxy-6-((4-methoxybenzyl)oxy)pyridin-3-yl)-2-fluorophenyl)-3-(3-(4-methyl-1H-imidazol-1-yl)-5-(trifluoromethyl)phenyl)urea

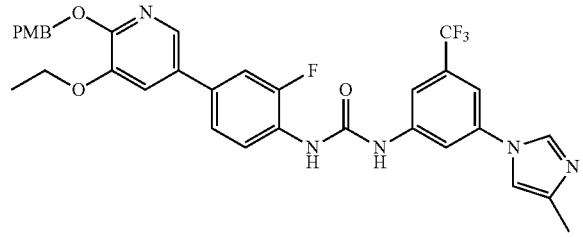

A suspension of 3(4-methyl-1H-imidazol-1-yl)-5-(trifluoromethyl)aniline (129 mg, 0.535 mmol) in THF (10 mL) was added to a solution of 3-ethoxy-5-(3-fluoro-4-isocyanatophenyl)-2-((4-methoxybenzyl)oxy)pyridine (212 mg, 0.535 mmol) in THF (10 mL). Et$_3$N (0.186 mL, 1.337 mmol) and DMAP (6.53 mg, 0.053 mmol) was added and the mixture was stirred at 60° C. for 10 h. The mixture was cooled to rt. Then the solution was concentrated and distributed between EA and saturated NaHCO$_3$ solution. The combined organic extract was washed with brine, dried over MgSO$_4$, filtered and concentrated. The residue was purified by preparative TLC (DCM/MeOH=20/1, R$_f$=0.4) to yield a light yellow solid of 1-(4-(5-ethoxy-6-((4-methoxybenzyl)oxy)pyridin-3-yl)-2-fluorophenyl)-3-(3-(4-methyl-1H-imidazol-1-yl)-5-(trifluoromethyl)phenyl)urea (80 mg, 0.126 mmol, 23.53% yield): $^1$H NMR (400 MHz, CD$_3$OD) δ 8.22 (s, 1H), 8.18 (s, 1H), 7.98 (s, 1H), 7.91 (s, 1H), 7.74 (s, 1H), 7.49 (s, 1H), 7.49-7.37 (m, 6H), 6.90-6.88 (m, 2H), 5.33 (s, 2H), 4.14-4.12 (m, 2H), 3.78 (s, 3H), 2.30 (s, 3H), 1.42-1.39 (t, J=7.0 Hz, 3H); ES-LCMS m/z 636.0 (M+H).

Step 5: 1-(4-(5-Ethoxy-6-oxo-1,6-dihydropyridin-3-yl)-2-fluorophenyl)-3-(3-(4-methyl-1H-imidazol-1-yl)-5-(trifluoromethyl)phenyl)urea

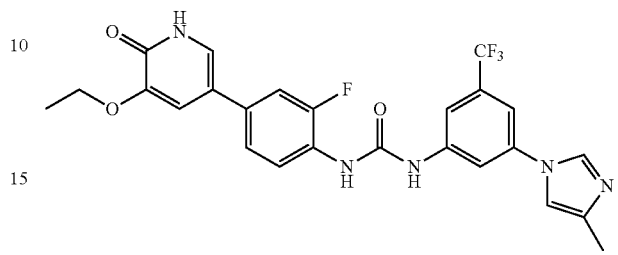

A suspension of 1-(4-(5-ethoxy-6-((4-methoxybenzyl)oxy)pyridin-3-yl)-2-fluorophenyl)-3-(3-(4-methyl-1H-imidazol-1-yl)-5-(trifluoromethyl)phenyl)urea (80 mg, 0.126 mmol) in MeOH (10 mL) was added to a solution of Pd/C (26.8 mg, 0.252 mmol)(10%) in MeOH (10 mL). The mixture was hydrogenated under H$_2$ atmosphere at 26° C. for 10 h. Then the solution was filtered and concentrated. The residue was purified by preparative HPLC (MeCN/H$_2$O as eluants, basic condition) to yield a white solid of 1-(4-(5-ethoxy-6-oxo-1,6-dihydropyridin-3-yl)-2-fluorophenyl)-3-(3-(4-methyl-1H-imidazol-1-yl)-5-(trifluoromethyl)phenyl)urea (14.40 mg, 0.028 mmol, 22.20% yield). TLC (DCM/MeOH=10/1, R$_f$=0.4): $^1$H NMR (400 MHz, CD$_3$OD) δ 8.16 (s, 1H), 8.11-8.10 (d, J=1.6 Hz, 1H), 7.97 (s, 1H), 7.74 (s, 1H), 7.49 (s, 1H), 7.36-7.35(m, 3H), 7.27 (s, 1H), 7.22 (s, 1H), 4.13-4.11 (m, 2H), 2.26 (s, 3H), 1.48-1.44 (t, J=7.0 Hz, 3H); ES-LCMS m/z 516.1 (M+H).

EXAMPLE 3

1-(4-Ethoxy-3-(trifluoromethyl)phenyl)-3-(2-fluoro-4-(1-oxo-2,5,6,7-tetrahydro-1H-cyclopenta[c]pyridin-4-yl)phenyl)urea

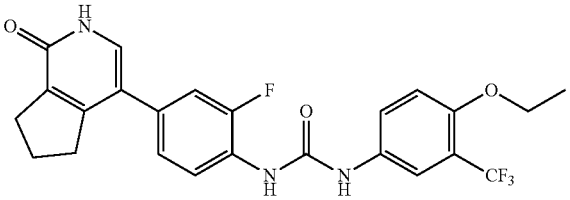 [SMILES: CCOc1ccc(NC(=O)Nc2ccc(-c3c[nH]c(=O)c4c3CCC4)cc2F)cc1C(F)(F)F]

Step 1: Ethyl 2-(2-ethoxy-2-oxoethyl)cyclopent-1-enecarboxylate

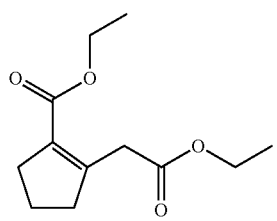 [SMILES: CCOC(=O)CC1=C(C(=O)OCC)CCC1]

A mixture of ethyl 2-(triphenylphosphoranylidene)acetate (89 g, 256 mmol), ethyl 2-oxocyclopentanecarboxylate (40 g, 256 mmol) in toluene (300 mL) was stirred at 120° C. for 34 h. The solvent was then removed and the residue was extracted with EA (2×200 mL), the combined organic phase was washed with brine (40 mL) and dried over anhydrous Na$_2$SO$_4$, filtered and the filtrate was concentrated, the residue was purified by column (PE:EA=20:1) to provide ethyl 2-(2-ethoxy-2-oxoethyl)cyclopent-1-enecarboxylate as yellow oil (15 g, 23% yield): $^1$H NMR (400 MHz, CDCl$_3$) δ 4.13 (m, 4H), 3.66 (s, 2H), 3.31 (m, 2H), 2.29 (m, 2H), 1.84 (m, 2H), 1.28 (m, 8H); ES-LCMS m/z 227.1 (M+H).

Step 2: Ethyl 1-oxo-1,5,6,7-tetrahydrocyclopenta[c]pyran-4-carboxylate

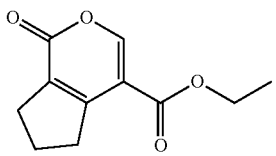

A mixture of ethyl 2-(2-ethoxy-2-oxoethyl)cyclopent-1-enecarboxylate (7.5 g, 33.1 mmol), 1,1-dimethoxy-N,N-dimethylmethanamine (3.95 g, 33.1 mmol) in DMF (50 mL) was stirred at 120° C. for 2 h, the solvent was removed and the residue was purified by column (PE:EA=5:1) to provide 1-oxo-1,5,6,7-tetrahydrocyclopenta[c]pyran-4-carboxylate as yellow oil (1.2 g, 10.61% yield): $^1$H NMR (400 MHz, CD$_3$OD) δ 4.18 (m, 5H), 1.88 (m, 2H), 1.21 (m, 5H); ES-LCMS m/z 209.1 (M+H).

Step 3: 2,5,6,7-Tetrahydro-1H-cyclopenta[c]pyridin-1-one

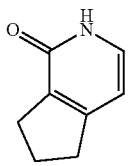

A mixture of ethyl 1-oxo-1,5,6,7-tetrahydrocyclopenta[c]pyran-4-carboxylate (200 mg, 0.961 mmol), ammonia (0.208 mL, 9.61 mmol) in EtOH (1 mL) was stirred at 80° C. for 2 h, the solvent was concentrated and the residue was purified by preparative TLC (DCM:MeOH=10:1) to provide us 2,5,6,7-tetrahydro-1H-cyclopenta[c]pyridin-1-one (23 mg, 16.67% yield): $^1$H NMR (400 MHz, CD$_3$OD) δ 7.25 (d, J=7.6 Hz, 1H), 6.40 (d, J=6.4 Hz, 1H), 2.9-2.72 (m, 4H), 2.06 (m, 2H); ES-LCMS m/z 136.1 (M+H).

Step 4: 4-Bromo-2,5,6,7-tetrahydro-1H-cyclopenta[c]pyridin-1-one

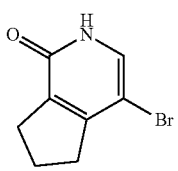 [SMILES: O=c1[nH]cc(Br)c2c1CCC2]

A mixture of 2,5,6,7-tetrahydro-1H-cyclopenta[c]pyridin-1-one (34 mg, 0.252 mmol), bromine (0.016 mL, 0.302 mmol) in AcOH (2 mL) was stirred at 25° C. for 1 h. Brown solid appeared and the solvent was removed and the residue was purified by preparative TLC (DCM:MeOH=40:1) to provide 4-bromo-2,5,6,7-tetrahydro-1H-cyclopenta[c]pyridin-1-one as a brown solid (50 mg, 91% yield): $^1$H NMR (400 MHz, CD$_3$OD) δ 7.48 (s, 1H), 2.94 (m, 4H), 2.15 (m, 2H); ES-LCMS m/z 215.9 (M+2H).

Step 5: 4-(4-Amino-3-fluorophenyl)-2,5,6,7-tetrahydro-1H-cyclopenta[c]pyridin-1-one

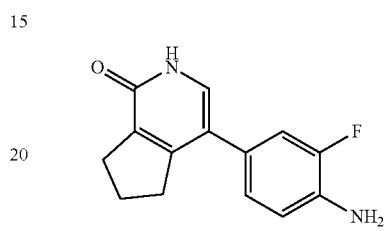

A mixture of 4-bromo-2,5,6,7-tetrahydro-1H-cyclopenta[c]pyridin-1-one (20 mg, 0.093 mmol), 2-fluoro-4-(4,4,5,5-tetramethyl-1,3,2-dioxaborolan-2-yl)aniline (22.15 mg, 0.093 mmol), PdCl$_2$(dppf) (6.84 mg, 9.34 μmol), K$_2$CO$_3$ (25.8 mg, 0.187 mmol) in 1,4-dioxane (3 mL) and water (1 mL) was stirred at 90° C. for 30 min under microwave. LCMS showed the reaction was complete, the solvent was concentrated and the residue was purified by preparative TLC (DCM:MeOH=10:1) to provide 4-(4-amino-3-fluorophenyl)-2,5,6,7-tetrahydro-1H-cyclopenta[c]pyridin-1-one (11 mg, 48.2% yield): $^1$H NMR (400 MHz, CD$_3$OD) δ 7.27-7.25 (m, 1H), 7.0-6.42 (m, 3H), 2.96-2.78 (m, 4H), 2.08 (m, 2H); ES-LCMS m/z 245.1 (M+H).

Step 6: 1-(4-Ethoxy-3-(trifluoromethyl)phenyl)-3-(2-fluoro-4-(1-oxo-2,5,6,7-tetrahydro-1H-cyclopenta[c]pyridin-4-yl)phenyl)urea

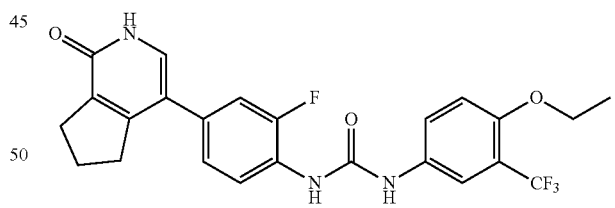

A mixture of 4-ethoxy-3-(trifluoromethyl)aniline (9.23 mg, 0.045 mmol), triphosgene (6.01 mg, 0.020 mmol) in THF (3 mL) was stirred at 60° C. for 0.5 h, LCMS showed the reaction was completed, the solvent was concentrated to provide 1-ethoxy-4-isocyanato-2-(trifluoromethyl)benzene (10.1 mg, 0.041 mmol, 92% yield). A mixture of 1-ethoxy-4-isocyanato-2-(trifluoromethyl)benzene (10 mg, 0.043 mmol), 4-(4-amino-3-fluorophenyl)-2,5,6,7-tetrahydro-1H-cyclopenta[c]pyridin-1-one (10.57 mg, 0.043 mmol), Et$_3$N (6.03 μL, 0.043 mmol) in THF (4 mL) was stirred at 60° C. for 30 min, the solvent was concentrated and the residue was purified by preparative HPLC to provide 1-(4-ethoxy-3-(trifluoromethyl)phenyl)-3-(2-fluoro-4-(1-oxo-2,5,6,7-tetrahydro-1H-cyclopenta[c]pyridine-4-yl)phenyl)urea (5 mg, 24.31% yield): $^1$H NMR (400 MHz, CD$_3$OD) δ 8.22 (t, J=8.80 Hz, 1H), 7.75 (d, J=2.4 Hz, 1H), 7.70 (s, 1H), 7.55 (m, 1H), 7.30 (d, J=12 Hz, 1H), 7.23 (d, J=7.2 Hz, 1H), 7.12 (d, J=8.8 Hz, 1H), 4.14 (t, J=6.8 Hz, 2H), 3.10 (t, J=7.6 Hz, 2H), 2.97 (t, J=7.6 Hz, 2H), 2.19 (m, 2H), 1.39 (t, J=7.2 Hz, 3H); ES-LCMS m/z 476.1 (M+H).

EXAMPLE 4

1-(2-Fluoro-4-(4-oxo-4,5-dihydro-1H-pyrazolo[4,3-c]pyridin-7-yl)phenyl)-3-(4-((3-methyloxetan-3-yl)oxy)-3-(trifluoromethyl)phenyl)urea

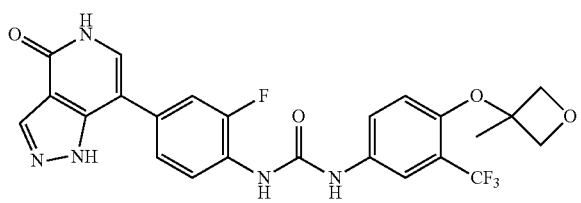 [SMILES: CC1(Oc2ccc(NC(=O)Nc3ccc(-c4c[nH]c(=O)c5cn[nH]c45)cc3F)cc2C(F)(F)F)COC1]

Step 1: 4-Chloro-1H-pyrazolo[4,3-c]pyridine

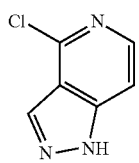

A mixture of 2,4-dichloronicotinaldehyde (800 mg, 4.55 mmol) and hydrazine (364 mg, 9.09 mmol) in DME (10 mL) was stirred at 80° C. for 2 h, the solvent was concentrated and the residue was purified by column chromatography (DCM:MeOH=20:1, 800 mL) to provide 4-chloro-1H-pyrazolo[4,3-c]pyridine (400 mg, 2.474 mmol, 54.4% yield): $^1$H NMR (400 MHz, CDCl$_3$) δ 13.85 (m, 1H), 8.31 (s, 1H), 8.13 (d, J=5.6 Hz, 1H), 7.60 (d, J=5.6 Hz, 1H); ES-LCMS m/z 154.0 (M+H).

Step 2: 1H-Pyrazolo[4,3-c]pyridin-4(5H)-one

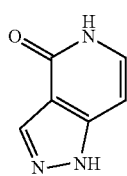

A mixture of 4-chloro-1H-pyrazolo[4,3-c]pyridine (400 mg, 2.60 mmol), AcOH (29.8 mL, 521 mmol) and water (0.1 mL) was stirred at 100° C. for 8 h, LCMS showed the reaction was completed, the solvent was concentrated to provide 1H-pyrazolo[4,3-c]pyridin-4-ol (300 mg, 2.027 mmol, 78% yield): $^1$H NMR (400 MHz, CDCl$_3$) δ 10.87 (m, 1H), 8.06 (s, 1H), 7.11 (d, J=6.8 Hz, 2H), 6.42 (d, J=6.8 Hz, 2H).

Step 3: 7-Bromo-1H-pyrazolo[4,3-c]pyridin-4(5H)-one

A mixture of 1H-pyrazolo[4,3-c]pyridin-4(5H)-one (80 mg, 0.592 mmol), Br$_2$ (0.031 mL, 0.592 mmol) in AcOH (5 mL) was stirred at 30° C. for 8 h, the solvent was concentrated and the residue was purified by preparative HPLC to provide 7-bromo-1H-pyrazolo[4,3-c]pyridin-4(5H)-one (65 mg, 0.301 mmol, 50.8% yield): $^1$H NMR (400 MHz, DMSO) δ 13.2-12.9 (m, 1H), 10.4-10.0 (m, 1H), 7.7-7.3 (m, 1H), 6.57-6.42 (m, 1H); ES-LCMS m/z 214.0, 216.0 (M+H).

Step 4: 1-(2-Fluoro-4-(4-oxo-4,5-dihydro-1H-pyrazolo[4,3-c]pyridin-7-yl)phenyl)-3-(4-((3-methyloxetan-3-yl)oxy)-3-(trifluoromethyl)phenyl)urea

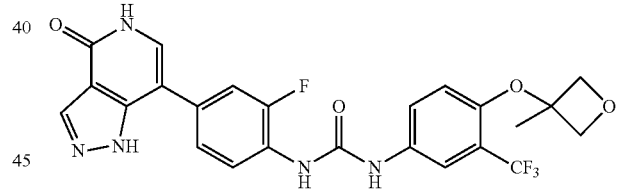

A mixture of 7-bromo-1H-pyrazolo[4,3-c]pyridin-4(5H)-one (20 mg, 0.093 mmol), 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (40.0 mg, 0.093 mmol), PdCl$_2$(dppf)-DCM adduct (7.63 mg, 9.34 μmol), K$_2$CO$_3$ (25.8 mg, 0.187 mmol) in DMF (2 mL) and water (0.2 mL) was stirred at 120° C. under microwave for 130 min, the solvent was concentrated and the residue was purified by preparative TLC (DCM:MeOH=10:1, R$_f$=0.35) and then purified by preparative HPLC to provide 1-(2-fluoro-4-(4-oxo-4,5-dihydro-1H-pyrazolo[4,3-c]pyridin-7-yl)phenyl)-3-(4-((3-methyloxetan-3-yl)oxy)-3-(trifluoromethyl)phenyl)urea (1.33 mg, 2.480 μmol, 2.65% yield): $^1$H NMR (400 MHz, CD$_3$OD+DMSO-d$_6$) δ 8.49-8.21 (m, 2H), 7.84 (d, J=2.8 Hz, 1H), 7.57-7.53 (m, 3H), 7.31 (s, 1H), 6.65 (d, J=8.8 Hz, 1H), 4.91 (m, 2H), 4.64 (m, 2H), 1.72 (s, 1H); ES-LCMS m/z 518.1 (M+H).

EXAMPLE 5

1-(5'-Ethoxy-6-methyl-6'-oxo-1',6'-dihydro-[2,3'-bipyridin]-5-yl)-3-(4-isopropoxy-3-(trifluoromethyl)phenyl)urea

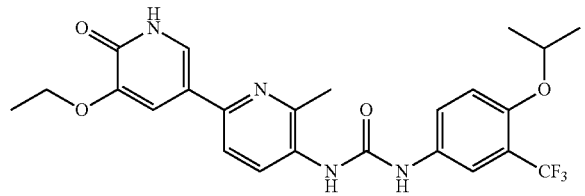 [SMILES: CCOc1cc(-c2ccc(NC(=O)Nc3ccc(OC(C)C)c(C(F)(F)F)c3)c(C)n2)c[nH]c1=O]

Step 1: 5-Amino-5'-ethoxy-6-methyl[2,3'-bipyridin]-6'(1'H)-one

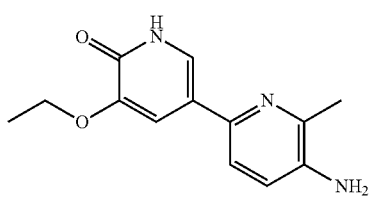 [SMILES: CCOc1cc(-c2ccc(N)c(C)n2)c[nH]c1=O]

A mixture of 6'-(benzyloxy)-5'-ethoxy-6-methyl-5-nitro-2,3'-bipyridine (150 mg, 0.411 mmol) and Pd/C (2.184 mg, 0.021 mmol) in MeOH (10 mL) was stirred for 1 h at 25° C. under a $H_2$ atmosphere. Then the mixture was concentrated to give the residue which was extracted with DCM (20 mL×2). The organic extract was washed with brine, dried over $Na_2SO_4$, filtered and concentrated. The residue was purified by preparative TLC (EA:PE=1:1) to yield 5-amino-5'-ethoxy-6-methyl-[2,3'-bipyridin]-6'(1'H)-one (80 mg, 0.245 mmol, 59.6% yield): $^1$H NMR (400 MHz, $CD_3OD$) δ 7.46 (d, J=2.00 Hz, 1H), 7.42 (d, J=2.00 Hz, 1H), 7.30-7.28 (m, 1H), 7.07-7.05 (d, J=8.40 Hz, 1H), 4.14-4.08 (m, 2H); 2.38 (s, 3H), 1.45(t, J=7.00 Hz, 3H); ES-LCMS m/z 246 (M+H).

Step 2: 4-Isocyanato-1-isopropoxy-2-(trifluoromethyl)benzene

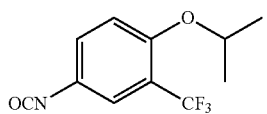

To a mixture of 4-isopropoxy-3-(trifluoromethyl)aniline hydrochloride (70 mg, 0.274 mmol) in THF (10 mL) was added $Et_3N$ (0.038 mL, 0.274 mmol). Then mixture was heated to 60° C. for 30 min, the mixture was concentrated to give 4-isocyanato-1-isopropoxy-2-(trifluoromethyl)benzene (60 mg, 0.224 mmol, 82% yield): ES-LCMS m/z 278 (M+33).

Step 3: 1-(5'-Ethoxy-6-methyl-6'-oxo-1',6'-dihydro-[2,3'-bipyridin]-5-yl)-3-(4-isopropoxy-3-(trifluoromethyl)phenyl)urea

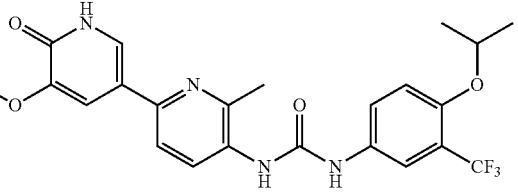

To a mixture of 5-amino-5'-ethoxy-6-methyl-[2,3'-bipyridin]-6'(1'H)-one (60 mg, 0.245 mmol) and 4-isocyanato-1-isopropoxy-2-(trifluoromethyl)benzene (60.0 mg, 0.245 mmol) in THF (10 mL) was added $Et_3N$ (0.102 mL, 0.734 mmol). Then mixture was heated to 60° C. for 30 min, the mixture was concentrated and then purified by preparative HPLC to yield a light yellow solid of 1-(5'-ethoxy-6'-hydroxy-6-methyl-[2,3'-bipyridin]-5-yl)-3-(4-isopropoxy-3-(trifluoromethyl)phenyl)urea hydrochloride (54.09 mg, 0.102 mmol, 41.6% yield): $^1$H NMR (400 MHz, $CD_3OD$) δ 8.83 (m, 1H), 7.93 (s, 1H), 7.79-7.73 (d, J=11.2 Hz, 1H), 7.59 (t, J=5.80 Hz, 1H), 7.44 (s, 1H), 7.20-7.17 (d, J=8.80 Hz, 1H), 4.72 (t, J=6.20 Hz, 1H), 4.17 (t, J=7.00 Hz, 2H), 2.77-2.75 (d, J=8.00 Hz, 3H), 1.51 (t, J=7.00 Hz, 3H), 1.36-1.34 (d, J=6.00 Hz, 6H); ES-LCMS m/z 491 (M+H).

EXAMPLE 6

1-(3-(Difluoromethyl)-4-isopropoxyphenyl)-3-(5'-ethoxy-6-methyl-6'-oxo-1',6'-dihydro-[2,3'-bipyridin]-5-yl)urea

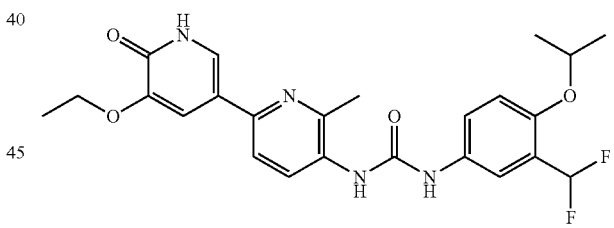

Step 1: 3-(Difluoromethyl)-4-isopropoxyaniline

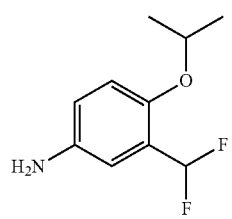

A mixture of 2-(difluoromethyl)-1-isopropoxy-4-nitrobenzene (200 mg, 0.865 mmol), $Na_4Cl$ (463 mg, 8.65 mmol) and zinc (566 mg, 8.65 mmol) in MeOH (20 mL) was stirred for 2 h at 25° C. The mixture was extracted with DCM (200 mL×2), dried over Na₂SO₄, and concentrated to give 3-(difluoromethyl)-4-isopropoxyaniline (150 mg, 0.482 mmol, 55.7% yield): ¹H NMR (400 MHz, CD₃OD) δ 6.90-6.80 (m, 3H), 6.85 (t, J=56.00 Hz, 1H), 4.50-4.38 (m, 1H), 1.26-1.25 (d, J=6.00 Hz, 1H); ES-LCMS m/z 202 (M+H).

Step 2: 2-(Difluoromethyl)-4-isocyanato-1-isopropoxybenzene

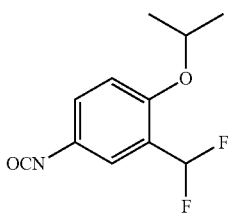

To a mixture of 3-(difluoromethyl)-4-isopropoxyaniline (200 mg, 0.994 mmol) in THF (10 mL) was added triphosgene (118 mg, 0.398 mmol). Then mixture was heated to 60° C. for 30 min, the mixture was concentrated to give 4-cyanato-2-(difluoromethyl)-1-isopropoxybenzene (210 mg, 0.620 mmol, 62.4% yield); ES-LCMS m/z 260 (M+33).

Step 3: 1-(3-(Difluoromethyl)-4-isopropoxyphenyl)-3-(5'-ethoxy-6-methyl-6'-oxo-1',6'-dihydro-[2,3'-bipyridin]-5-yl)urea

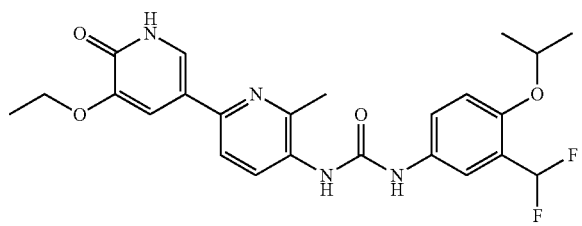 [SMILES: CCOc1cc(-c2ccc(NC(=O)Nc3ccc(OC(C)C)c(C(F)F)c3)c(C)n2)c[nH]c1=O]

To a mixture of 5-amino-5'-ethoxy-6-methyl-[2,3'-bipyridin]-6'(1'H)-one (100 mg, 0.408 mmol), 4-cyanato-2-(difluoromethyl)-1-isopropoxybenzene (93 mg, 0.408 mmol) in THF (10 mL) was added Et₃N (0.114 mL, 0.815 mmol). Then mixture was heated to 60° C. for 30 min, concentrated, and then purified by preparative HPLC to yield a yellow solid of 1-(3-(difluoromethyl)-4-isopropoxyphenyl)-3-(5'-ethoxy-6-methyl-6'-oxo-1',6'-dihydro-[2,3'-bipyridin]-5-yl)urea hydrochloride (16.72 mg, 0.032 mmol, 7.80% yield): ¹H NMR (400 MHz, CD₃OD) δ 8.71-8.69 (d, J=8.40 Hz, 1H), 7.85-7.82 (d, J=9.20 Hz, 1H), 7.68 (d, J=2.00 Hz, 1H), 7.52-7.49 (m, 1H), 7.43 (d, J=2.40, 1H), 7.07 (d, J=1.60 Hz, 1H), 6.93 (t, J=52.0 Hz, 1H), 4.66-4.60 (m, 2H), 4.17-4.12 (m, 3H), 2.69 (s, 3H), 1.47 (t, J=7.00 Hz, 3H), 1.33-1.31 (d, J=6.00 Hz, 6H); ES-LCMS m/z 473 (M+H).

EXAMPLE 7

1-(2-fluoro-4-(5-methyl-6-oxo-1,6-dihydropyridin-3-yl)phenyl)-3-(4-((3-methyloxetan-3-yl)oxy)-3-(trifluoromethyl)phenyl)urea

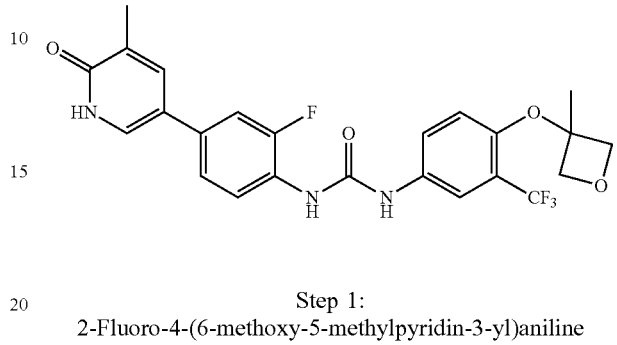

Step 1:
2-Fluoro-4-(6-methoxy-5-methylpyridin-3-yl)aniline

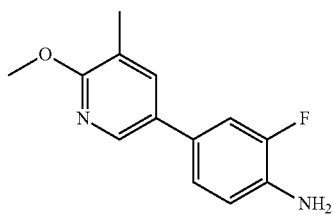 [SMILES: COc1ncc(-c2ccc(N)c(F)c2)cc1C]

To a mixture of (6-methoxy-5-methylpyridin-3-yl)boronic acid (300 mg, 1.797 mmol), 4-bromo-2-fluoroaniline (341 mg, 1.797 mmol) in water (3 mL) and 1,4-dioxane (9 mL) was added Cs₂CO₃ (1171 mg, 3.59 mmol) and PdCl₂(dppf) (65.7 mg, 0.090 mmol). Then the mixture was stirred at 100° C. for 3 h. The mixture was concentrated to give a residue, which was dissolve in EA and water, extracted with EA to give the organic layer. The organic layer was concentrated to give a residue. The residue was purified by silica gel column chormatography to give 2-fluoro-4-(6-methoxy-5-methylpyridin-3-yl)aniline (320 mg, 1.378 mmol, 77% yield) as a yellow oil. ¹H NMR (400 MHz, CDCl₃) δ 8.12 (d, J=2.8 Hz 1H), 7.51 (s, 1H), 7.17 (dd, J=2.0 Hz and 12 Hz, 1H), 7.19 (dd, J=2.0 Hz and 12 Hz,1H), 6.84 (dd, J=9.2 Hz and 8.0 Hz, 1H) 3.97 (s, 3H), 2.75 (s,2H), 2.22 (s, 3H), ES-LCMS m/z 233.1 (M+H).

Step 2: 5-(4-amino-3-fluorophenyl)-3-methylpyridin-2(1H)-one

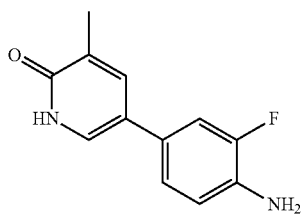 [SMILES: Cc1cc(-c2ccc(N)c(F)c2)c[nH]c1=O]

A solution of 2-fluoro-4-(6-methoxy-5-methylpyridin-3-yl)aniline (170 mg, 0.732 mmol) in HBr/H₂O (10 mL)

stirred under N₂ at 100° C. for 16 h. The reaction mixture was concentrated to give a residue and the residue was disscolve in EA. The organic phase was washed with saturated NaHCO₃ solution (10 mL), water (10 mL) and brine (10 mL), dried over Na₂SO₄, and evaporated in vacuo to 5-(4-amino-3-fluorophenyl)-3-methylpyridin-2(1H)-one (120 mg, 0.550 mmol, 75% yield) as a yellow solid. ¹H NMR (400 MHz, CD₃OD) δ 8.01 (d, J=6 Hz 1H), 7.86(d, J=6 Hz 1H) 7.71 (d, J=12 Hz,1H), 7.60 (m, 2H), 2.26 (s, 3H), ES-LCMS m/z 219.1 (M+H).

Step 3: 1-(2-fluoro-4-(5-methyl-6-oxo-1,6-dihydropyridin-3-yl)phenyl)-3-(4-((3-methyloxetan-3-yl)oxy)-3-(trifluoromethyl)phenyl)urea

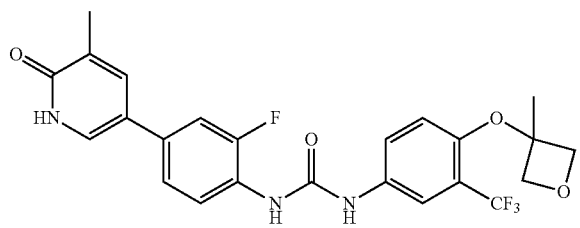 [SMILES: Cc1cc(-c2ccc(NC(=O)Nc3ccc(OC4(C)COC4)c(C(F)(F)F)c3)c(F)c2)c[nH]c1=O]

To a solution of 4-((3-methyloxetan-3-yl)oxy)-3-(trifluoromethyl)aniline (50 mg, 0.202 mmol) in THF (10 mL) stirred under N₂ at it was added triphosgene (24.01 mg, 0.081 mmol). The mixture was stirred at 50° C. for 40 min. 5-(4-amino-3-fluorophenyl)-3-methylpyridin-2(1H)-one (44.1 mg, 0.202 mmol) and Et₃N (0.085 mL, 0.607 mmol) was added to the mixture. The mixture was stirred at 50° C. for 4 h and then purified by HPLC to give 1-(2-fluoro-4-(5-methyl-6-oxo-1,6-dihydropyridin-3-yl)phenyl)-3-(4-((3-methyloxetan-3-yl)oxy)-3-(trifluoromethyl)phenyl)urea (26 mg, 0.052 mmol, 25.9% yield): ¹H NMR (400 MHz, CD₃OD) δ 8.17 (t, J=8.4 Hz 1H), 7.86 (dd, J=1.6 Hz and 8 Hz 2H) 7.59 (m, 2H), 7.40 (m, 2H), 6.66 (d, J=8 Hz 1H), ES-LCMS m/z 492.1 (M+H).

EXAMPLE 8

1-(5'-Ethoxy-2-methyl-6'-oxo-1',6'-dihydro-[3,3'-bipyridin]-6-yl)-3-(4-isopropoxy-3-(trifluoromethyl)phenyl)urea

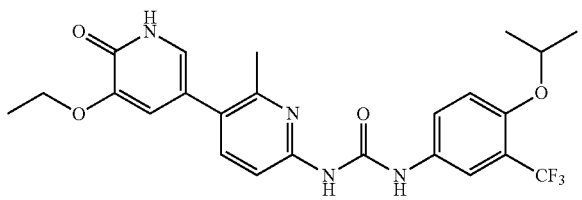 [SMILES: CCOc1cc(-c2ccc(NC(=O)Nc3ccc(OC(C)C)c(C(F)(F)F)c3)nc2C)c[nH]c1=O]

Step 1: 5-Bromo-6-methylpyridin-2-amine

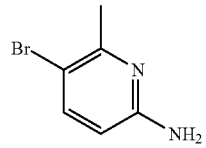

A solution of 6-methylpyridin-2-amine (5 g, 46.2 mmol) in MeOH (20 mL) stirred under N₂ at 0° C. NBS (8.23 g, 46.2 mmol) was added to the solution slowly, the reaction mixture was stirred at 0° C. for 1 h. The reaction mixture was stirred at rt for 16 h. Then the solution was concentrated and distributed between EA and saturated NaHCO₃ solution. The combined organic extract was washed with brine, dried over MgSO₄, filtered and concentrated. The residue was purified by silica column chromatography to give 5-bromo-6-methylpyridin-2-amine (3 g, 16.04 mmol, 34.7% yield). ¹H NMR (400 MHz, CD₃OD) δ 7.49 (d, J=8.8 Hz, 1H), 6.33 (d, J=8.8 Hz, 1H), 2.39 (s, 3H), ES-LCMS m/z 188.9 (M+H).

Step 2: 4-Isopropoxy-3-(trifluoromethyl)aniline

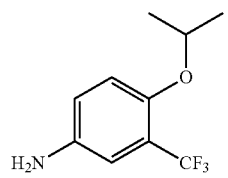

A suspension of 1-isopropoxy-4-nitro-2-(trifluoromethyl)benzene (2 g, 8.03 mmol) and Pd/C (0.2 g, 1.879 mmol) in MeOH (30 mL) stirred under a H₂ atmosphere at 30° C. The reaction mixture was stirred at 30° C. for 4 h. The reaction mixture was filtered and the filtrate was concentrated to give 4-isopropoxy-3-(trifluoromethyl)aniline (1.8 g, 7.06 mmol, 88% yield). ¹H NMR (400 MHz, CDCl₃) δ 7.84 (m, 2H), 6.90 (t, J=2.8 Hz, 1H), 6.85 (s, 1H), 6.79 (t, J=2.8 Hz, 1H), 4.52-4.43 (m, 1H), 2.60 (s, 3H), 1.32 (d, J=2.8 Hz, 6H); ES-LCMS m/z 220.0 (M+H).

Step 3: 1-(5-Bromo-6-methylpyridin-2-yl)-3-(4-isopropoxy-3-(trifluoromethyl)phenyl)urea

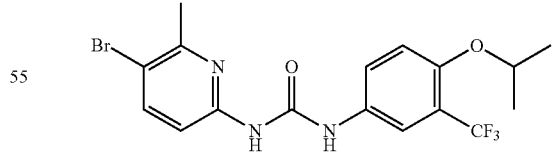

A solution of 5-bromo-6-methylpyridin-2-amine (1 g, 5.35 mmol) and triphosgene (0.714 g, 2.406 mmol) in THF (20 mL) stirred under a N₂ atmosphere at 60° C. The reaction mixture was stirred at 60° C. for 15 min. Et₃N (2.236 mL, 16.04 mmol) and 4-isopropoxy-3-(trifluoromethyl)aniline (1.172 g, 5.35 mmol) was added to the reaction mixture. The reaction mixture was stirred at 60° C. for 16 h. Then the solution was cooled to rt and filtered through a Celite® pad to give 11-(5-bromo-6-methylpyridin-2-yl)-3-(4-isopropoxy-3-(trifluoromethyl)phenyl)urea (500 mg, 1.157 mmol, 21.64% yield); $^1$H NMR (400 MHz, CD$_3$OD) δ 7.84 (m, 2H), 7.59 (dd, J=9.6 Hz, J=2.8 Hz, 1H), 7.16 (d, J=9.2 Hz, 1H), 7.01 (d, J=8.8 Hz, 1H), 4.72 (m, 1H), 2.60 (s, 3H), 1.30 (s, 6H). ES-LCMS m/z 432.0 (M+H).

Step 4: 1-(5'-Ethoxy-6'-((4-methoxybenzyl)oxy)-2-methyl-[3,3'-bipyridin]-6-yl)-3-(4-isopropoxy-3-(trifluoromethyl)phenyl)urea

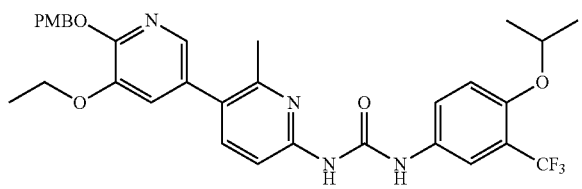

A solution of Cs$_2$CO$_3$ (0.846 g, 2.60 mmol), PdCl$_2$(dppf) (0.095 g, 0.130 mmol), 3-ethoxy-2-((4-methoxybenzyl)oxy)-5-(4,4,5,5-tetramethyl-1,3,2-dioxaborolan-2-yl)pyridine (1 g, 2.60 mmol) and 1-(4-bromo-2-fluorophenyl)-3-(4-isopropoxy-3-(trifluoromethyl)phenyl)urea (1.130 g, 2.60 mmol) in dioxane/water (20 mL) was stirred under N$_2$. The reaction mixture was stirred at 120° C. for 16 h. Then the solution was concentrated and the residue was purified by silica column chromatography (PE/EA=3:1) to give 1-(5'-ethoxy-6'-((4-methoxybenzyl)oxy)-2-methyl-[3,3'-bipyridin]-6-yl)-3-(4-isopropoxy-3-(trifluoromethyl)phenyl)urea (400 mg, 0.652 mmol, 25.1% yield); $^1$H NMR (400 MHz, CD$_3$OD) δ 7.65 (d, J=2 Hz, 1H), 7.62 (m, 3H), 7.41 (d, J=8.4 Hz, 2H), 7.22 (d, J=2 Hz, 1H), 7.17 (d, J=9.2 Hz, 1H), 7.04 (d, J=8.4 Hz, 1H), 6.92 (d, J=8.4 Hz, 2H), 5.36 (s, 2H), 4.70 (m, 1H), 4.09 (m, 2H), 3.79 (s, 3H), 3.14 (d, J=2 Hz, 3H), 1.44 (s, 3H), 1.20 (s, 6H). ES-LCMS m/z 611.1 (M+H).

Step 5: 1-(5'-Ethoxy-2-methyl-6'-oxo-1',6'-dihydro-[3,3'-bipyridin]-6-yl)-3-(4-isopropoxy-3-(trifluoromethyl)phenyl)urea

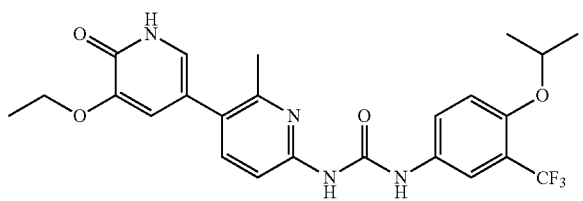 [SMILES: CCOc1cc(-c2ccc(NC(=O)Nc3ccc(OC(C)C)c(C(F)(F)F)c3)nc2C)c[nH]c1=O]

A solution of 1-(5'-ethoxy-6'-((4-methoxybenzyl)oxy)-2-methyl-[3,3'-bipyridin]-6-yl)-3-(4-isopropoxy-3-(trifluoromethyl)phenyl)urea (400 mg, 0.655 mmol) in TFA:DCM (20 mL) stirred under N$_2$ at 25° C. The reaction mixture was stirred at 25° C. for 2 h. The reaction mixture was concentrated in vacuo. The residue was purified by preparative HPLC (MeCN/H$_2$O as eluants, acidic condition) to give 1-(5'-ethoxy-2-methyl-6'-oxo-1',6'-dihydro-[3,3'-bipyridin]-6-yl)-3-(4-isopropoxy-3-(trifluoromethyl)phenyl)urea (34.63 mg, 0.071 mmol, 10.78% yield), $^1$H NMR (400 MHz, CD$_3$OH) δ 7.84 (d, J=2.4 Hz, 1H), 7.60 (m, 2H), 7.17 (d, J=9.2 Hz, 1H), 7.03 (d, J=8.4 Hz, 1H), 6.98 (dd, J=7.6 Hz, J=2.0 Hz 2H), 4.57 (s, 1H), 4.15 (m, 2H), 2.52 (s, 3H), 1.45 (t, J=6.8 Hz, 3H), 1.33 (d, J=6.0 Hz, 3H), ES-LCMS m/z 491.2 (M+H).

EXAMPLE 9

1-(5'-Ethoxy-5-methyl-6'-oxo-1',6'-dihydro-[3,3'-bipyridin]-6-yl)-3-(4-(3-hydroxy-2,2-dimethylpropyl)-3-(trifluoromethyl)phenyl)urea

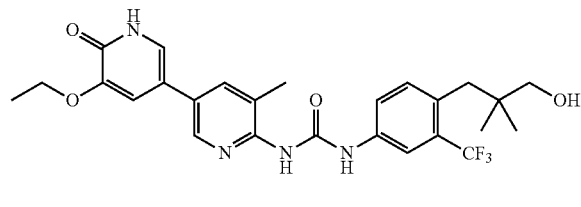 [SMILES: CCOc1cc(-c2cnc(NC(=O)Nc3ccc(CC(C)(C)CO)c(C(F)(F)F)c3)c(C)c2)c[nH]c1=O]

Step 1: Ethyl 3-(4-isocyanato-2-(trifluoromethyl)phenyl)-2,2-dimethylpropanoate

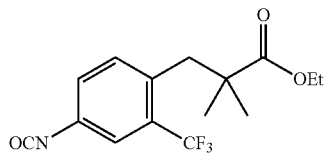

To a solution of ethyl 3-(4-amino-2-(trifluoromethyl)phenyl)-2,2-dimethylpropanoate (300 mg, 1.037 mmol) in THF (30 mL) was added triphosgene (108 mg, 0.363 mmol) in portions. The mixture was stirred at 60° C. to reflux for 30 min. After LCMS analysis showed the starting material was disappeared. The reaction solution was evaporated to dryness to afford ethyl 3-(4-isocyanato-2-(trifluoromethyl)phenyl)-2,2-dimethylpropanoate (250 mg, 0.725 mmol, 69.9% yield): ES-LCMS m/z 348.1 (M+MeOH).

Step 2: Ethyl 3-(4-(3-(5-bromo-3-methylpyridin-2-yl)ureido)-2-(trifluoromethyl)phenyl)-2,2-dimethylpropanoate

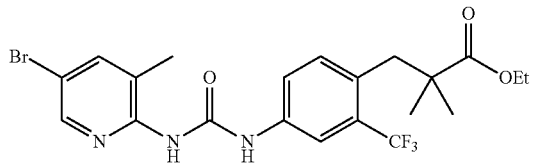 [SMILES: CCOC(=O)C(C)(C)Cc1ccc(NC(=O)Nc2ncc(Br)cc2C)cc1C(F)(F)F]

To a solution of 2-43-(4-isocyanato-2-(trifluoromethyl)phenyl)-2,2-dimethylpropanoyl)oxy)ethan-1-ylium (250 mg, 0.795 mmol), 5-bromo-3-methylpyridin-2-amine (149 mg, 0.795 mmol) in THF (30 mL) was added DMAP (194 mg, 1.591 mmol) and Et$_3$N (0.222 mL, 1.591 mmol). The mixture was stirred at 60° C. for 3 h. After LCMS analysis showed the starting material was disappeared, the reaction mixture was extracted with EA (40 mL) and the organic layer was washed with water (15 mL) and brine (15 mL). The organic phase was evaporated to dryness and the residue was purified by preparative TLC (PE/EA=1/1, $R_f$=0.4) to give pure product ethyl 3-(4-(3-(5-bromo-3-methylpyridin-2-yl)ureido)-2-(trifluoromethyl)phenyl)-2,2-dimethylpropanoate (200 mg, 0.262 mmol, 32.9% yield): $^1$H NMR (400 MHz, CDCl$_3$) δ 8.32 (d, J=2.4 Hz, 1H), 8.03 (d, J=2.4 Hz, 1H), 7.81 (d, J=1.6 Hz, 1H), 7.63 (d, J=8.8 Hz, 1H), 7.24 (d, J=5.6 Hz, 1H), 4.17 (d, J=7.2 Hz, 2H), 3.10 (s, 2H), 2.32 (s, 3H), 1.26 (s, 3H), 1.18 (s, 6H); ES-LCMS m/z 502.1 (M+H).

Step 3: Ethyl 3-(4-(3-(5'-ethoxy-6'-((4-methoxybenzyl)oxy)-5-methyl-[3,3'-bipyridin]-6-yl)ureido)-2-(trifluoromethyl)phenyl)-2,2-dimethylpropanoate

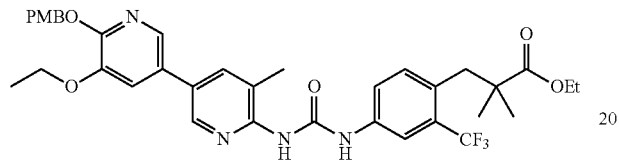

The reaction vessel with a solution of 2-((3-(4-(3-(5-bromo-3-methylpyridin-2-yl)ureido)-2-(trifluoromethyl)phenyl)-2,2-dimethylpropanoyl)oxy)ethan-1-ylium (100 mg, 0.199 mmol), 3-ethoxy-2-((4-methoxybenzyl)oxy)-5-(4,4,5,5-tetramethyl-1,3,2-dioxaborolan-2-yl)pyridine (77 mg, 0.199 mmol), PdCl$_2$(dppf) (14.60 mg, 0.020 mmol) and Cs$_2$CO$_3$ (195 mg, 0.598 mmol) in 1,4-dioxane (3 mL) and water (1 mL) was sealed and heated in microwave at 110° C. for 20 min. After LCMS analysis showed the correct product was observed, the reaction solution was evaporated to dryness and the residue was extracted with DCM (40 mL) and washed with H$_2$O (15 mL) and brine (15 mL). The organic layer was dried over Na$_2$SO$_4$, filtered and concentrated. The residue was purified by preparative TLC (DCM/MeOH=20/1, $R_f$=0.45) to afford pure product 2-((3-(4-(3-(5'-ethoxy-6'-((4-methoxybenzyl)oxy)-5-methyl-[3,3'-bipyridin]-6-yl)ureido)-2-(trifluoromethyl)phenyl)-2,2-dimethylpropanoyl)oxy)ethan-1-ylium (50 mg, 0.067 mmol, 33.6% yield): $^1$H NMR (400 MHz, DMSO-d$_6$) δ 8.88 (br. s., 1H), 8.59 (s, 1H), 8.02-8.07 (m, 2H), 7.74 (d, J=8.4 Hz, 1H), 7.60 (d, J=1.8 Hz, 1H), 7.41 (d, J=8.8 Hz, 2H), 7.23 (d, J=8.4 Hz, 1H), 6.95 (d, J=8.8 Hz, 2H), 5.34 (s, 2H), 4.06-4.21 (m, 4H), 3.76 (s, 3H), 3.01 (s, 2H), 2.36 (s, 3H), 1.35 (t, J=7.0 Hz, 3H), 1.08-1.31 (m, 9H); ES-LCMS m/z 681.2 (M+H).

Step 4: 1-(5'-Ethoxy-6'-((4-methoxybenzyl)oxy)-5-methyl-[3,3'-bipyridin]-6-yl)-3-(4-(3-hydroxy-2,2-dimethylpropyl)-3-(trifluoromethyl)phenyl)urea

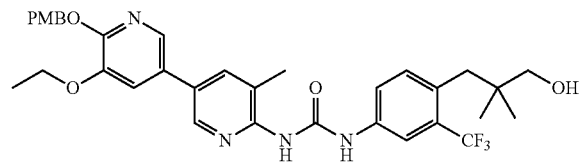

To a solution of ethyl 3-(4-(3-(5'-ethoxy-6'-((4-methoxybenzyl)oxy)-5-methyl-[3,3'-bipyridin]-6-yl)ureido)-2-(trifluoromethyl)phenyl)-2,2-dimethylpropanoate (50 mg, 0.073 mmol) in THF (10 mL) was added LAH (8.36 mg, 0.220 mmol) in portions. The mixture was stirred at 0° C. for 1 h. After LCMS analysis showed the starting material was disappeared, the reaction solution was quenched by water (2 mL), NaOH (6 mL) and water (2 mL). Then the mixture was extracted with DCM (30 mL) and washed with brine (10 mL). The organic layer was dried over Na$_2$SO$_4$, filtered and concentrated. The residue was purified by preparative TLC (DCM/MeOH=40/1, $R_f$=0.54) to afford pure product 1-(5'-ethoxy-6'-((4-methoxybenzyl)oxy)-5-methyl-[3,3'-bipyridin]-6-yl)-3-(4-(3-hydroxy-2,2-dimethylpropyl)-3-(trifluoromethyl)phenyl)urea (40 mg, 0.047 mmol, 63.6% yield): $^1$H NMR (400 MHz, CD$_3$OD) δ 8.50 (s, 1H), 8.02-7.95 (m, 2H), 7.91 (br.s., 1H), 7.70 (d, J=8.6 Hz, 1H), 7.50-7.44 (m, 2H), 7.41 (d, J=8.6 Hz, 2H), 6.92 (d, J=8.8 Hz, 2H), 5.38 (s, 2H), 4.60 (s, 2H), 4.17 (q, J=7.0 Hz, 2H), 3.82-3.76 (m, 3H), 2.80 (s, 2H), 2.40 (s, 3H), 1.44 (t, J=7.0 Hz, 3H), 0.86 (s, 6H); ES-LCMS m/z 639.2 (M+H).

Step 5: 1-(5'-Ethoxy-5-methyl-6'-oxo-1',6'-dihydro-[3,3'-bipyridin]-6-yl)-3-(4-(3-hydroxy-2,2-dimethylpropyl)-3-(trifluoromethyl)phenyl)urea

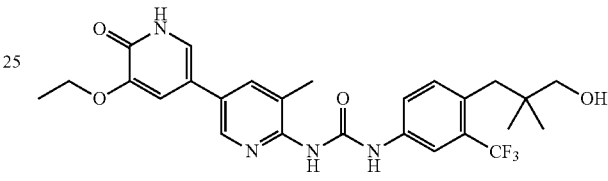

A solution of 1-(5'-ethoxy-6'-((4-methoxybenzyl)oxy)-5-methyl-[3,3'-bipyridin]-6-yl)-3-(4-(3-hydroxy-2,2-dimethylpropyl)-3-(trifluoromethyl)phenyl)urea (20 mg, 0.031 mmol) in HCl in MeOH (8 mL, 32.0 mmol) was stirred at 20° C. for 30 min. After LCMS analysis showed the starting material was disappeared, the reaction mixture was evaporated to dryness and purified by preparative HPLC (Instrument: DB/Column: ASB C18 150*25 mm/Mobile phase A: Water+0.1% HCl/Mobile phase B: MeCN/Flowrate: 25 mL/min/Gradient Profile Description: 40-60(B %)) to yield a off white solid 1-(5'-ethoxy-5-methyl-6'-oxo-1',6'-dihydro-[3,3'-bipyridin]-6-yl)-3-(4-(3-hydroxy-2,2-dimethylpropyl)-3-(trifluoromethyl)phenyl)urea (7.36 mg, 0.014 mmol, 44.1% yield): $^1$H NMR (400 MHz, CD$_3$OD) δ 8.50 (s, 1H), 8.37 (d, J=2.0 Hz, 1H), 8.03 (d, J=2.0 Hz, 1H), 7.63 (d, J=8.8 Hz, 1H), 7.52 (d, J=8.4 Hz, 1H), 7.47 (d, J=2.4 Hz, 1H), 7.25 (d, J=2.2 Hz, 1H), 4.18-4.136 (m, 2H), 3.32 (br. s., 2H), 2.82 (s, 2H), 2.54 (s, 3H), 1.49 (t, J=7.0 Hz, 3H), 0.86 (s, 6H); ES-LCMS m/z 519.1 (M+H).

EXAMPLE 10

1-(2-(5-Ethoxy-6-oxo-1,6-dihydropyridin-3-yl)-4-methylpyrimidin-5-yl)-3-(4-(1-hydroxyethyl)-3-(trifluoromethyl)phenyl)urea

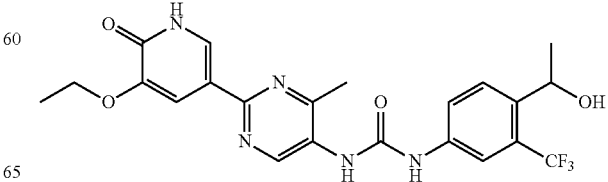

Step 1: 2-Chloro-5-isocyanato-4-methylpyrimidine

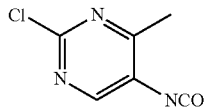

To a solution of 2-chloro-4-methylpyrimidin-5-amine (300 mg, 2.090 mmol) in THF (20 mL) was added triphosgene (620 mg, 2.090 mmol) in one portion. The mixture was stirred at 60° C. for 20 min. LCMS analysis showed the starting material had disappeared: ES-LCMS m/z 202.1 (M+MeOH).

Step 2: 1-(4-Acetyl-3-(trifluoromethyl)phenyl)-3-(2-chloro-4-methylpyrimidin-5-yl)urea

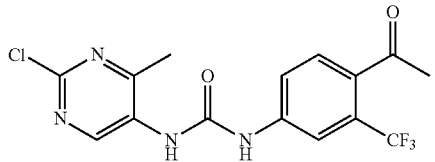 [SMILES: CC(=O)c1ccc(NC(=O)Nc2cnc(Cl)nc2C)cc1C(F)(F)F]

To a solution of 1-(4-amino-2-(trifluoromethyl)phenyl) ethanone (419 mg, 2.064 mmol) in THF (20 mL) was added DMAP (126 mg, 1.032 mmol), Et$_3$N (0.863 mL, 6.19 mmol) and a solution of 2-chloro-5-isocyanato-4-methylpyrimidine (350 mg, 2.064 mmol) in THF (5 mL). The mixture was stirred at 60° C. to reflux for 1 h. After LCMS analysis showed the starting material was disappeared. The reaction solution was extracted with DCM (60 mL) and washed with H$_2$O (20 mL) and brine (20 mL). The organic layer was dried over Na$_2$SO$_4$, filtered and concentrated. The residue was purified by silica column chromatography (PE/EA=2/1 to 1/2) to give pure product 1-(4-acetyl-3-(trifluoromethyl) phenyl)-3-(2-chloro-4-methylpyrimidin-5-yl)urea (300 mg, 0.757 mmol, 36.7% yield): $^1$H NMR (400 MHz, CD$_3$OD) δ 9.05 (s, 1H), 7.97 (s, 1H), 7.77-7.71 (m, 2H), 2.55 (s, 3H), 2.51 (s, 3H); ES-LCMS m/z 373.0 (M+H).

Step 3: 1-(4-Acetyl-3-(trifluoromethyl)phenyl)-3-(2-(5-ethoxy-6-((4-methoxybenzyl)oxy)pyridin-3-yl)-4-methylpyrimidin-5-yl)urea

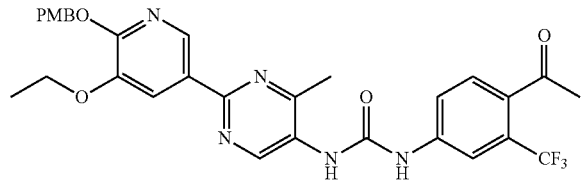

A solution of 1-(4-acetyl-3-(trifluoromethyl)phenyl)-3-(2-chloro-4-methylpyrimidin-5-yl)urea (200 mg, 0.537 mmol), 3-ethoxy-2-((4-methoxybenzyl)oxy)-5-(4,4,5,5-tetramethyl-1,3,2-dioxaborolan-2-yl)pyridine (207 mg, 0.537 mmol), PdCl$_2$(dppf) (39.3 mg, 0.054 mmol) and Cs$_2$CO$_3$ (524 mg, 1.610 mmol) in 1,4-dioxane (3 mL) and water (1 mL) was stirred at 110° C. in the microwave for 20 min. After LCMS analysis showed correct mass was observed. The reaction solution was evaporated to dryness and extracted with DCM (40 mL) and washed with H$_2$O (10 mL) and brine (10 mL). The residue was purified by preparative TLC (DCM/MeOH=20/1, R$_f$=0.52) to give product 1-(4-acetyl-3-(trifluoromethyl)phenyl)-3-(2-(5-ethoxy-6-((4-methoxybenzyl)oxy)pyridin-3-yl)-4-methylpyrimidin-5-yl) urea (250 mg, 0.243 mmol, 45.4% yield): $^1$H NMR (400 MHz, CD$_3$OD) δ 9.09 (s, 1H), 8.66 (d, J=2.0 Hz, 1H), 8.06 (d, J=1.6 Hz, 1H), 7.98 (s, 1H), 7.74 (d, J=2.0 Hz, 1H), 7.71 (s, 1H), 7.39 (d, J=8.8 Hz, 2H), 6.89 (d, J=8.8 Hz, 2H), 5.36 (s, 2H), 4.17-4.12 (m, 2H), 3.77 (s, 3H), 2.56 (s, 3H), 2.54 (s, 3H), 1.42 (t, J=7.0 Hz, 3H); ES-LCMS m/z 476.1 (M-PMB+H), 596.1 (M+H).

Step 4: 1-(2-(5-Ethoxy-6-((4-methoxybenzyl)oxy) pyridin-3-yl)-4-methylpyrimidin-5-yl)-3-(4-(1-hydroxyethyl)-3-(trifluoromethyl)phenyl)urea

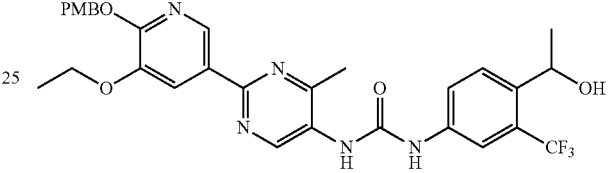

To a solution of 1-(4-acetyl-3-(trifluoromethyl)phenyl)-3-(2-(5-ethoxy-6-((4-methoxybenzyl)oxy)pyridin-3-yl)-4-methylpyrimidin-5-yl)urea (140 mg, 0.235 mmol) in THF (5 mL) was added NaBH$_4$ (44.5 mg, 1.175 mmol) in portions. The mixture was stirred at 20° C. for 3 h. After LCMS analysis showed the starting material was disappeared. Water (10 mL) was added dropwise to quench the reaction solution. The mixture was extracted with EA (30 mL) and washed with brine (10 mL). The organic layer was dried over Na$_2$SO$_4$, filtered and concentrated. The residue was purified by preparative TLC (DCM/MeOH=20/1, R$_f$=0.56) to give product 1-(2-(5-ethoxy-6-((4-methoxybenzyl)oxy) pyridin-3-yl)-4-methylpyrimidin-5-yl)-3-(4-(1-hydroxyethyl)-3-(trifluoromethyl)phenyl)urea (100 mg, 0.100 mmol, 42.7% yield): $^1$H NMR (400 MHz, CD$_3$OD) δ 9.10 (s, 1H), 8.67 (d, J=1.8 Hz, 1H), 8.08 (d, J=1.8 Hz, 1H), 7.87 (d, J=2.0 Hz, 1H), 7.75 (d, J=8.8 Hz, 1H), 7.65 (d, J=8.8 Hz, 1H), 7.40 (d, J=8.4 Hz, 2H), 6.91 (d, J=8.8 Hz, 2H), 5.38 (s, 2H), 5.16 (d, J=6.0 Hz, 1H), 4.18-4.13 (m, 2H), 3.78 (s, 3H), 2.57 (s, 3H), 1.47-1.42 (m, 3H), 1.40 (d, J=7.2 Hz, 3H); ES-LCMS m/z 598.1 (M+H).

Step 5: 1-(2-(5-Ethoxy-6-oxo-1,6-dihydropyridin-3-yl)-4-methylpyrimidin-5-yl)-3-(4-(1-hydroxyethyl)-3-(trifluoromethyl)phenyl)urea

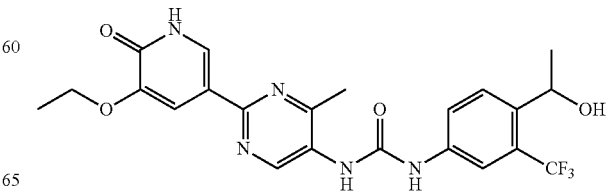

To a solution of 1-(2-(5-ethoxy-6-((4-methoxybenzyl)oxy)pyridin-3-yl)-4-methylpyrimidin-5-yl)-3-(4-(1-hydroxyethyl)-3-(trifluoromethyl)phenyl)urea (80 mg, 0.134 mmol) in MeOH (20 mL) was added 10% Pd/C (14.25 mg, 0.134 mmol) in portions. The mixture was stirred at a $H_2$ atmosphere at rt for 1 h. After LCMS analysis showed the starting material was disappeared. The reaction mixture was filtered and the filtrate was evaporated to dryness. Then the residue was purified by preparative HPLC (Instrument: Gilson 215/Column: Gemini C18 10 u 150*25 mm/Mobile phase A: Water (0.01 mol/L $(NH_4)HCO_3$)/Mobile phase B: MeCN/Flowrate: 25 mL/min/Gradient Profile Description: 28-58(B %)) to give pure product 1-(2-(5-ethoxy-6-oxo-1,6-dihydropyridin-3-yl)-4-methylpyrimidin-5-yl)-3-(4-(1-hydroxyethyl)-3-(trifluoromethyl)phenyl)urea (8.61 mg, 0.018 mmol, 13.35% yield): $^1$H NMR (400 MHz, $CD_3OD$) δ 9.05 (s, 1H), 8.08 (d, J=2.0 Hz, 1H), 7.88 (br. s., 2H), 7.77 (d, J=8.6 Hz, 1H), 7.67 (d, J=8.6 Hz, 1H), 5.18 (d, J=6.0 Hz, 1H), 4.18-4.13 (m, 2H), 2.56 (s, 3H), 1.49 (t, J=7.0 Hz, 3H), 1.42 (d, J=6.6 Hz, 3H); ES-LCMS m/z 478.1 (M+H).

EXAMPLE 11

1-(4-(5-Ethoxy-6-oxo-1,6-dihydropyridin-3-yl)-2-fluorophenyl)-3-(5-(1,1,1-trifluoro-2-methylpropan-2-yl)isoxazol-3-yl)urea

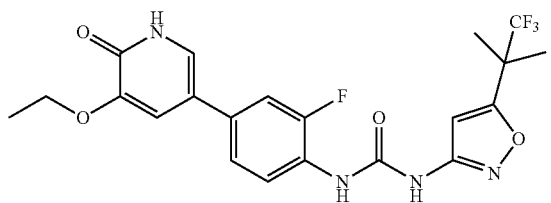 [SMILES: CCOc1cc(-c2ccc(NC(=O)Nc3cc(C(C)(C)C(F)(F)F)on3)c(F)c2)c[nH]c1=O]

Step 1: 4-Bromo-2-fluoro-1-isocyanatobenzene

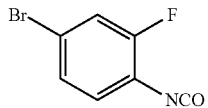

A mixture of 4-bromo-2-fluoroaniline (720 mg, 3.79 mmol) in THF (30 mL) was added triphosgene (450 mg, 1.516 mmol). The mixture was stirred at 50° C. for 1 h. The mixture was concentrated to yield a light yellow oil of 4-bromo-2-fluoro-1-isocyanatobenzene (750 mg, 3.47 mmol, 92% yield); ES-LCMS m/z 249.9 (M+MeOH+H).

Step 2: 1-(4-Bromo-2-fluorophenyl)-3-(5-(1,1,1-trifluoro-2-methylpropan-2-yl)isoxazol-3-yl)urea

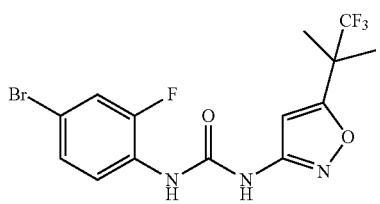 [SMILES: CC(C)(c1cc(NC(=O)Nc2ccc(Br)cc2F)no1)C(F)(F)F]

To a mixture of 4-bromo-2-fluoro-1-isocyanatobenzene (751 mg, 3.48 mmol) in THF (50 mL) was added 5-(1,1,1-trifluoro-2-methylpropan-2-yl)isoxazol-3-amine (450 mg, 2.318 mmol) and $Et_3N$ (0.645 mL, 4.64 mmol). Then the mixture was stirred at 50° C. for 4 h. The mixture was concentrated. The residue was purified on silica column chromatography (PE/EA=5:1). All fractions found to contain product by TLC (PE/EA=2:1, $R_f$=0.6) were combined and concentrated to yield a light yellow solid of 1-(4-bromo-2-fluorophenyl)-3-(5-(1,1,1-trifluoro-2-methylpropan-2-yl)isoxazol-3-yl)urea (220 mg, 0.536 mmol, 23.14% yield): $^1$H NMR (400 MHz, MeOD) δ: 8.07 (t, J=4.8 Hz, 1H), 7.38 (dd, J=2.4, 10.8 Hz, 1H), 7.32-7.29 (m, 1H), 6.76 (s, 1H), 1.58 (s, 6H); ES-LCMS m/z 412.0, 410.0 (M+H).

Step 3: 1-(4-(5-Ethoxy-6-((4-methoxybenzyl)oxy)pyridin-3-yl)-2-fluorophenyl)-3-(5-(1,1,1-trifluoro-2-methylpropan-2-yl)isoxazol-3-yl)urea

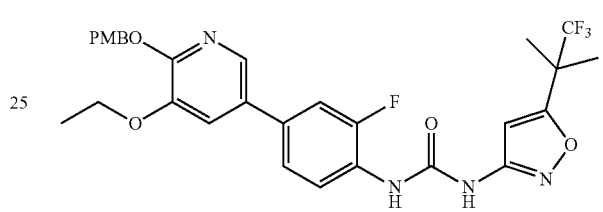

To a mixture of 3-ethoxy-2-((4-methoxybenzyl)oxy)-5-(4,4,5,5-tetramethyl-1,3,2-dioxaborolan-2-yl)pyridine (250 mg, 0.649 mmol), 1-(4-bromo-2-fluorophenyl)-3-(5-(1,1,1-trifluoro-2-methylpropan-2-yl)isoxazol-3-yl)urea (220 mg, 0.536 mmol) in water (1 mL) and 1,4-dioxane (3 mL) was added $Cs_2CO_3$ (423 mg, 1.298 mmol) and $PdCl_2$(dppf)-DCM adduct (53.0 mg, 0.065 mmol) under a $N_2$ atmosphere. Then the mixture was stirred and irradiated in a microwave oven at 130° C. for 30 min. The mixture was concentrated and extracted with EA. The combined organic was concentrated. The residue was purified by preparative TLC (PE/EA=2:1, $R_f$=0.5) to yield an off white solid of 1-(4-(5-ethoxy-6-((4-methoxybenzyl)oxy)pyridin-3-yl)-2-fluorophenyl)-3-(5-(1,1,1-trifluoro-2-methylpropan-2-yl)isoxazol-3-yl)urea (150 mg, 0.161 mmol, 24.74% yield): $^1$H NMR (400 MHz, MeOD) δ: 8.22 (t, J=4.8 Hz, 1H), 7.95 (d, J=2.4 Hz, 1H), 7.48-7.37 (m, 5H), 6.95-6.81 (m, 3H), 5.38-5.35 (m, 2H), 4.20-4.14 (m, 2H), 3.81 (s, 3H), 1.62-1.37 (m, 9H); ES-LCMS m/z 589.0 (M+H).

Step 4: 1-(4-(5-Ethoxy-6-oxo-1,6-dihydropyridin-3-yl)-2-fluorophenyl)-3-(5-(1,1,1-trifluoro-2-methylpropan-2-yl)isoxazol-3-yl)urea

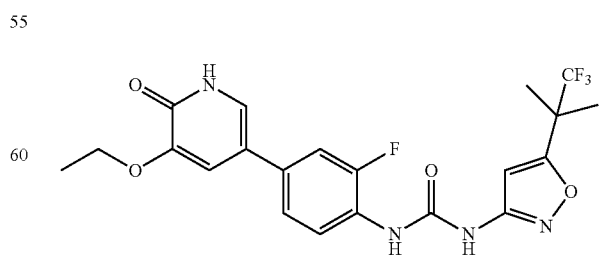

A mixture of 1-(4-(5-ethoxy-6-((4-methoxybenzyl)oxy)pyridin-3-yl)-2-fluorophenyl)-3-(5-(1,1,1-trifluoro-2-methylpropan-2-yl)isoxazol-3-yl)urea (150 mg, 0.255 mmol) and TFA (10% in DCM, 100 mL) was stirred at 25° C. for 2 h. The mixture was concentrated, and the residue was purified by preparative HPLC (MeCN/H$_2$O as eluants, acidic condition) to yield an off white solid of 1-(4-(5-ethoxy-6-oxo-1,6-dihydropyridin-3-yl)-2-fluorophenyl)-3-(5-(1,1,1-trifluoro-2-methylpropan-2-yl)isoxazol-3-yl)urea (84.37 mg, 0.177 mmol, 87% yield): $^1$H NMR (400 MHz, MeOD) δ: 8.17 (t, J=8.4 Hz, 1H), 7.40 (dd, J=2.0, 12.4 Hz, 1H), 7.36-7.33 (m, 1H), 7.27 (d, J=2.4 Hz, 1H), 7.22 (d, J=2.0 Hz, 1H), 6.77 (s, 1H), 4.12 (q, J=7.2 Hz, 2H), 1.59 (s, 6H), 1.46 (t, J=7.2 Hz, 3H); ES-LCMS m/z 469.1 (M+H).

EXAMPLE 12

1-(2-(4-Ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea

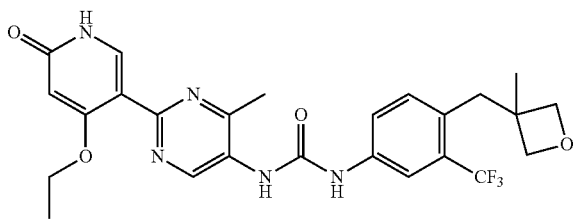 [SMILES: CCOc1cc(=O)[nH]cc1-c1ncc(NC(=O)Nc2ccc(CC3(C)COC3)c(C(F)(F)F)c2)c(C)n1]

Step 1: 1-(2-(4-Ethoxy-6-((4-methoxybenzyl)oxy)pyridin-3-yl)-4-methylpyrimidin-5-yl)3-(4-((3-methyloxetan-3-yl)methyl)-3-(trifluoromethyl)phenyl)urea

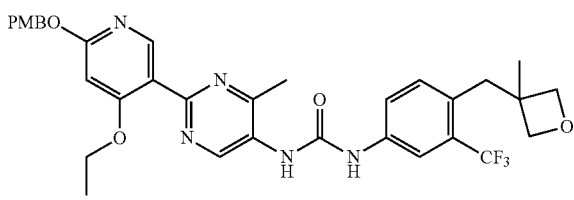

To a mixture of 2-(4-ethoxy-6-((4-methoxybenzyl)oxy)pyridin-3-yl)-4-methylpyrimidine-5-carboxylic acid (200 mg, 0.506 mmol) in 1,4-dioxane (30 mL) was added Et$_3$N (0.106 mL, 0.759 mmol) and stirred at 25° C. for 15 min. Then to the mixture was added DPPA (209 mg, 0.759 mmol) and stirred for 15 min. To the mixture was added 4-((3-methyloxetan-3-yl)methyl)-3-(trifluoromethyl)aniline (124 mg, 0.506 mmol) and stirred at 80° C. for 3 h. The mixture was concentrated and the residue was purified by preparative TLC (DCM/MeOH=15:1, R$_f$=0.45) to yield a light yellow solid of 1-(2-(4-ethoxy-6-((4-methoxybenzyl)oxy)pyridin-3-yl)-4-methylpyrimidin-5-yl)-3-(4-((3-methyloxetan-3-yl)methyl)-3-(trifluoromethyl)phenyl)urea (80 mg, 0.107 mmol, 21.08% yield): $^1$H NMR (400 MHz, CD$_3$OD) δ 9.16 (s, 1H), 8.08 (s, 1H), 7.90 (s, 1H), 7.81-7.75 (m, 1H), 7.64-7.62 (m, 1H), 7.55 (s, 1H), 7.26-7.20 (m, 2H), 6.88-6.86 (m, 2H), 5.99-5.96 (m, 2H), 4.71-4.64 (m, 2H), 4.33-4.25 (m, 2H), 4.12-4.05 (m, 2H), 3.76 (s, 3H), 2.56 (s, 2H), 2.50-2.30 (m, 3H), 1.37-1.35 (m, 3H), 1.18 (s, 3H); ES-LCMS (m/z): 638.2 (M+H).

Step 2: 1-(2-(4-Ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea

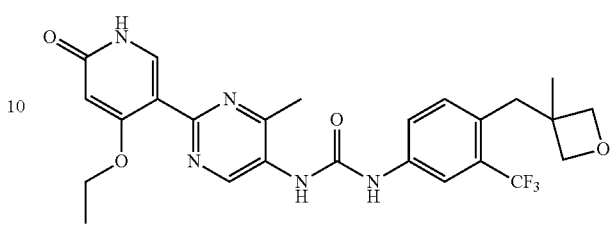

A mixture of 1-(2-(4-ethoxy-6-((4-methoxybenzyl)oxy)pyridin-3-yl)-4-methylpyrimidin-5-yl)-3-(4-((3-methyloxetan-3-yl)methyl)-3-(trifluoromethyl)phenyl)urea (80 mg, 0.125 mmol) and TFA (10% in DCM, 30 mL) was stirred at 25° C. for 2 h. The mixture was concentrated. The residue was purified by preparative HPLC (Instrument: Gilson GX 281; Column: Gemini 150*25 mm*5 um; Mobile phase A: Water (0.05% ammonia solution); Mobile phase B: MeCN; Gradient: 36-66(B %); Flowrate: 25 mL/min; Run time: 10 min) to give a white solid of 1-(2-(4-ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea (4.58 mg, 8.85 mol, 7.05% yield): $^1$H NMR (400 MHz, CD$_3$OD) δ 9.15 (s, 1H), 7.90 (d, J=2.4 Hz, 1H), 7.77 (s, 1H), 7.63 (d, J=8.4 Hz, 1H), 7.23 (d, J=8.4 Hz, 1H), 5.99 (s, 1H), 4.68 (d, J=6.0 Hz, 2H), 4.30 (d, J=5.6 Hz, 2H), 4.11 (q, J=6.8 Hz, 2H), 3.03 (s, 2H), 2.55 (s, 3H), 1.44-1.29 (m, 6H); ES-LCMS m/z: 518.1 (M+H).

EXAMPLE 13

1-(2-(5-Ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea

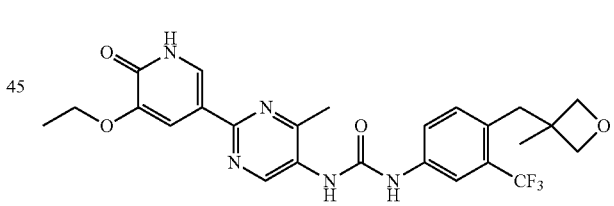

Step 1: 1-(2-(5-Ethoxy-6-((4-methoxybenzyl)oxy)pyridin-3-yl)-4-methylpyrimidin-5-yl)-3-(4-((3-methyloxetan-3-yl)methyl)-3-(trifluoromethyl)phenyl)urea

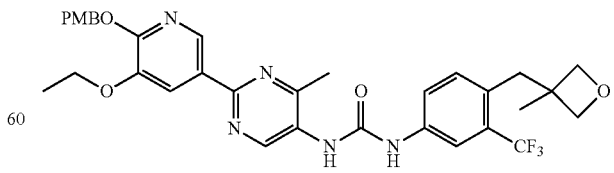

To a mixture of 2-(5-ethoxy-6-((4-methoxybenzyl)oxy)pyridin-3-yl)-4-methylpyrimidine-5-carboxylic acid (180 mg, 0.455 mmol) in 1,4-dioxane (30 mL) was added Et$_3$N (0.095 mL, 0.683 mmol) and stirred at 25° C. for 15 min.

Then to the mixture was added DPPA (188 mg, 0.683 mmol) and stirred for 15 min. To the mixture was added 4-((3-methyloxetan-3-yl)methyl)-3-(trifluoromethyl)aniline (112 mg, 0.455 mmol) and stirred at 80° C. for 3 h. The mixture was concentrated and the residue was purified by preparative TLC (DCM/MeOH=20:1, R$_f$=0.5) to yield a light yellow solid of 1-(2-(5-ethoxy-6-((4-methoxybenzyl)oxy)pyridin-3-yl)-4-methylpyrimidin-5-yl)-3-(4-((3-methyloxetan-3-yl)methyl)-3-(trifluoromethyl)phenyl)urea (100 mg, 0.133 mmol, 29.3% yield): $^1$H NMR (400 MHz, CD$_3$OD) δ 9.10 (s, 1H), 8.66 (s, 1H), 8.07-8.06 (m, 1H), 7.90 (s, 1H), 7.61 (d, J=8.4 Hz, 1H), 7.40 (d, J=8.4 Hz, 2H), 7.22 (d, J=8.4 Hz, 1H), 6.91 (d, J=8.4 Hz, 2H), 5.38 (s, 2H), 4.68 (d, J=5.6 Hz, 2H), 4.30 (d, J=5.6 Hz, 2H), 4.19-4.12 (m, 2H), 3.81-3.74 (m, 3H), 3.02 (s, 2H), 2.59-2.52 (m, 3H), 1.43 (t, J=7.2 Hz, 3H), 1.35 (s, 3H); ES-LCMS (m/z): 638.1 (M+H).

Step 2: 1-(2-(5-Ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea

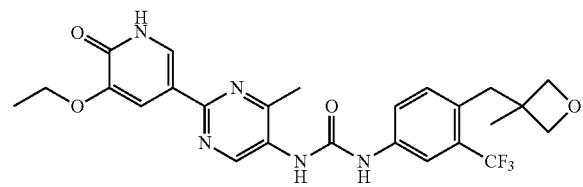 [SMILES: CCOc1cc(-c2ncc(NC(=O)Nc3ccc(CC4(C)COC4)c(C(F)(F)F)c3)c(C)n2)c[nH]c1=O]

A mixture of 1-(2-(5-ethoxy-6-((4-methoxybenzyl)oxy)pyridin-3-yl)-4-methylpyrimidin-5-yl)-3-(4-((3-methyloxetan-3-yl)methyl)-3-(trifluoromethyl)phenyl)urea (100 mg, 0.157 mmol) and TFA (10% in DCM, 30 mL) was stirred at 25° C. for 2 h. The mixture was concentrated. The residue was purified by preparative HPLC (Instrument: Gilson GX 281; Column: Gemini 150*25 mm*5 um; Mobile phase A: Water (0.05% ammonia solution); Mobile phase B: MeCN; Gradient: 40-70(B %); Flowrate: 25 mL/min; Run time: 10 min) to give a white solid of 1-(2-(5-ethoxy-6-oxo-1,6-dihydropyridin-3-yl)-4-methylpyrimidin-5-yl)-3-(4-((3-methyloxetan-3-yl)methyl)-3-(trifluoromethyl)phenyl)urea (49 mg, 0.092 mmol, 58.8% yield): $^1$H NMR (400 MHz, CD$_3$OD) δ 9.03 (s, 1H), 8.06 (s, 1H), 7.90 (s, 1H), 7.85 (d, J=2.0 Hz, 1H), 7.63-7.61 (m, 1H), 7.24-7.22 (m, 1H), 4.69 (d, J=6.0 Hz, 2H), 4.30 (d, J=6.0 Hz, 2H), 4.14 (q, J=6.8 Hz, 2H), 3.03 (s, 2H), 2.55 (s, 3H), 1.48 (t, J=7.2 Hz, 3H), 1.35 (s, 6H); ES-LCMS m/z: 518.1 (M+H).

EXAMPLE 14

1-(4-(2-Cyano-2-methylpropyl)-3-(trifluoromethyl)phenyl)-3-(2-(5-ethoxy-6-oxo-1,6-dihydropyridin-3-yl)-4-methylpyrimidin-5-yl)urea

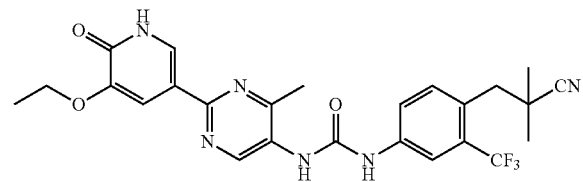 [SMILES: CCOc1cc(-c2ncc(NC(=O)Nc3ccc(CC(C)(C)C#N)c(C(F)(F)F)c3)c(C)n2)c[nH]c1=O]

Step 1: 2,2-Dimethyl-3-(4-nitro-2-(trifluoromethyl)phenyl)propanoic acid

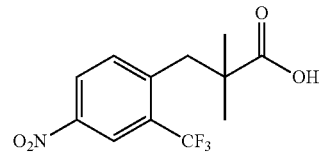 [SMILES: CC(C)(Cc1ccc([N+](=O)[O-])cc1C(F)(F)F)C(=O)O]

A mixture of ethyl 2,2-dimethyl-3-(4-nitro-2-(trifluoromethyl)phenyl)propanoate (2 g, 6.26 mmol) in MeOH (30 mL) was added a solution of LiOH (0.450 g, 18.79 mmol) in water (30 mL). Then the mixture was stirred at 60° C. for 10 h. The mixture was acified by 6.0 mol/L HCl to pH=6.0, and then extracted with DCM/MeOH (10/1, 50 mL×3). The combined organic layer was dried over Na$_2$SO$_4$ and concentrated to give a white solid of 2,2-dimethyl-3-(4-nitro-2-(trifluoromethyl)phenyl)propanoic acid (1.5 g, 4.48 mmol, 71.5% yield): $^1$H NMR (400 MHz, CD$_3$OD) δ: 8.48 (d, J=2.4 Hz, 1H), 8.37 (dd, J=2.4, 8.8 Hz, 1H), 7.75 (d, J=8.8 Hz, 1H), 3.24 (s, 2H), 1.17 (s, 6H).

Step 2: 2,2-dimethyl-3-(4-nitro-2-(trifluoromethyl)phenyl)propanamide

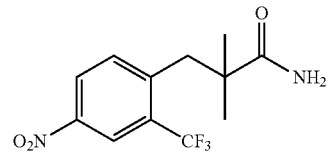

A mixture of 2,2-dimethyl-3-(4-nitro-2-(trifluoromethyl)phenyl)propanoic acid (8.5 g, 29.2 mmol) and DMF (0.2 mL) in DCM (250 mL) cooled to 0° C. was added oxalyl dichloride (3.07 mL, 35.0 mmol) and the mixture was stirred at 25° C. for 1 h. The mixture was concentrated, and the residue was added DCM (250 mL). The mixture was stirred at 25° C. for 2 h under NH$_3$. The mixture was concentrated. The residue was partioned between EA (200 mL) and H$_2$O (200 mL). The organic layer was washed with brine, dried over Na$_2$SO$_4$, filtered and concentrated to give a yellow oil of 2,2-dimethyl-3-(4-nitro-2-(trifluoromethyl)phenyl)propanamide (5.5 g, 10.74 mmol, 36.8% yield): $^1$H NMR (400 MHz, CD$_3$OD) δ: 8.49 (d, J=2.0 Hz, 1H), 8.37 (dd, J=2.4, 8.8 Hz, 1H), 7.73 (d, J=8.8 Hz, 1H), 3.22 (s, 2H), 1.18 (s, 6H); ES-LCMS (m/z): 291.0 (M+H).

Step 3: 2,2-Dimethyl-3-(4-nitro-2-(trifluoromethyl)phenyl)propanenitrile

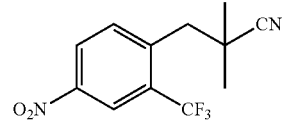

A mixture of 2,2-dimethyl-3-(4-nitro-2-(trifluoromethyl)phenyl)propanamide (5 g, 17.23 mmol) and Et$_3$N (7.20 mL, 51.7 mmol) in DCM (50 mL) was added TFAA (3.65 mL, 25.8 mmol). The mixture was stirred at 25° C. for 10 h. The mixture was washed with saturated NaHCO₃ and brine (50 mL×2). The organic layer was dried over MgSO₄ and concentrated. The residue was purified on silica column chromatography (PE/EA=10:1). All fractions found to contain product by TLC (PE/EA=5:1, R$_f$=0.6) were combined and concentrated to yield a light yellow solid of 2,2-dimethyl-3-(4-nitro-2-(trifluoromethyl)phenyl)propanenitrile (4 g, 13.55 mmol, 79% yield): ¹H NMR (400 MHz, CD₃OD) δ: 8.56 (d, J=2.4 Hz, 1H), 8.50 (dd, J=2.0, 8.4 Hz, 1H), 8.05 (d, J=8.4 Hz, 1H), 3.21 (s, 2H), 1.43 (s, 6H); ES-LCMS (m/z): 290.0 (M+H₂O).

Step 4: 3-(4-Amino-2-(trifluoromethyl)phenyl)-2,2-dimethylpropanenitrile

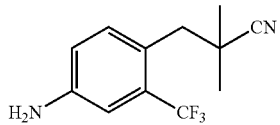

A mixture of 2,2-dimethyl-3-(4-nitro-2-(trifluoromethyl)phenyl)propanenitrile (4 g, 14.69 mmol) in EA (100 mL) was added SnCl₂.H₂O (12.20 g, 58.8 mmol) and refluxed for 2 h. After cooled, the mixture was neutralized with saturated NaHCO₃ solution to pH=7.5. The mixture was extracted with EA (100 mL×4). The combined organic extract was washed with brine, dried over MgSO₄, filtered and concentrated. The residue was purified on silica column chromatography (PE/EA=5:1). All fractions found to contain product by TLC (PE/EA=2:1, R$_f$=0.45) were combined and concentrated to yield a light yellow solid of 3-(4-amino-2-(trifluoromethyl)phenyl)-2,2-dimethylpropanenitrile (3.5 g, 13.29 mmol, 90% yield): ¹H NMR (400 MHz, CD₃OD) δ: 7.40 (d, J=8.4 Hz, 1H), 6.98 (d, J=2.4 Hz, 1H), 6.86 (dd, J=2.4, 8.4 Hz, 1H), 2.90 (s, 2H), 1.34 (s, 6H); ES-LCMS m/z: 243.1 (M+H).

Step 5: 1-(4-(2-Cyano-2-methylpropyl)-3-(trifluoromethyl)phenyl)-3-(2-(5-ethoxy-6-((4-methoxybenzyl)oxy)-1,6-dihydropyridin-3-yl)-4-methylpyrimidin-5-yl)urea

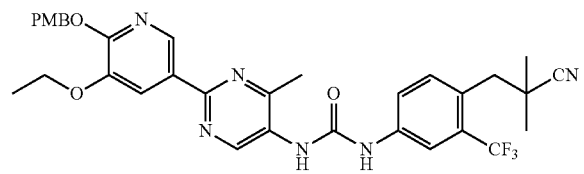

To a mixture of 2-(5-ethoxy-6-((4-methoxybenzyl)oxy)pyridin-3-yl)-4-methylpyrimidine-5-carboxylic acid (200 mg, 0.503 mmol) in 1,4-dioxane (30 mL) was added Et₃N (0.105 mL, 0.755 mmol) and stirred at 25° C. for 15 min. Then to the mixture was added DPPA (208 mg, 0.755 mmol) and stirred for 15 min. To the mixture was added 3-(4-amino-2-(trifluoromethyl)phenyl)-2,2-dimethylpropanenitrile (122 mg, 0.503 mmol) and stirred at 80° C. for 3 h. The mixture was concentrated and the residue was purified by preparative TLC (DCM/MeOH=20:1, R$_f$=0.5) to yield a light yellow solid of 1-(4-(2-cyano-2-methylpropyl)-3-(trifluoromethyl)phenyl)-3-(2-(5-ethoxy-6-((4-methoxybenzyl)oxy)-1,6-dihydropyridin-3-yl)-4-methylpyrimidin-5-yl)urea (80 mg, 0.113 mmol, 22.5% yield): ¹H NMR (400 MHz, CD₃OD) δ: 9.04 (s, 1H), 8.08-8.04 (m, 1H), 7.96 (s, 1H), 7.85 (s, 1H), 7.80-7.75 (m, 1H), 7.67-7.65 (m, 1H), 7.25 (d, J=8.4 Hz, 2H), 6.91-6.84 (m, 2H), 4.59 (s, 2H), 4.16-4.11 (m, 2H), 3.77 (s, 3H), 3.03 (s, 2H), 2.55 (s, 3H), 1.50-1.45 (m, 3H), 1.38 (s, 6H); ES-LCMS (m/z): 515.1 (M-PMB+H).

Step 6: 1-(4-(2-Cyano-2-methylpropyl)-3-(trifluoromethyl)phenyl)-3-(2-(5-ethoxy-6-oxo-1,6-dihydropyridin-3-yl)-4-methylpyrimidin-5-yl)urea

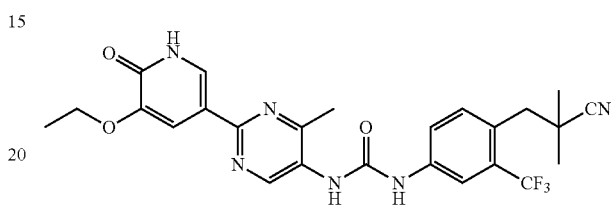

A mixture of 1-(4-(2-cyano-2-methylpropyl)-3-(trifluoromethyl)phenyl)-3-(2-(5-ethoxy-6-((4-methoxybenzyl)oxy)pyridin-3-yl)-4-methylpyrimidin-5-yl)urea (80 mg, 0.126 mmol) and TFA (10% in DCM, 30 mL) was stirred at 25° C. for 2 h. The mixture was concentrated. The residue was purified by preparative HPLC (Instrument: Gilson GX 281; Column: Gemini 150*25 mm*5 um; Mobile phase A: Water (0.05% ammonia solution); Mobile phase B: MeCN; Gradient: 42-72(B %); Flowrate: 25 mL/min; Run time: 10 min) to give a white solid of 1-(4-(2-cyano-2-methylpropyl)-3-(trifluoromethyl)phenyl)-3-(2-(5-ethoxy-6-oxo-1,6-dihydropyridin-3-yl)-4-methylpyrimidin-5-yl)urea (22.67 mg, 0.043 mmol, 34.3% yield): ¹H NMR (400 MHz, CD₃OD) δ: 9.03 (s, 1H), 8.06 (s, 1H), 7.96 (s, 1H), 7.86-7.85 (m, 1H), 7.68-7.66 (m, 2H), 4.14 (q, J=7.2 Hz, 2H), 3.03 (s, 2H), 2.55 (s, 3H), 1.48 (t, J=7.2 Hz, 3H), 1.38 (s, 6H); ES-LCMS m/z: 515.1 (M+H).

EXAMPLE 15

1-(2-(5-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea

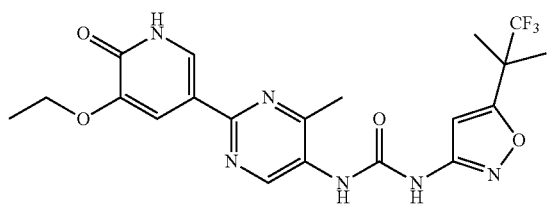

Step 1: 2-Chloro-4-methylpyrimidin-5-amine

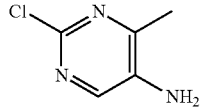

To a solution of 2,4-dichloro-6-methyl-5-nitropyrimidine (10 g, 48.1 mmol) and NH₄Cl (25.7 g, 481 mmol) in MeOH (100 mL) stirred under N₂ at 20° C. was added zinc (31.4 g, 481 mmol) in one charge. The reaction mixture was stirred at 70° C. for 50 h. The mixture was filtered, and the filtrate was concentrated in vacuo. The residue was purified by silica column chromatography (DCM/MeOH=30:1). All fractions found to contain product by TLC (EA/EA=1=1:1, R$_f$=0.6) were combined and concentrated to yield a light yellow solid of 2-chloro-4-methylpyrimidin-5-amine (2 g, 13.93 mmol, 29.0% yield): ¹H NMR (400 MHz, CDCl₃) δ: 7.95 (s, 1H), 3.66 (s, 2H), 2.88 (s, 3H); ES-LCMS m/z: 144.2 (M+H).

Step 2: 2-(5-Ethoxy-6-((4-methoxybenzyl)oxy)pyridin-3-yl)-4-methylpyrimidin-5-amine

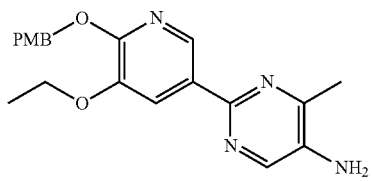

To a solution of 3-ethoxy-2-((4-methoxybenzyl)oxy)-5-(4,4,5,5-tetramethyl-1,3,2-dioxaborolan-2-yl)pyridine (3.22 g, 8.36 mmol), 2-chloro-4-methylpyrimidin-5-amine (1 g, 6.97 mmol) and Cs₂CO₃ (5.67 g, 17.41 mmol) in DMF (3 mL) and water (1 mL) stirred under N₂ at 20° C. was added PdCl₂(PPh₃)₂ (0.244 g, 0.348 mmol) in one charge. The reaction vessel was heated in 110° C. for 3 h. Then the solution was concentrated and distributed between EA and water. The combined organic extract was washed with brine, dried over MgSO₄, filtered and concentrated. The residue was purified by silica column chromatography (PE/EA=1:1). All fractions found to contain product by TLC (PE/EA=1:1, R$_f$=0.3) were combined and concentrated to yield a light yellow solid of 2-(5-ethoxy-6-((4-methoxybenzyl)oxy)pyridin-3-yl)-4-methylpyrimidin-5-amine (1.6 g, 4.37 mmol, 62.7% yield): ¹H NMR (400 MHz, CDCl₃) δ: 8.68 (s, 1H), 8.11 (s, 1H), 7.97 (s, 1H), 7.46 (d, J=8.4 Hz, 2H), 6.89 (d, J=8.4 Hz, 2H), 5.48 (s, 2H), 4.20 (q, J=7.2 Hz, 2H), 3.80 (s, 3H), 3.64 (s, 2H), 2.45 (s, 3H), 1.47 (t, J=7.2 Hz, 3H); ES-LCMS m/z: 367.1 (M+H).

Step 3: 3-Isocyanato-5-(1,1,1-trifluoro-2-methylpropan-2-yl)isoxazole

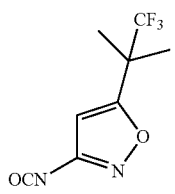

A mixture of 5-(1,1,1-trifluoro-2-methylpropan-2-yl)isoxazol-3-amine (300 mg, 1.545 mmol) and triphosgene (183 mg, 0.618 mmol) in THF (30 mL) was stirred at 50° C. for 0.5 h. The mixture was concentrated to give a yellow solid of 3-isocyanato-5-(1,1,1-trifluoro-2-methylpropan-2-yl)isoxazole (300 mg, 1.186 mmol, 77% yield): ES-LCMS m/z: 253.0 (M+MeOH).

Step 4: 1-(2-(5-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea

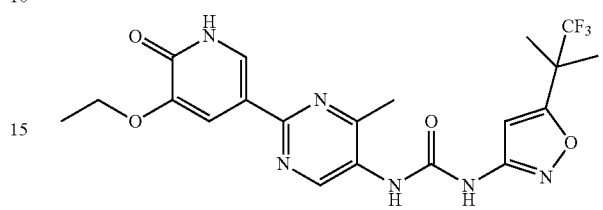

To a mixture of 3-isocyanato-5-(1,1,1-trifluoro-2-methylpropan-2-yl)isoxazole (100 mg, 0.454 mmol) in THF (50 mL) was added 2-(5-ethoxy-6-((4-methoxybenzyl)oxy)pyridin-3-yl)-4-methylpyrimidin-5-amine (100 mg, 0.273 mmol) and Et₃N (0.126 mL, 0.908 mmol). Then the mixture was stirred at 50° C. for 1 h. To the mixture was added another solution of 3-isocyanato-5-(1,1,1-trifluoro-2-methylpropan-2-yl)isoxazole (100 mg, 0.454 mmol) in THF (15 mL) and the mixture was stirred at 50° C. for 4 h. The mixture was concentrated. The residue was purified by preparative TLC (DCM/MeOH=10:1, R$_f$=0.6) to give a yellow solid of 1-(2-(5-ethoxy-6-((4-methoxybenzyl)oxy)pyridin-3-yl)-4-methylpyrimidin-5-yl)-3-(5-(1,1,1-trifluoro-2-methylpropan-2-yl)isoxazol-3-yl)urea (60 mg, 0.102 mmol). A solution of 1-(2-(5-ethoxy-6-((4-methoxybenzyl)oxy)pyridin-3-yl)-4-methylpyrimidin-5-yl)-3-(5-(1,1,1-trifluoro-2-methylpropan-2-yl)isoxazol-3-yl)urea (60 mg, 0.102 mmol) in TFA (10% in DCM, 30 mL) was stirred at 25° C. for 1 h. The mixture was concentrated and the residue was purified by preparative HPLC (MeCN/H₂O as eluants, basic condition) to yield a white solid of 1-(2-(5-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (5.97 mg, 0.013 mmol, 2.82% yield): ¹H NMR (400 MHz, CD₃OD+CDCl₃) δ: 9.09 (s, 1H), 8.05 (d, J=2.0 Hz, 1H), 7.82 (d, J=2.0 Hz, 1H), 6.70 (s, 1H), 4.14 (q, J=7.2 Hz, 2H), 2.55 (s, 3H), 1.58 (s, 6H), 1.48 (t, J=6.8 Hz, 3H); ES-LCMS m/z 467.1 (M+H).

EXAMPLE 16

1-(5-(5-Ethoxy-6-oxo-1,6-dihydropyridin-3-yl)-3-methylpyrazin-2-yl)-3-(5-(1,1,1-trifluoro-2-methylpropan-2-yl)isoxazol-3-yl)urea

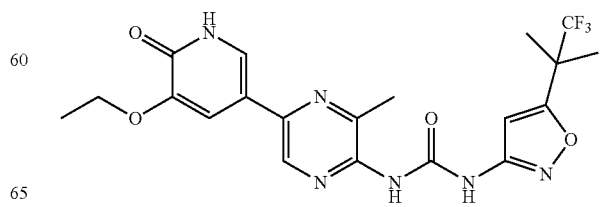

Step 1: 5-Bromo-2-isocyanato-3-methylpyrazine

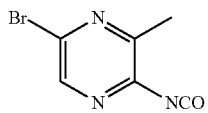

A mixture of 5-bromo-3-methylpyrazin-2-amine (450 mg, 2.393 mmol) in THF (30 mL) was added triphosgene (284 mg, 0.957 mmol). The mixture was stirred at 50° C. for 1 h. The mixture was concentrated to yield a light yellow oil of 5-bromo-2-isocyanato-3-methylpyrazine (500 mg, 0.963 mmol, 40.2% yield): ES-LCMS m/z 247.9 (M+MeOH+H).

Step 2: 1-(5-Bromo-3-methylpyrazin-2-yl)-3-(5-(1,1,1-trifluoro-2-methylpropan-2-yl)isoxazol-3-yl)urea

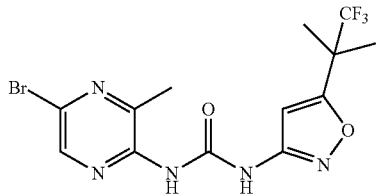 [SMILES: Cc1nc(Br)cnc1NC(=O)Nc1cc(C(C)(C)C(F)(F)F)on1]

To a mixture of 5-bromo-2-isocyanato-3-methylpyrazine (507 mg, 2.369 mmol) in THF (50 mL) was added 5-(1,1,1-trifluoro-2-methylpropan-2-yl)isoxazol-3-amine (400 mg, 2.060 mmol) and Et$_3$N (0.573 mL, 4.12 mmol). Then the mixture was stirred at 50° C. for 4 h. The mixture was concentrated. The residue was purified on silica column chromatography (PE/EA=5:1). All fractions found to contain product by TLC (PE/EA=2:1, R$_f$=0.6) were combined and concentrated to yield a light yellow solid of 1-(5-bromo-3-methylpyrazin-2-yl)-3-(5-(1,1,1-trifluoro-2-methylpropan-2-yl)isoxazol-3-yl)urea (150 mg, 0.187 mmol, 9.10% yield): $^1$H NMR (400 MHz, CD$_3$OD) δ: 7.79 (s, 1H), 6.92 (s, 1H), 2.58 (s, 3H), 1.52 (s, 6H); ES-LCMS m/z 409.9 (M+2).

Step 3: 1-(5-(5-ethoxy-6-((4-methoxybenzyl)oxy)pyridin-3-yl)-3-methylpyrazin-2-yl)-3-(5-(1,1,1-trifluoro-2-methylpropan-2-yl)isoxazol-3-yl)urea

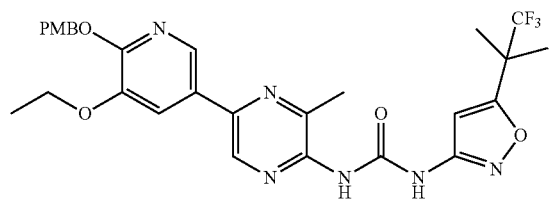

To a mixture of 3-ethoxy-2-((4-methoxybenzyl)oxy)-5-(4,4,5,5-tetramethyl-1,3,2-dioxaborolan-2-yl)pyridine (80 mg, 0.208 mmol), 1-(5-bromo-3-methylpyrazin-2-yl)-3-(5-(1,1,1-trifluoro-2-methylpropan-2-yl)isoxazol-3-yl)urea (85 mg, 0.208 mmol) in water (1 mL) and 1,4-dioxane (3 mL) was added Cs$_2$CO$_3$ (135 mg, 0.415 mmol) and PdCl$_2$(dppf) (15.19 mg, 0.021 mmol) under N$_2$ atmosphere. Then the mixture was stirred and irradiated in a microwave oven at 120° C. for 30 min. The mixture was concentrated and extracted with EA. The combined organic was concentrated. The residue was purified by preparative TLC (PE/EA=2:1, R$_f$=0.5) to give a yellow solid of 1-(5-(5-ethoxy-6-((4-methoxybenzyl)oxy)pyridin-3-yl)-3-methylpyrazin-2-yl)-3-(5-(1,1,1-trifluoro-2-methylpropan-2-yl)isoxazol-3-yl)urea (20 mg, 0.014 mmol, 6.57% yield): $^1$H NMR (400 MHz, CD$_3$OD) δ: 8.71 (d, J=6.4 Hz, 1H), 8.38 (s, 1H), 7.89 (d, J=12.0 Hz, 2H), 7.44 (d, J=8.4 Hz, 2H), 6.94 (d, J=8.4 Hz, 2H), 5.42 (d, J=3.6 Hz, 2H), 4.62 (s, 2H), 4.23-4.17 (m, 2H), 3.82 (s, 3H), 1.72-1.51 (m, 6H), 1.47 (t, J=6.8 Hz, 3H); ES-LCMS m/z 587.1 (M+H).

Step 4: 1-(5-(5-Ethoxy-6-oxo-1,6-dihydropyridin-3-yl)-3-methylpyrazin-2-yl)-3-(5-(1,1,1-trifluoro-2-methylpropan-2-yl)isoxazol-3-yl)urea

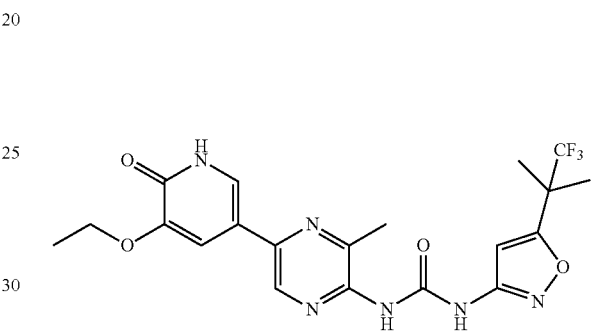

A mixture of 1-(5-(5-ethoxy-6-((4-methoxybenzyl)oxy)pyridin-3-yl)-3-methylpyrazin-2-yl)-3-(5-(1,1,1-trifluoro-2-methylpropan-2-yl)isoxazol-3-yl)urea (20 mg, 0.034 mmol) and HCl (4 mol/L in dioxane, 20 mL) was stirred at 25° C. for 2 h. The mixture was concentrated. The residue was purified by preparative HPLC (MeCN/H$_2$O as eluants, acidic condition) to give a white solid of 1-(5-(5-ethoxy-6-oxo-1,6-dihydropyridin-3-yl)-3-methylpyrazin-2-yl)-3-(5-(1,1,1-trifluoro-2-methylpropan-2-yl)isoxazol-3-yl)urea hydrochloride (1.2 mg, 2.386 μmol, 7.00% yield): $^1$H NMR (400 MHz, DMSO-d$_6$) δ: 11.92 (s, 1H), 11.13 (s, 1H), 9.28 (s, 1H), 8.73 (s, 1H), 7.72 (s, 1H), 7.43 (d, J=2.0 Hz, 1H), 6.89 (s, 1H), 4.02 (q, J=7.1 Hz, 2H), 2.51 (s, 3H), 1.53 (s, 6H), 1.33 (t, J=6.9 Hz, 3H); ES-LCMS m/z 467.2 (M+H).

EXAMPLE 17

1-(4-(6-Oxo-1,6-dihydropyridin-3-yl)phenyl)-3-(4-(piperazin-1-ylmethyl)-3-(trifluoromethyl)phenyl)urea

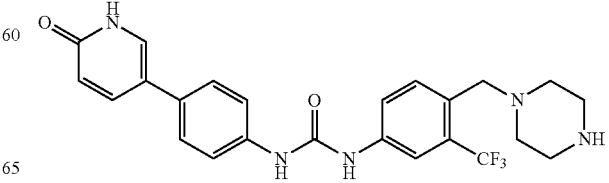

Step 1: tert-butyl (4-(6-oxo-1,6-dihydropyridin-3-yl)phenyl)carbamate

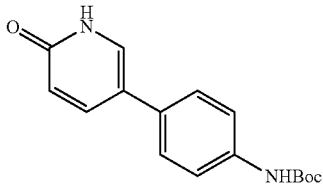 [SMILES: CC(C)(C)OC(=O)Nc1ccc(-c2ccc(=O)[nH]c2)cc1]

To a mixture of 5-bromopyridin-2-ol (600 mg, 3.45 mmol), (4-((tert-butoxycarbonyl)amino)phenyl)boronic acid (817 mg, 3.45 mmol) in water (3 mL) and 1,4-dioxane (9 mL) was added $Cs_2CO_3$ (2247 mg, 6.90 mmol), $PdCl_2$(dppf) (126 mg, 0.172 mmol) under $N_2$ atmosphere. Then the mixture was stirred and irradiated in a microwave oven at 100° C. for 1 h. The mixture was concentrated, extracted with EA. The organic phase was concentrated. The residue was purified by preparative TLC (DCM/MeOH=10: 1) to give tert-butyl (4-(6-oxo-1,6-dihydropyridin-3-yl)phenyl)carbamate (100 mg, 0.349 mmol, 10.13% yield): $^1$H NMR (400 MHz, $CDCl_3$) δ: 7.67 (dd, J=2.4, 9.6 Hz, 1H), 7.43-7.40 (m, 1H), 7.35 (d, J=8.8 Hz, 2H), 7.26 (d, J=8.4 Hz, 2H), 6.60 (d, J=9.6 Hz, 1H), 1.40 (s, 9H); ES-LCMS m/z 287.2 (M+H).

Step 2: 5-(4-Aminophenyl)pyridin-2(1H)-one

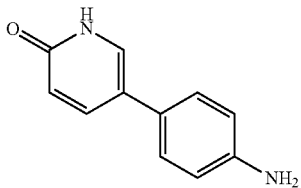

To a solution of tert-butyl (4-(6-oxo-1,6-dihydropyridin-3-yl)phenyl)carbamate (100 mg, 0.349 mmol) in DCM (10 mL) was added TFA (39.8 mg, 0.349 mmol), and then stirred at 25° C. for 2 h. The mixture was concentrated to give 5-(4-aminophenyl)pyridin-2(1H)-one (60 mg, 0.322 mmol, 92% yield): ES-LCMS m/z 187.1 (M+H).

Step 3: 4-Isocyanato-2-(trifluoromethyl)benzaldehyde

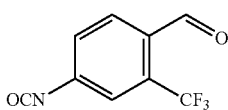

To a mixture of 4-amino-2-(trifluoromethyl)benzaldehyde (90 mg, 0.476 mmol) in THF (30 mL) was added carbonic acid ditrichloromethyl ester (56.5 mg, 0.190 mmol). Then the mixture was stirred at 50° C. for 0.5 h. The mixture was concentrated to give 4-isocyanato-2-(trifluoromethyl)benzaldehyde (100 mg, 0.465 mmol, 98% yield).

Step 4: 1-(4-Formyl-3-(trifluoromethyl)phenyl)-3-(4-(6-oxo-1,6-dihydropyridin-3-yl)phenyl)urea

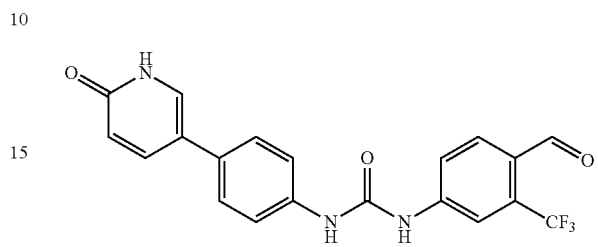

To a mixture of 5-(4-aminophenyl)pyridin-2(1H)-one (60 mg, 0.322 mmol) in THF (15 mL) was added 4-isocyanato-2-(trifluoromethyl)benzaldehyde (90 mg, 0.419 mmol), $Et_3N$ (65.2 mg, 0.644 mmol). Then the mixture was stirred at 50° C. for 4 h. The mixture was concentrated, and the residue was purified by preparative TLC (DCM:MeOH= 10 : 1) to give 1-(4-formyl-3-(trifluoromethyl)phenyl)-3-(4-(6-oxo-1,6-dihydropyridin-3-yl)phenyl)urea (20 mg, 0.050 mmol, 15.47% yield): $^1$H NMR (400 MHz, $CD_3OD$) δ 10.20 (t, J=2.0 Hz, 1H), 8.17 (d, J=2.0 Hz, 1H), 8.10 (d, J=8.4 Hz, 1H), 7.95 (dd, J=2.8, 9.6 Hz, 1H), 7.81 (dd, J=2.4, 8.8 Hz, 1H), 7.70 (d, J=2.8 Hz, 1H), 7.58 (dd, J=2.0, 6.8 Hz, 2H), 7.53 (dd, J=2.0, 8.4 Hz, 2H), 6.63 (d, J=7.2 Hz, 1H); ES-LCMS m/z 402.1 (M+H).

Step 5: tert-Butyl 4-(4-(3-(4-(6-oxo-1,6-dihydropyridin-3-yl)phenyl)ureido)-2-(trifluoromethyl)benzyl)piperazine-1-carboxylate

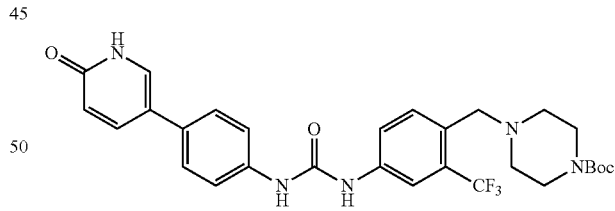

A mixture of 1-(4-formyl-3-(trifluoromethyl)phenyl)-3-(4-(6-oxo-1,6-dihydropyridin-3-yl)phenyl)urea (35 mg, 0.087 mmol), tert-butyl piperazine-1-carboxylate (0.031 mL, 0.174 mmol), tert-butyl piperazine-1-carboxylate (0.031 mL, 0.174 mmol) in DCM (10 mL) was stirred at 25° C. for 2 h. Then to the mixture was added $NaBH(OAc)_3$ (18.48 mg, 0.087 mmol) in portions, then stirred at 25° C. for 12 h. The mixture was concentrated, and the residue was purified by preparative TLC to give tert-butyl 4-(4-(3-(4-(6-oxo-1,6-dihydropyridin-3-yl)phenyl)ureido)-2-(trifluoromethyl)benzyl)piperazine-1-earboxylate (20 mg, 0.035 mmol, 40.1% yield): ES-LCMS m/z 572.2 (M+H).

Step 6: 1-(4-(6-Oxo-1,6-dihydropyridin-3-yl)phenyl)-3-(4-(piperazin-1-ylmethyl)-3-(trifluoromethyl)phenyl)urea

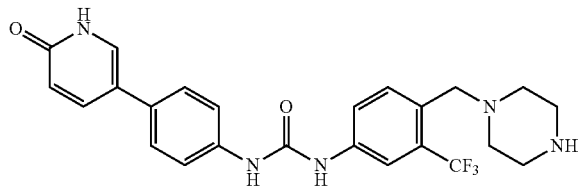 [SMILES: O=C(Nc1ccc(-c2ccc(=O)[nH]c2)cc1)Nc1ccc(CN2CCNCC2)c(C(F)(F)F)c1]

A mixture of tert-butyl 4-(4-(3-(4-(6-oxo-1,6-dihydropyridin-3-yl)phenyl)ureido)-2-(trifluoromethyl)benzyl)piperazine-1-carboxylate (20 mg, 0.035 mmol) and HCl/MeOH (4 mol/L, 10 mL, 40.0 mmol) was stirred at 25° C. for 2 h. The mixture was concentrated, purified by preparative HPLC to give 1-(4-(6-oxo-1,6-dihydropyridin-3-yl)phenyl)-3-(4-(piperazin-1-ylmethyl)-3-(trifluoromethyl)phenyl)urea dihydrochloride (2.48 mg, 4.56 µmol, 13.02% yield): $^1$H NMR (400 MHz, CD$_3$OD) δ: 8.27 (d, J=8.0 Hz, 1H), 8.11 (s, 1H), 8.03 (s, 1H), 7.92 (d, J=8.0 Hz, 1H), 7.79 (d, J=8.4 Hz, 1H), 7.60-7.59 (m, 4H), 6.96 (d, J=9.2 Hz, 1H), 4.35 (s, 2H), 3.56 (s, 4H), 3.39 (s, 4H); ES-LCMS m/z 472.2 (M+H).

EXAMPLE 18

1-(4-(4-Ethoxy-6-oxo-1,6-dihydropyridin-3-yl)-2-fluorophenyl)-3-(4-((3-methyloxetan-3-yl)oxy)-3-(trifluoromethyl)phenyl)urea

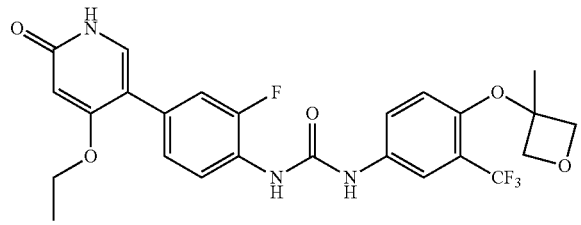

Step 1: 1-(4-(6-(Benzyloxy)-4-ethoxypyridin-3-yl)-2-fluorophenyl)-3-(4-((3-methyloxetan-3-yl)oxy)-3-(trifluoromethyl)phenyl)urea

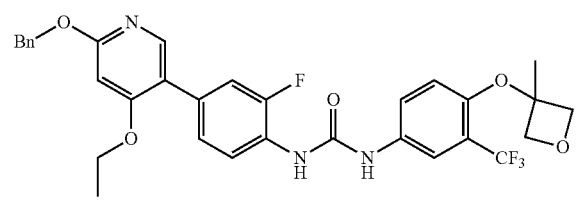 [SMILES: CCOc1cc(OCc2ccccc2)ncc1-c1ccc(NC(=O)Nc2ccc(OC3(C)COC3)c(C(F)(F)F)c2)c(F)c1]

To a mixture of 2-(benzyloxy)-4-ethoxy-5-iodopyridine (150 mg, 0.422 mmol) in 1,4-dioxane (3 mL) and water (1 mL) was added 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (237 mg, 0.465 mmol), Cs$_2$CO$_3$ (275 mg, 0.845 mmol) and PdCl$_2$(dppf) (30.9 mg, 0.042 mmol). The mixture was stirred under a N$_2$ atmosphere at 110° C. for 30 min under microwave. Then the reaction residue was filtered and the filtrate was concentrated and purified by TLC (PE/EA=1:1, R$_f$=0.6) to yield a yellow solid of 1-(4-(6-(benzyloxy)-4-ethoxypyridin-3-yl)-2-fluorophenyl)-3-(4-((3-methyloxetan-3-yl)oxy)-3-(trifluoromethyl)phenyl)urea (100 mg, 0.147 mmol, 34.8% yield): $^1$H NMR (400 MHz, CD$_3$OD) δ 8.08 (t, J=8.4 Hz, 1H), 7.94 (s, 1H), 7.78 (d, J=2.4 Hz, 1H), 7.55 (d, J=8.4 Hz, 1H), 7.45-7.43 (m, 2H), 7.37-7.35 (m, 1H), 7.32-7.29 (m, 3H), 7.26-7.23 (m, 1H), 6.62 (d, J=8.4 Hz, 1H), 6.47 (s, 1H), 5.35 (s, 2H), 4.89 (d, J=6.4 Hz, 2H), 4.62 (d, J=7.2 Hz, 2H), 4.16-4.10 (m, 2H), 1.72 (s, 3H), 1.38 (t, J=6.8 Hz, 3H); ES-LCMS m/z 612.2 (M+H).

Step 2: 1-(4-(4-Ethoxy-6-oxo-1,6-dihydropyridin-3-yl)-2-fluorophenyl)-3-(4-((3-methyloxetan-3-yl)oxy)-3-(trifluoromethyl)phenyl)urea

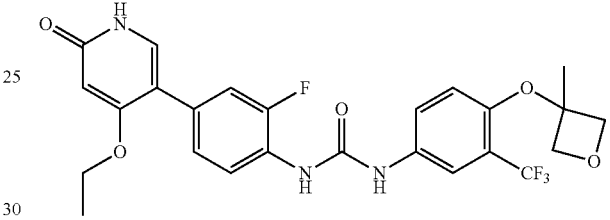

To a mixture of 1-(4-(6-(benzyloxy)-4-ethoxypyridin-3-yl)-2-fluorophenyl)-3-(4-((3-methyloxetan-3-yl)oxy)-3-(trifluoromethyl)phenyl)urea (100 mg, 0.164 mmol) in MeOH (10 mL) was added Pd/C (20 mg, 10%). The mixture was stirred at 25° C. for 16 h under a H$_2$ atmosphere. The reaction residue was filtered and concentrated. The residue was purified by preparative HPLC (MeCN/H$_2$O as eluants, acidic condition) to yield a white solid of 1-(4-(4-ethoxy-6-oxo-1,6-dihydropyridin-3-yl)-2-fluorophenyl)-3-(4-((3-methyloxetan-3-yl)oxy)-3-(trifluoromethyl)phenyl)urea (40.13 mg, 0.077 mmol, 47.1% yield): $^1$H NMR (400 MHz, CD$_3$OD) δ 8.11 (t, J=8.8 Hz, 1H), 7.80 (d, J=2.8 Hz, 1H), 7.57 (dd, J=2.8 Hz, 8.4 Hz, 1H), 7.38 (s, 1H), 7.30 (dd, J=2.4, 8.4 Hz, 1H), 7.21 (d, J=8.8 Hz, 1H), 6.65 (d, J=8.8 Hz, 1H), 6.01 (s, 1H), 4.92 (d, J=6.8 Hz, 2H), 4.65 (d, J=6.8 Hz, 2H), 4.16-4.11 (m, 2H), 1.75 (s, 3H), 1.41 (t, J=7.2 Hz, 2H); ES-LCMS m/z 522.2 (M+H).

EXAMPLE 19

1-(2-Fluoro-4-(4-oxo-4,5-dihydrofuro[3,2-c]pyridin-7-yl)phenyl)-3-(4-((3-methyloxetan-3-yl)oxy)-3-(trifluoromethyl)phenyl)urea

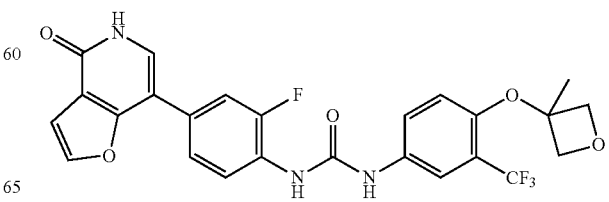

Step 1: (E)-3-(Furan-2-yl)acrylic acid

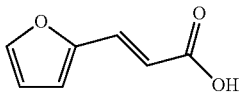

To a mixture of furan-2-carbaldehyde (30 g, 312 mmol) and malonic acid (35.7 g, 343 mmol) in pyridine (300 mL) was added piperidine (3.09 mL, 31.2 mmol) at rt, and the mixture was stirred at 100° C. for 16 h. The reaction solution was poured into water (200 mL) and acidified with 6M hydrochloric acid. The resulting precipitate was collected by filtration to give (E)-3-(furan-2-yl)acrylic acid (32 g, 227 mmol, 72.7% yield): $^1$H NMR (400 MHz, CD$_3$OD) δ 7.61 (d, J=1.6 Hz, 1H), 7.42 (d, J=15.6 Hz, 1H), 6.73 (d, J=3.2 Hz, 1H), 6.53 (dd, J=2.0, 3.6 Hz, 1H), 6.22 (d, J=15.6 Hz, 1H); ES-LCMS m/z 139.1 (M+H).

Step 2: (E)-3-(Furan-2-yl)acryloyl azide

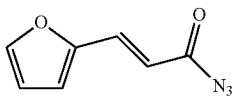 [SMILES: [N-]=[N+]=NC(=O)/C=C/c1ccco1]

To a mixture of (E)-3-(furan-2-yl)acrylic acid (25 g, 181 mmol) and Et$_3$N (30.3 mL, 217 mmol) in THF (50 mL) was added DPPA (54.8 g, 199 mmol) under ice-cooling. The mixture was stirred at 25° C. for 4 h. The reaction solution was poured into a mixture of EA (300 mL) and saturated aqueous NaHCO$_3$ solution (300 mL), and the mixture was extracted with EA (200 mL). The extract was dried over anhydrous Na$_2$SO$_4$, and the solvent was evaporated under reduced pressure. The residue was washed with MeOH to give (E)-3-(furan-2-yl)acryloyl azide (24 g, 144 mmol, 80% yield): $^1$H NMR (400 MHz, CDCl$_3$) δ 7.53-7.50 (m, 1H), 7.47 (s, 1H), 6.71 (d, J=3.2 Hz, 1H), 6.50 (dd, J=2.0, 3.6 Hz, 1H), 6.30 (d, J=3.6 Hz, 1H).

Step 3: Furo[3,2-c]pyridin-4(5H)-one

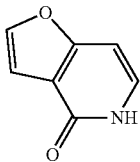

A mixture of (E)-3-(furan-2-yl)acryloyl azide (10 g, 61.3 mmol) in toluene (100 mL) was stirred at 100° C. for 30 min. The solvent was evaporated. The residue was dissolved in 1,2-dichlorobenzene (90 g, 613 mmol) and iodine (0.062 g, 0.245 mmol). The mixture was stirred at 180° C. for 2 h. The solvent was evaporated. The residue was dissolved in MeOH (200 mL). The precipitate was filtered off, and the filtrate was concentrated and washed with TBME (50 mL) to give furo[3,2-c]pyridin-4(5H)-one (5 g, 31.5 mmol, 51.3% yield): $^1$H NMR (400 MHz, CD$_3$OD) δ 7.71 (d, J=2.0 Hz, 1H), 7.32 (d, J=7.2 Hz, 1H), 6.95 (dd, J=1.2, 2.4 Hz, 1H), 6.75 (dd, J=0.8, 7.2 Hz, 1H); ES-LCMS m/z 136.1 (M+H).

Step 4: 7-Bromofuro[3,2-c]pyridin-4(5H)-one

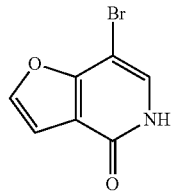 [SMILES: O=c1[nH]cc(Br)c2occc12]

To a mixture of furo[3,2-c]pyridin-4(5H)-one (5 g, 37.0 mmol) in MeCN (50 mL) was added a solution of NBS (8.56 g, 48.1 mmol) in MeCN at 0° C. over 10 min. The resulting suspension was stirred at 0° C. for 1 h and warmed to rt for 10 min. Water (250 mL) and saturated aqueous NaHCO$_3$ (10 mL) ware added to the mixture. Off-white solids ware collected by filtration and dried to afford 7-bromofuro[3,2-c]pyridin-4(5H)-one (1.5 g, 5.96 mmol, 16.10% yield): $^1$H NMR (400 MHz, CD$_3$OD) δ 7.82 (d, J=2.0 Hz, 1H), 7.51 (s, 1H), 7.05 (d, J=2.4 Hz, 1H); ES-LCMS m/z 214.0, 215.9 (M+H).

Step 5: 1-(2-Fluoro-4-(4-oxo-4,5-dihydrofuro[3,2-c]pyridin-7-yl)phenyl)-3-(4-((3-methyloxetan-3-yl)oxy)-3-(trifluoromethyl)phenyl)urea

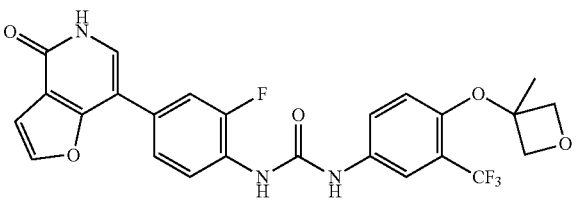

To a mixture of 7-bromofuro[3,2-c]pyridin-4(5H)-one (250 mg, 1.168 mmol) in 1,4-dioxane (12 mL) and water (4 mL) was added 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (656 mg, 1.285 mmol), PdCl$_2$(dppf) (85 mg, 0.117 mmol)and Cs$_2$CO$_3$ (761 mg, 2.336 mmol). The mixture was stirred at 110° C. for 30 min under a N$_2$ atmosphere under microwave. The residue was purified by preparative HPLC (MeCN/H$_2$O as eluants, acidic condition) to yield a white solid of 1-(2-fluoro-4-(4-oxo-4,5-dihydrofuro[3 ,2-c]pyridin-7-yl)phenyl)-3-(4-((3-methyloxetan-3-yl)oxy)-3-(trifluoromethyl)phenyl)urea (48.18 mg, 0.089 mmol, 7.63% yield): $^1$H NMR (400 MHz, CD$_3$OD) δ 8.20 (t, J=8.4 Hz, 1H), 7.85 (d, J=2.0 Hz, 1H), 7.80 (d, J=2.4 Hz, 1H), 7.61-7.51 (m, 4H), 7.07 (d, J=2.0 Hz, 1H), 6.62 (d, J=8.8 Hz, 1H), 4.89 (d, J=6.8 Hz, 2H), 4.63 (d, J=7.2 Hz, 2H), 1.72 (s, 3H); ES-LCMS m/z 518.0 (M+H).

EXAMPLE 20

1-(4-(5-Cyclopropoxy-6-oxo-1,6-dihydropyridin-3-yl)-2-fluorophenyl)-3-(4-((3-methyloxetan-3-yl)oxy)-3-(trifluoromethyl)phenyl)urea

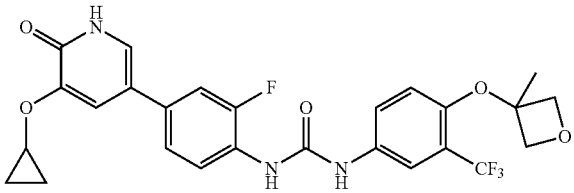 [SMILES: CC1(Oc2ccc(NC(=O)Nc3ccc(-c4c[nH]c(=O)c(OC5CC5)c4)cc3F)cc2C(F)(F)F)COC1]

Step 1: 3-Bromo-5-cyclopropoxypyridine

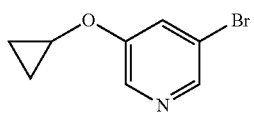

To a mixture of 5-bromopyridin-3-ol (5 g, 28.7 mmol) in DMF (50 mL) was added bromocyclopropane (3.82 g, 31.6 mmol), NaI (0.431 g, 2.87 mmol) and K₂CO₃ (7.94 g, 57.5 mmol). The mixture was stirred at 150° C. for 32 h. The reaction was filtered, concentrated, and purified by silica column chromatography (PE/EA=5:1). All fractions found to contain product by TLC (PE/EA=5:1, R$_f$=0.6) were combined and concentrated to yield a yellow oil of 3-bromo-5-cyclopropoxypyridine (1.5 g, 5.61 mmol, 19.51% yield): ¹H NMR (400 MHz, CDCl₃) δ 8.31-8.28 (m, 2H), 7.52 (t, J=2.4 Hz, 1H), 3.78-3.75 (m, 1H), 0.84-0.78 (m, 4H); ES-LCMS m/z 214.0, 216.0 (M+H).

Step 2: 3-Bromo-5-cyclopropoxypyridine 1-oxide

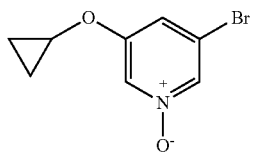

To a mixture of 3-bromo-5-cyclopropoxypyridine (1.5 g, 7.01 mmol) in DCM (50 mL) was added m-CPBA (1.814 g, 10.51 mmol). The mixture was stirred at 25° C. for 16 h. The mixture was distributed between DCM (50 mL) and saturated Na₂SO₃ solution (50 mL×3). The combined organic extract was washed with brine, dried over MgSO₄, filtered and concentrated. The resulting 3-bromo-5-cyclopropoxypyridine 1-oxide (1.2 g, 3.91 mmol, 55.8% yield): ¹H NMR (400 MHz, CDCl₃) δ 8.08-8.07 (m, 1H), 8.04-8.03 (m, 1H), 7.16-7.15 (m, 1H), 3.82-3.79 (m, 1H), 0.87-0.81 (m, 4H); ES-LCMS m/z 229.9, 231.9 (M+H).

Step 3: 5-Bromo-2-chloro-3-cyclopropoxypyridine

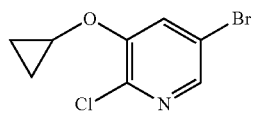 [SMILES: Clc1ncc(Br)cc1OC1CC1]

To a mixture of 3-bromo-5-cyclopropoxypyridine 1-oxide (1.2 g, 5.22 mmol) in DCM (20 mL) was added POCl₃ (9.72 mL, 104 mmol). The mixture was stirred at 45° C. for 16 h. The reaction was distributed between DCM (100 mL) and saturated NaHCO₃ solution (150 mL). The combined organic extract was washed with brine, dried over Na₂SO₄, filtered and concentrated. The residue was purified by silica column chromatography (PE/EA=5:1). All fractions found to contain product by TLC (PE/EA=5:1, R$_f$=0.6) were combined and concentrated to yield a yellow oil of 5-bromo-2-chloro-3-cyclopropoxypyridine (1 g, 3.42 mmol, 65.6% yield): ¹H NMR (400 MHz, CDCl₃) δ 8.08 (d, J=2.0 Hz, 1H), 7.69 (d, J=2.0 Hz, 1H), 3.84-3.79 (m, 1H), 0.91-0.89 (m, 4H); ES-LCMS m/z 247.9, 249.9 (M+H).

Step 4: 5-Bromo-3-cyclopropoxy-2-((4-methoxybenzyl)oxy)pyridine

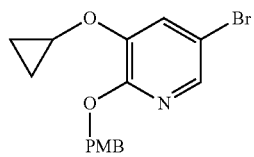

To a mixture of 5-bromo-2-chloro-3-cyclopropoxypyridine (1 g, 4.02 mmol) in DMF (10 mL) was added (4-methoxyphenyl)methanol (0.612 g, 4.43 mmol) and NaH (0.241 g, 6.04 mmol). The mixture was stirred at 120° C. for 16 h. The mixture was evaporated and distributed between DCM (50 mL×2) and water (50 mL). The combined organic extract was washed with brine, dried over MgSO₄, filtered and concentrated. The residue was purified by silica column chromatography (PE/EA=5:1). All fractions found to contain product by TLC (PE/EA=5:1, R$_f$=0.6) were combined and concentrated to yield a yellow solid of 5-bromo-3-cyclopropoxy-2-((4-methoxybenzyl)oxy)pyridine (1.2 g, 2.399 mmol, 59.6% yield): ¹H NMR (400 MHz, CDCl₃) δ 7.77 (d, J=2.0 Hz, 1H), 7.48 (d, J=2.4 Hz, 1H), 7.39-7.37 (m, 2H), 6.86 (dd, J=2.4, 6.8 Hz, 2H), 5.34 (s, 2H), 3.79 (s, 2H), 3.72-3.68 (m, 11-I), 0.84-0.79 (m, 4H); ES-LCMS m/z 350.0, 352.0 (M+H).

Step 5: 1-(4-(5-Cyclopropoxy-6-((4-methoxybenzyl)oxy)pyridin-3-yl)-2-fluorophenyl)-3-(4-((3-methyloxetan-3-yl)oxy)-3-(trifluoromethyl)phenyl)urea

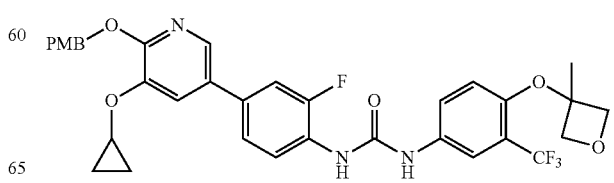

To a mixture of 5-bromo-3-cyclopropoxy-2-((4-methoxybenzyl)oxy)pyridine (180 mg, 0.514 mmol) in 1,4-dioxane (12 mL) and water (4 mL) was added 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (289 mg, 0.565 mmol), Cs$_2$CO$_3$ (335 mg, 1.028 mmol) and PdCl$_2$(dppf) (37.6 mg, 0.051 mmol). The mixture was stirred at 110° C. under a N$_2$ atmosphere for 16 h. The reaction was filtered and the filtrate was evaporated. The residue was purified by preparative TLC (PE/EA=3:1, R$_f$=0.6) to yield a yellow oil of 1-(4-(5-cyclopropoxy-6-((4-methoxybenzyl)oxy)pyridin-3-yl)-2-fluorophenyl)-3-(4-((3-methylthyloxetan-3-yl)oxy)-3-(trifluoromethyl)phenyl)urea (180 mg, 0.275 mmol, 53.6% yield): $^1$H NMR (400 MHz, CDCl$_3$) δ 8.14 (t, J=8.0 Hz, 1H), 7.90 (d, J=2.0 Hz, 1H), 7.53 (dd, J=2.0, 4.0 Hz, 3H), 7.40 (d, J=8.8 Hz, 2H), 7.14 (s, 1H), 7.07 (d, J=2.8 Hz, 1H), 6.86 (dd, J=2.0, 6.4 Hz, 2H), 6.40-6.37 (m, 1H), 5.41 (s, 2H), 4.94 (d, J=6.4 Hz, 2H), 4.56 (d, J=7.2 Hz, 2H), 3.78 (s, 3H), 2.17 (s, 1H), 1.71 (s, 3H), 0.85-0.80 (m, 4H); ES-LCMS m/z 534.0 (M-PMB+H).

Step 6: 1-(4-(5-Cyclopropoxy-6-oxo-1,6-dihydropyridin-3-yl)-2-fluorophenyl)-3-(4-((3-methyloxetan-3-yl)oxy)-3-(trifluoromethyl)phenyl)urea

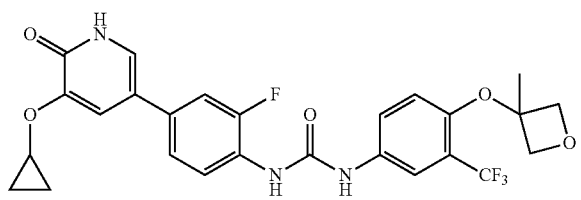 [SMILES: CC1(Oc2ccc(NC(=O)Nc3ccc(-c4c[nH]c(=O)c(OC5CC5)c4)cc3F)cc2C(F)(F)F)COC1]

To a mixture of 1-(4-(5-cyclopropoxy-6-((4-methoxybenzyl)oxy)pyridin-3-yl)-2-fluorophenyl)-3-(4-((3-methyloxetan-3-yl)oxy)-3-(trifluoromethyl)phenyl)urea (180 mg, 0.275 mmol) in MeOH (10 mL) was added Pd/C (18 mg, 10%). The mixture was stirred at 25° C. under a H$_2$ atmosphere for 16 h. The reaction was evaporated and purified by preparative HPLC (MeCN/H$_2$O as eluants, acidic condition) to yield a white solid of 1-(4-(5-cyclopropoxy-6-oxo-1,6-dihydropyridin-3-yl)-2-fluorophenyl)-3-(4-((3-methyloxetan-3-yl)oxy)-3-(trifluoromethyl)phenyl)urea (46.27 mg, 0.085 mmol, 30.9% yield): $^1$H NMR (400 MHz, CD$_3$OD) δ 8.14 (t, J=8.8 Hz, 1H), 7.79 (d, J=2.8 Hz, 1H), 7.54 (dd, J=2.4 Hz, 9.2 Hz, 2H), 7.39-7.32 (m, 2H), 7.28 (d, J=2.4 Hz, 1H), 6.62 (d, J=9.2 Hz, 1H), 4.90 (d, J=6.4 Hz, 2H), 4.62 (d, J=7.6 Hz, 2H), 3.94-3.89 (m, 1H), 1.72 (s, 3H), 0.89-0.77 (m, 4H); ES-LCMS m/z 534.2 (M+H).

EXAMPLE 21

1-(4-(5-Methoxy-6-oxo-1,6-dihydropyridin-3-yl)phenyl)-3-(4-((3-methyloxetan-3-yl)oxy)-3-(trifluoromethyl)phenyl)urea

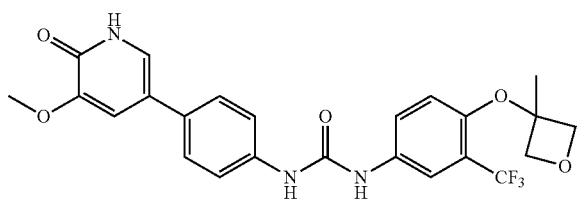 [SMILES: COc1cc(-c2ccc(NC(=O)Nc3ccc(OC4(C)COC4)c(C(F)(F)F)c3)cc2)c[nH]c1=O]

Step 1: 3-Bromo-5-methoxypyridine 1-oxide

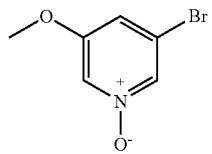

To a mixture of 3-bromo-5-methoxypyridine (3.6 g, 19.15 mmol) in DCM (50 mL) was added m-CPBA (3.96 g, 22.98 mmol). The mixture was stirred at 25° C. for 16 h. The reaction residue was distributed between DCM (100 mL) and saturated Na$_2$SO$_3$ solution (100 mL×2). The combined organic extract was washed with brine, dried over MgSO$_4$, filtered and concentrated. The resulting 3-bromo-5-methoxypyridine 1-oxide (4 g, 14.70 mmol, 77% yield): $^1$H NMR (400 MHz, CDCl$_3$) δ 8.02-8.01 (m 1H), 7.92-7.91 (m 1H), 7.03 (t, J=1.6 Hz, 1H), 3.93 (s, 3H); ES-LCMS m/z 204.1, 206.1 (M+H).

Step 2: 5-Bromo-2-chloro-3-methoxypyridine

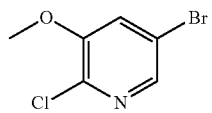

To a mixture of 3-bromo-5-methoxypyridine 1-oxide (2 g, 9.80 mmol) in DCM (40 mL) was added POCl$_3$ (18.27 mL, 196 mmol). The mixture was stirred at 40° C. for 16 h. The mixture was evaporated and distributed between EA (100 mL×2) and saturated NaHCO$_3$ solution (200 mL). The combined organic extract was washed with brine, dried over MgSO$_4$, filtered and concentrated. The residue was purified by silica column chromatography (PE/EA=10:1). All fractions found to contain product by TLC (PE/EA=10:1, R$_f$=0.6) were combined and concentrated to yield a light yellow oil of 5-bromo-2-chloro-3-methoxypyridine (1 g, 4.27 mmol, 43.6% yield): $^1$H NMR (400 MHz, CDCl$_3$) δ 8.05 (d, J=2.0 Hz, 1H), 7.33 (d, J=2.0 Hz, 1H), 3.93 (s, 3H); ES-LCMS m/z 222.0, 224.0 (M+H).

Step 3: 2-(Benzyloxy)-5-bromo-3-methoxypyridine

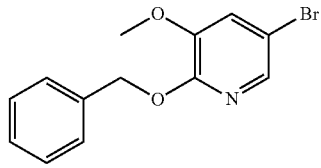 [SMILES: COc1cc(Br)cnc1OCc1ccccc1]

To a mixture of 5-bromo-2-chloro-3-methoxypyridine (1 g, 4.50 mmol) in phenylmethanol (4.86 g, 45.0 mmol) was added sodium (0.310 g, 13.49 mmol). The mixture was stirred at 100° C. for 16 h. The mixture was distributed between DCM (100 mL×2) and water (80 mL). The combined organic extract was washed with brine, dried over MgSO$_4$, filtered and concentrated. The residue was purified by silica column chromatography (PE/EA=10:1). All fractions found to contain product by TLC (PE/EA=10:1, R$_f$=0.6) were combined and concentrated to yield a light yellow oil of 2-(benzyloxy)-5-bromo-3-methoxypyridine (1.5 g, 4.33 mmol, 96% yield): $^1$H NMR (400 MHz, CDCl$_3$) δ 7.81 (d, J=2.0 Hz, 1H), 7.50-7.48 (m, 2H), 7.31-7.29 (m, 3H), 7.15 (d, J=2.0 Hz, 1H), 5.46 (s, 2H), 3.81 (s, 3H); ES-LCMS m/z 294.0, 296.0 (M+H).

Step 4:
4-(6-(Benzyloxy)-5-methoxypyridin-3-yl)aniline

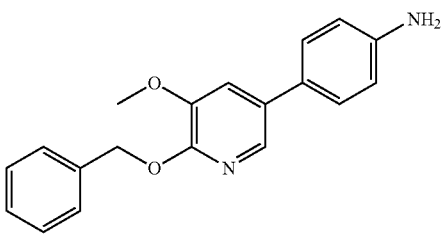 [SMILES: COc1cc(-c2ccc(N)cc2)cnc1OCc1ccccc1]

To a mixture of 2-(benzyloxy)-5-bromo-3-methoxypyridine (1 g, 3.40 mmol) in 1,4-dioxane (30 mL) and water (10.0 mL) was added (4-aminophenyl)boronic acid hydrochloride (0.394 mL, 3.74 mmol), Cs$_2$CO$_3$ (4.43 g, 13.60 mmol) and PdCl$_2$(dppf) (0.249 g, 0.340 mmol). The mixture was stirred at 110° C. under a N$_2$ atmosphere for 16 h. The residue was filtered and the filtrate was evaporated and purified by silica column chromatography (PE/EA=5:1). All fractions found to contain product by TLC (PE/EA=5:1, R$_f$=0.6) were combined and concentrated to give 4-(6-(benzyloxy)-5-methoxypyridin-3-yl)aniline (800 mg, 2.481 mmol, 73.0% yield): $^1$H NMR (400 MHz, CDCl$_3$) δ 7.88 (d, J=2.0 Hz, 1H), 7.51 (d, J=7.2 Hz, 2H), 7.38-7.30 (m, 5H), 7.22 (d, J=2.0 Hz, 1H), 6.78-6.73 (m, 2H), 5.51 (s, 2H), 3.92 (s, 3H), 3.74 (s, 2H); ES-LCMS m/z 307.0 (M+H).

Step 5:
5-(4-Aminophenyl)-3-methoxypyridin-2(1H)-one

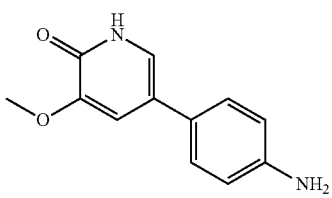 [SMILES: COc1cc(-c2ccc(N)cc2)c[nH]c1=O]

A mixture of 4-(6-(benzyloxy)-5-methoxypyridin-3-yl)aniline (800 mg, 2.61 mmol) in hydrochloric acid (1587 μl, 52.2 mmol) was stirred at 80° C. for 16 h. The reaction residue was concentrated to afford 5-(4-aminophenyl)-3-methoxypyridin-2(1H)-one (500 mg, 2.312 mmol, 89% yield): $^1$H NMR (400 MHz, CD$_3$OD) δ 7.67-7.62 (m, 4H), 7.32 (d, J=8.4 Hz, 2H), 3.84 (s, 3H); ES-LCMS m/z 217.2 (M+H).

Step 6: 1-(4-(5-Methoxy-6-oxo-1,6-dihydropyridin-3-yl)phenyl)-3-(4-((3-methyloxetan-3-yl)oxy)-3-(trifluoromethyl)phenyl)urea

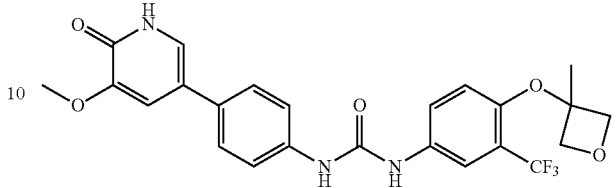

To a mixture of 3-(4-isocyanato-2-(trifluoromethyl)phenoxy)-3-methyloxetane (250 mg, 0.915 mmol) in THF (10 mL) was added 5-(4-aminophenyl)-3-methoxypyridin-2(1H)-one (218 mg, 1.007 mmol) and Et$_3$N (0.255 mL, 1.830 mmol). The mixture was stirred at 60° C. for 1 h. Then the reaction residue was concentrated and purified by preparative HPLC (MeCN/H$_2$O as eluants, acidic condition) to yield a pink solid of 1-(4-(5-methoxy-6-oxo-1,6-dihydropyridin-3-yl)phenyl)-3-(4-((3-methyloxetan-3-yl)oxy)-3-(trifluoromethyl)phenyl)urea (131.55 mg, 0.269 mmol, 29.4% yield): $^1$H NMR (400 MHz, CD$_3$OD) δ 7.80 (d, J=2.8 Hz, 1H), 7.58-7.57 (m, 1H), 7.56-7.53 (m, 4H), 7.35 (d, J=2.0 Hz, 1H), 7.31 (d, J=2 Hz, 1H), 6.65 (d, J=9.2 Hz, 1H), 4.93 (d, J=6.8 Hz, 2H), 4.66 (d, J=7.2 Hz, 2H), 3.95 (s, 3H), 1.75 (s, 3H); ES-LCMS m/z 490.1 (M+H).

EXAMPLE 22

1-(2-Fluoro-4-(4-oxo-2,3,4,5-tetrahydrofuro[3,2-c]pyridin-7-yl)phenyl)-3-(4-((3-methyloxetan-3-yl)oxy)-3-(trifluoromethyl)phenyl)urea

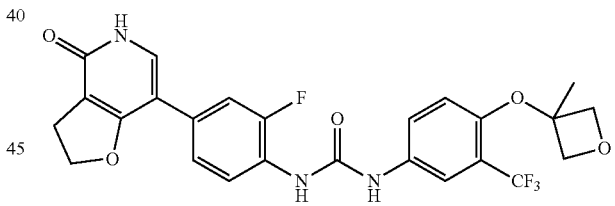

Step 1: (E)-3-(Furan-2-yl)acrylic acid

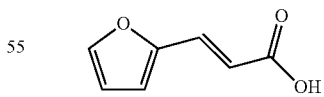

To a mixture of furan-2-carbaldehyde (30 g, 312 mmol) and malonic acid (35.7 g, 343 mmol) in pyridine (300 mL) was added piperidine (3.09 mL, 31.2 mmol) at rt, and the mixture was stirred at 100° C. for 16 h. The reaction solution was poured into water (200 mL) and acidified with 6M hydrochloric acid. The resulting precipitate was collected by filtration to give (E)-3-(furan-2-yl)acrylic acid (32 g, 227 mmol, 72.7% yield): $^1$H NMR (400 MHz, CD$_3$OD) δ 7.61 (d, J=1.6 Hz, 1H), 7.42 (d, J=15.6 Hz, 1H), 6.73 (d, J=3.2

Hz, 1H), 6.53 (dd, J=2.0, 3.6 Hz, 1H), 6.22 (d, J=15.6 Hz, 1H); ES-LCMS m/z 139.1 (M+H).

Step 2: (E)-3-(Furan-2-yl)acryloyl azide

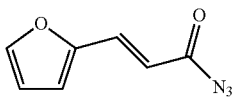

To a mixture of (E)-3-(furan-2-yl)acrylic acid (25 g, 181 mmol) and Et$_3$N (30.3 mL, 217 mmol) in THF (50 mL) was added DPPA (54.8 g, 199 mmol) under ice-cooling. The mixture was stirred at 25° C. for 4 h. The reaction solution was poured into a mixture of EA (300 mL) and saturated aqueous NaHCO$_3$ solution (300 mL), and the mixture was extracted with EA (200 mL). The extract was dried over anhydrous Na$_2$SO$_4$, and the solvent was evaporated under reduced pressure. The residue was washed with MeOH to give (E)-3-(furan-2-yl)acryloyl azide (24 g, 144 mmol, 80% yield): $^1$H NMR (400 MHz, CDCl$_3$) δ 7.53-7.50 (m, 1H), 7.47 (s, 1H), 6.71 (d, J=3.2 Hz, 1H), 6.50 (dd, J=2.0, 3.6 Hz, 1H), 6.30 (d, J=3.6 Hz, 1H).

Step 3: Furo[3,2-c]pyridin-4(5H)-one

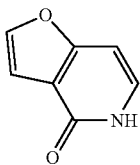

A mixture of (E)-3-(furan-2-yl)acryloyl azide (10 g, 61.3 mmol) in toluene (100 mL) was stirred at 100° C. for 30 min. The solvent was evaporated. The residue was dissolved in 1,2-dichlorobenzene (90 g, 613 mmol) and iodine (0.062 g, 0.245 mmol). The mixture was stirred at 180° C. for 2 h. The solvent was evaporated. The residue was dissolved in MeOH (200 mL). The precipitate was filtered off, and the filtrate was concentrated and washed with TBME (50 mL) to give furo[3,2-c]pyridin-4(5H)-one (5 g, 31.5 mmol, 51.3% yield): $^1$H NMR (400 MHz, CD$_3$OD) δ 7.71 (d, J=2.0 Hz, 1H), 7.32 (d, J=7.2 Hz, 1H), 6.95 (dd, J=1.2, 2.4 Hz, 1H), 6.75 (dd, J=0.8, 7.2 Hz, 1H); ES-LCMS m/z 136.1 (M+H).

Step 4: 7-Bromofuro[3,2-c]pyridin-4(5H)-one

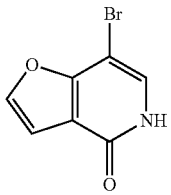

To a mixture of furo[3,2-c]pyridin-4(5H)-one (5 g, 37.0 mmol) in MeCN (50 mL) was added a solution of NBS (8.56 g, 48.1 mmol) in MeCN at 0° C. over 10 min. The resulting suspension was stirred at 0° C. for 1 h and warmed to rt for 10 min. Water (250 mL) and saturated aqueous NaHCO$_3$ (10 mL) ware added to the mixture. Off-white solids ware collected by filtration and dried to afford 7-bromofuro[3,2-c]pyridin-4(5H)-one (1.5 g, 5.96 mmol, 16.10% yield): $^1$H NMR (400 MHz, CD$_3$OD) δ 7.82 (d, J=2.0 Hz, 1H), 7.51 (s, 1H), 7.05 (d, J=2.4 Hz, 1H); ES-LCMS m/z 214.0, 215.9 (M+H).

Step 5: 1-(2-Fluoro-4-(4-oxo-4,5-dihydrofuro[3,2-c]pyridin-7-yl)phenyl)-3-(4-((3-methyloxetan-3-yl)oxy)-3-(trifluoromethyl)phenyl)urea

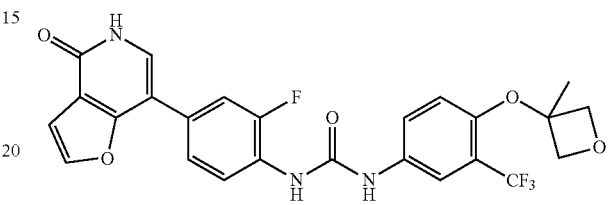

To a mixture of 7-bromofuro[3,2-c]pyridin-4(5H)-one (250 mg, 1.168 mmol) in 1,4-dioxane (3 mL) and water (1 mL) was added 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (656 mg, 1.285 mmol), PdCl$_2$(dppf) (85 mg, 0.117 mmol) and Cs$_2$CO$_3$ (761 mg, 2.336 mmol). The mixture was stirred at 110° C. for 30 min under a N$_2$ atmosphere under microwave. The mixture was filtered and the filtrate was concentrated. The residue was purified by preparative TLC (DCM/MeOH=15:1, R$_f$=0.6) to yield a yellow solid of 1-(2-fluoro-4-(4-oxo-4,5-dihydrofuro[3,2-c]pyridin-7-yl)phenyl)-3-(4-((3-methyloxetan-3-yl)oxy)-3-(trifluoromethyl)phenyl)urea (45 mg, 0.082 mmol, 7.00% yield): $^1$H NMR (400 MHz, CD$_3$OD) δ 8.20 (t, J=8.8 Hz, 1H), 7.84 (d, J=2.0 Hz, 1H), 7.80 (d, J=2.8 Hz, 1H), 7.61-7.51 (m, 4H), 7.06 (d, J=2.4 Hz, 1H), 6.62 (d, J=9.2 Hz, 1H), 4.89 (d, J=6.8 Hz, 2H), 4.63 (d, J=7.2 Hz, 2H), 1.72 (s, 3H); ES-LCMS m/z 518.0 (M+H).

Step 6: 1-(2-Fluoro-4-(4-oxo-2,3,4,5-tetrahydrofuro[3,2-c]pyridin-7-yl)phenyl)-3-(4-((3-methyloxetan-3-yl)oxy)-3-(trifluoromethyl)phenyl)urea

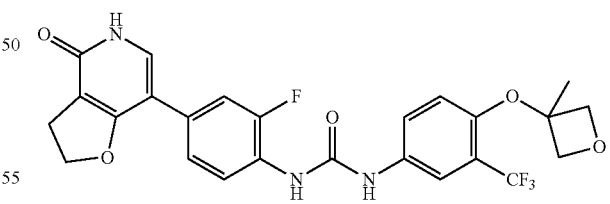

To a mixture of 1-(2-fluoro-4-(4-oxo-4,5-dihydrofuro[3,2-c]pyridin-7-yl)phenyl)-3-(4-((3-methyloxetan-3-yl)oxy)-3-(trifluoromethyl)phenyl)urea (30 mg, 0.058 mmol) in MeOH (10 mL) was added Pd/C (3 mg, 0.028 mmol). The mixture was stirred at 25° C. under a H$_2$ atmosphere for 48 h. The reaction residue was filtered and concentrated. The residue was purified by preparative HPLC (MeCN/H$_2$O as eluants, basic condition) to yield a white solid of 1-(2-fluoro-4-(4-oxo-2,3,4,5-tetrahydrofuro[3,2-c]pyridin-7-yl)phenyl)-3-(4-((3-methyloxetan-3-yl)oxy)-3-(trifluoromethyl)phenyl)urea (17.18 mg, 0.032 mmol, 55.6% yield): $^1$H NMR (400 MHz, CD$_3$OD) δ 8.14 (t, J=8.4 Hz, 1H), 7.81 (d, J=2.4 Hz, 1H), 7.57-7.56 (m, 2H), 7.45 (d, J=12.8 Hz, 1H), 7.36 (d, J=7.6 Hz, 1H), 6.65 (d, J=9.2 Hz, 1H), 4.92 (d, J=6.4 Hz, 2H), 4.65 (d, J=7.2 Hz, 2H), 4.60 (s, 2H), 3.15 (t, J=9.2 Hz, 2H), 1.75 (s, 3H); ES-LCMS m/z 520.0 (M+H).

EXAMPLE 23

1-(4-(2-Cyanopropan-2-yl)-3-(trifluoromethyl)phenyl)-3-(2-(5-ethoxy-6-oxo-1,6-dihydropyridin-3-yl)-4-methylpyrimidin-5-yl)urea

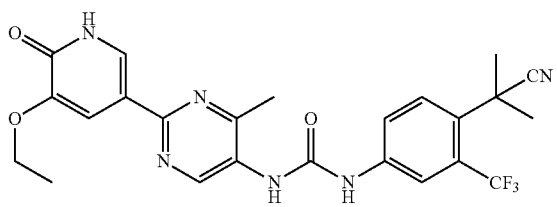 [SMILES: CCOc1cc(-c2ncc(NC(=O)Nc3ccc(C(C)(C)C#N)c(C(F)(F)F)c3)c(C)n2)c[nH]c1=O]

Step 1: 2-Methyl-2-(2-(trifluoromethyl)phenyl)propanenitrile

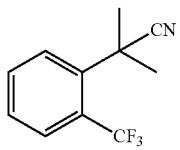

To a mixture of 2-(2-(trifluoromethyl)phenyl)acetonitrile (5 g, 27.0 mmol) in DMF (50 mL) was added NaH (1.620 g, 67.5 mmol) and MeI (4.22 mL, 67.5 mmol). The mixture was stirred at 25° C. for 16 h. The mixture was washed with water (100 mL) and extracted with DCM (120 mL×2). The combined organic extract was washed with brine, dried over MgSO$_4$, filtered and concentrated. The residue was purified by silica column chromatography (PE/EA=10:1). All fractions found to contain product by TLC (PE/EA=10:1, R$_f$=0.6) were combined and concentrated to yield a light yellow oil of 2-methyl-2-(2-(trifluoromethyl)phenyl)propanenitrile (4.8 g, 19.14 mmol, 70.9% yield): $^1$H NMR (400 MHz, CD$_3$OD) δ 7.83 (dd, J=8.4, 14.4 Hz, 1H), 7.70 (t, J=8.0 Hz, 1H), 7.62-7.54 (m, 1H), 1.89 (s, 6H); ES-LCMS m/z 214.1 (M+H).

Step 2: 2-Methyl-2-(4-nitro-2-(trifluoromethyl)phenyl)propanenitrile

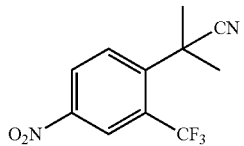 [SMILES: CC(C)(C#N)c1ccc([N+](=O)[O-])cc1C(F)(F)F]

To a mixture of 2-methyl-2-(2-(trifluoromethyl)phenyl) propanenitrile (4.8 g, 22.51 mmol) in H$_2$SO$_4$ (22.08 g, 225 mmol) was added potassium nitroperoxous acid (2.73 g, 27.0 mol). The mixture was stirred at 0° C. for 15 min. The mixture was extracted with EA (50 mL×2) and washed with water (50 mL) to give the organic layer. The combined organic extract was washed with brine, dried over Na$_2$SO$_4$, concentrated to yield a light yellow oil of 2-methyl-2-(4-nitro-2-(trifluoromethyl)phenyl)propanenitrile (5 g, 17.04 mmol, 76% yield): $^1$H NMR (400 MHz, CD$_3$OD) δ 8.66 (d, J=2.4 Hz, 1H) 8.53 (dd, J=2.4, 9.2 Hz, 1H) 8.11 (d, J=9.2 Hz, 1H) 1.95 (s, 6H); ES-LCMS m/z 259.0 (M+H).

Step 3: 2-(4-Amino-2-(trifluoromethyl)phenyl)-2-methylpropanenitrile

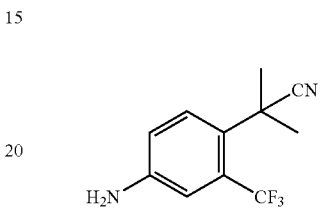

To a mixture of 2-methyl-2-(4-nitro-2-(trifluoromethyl) phenyl)propanenitrile (8 g, 31.0 mmol) in MeOH (100 mL) was added Pd/C (800 mg, 10%). The mixture was stirred at 25° C. for 15 h. The mixture was filtered and concentrated. The combined organic extract was washed with brine, dried over MgSO$_4$, filtered and concentrated. The residue was purified by silica column chromatography (PE/EA=3:1). All fractions found to contain product by TLC (PE/EA=3:1, R$_f$=0.6) were combined and concentrated to yield a red oil of 2-(4-amino-2-(trifluoromethyl)phenyl)-2-methylpropanenitrile (6.7 g, 24.95 mmol, 81% yield): $^1$H NMR (400 MHz, CD$_3$OD) δ 7.39 (d, J=8.8 Hz, 1H), 7.05 (d, J=2.4 Hz, 1H), 6.84 (dd, J=2.4, 8.8 Hz, 1H), 1.77 (s, 6H); ES-LCMS m/z 229.1 (M+H).

Step 4: 1-(4-(2-Cyanopropan-2-yl)-3-(trifluoromethyl)phenyl)-3-(2-(5-ethoxy-6-((4-methoxybenzyl)oxy)pyridin-3-yl)-4-methylpyrimidin-5-yl)urea

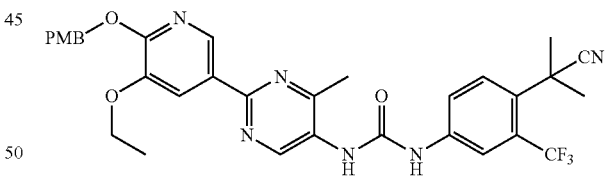

To a mixture of 2-(5-ethoxy-6-((4-methoxybenzyl)oxy) pyridin-3-yl)-4-methylpyrimidine-5-carboxylic acid (100 mg, 0.253 mmol) in 1,4-dioxane (10 mL) was added Et$_3$N (0.053 mL, 0.379 mmol) and DPPA (84 mg, 0.303 mmol). The mixture was stirred at 25° C. for 15 min. Then to the mixture was added 2-(4-amino-2-(trifluoromethyl)phenyl)-2-methylpropanenitrile (69.3 mg, 0.303 mmol). The mixture was stirred at 80° C. for 2 h. The mixture was concentrated and purified by preparative TLC (DCM/MeOH=20:1, R$_f$=0.6) to yield a yellow solid of 1-(4-(2-cyanopropan-2-yl)-3-(trifluoromethyl)phenyl)-3-(2-(5-ethoxy-6-((4-methoxybenzyl)oxy)pyridin-3-yl)-4-methylpyrimidin-5-yl) urea (100 mg, 0.137 mmol, 54.2% yield): $^1$H NMR (400 MHz, CD$_3$OD) δ 9.09 (s, 1H), 8.66 (d, J=2.0 Hz, 1H), 8.07 (d, J=1.6 Hz, 1H), 8.01 (d, J=2.0 Hz, 1H), 7.77-7.65 (m, 3H), 7.40 (d, J=8.8 Hz, 2H), 6.90 (d, J=8.8 Hz, 2H), 5.37 (s, 2H), 4.19-4.14 (m, 2H), 3.78 (s, 3H), 2.57 (s, 3H), 1.84 (s, 6H), 1.43 (t, J=7.2 Hz, 3H); ES-LCMS m/z 621.1 (M+H).

Step 5: 1-(4-(2-Cyanopropan-2-yl)-3-(trifluoromethyl)phenyl)-3-(2-(5-ethoxy-6-oxo-1,6-dihydropyridin-3-yl)-4-methylpyrimidin-5-yl)urea

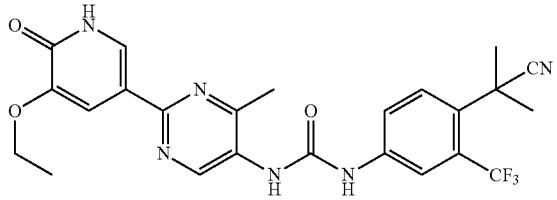 [SMILES: CCOc1cc(-c2ncc(NC(=O)Nc3ccc(C(C)(C)C#N)c(C(F)(F)F)c3)c(C)n2)c[nH]c1=O]

To a mixture of 1-(4-(2-cyanopropan-2-yl)-3-(trifluoromethyl)phenyl)-3-(2-(5-ethoxy-6-((4-methoxybenzyl)oxy)pyridin-3-yl)-4-methylpyrimidin-5-yl)urea (100 mg, 0.161 mmol) in DCM (10 mL) was added TFA (1 mL, 12.98 mmol). The mixture was stirred at 25° C. for 2 h. NH$_4$OH (5 mL) was added to the mixture and then the reaction residue was concentrated. The residue was purified by preparative HPLC (acidic condition; Instrument: DC; Column: Gemini: C18 150*25 mm*10 uL; Mobile phase A: Water+0.1% HCl; Mobile phase B: MeCN; Flowrate: 25 mL/min; Run time: 15 min; Gradient Profile Description: 25-55(B%)) to yield a yellow solid of 1-(4-(2-cyanopropan-2-yl)-3-(trifluoromethyl)phenyl)-3-(2-(5-ethoxy-6-oxo-1,6-dihydropyridin-3-yl)-4-methylpyrimidin-5-yl)urea hydrochloride (19.12 mg, 0.036 mmol, 22.10% yield): $^1$H NMR (400 MHz, CD$_3$OD) δ 9.08 (s, 1H), 8.10 (d, J=2.0 Hz, 1H), 8.02 (d, J=2.4 Hz, 1H), 7.87 (d, J=2.0 Hz, 1H), 7.76-7.68 (m, 2H), 4.15 (q, J=7.2 Hz, 2H), 2.57 (s, 3H), 1.84 (s, 6H), 1.48 (t, J=7.2 Hz, 3H); ES-LCMS m/z 501.1 (M+H).

EXAMPLE 24

1-(4-(1-Cyanoethyl)-3-(trifluoromethyl)phenyl)-3-(2-(4-ethoxy-6-oxo-1,6-dihydropyridin-3-yl)-4-methylpyrimidin-5-yl)urea

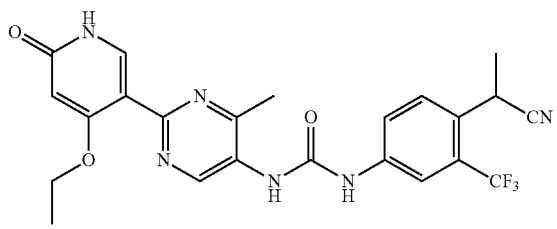 [SMILES: CCOc1cc(=O)[nH]cc1-c1ncc(NC(=O)Nc2ccc(C(C)C#N)c(C(F)(F)F)c2)c(C)n1]

Step 1: 2-Methyl-2-(2-(trifluoromethyl)phenyl)propanenitrile

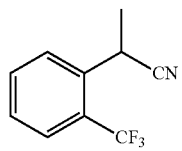

To a mixture of 2-(2-(trifluoromethyl)phenyl)acetonitrile (10 g, 54.0 mmol) in DMF (100 mL) was added MeI (3.38 mL, 54.0 mmol) and NaH (2.59 g, 64.8 mmol). The mixture was stirred at 25° C. for 16 h. The mixture was concentrated, washed with water and extracted with DCM. The combined organic extract was washed with brine, dried over MgSO4, filtered and concentrated. The residue was purified by silica column chromatography (PE/EA=5:1). All fractions found to contain product by TLC (PE/EA=5:1, R$_f$=0.6) were combined and concentrated to yield a light yellow oil of 2-(2-(trifluoromethyl)phenyl)propanenitrile (8 g, 34.1 mmol, 63.2% yield): $^1$H NMR (400 MHz, CD$_3$OD) δ 7.87-7.81 (m, 1H), 7.80-7.72 (m, 2H), 7.61-7.53 (m, 1H), 4.39 (q, J=7.2 Hz, 1H), 1.68 (d, J=7.2 Hz, 3H).

Step 2: 2-Methyl-2-(4-nitro-2-(trifluoromethyl)phenyl)propanenitrile

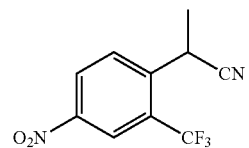

To a mixture of 2-(2-(trifluoromethyl)phenyl)propanenitrile (8 g, 40.2 mmol) in H$_2$SO$_4$ (39.4 g, 402 mmol) was added potassium nitroperoxous acid (4.87 g, 48.2 mmol). The mixture was stirred at 0° C. for 15 min. The mixture was extracted with EA (50 mL×2) and washed with water (50 mL) to give the organic layer. The combined organic extract was washed with brine, dried over Na$_2$SO$_4$, concentrated to yield a light yellow mixture (7.8 g, 19.17 mmol, 47.7% yield) of 2-(4-nitro-2-(trifluoromethyl)phenyl)propanenitrile and 2-(4-nitro-2-(trifluoromethyl)phenyl)propanamide. TLC (PE/EA=5:1, R$_f$=0.6): $^1$H NMR (400 MHz, CD$_3$OD) δ 8.65-8.58 (m, 2H), 8.15 (d, J=8.4 Hz, 1H), 4.55 (q, J=7.2 Hz, 1H), 1.73 (d, J=7.2 Hz, 3H).

Step 3: 2-Methyl-2-(4-nitro-2-(trifluoromethyl)phenyl)propanenitrile

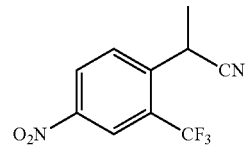

To a mixture of 2-(4-nitro-2-(trifluoromethyl)phenyl)propanamide (7.8 g, 29.7 mmol) in DCM (100 mL) was added Et$_3$N (8.29 mL, 59.5 mmol) and TFAA (6.30 mL, 44.6 mmol). The mixture was stirred at 25° C. for 16 h. The mixture was washed with water. The combined organic extract was washed with brine, dried over MgSO$_4$, filtered and concentrated. The resulting 2-(4-nitro-2-(trifluoromethyl)phenyl)propanenitrile (7.5 g, 26.1 mmol, 88% yield). TLC (PE/EA=5:1, R$_f$=0.6): $^1$H NMR (400 MHz, CD$_3$OD) δ 8.65-8.58 (m, 2H), 8.15 (d, J=8.4 Hz, 1H), 4.55 (q, J=7.2 Hz, 1H), 1.73 (d, J=7.2 Hz, 3H).

Step 4: 2-(4-Amino-2-(trifluoromethyl)phenyl)-2-methylpropanenitrile

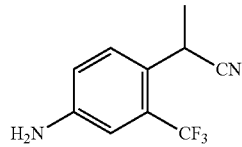

To a mixture of 2-(4-nitro-2-(trifluoromethyl)phenyl)propanenitrile (9 g, 36.9 mmol) in MeOH (100 mL) was added Pd/C (90 mg, 10%). The mixture was stirred at 25° C. for 16 h under a $H_2$ atmosphere. The reaction residue was filtered and concentrated. The residue was purified by silica column chromatography (PE/EA=3:1). All fractions found to contain product by TLC (PE/EA=3:1, $R_f$=0.6) were combined and concentrated to yield a light yellow oil of 2-(4-amino-2-(trifluoromethyl)phenyl)propanenitrile (7 g, 29.4 mmol, 80% yield): $^1$H NMR (400 MHz, $CD_3OD$) δ 7.44 (d, J=8.4 Hz, 1H), 6.99 (d, J=2.4 Hz, 1H), 6.96-6.92 (m, 1H), 4.19 (q, J=7.2 Hz, 1H), 1.59 (d, J=7.2 Hz, 3H); ES-LCMS m/z 215.1 (M+H).

Step 5: 1-(4-(1-Cyanoethyl)-3-(trifluoromethyl)phenyl)-3-(2-(4-ethoxy-6-((4-methoxybenzyl)oxy)pyridin-3-yl)-4-methylpyrimidin-5-yl)urea

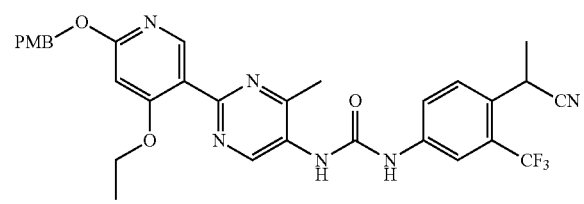

To a mixture of 2-(4-ethoxy-6-((4-methoxybenzyl)oxy)pyridin-3-yl)-4-methylpyrimidine-5-carboxylic acid (200 mg, 0.506 mmol) in 1,4-dioxane (10 mL) was added $Et_3N$ (0.106 mL, 0.759 mmol) and DPPA (167 mg, 0.607 mmol). The mixture was stirred at 25° C. for 15 min. Then to the mixture was added 2-(4-amino-2-(trifluoromethyl)phenyl)propanenitrile (130 mg, 0.607 mmol). The mixture was stirred at 80° C. for 2 h. The mixture was concentrated and purified by preparative TLC (DCM/MeOH=15:1, $R_f$=0.6) to yield a yellow solid of 1-(4-(1-cyanoethyl)-3-(trifluoromethyl)phenyl)-3-(2-(4-ethoxy-6-((4-methoxybenzyl)oxy)pyridin-3-yl)-4-methylpyrimidin-5-yl)urea (10 mg, 0.014 mmol, 2.77% yield): $^1$H NMR (400 MHz, $CD_3OD$) δ 9.19 (s, 1H), 8.26 (s, 1H), 8.00 (s, 1H), 7.78-7.73 (m, 2H), 7.37 (d, J=7.6 Hz, 2H), 6.90 (d, J=7.6 Hz, 2H), 6.47 (s, 1H), 5.30 (s, 2H), 4.31 (m, 1H), 4.14-4.10 (m, 2H), 3.78 (s, 3H), 2.70 (s, 3H), 1.63 (d, J=6.8 Hz, 3H), 1.34 (t, J=7.2 Hz, 3H); ES-LCMS ni/z 607.1 (M+H).

Step 6: 1-(4-(1-Cyanoethyl)-3-(trifluoromethyl)phenyl)-3-(2-(4-ethoxy-6-oxo-1,6-dihydropyridin-3-yl)-4-methylpyrimidin-5-yl)urea

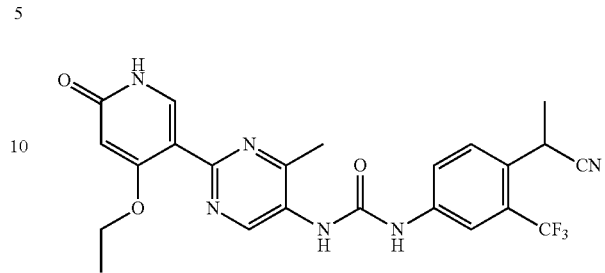

To a mixture of 1-(4-(1-cyanoethyl)-3-(trifluoromethyl)phenyl)-3-(2-(4-ethoxy-6-((4-methoxybenzyl)oxy)pyridin-3-yl)-4-methylpyrimidin-5-yl)urea (10 mg, 0.016 mmol) in DCM (10 mL) was added TFA (1 mL, 12.98 mmol). The mixture was stirred at 25° C. for 2 h. The mixture was concentrated and $NH_4OH$ (0.5 mL) was added. Then the reaction residue was concentrated and purified by preparative HPLC (Column: ASB C18 150*25 mm; Mobile phase A: Water+0.1% HCl; Mobile phase B: MeCN; Flowrate: 25 mL/min; Gradient Profile Description: 32-62(B %)) to yield an off-white solid of 1-(4-(1-cyanoethyl)-3-(trifluoromethyl)phenyl)-3-(2-(4-ethoxy-6-oxo-1,6-dihydropyridin-3-yl)-4-methylpyrimidin-5-yl)urea hydrochloride (3.14 mg, 5.91 μmol, 35.9% yield): $^1$H NMR (400 MHz, $CD_3OD$) δ 9.19 (s, 1H), 8.26 (s, 1H), 8.00 (s, 1H), 7.78-7.73 (m, 2H), 7.37 (d, J=8.0 Hz, 2H), 6.90 (d, J=8.0 Hz, 2H), 6.47 (s, 1H), 5.30 (s, 2H), 4.31 (m, 1H), 4.14-4.10 (m, 2H), 3.78 (s, 3H), 2.70 (s, 3H), 1.63 (d, J=6.8 Hz, 3H), 1.34 (t, J=7.2 Hz, 3H); ES-LCMS m/z 487.1 (M+H); TLC (DCM/MeOH=10:1, $R_f$=0.4).

EXAMPLE 25

1-(4-(1-Cyanoethyl)-3-(trifluoromethyl)phenyl)-3-(2-(5-ethoxy-6-oxo-1,6-dihydropyridin-3-yl)-4-methylpyrimidin-5-yl)urea

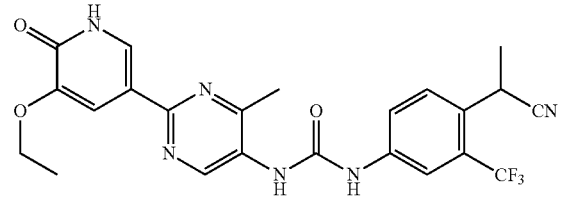 [SMILES: CCOc1cc(-c2ncc(NC(=O)Nc3ccc(C(C)C#N)c(C(F)(F)F)c3)c(C)n2)c[nH]c1=O]

Step 1: 2-Methyl-2-(2-(trifluoromethyl)phenyl)propanenitrile

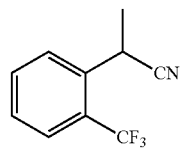

To a mixture of 2-(2-(trifluoromethyl)phenyl)acetonitrile (10 g, 54.0 mmol) in DMF (100 mL) was added MeI (3.38 mL, 54.0 mmol) and NaH (2.59 g, 64.8 mmol). The mixture was stirred at 25° C. for 16 h. The mixture was concentrated, washed with water and extracted with DCM. The combined organic extract was washed with brine, dried over MgSO4, filtered and concentrated. The residue was purified by silica column chromatography (PE/EA=5:1). All fractions found to contain product by TLC (PE/EA=5:1, R$_f$=0.6) were combined and concentrated to yield a light yellow oil of 2-(2-(trifluoromethyl)phenyl)propanenitrile (8 g, 34.1 mmol, 63.2% yield): $^1$H NMR (400 MHz, CD$_3$OD) δ 7.87-7.81 (m, 1H), 7.80-7.72 (m, 2H), 7.61-7.53 (m, 1H), 4.39 (q, J=7.2 Hz, 1H), 1.68 (d, J=7.2 Hz, 3H).

Step 2: 2-Methyl-2-(4-nitro-2-(trifluoromethyl)phenyl)propanenitrile

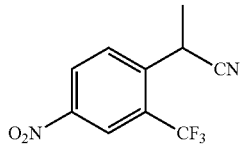 [SMILES: CC(C#N)c1ccc([N+](=O)[O-])cc1C(F)(F)F]

To a mixture of 2-(2-(trifluoromethyl)phenyl)propanenitrile (8 g, 40.2 mmol) in H$_2$SO$_4$ (39.4 g, 402 mmol) was added potassium nitroperoxous acid (4.87 g, 48.2 mmol). The mixture was stirred at 0° C. for 15 min. The mixture was extracted with EA (50 mL×2) and washed with water (50 mL) to give the organic layer. The combined organic extract was washed with brine, dried over Na$_2$SO$_4$, concentrated to yield a light yellow mixture (7.8 g, 19.17 mmol, 47.7% yield) of 2-(4-nitro-2-(trifluoromethyl)phenyl)propanenitrile and 2-(4-nitro-2-(trifluoromethyl)phenyl)propanamide. TLC(PE/EA=5:1, R$_f$=0.6): $^1$H NMR (400 MHz, CD$_3$OD) δ 8.65-8.58 (m, 2H), 8.15 (d, J=8.4 Hz, 1H), 4.55 (q, J=7.2 Hz, 1H), 1.73 (d, J=7.2 Hz, 3H).

Step 3: 2-Methyl-2-(4-nitro-2-(trifluoromethyl)phenyl)propanenitrile

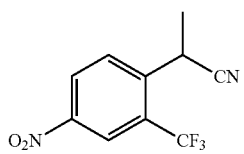 [SMILES: CC(C#N)c1ccc([N+](=O)[O-])cc1C(F)(F)F]

To a mixture of 2-(4-nitro-2-(trifluoromethyl)phenyl)propanamide (7.8 g, 29.7 mmol) in DCM (100 mL) was added Et$_3$N (8.29 mL, 59.5 mmol) and TFAA (6.30 mL, 44.6 mmol). The mixture was stirred at 25° C. for 16 h. The mixture was washed with water. The combined organic extract was washed with brine, dried over MgSO$_4$, filtered and concentrated. The resulting 2-(4-nitro-2-(trifluoromethyl)phenyl)propanenitrile (7.5 g, 26.1 mmol, 88% yield). TLC (PE/EA=5:1, R$_f$=0.6): $^1$H NMR (400 MHz, CD$_3$OD) δ 8.65-8.58 (m, 2H), 8.15 (d, J=8.4 Hz, 1H), 4.55 (q, J=7.2 Hz, 1H), 1.73 (d, J=7.2 Hz, 3H).

Step 4: 2-(4-Amino-2-(trifluoromethyl)phenyl)-2-methylpropanenitrile

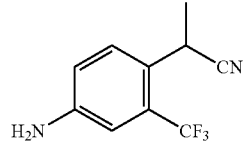

To a mixture of 2-(4-nitro-2-(trifluoromethyl)phenyl)propanenitrile (9 g, 36.9 mmol) in MeOH (100 mL) was added Pd/C (90 mg, 10%). The mixture was stirred at 25° C. for 16 h under a H$_2$ atmosphere. The reaction residue was filtered and concentrated. The residue was purified by silica column chromatography (PE/EA=3:1). All fractions found to contain product by TLC (PE/EA=3:1, R$_f$=0.6) were combined and concentrated to yield a light yellow oil of 2-(4-amino-2-(trifluoromethyl)phenyl)propanenitrile (7 g, 29.4 mmol, 80% yield): $^1$H NMR (400 MHz, CD$_3$OD) δ 7.44 (d, J=8.5 Hz, 1H), 6.99 (d, J=2.4 Hz, 1H), 6.96-6.92 (m, 1H), 4.19 (q, J=7.2 Hz, 1H), 1.59 (d, J=7.2 Hz, 3H); ES-LCMS m/z 215.1 (M+H).

Step 5: 1-(4-(1-Cyanoethyl)-3-(trifluoromethyl)phenyl)-3-(2-(5-ethoxy-6-((4-methoxybenzyl)oxy)pyridin-3-yl)-4-methylpyrimidin-5-yl)urea

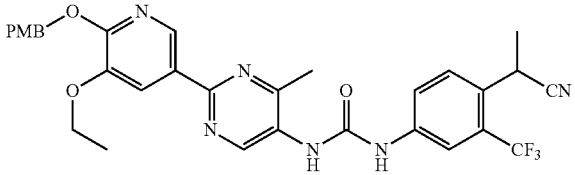

To a mixture of 2-(5-ethoxy-6-((4-methoxybenzyl)oxy)pyridin-3-yl)-4-methylpyrimidine-5-carboxylic acid (100 mg, 0.253 mmol) in 1,4-dioxane (10 mL) was added Et$_3$N (0.053 mL, 0.379 mmol) and DPPA (84 mg, 0.303 mmol). The mixture was stirred at 25° C. for 15 min. Then to the mixture was added 2-(4-amino-2-(trifluoromethyl)phenyl)propanenitrile (65.0 mg, 0.303 mmol). The mixture was stirred at 80° C. for 2 h. The mixture was concentrated and purified by preparative TLC (DCM/MeOH=20:1, R$_f$=0.6) to yield a yellow solid of 1-(4-(1-cyanoethyl)-3-(trifluoromethyl)phenyl)-3-(2-(5-ethoxy-6-((4-methoxybenzyl)oxy)pyridin-3-yl)-4-methylpyrimidin-5-yl)urea (100 mg, 0.132 mmol, 52.1% yield): $^1$H NMR (400 MHz, CD$_3$OD) δ 9.09 (s, 1H), 8.67 (d, J=2.0 Hz, 1H), 8.08 (d, J=1.6 Hz, 1H), 7.99 (s, 1H), 7.77-7.69 (m, 3H), 7.40 (d, J=8.8 Hz, 2H), 6.90 (d, J=8.8 Hz, 2H), 5.38 (s, 2H), 4.19-4.14 (m, 2H), 4.14-4.10 (m, 1H), 3.78 (s, 3H), 2.57 (s, 3H), 1.63 (d, J=7.2 Hz, 3H), 1.43 (t, J=7.2 Hz, 3H); ES-LCMS m/z 607.1 (M+H).

Step 6: 1-(4-(1-Cyanoethyl)-3-(trifluoromethyl)phenyl)-3-(2-(5-ethoxy-6-oxo-1,6-dihydropyridin-3-yl)-4-methylpyrimidin-5-yl)urea

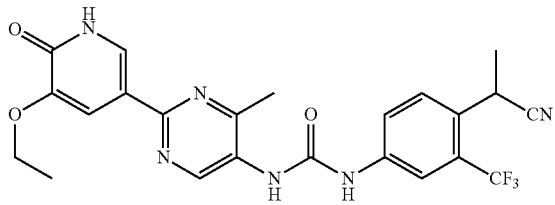 [SMILES: CCOc1cc(-c2ncc(NC(=O)Nc3ccc(C(C)C#N)c(C(F)(F)F)c3)c(C)n2)c[nH]c1=O]

To a mixture of 1-(4-(1-cyanoethyl)-3-(trifluoromethyl)phenyl)-3-(2-(5-ethoxy-6-((4-methoxybenzyl)oxy)pyridin-3-yl)-4-methylpyrimidin-5-yl)urea (100 mg, 0.165 mmol) in DCM (10 mL) was added TFA (1 mL, 12.98 mmol). The mixture was stirred at 25° C. for 2 h. NH$_4$OH (5 mL) was added and the mixture was concentrated. The residue was purified by preparative HPLC (acidic condition; Column: ASB C18 150*25 mm; Mobile phase A: Water+0.1% HCl; Mobile phase B: MeCN; Flowrate: 25 mL/min; Run time: 15 min; Gradient Profile Description: 36-66(B %)) to yield a yellow solid of 1-(4-(1-cyanoethyl)-3-(trifluoromethyl)phenyl)-3-(2-(5-ethoxy-6-oxo-1,6-dihydropyridin-3-yl)-4-methylpyrimidin-5-yl)urea hydrochloride (18.56 mg, 0.035 mmol, 21.41% yield): $^1$H NMR (400 MHz, CD$_3$OD) δ 9.13 (s, 1H), 8.12 (d, J=2.4 Hz, 1H), 8.01 (s, 1H), 7.87 (d, J=2.0 Hz, 1H), 7.76-7.71 (m, 2H), 4.31 (q, J=7.2 Hz, 1H), 4.16 (q, J=6.8 Hz, 2H), 2.60 (s, 3H), 1.63 (d, J=7.2 Hz, 3H), 1.48 (t, J=7.2 Hz, 3H); ES-LCMS m/z 487.1 (M+H).

EXAMPLE 26

1-(4-(2-Cyanopropan-2-yl)-3-(trifluoromethyl)phenyl)-3-(2-(4-ethoxy-6-oxo-1,6-dihydropyridin-3-yl)-4-methylpyrimidin-5-yl)urea

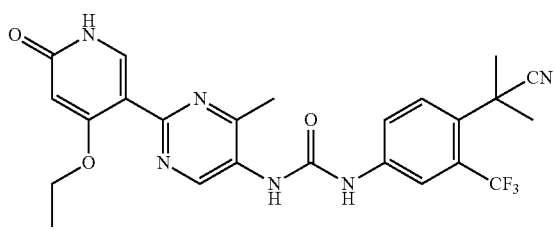 [SMILES: CCOc1cc(=O)[nH]cc1-c1ncc(NC(=O)Nc2ccc(C(C)(C)C#N)c(C(F)(F)F)c2)c(C)n1]

Step 1: 2-Methyl-2-(2-(trifluoromethyl)phenyl)propanenitrile

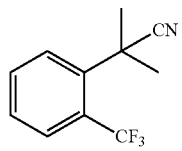

To a mixture of 2-(2-(trifluoromethyl)phenyl)acetonitrile (5 g, 27.0 mmol) in DMF (50 mL) was added NaH (1.620 g, 67.5 mmol) and MeI (4.22 mL, 67.5 mmol). The mixture was stirred at 25° C. for 16 h. The mixture was washed with water (100 mL) and extracted with DCM (120 mL×2). The combined organic extract was washed with brine, dried over MgSO4, filtered and concentrated. The residue was purified by silica column chromatography (PE/EA=10:1). All fractions found to contain product by TLC (PE/EA=10:1, R$_f$=0.6) were combined and concentrated to yield a light yellow oil of 2-methyl-2-(2-(trifluoromethyl)phenyl)propanenitrile (4.8 g, 19.14 mmol, 70.9% yield): $^1$H NMR (400 MHz, CD$_3$OD) δ 7.83 (dd, J=8.4, 14.4 Hz, 1H), 7.70 (t, J=8.0 Hz, 1H), 7.62-7.54 (m, 1H), 1.89 (s, 6H); ES-LCMS m/z 214.1 (M+H).

Step 2: 2-Methyl-2-(4-nitro-2-(trifluoromethyl)phenyl)propanenitrile

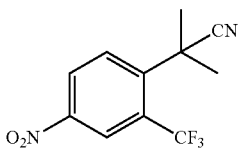 [SMILES: CC(C)(C#N)c1ccc([N+](=O)[O-])cc1C(F)(F)F]

To a mixture of 2-methyl-2-(2-(trifluoromethyl)phenyl)propanenitrile (4.8 g, 22.51 mmol) in H$_2$SO$_4$ (22.08 g, 225 mmol) was added potassium nitroperoxous acid (2.73 g, 27.0 mol). The mixture was stirred at 0° C. for 15 min. The mixture was extracted with EA (50 mL×2) and washed with water (50 mL) to give the organic layer. The combined organic extract was washed with brine, dried over Na$_2$SO$_4$, concentrated to yield a light yellow oil of 2-methyl-2-(4-nitro-2-(trifluoromethyl)phenyl)propanenitrile (5 g, 17.04 mmol, 76% yield): $^1$H NMR (400 MHz, CD$_3$OD) δ 8.66 (d, J=2.4 Hz, 1H), 8.53 (dd, J=2.4, 9.2 Hz, 1H), 8.11 (d, J=9.2 Hz, 1H), 1.95 (s, 6H); ES-LCMS m/z 259.0 (M+H).

Step 3: 2-(4-Amino-2-(trifluoromethyl)phenyl)-2-methylpropanenitrile

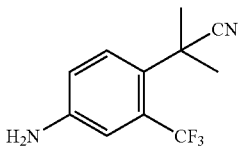

To a mixture of 2-methyl-2-(4-nitro-2-(trifluoromethyl)phenyl)propanenitrile (8 g, 31.0 mmol) in MeOH (100 mL) was added Pd/C (800 mg, 10%). The mixture was stirred at 25° C. for 15 h under a H$_2$ atmosphere. The mixture was filtered and concentrated. The combined organic extract was washed with brine, dried over MgSO$_4$, filtered and concentrated. The residue was purified by silica column chromatography (PE/EA=3:1). All fractions found to contain product by TLC (PE/EA=3:1, R$_f$=0.6) were combined and concentrated to yield a red oil of 2-(4-amino-2-(trifluoromethyl)phenyl)-2-methylpropanenitrile (6.7 g, 24.95 mmol, 81% yield): $^1$H NMR (400 MHz, CD$_3$OD) δ 7.39 (d, J=8.8 Hz, 1H), 7.05 (d, J=2.4 Hz, 1H), 6.84 (dd, J=2.4, 8.8 Hz, 1H), 1.77 (s, 6H); ES-LCMS m/z 229.1 (M+H).

Step 4: 1-(4-(2-Cyanopropan-2-yl)-3-(trifluoromethyl)phenyl)-3-(2-(4-ethoxy-6-((4-methoxybenzyl)oxy)pyridin-3-yl)-4-methylpyrimidin-5-yl)urea

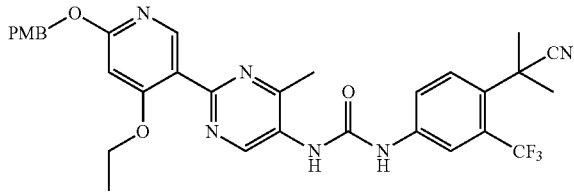

To a mixture of 2-(4-ethoxy-6-((4-methoxybenzyl)oxy)pyridin-3-yl)-4-methylpyrimidine-5-carboxylic acid (200 mg, 0.506 mmol) in 1,4-dioxane (10 mL) was added Et$_3$N (0.106 mL, 0.759 mmol) and DPPA (167 mg, 0.607 mmol). The mixture was stirred at 25° C. for 15 min. Then to the mixture was added 2-(4-amino-2-(trifluoromethyl)phenyl)-2-methylpropanenitrile (139 mg, 0.607 mmol). The mixture was stirred at 80° C. for 2 h. The mixture was concentrated and purified by preparative TLC (DCM/MeOH=15:1, R$_f$=0.6) to yield a yellow solid of 1-(4-(2-cyanopropan-2-yl)-3-(trifluoromethyl)phenyl)-3-(2-(4-ethoxy-6-((4-methoxybenzyl)oxy)pyridin-3-yl)-4-methylpyrimidin-5-yl)urea (10 mg, 0.014 mmol, 2.71% yield): $^1$H NMR (400 MHz, CD$_3$OD) δ 9.19 (s, 1H), 8.27 (s, 1H), 8.00 (s., 1H), 7.76 (d, J=8.4 Hz, 1H), 7.71-7.67 (m, 1H), 7.37 (d, J=8.0 Hz, 2H), 6.90 (d, J=8.0 Hz, 2H), 6.47 (s, 1H), 5.30 (s, 2H), 4.14-4.10 (m, 2H), 3.78 (s, 3H), 2.57 (s, 3H), 1.84 (s, 6H), 1.34 (t, J=7.2 Hz, 3H); ES-LCMS m/z 501.2 (M-PMB+H).

Step 5: 1-(4-(2-Cyanopropan-2-yl)-3-(trifluoromethyl)phenyl)-3-(2-(4-ethoxy-6-oxo-1,6-dihydropyridin-3-yl)-4-methylpyrimidin-5-yl)urea

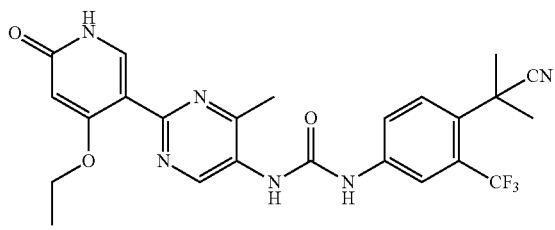 [SMILES: CCOc1cc(=O)[nH]cc1-c1ncc(NC(=O)Nc2ccc(C(C)(C)C#N)c(C(F)(F)F)c2)c(C)n1]

To a mixture of 1-(4-(2-cyanopropan-2-yl)-3-(trifluoromethyl)phenyl)-3-(2-(4-ethoxy-6-((4-methoxybenzyl)oxy)pyridin-3-yl)-4-methylpyrimidin-5-yl)urea (10 mg, 0.016 mmol) in DCM (10 mL) was added TFA (1 mL, 12.98 mmol). The mixture was stirred at 25° C. for 2 h. The mixture was concentrated and NH$_4$OH (1 mL) was added. The residue was purified by preparative HPLC (Instrument: DC; Column: Gemini: C18 150*25 mm*10 uL; Mobile phase A: Water+0.1% HCl; Mobile phase B: MeCN; Flow-rate: 25 mL/min; Run time: 15 min; Gradient Profile Description: 30-60(B %)) to yield an off-white solid of 1-(4-(2-cyanopropan-2-yl)-3-(trifluoromethyl)phenyl)-3-(2-(4-ethoxy-6-oxo-1,6-dihydropyridin-3-yl)-4-methylpyrimidin-5-yl)urea hydrochloride (5.81 mg, 10.28 µmol, 63.8% yield): $^1$H NMR (400 MHz, CD$_3$OD) δ 9.48 (s, 1H), 8.33 (s, 1H), 8.08 (s, 1H), 7.76-7.71 (m, 2H), 6.13 (s, 1H), 4.32 (q, J=6.8 Hz, 2H), 2.74 (s, 3H), 1.85 (s, 6H), 1.46 (t, J=6.8 Hz, 3H); ES-LCMS m/z 501.1 (M+H).

EXAMPLE 27

1-(5'-Ethoxy-6'-oxo-1',6'-dihydro-[3,3'-bipyridin]-6-yl)-3-(4-((3-methyloxetan-3-yl)oxy)-3-(trifluoromethyl)phenyl)urea

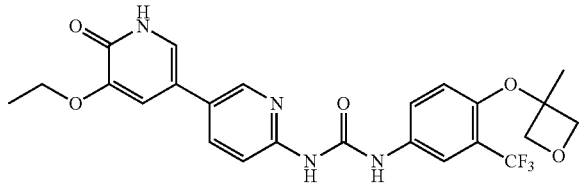 [SMILES: CCOc1cc(-c2ccc(NC(=O)Nc3ccc(OC4(C)COC4)c(C(F)(F)F)c3)nc2)c[nH]c1=O]

Step 1: 5-Bromo-2-isocyanatopyridine

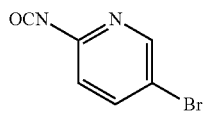

A mixture of 5-bromopyridin-2-amine (900 mg, 5.20 mmol) in THF (20 mL) was added triphosgene (509 mg, 1.717 mmol). The mixture was stirred at 60° C. for 1 h. LCMS showed the reaction was finished. The mixture was concentrated to give 5-bromo-2-isocyanatopyridine (912 mg, 3.97 mmol, 76% yield).

Step 2: 1-(5-Bromopyridin-2-yl)-3-(4-((3-methyloxetan-3-yl)oxy)-3-(trifluoromethyl)phenyl)urea

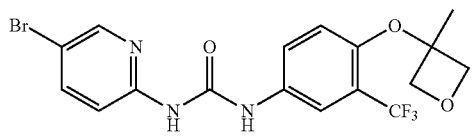 [SMILES: CC1(Oc2ccc(NC(=O)Nc3ccc(Br)cn3)cc2C(F)(F)F)COC1]

To a mixture of 5-bromo-2-isocyanatopyridine (500 mg, 2.51 mmol) in THF (20 mL) was added Et$_3$N (0.700 mL, 5.03 mmol) and 4-((3-methyloxetan-3-yl)oxy)-3-(trifluoromethyl)aniline (621 mg, 2.51 mmol). The mixture was stirred at 60° C. for 12 h. LCMS showed the reaction was finished. The mixture was concentrated and purified by column chromatography (PE/EA=2:1, R$_f$ 0.2) to give 1-(5-bromopyridin-2-yl)-3-(4-((3-methyloxetan-3-yl)oxy)-3-(trifluoromethyl)phenyl)urea (426 mg, 0.834 mmol, 33.2% yield). $^1$H NMR (400 MHz, CD$_3$OD) 8.34 (d, J=2.0 Hz, 1H), 7.83(dd, J=2.4, 8.8 Hz, 2H), 7.61(dd, J=2.4, 9.2 Hz, 1H), 7.25(d, J=8.4 Hz, 1H), 6.67(d, J=8.8 Hz, 1H), 4.89 (d, J=6.8 Hz, 2H), 4.63 (d, J=7.2 Hz, 2H), 1.72 (s, 3H); ES-LCMS m/z 446.0 (M+H).

Step 3: 1-(5'-Ethoxy-6'-((4-methoxybenzyl)oxy)-[3, 3'-bipyridin]-6-yl)-3-(4-((3-methyloxetan-3-yl)oxy)-3-(trifluoromethyl)phenyl)urea

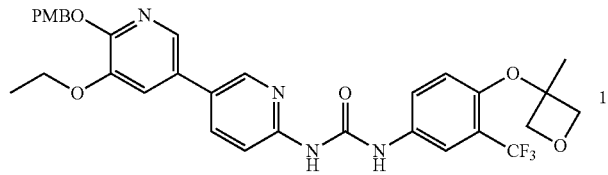

To a mixture of 1-(5-bromopyridin-2-yl)-3-(4-((3-methyloxetan-3-yl)oxy)-3-(trifluoromethyl)phenyl)urea (200 mg, 0.448 mmol) in 1,4-dioxane (3 mL) and water (1 mL) was added 3-ethoxy-2-((4-methoxybenzyl)oxy)-5-(4,4,5,5-tetramethyl-1,3,2-dioxaborolan-2-yl)pyridine (173 mg, 0.448 mmol), $PdCl_2$(dppf) ($_{32.8}$ mg, 0.045 mmol) and $Cs_2CO_3$ (292 mg, 0.896 mmol) under $N_2$. The mixture was stirred at 110° C. under microwave for 30 min. LCMS showed the reaction was finished. The mixture was filtered, and the filtrate was concentrated and purified by TLC (DCM/MeOHc=30:1, $R_f$ 0.3) to obtain 1-(5'-ethoxy-6'-((4-methoxybenzyl)oxy)-[3,3'-bipyridin]-6-yl)-3-(4-((3-methyloxetan-3-yl)oxy)-3-(trifluoromethyl)phenyl)urea (112 mg, 0.157 mmol, 35.0% yield). $^1$H NMR (400 MHz, $CDCl_3$) 8.38 (d, J=2.0 Hz, 1H), 7.83 (d, J=2.0 Hz, 1H), 7.75 (d, J=2.4 Hz, 2H), 7.73 (d, J=2.8 Hz, 1H), 7.37 (d, J=8.4 Hz, 2H), 7.12 (d, J=2.0 Hz, 1H), 6.84-6.82 (m, 2H), 6.76 (d, J=8.4 Hz, 1H), 6.39 (d, J=9.2 Hz, 1H), 5.39 (s, 2H), 4.92 (d, J=6.4 Hz, 2H), 4.52 (d, J=7.2 Hz, 2H), 4.09 (d, J=6.8 Hz, 2H), 3.74 (s, 3H), 1.68 (s, 3H), 1.43 (t, J=7.2 Hz, 3H); ES-LCMS m/z 625.1 (M+H).

Step 4: 1-(5'-Ethoxy-6'-oxo-1',6'-dihydro-[3,3'-bipyridin]-6-yl)-3-(4-((3-methyloxetan-3-yl)oxy)-3-(trifluoromethyl)phenyl)urea

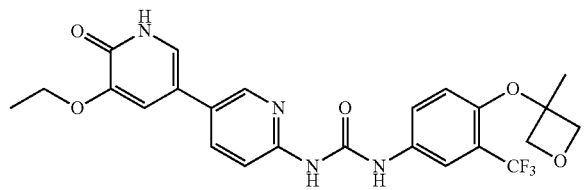 [SMILES: CCOc1cc(-c2ccc(NC(=O)Nc3ccc(OC4(C)COC4)c(C(F)(F)F)c3)nc2)c[nH]c1=O]

To a mixture of 1-(5'-ethoxy-6'-((4-methoxybenzyl)oxy)-[3,3'-bipyridin]-6-yl)-3-(4-((3-methyloxetan-3-yl)oxy)-3-(trifluoromethyl)phenyl)urea (100 mg, 0.160 mmol) in MeOH (5 mL) was added Pd/C (17.04 mg, 0.160 mmol). The mixture was stirred at 20° C. under $H_2$ for 12 h. LCMS showed the reaction was finished. The mixture was filtered, and the filtrate was concentrated and purified by HPLC to give 1-(5'-ethoxy-6'-oxo-1',6'-dihydro-[3,3'-bipyridin]-6-yl)-3-(4-((3-methyloxetan-3-yl)oxy)-3-(trifluoromethyl)phenyl)urea (31.83 mg, 0.063 mmol, 39.4% yield). $^1$H NMR (400 MHz, DMSO-$d_6$) 11.80 (s, 1H), 10.43 (s, 1H), 9.46 (s, 1H), 8.50 (d, J=2.4 Hz, 1H), 7.97 (dd, J=2.4,8.8 Hz, 1H), 7.88 (d, J=2.8 Hz, 1H), 7.57-7.50 (m, 2H), 7.28 (d, J=2.4 Hz, 1H), 7.12 (d, J=2.4 Hz, 1H), 6.69 (d, J=8.8 Hz, 1H), 4.72 (d, J=6.8 Hz, 2H), 4.57 (d, J=7.2 Hz, 2H), 4.02 (d, J=6.8 Hz, 214), 1.63(s, 3H), 1.32 (t, J=6.8 Hz, 3H); ES-LCMS m/z 505.0(M+H).

EXAMPLE 28

1-(2-(4-Ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea

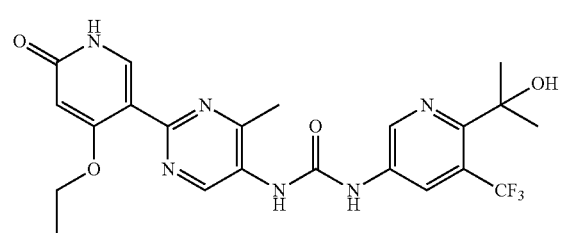 [SMILES: CCOc1cc(=O)[nH]cc1-c1ncc(NC(=O)Nc2cnc(C(C)(C)O)c(C(F)(F)F)c2)c(C)n1]

Step 1: 1-(6-Acetyl-5-(trifluoromethyl)pyridin-3-yl)-3-(2-(4-ethoxy-6-((4-methoxybenzyl)oxy)pyridin-3-yl)-4-methylpyrimidin-5-yl)urea

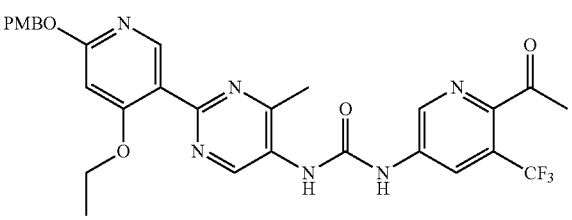

To a mixture of 2-(4-ethoxy-6-((4-methoxybenzyl)oxy) pyridin-3-yl)-4-methylpyrimidine-5-carboxylic acid (0.2 g, 0.506 mmol) in 1,4-dioxane (10 mL) was added $Et_3N$ (0.102 g, 1.012 mmol), DPPA (0.209 g, 0.759 mmol) and 1-(5-amino-3-(trifluoromethyl)pyridin-2-yl)ethanone (0.103 g, 0.506 mmol) at 20° C. The mixture was stirred at 80° C. for 2 h. TLC (DCM/MeOH=15:1, $R_f$ 0.3) and LCMS showed the reaction was finished. The mixture was concentrated and purified by TLC (DCM/MeOH=15:1, $R_f$ 0.3) to give 1-(6-acetyl-5-(trifluoromethyl)pyridin-3-yl)-3-(2-(4-ethoxy-6-((4-methoxybenzyl)oxy)pyridin-3-yl)-4-methylpyrimidin-5-yl)urea (45 mg, 0.075 mmol, 14.91% yield): $^1$H NMR (400 MHz, $CD_3OD$) 8.55 (s, 1H), 8.31-8.24 (m, 1H), 8.08 (d, J=1.2 Hz, 1H), 7.36 (d, J=5.6 Hz, 2H), 6.87-6.83 (m, 3H), 6.43 (s, 1H), 5.30 (s, 2H), 4.12 (d, J=6.6 Hz, 2H), 3.76 (s, 3H), 2.64 (s, 3H), 2.40 (s, 3H), 1.33 (d, J=1.5 Hz, 3H);ES-LCMS m/z 597.2 (M+H).

Step 2: 1-(2-(4-Ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea

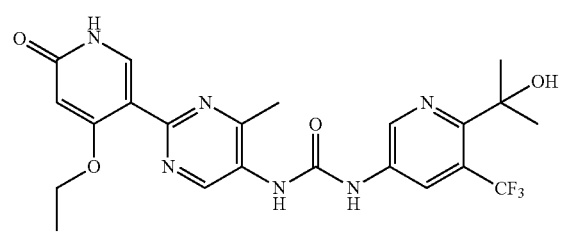 [SMILES: CCOc1cc(=O)[nH]cc1-c1ncc(NC(=O)Nc2cnc(C(C)(C)O)c(C(F)(F)F)c2)c(C)n1]

To a mixture of 1-(6-acetyl-5-(trifluoromethyl)pyridin-3-yl)-3-(2-(4-ethoxy-6-((4-methoxybenzyl)oxy)pyridin-3-yl)-4-methylpyrimidin-5-yl)urea (22 mg, 0.037 mmol) in THF (10 mL) was added MeMgBr (0.111 mL, 0.111 mmol) at 0° C. The mixture was stirred for 1 h. TLC (DCM/MeOH=15:1, $R_f$ 0.4) showed the reaction was finished. The reaction was quenched by H$_2$O (0.2 mL) and aqueous HCl (0.1 mL, 1N). The mixture was filtered, and the filtrate was dried, concentrated in vacuo and the residue was purified by TLC (DCM/MeOH=10:1, $R_f$ 0.2) and preparative HPLC to give 1-(2-(4-ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea (2.07 mg, 4.18 umol, 11.32% yield): $^1$H NMR (400 MHz, CD$_3$OD) 9.14 (s, 1H), 8.75 (d, J=2.4 Hz, 1H), 8.40 (d, J=2.4 Hz, 1H), 7.79 (s, 1H), 5.99 (s, 1H), 4.11 (t, J=7.2 Hz, 2H), 2.56 (s, 3H), 1.60 (s, 6H), 1.37 (t, J=7.2 Hz, 3H); ES-LCMS m/z 493.1 (M+H).

EXAMPLE 29

1-(2-(5-Ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea

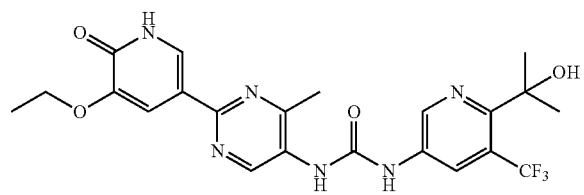 [SMILES: CCOc1cc(-c2ncc(NC(=O)Nc3cnc(C(C)(C)O)c(C(F)(F)F)c3)c(C)n2)c[nH]c1=O]

Step 1: 1-(6-Acetyl-5-(trifluoromethyl)pyridin-3-yl)-3-(2-(5-ethoxy-6-((4-methoxybenzyl)oxy)pyridin-3-yl)-4-methylpyrimidin-5-yl)urea

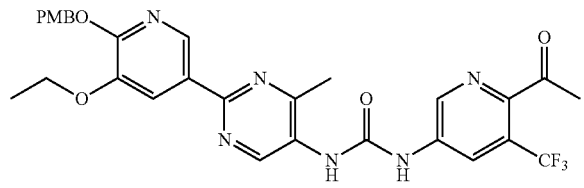

To a mixture of 2-(5-ethoxy-6-((4-methoxybenzyl)oxy)pyridin-3-yl)-4-methylpyrimidine-5-carboxylic acid (0.2 g, 0.506 mmol) in dioxane (10 mL) was added Et$_3$N (0.102 g, 1.012 mmol), DPPA (0.209 g, 0.759 mmol) and 1-(5-amino-3-(trifluoromethyl)pyridin-2-yl)ethanone (0.103 g, 0.506 mmol) at 20° C. The mixture was stirred at 80° C. for 2 h. TLC (DCM/MeOH=15:1, $R_f$ 0.3) and LCMS showed the reaction was finished. The mixture was concentrated in vacuo and the residue was purified by TLC (DCM/MeOH=15:1, $R_f$ 0.3) to give 1-(6-acetyl-5-(trifluoromethyl)pyridin-3-yl)-3-(2-(5-ethoxy-6-((4-methoxybenzyl)oxy)pyridin-3-yl)-4-methylpyrimidin-5-yl)urea (50 mg, 0.064 mmol, 12.68% yield): $^1$H NMR (400 MHz, CD$_3$OD) 8.53 (s, 1H), 8.08 (d, J=1.7 Hz, 1H), 7.41-7.40 (m, 2H), 7.24 (d, J=8.6 Hz, 1H), 6.91-6.87 (m, 3H), 5.38 (s, 2H), 4.15 (d, J=2.7 Hz, 2H), 3.76 (s, 3H), 2.63 (s, 3H), 2.59 (s, 3H), 1.45 (d, J=2.0 Hz, 3H); ES-LCMS m/z 597.1 (M+H).

Step 2: 1-(2-(5-Ethoxy-6-((4-methoxybenzyl)oxy)pyridin-3-yl)-4-methylpyrimidin-5-yl)-3-(6-(2-hydroxypropan-2-yl)-5-(trifluoromethyl)pyridin-3-yl)urea

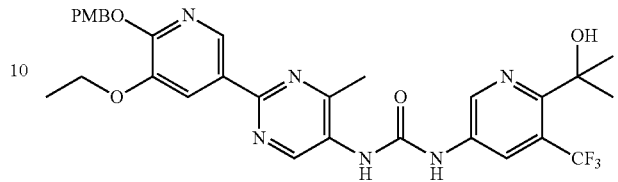

To a mixture of 1-(6-acetyl-5-(trifluoromethyl)pyridin-3-yl)-3-(2-(5-ethoxy-6-((4-methoxybenzyl)oxy)pyridin-3-yl)-4-methylpyrimidin-5-yl)urea (50 mg, 0.084 mmol) in THF (10 mL) was added MeMgBr (0.251 mL, 0.251 mmol) at 20° C. The mixture was stirred 1 h. TLC (DCM/MeOH=10:1, $R_f$=0.5) showed the reaction was finished. The reaction was quenched by water (0.3 mL). The mixture was filtered and the filtrate was concentrated in vacuo and the residue was purified by TLC (DCM/MeOH=10:1, $R_f$ 0.5) to give 1-(2-(5-ethoxy-6-((4-methoxybenzyl)oxy)pyridin-3-yl)-4-methylpyrimidin-5-yl)-3-(6-(2-hydroxypropan-2-yl)-5-(trifluoromethyl)pyridin-3-yl)urea (20 mg, 0.023 mmol, 27.4% yield): $^1$H NMR (400 MHz, CD$_3$OD) 8.41 (t, J=2.3 Hz, 1H), 8.07 (dd, J=1.8, 4.8 Hz, 1H), 7.85 (d, J=2.0 Hz, 1H), 7.40 (d, J=8.6 Hz, 1H), 7.25 (d, J=8.6 Hz, 2H), 6.89-6.85 (m, 3H), 5.37 (s, 2H), 4.19-4.12 (m, 2H), 3.80 (s, 3H), 2.59 (s, 3H), 1.59 (s, 6H), 1.49-1.42 (m, 3H); ES-LCMS m/z 493.1 (M-PMB+H).

Step 3: 1-(2-(5-Ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea

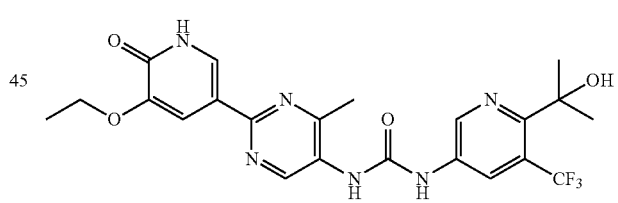

To a mixture of 1-(2-(5-ethoxy-6-((4-methoxybenzyl)oxy)pyridin-3-yl)-4-methylpyrimidin-5-yl)-3-(6-(2-hydroxypropan-2-yl)-5-(trifluoromethyl)pyridin-3-yl)urea (20 mg, 0.033 mmol) in MeOH (10 mL) was added Pd/C (3.47 mg, 0.033 mmol, 10%) under N$_2$. The mixture was stirred under a H$_2$ atmosphere for 1 h. LCMS and TLC (DCM/MeOH=10:1, $R_f$=0.3) showed the reaction was finished. The mixture was filtered and the filtrate was purified by preparative HPLC to give 1-(2-(5-ethoxy-6-oxo-1,6-dihydropyridin-3-yl)-4-methylpyrimidin-5-yl)-3-(6-(2-hydroxypropan-2-yl)-5-(trifluoromethyl)pyridin-3-yl)urea (3.91 mg, 7.83 μmol, 23.97% yield): $^1$H NMR (400 MHz, CD$_3$OD) 9.01 (s, 1H), 8.74 (d, J=2.4 Hz, 1H), 8.40 (d, J=2.4 Hz, 1H), 8.07 (d, J=2.0 Hz, 1H), 7.86 (d, J=2.0 Hz, 1H), 4.16-4.11 (m, 2H), 2.55 (s, 3H), 1.60 (s, 6H), 1.48 (t, J=6.8 Hz, 3H); ES-LCMS m/z 493.1 (M+H).

EXAMPLE 30

1-(2-(Difluoromethyl)-4-(5-ethoxy-6-oxo-1,6-dihydropyridin-3-yl)phenyl)-3-(4-((4-ethylpiperazin-1-yl)methyl)-3-(trifluoromethyl)phenyl)urea

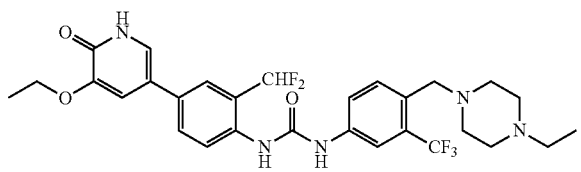

Step 1: 4-Bromo-2-(difluoromethyl)-1-nitrobenzene

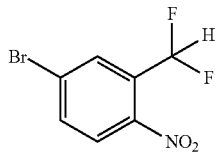

To a solution of 5-bromo-2-nitrobenzaldehyde (0.5 g, 2.174 mmol) in DCM (20 mL) was added DAST (0.431 mL, 3.26 mmol) at 0° C. The resulting mixture was stirred at rt. After 2 h, TLC analysis (PE/EA=3/1) showed the starting material was disappeared. The mixture was poured to ice. The resulting mixture was extracted by DCM (50 mL). The organic layer was dried and concentrated to give 4-bromo-2-(difluoromethyl)-1-nitrobenzene (0.5 g, 1.936 mmol, 89% yield), which: $^1$H NMR (400 MHz, CD$_3$OD) δ 8.12-8.09 (m, 1H), 8.04-8.03 (m, 1H), 7.96-7.93 (m, 1H), 7.51-7.24 (m, 1H).

Step 2: 4-Bromo-2-(difluoromethyl)aniline

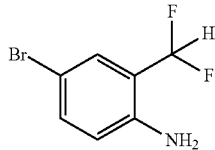

To a solution of 4-bromo-2-(difluoromethyl)-1-nitrobenzene (0.5 g, 1.984 mmol) and zinc (1.297 g, 19.84 mmol) in MeOH (30 mL) was added NH$_4$Cl (1.061 g, 19.84 mmol). The resulting mixture was stirred at 25° C. overnight. After TLC analysis (PE/EA=3/1) showed the starting material was disappeared. The mixture was filtered. The filtrate was concentrated to give the residue, which was dissolved in EA (60 mL) and washed with H$_2$O (30 mL) and brine (30 mL). The organic layer was dried over Na$_2$SO$_4$, filtered and concentrated. The residue was purified by preparative TLC (PE/EA=3/1) to yield a yellow solid of 4-bromo-2-(difluoromethyl)aniline (0.26 g, 0.713 mmol, 36.0% yield): $^1$H NMR (400 MHz, CDCl$_3$) δ 7.35 (s, 1H), 7.34-7.31 (m, 1H), 6.69-6.41 (m, 1H), 6.61 (d, J=8.4 Hz, 1H), 4.07 (brs, 2H); ES-LCMS m/z 221.9, 224.0 (M+H).

Step 3: 1-(4-Bromo-2-(difluoromethyl)phenyl)-3-(4-((4-ethylpiperazin-1-yl)methyl)-3-(trifluoromethyl)phenyl)urea

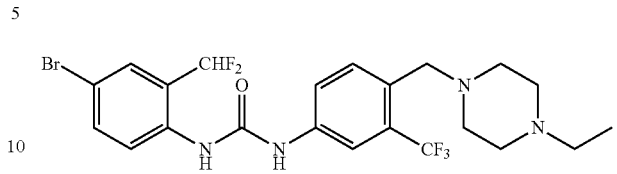

To a solution of 4-bromo-2-(difluoromethyl)aniline (100 mg, 0.450 mmol) in THF (10 mL) was added triphosgene (46.8 mg, 0.158 mmol). The resulting mixture was stirred at 70° C. After 30 min, LCMS analysis showed the starting material was disappeared. The solvent was removed in vacuo to give 4-bromo-2-(difluoromethyl)-1-isocyanatobenzene (110 mg, 0.417 mmol, 93% yield). To a solution of 4-((4-ethylpiperazin-1-yl)methyl)-3-(trifluoromethyl)aniline (153 mg, 0.532 mmol), Et$_3$N (0.124 mL, 0.887 mmol) and DMAP (10.84 mg, 0.089 mmol) in THF (10 mL) was added a solution of 4-bromo-2-(difluoromethyl)-1-isocyanatobenzene (110 mg, 0.444 mmol) in THF (10 mL). The resulting mixture was stirred at 70° C. After LCMS analysis showed the starting material was disappeared. The solvent was removed in vacuo. The residue was purified by preparative TLC (DCM/MeOH=10/1) to yield a solid of 1-(4-bromo-2-(difluoromethyl)phenyl)-3-(4-((4-ethylpiperazin-1-yl)methyl)-3-(trifluoromethyl)phenyl)urea (130 mg, 0.172 mmol, 38.9% yield): $^1$H NMR (400 MHz, CD$_3$OD) δ 7.86 (s, 1H), 7.75 (d, J=8.8 Hz, 1H), 7.67-7.63 (m, 4H), 7.03-6.76 (m, 1H), 3.67 (s, 2H), 3.20-3.18 (m, 2H), 2.96 (m, 8H), 1.30 (m, 3H); ES-LCMS m/z 535.1, 537.1 (M+H).

Step 4: 1-(2-(Difluoromethyl)-4-(5-ethoxy-6-((4-methoxybenzyl)oxy)pyridin-3-yl)phenyl)-3-(4-((4-ethylpiperazin-1-yl)methyl)-3-(trifluoromethyl)phenyl)urea

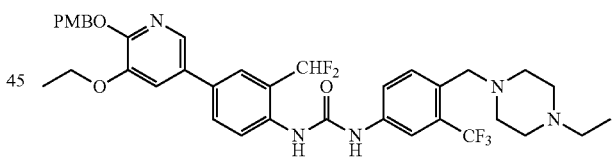

A solution of 3-ethoxy-2-((4-methoxybenzyl)oxy)-5-(4,4,5,5-tetramethyl-1,3,2-dioxaborolan-2-yl)pyridine (72.0 mg, 0.187 mmol), 1-(4-bromo-2-(difluoromethyl)phenyl)-3-(4-((4-ethylpiperazin-1-yl)methyl)-3-(trifluoromethyl)phenyl)urea (100 mg, 0.187 mmol), PdCl$_2$(dppf)-DCM adduct (15.25 mg, 0.019 mmol) and Cs$_2$CO$_3$ (122 mg, 0.374 mmol) in 1,4-dioxane (3 mL) and water (3.00 mL) was stirred at 110° C. for 15 min. After LCMS analysis showed the starting material was disappeared. The solvent was removed in vacuo. The residue was dissolved in DCM (60 mL) and washed with H$_2$O (20 mL) and brine (20 mL). The organic layer was dried over Na$_2$SO$_4$, filtered and concentrated. The residue was purified by preparative TLC (DCM/MeOH=10/1) to yield 1-(2-(difluoromethyl)-4-(5-ethoxy-6-((4-methoxybenzyl)oxy)pyridin-3-yl)phenyl)-3-(4-((4-ethylpiperazin-1-yl)methyl)-3-(trifluoromethyl)phenyl)urea (60 mg, 0.063 mmol, 33.8% yield): $^1$H NMR (400 MHz, CD$_3$OD) δ 7.95-7.88 (m, 3H), 7.75 (m, 2H), 7.67-7.50 (m, 2H), 7.46 (d, J=2.0 Hz, 1H), 7.41-7.39 (m, 1H), 6.96-6.90 (m, 3H), 5.36 (s, 2H), 4.17-4.15 (m, 2H), 3.79 (s, 3H), 3.66-3.65 (m, 2H), 3.56-3.55 (m, 2H), 2.70-2.61 (m, 8H), 1.42 (t, J=7.0 Hz, 3H), 1.17 (t, J=7.2 Hz, 3H); ES-LCMS m/z 714.3 (M+H).

Step 5: 1-(2-(Difluoromethyl)-4-(5-ethoxy-6-oxo-1,6-dihydropyridin-3-yl)phenyl)-3-(4-((4-ethylpiperazin-1-yl)methyl)-3-(trifluoromethyl)phenyl)urea

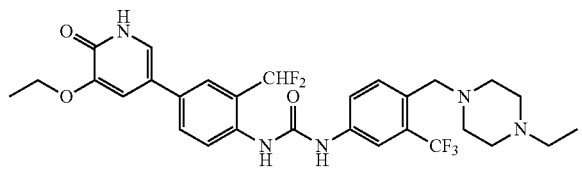 [SMILES: CCOc1cc(-c2ccc(NC(=O)Nc3ccc(CN4CCN(CC)CC4)c(C(F)(F)F)c3)c(C(F)F)c2)c[nH]c1=O]

A solution of 1-(2-(difluoromethyl)-4-(5-ethoxy-6-((4-methoxybenzyl)oxy)pyridin-3-yl)phenyl)-3-(4-((4-ethylpiperazin-1-yl)methyl)-3-(trifluoromethyl)phenyl)urea (60 mg, 0.084 mmol) in HCl in MeOH (10 mL, 175 mmol) was stirred at 25° C. After LCMS analysis showed the starting material was disappeared. The solvent was removed in vacuo. The residue was purified by preparative HPLC to yield a white solid of 1-(2-(difluoromethyl)-4-(5-ethoxy-6-oxo-1,6-dihydropyridin-3-yl)phenyl)-3-(4-((4-ethylpiperazin-1-yl)methyl)-3-(trifluoromethyl)phenyl)urea dihydrochloride (21.83 mg, 0.033 mmol, 39.0% yield): $^1$H NMR (400 MHz, CD$_3$OD) δ 8.04 (s, 1H), 7.95 (d, J=8.0 Hz, 1H), 7.83 (m, 1H), 7.75-7.73 (m, 3H), 7.52-7.50 (m, 2H), 7.10-5.83 (m, 1H), 4.24-4.19 (m, 4H), 3.72-3.26 (m, 8H), 3.12 (m, 2H), 1.49 (t, J=6.8 Hz, 3H), 1.37 (t, J=7.2 Hz, 3H); ES-LCMS m/z 594.2 (M+H).

EXAMPLE 31

1-(4-((5-Ethoxy-6-oxo-1,6-dihydropyridin-3-yl)oxy)phenyl)-3-(4-((4-ethylpiperazin-1-yl)methyl)-3-(trifluoromethyl)phenyl)urea

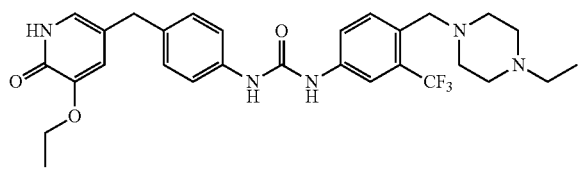

Step 1:
5-Ethoxy-6-((4-methoxybenzyl)oxy)pyridin-3-ol

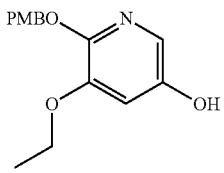

To a solution of 3-ethoxy-2-((4-methoxybenzyl)oxy)-5-(4,4,5,5-tetramethyl-1,3,2-dioxaborolan-2-yl)pyridine (2 g, 5.19 mmol) and NaHCO$_3$ (3.05 g, 36.3 mmol) in acetone (60 mL) and water (60 mL) was added dihydrate (3.12 g, 26.0 mmol) by dropwise at 0° C. overnight. After LCMS analysis showed the starting material was disappeared. The solvent was removed in vacuo. The residue was dissolved in DCM (100 mL) and washed with H$_2$O (30 mL) and brine (30 mL). The organic layer was dried over Na$_2$SO$_4$, filtered and concentrated. The residue was purified by silica column chromatography (PE/EA=3/1) to give a yellow solid of 5-ethoxy-6-((4-methoxybenzyl)oxy)pyridin-3-ol (1.3 g, 4.72 mmol, 91% yield): $^1$H NMR (400 MHz, CD$_3$OD) δ 7.35-7.32 (m, 2H), 7.22 (d, J=2.4 Hz, 1H), 6.89-6.87 (m, 2H), 6.78 (d, J=2.4 Hz, 1H), 5.19 (s, 2H), 4.04-3.98 (m, 2H), 3.77 (s, 3H), 1.37 (t, J=7.0 Hz, 3H); ES-LCMS nilz 276.1 (M+H).

Step 2: 3-Ethoxy-2-((4-methoxybenzyl)oxy)-5-(4-nitrophenoxy)pyridine

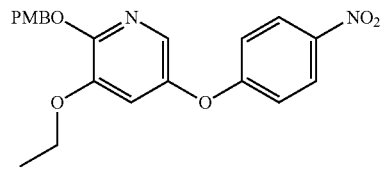

A solution of 5-ethoxy-6-((4-methoxybenzyl)oxy)pyridin-3-ol (0.3 g, 1.090 mmol), 1-fluoro-4-nitrobenzene (0.161 g, 1.144 mmol) and K$_2$CO$_3$ (0.301 g, 2.179 mmol) in MeCN (30 mL) was stirred at 70° C. overnight. After LCMS analysis showed the starting material was disappeared. The solvent was removed in vacuo. The residue was dissolved in DCM (60 mL) and washed with H$_2$O (20 mL) and brine (20 mL). The organic layer was dried over Na$_2$SO$_4$, filtered and concentrated. The residue was purified by silica column chromatography (PE/EA=5/1) to yield a yellow solid of 3-ethoxy-2-((4-methoxybenzyl)oxy)-5-(4-nitrophenoxy)pyridine (0.39 g, 0.924 mmol, 85% yield): $^1$H NMR (400 MHz, CD$_3$OD) δ 8.23 (d, J=9.2 Hz, 2H), 7.54 (d, J=2.4 Hz, 1H), 7.38 (d, J=8.4 Hz, 2H), 7.11-7.07 (m, 3H), 6.90 (d, J=8.4 Hz, 2H), 5.33 (s, 2H), 4.06-4.01 (m, 2H), 3.79 (s, 3H), 1.38 (t, J=7.0 Hz, 3H); ES-LCMS m/z 397.1 (M+H).

Step 3: 4-((5-Ethoxy-6-((4-methoxybenzyl)oxy)pyridin-3-yl)oxy)aniline

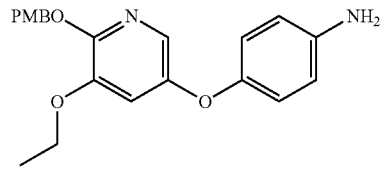

To a solution of 3-ethoxy-2-((4-methoxybenzyl)oxy)-5-(4-nitrophenoxy)pyridine (390 mg, 0.981 mmol) and zinc (642 mg, 9.81 mmol) in MeOH (80 mL) was added NH$_4$Cl (525 mg, 9.81 mmol). The resulting mixture was stirred at 25° C. After LCMS analysis showed the starting material was disappeared. The mixture was filtered. The filtrate was concentrated, which was dissolved in DCM (60 mL) and washed with H$_2$O (20 mL) and brine (20 mL). The organic layer was dried over Na$_2$SO$_4$, filtered and concentrated. The residue was purified by silica column chromatography (PE/EA=2/1) to give 4-((5-ethoxy-6-((4-methoxybenzyl)oxy)pyridin-3-yl)oxy)aniline (250 mg, 0.646 mmol, 65.9% yield): $^1$H NMR (400 MHz, CD$_3$OD) δ 7.36-7.34 (m, 2H), 7.27 (d, J=2.4 Hz, 1H), 6.91-6.89 (m, 3H), 6.79 (dd, J=6.8, 2.4 Hz, 2H), 6.77-6.71 (m, 2H), 5.25 (s, 2H), 4.00-3.95 (m, 2H), 3.78 (s, 3H), 1.35 (t, J=7.0 Hz, 3H); ES-LCMS m/z 367.0 (M+H).

Step 4: 1-(4-((5-Ethoxy-6-((4-methoxybenzyl)oxy)pyridin-3-yl)oxy)phenyl)-3-(4-((4-ethylpiperazin-1-yl)methyl)-3-(trifluoromethyl)phenyl)urea

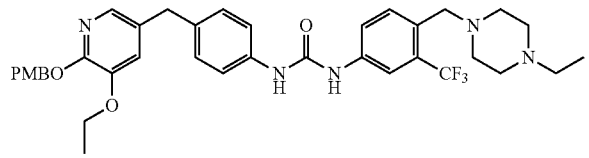

To a solution of 4-((4-ethylpiperazin-1-yl)methyl)-3-(trifluoromethyl)aniline (60 mg, 0.209 mmol) in THF (10 mL) was added triphosgene (21.69 mg, 0.073 mmol). The resulting mixture was stirred at 70° C. After 30 mm, TLC analysis (PE/EA=3/1) showed the starting material was disappeared. The solvent was removed in vacuo to give a brown oil of 1-ethyl-4-(4-isocyanato-2-(trifluoromethyl)benzyl)piperazine (65 mg, 0.197 mmol, 94% yield). To a solution of 4-((5-ethoxy-6-((4-methoxybenzyl)oxy)pyridin-3-yl)oxy)aniline (50 mg, 0.136 mmol) and Et$_3$N (44 mg, 0.4 mmol) in THF (10 mL) was added a solution of 1-ethyl-4-(4-isocyanato-2-(trifluoromethyl)benzyl)piperazine (64.1 mg, 0.205 mmol) in THF (10 mL). The resulting mixture was stirred at 70° C. After LCMS analysis showed the starting material was disappeared. The solvent was removed in vacuo. The residue was washed with H$_2$O. The residue was purified by preparative TLC to yield a white solid of 1-(4-((5-ethoxy-6-((4-methoxybenzyl)oxy)pyridin-3-yl)oxy)phenyl)-3-(4-((4-ethylpiperazin-1-yl)methyl)-3-(trifluoromethyl)phenyl)urea (50 mg, 0.070 mmol, 51.2% yield): $^1$H NMR (400 MHz, CD$_3$OD) δ 7.85 (d, J=2.0 Hz, 1H), 7.66-7.64 (m, 2H), 7.42-7.36 (m, 5H), 6.99-6.95 (m, 3H), 6.89 (dd, J=6.8, 2.0 Hz, 2H), 5.29 (s, 2H), 4.03-3.98 (m, 2H), 3.79 (s, 3H), 3.69 (s, 2H), 3.31-2.65 (m, 8H), 1.37 (t, J=7.0 Hz, 3H), 1.27 (t, J=7.2 Hz, 3H); ES-LCMS m/z 680.1 (M+H).

Step 5: 1-(4-((5-Ethoxy-6-oxo-1,6-dihydropyridin-3-yl)oxy)phenyl)-3-(4-((4-ethylpiperazin-1-yl)methyl)-3-(trifluoromethyl)phenyl)urea

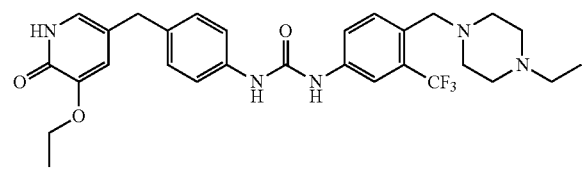 [SMILES: CCOc1cc(Cc2ccc(NC(=O)Nc3ccc(CN4CCN(CC)CC4)c(C(F)(F)F)c3)cc2)c[nH]c1=O]

A solution of 1-(4-((5-ethoxy-6-((4-methoxybenzyl)oxy)pyridin-3-yl)oxy)phenyl)-3-(4-((4-ethylpiperazin-1-yl)methyl)-3-(trifluoromethyl)phenyl)urea (50 mg, 0.074 mmol) in HCl in MeOH (5 mL, 20.00 mmol) was stirred at 25° C. After LCMS analysis showed the starting material was disappeared. The solvent was removed in vacuo. The residue was purified by preparative HPLC to give a colorless oil of 1-(4-((5-ethoxy-6-oxo-1,6-dihydropyridin-3-yl)oxy)phenyl)-3-(4-((4-ethylpiperazin-1-yl)methyl)-3-(trifluoromethyl)phenyl)urea dihydrochloride (34.97 mg, 0.054 mmol, 74.0% yield): $^1$H NMR (400 MHz, CD$_3$OD) δ 8.02 (d, J=2.4 Hz, 1H), 7.83 (d, J=8.8 Hz, 1H), 7.74-7.71 (m, 1H), 7.46-7.44 (dd, J=6.8, 2.0 Hz, 2H), 7.08 (d, J=2.8 Hz, 1H), 7.01 (dd, J=6.8, 2.4 Hz, 2H), 6.91 (d, J=2.8 Hz, 1H), 4.25 (s, 2H), 4.09-4.04 (m, 2H), 3.70-3.47 (m, 8H), 3.30-3.19 (m, 2H), 1.44-1.36 (m, 6H); ES-LCMS m/z 560.2 (M+H).

EXAMPLE 32

1-(2-(5-Ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea

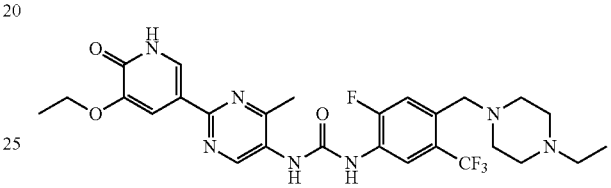

Step 1: 1-Ethyl-4-(5-fluoro-2-(trifluoromethyl)benzyl)piperazine

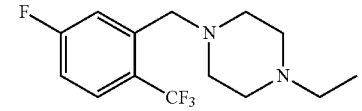

A solution of 5-fluoro-2-(trifluoromethyl)benzaldehyde (2 g, 10.41 mmol) and 1-ethylpiperazine (1.783 g, 15.62 mmol) in DCM (60 mL) was stirred at 20° C. After 2 h, NaBH(OAc)$_3$ (6.62 g, 31.2 mmol) was added. The resulting mixture was stirred at 20° C. overnight. After LCMS analysis showed the starting material was disappeared. The mixture was dissolved in H$_2$O (30 mL) and adjusted to pH 8 by aq NaHCO$_3$. The organic layer was washed with brine and dried over Na$_2$SO$_4$. After filtered, the filtrate was concentrated, which was purified by column chromatography (DCM/MeOH=0 to 20/1) to yield a yellow oil of 1-ethyl-4-(5-fluoro-2-(trifluoromethyl)benzyl)piperazine (3 g, 8.74 mmol, 84% yield): $^1$H NMR (400 MHz, CD$_3$OD) δ7.78-7.75 (m, 1H), 7.64-7.62 (m, 1H), 7.21-7.18 (m, 1H), 3.80 (s, 2H), 3.24 (br. s., 4H), 3.13 (m, 2H), 2.77 (br. s., 4H), 1.34 (t, J=7.4 Hz, 3H); ES-LCMS m/z 291.1 (M+H).

Step 2: 1-Ethyl-4-(5-fluoro-4-nitro-2-(trifluoromethyl)benzyl)piperazine

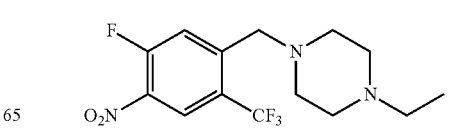

To a solution of 1-ethyl-4-(5-fluoro-2-(trifluoromethyl)benzyl)piperazine (3 g, 10.33 mmol) in $H_2SO_4$ (6 mL, 113 mmol) was added nitric acid (0.716 g, 11.37 mmol). The resulting mixture was stirred at rt overnight. The mixture was stirred at 50° C. for 2 h. After TLC analysis (PE/EA=10/1) showed the starting material was disappeared. The mixture was adjusted to pH 8 by aq NaOH and extracted by EA (50 mL×2). The organic layer was washed with $H_2O$ (50 mL) and brine (50 mL). After dried over $Na_2SO_4$ and filtered. The filtrate was concentrated to give a yellow oil of 1-ethyl-4-(5-fluoro-4-nitro-2-(trifluoromethyl)benzyl)piperazine (2.2 g, 6.56 mmol, 63.5% yield): $^1$H NMR (400 MHz, $CD_3OD$) δ8.39 (d, J=7.2 Hz, 1H), 7.92 (d, J=12.8 Hz, 1H), 3.75 (s, 2H), 2.60-2.47 (m, 10H), 1.14-1.10 (m, 3H); ES-LCMS m/z 336.1 (M+H).

Step 3: 4-((4-Ethylpiperazin-1-yl)methyl)-2-fluoro-5-(trifluoromethyl)aniline

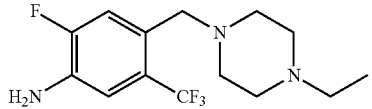 [SMILES: CCN1CCN(Cc2cc(F)c([N+](=O)[O-])cc2C(F)(F)F)CC1]

To a solution of 1-ethyl-4-(5-fluoro-4-nitro-2-(trifluoromethyl)benzyl)piperazine (2.2 g, 6.56 mmol) and zinc (4.29 g, 65.6 mmol) in MeOH (100 mL) was added $NH_4Cl$ (3.51 g, 65.6 mmol) by portion. The resulting mixture was stirred at 20° C. for 12 h. After LCMS analysis showed the starting material was disappeared. The mixture was filtered. The filtrate was concentrated, which was purified by preparative HPLC (Mobile phase A: water with 0.05% $NH_3.H_2O$ solution/Mobile phase B: MeCN/Flow rate: 80 mL/min/Detection: UV 220 nm/254 nm/Column: Phenomenex Gemini C18 250*50 mm,10 um/Column temperature: RT/Gradient Profile Description: 40-70(B %)) to yield a yellow solid of 4-((4-ethylpiperazin-1-yl)methyl)-2-fluoro-5-(trifluoromethyl)aniline (0.7 g, 2.265 mmol, 34.5% yield): $^1$H NMR (400 MHz, $CD_3OD$) δ7.31 (d, J=12.8 Hz, 1H), 7.10 (d, J=8.4 Hz, 1H), 3.51 (s, 2H), 2.74-2.15 (m, 10H), 1.10 (t, J=7.4 Hz, 3H); ES-LCMS m/z 306.1 (M+H).

Step 4: 1-(2-(5-Ethoxy-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea

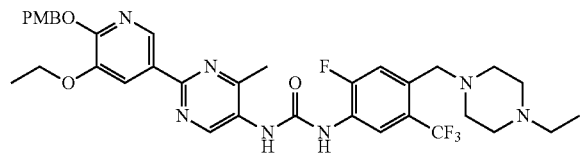

A solution of 2-(5-ethoxy-6-((4-methoxybenzyl)oxy)pyridin-3-yl)-4-methylpyrimidine-5-carboxylic acid (300 mg, 0.759 mmol), 4-((4-ethylpiperazin-1-yl)methyl)-2-fluoro-5-(trifluoromethyl)aniline (232 mg, 0.759 mmol), DPPA (313 mg, 1.138 mmol) and $Et_3N$ (0.159 mL, 1.138 mmol) in 1,4-dioxane (10 mL) was stirred at 70° C. under a $N_2$ atmosphere for 12 hr. After LCMS analysis showed the starting material was disappeared. The solvent was removed in vacuo. The residue was distributed between EA (30 mL) and $H_2O$ (20 mL), extracted with EA (30 mL×2). The combined organic layer was washed with brine (20 mL), dried over $Na_2SO_4$, filtered and concentrated to give the product, which was purified preparative TLC (DCM/MeOH=15/1, $R_f$=0.4) to yield a brown solid of 1-(2-(5-ethoxy-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea (200 mg, 0.272 mmol, 35.9% yield): $^1$H NMR (400 MHz, $CD_3OD$) δ 9.20 (s, 1H), 8.66 (s, 1H), 8.61 (d, J=7.6 Hz, 1H), 8.07 (s, 1H), 7.58 (d, J=12.0 Hz, 1H), 7.41 (d, J=8.8 Hz, 2H), 6.92 (d, J=8.4 Hz, 2H), 5.38 (s, 2H), 4.16 (m, 2H), 3.79 (s, 3H), 3.67 (s, 2H), 3.18 (m, 3H), 3.04-2.87 (m, 4H), 2.83-2.52 (m, 7H), 1.44 (t, J=6.8 Hz, 3H), 1.27-1.20 (m, 3H); ES-LCMS m/z 578.2 (M+H-PMB).

Step 5: 1-(2-(5-Ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea

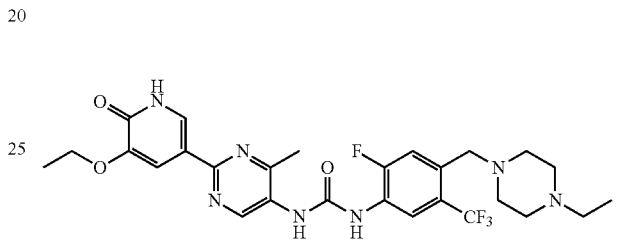

A solution of 1-(2-(5-ethoxy-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea (200 mg, 0.287 mmol) in TFA in DCM (5 mL, 3.72 mmol) was stirred at 25° C. After 0.5 hr, LCMS analysis showed the starting material was disappeared. The solvent was removed in vacuo. The residue was dissolved in MeCN and adjusted to pH 8 by $NH_3.H_2O$. The mixture was concentrated, which was purified by preparative HPLC (Instrument: Gilson GX 281/Column: Gemini 150*25 mm*5 um/Column temperature: 30° C./Mobile phase: A: water with 0.05% ammonia solution B: MeCN/Flow rate: 25 mL/min/Gradient Profile Description: 40-70(B %)). After lyophilization, a white solid of 1-(2-(5-ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea (40 mg, 0.069 mmol, 24.16% yield) was obtained: $^1$H NMR (400 MHz, $CD_3OD$) δ 9.17 (s, 1H), 8.61 (d, J=8.0 Hz, 1H), 8.08 (s, 1H), 7.88 (s, 1H), 7.63 (d, J=12.4 Hz, 1H), 4.17 (m, 2H), 3.66 (s, 2H), 2.78-2.38 (m, 13H), 1.51 (t, J=7.0 Hz, 3H), 1.14 (t, J=7.4 Hz, 3H); ES-LCMS m/z 578.3 (M+H).

EXAMPLE 33

1-(2-(5-Ethoxy-6-oxo-1,6-dihydropyridin-3-yl)-4,6-dimethylpyrimidin-5-yl)-3-(4-((4-ethylpiperazin-1-yl)methyl)-3-(trifluoromethyl)phenyl)urea

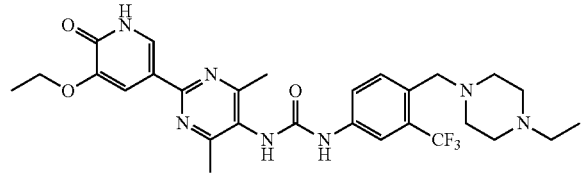 [SMILES: CCOc1cc(-c2nc(C)c(NC(=O)Nc3ccc(CN4CCN(CC)CC4)c(C(F)(F)F)c3)c(C)n2)c[nH]c1=O]

Step 1: 4,6-Dimethyl-5-nitropyrimidin-2-ol

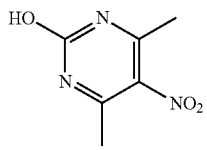

To a solution of 4,6-dimethylpyrimidin-2-ol (3 g, 24.17 mmol) in sulfamic acid (10 mL, 24.17 mmol) was added nitric acid (1.620 mL, 36.2 mmol) at 0° C. The resulting mixture was stirred at rt overnight. The mixture was added to aq NaOH at 0° C. adjusted to pH 8. The mixture was filtered. The filtrate was concentrated and salt. The mixture was suspended in MeOH (200 mL) and filtered. The filtrate was concentrated, which was purified by column chromatography (DCM/MeOH=30/1 to 10/1) to yield a yellow solid of 4,6-dimethyl-5-nitropyrimidin-2-ol (1.6 g, 8.99 mmol, 37.2% yield): $^1$H NMR (400 MHz, CD$_3$OD) δ 2.51 (s, 6H); ES-LCMS m/z 170.1 (M+H).

Step 2: 2-Chloro-4,6-dimethyl-5-nitropyrimidine

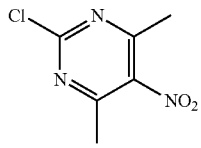

To a solution of 4,6-dimethyl-5-nitropyrimidin-2-ol (0.5 g, 2.96 mmol) in POCl$_3$ (5 mL, 53.8 mmol) was added N,N-dimethylaniline (0.036 g, 0.296 mmol). The resulting mixture was stirred at 60° C. overnight. After LCMS analysis showed the starting material was disappeared. The solvent was removed in vacuo. The residue was added to ice water and adjusted to pH 8 by aq Na$_2$CO$_3$. The mixture was filtered. The cake was dried and purified by column chromatography (PE/EA=3/1) to yield 2-chloro-4,6-dimethyl-5-nitropyrimidine (130 mg, 0.606 mmol, 20.52% yield): $^1$H NMR (400 MHz, CD$_3$OD) δ 2.54 (s, 6H); ES-LCMS m/z 188.1 (M+H).

Step 3: 2-Chloro-4,6-dimethylpyrimidin-5-amine

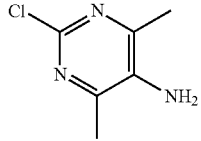

To a solution of 2-chloro-4,6-dimethyl-5-nitropyrimidine (130 mg, 0.693 mmol) and zinc (45.3 mg, 0.693 mmol) in MeOH (20 mL) was added NH$_4$Cl (37.1 mg, 0.693 mmol). The resulting mixture was stirred at 25° C. overnight. After LCMS analysis showed the starting material was disappeared. The mixture was filtered. The filtrate was concentrated, which was purified by column chromatography (PE/EA=3/1) to yield a white solid of 2-chloro-4,6-dimethylpyrimidin-5-amine (80 mg, 0.508 mmol, 73.2% yield): $^1$H NMR (400 MHz, CD$_3$OD) δ 2.33 (s, 6H).

Step 4: 1-(2-Chloro-4,6-dimethylpyrimidin-5-yl)-3-(4-((4-ethylpiperazin-1-yl)methyl)-3-(trifluoromethyl)phenyl)urea

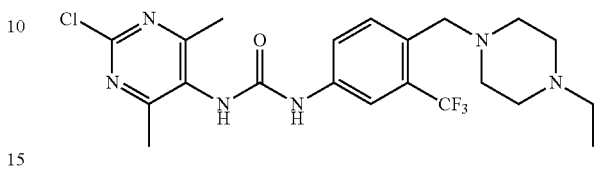

To a solution of 2-chloro-4,6-dimethylpyrimidin-5-amine (50 mg, 0.317 mmol) in THF (10 mL) was added triphosgene (33.0 mg, 0.111 mmol). The resulting mixture was stirred at 70° C. After LCMS analysis showed the starting material was disappeared. The solvent was removed in vacuo to give 2-chloro-5-isocyanato-4,6-dimethylpyrimidine (50 mg, 0.257 mmol, 81% yield). To a solution of 4-((4-ethylpiperazin-1-yl)methyl)-3-(trifluoromethyl)aniline (94 mg, 0.327 mmol) and Et$_3$N (0.114 mL, 0.817 mmol) in THF (10 mL) was added a solution of 2-chloro-5-isocyanato-4,6-dimethylpyrimidine (50 mg, 0.272 mmol) in THF (10 mL). The resulting mixture was stirred at 70° C. After LCMS analysis showed the starting material was disappeared. The solvent was removed in vacuo. The residue was dissolved in DCM (60 mL) and washed with H$_2$O (20 mL) and brine (20 mL). The organic layer was dried over Na$_2$SO$_4$, filtered and concentrated. The residue was purified by preparative HPLC (DCM/MeOH=10/1) to yield a white solid of 1-(2-chloro-4,6-dimethylpyrimidin-5-yl)-3-(4-((4-ethylpiperazin-1-yl)methyl)-3-(trifluoromethyl)phenyl)urea (80 mg, 0.167 mmol, 61.2% yield): $^1$H NMR (400 MHz, CD$_3$OD) δ 7.88 (s, 1H), 7.39 (d, J=8.0 Hz, 1H), 6.99 (d, J=2.8 Hz, 1H), 3.75 (s, 2H), 3.04 (m, 8H), 2.49 (m, 8H), 1.37 (m, 3H); ES-LCMS m/z 471.0 (M+H).

Step 5: 1-(2-(5-Ethoxy-6-((4-methoxybenzyl)oxy)pyridin-3-yl)-4,6-dimethylpyrimidin-5-yl)-3-(4-((4-ethylpiperazin-1-yl)methyl)-3-(trifluoromethyl)phenyl)urea

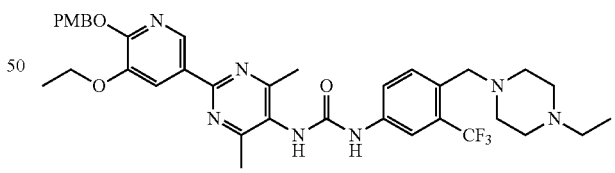

A solution of 3-ethoxy-2-((4-methoxybenzyl)oxy)-5-(4,4,5,5-tetramethyl-1,3,2-dioxaborolan-2-yl)pyridine (40.9 mg, 0.106 mmol), 1-(2-chloro-4,6-dimethylpyrimidin-5-yl)-3-(4-((4-ethylpiperazin-1-yl)methyl)-3-(trifluoromethyl)phenyl)urea (50 mg, 0.106 mmol), PdCl$_2$(dppf)-DCM adduct (8.67 mg, 10.62 μmol) and Cs$_2$CO$_3$ (69.2 mg, 0.212 mmol) in 1,4-dioxane (3 mL) and water (1 mL) was stirred at 110° C. After LCMS analysis showed the starting material was disappeared. The mixture was dissolved in EA (60 mL) and washed with H$_2$O (20 mL) and brine (20 mL). The organic layer was dried over Na$_2$SO$_4$, filtered and concentrated. The residue was purified by preparative TLC (DCM/MeOH=10/

1) to yield a white solid of 1-(2-(5-ethoxy-6-((4-methoxybenzyl)oxy)pyridin-3-yl)-4,6-dimethylpyrimidin-5-yl)-3-(4-((4-ethylpiperazin-1-yl)methyl)-3-(trifluoromethyl)phenyl)urea (20 mg, 0.024 mmol, 22.77% yield): $^1$H NMR (400 MHz, CD$_3$OD) δ 8.71 (d, J=2.0 Hz, 1H), 8.12 (d, J=1.6 Hz, 1H), 7.85 (s, 1H), 7.66 (m, 2H), 7.40 (d, J=8.4 Hz, 2H), 6.91 (d, J=8.4 Hz, 2H), 5.39 (s, 2H), 4.19-4.14 (m, 2H), 3.78 (s, 3H), 3.66 (s, 2H), 2.81-2.62 (m, 10H), 2.53 (s, 6H), 1.43 (t, J=7.0 Hz, 3H), 1.21 (t, J=7.2 Hz, 3H); ES-LCMS m/z 694.2 (M+H).

Step 6: 1-(2-(5-Ethoxy-6-oxo-1,6-dihydropyridin-3-yl)-4,6-dimethylpyrimidin-5-yl)-3-(4-((4-ethylpiperazin-1-yl)methyl)-3-(trifluoromethyl)phenyl)urea

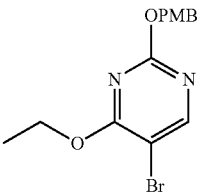

A solution of 1-(2-(5-ethoxy-6-((4-methoxybenzyl)oxy)pyridin-3-yl)-4,6-dimethylpyrimidin-5-yl)-3-(4-((4-ethylpiperazin-1-yl)methyl)-3-(trifluoromethyl)phenyl)urea (40 mg, 0.058 mmol) in HCl in MeOH (10 mL, 175 mmol) was stirred at 20° C. After LCMS analysis showed the starting material was disappeared. The solvent was removed in vacuo. The residue was purified by preparative HPLC to give 1-(2-(5-ethoxy-6-oxo-1,6-dihydropyridin-3-yl)-4,6-dimethylpyrimidin-5-yl)-3-(4-((4-ethylpiperazin-1-yl)methyl)-3-(trifluoromethyl)phenyl)urea trihydrochloride (7.79 mg, 10.92 μmol, 18.94% yield) as a yellow solid: $^1$H NMR (400 MHz, CD$_3$OD) δ 8.19 (s, 1H), 7.98 (s, 1H), 7.91 (d, J=2.0 Hz, 1H), 7.81-7.77 (m, 2H), 4.19-4.13 (m, 4H), 3.68-3.47 (m, 8H), 2.95 (m, 2H), 2.55 (s, 6H), 1.49 (t, J=7.2 Hz, 3H), 1.36 (d, J=7.2 Hz, 3H); ES-LCMS m/z 574.2 (M+H).

EXAMPLE 34

1-(4-(4-Ethoxy-2-oxo-1,2-dihydropyrimidin-5-yl)-2-fluorophenyl)-3-(4-((3-methyloxetan-3-yl)oxy)-3-(trifluoromethyl)phenyl)urea

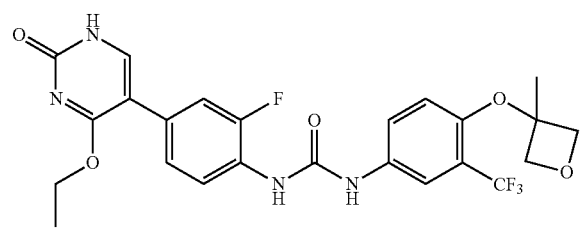 [SMILES: CCOc1nc(=O)[nH]cc1-c1ccc(NC(=O)Nc2ccc(OC3(C)COC3)c(C(F)(F)F)c2)c(F)c1]

Step 1: 5-Bromo-2-chloro-4-ethoxypyrimidine

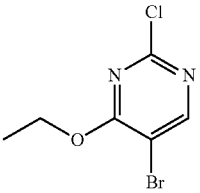

Fresh cut sodium (0.202 g, 8.78 mmol) was added to EtOH (50 mL). The resulting mixture was stirred at 25° C. After the sodium was disappeared, 5-bromo-2,4-dichloropyrimidine (2 g, 8.78 mmol) was added to the mixture. The resulting mixture was stirred at 25° C. overnight. After LCMS analysis showed the starting material was disappeared. The solvent was removed in vacuo to give a white solid of 5-bromo-2-chloro-4-ethoxypyrimidine (2 g, 6.22 mmol, 70.9% yield): $^1$H NMR (400 MHz, CD$_3$OD) δ 8.51 (s, 1H), 4.54-4.49 (m, 2H), 1.42 (t, J=7.0 Hz, 3H); ES-LCMS m/z 236.9, 238.9 (M+H).

Step 2: 5-Bromo-4-ethoxy-2-((4-methoxybenzyl)oxy)pyrimidine

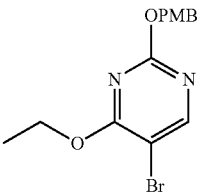

To a solution of (4-methoxyphenyl)methanol (0.640 g, 4.63 mmol) in DMF (30 mL) was added NaH (0.202 g, 5.05 mmol). The resulting mixture was stirred at rt. After 30 min, 5-bromo-2-chloro-4-ethoxypyrimidine (1 g, 4.21 mmol) was added. The resulting mixture was stirred at 90° C. overnight. After LCMS analysis showed the starting material was disappeared. The solvent was removed in vacuo. The residue was dissolved in DCM (60 mL) and washed with H$_2$O (20 mL) and brine (20 mL). The organic layer was dried over Na$_2$SO$_4$, filtered and concentrated. The residue was purified by silica column chromatography to give 5-bromo-4-ethoxy-2-((4-methoxybenzyl)oxy)pyrimidine (180 mg, 0.425 mmol, 10.08% yield): $^1$H NMR (400 MHz, CD$_3$OD) δ 8.36 (s, 1H), 7.39 (d, J=8.8 Hz, 2H), 6.93 (d, J=8.4 Hz, 2H), 5.34 (s, 2H), 4.55-4.50 (m, 2H), 3.81 (s, 3H), 1.43 (t, J=7.2 Hz, 3H); ES-LCMS m/z 338.9, 340.9 (M+H).

Step 3: 1-(4-(4-Ethoxy-2-((4-methoxybenzyl)oxy)pyrimidin-5-yl)-2-fluorophenyl)-3-(4-((3-methyloxetan-3-yl)oxy)-3-(trifluoromethyl)phenyl)urea

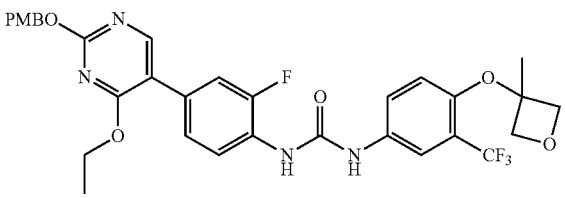

A solution of 5-bromo-4-ethoxy-2-((4-methoxybenzyl)oxy)pyrimidine (100 mg, 0.295 mmol), (3-fluoro-4-(3-(4-((3-methyloxetan-3-yl)oxy)-3-(trifluoromethyl)phenyl)

ureido)phenyl)boronic acid (126 mg, 0.295 mmol), PdCl₂ (dppf) (21.57 mg, 0.029 mmol) and Cs₂CO₃ (192 mg, 0.590 mmol) in 1,4-Dioxane (9 mL) and water (3 mL) was stirred at 110° C. for 15 min on microwave. After LCMS analysis showed the starting material was disappeared. The solvent was removed in vacuo. The residue was dissolved in DCM (60 mL) and washed with H₂O (20 mL) and brine (20 mL). The organic layer was dried over Na₂SO₄, filtered and concentrated. The residue was purified by preparative TLC (PE/EA=2/1) to give a oil of 1-(4-(4-ethoxy-2-((4-methoxybenzyl)oxy)pyrimidin-5-yl)-2-fluorophenyl)-3-(4-((3-methyloxetan-3-yl)oxy)-3-(trifluoromethyl)phenyl)urea (70 mg, 0.086 mmol, 29.2% yield): ¹H NMR (400 MHz, CD₃OD) δ 8.29 (s, 1H), 8.13 (s, 1H), 7.78 (s, 1H), 7.54 (m, 1H), 7.40-7.31 (m, 4H), 6.92 (m, 2H), 6.62 (m, 1H), 5.38 (s, 2H), 4.89 (m, 2H), 4.63-4.53 (m, 4H), 3.79 (s, 3H), 1.72 (s, 3H), 1.39 (m, 3H); ES-LCMS m/z 643.1 (M+H).

Step 4: 1-(4-(4-Ethoxy-2-oxo-1,2-dihydropyrimidin-5-yl)-2-fluorophenyl)-3-(4-((3-methyloxetan-3-yl)oxy)-3-(trifluoromethyl)phenyl)urea

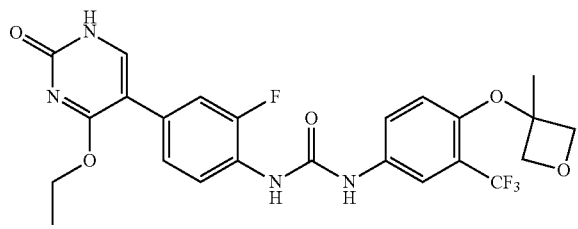 [SMILES: CCOc1nc(=O)[nH]cc1-c1ccc(NC(=O)Nc2ccc(OC3(C)COC3)c(C(F)(F)F)c2)c(F)c1]

A solution of 1-(4-(4-ethoxy-2-((4-methoxybenzyl)oxy)pyrimidin-5-yl)-2-fluorophenyl)-3-(4-((3-methyloxetan-3-yl)oxy)-3-(trifluoromethyl)phenyl)urea (40 mg, 0.062 mmol) in TFA in DCM (5 mL, 7.44 mmol) was stirred at 25° C. After LCMS analysis showed the starting material was disappeared. The mixture was adjusted to pH 8 by aq K₂CO₃. The solvent was removed in vacuo. The residue was dissolved in MeOH and filtered. The filtrate was purified by preparative HPLC to yield a white solid of 1-(4-(4-ethoxy-2-oxo-1,2-dihydropyrimidin-5-yl)-2-fluorophenyl)-3-(4-((3-methyloxetan-3-yl)oxy)-3-(trifluoromethyl)phenyl)urea (18 mg, 0.034 mmol, 55.3% yield): ¹H NMR (400 MHz, CD₃OD) δ 8.12 (t, J=8.4 Hz, 1H), 7.82-7.79 (m, 2H), 7.58-7.55 (m, 1H), 7.33 (dd, J=12.4, 2.0 Hz, 1H), 7.27-7.24 (m, 1H), 6.64 (d, J=8.8 Hz, 1H), 4.93-4.91 (m, 2H), 4.65 (d, J=7.6 Hz, 2H), 4.52-4.47 (m, 2H), 1.75 (s, 3H), 1.39 (t, J=7.2 Hz, 3H); ES-LCMS m/z 523.2 (M+H).

EXAMPLE 35

1-(4-(2-Ethoxy-6-oxo-1,6-dihydropyridin-3-yl)-2-fluorophenyl)-3-(4-((3-methyloxetan-3-yl)oxy)-3-(trifluoromethyl)phenyl)urea

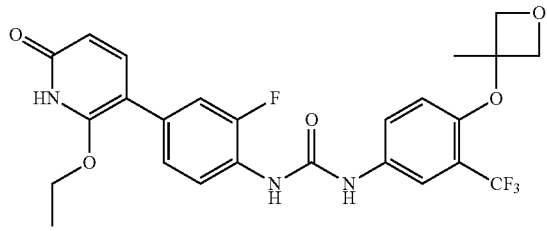 [SMILES: CCOc1[nH]c(=O)ccc1-c1ccc(NC(=O)Nc2ccc(OC3(C)COC3)c(C(F)(F)F)c2)c(F)c1]

Step 1: 3-Bromo-6-chloro-2-ethoxypyridine

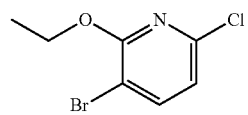

Fresh cut sodium (0.101 g, 4.41 mmol) was added to EtOH (50 mL). The resulting mixture was stirred at rt. After the solid dissolved, 3-bromo-2,6-dichloropyridine (1 g, 4.41 mmol) was added. The resulting mixture was stirred at 70° C. overnight. After LCMS analysis showed the starting material was disappeared. The solvent was removed in vacuo. The residue was dissolved in DCM (60 mL) and washed with H₂O (20 mL) and brine (20 mL). The organic layer was dried over Na₂SO₄, filtered and concentrated. The residue was purified by silica column chromatography (PE/EA=20/1) to yield a white solid of a mixture of 3-bromo-2-chloro-6-ethoxypyridine, 3-bromo-2,6-diethoxypyridine and 3-bromo-6-chloro-2-ethoxypyridine (930 mg, 3.85 mmol, 87% yield): ¹H NMR (400 MHz, CD₃OD) δ 7.85 (d, J=1.2 Hz, 1H), 6.88 (d, J=8.0 Hz, 1H), 4.42-4.36 (m, 2H), 1.39 (t, J=7.2 Hz, 3H); ES-LCMS m/z 235.9, 237.9 (M+H).

Step 2: 3-Bromo-2-ethoxy-6-((4-methoxybenzyl)oxy)pyridine

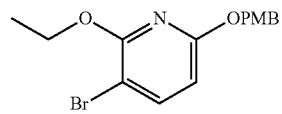

To a solution of (4-methoxyphenyl)methanol (257 mg, 1.861 mmol) in DMF (20 mL) was added NaH (135 mg, 3.38 mmol) at 0° C. The resulting mixture was stirred at rt. After 0.5 h, 3-bromo-6-chloro-2-ethoxypyridine (400 mg, 1.691 mmol) was added. The resulting mixture was stirred at 80° C. overnight. After LCMS analysis showed the starting material was disappeared. The solvent was removed in vacuo. The residue was dissolved in DCM (60 mL) and washed with H₂O (20 mL) and brine (20 mL). The organic layer was dried over Na₂SO₄, filtered and concentrated. The residue was purified by silica column chromatography and chiral HPLC to yield a white solid of 3-bromo-2-ethoxy-6-((4-methoxybenzyl)oxy)pyridine (100 mg, 0.296 mmol, 17.48% yield): ¹H NMR (400 MHz, CDCl₃) δ 7.61 (d, J=8.4 Hz, 1H), 7.33 (d, J=8.8 Hz, 2H), 6.88 (dd, J=6.8, 2.0 Hz, 2H), 6.23 (d, J=8.0 Hz, 1H), 5.24 (s, 2H), 4.44-4.39 (m, 2H), 3.79 (s, 3H), 1.41 (t, J=7.0 Hz, 3H); ES-LCMS m/z 338.0, 340.0 (M+H).

Step 3: 1-(4-(2-Ethoxy-6-((4-methoxybenzyl)oxy)
pyridin-3-yl)-2-fluorophenyl)-3-(4-((3-methylox-
etan-3-yl)oxy)-3-(trifluoromethyl)phenyl)urea

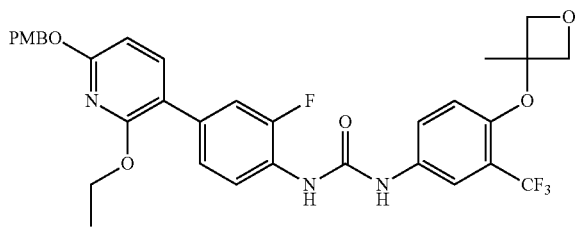

A solution of 3-bromo-2-ethoxy-6-((4-methoxybenzyl)oxy)pyridine (30 mg, 0.089 mmol), (3-fluoro-4-(3-(4-((3-methyloxetan-3-yl)oxy)-3-(trifluoromethyl)phenyl)ureido)phenyl)boronic acid (45.6 mg, 0.106 mmol), PdCl$_2$(dppf)-DCM adduct (7.24 mg, 8.87 μmol) and Cs$_2$CO$_3$ (57.8 mg, 0.177 mmol) in 1,4-dioxane (3 mL) and water (1 mL) was stirred at 110° C. on microwave for 15 min After LCMS analysis showed the starting material was disappeared. The mixture was extracted by EA (20 mL) and washed with H$_2$O (10 mL) and brine (10 mL). The organic layer was dried over Na$_2$SO$_4$, filtered and concentrated. The residue was purified by preparative TLC (PE/EA=3/1) to yield a white solid of 1-(4-(2-ethoxy-6-((4-methoxybenzyl)oxy)pyridin-3-yl)-2-fluorophenyl)-3-(4-((3-methyloxetan-3-yl)oxy)-3-(trifluoromethyl)phenyl)urea (30 mg, 0.044 mmol, 49.5% yield): $^1$H NMR (400 MHz, CD$_3$OD) δ 8.03 (t, J=8.6 Hz, 1H), 7.77 (d, J=2.4 Hz, 1H), 7.64 (d, J=8.0 Hz, 1H), 7.55-7.52 (m, 1H), 7.39-7.33 (m, 3H), 7.29 (d, J=8.8 Hz, 1H), 6.91-6.89 (m, 2l), 6.61 (d, J=8.8 Hz, 1H), 6.41 (d, J=8.0 Hz, 1H), 5.31 (s, 2H), 4.89-4.88 (m, 2H), 4.62 (d, J=7.2 Hz, 2H), 4.44-4.39 (m, 2H), 3.78 (s, 3H), 1.72 (s, 3H), 1.35 (t, J=7.0 Hz, 3H); ES-LCMS m/z 642.2 (M+H).

Step 4: 1-(4-(2-Ethoxy-6-oxo-1,6-dihydropyridin-3-
yl)-2-fluorophenyl)-3-(4-((3-methyloxetan-3-yl)
oxy)-3-(trifluoromethyl)phenyl)urea

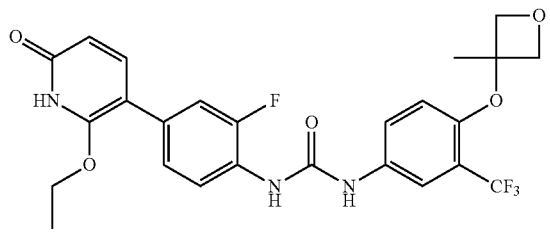 [SMILES: CCOc1[nH]c(=O)ccc1-c1ccc(NC(=O)Nc2ccc(OC3(C)COC3)c(C(F)(F)F)c2)c(F)c1]

A solution of 1-(4-(2-ethoxy-6-((4-methoxybenzyl)oxy)pyridin-3-yl)-2-fluorophenyl)-3-(4-((3-methyloxetan-3-yl)oxy)-3-(trifluoromethyl)phenyl)urea (30 mg, 0.047 mmol) in TFA in DCM (5 mL, 3.72 mmol) was stirred at 25° C. After LCMS analysis showed the starting material was disappeared. The mixture was adjusted to pH 7 by aq Na$_2$CO$_3$. The solvent was removed in vacuo. The residue was dissolved in MeOH (5 mL), filtered, and purified by preparative HPLC to yield a white solid of 1-(4-(2-ethoxy-6-oxo-1,6-dihydropyridin-3-yl)-2-fluorophenyl)-3-(4-((3-methyloxetan-3-yl)oxy)-3-(trifluoromethyl)phenyl)urea (3 mg, 5.70 μmol, 12.20% yield): $^1$H NMR (400 MHz, CD$_3$OD) δ 8.02 (t, J=8.6 Hz, 1H), 7.77 (d, J=2.8 Hz, 1H), 7.59 (d, J=8.4 Hz, 1H), 7.54 (dd, J=8.8, 2.8 Hz, 1H), 7.36 (dd, J=12.8, 2.0 Hz, 1H), 7.27 (d, J=8.4 Hz, 1H), 6.61 (d, J=9.2 Hz, 1H), 6.26 (d, J=8.4 Hz, 1H), 4.90-4.88 (m, 2H), 4.62 (d, J=7.2 Hz, 2H), 4.38-4.33 (m, 2H), 1.72 (s, 3H), 1.34 (t, J=7.2 Hz, 3H); ES-LCMS m/z 522.0 (M+H).

EXAMPLE 36

1-(2-Fluoro-4-(5-fluoro-6-oxo-1,6-dihydropyridin-3-
yl)phenyl)-3-(4-((3-methyloxetan-3-yl)oxy)-3-(trif-
luoromethyl)phenyl)urea

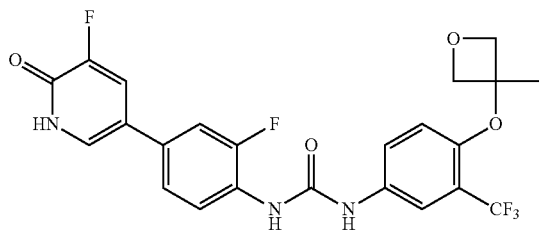 [SMILES: CC1(Oc2ccc(NC(=O)Nc3ccc(-c4c[nH]c(=O)c(F)c4)cc3F)cc2C(F)(F)F)COC1]

Step 1: 5-Bromo-3-fluoropyridin-2-ol

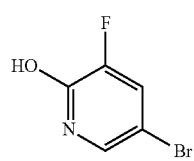

A sloution of 5-bromo-3-fluoro-2-methoxypyridine (300 mg, 1.456 mmol) in aq HBr (5 mL, 48%) was stirred at 80° C. overnight. After TLC analysis (DCM/MeOH=10/1) showed the starting material was disappeared. The solvent was removed in vacuo to yield of a off white solid of 5-bromo-3-fluoropyridin-2-ol (0.2 g, 1.042 mmol, 71.5% yield): $^1$H NMR (400 MHz, CD$_3$OD) δ 7.57 (dd, J=10.0, 2.4 Hz, 1H), 7.46 (d, J=2.4, 1.6 Hz, 1H); ES-LCMS m/z 192.0; 193.9 (M+H).

Step 2: 1-(2-Fluoro-4-(5-fluoro-6-oxo-1,6-dihydro-
pyridin-3-yl)phenyl)-3-(4-((3-methyloxetan-3-yl)
oxy)-3-(trifluoromethyl)phenyl)urea

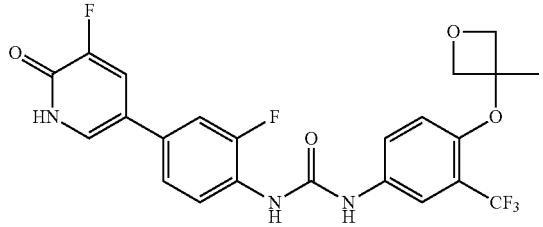 [SMILES: CC1(Oc2ccc(NC(=O)Nc3ccc(-c4c[nH]c(=O)c(F)c4)cc3F)cc2C(F)(F)F)COC1]

A solution of 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (300 mg, 0.588 mmol), 5-bromo-3-fluoropyridin-2-ol (135 mg, 0.705 mmol), PdCl$_2$ (dppf)-DCM adduct (48.0 mg, 0.059 mmol) and Cs$_2$CO$_3$ (575 mg, 1.764 mmol) in 1,4-dioxane (6 mL) and water (2 mL) was stirred at 110° C. on microwave for 15 min. After LCMS analysis showed the starting material was disappeared. The mixture was dissolved in H$_2$O (20 mL) and extracted with EA (30 mL). The organic layer was dried over Na$_2$SO$_4$ and concentrated, which was purified by preparative TLC (DCM/MeOH=10/1) and preparative HPLC (neutral condition) to yield a white solid of 1-(2-fluoro-4-(5-fluoro-6-oxo-1,6-dihydropyridin-3-yl)phenyl)-3-(4-((3-methyloxetan-3-yl)oxy)-3-(trifluoromethyl)phenyl)urea (8 mg, 0.016 mmol, 2.75% yield): $^1$H NMR (400 MHz, CD$_3$OD) δ 8.18 (t, J=8.4 Hz, 1H), 7.84-7.80 (m, 2H), 7.58-7.55 (m, 2H), 7.43-7.39 (m, 1H), 7.36-7.34 (m, 1H), 6.65 (d, J=9.2 Hz, 1H), 4.93-4.88 (m, 2H), 4.66 (d, J=7.2 Hz, 1H), 1.75 (s, 3H); ES-LCMS m/z 496.0 (M+H).

EXAMPLE 37

1-(2-Fluoro-4-(4-fluoro-6-oxo-1,6-dihydropyridin-3-yl)phenyl)-3-(4-((3-methyloxetan-3-yl)oxy)-3-(trifluoromethyl)phenyl)urea

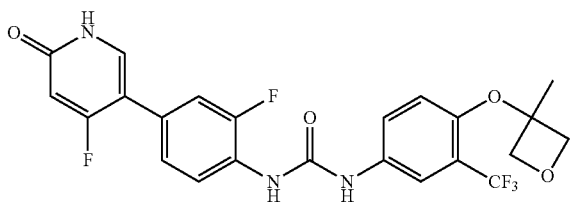 [SMILES: CC1(Oc2ccc(NC(=O)Nc3ccc(-c4c[nH]c(=O)cc4F)cc3F)cc2C(F)(F)F)COC1]

Step 1: tert-Butyl (4-fluoropyridin-2-yl)carbamate

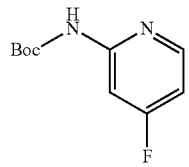 [SMILES: CC(C)(C)OC(=O)Nc1cc(F)ccn1]

A solution of dicyclohexyl(2',4',6'-triisopropyl-[1,1'-biphenyl]-2-yl)phosphine (0.072 g, 0.152 mmol), 2-chloro-4-fluoropyridine (1 g, 7.60 mmol), tert-butyl carbamate (4.45 g, 38.0 mmol), Pd$_2$(dba)$_3$ (0.070 g, 0.076 mmol) and Cs$_2$CO$_3$ (12.39 g, 38.0 mmol) in THF (80 mL) was stirred at 80° C. under N$_2$ overnight. After LCMS analysis showed the starting material was disappeared. The mixture was washed with H$_2$O (100 mL) and extracted by EA (100 mL). The organic layer was dried and concentrated, which was purified by column chromatography to give tert-butyl (4-fluoropyridin-2-yl)carbamate (1.3 g, 5.55 mmol, 73.1% yield) as a light yellow solid: $^1$H NMR (400 MHz, CD$_3$OD) δ 8.20-8.16 (m, 1H), 7.65 (dd, J=12.0, 2.4 Hz, 1H), 6.81-6.77 (m, 1H), 1.52 (s, 9H); ES-LCMS m/z 213.1 (M+H).

Step 2: 4-Fluoropyridin-2-amine

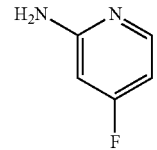

A solution of tert-butyl (4-fluoropyridin-2-yl)carbamate (0.7 g, 3.30 mmol) in HCl in MeOH (50 mL, 200 mmol) was stirred at 25° C. After TLC analysis showed the starting material was disappeared. The solvent was removed in vacuo to yield a solid of 4-fluoropyridin-2-amine hydrochloride (0.5 g, 3.20 mmol, 97% yield): $^1$H NMR (400 MHz, CD$_3$OD) δ 7.96 (t, J=6.6 Hz, 1H), 6.83-6.78 (m, 1H), 6.74-6.71 (m, 1H); ES-LCMS m/z 134.9 (M+Na).

Step 3: 5-Bromo-4-fluoropyridin-2-amine

To a suspension of 4-fluoropyridin-2-amine (0.6 g, 4.04 mmol) in MeCN (20 mL) was added Et$_3$N (0.563 mL, 4.04 mmol). The solid all dissolved. Then NBS (0.719 g, 4.04 mmol) was added. The resulting mixture was stirred at 25° C. overnight. LCMS analysis showed only 50% of product. NBS (0.719 g, 4.04 mmol) was added. The resulting mixture was stirred at 25° C. overnight. After LCMS analysis showed the starting material was disappeared. The solvent was removed in vacuo. The residue was dissolved in DCM (100 mL) and washed with H$_2$O (50 mL) and brine (50 mL). The organic layer was dried over Na$_2$SO$_4$, filtered and concentrated. The residue was purified by preparative TLC (PE/EA=3/1) to yield a off white solid of 5-bromo-4-fluoropyridin-2-amine (0.3 g, 1.319 mmol, 32.7% yield): $^1$H NMR (400 MHz, CDCl$_3$) δ 8.11 (d, J=9.6 Hz, 1H), 6.26 (d, J=10.0 Hz, 1H), 4.55 (brs, 2H); ES-LCMS m/z 192.9 (M+H).

Step 4: 5-Bromo-4-fluoropyridin-2-ol

5-bromo-4-fluoropyridin-2-amine (100 mg, 0.524 mmol) was mixed with a 50% aqueous solution of H$_3$PO$_2$ (691 mg, 5.24 mmol) and water (3 mL). The mixture was cooled to about 2° C. and a solution of NaNO$_2$ (43.3 mg, 0.628 mmol) in water (1 mL) was added with vigorous stirring keeping the temperature below 5° C. The mixture was stirred for 30 min at a lower temperature and then for an additional 12 h at rt. After LCMS analysis showed the starting material was disappeared. The resulting precipitate was filtered and washed with water. The cake was dried and concentrated to give a yellow oil of 5-bromo-4-fluoropyridin-2-ol (80 mg, 0.417 mmol, 80% yield): $^1$H NMR (400 MHz, CD$_3$OD) δ 7.77 (d, J=8.8 Hz, 1H), 6.31 (d, J=10.8 Hz, 1H); ES-LCMS m/z 191.9, 193.9 (M+H).

Step 5: 1-(2-Fluoro-4-(4-fluoro-6-oxo-1,6-dihydropyridin-3-yl)phenyl)-3-(4-((3-methyloxetan-3-yl)oxy)-3-(trifluoromethyl)phenyl)urea

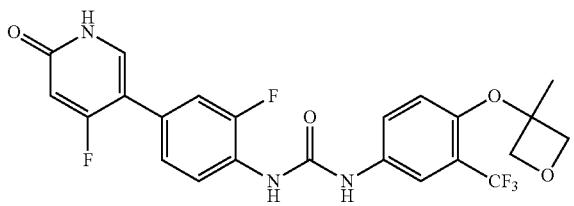 [SMILES: CC1(Oc2ccc(NC(=O)Nc3ccc(-c4c[nH]c(=O)cc4F)cc3F)cc2C(F)(F)F)COC1]

A solution of 5-bromo-4-fluoropyridin-2-ol (40 mg, 0.208 mmol), (3-fluoro-4-(3-(4-((3-methyloxetan-3-yl)oxy)-3-(trifluoromethyl)phenyl)ureido)phenyl)boronic acid (107 mg, 0.250 mmol), Cs$_2$CO$_3$ (136 mg, 0.417 mmol) and PdCl$_2$(dppf) (15.24 mg, 0.021 mmol) in 1,4-dioxane (3 mL) and water (1 mL) was stirred at 110° C. for 15 min. After LCMS analysis showed the starting material was disappeared. The solvent was removed in vacuo. The residue was dissolved in EA (20 mL) and washed with H$_2$O (10 mL) and brine (10 mL). The organic layer was dried over Na$_2$SO$_4$, filtered and concentrated. The residue was purified by preparative TLC (DCM/MeOH=10/1) to give 1-(2-fluoro-4-(4-fluoro-6-oxo-1,6-dihydropyridin-3-yl)phenyl)-3-(4-((3-methyloxetan-3-yl)oxy)-3-(trifluoromethyl)phenyl)urea (2.88 mg, 5.81 μmol, 2.79% yield): $^1$H NMR (400 MHz, CD$_3$OD) δ 8.17 (t, J=8.4 Hz, 1H), 7.78 (d, J=2.4 Hz, 1H), 7.64 (d, J=9.6 Hz, 1H), 7.55-7.52 (m, 1H), 7.30-7.21 (m, 2H), 6.62 (d, J=8.8 Hz, 1H), 6.30 (d, J=12.8 Hz, 1H), 4.89 (d, J=6.4 Hz, 2H), 4.62 (d, J=7.6 Hz, 2H), 1.72 (s, 3H); ES-LCMS m/z 496.1 (M+H).

EXAMPLE 38

1-(2-(4-Ethoxy-6-oxo-1,6-dihydropyridin-3-yl)-4-methylpyrimidin-5-yl)-3-(3-(trifluoromethyl)phenyl)urea

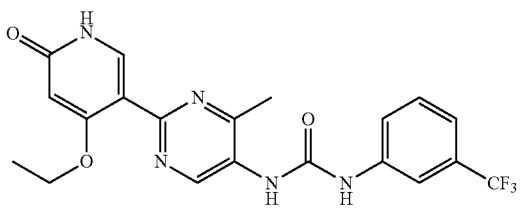 [SMILES: CCOc1cc(=O)[nH]cc1-c1ncc(NC(=O)Nc2cccc(C(F)(F)F)c2)c(C)n1]

Step 1: 1-(2-(4-Ethoxy-6-((4-methoxybenzyl)oxy)pyridin-3-yl)-4-methylpyrimidin-5-yl)-3-(3-(trifluoromethyl)phenyl)urea

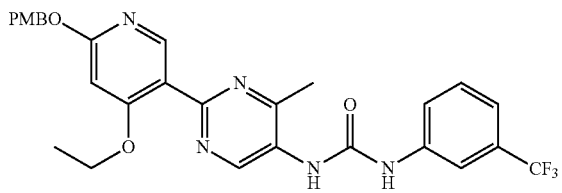

To a solution of 2-(4-ethoxy-6-((4-methoxybenzyl)oxy)pyridin-3-yl)-4-methylpyrimidine-5-carboxylic acid (100 mg, 0.253 mmol) and Et$_3$N (0.053 mL, 0.379 mmol) in 1,4-dioxane (5 mL) was added DPPA (84 mg, 0.303 mmol). After 10 min, 3-(trifluoromethyl)aniline (61.1 mg, 0.379 mmol) was added. The resulting mixture was stirred at 60° C. overnight. After LCMS analysis showed the starting material was disappeared. The solvent was removed in vacuo. The residue was purified by preparative TLC (DCM/MeOH=20/1) to yield a white solid of 1-(2-(4-ethoxy-6-((4-methoxybenzyl)oxy)pyridin-3-yl)-4-methylpyrimidin-5-yl)-3-(3-(trifluoromethyl)phenyl)urea (10 mg, 0.018 mmol, 7.14% yield): $^1$H NMR (400 MHz, CD$_3$OD) δ $^1$H NMR (400 MHz, CD$_3$OD) δ 9.21 (s, 1H), 8.27 (s, 1H), 7.93 (br. s., 1H), 7.63 (m, 1H), 7.49 (t, J=8.0 Hz, 1H), 7.38 (d, J=8.8 Hz, 2H), 7.32 (d, J=8.4 Hz, 1H), 6.91 (d, J=8.8 Hz, 2H), 6.48 (s, 1H), 5.31 (s, 2H), 4.14 (m, 2H), 3.79 (s, 3H), 2.58 (s, 3H), 1.35 (t, J=7.0 Hz, 3H); ES-LCMS m/z 554.1 (M+H).

Step 2: 1-(2-(4-Ethoxy-6-oxo-1,6-dihydropyridin-3-yl)-4-methylpyrimidin-5-yl)-3-(3-(trifluoromethyl)phenyl)urea

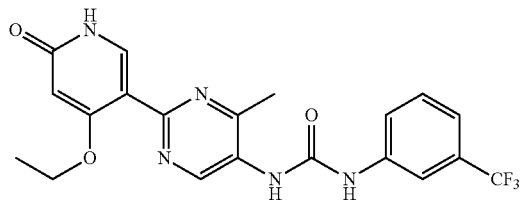 [SMILES: CCOc1cc(=O)[nH]cc1-c1ncc(NC(=O)Nc2cccc(C(F)(F)F)c2)c(C)n1]

A solution of 1-(2-(4-ethoxy-6-oxo-1,6-dihydropyridin-3-yl)-4-methylpyrimidin-5-yl)-3-(3-(trifluoromethyl)phenyl)urea (10 mg, 0.018 mmol) in HCl in MeOH (2 mL, 8.00 mmol) was stirred at 25° C. After LCMS analysis showed the starting material was disappeared. The solvent was removed in vacuo. The residue was purified by preparative HPLC (Instrument: DB/Column: ASB C18 150*25 mm/Mobile phase A: Water+0.1% HCl/Mobile phase B: MeCN/Flowrate: 25 mL/min/Gradient Profile Description: 30-60(B %)). After lyophilization, a yellow solid of 1-(2-(4-ethoxy-6-oxo-1,6-dihydropyridin-3-yl)-4-methylpyrimidin-5-yl)-3-(3-(trifluoromethyl)phenyl)urea hydrochloride (3 mg, 6.23 μmol, 34.5% yield) was obtained: $^1$H NMR (400 MHz, CD$_3$OD) δ 9.52 (s, 1H), 8.37 (s, 1H), 7.98 (s, 1H), 7.63 (d, J=8.0 Hz, 1H), 7.51 (t, J=8.0 Hz, 1H), 7.36 (d, J=7.6 Hz, 1H), 6.14 (s, 1H), 4.34 (m, 2H), 2.75 (s, 3H), 1.47 (t, J=6.8 Hz, 3H); ES-LCMS m/z 434.1 (M+H).

EXAMPLE 39

1-(6-(2-Hydroxypropan-2-yl)-5-(trifluoromethyl)pyridin-3-yl)-3-(4-methyl-2-(7-oxo-6,7-dihydrofuro[2,3-c]pyridin-4-yl)pyrimidin-5-yl)urea

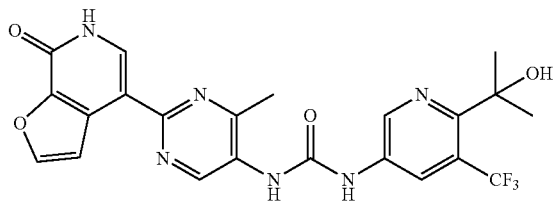 [SMILES: Cc1nc(-c2c[nH]c(=O)c3occc23)ncc1NC(=O)Nc1cnc(C(C)(C)O)c(C(F)(F)F)c1]

Step 1: 1-(6-Acetyl-5-(trifluoromethyl)pyridin-3-yl)-3-(2-chloro-4-methylpyrimidin-5-yl)urea

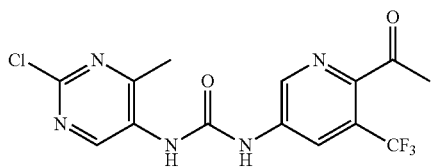 [SMILES: CC(=O)c1ncc(NC(=O)Nc2cnc(Cl)nc2C)cc1C(F)(F)F]

To a solution of 2-chloro-4-methylpyrimidin-5-amine (65 mg, 0.453 mmol) in THF (5 mL) was added triphosgene (53.7 mg, 0.181 mmol). The resulting mixture was stirred at 50° C. After 30 min, LCMS analysis showed the starting material was disappeared. The solvent was removed in vacuo to yield 2-chloro-5-isocyanato-4-methylpyrimidine (70 mg, 0.397 mmol, 88% yield). To a solution of 1-(5-amino-3-(trifluoromethyl)pyridin-2-yl)ethanone(75 mg, 0.367 mmol) and Et$_3$N (0.154 mL, 1.102 mmol) in THF (5 mL) was added a solution of 2-chloro-5-isocyanato-4-methylpyrimidine (68.5 mg, 0.404 mmol) in THF (5 mL). The resulting mixture was stirred at 50° C. After LCMS analysis showed the starting material was disappeared. The solvent was removed in vacuo. The residue was dissolved in EA and washed with H$_2$O. The organic layer was dried and concentrated, which was purified by preparative TLC (DCM/MeOH=20/1) to yield a yellow solid of 1-(6-acetyl-5-(trifluoromethyl)pyridin-3-yl)-3-(2-chloro-4-methylpyrimidin-5-yl)urea (50 mg, 0.134 mmol, 36.4% yield): $^1$H NMR (400 MHz, CD$_3$OD)δ9.03 (s, 1H), 8.83 (d, J=2.4 Hz, 1H), 8.52 (s, 1H), 2.64 (s, 3H), 2.52 (s, 3H); ES-LCMS m/z 374.0 (M+H).

Step 2: 1-(6-Acetyl-5-(trifluoromethyl)pyridin-3-yl)-3-(2-(7-(benzyloxy)furo[2,3-c]pyridine-4-yl)-4-methylpyrimidin-5-yl)urea

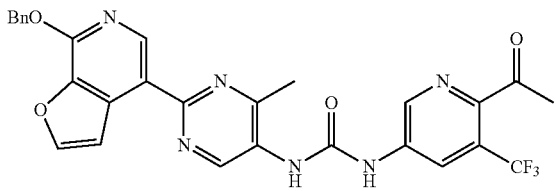 [SMILES: CC(=O)c1ncc(NC(=O)Nc2cnc(-c3cnc(OCc4ccccc4)c4occc34)nc2C)cc1C(F)(F)F]

A solution of 7-(benzyloxy)-4-(4,4,5,5-tetramethyl-1,3-dioxolan-2-yl)furo[2,3-c]pyridine (56.4 mg, 0.161 mmol), 1-(6-acetyl-5-(trifluoromethyl)pyridin-3-yl)-3-(2-chloro-4-methylpyrimidin-5-yl)urea (60 mg, 0.161 mmol), PdCl$_2$(dppf) (11.75 mg, 0.016 mmol) and Cs$_2$CO$_3$ (105 mg, 0.321 mmol) in 1,4-dioxane (9 mL) and water (3 mL) was stirred at 110° C. on microwave for 15 min. After LCMS analysis showed the starting material was disappeared. The solvent was removed in vacuo. The residue was dissolved in EA (30 mL) and washed with H$_2$O (10 mL) and brine (10 mL). The organic layer was dried over Na$_2$SO$_4$, filtered and concentrated. The residue was purified by preparative TLC (PE/EA=1/1) to yield a brown solid of 1-(6-acetyl-5-(trifluoromethyl)pyridin-3-yl)-3-(2-(7-(benzyloxy)furo[2,3-c]pyridin-4-yl)-4-methylpyrimidin-5-yl)urea (60 mg, 0.107 mmol, 66.4% yield): $^1$H NMR (400 MHz, CD$_3$OD)δ9.18 (s, 1H), 8.97-8.92 (m, 2H), 8.56 (d, J=8.0 Hz, 1H), 8.03 (s, 1H), 7.81 (s, 1H), 7.56 (d, J=7.6 Hz, 2H), 7.42-7.35 (m, 3H), 5.66 (s, 2H), 2.68 (s, 3H), 2.18 (s, 3H); ES-LCMS m/z 563.0 (M+H).

Step 3: 1-(2-(7-(Benzyloxy)furo[2,3-c]pyridin-4-yl)-4-methylpyrimidin-5-yl)-3-(6-(2-hydroxypropan-2-yl)-5-(trifluoromethyl)pyridin-3-yl)urea

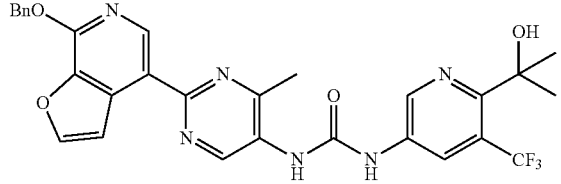 [SMILES: Cc1nc(-c2cnc(OCc3ccccc3)c3occc23)ncc1NC(=O)Nc1cnc(C(C)(C)O)c(C(F)(F)F)c1]

To a solution of 1-(6-acetyl-5-(trifluoromethyl)pyridin-3-yl)-3-(2-(7-(benzyloxy)furo[2,3-c]pyridin-4-yl)-4-methylpyrimidin-5-yl)urea (60 mg, 0.107 mmol) in THF (5 mL) was added methylmagnesium chloride (0.356 mL, 1.067 mmol) at 20° C. After LCMS analysis showed the starting material was disappeared. The mixture was quenched by saturated NH$_4$Cl. The mixture was filtered. The filtrate was concentrated, which was purified by preparative TLC (DCM/MeOH=20/1) to yield 1-(2-(7-(benzyloxy)furo[2,3-c]pyridin-4-yl)-4-methylpyrimidin-5-yl)-3-(6-(2-hydroxypropan-2-yl)-5-(trifluoromethyl)pyridin-3-yl)urea (30 mg, 0.051 mmol, 47.8% yield): $^1$H NMR (400 MHz, CD$_3$OD) δ9.15 (s, 1H), 8.92 (s, 1H), 8.76 (d, J=2.0 Hz, 1H), 8.41 (d, J=2.4 Hz, 1H), 7.99 (s, 1H), 7.78 (d, J=2.0 Hz, 1H), 7.53 (d, J=7.2 Hz, 2H), 7.38-7.29 (m, 3H), 5.62 (s, 2H), 2.63 (s, 3H), 1.60 (s, 6H); ES-LCMS m/z 579.1 (M+H).

Step 4: 1-(6-(2-Hydroxypropan-2-yl)-5-(trifluoromethyl)pyridin-3-yl)-3-(4-methyl-2-(7-oxo-6,7-dihydrofuro[2,3-c]pyridin-4-yl)pyrimidin-5-yl)urea

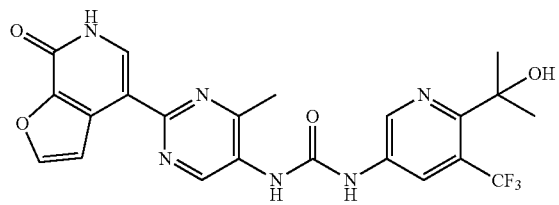 [SMILES: Cc1nc(-c2c[nH]c(=O)c3occc23)ncc1NC(=O)Nc1cnc(C(C)(C)O)c(C(F)(F)F)c1]

A solution of 1-(2-(7-(benzyloxy)furo[2,3-c]pyridin-4-yl)-4-methylpyrimidin-5-yl)-3-(6-(2-hydroxypropan-2-yl)-5-(trifluoromethyl)pyridin-3-yl)urea (15 mg, 0.026 mmol) and Pd/C (10 mg, 10%) in MeOH (5 mL) was stirred at 20° C. under a H$_2$ atmosphere. After 0.5 h, TLC analysis (DCM/MeOH=20/1) showed the starting material was disappeared. The mixture was filtered. The filtrate was concentrated, which was purified by preparative HPLC (under neutral condition) to yield a white solid of 1-(6-(2-hydroxypropan-2-yl)-5-(trifluoromethyl)pyridin-3-yl)-3-(4-methyl-2-(7-oxo-6,7-dihydrofuro[2,3-c]pyridin-4-yl)pyrimidin-5-yl)urea (3.29 mg, 6.74 μmol, 26.0% yield) $^1$H NMR (400 MHz, CD$_3$OD)δ9.08 (s, 1H), 8.77 (br. s., 1H), 8.41 (br. s., 1H), 8.34 (s, 1H), 8.06 (s, 1H), 7.82 (s, 1H), 2.61 (s, 3H), 1.61 (s, 6H); ES-LCMS m/z 489.1 (M+H).

EXAMPLE 40

1-(2-Fluoro-4-(2-methyl-6-oxo-1,6-dihydropyridin-3-yl)phenyl)-3-(4-((3-methyloxetan-3-yl)oxy)-3-(trifluoromethyl)phenyl)urea

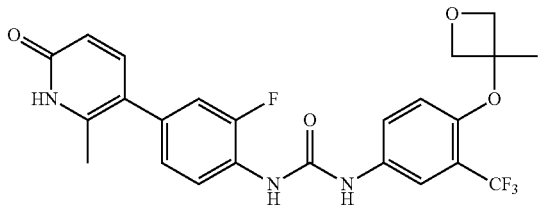 [SMILES: Cc1[nH]c(=O)ccc1-c1ccc(NC(=O)Nc2ccc(OC3(C)COC3)c(C(F)(F)F)c2)c(F)c1]

A solution of 5-bromo-6-methylpyridin-2-ol (17.69 mg, 0.094 mmol), 1-(2-fluoro-4-(4,4,5,5-tetramethyl-1,3,2-dioxaborolan-2-yl)phenyl)-3-(4-((3-methyloxetan-3-yl)oxy)-3-(trifluoromethyl)phenyl)urea (40 mg, 0.078 mmol), PdCl$_2$(dppf) (5.74 mg, 7.84 μmol) and Cs$_2$CO$_3$ (51.1 mg, 0.157 mmol) in 1,4-dioxane (1.5 mL) and water (0.5 mL) was stirred at 110° C. on microwave for 15 min. After LCMS analysis showed the starting material was disappeared. The mixture was dissolved in EA (20 mL) and washed with H$_2$O (10 mL). The combined organic extract was washed with brine (10 mL), dried over Na$_2$SO$_4$, filtered and concentrated. The residue was purified by preparative HPLC. After lyophilization, a white solid of 1-(2-fluoro-4-(2-methyl-6-oxo-1,6-dihydropyridin-3-yl)phenyl)-3-(4-((3-methyloxetan-3-yl)oxy)-3-(trifluoromethyl)phenyl)urea (10.21 mg, 0.020 mmol, 26.1% yield) was obtained: $^1$H NMR (400 MHz, CD$_3$OD) δ 8.13 (t, J=8.6 Hz, 1H), 7.78 (d, J=2.4 Hz, 1H), 7.55-7.50 (m, 2H), 7.14-7.06 (m, 2H), 6.62 (d, J=8.8 Hz, 1H), 6.42 (d, J=9.2 Hz, 1H), 4.89-4.88 (m, 2H), 4.62 (d, J=7.2 Hz, 2H), 2.28 (s, 3H), 1.72 (s, 3H); ES-LCMS m/z 492.1 (M+H).

EXAMPLE 41

1-(5-(5-Ethoxy-6-oxo-1,6-dihydropyridin-3-yl)-3-methylpyrazin-2-yl)-3-(4-(3-hydroxy-2,2-dimethyl-propyl)-3-(trifluoromethyl)phenyl)urea

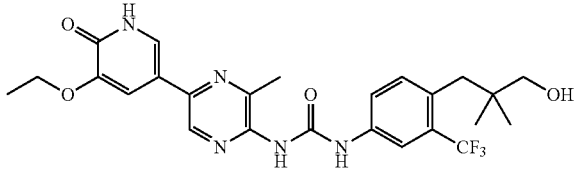 [SMILES: CCOc1cc(-c2cnc(NC(=O)Nc3ccc(CC(C)(C)CO)c(C(F)(F)F)c3)c(C)n2)c[nH]c1=O]

Step 1: Ethyl 3-(4-(3-(5-bromo-3-methylpyrazin-2-yl)ureido)-2-(trifluoromethyl)phenyl)-2,2-dimethyl-propanoate

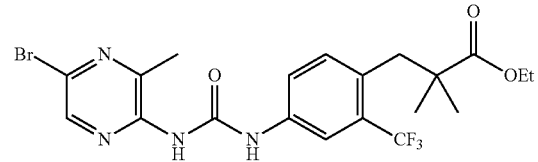 [SMILES: CCOC(=O)C(C)(C)Cc1ccc(NC(=O)Nc2ncc(Br)nc2C)cc1C(F)(F)F]

To a solution of 5-bromo-3-methylpyrazin-2-amine (200 mg, 1.064 mmol) in THF (30 mL) was added triphosgene (110 mg, 0.372 mmol). The resulting mixture was stirred at 70° C. After LCMS analysis showed the starting material was disappeared. The solvent was removed in vacuo to give 5-bromo-2-isocyanato-3-methylpyrazine (220 mg, 0.977 mmol, 92% yield). A solution of ethyl 3-(4-amino-2-(trifluoromethyl)phenyl)-2,2-dimethylpropanoate (270 mg, 0.934 mmol) in THF (20 mL) was added NaH (112 mg, 2.80 mmol). The resulting mixture was stirred at rt. After 30 min, a solution of 5-bromo-2-isocyanato-3-methylpyrazine (200 mg, 0.934 mmol) in THF (20 mL) was added. The resulting mixture was stirred at 70° C. After 2 h, LCMS analysis showed the starting material was disappeared. The solvent was removed in vacuo. The residue was dissolved in EA (60 mL) and washed with H$_2$O (20 mL) and brine (20 mL). The organic layer was dried over Na$_2$SO$_4$, filtered and concentrated. The residue was purified by silica column chromatography (PE/EA=3/1) to yield a white solid of ethyl 3-(4-(3-(5-bromo-3-methylpyrazin-2-yl)ureido)-2-(trifluoromethyl)phenyl)-2,2-dimethylpropanoate (330 mg, 0.357 mmol, 38.2% yield): $^1$H NMR (400 MHz, CD$_3$OD) δ 8.33 (s, 1H), 7.98 (s, 1H), 7.63 (d, J=7.2 Hz, 1H), 7.24 (d, J=8.8 Hz, 1H), 4.18-4.13 (m, 2H), 3.08 (d, J=8.0 Hz, 2H), 2.54 (s, 3H), 1.26-1.22 (m, 3H), 1.16 (s, 6H); ES-LCMS m/z 503.0, 505.0 (M+H).

Step 2: Ethyl 3-(4-(3-(5-(5-ethoxy-6-((4-methoxybenzyl)oxy)pyridin-3-yl)-3-methylpyrazin-2-yl)ureido)-2-(trifluoromethyl)phenyl)-2,2-dimethylpropanoate

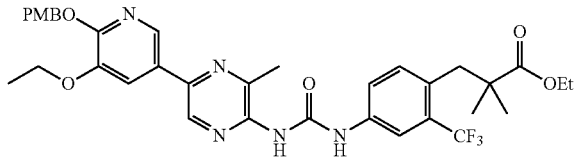

A solution of ethyl 3-(4-(3-(5-bromo-3-methylpyrazin-2-yl)ureido)-2-(trifluoromethyl)phenyl)-2,2-dimethylpropanoate (240 mg, 0.477 mmol), 3-ethoxy-2-((4-methoxybenzyl)oxy)-5-(4,4,5,5-tetramethyl-1,3,2-dioxaborolan-2-yl)pyridine (184 mg, 0.477 mmol), PdCl$_2$(dppf) (34.9 mg, 0.048 mmol) and Cs$_2$CO$_3$ (311 mg, 0.954 mmol) in 1,4-dioxane (9 mL) and water (3 mL) was stirred at 110° C. on microwave for 15 min. After LCMS analysis showed the starting material was disappeared. The solvent was removed in vacuo. The residue was dissolved in EA (60 mL) and washed with H$_2$O (20 mL) and brine (20 mL). The organic layer was dried over Na$_2$SO$_4$, filtered and concentrated. The residue was purified by preparative TLC (DCM/MeOH=40/1) to yield a yellow solid of ethyl 3-(4-(3-(5-(5-ethoxy-6-((4-methoxybenzyl)oxy)pyridin-3-yl)-3-methylpyrazin-2-yl)ureido)-2-(trifluoromethyl)phenyl)-2,2-dimethylpropanoate (160 mg, 0.192 mmol, 40.2% yield): $^1$H NMR (400 MHz, CD$_3$OD) 8.69 (br. s., 1H), 8.34 (br. s., 1H), 7.82 (d, J=2.0 Hz, 2H), 7.55 (d, J=8.4 Hz, 2H), 7.40 (d, J=8.4 Hz, 1H), 7.21 (d, J=8.4 Hz, 2H), 6.91 (d, J=8.8 Hz, 1H), 5.39 (s, 2H), 4.18-4.14 (m, 4H), 3.78 (s, 3H), 3.07 (s, 3H), 2.56 (s, 2H), 1.24 (t, J=7.0 Hz, 6H), 1.16 (s, 6H); ES-LCMS m/z 682.2 (M+H).

Step 3: 1-(5-(5-Ethoxy-6-((4-methoxybenzyl)oxy)pyridin-3-yl)-3-methylpyrazin-2-yl)-3-(4-(3-hydroxy-2,2-dimethylpropyl)-3-(trifluoromethyl)phenyl)urea

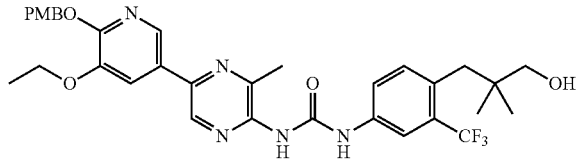

To a solution of ethyl 3-(4-(3-(5-(5-ethoxy-6-((4-methoxybenzyl)oxy)pyridin-3-yl)-3-methylpyrazin-2-yl)ureido)-2-(trifluoromethyl)phenyl)-2,2-dimethylpropanoate (80 mg, 0.117 mmol) in THF (10 mL) was added LAH (8.91 mg, 0.235 mmol) at 0° C. The resulting mixture was stirred at rt overnight. After LCMS analysis showed the starting material was disappeared. The mixture was quenched by H$_2$O and NaOH (10%). The solvent was removed in vacuo. The residue was dissolved in DCM (40 mL) and washed with H$_2$O (20 mL) and brine (20 mL). The organic layer was dried over Na$_2$SO$_4$, filtered and concentrated. The residue was purified by preparative TLC (DCM/MeOH=40/1) to yield a light yellow solid of 1-(5-(5-ethoxy-6-((4-methoxybenzyl)oxy)pyridin-3-yl)-3-methylpyrazin-2-yl)-3-(4-(3-hydroxy-2,2-dimethylpropyl)-3-(trifluoromethyl)phenyl)urea (40 mg, 0.054 mmol, 46.3% yield): $^1$H NMR (400 MHz, CD$_3$OD) 8.63 (s, 1H), 8.29 (d, J=1.6 Hz, 1H), 7.91 (s, 1H), 7.78 (s, 1H), 7.67 (d, J=6.0 Hz, 1H), 7.43-7.38 (m, 3H), 6.89 (d, J=8.8 Hz, 2H), 5.38 (s, 2H), 4.20-4.14 (m, 2H), 3.78 (s, 3H), 3.42-3.33 (m, 2H), 2.78 (s, 2H), 2.64 (s, 3H), 1.44 (t, J=7.0 Hz, 3H), 0.84 (s, 6H); ES-LCMS m/z 640.2 (M+H).

Step 4: 1-(5-(5-Ethoxy-6-oxo-1,6-dihydropyridin-3-yl)-3-methylpyrazin-2-yl)-3-(4-(3-hydroxy-2,2-dimethylpropyl)-3-(trifluoromethyl)phenyl)urea

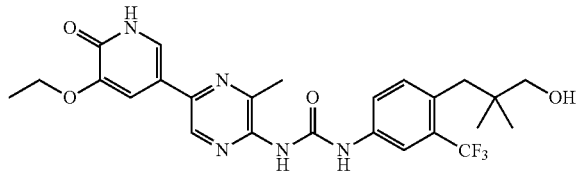 [SMILES: CCOc1cc(-c2cnc(NC(=O)Nc3ccc(CC(C)(C)CO)c(C(F)(F)F)c3)c(C)n2)c[nH]c1=O]

A solution of 1-(5-(5-ethoxy-6-((4-methoxybenzyl)oxy)pyridin-3-yl)-3-methylpyrazin-2-yl)-3-(4-(3-hydroxy-2,2-dimethylpropyl)-3-(trifluoromethyl)phenyl)urea (40 mg, 0.063 mmol) in HCl in MeOH (10 mL, 175 mmol) was stirred at 20° C. After LCMS analysis showed the starting material was disappeared. The solvent was removed in vacuo. The residue was purified by preparative HPLC to give 1-(5-(5-ethoxy-6-oxo-1,6-dihydropyridin-3-yl)-3-methylpyrazin-2-yl)-3-(4-(3-hydroxy-2,2-dimethylpropyl)-3-(trifluoromethyl)phenyl)urea hydrochloride (7.06 mg, 0.013 mmol, 20.31% yield) as a yellow solid: $^1$H NMR (400 MHz, CD$_3$OD and DMSO-d$_6$) 8.68 (s, 1H), 8.03 (s, 1H), 7.82 (s, 1H), 7.78 (m, 1H), 7.63 (s, 1H), 7.59 (m, 1H), 4.20-4.14 (m, 2H), 3.50 (s, 2H), 2.83 (s, 2H), 2.09 (s, 3H), 1.53 (m, 3H), 0.89 (s, 6H); ES-LCMS m/z 520.1 (M+H).

EXAMPLE 42

1-(2-(5-Ethoxy-6-oxo-1,6-dihydropyridin-3-yl)-4-methylpyrimidin-5-yl)-3-(3-(trifluoromethyl)phenyl)urea

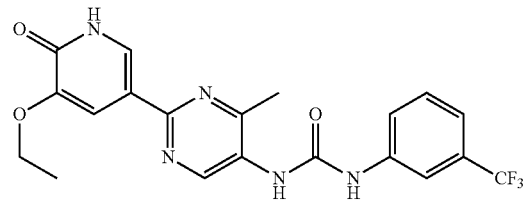 [SMILES: CCOc1cc(-c2ncc(NC(=O)Nc3cccc(C(F)(F)F)c3)c(C)n2)c[nH]c1=O]

Step 1: 1-(2-(5-Ethoxy-6-((4-methoxybenzyl)oxy)pyridin-3-yl)-4-methylpyrimidin-5-yl)-3-(3-(trifluoromethyl)phenyl)urea

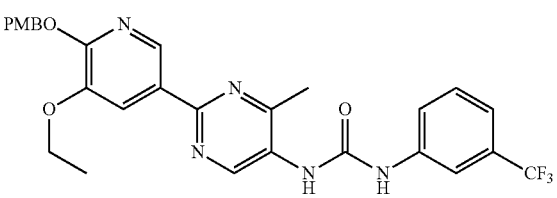

To a solution of 2-(5-ethoxy-6-((4-methoxybenzyl)oxy)pyridin-3-yl)-4-methylpyrimidine-5-carboxylic acid (100 mg, 0.253 mmol) and Et$_3$N (0.053 mL, 0.379 mmol) in 1,4-dioxane (5 mL) was added DPPA (84 mg, 0.303 mmol). After 10 min, 3-(trifluoromethyl)aniline (61.1 mg, 0.379 mmol) was added. The resulting mixture was stirred at 60° C. overnight. After LCMS analysis showed the starting material was disappeared. The solvent was removed in vacuo. The residue was purified by preparative TLC (DCM/MeOH=20/1) to yield a white solid of 1-(2-(5-ethoxy-6-((4-methoxybenzyl)oxy)pyridin-3-yl)-4-methylpyrimidin-5-yl)-3-(3-(trifluoromethyl)phenyl)urea (60 mg, 0.108 mmol, 42.9% yield): $^1$H NMR (400 MHz, CD$_3$OD) δ 9.14 (s, 1H), 8.71 (d, J=2.0 Hz, 1H), 8.12 (d, J=2.0 Hz, 1H), 7.96 (br. s., 1H), 7.65 (d, J=8.0 Hz, 1H), 7.51 (m, 1H), 7.44 (d, J=8.8 Hz, 2H), 7.27 (m, 1H), 6.94 (m, 2H), 5.42 (s, 2H), 4.21-4.16 (m, 2H), 3.82 (s, 3H), 2.61 (s, 3H), 1.49-1.45 (m, 3H); ES-LCMS m/z 554.1 (M+H).

Step 2: 1-(2-(5-Ethoxy-6-oxo-1,6-dihydropyridin-3-yl)-4-methylpyrimidin-5-yl)-3-(3-(trifluoromethyl)phenyl)urea

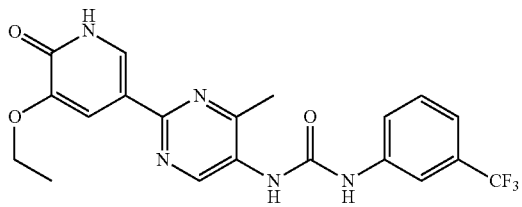 [SMILES: CCOc1cc(-c2ncc(NC(=O)Nc3cccc(C(F)(F)F)c3)c(C)n2)c[nH]c1=O]

A solution of 1-(2-(5-ethoxy-6-((4-methoxybenzyl)oxy)pyridin-3-yl)-4-methylpyrimidin-5-yl)-3-(3-(trifluoromethyl)phenyl)urea (60 mg, 0.108 mmol) in TFA in DCM (5 mL, 37.2 mmol) was stirred at 25° C. After LCMS analysis showed the starting material was disappeared. The solvent was removed in vacuo. The residue was purified by preparative HPLC (Instrument: DB/Column: ASB C18 150*25 mm/Mobile phase A: Water+0.1% HCl/Mobile phase B: MeCN/Flowrate: 25 mL/min/Gradient Profile Description: 38-68(B %)). After lyophilization, a yellow solid of 1-(2-(5-ethoxy-6-oxo-1,6-dihydropyridin-3-yl)-4-methylpyrimidin-5-yl)-3-(3-(trifluoromethyl)phenyl)urea hydrochloride (17 mg, 0.036 mmol, 33.0% yield) was obtained: $^1$H NMR (400 MHz, CD$_3$OD) δ 9.13 (s, 1H), 8.12 (d, J=2.0 Hz, 1H), 7.94 (s, 1H), 7.87 (d, J=2.0 Hz, 1H), 7.61 (d, J=8.4 Hz, 1H), 7.49 (m, 1H), 7.32 (d, J=7.2 Hz, 1H), 4.17 (m, 2H), 2.60 (s, 3H), 1.49 (t, J=7.2 Hz, 3H); ES-LCMS m/z 434.0 (M+H).

EXAMPLE 43

1-(4-Cyano-3-(trifluoromethyl)phenyl)-3-(2-(5-ethoxy-6-oxo-1,6-dihydropyridin-3-yl)-4-methylpyrimidin-5-yl)urea

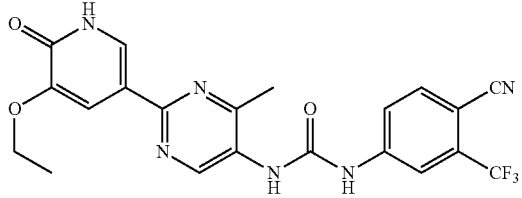 [SMILES: CCOc1cc(-c2ncc(NC(=O)Nc3ccc(C#N)c(C(F)(F)F)c3)c(C)n2)c[nH]c1=O]

Step 1: 1-(4-Cyano-3-(trifluoromethyl)phenyl)-3-(2-(5-ethoxy-6-((4-methoxybenzyl)oxy)pyridin-3-yl)-4-methylpyrimidin-5-yl)urea

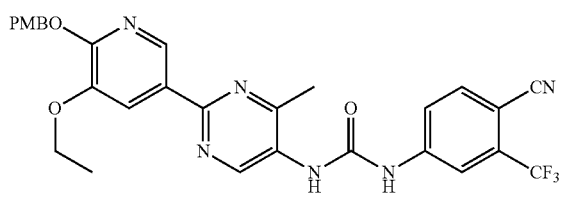

To a solution of 2-(5-ethoxy-6-((4-methoxybenzyl)oxy)pyridin-3-yl)-4-methylpyrimidine-5-carboxylic acid (300 mg, 0.759 mmol) and Et$_3$N (0.159 mL, 1.138 mmol) in 1,4-dioxane (10 mL) was added DPPA (251 mg, 0.910 mmol). After 10 min, 4-amino-2-(trifluoromethyl)benzonitrile (212 mg, 1.138 mmol) was added. The resulting mixture was stirred at 60° C. overnight. After LCMS analysis showed the starting material was disappeared. The solvent was removed in vacuo. The residue was purified by column chromatography (eluted with DCM to DCM/MeOH=20/1). All fractions found to contain product by TLC (DCM/MeOH=20/1, R$_f$=0.4) were combined and concentrated in vacuo and the residue was re-purified by preparative TLC (DCM/MeOH=20/1) to yield a brown solid of 1-(4-cyano-3-(trifluoromethyl)phenyl)-3-(2-(5-ethoxy-6-((4-methoxybenzyl)oxy)pyridin-3-yl)-4-methylpyrimidin-5-yl)urea (40 mg, 0.069 mmol, 9.11% yield): $^1$H NMR (400 MHz, CD$_3$OD) δ 9.09 (s, 1H), 8.69 (d, J=2.0 Hz, 1H), 8.17 (s, 1H), 8.10 (s, 1H), 7.90-7.88 (m, 1H), 7.82-7.80 (m, 1H), 7.41 (d, J=8.4 Hz, 2H), 6.91 (d, J=8.8 Hz, 2H), 5.39 (s, 2H), 4.19-4.15 (m, 2H), 3.79 (s, 3H), 2.58 (s, 3H), 1.44 (t, J=7.0 Hz, 3H), LCMS m/z 579.1 (M+H).

Step 2: 1-(4-Cyano-3-(trifluoromethyl)phenyl)-3-(2-(5-ethoxy-6-oxo-1,6-dihydropyridin-3-yl)-4-methylpyrimidin-5-yl)urea

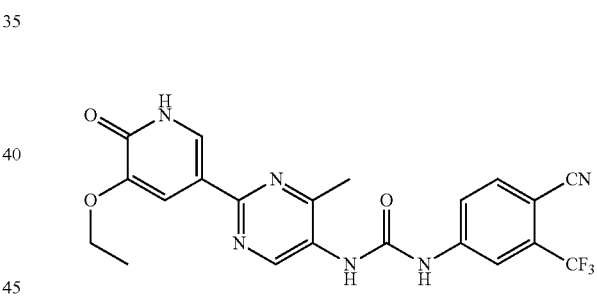

A solution of 1-(4-cyano-3-(trifluoromethyl)phenyl)-3-(2-(5-ethoxy-6-((4-methoxybenzyl)oxy)pyridin-3-yl)-4-methylpyrimidin-5-yl)urea (40 mg, 0.069 mmol) in TFA in DCM (3 mL, 2.232 mmol) was stirred at 25° C. After LCMS analysis showed the starting material was disappeared. The solvent was removed in vacuo. The residue was purified by preparative HPLC (Instrument: DB/Column: ASB C18 150*25 mm/Mobile phase A: Water+0.1% HCl/Mobile phase B: MeCN/Flowrate: 25 mL/min/Gradient Profile Description: 38-68(B %)). After lyophilization, a yellow solid of 1-(4-cyano-3-(trifluoromethyl)phenyl)-3-(2-(5-ethoxy-6-oxo-1,6-dihydropyridin-3-yl)-4-methylpyrimidin-5-yl)urea hydrochloride (18 mg, 0.036 mmol, 52.2% yield) was obtained: $^1$H NMR (400 MHz, DMSO-d$_6$) δ 11.91 (br. s., 1H), 9.96 (s, 1H), 8.91 (s, 1H), 8.64 (s, 1H), 8.17 (s, 1H), 8.04 (d, J=8.4 Hz, 1H), 7.91 (br. s., 1H), 7.80 (d, J=8.8 Hz, 1H), 7.57 (s, 1H), 4.03-3.98 (m, 2H), 2.43 (br. s., 3H), 1.34 (t, J=7.0 Hz, 3H); ES-LCMS m/z 459.0 (M+H).

EXAMPLE 44

1-(4-Cyano-3-(trifluoromethyl)phenyl)-3-(2-(4-ethoxy-6-oxo-1,6-dihydropyridin-3-yl)-4-methylpyrimidin-5-yl)urea

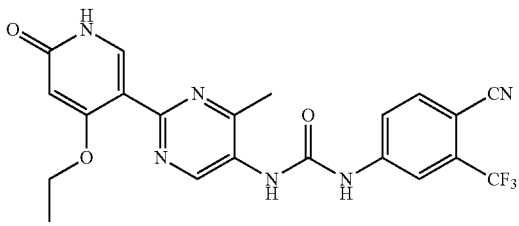 [SMILES: CCOc1cc(=O)[nH]cc1-c1ncc(NC(=O)Nc2ccc(C#N)c(C(F)(F)F)c2)c(C)n1]

Step 1: 1-(4-Cyano-3-(trifluoromethyl)phenyl)-3-(2-(4-ethoxy-6-((4-methoxybenzyl)oxy)pyridin-3-yl)-4-methylpyrimidin-5-yl)urea

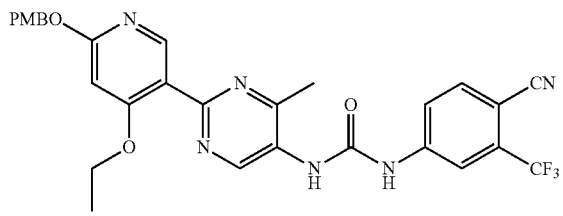

To a solution of 2-(4-ethoxy-6-((4-methoxybenzyl)oxy)pyridin-3-yl)-4-methylpyrimidine-5-carboxylic acid (200 mg, 0.506 mmol) and Et₃N (0.106 mL, 0.759 mmol) in 1,4-dioxane (10 mL) was added DPPA (167 mg, 0.607 mmol). After 10 min, 4-amino-2-(trifluoromethyl)benzonitrile (141 mg, 0.759 mmol) was added. The resulting mixture was stirred at 60° C. overnight. After LCMS analysis showed the starting material was disappeared. The solvent was removed in vacuo. The residue was purified by preparative TLC (DCM/MeOH=20/1) to yield a brown solid of 1-(4-cyano-3-(trifluoromethyl)phenyl)-3-(2-(4-ethoxy-6-((4-methoxybenzyl)oxy)pyridin-3-yl)-4-methylpyrimidin-5-yl)urea (30 mg, 0.052 mmol, 10.25% yield): ¹H NMR (400 MHz, CD₃OD) δ 8.12-8.08 (m, 2H), 7.39-7.36 (m, 3H), 6.92-6.86 (m, 4H), 6.44 (s, 1H), 5.28 (s, 2H), 4.10-4.07 (m, 2H), 3.78 (s, 3H), 2.40 (s, 3H), 1.34-1.31 (m, 3H); LCMS m/z 579.1 (M+H).

Step 2: 1-(4-Cyano-3-(trifluoromethyl)phenyl)-3-(2-(4-ethoxy-6-oxo-1,6-dihydropyridin-3-yl)-4-methylpyrimidin-5-yl)urea

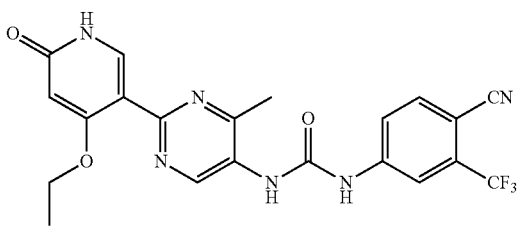 [SMILES: CCOc1cc(=O)[nH]cc1-c1ncc(NC(=O)Nc2ccc(C#N)c(C(F)(F)F)c2)c(C)n1]

A solution of 1-(4-cyano-3-(trifluoromethyl)phenyl)-3-(2-(4-ethoxy-6-((4-methoxybenzyl)oxy)pyridin-3-yl)-4-methylpyrimidin-5-yl)urea (40 mg, 0.069 mmol) in HCl in MeOH (2 mL, 8.00 mmol) was stirred at 25° C. After LCMS analysis showed the starting material was disappeared. The solvent was removed in vacuo. The residue was purified by preparative HPLC (Instrument: DB/Column: ASB C18 150*25 mm/Mobile phase A: Water+0.1% HCl/Mobile phase B: MeCN/Flowrate: 25 mL/min/Gradient Profile Description: 28-58(B %)). After lyophilization, a yellow solid of 1-(4-cyano-3-(trifluoromethyl)phenyl)-3-(2-(4-ethoxy-6-oxo-1,6-dihydropyridin-3-yl)-4-methylpyrimidin-5-yl)urea hydrochloride (8 mg, 0.016 mmol, 23.38% yield) was obtained. ¹H NMR (400 MHz, CD₃OD) δ 9.43 (s, 1H), 8.30 (s, 1H), 8.21 (s, 1H), 7.92 (d, J=8.8 Hz, 1H), 7.82 (d, J=10.4 Hz, 1H), 6.14 (s, 1H), 4.31 (m, 2H), 2.72 (s, 3H), 1.46 (t, J=7.2 Hz, 3H); ES-LCMS m/z 459.1 (M+H).

EXAMPLE 45

1-(4-(5-Ethoxy-6-oxo-1,6-dihydropyridin-3-yl)-2-fluorophenyl)-3-(4-(morpholinomethyl)-3-(trifluoromethyl)phenyl)urea

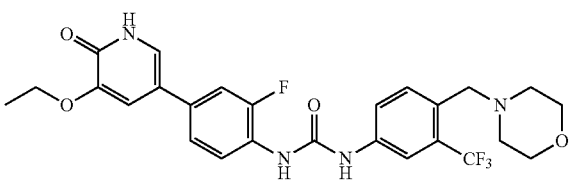 [SMILES: CCOc1cc(-c2ccc(NC(=O)Nc3ccc(CN4CCOCC4)c(C(F)(F)F)c3)c(F)c2)c[nH]c1=O]

Step 1: (4-Amino-2-(trifluoromethyl)phenyl)(morpholino)methanone

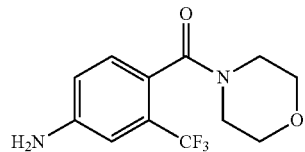

A solution of 4-amino-2-(trifluoromethyl)benzoic acid (1 g, 4.87 mmol), morpholine (0.637 g, 7.31 mmol), EDC (1.402 g, 7.31 mmol), HOBt (1.120 g, 7.31 mmol) and DIEA (2.55 mL, 14.62 mmol) in DCM (60 mL) was stirred at 25° C. After 2 h, LCMS analysis showed the starting material was disappeared. The solvent was removed in vacuo and the residue was purified by column chromatography (DCM/MeOH=20/1) to give a colorless oil of (4-amino-2-(trifluoromethyl)phenyl)(morpholino)methanone (1.3 g, 4.59 mmol, 94% yield): ¹H NMR (400 MHz, CD₃OD) δ 7.06 (d, J=8.4 Hz, 1H), 6.96 (d, J=2.0 Hz, 1H), 6.87-6.85 (m, 1H), 3.74-3.66 (m, 6H), 3.58-3.53 (m, 2H); ES-LCMS m/z 275.1 (M+H).

Step 2:
4-(Morpholinomethyl)-3-(trifluoromethyl)aniline

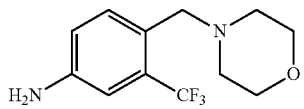

To a solution of (4-amino-2-(trifluoromethyl)phenyl)(morpholino)methanone (0.8 g, 2.92 mmol) in THF (50 mL) was added BH$_3$.THF (8.75 mL, 8.75 mmol). The resulting mixture was stirred at 70° C. overnight. After LCMS analysis showed the starting material was disappeared. The mixture was quenched by MeOH and stirred at 70° C. overnight. The solvent was removed in vacuo to give a light yellow oil of 4-(morpholinomethyl)-3-(trifluoromethyl)aniline (0.8 g, 1.784 mmol, 61.2% yield): $^1$H NMR (400 MHz, CD$_3$OD) δ 7.86 (d, J=8.4 Hz, 1H), 7.46 (d, J=2.4 Hz, 1H), 7.36 (d, J=8.0 Hz, 1H), 4.48 (s, 2H), 4.04-4.01 (m, 2H), 3.88-3.81 (m, 2H), 3.45-3.40 (m, 2H), 3.34-3.28 (m, 2H); ES-LCMS m/z 261.1 (M+H).

Step 3: 1-(4-(5-Ethoxy-6-oxo-1,6-dihydropyridin-3-yl)-2-fluorophenyl)-3-(4-(morpholinomethyl)-3-(trifluoromethyl)phenyl)urea

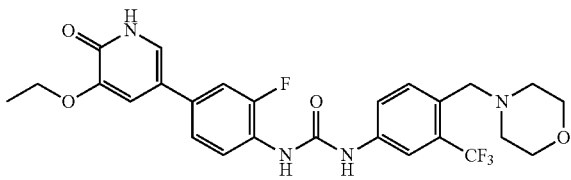 [SMILES: CCOc1cc(-c2ccc(NC(=O)Nc3ccc(CN4CCOCC4)c(C(F)(F)F)c3)c(F)c2)c[nH]c1=O]

To a solution of 4-(5-ethoxy-6-((4-methoxybenzyl)oxy)pyridin-3-yl)-2-fluoroaniline (100 mg, 0.271 mmol) and Et$_3$N (0.038 mL, 0.271 mmol) in anhydrous THF (20 mL) was added triphosgene (28.2 mg, 0.095 mmol). The resulting mixture was stirred at 70° C. under a N$_2$ atmosphere. After 30 min, TLC analysis (PE/EA=3/1) showed the starting material was disappeared. The solvent was removed in vacuo to yield 3-ethoxy-5-(3-fluoro-4-isocyanatophenyl)-2-((4-methoxybenzyl)oxy)pyridine (100 mg, 0.254 mmol, 93% yield). To a solution of 4-(morpholinomethyl)-3-(trifluoromethyl)aniline (117 mg, 0.394 mmol) and Et$_3$N (0.110 mL, 0.789 mmol) in THF (20 mL) was added a solution of 3-ethoxy-5-(3-fluoro-4-isocyanatophenyl)-2-((4-methoxybenzyl)oxy)pyridine (100 mg, 0.263 mmol) in THF (20 mL) by drop wise at 80° C. under a N$_2$ atmosphere. After LC-MS analysis showed the starting material was disappeared. The mixture was filtered. The filtrate was concentrated, which was purified by preparative TLC (DCM/MeOH=15/1) and preparative HPLC to yield a pink solid of 1-(4-(5-ethoxy-6-oxo-1,6-dihydropyridin-3-yl)-2-fluorophenyl)-3-(4-(morpholinomethyl)-3-(trifluoromethyl)phenyl)urea hydrochloride (23.07 mg, 0.040 mmol, 15.13% yield): $^1$H NMR (400 MHz, CD$_3$OD) δ 8.16 (t, J=8.4 Hz, 1H), 8.08 (d, J=2.0 Hz, 1H), 7.81 (dd, J=8.6, 2.2 Hz, 1H), 7.75 (d, J=8.8 Hz, 1H), 7.43 (dd, J=8.4, 2.0 Hz, 1H), 7.40-7.35 (m, 3H), 4.49 (s, 2H), 4.19-4.13 (m, 2H), 4.07-4.04 (m, 2H), 3.84-3.78 (m, 2H), 3.49-3.46 (m, 2H), 3.36-3.33 (m, 2H), 1.46 (t, J=7.0 Hz, 3H); ES-LCMS m/z 535.2 (M+H).

EXAMPLE 46

1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A)

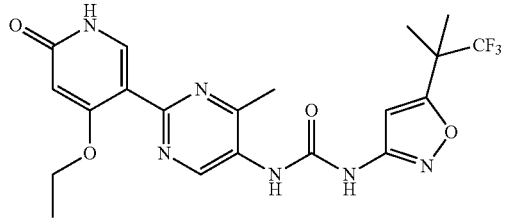 [SMILES: CCOc1cc(=O)[nH]cc1-c1ncc(NC(=O)Nc2cc(C(C)(C)C(F)(F)F)on2)c(C)n1]

To a mixture of 2-(4-ethoxy-6-((4-methoxybenzyl)oxy)pyridin-3-yl)-4-methylpyrimidine-5-carboxylic acid (100 mg, 0.253 mmol) in 1,4-dioxane (30 mL) were added Et$_3$N (0.38.4 mg, 0.379 mmol) and DMAP (3.09 mg, 0.025 mmol) and the mixture was stirred at 25° C. for 15 min. Then DPPA (104 mg, 0.379 mmol) was added and the mixture stirred for 15 min. 5-(1,1,1-trifluoro-2-methylpropan-2-yl)isoxazol-3-amine (49.1 mg, 0.253 mmol) was added and the mixture was stirred at 80° C. for 3 h. The mixture was concentrated and the residue was purified by preparative TLC (DCM/MeOH=15:1, R$_f$=0.5) to give 1-(2-(5-ethoxy-6-((4-methoxybenzyl)oxy)pyridin-3-yl)-4-methylpyrimidin-5-yl)-3-(5-(1,1,1-trifluoro-2-methylpropan-2-yl)isoxazol-3-yl)urea (20 mg), to which was added TFA (20 mL, 10% in DCM) and the mixture was stirred at 25° C. for 1 h. The mixture was concentrated and the residue was purified by preparative HPLC (Instrument: Gilson GX 281; Column: Gemini 150*25 mm*5 um; Mobile phase A: Water (0.05% ammonia solution); Mobile phase B: MeCN; Gradient: 36-66(B %); Flowrate: 25 mL/min; Run time: 10 min) to give a white solid of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (1.83 mg, 3.92 timol, 1.551% yield): $^1$H NMR (400 MHz, CD$_3$OD) δ 9.18 (s, 1H), 7.78 (s, 1H), 6.74 (s, 1H), 5.99 (s, 1H), 4.11 (q, J=6.8 Hz, 2H), 2.56 (s, 3H), 1.58 (s, 6H), 1.36 (t, J=7.2 Hz, 3H); ES-LCMS (m/z): 467.1 (M+H).

EXAMPLE 47

1-(2-(4-Ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea

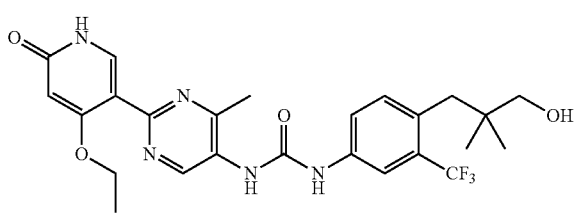 [SMILES: CCOc1cc(=O)[nH]cc1-c1ncc(NC(=O)Nc2ccc(CC(C)(C)CO)c(C(F)(F)F)c2)c(C)n1]

Step 1: 1-(4-(3-((tert-Butyldimethylsilyl)oxy)-2,2-dimethylpropyl)-3-(trifluoromethyl)phenyl)-3-(2-(4-ethoxy-6-((4-methoxybenzyl)oxy)pyridin-3-yl)-4-methylpyrimidin-5-yl)urea

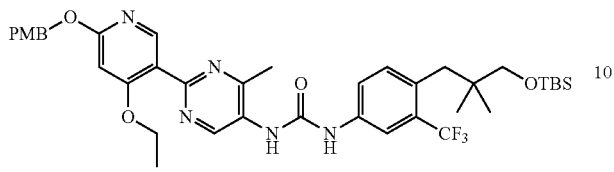

To a solution of 2-(4-ethoxy-6-((4-methoxybenzyl)oxy)pyridin-3-yl)-4-methylpyrimidine-5-carboxylic acid (0.2 g, 0.506 mmol) in dioxane (5 mL) stirred under N$_2$ at 20° C. was added Et$_3$N (0.106 mL, 0.759 mmol) and DPPA (0.167 g, 0.607 mmol) in one charge. The reaction mixture was stirred at rt for 30 mins. To the mixture, a solution of 4-(3-((tert-butyldimethylsilyl)oxy)-2,2-dimethylpropyl)-3-(trifluoromethyl)aniline (0.146 g, 0.405 mmol) in 1 mL of 1,4-dioxane (1 mL) was added. The reaction solution was heated to 100° C. with stirring for 3 hr. The solution was concentrated in vacuo and the residue was purified by preparative TLC (DCM/MeOH=20:1, R$_f$=0.5) to yield a light yellow solid of 1-(4-(3-((tert-butyldimethylsilyl)oxy)-2,2-dimethylpropyl)-3-(trifluoromethyl)phenyl)-3-(2-(4-ethoxy-6-((4-methoxybenzyl)oxy)pyridin-3-yl)-4-methylpyrimidin-5-yl)urea (40 mg, 0.053 mmol, 10.5% yield): $^1$H NMR (400 MHz, CDCl$_3$) δ 9.09 (s, 1H), 8.39 (br. s., 1H), 7.57-7.55 (m, 1H), 7.51 (s, 1H), 7.44-7.40 (m, 1H), 7.34-7.32 (m, 2H), 6.85-6.82 (m, 2H), 6.24 (s, 1H), 5.28 (s, 2H), 4.04-4.01 (m, 2H), 3.75 (s, 3H), 3.21 (s, 2H), 2.70 (s, 2H), 2.48 (s, 3H), 1.31 (t, J=6.9 Hz, 3H), 0.87 (s, 9H), 0.74 (s, 6H), 0.01 (s, 6H); ES-LCMS m/z 754.3 (M+H).

Step 2: 1-(2-(4-Ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea

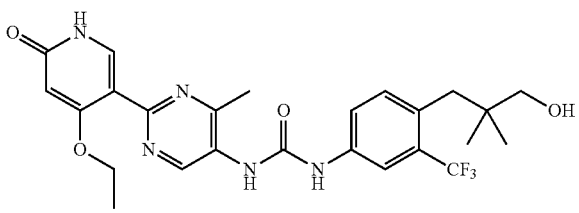 [SMILES: CCOc1cc(=O)[nH]cc1-c1ncc(NC(=O)Nc2ccc(CC(C)(C)CO)c(C(F)(F)F)c2)c(C)n1]

To a solution of 1-(4-(3-((tert-butyldimethylsilyl)oxy)-2,2-dimethylpropyl)-3-(trifluoromethyl)phenyl)-3-(2-(4-ethoxy-6-((4-methoxybenzyl)oxy)pyridin-3-yl)-4-methylpyrimidin-5-yl)urea (40 mg, 0.053 mmol) in DCM (3 mL) stirred under N$_2$ at 20° C. was added HCl in MeOH (0.5 mL, 2.000 mmol) in one charge. The reaction mixture was stirred at 20° C. for 1 hr. Then the solution was concentrated. The residue was purified by preparative HPLC (Instrument: DC/Column: ASB C18 150*25 mm/Mobile phase A: Water+ 0.1% HCl/Mobile phase B: MeCN/Flowrate: 25 mL/min/ Gradient Profile Description: 12-42(B %)) to yield a white solid of 1-(2-(4-ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea hydrochloride (10.12 mg, 0.018 mmol, 34.2% yield). TLC (DCM/MeOH=5:1, R$_f$=0.4): $^1$H NMR (400 MHz, CD$_3$OD) δ 9.47 (s, 1H), 8.30 (s, 1H), 7.90 (d, J=2.2 Hz, 1H), 7.59-7.57 (m, 1H), 7.45-7.43 (m, 1H), 6.12 (s, 1H), 4.33-4.28 (m, 2H), 3.33-3.31 (m, 2H), 2.78 (s, 2H), 2.73 (s, 3H), 1.46 (t, J=7.1 Hz, 3H), 0.84 (s, 6H); ES-LCMS m/z 520.1 (M+H).

EXAMPLE 48

1-(2-(5-Ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea

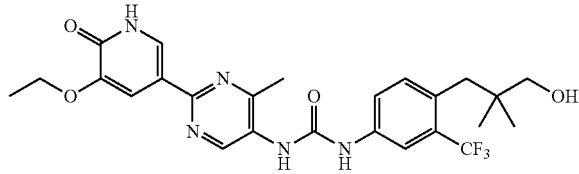 [SMILES: CCOc1cc(-c2ncc(NC(=O)Nc3ccc(CC(C)(C)CO)c(C(F)(F)F)c3)c(C)n2)c[nH]c1=O]

Step 1: 1-(4-(3-((tert-Butyldimethylsilyl)oxy)-2,2-dimethylpropyl)-3-(trifluoromethyl)phenyl)-3-(2-(5-ethoxy-6-((4-methoxybenzyl)oxy)pyridin-3-yl)-4-methylpyrimidin-5-yl)urea

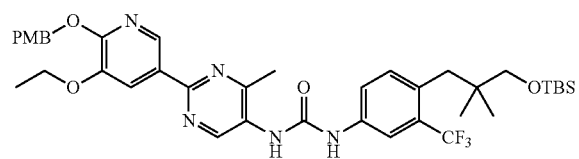

To a solution of 2-(5-ethoxy-6-((4-methoxybenzyl)oxy)pyridin-3-yl)-4-methylpyrimidine-5-carboxylic acid (0.1 g, 0.253 mmol) in 1,4-dioxane (5 mL) stirred at a N$_2$ atomsphere at 20° C. was added Et$_3$N (0.053 mL, 0.379 mmol) and DPPA (0.084 g, 0.303 mmol) in one charge. The reaction mixture was stirred at rt for 30 mins. To the mixture, a solution of 4-(3-((tert-butyldimethylsilyl)oxy)-2,2-dimethylpropyl)-3-(trifluoromethyl)aniline (0.091 g, 0.253 mmol) in 1 mL of 1,4-dioxane was added. The reaction solution was heated to 100° C. with stirring for 3 hr. Then the solution was concentrated in vacuo and the residue was purified by preparative TLC (DCM/MeOH=20:1, R$_f$=0.6) to yield a light yellow solid of 1-(4-(3-((tert-butyldimethylsilyl)oxy)-2,2-dimethylpropyl)-3-(trifluoromethyl)phenyl)-3-(2-(5-ethoxy-6-((4-methoxybenzyl)oxy)pyridin-3-yl)-4-methylpyrimidin-5-yl)urea (80 mg, 0.106 mmol, 42.0% yield): $^1$H NMR (400 MHz, CDCl$_3$) δ 8.91 (s, 1H), 8.71 (s, 1H), 7.95 (s, 1H), 7.48 (s, 1H), 7.38 (d, J=7.3 Hz, 2H), 6.88 (br. s., 1H), 6.80 (d, J=7.3 Hz, 1H), 6.44 (br. s., 1H), 5.42 (s, 2H), 4.13-4.10 (m, 2H), 3.72 (s, 3H), 3.21 (s, 2H), 2.70 (s, 2H), 2.43 (s, 3H), 1.40 (t, J=6.7 Hz, 3H), 0.86 (s, 9H), 0.74 (s, 6H), 0.00 (s, 6H).

Step 2: 1-(2-(5-Ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea

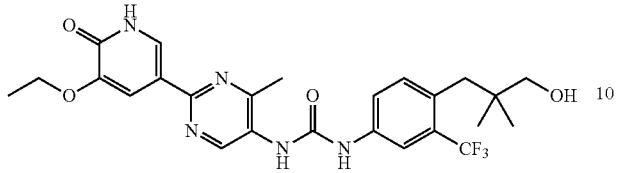

To a solution of 1-(4-(3-((tert-butyldimethylsilyl)oxy)-2,2-dimethylpropyl)-3-(trifluoromethyl)phenyl)-3-(2-(5-ethoxy-6-((4-methoxybenzyl)oxy)pyridin-3-yl)-4-methyl-pyrimidin-5-yl)urea (80 mg, 0.106 mmol) in DCM (2 mL) stirred at a N₂ atomsphere at 20° C. was added HCl in MeOH (0.5 mL, 2.000 mmol) in one charge. The reaction mixture was stirred at 20° C. for 1 hr. Then the solution was concentrated. The residue was purified by preparative HPLC (Column: ASB C18 150*25 mm; Mobile phase A: Water+0.1% HCl; Mobile phase B: MeCN; Flowrate: 25 mL/min; Gradient Profile Description: 34-64(B %)) to give a yellow solid of 1-(2-(5-ethoxy-6-oxo-1,6-dihydropyridin-3-yl)-4-methylpyrimidin-5-yl)-3-(4-(3-hydroxy-2,2-dimethylpropyl)-3-(trifluoromethyl)phenyl)urea hydrochloride (29.96 mg, 0.052 mmol, 49.3% yield). TLC (DCM/MeOH=5:1, R$_f$=0.4): ¹H NMR (400 MHz, CD₃OD) δ 9.10 (s, 1H), 8.10 (s, 1H), 7.88-7.82 (m, 2H), 7.58 (d, J=8.8 Hz, 1H), 7.42 (d, J=8.6 Hz, 1H), 4.16-4.13 (m, 2H), 3.33-3.31 (m, 2H), 2.77 (s, 2H), 2.58 (s, 3H), 1.48 (t, J=7.1 Hz, 3H), 0.84 (s, 6H); ES-LCMS m/z 520.1 (M+H).

EXAMPLE 49

1-(4-((5-Ethoxy-6-oxo-1,6-dihydropyridin-3-yl)oxy)phenyl)-3-(4-((3-methyloxetan-3-yl)oxy)-3-(trifluoromethyl)phenyl)urea

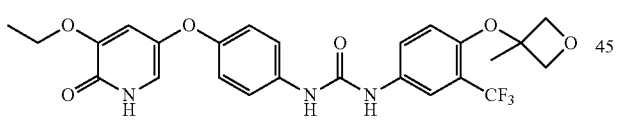

Step 1:
5-Ethoxy-6-((4-methoxybenzyl)oxy)pyridin-3-ol

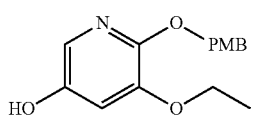

To a solution of 3-ethoxy-2-((4-methoxybenzyl)oxy)-5-(4,4,5,5-tetramethyl-1,3,2-dioxaborolan-2-yl)pyridine (1.1 g, 2.86 mmol) and NaHCO₃ (1.679 g, 19.99 mmol) in acetone (15 mL) and water (5.00 mL) stirred in air at 0° C. was added H₂O₂ (0.971 g, 8.57 mmol) dropwise during 15 min. The reaction mixture was stirred at 20° C. for 12 hr. The the solution was added saturated NaHSO₃ solution. The combined organic extract was washed with brine, dried over MgSO₄, filtered and concentrated. The residue was purified by preparative TLC (PE/EA=1:1, R$_f$ 0.6) to yield a light yellow solid of 5-ethoxy-6-((4-methoxybenzyl)oxy)pyridin-3-ol (0.6 g, 1.744 mmol, 61.1% yield): ¹H NMR (400 MHz, CDCl₃) δ 7.39-7.37 (m, 2H), 7.30 (d, J=2.4 Hz, 1H), 6.87-6.84 (m, 2H), 6.70 (d, J=2.4 Hz, 1H), 5.38 (br, 1H), 5.31 (s, 2H), 4.03-4.01 (m, 2H), 3.78 (s, 3H), 1.44 (t, J=7.0 Hz, 3H); ES-LCMS m/z 276.1 (M+H).

Step 2: 3-Ethoxy-2-((4-methoxybenzyl)oxy)-5-(4-nitrophenoxy)pyridine

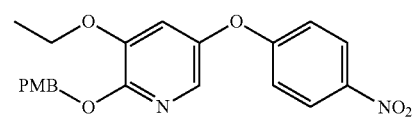

To a solution of 1-fluoro-4-nitrobenzene (141 mg, 0.999 mmol) and 5-ethoxy-6-((4-methoxybenzyl)oxy)pyridin-3-ol (250 mg, 0.908 mmol) in MeCN (20 mL) stirred under N₂ at 20° C. was added Cs₂CO₃ (888 mg, 2.72 mmol) in one charge. The reaction mixture was stirred at 80° C. for 12 hr. The mixture was filtered, the filtrate was concentrated in vacuo and the residue was purified by silica column chromatography (PE/EA=3:1). All fractions found to contain product by TLC (PE/EA=3:1, R$_f$ 0.5) were combined and concentrated to yield a light yellow solid of 3-ethoxy-2-((4-methoxybenzyl)oxy)-5-(4-nitrophenoxy)pyridine (250 mg, 0.378 mmol, 41.7% yield): ¹H NMR (400 MHz, CDCl₃) δ 8.20 (d, J=9.2 Hz, 2H), 7.57 (d, J=2.4 Hz, 1H), 7.44 (d, J=8.8 Hz, 2H), 7.00 (d, J=9.2 Hz, 2H), 6.91 (d, J=8.8 Hz, 2H), 6.82 (d, J=2.4 Hz, 1H), 5.40 (s, 2H), 4.03-4.01 (m, 2H), 3.80 (s, 3H), 1.44 (t, J=7.0 Hz, 3H); ES-LCMS m/z 397.1 (M+H).

Step 3: 3-(4-Isocyanato-2-(trifluoromethyl)phenoxy)-3-methyloxetane

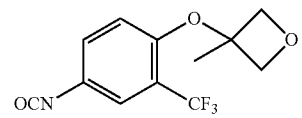

To a solution of 4-((3-methyloxetan-3-yl)oxy)-3-(trifluoromethyl)aniline (100 mg, 0.405 mmol) in THF (6 mL) stirred under N₂ at 20° C. was added triphosgene (42.0 mg, 0.142 mmol) in one charge. The reaction mixture was stirred at 60° C. for 2 hr.

Step 4:
5-(4-Aminophenoxy)-3-ethoxypyridin-2(1H)-one

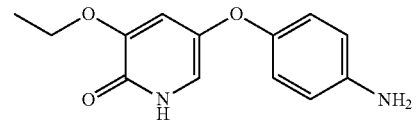 [SMILES: CCOc1cc(Oc2ccc(N)cc2)c[nH]c1=O]

The mixture of 3-ethoxy-2-((4-methoxybenzyl)oxy)-5-(4-nitrophenoxy)pyridine (250 mg, 0.631 mmol) and Pd/C (6.71 mg, 0.063 mmol, 10%) in MeOH (15 mL) was stirred at rt. The reaction was hydrogenated using an H-cube® (settings: 20° C., flow rate) and 10% Pd/C as the catalyst. TLC showed the mixture was finished. The mixture was filtered and the filtrate was concentrated in vacuo to afford a brown solid of 5-(4-aminophenoxy)-3-ethoxypyridin-2 (1H)-one (100 mg, 0.268 mmol, 42.5% yield): $^1$H NMR (400 MHz, CDCl$_3$) δ 6.80-6.78 (m, 2H), 6.66-6.63 (m, 4H), 3.99-3.97 (m, 2H), 3.56 (br, 2H), 1.48 (t, J=7.0 Hz, 3H); ES-LCMS m/z 247.1 (M+H).

Step 5: 1-(4-((5-Ethoxy-6-oxo-1,6-dihydropyridin-3-yl)oxy)phenyl)-3-(4-((3-methyloxetan-3-yl)oxy)-3-(trifluoromethyl)phenyl)urea

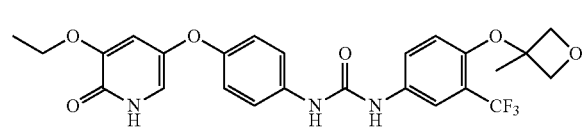 [SMILES: CCOc1cc(Oc2ccc(NC(=O)Nc3ccc(OC4(C)COC4)c(C(F)(F)F)c3)cc2)c[nH]c1=O]

To a solution of 5-(4-aminophenoxy)-3-ethoxypyridin-2 (1H)-one (100 mg, 0.406 mmol), DMAP (2.480 mg, 0.020 mmol) and Et$_3$N (0.170 mL, 1.218 mmol) in THF (15 mL) stirred under N$_2$ at 40° C. was added 3-(4-isocyanato-2-(trifluoromethyl)phenoxy)-3-methyloxetane (222 mg, 0.812 mmol) in one charge. The reaction mixture was stirred at 40° C. for 1 hr. The solution was concentrated in vacuo and the residue was purified by preparative HPLC (MeCN/H$_2$O as eluants, basic condition) to yield a off white solid of 1-(4-((5-ethoxy-6-oxo-1,6-dihydropyridin-3-yl)oxy)phenyl)-3-(4-((3-methyloxetan-3-yl)oxy)-3-(trifluoromethyl)phenyl) urea (126.16 mg, 0.234 mmol, 57.5% yield): $^1$H NMR (400 MHz, CD$_3$OD) δ 7.75 (d, J=2.4 Hz, 1H), 7.53-7.50 (m,1H), 7.40-7.36 (m, 2H), 6.96(dd, J=2.0 Hz, 6.8 Hz, 2H), 6.83 (d, J=2.4 Hz, 1H), 6.74 (d, J=2.8 Hz, 1H), 6.61(d, J=8.8 Hz, 1H), 4.89-4.83 (m, 2H), 4.63 (d, J=7.2 Hz, 2H), 4.00-3.97 (m, 2H), 1.71(s, 3H), 1.42 (t, J=7.0 Hz, 3H); ES-LCMS m/z 520.1 (M+H).

EXAMPLE 50

1-(5'-Ethoxy-6-methyl-6'-oxo-1',6'-dihydro-[2,3'-bipyridin]-5-yl)-3-(4-((3-methyloxetan-3-yl)oxy)-3-(trifluoromethyl)phenyl)urea hydrochloride

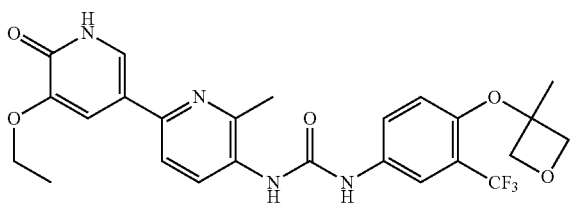 [SMILES: CCOc1cc(-c2ccc(NC(=O)Nc3ccc(OC4(C)COC4)c(C(F)(F)F)c3)c(C)n2)c[nH]c1=O]

Step 1: 3-Bromo-5-ethoxypyridine

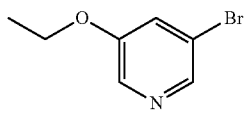

To a mixture of 5-bromopyridin-3-ol (45 g, 259 mmol) in DMF (400 mL) was added K$_2$CO$_3$ (71.5 g, 517 mmol) and EtI (48.4 g, 310 mmol) at rt. The mixture was stirred at 70° C. for 12 hrs. LCMS and TLC (PE/EA=5:1, R$_f$ 0.4) showed the reaction was finished. The mixture was filtered, and the filtrate was concentrated in vacuo and the residue was purified by column to obtain 3-bromo-5-ethoxypyridine (30 g, 135 mmol, 52.2% yield): $^1$H NMR (400 MHz, CD$_3$OD) δ 8.18 (d, J=2.8 Hz, 2H), 7.59 (d, J=2.4 Hz, 1H), 4.11 (d, J=7.2 Hz, 2H), 1.40 (t, J=7.2 Hz, 3H); ES-LCMS m/z 204 (M+2H).

Step 2: 3-Bromo-5-ethoxypyridine 1-oxide

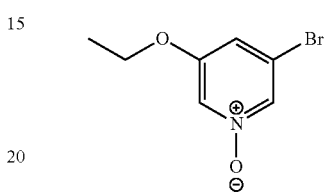

A mixture of 3-bromo-5-ethoxypyridine (28 g, 139 mmol) in DCM (500 mL) was added m-CPBA (28.7 g, 166 mmol). The mixture was stirred at 20° C. for 10 hrs. LCMS and TLC (DCM/MeOH=40:1, R$_f$ 0.4) showed the reaction was finished. The mixture was washed with NaSO$_3$ and saturated NaHCO$_3$ solution. The combined organic extract was washed with brine, dried over MgSO$_4$, filtered and concentrated to give 3-bromo-5-ethoxypyridine 1-oxide (30 g, 128 mmol, 92% yield): $^1$H NMR (400 MHz, CD$_3$OD) δ 8.16 (d, J=3.2 Hz, 1H), 8.05 (d, J=3.6 Hz, 1H), 7.47 (d, J=3.2 Hz, 1H), 4.12 (d, J=7.2 Hz, 2H), 1.38 (t, J=7.2 Hz, 3H); ES-LCMS m/z 220 (M+2H).

Step 3: 5-Bromo-2-chloro-3-ethoxypyridine

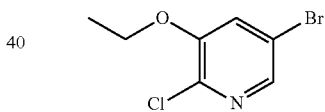

A mixture of 3-bromo-5-ethoxypyridine 1-oxide (28 g, 128 mmol) in DCM (300 mL) was added POCl$_3$ (168 mL, 1798 mmol). The mixture was stirred at 40° C. for 12 hrs. LCMS and TLC (PE/EA=5:1, R$_f$ 0.6) showed the reaction was finished. The mixture was concentrated, and then distributed between EA and saturated NaHCO$_3$ solution. The combined organic extract was washed with brine, dried over MgSO$_4$, filtered and concentrated, which was purified by silica column chromatography (PE/EA=10:1) to give 5-bromo-2-chloro-3-ethoxypyridine (26 g, 106 mmol, 82% yield): $^1$H NMR (400 MHz, CD$_3$OD) δ 8.00 (d, J=2.0 Hz, 1H), 7.65 (d, J=2.0 Hz, 1H), 4.16 (d, J=7.2 Hz, 2H), 1.43 (t, J=7.2 Hz, 3H); ES-LCMS m/z 238 (M+2H).

Step 4: 2-(Benzyloxy)-5-bromo-3-ethoxypyridine

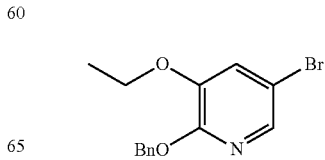

To a mixture of 5-bromo-2-chloro-3-ethoxypyridine (700 mg, 2.96 mmol) in phenylmethanol (10 mL) was added sodium (340 mg, 14.80 mmol). The mixture was stirred at 100° C. for 3 hrs. LCMS showed the reaction was finished. The mixture was diluted with water, and the mixture was extracted with EA, was concentrated in vacuo and the residue was purified silica column chromatography (PE/EA=5:1) to give 2-(benzyloxy)-5-bromo-3-ethoxypyridine (751 mg, 2.193 mmol, 74.1% yield): $^1$H NMR (400 MHz, CDCl$_3$) δ 7.74 (d, J=6.8 Hz, 1H), 7.46 (d, J=2.0 Hz, 2H), 7.36-7.24 (m, 3H), 7.13 (d, J=2.4 Hz, 1H), 5.43 (s, 2H), 4.07 (d, J=6.8 Hz, 2H), 1.44 (t, J=6.8 Hz, 3H); ES-LCMS m/z 309 (M+2H).

Step 5: 2-(Benzyloxy)-3-ethoxy-5-(4,4,5,5-tetramethyl-1,3,2-dioxaborolan-2-yl)pyridine

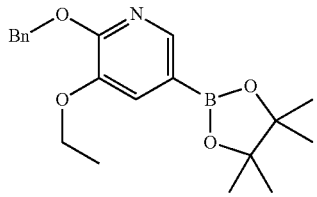 [SMILES: CCOc1cc(B2OC(C)(C)C(C)(C)O2)cnc1OCc1ccccc1]

To a solution of 2-(benzyloxy)-5-bromo-3-ethoxypyridine (1.5 g, 4.87 mmol), 4,4,4',4',5,5,5',5'-octamethyl-2,2'-bi(1,3,2-dioxaborolane) (1.483 g, 5.84 mmol) and KOAc (0.955 g, 9.73 mmol) in 1,4-dioxane (15 mL) stirred under N$_2$ at 20° C. was added PdCl$_2$(dppf) (0.178 g, 0.243 mmol) in one charge. The reaction mixture was stirred at 100° C. for 3 hr. The solution was concentrated in vacuo and the residue was purified by silica column chromatography (PE/EA=5:1). All fractions found to contain product by TLC (PE/EA=5:1, R$_f$ 0.6) were combined and concentrated to yield a light yellow oil of 2-(benzyloxy)-3-ethoxy-5-(4,4,5,5-tetramethyl-1,3,2-dioxaborolan-2-yl)pyridine (1.2 g, 1.858 mmol, 38.2% yield): $^1$H NMR (400 MHz, CDCl$_3$) δ 8.10 (s, 1H), 7.48 (d, J=7.6 Hz, 2H), 7.35-7.26 (m, 4H), 5.50 (s, 2H), 4.13-4.08 (m, 2H), 1.48 (t, J=7.0 Hz, 3H), 1.32 (s, 12H); ES-LCMS m/z 356.2 (M+H).

Step 6: 6'-(Benzyloxy)-5'-ethoxy-6-methyl-5-nitro-2,3'-bipyridine

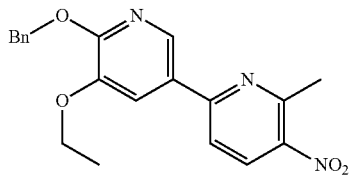 [SMILES: CCOc1cc(-c2ccc([N+](=O)[O-])c(C)n2)cnc1OCc1ccccc1]

To a solution of 2-(benzyloxy)-3-ethoxy-5-(4,4,5,5-tetramethyl-1,3,2-dioxaborolan-2-yl)pyridine (491 mg, 1.382 mmol), 6-bromo-2-methyl-3-nitropyridine (250 mg, 1.152 mmol) and Cs$_2$CO$_3$ (938 mg, 2.88 mmol) in 1,4-dioxane (6 mL) and water (2.000 mL) stirred under N$_2$ at 20° C. was added PdCl$_2$(dppf) (42.1 mg, 0.058 mmol) in one charge. The reaction vessel was sealed and heated in CEM discover using initial 100 W to 110° C. for 15 min. After cooling the reaction was concentrated in vacuo and the residue was purified by TLC (DCM:MeOH=10:1, R$_f$=0.5) to give the desired product 6'-(benzyloxy)-5'-ethoxy-6-methyl-5-nitro-2,3'-bipyridine (250 mg, 0.643 mmol, 55.8% yield): $^1$H NMR (400 MHz, CDCl$_3$) δ 8.36-8.34 (m, 2H), 7.87 (d, J=2.0 Hz, 1H), 7.69 (d, J=8.4 Hz, 1H), 7.50-7.48 (m, 2H), 7.38-7.29 (m, 3H), 5.55 (s, 2H), 4.24-4.19 (m, 2H), 2.93 (s, 3H), 1.50 (t, J=7.0 Hz, 3H); ES-LCMS m/z 366.1 (M+H).

Step 7: 5-Amino-5'-ethoxy-6-methyl-[2,3'-bipyridin]-6'(1'H)-one

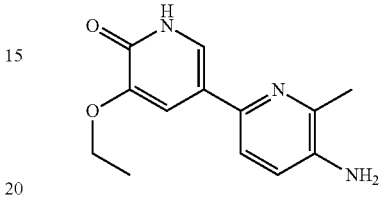

The mixture of 6'-(benzyloxy)-5'-ethoxy-6-methyl-5-nitro-2,3'-bipyridine (250 mg, 0.684 mmol) and 10% Pd/C (7.28 mg, 0.068 mmol) in MeOH (15 mL) was stirred at rt. The reaction was hydrogenated using the H-cube (settings: 20° C., flow rate) and 10% Pd/C as the catalyst. TLC showed the mixture was finished. The mixture was filtered and the filtrate was concentrated in vacuo to afford yellow oil of 5-amino-5'-ethoxy-6-methyl[2,3'-bipyridin]-6'(1'H)-one (150 mg, 0.605 mmol, 88% yield): $^1$H NMR (400 MHz, CDCl$_3$) δ 7.27 (d, J=2.8 Hz, 2H), 7.10 (d, J=8.0 Hz, 1H), 6.91 (d, J=8.4 Hz, 1H), 4.04-3.99 (m, 2H), 3.86 (br, 2H), 2.32 (s, 3H), 1.38 (t, J=7.0 Hz, 3H); ES-LCMS m/z 246.1 (M+H).

Step 8: 3-(4-Isocyanato-2-(trifluoromethyl)phenoxy)-3-methyloxetane

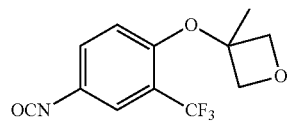

To a solution of 4-((3-methyloxetan-3-yl)oxy)-3-(trifluoromethyl)aniline (50 mg, 0.202 mmol) in THF (6 mL) stirred under N$_2$ at 20° C. was added triphosgene (21.01 mg, 0.071 mmol) in one charge. The reaction mixture was stirred at 60° C. for 2 hr.

Step 9: 1-(5'-Ethoxy-6-methyl-6'-oxo-1',6'-dihydro-[2,3'-bipyridin]-5-yl)-3-(4-((3-methyloxetan-3-yl)oxy)-3-(trifluoromethyl)phenyl)urea hydrochloride

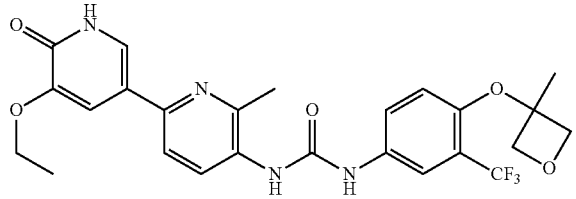 [SMILES: CCOc1cc(-c2ccc(NC(=O)Nc3ccc(OC4(C)COC4)c(C(F)(F)F)c3)c(C)n2)c[nH]c1=O]

To a solution of 5-amino-5'-ethoxy-6-methyl[2,3'-bipyridin]-6'(1'H)-one (40 mg, 0.163 mmol), DMAP (0.996 mg, 8.15 timol) and Et₃N (0.068 mL, 0.489 mmol) in THF (10 mL) stirred under N₂ at 40° C. was added 3-(4-isocyanato-2-(trifluoromethyl)phenoxy)-3-methyloxetane (66.8 mg, 0.245 mmol) in one charge. The reaction mixture was stirred at 40° C. for 1 hr. The solution was concentrated in vacuo and the residue was purified by preparative HPLC (MeCN/H₂O as eluants, acidic condition) to yield a yellow solid of 1-(5'-ethoxy-6-methyl-6'-oxo-1',6'-dihydro-[2,3'-bipyridin]-5-yl)-3-(4-((3-methyloxetan-3-yl)oxy)-3-(trifluoromethyl)phenyl)urea hydrochloride (41.7 mg, 0.074 mmol, 45.2% yield): ¹H NMR (400 MHz, CD₃OD) δ 8.97 (d, J=8.8 Hz, 1H), 8.00 (d, J=8.8 Hz, 1H), 7.85 (d, J=2.8 Hz, 1H), 7.72 (d, J=2.4 Hz, 1H), 7.58 (dd, J=2.4 Hz, 8.8 Hz, 1H), 7.37 (d, J=2.0 Hz, 1H), 6.65 (d, J=9.2 Hz, 1H), 4.89-4.88 (m, 2H), 4.64 (d, J=7.6 Hz, 2H), 4.18-4.12 (m, 2H), 2.77 (s, 3H), 1.72 (s, 3H), 1.50 (t, J=7.0 Hz, 3H); ES-LCMS m/z 519.2 (M+H).

EXAMPLE 51

1-(2-(4-Ethoxy-6-oxo-1,6-dihydropyridin-3-yl)-4-methylpyrimidin-5-yl)-3-(4-(2-hydroxypropan-2-yl)-3-(trifluoromethyl)phenyl)urea

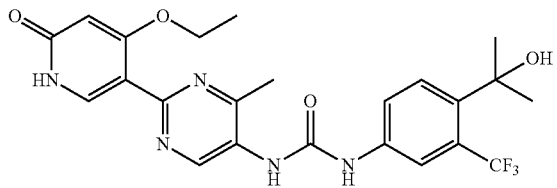 [SMILES: CCOc1cc(=O)[nH]cc1-c1ncc(NC(=O)Nc2ccc(C(C)(C)O)c(C(F)(F)F)c2)c(C)n1]

Step 1: 4-Ethoxy-2-((4-methoxybenzyl)oxy)-5-(4,4,5,5-tetramethyl-1,3,2-dioxaborolan-2-yl)pyridine

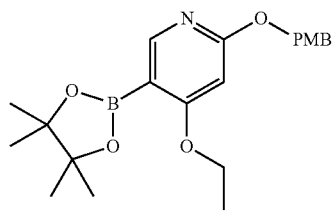

To a solution of 5-bromo-4-ethoxy-2-((4-methoxybenzyl)oxy)pyridine (5.5 g, 16.26 mmol) in THF (40 mL) stirred under N₂ at −70° C. was added n-BuLi (7.81 mL, 19.52 mmol) portionwise during 1 min. The reaction mixture was stirred at −70° C. for 1 hr. Then to the solution was added 4-ethoxy-2-((4-methoxybenzyl)oxy)-5-(4,4,5,5-tetramethyl-1,3,2-dioxaborolan-2-yl)pyridine (1.7 g, 4.41 mmol, 27.1% yield) in THF (1 mL) at −70° C. with stirring. The solution was stirred at −70° C. for 1 hr. To the mixture was added saturated NH₄Cl solution. Then the solution was concentrated and distributed between EA and water. The combined organic extract was washed with brine, dried over Na₂SO₄, filtered and concentrated. The residue was purified by silica column chromatography (PE/EA=5:1). All fractions found to contain product by TLC (PE/EA=5:1, R𝑓=0.4) were combined and concentrated to yield light yellow oil of 4-ethoxy-2-((4-methoxybenzyl)oxy)-5-(4,4,5,5-tetramethyl-1,3,2-dioxaborolan-2-yl)pyridine (1.7 g, 4.41 mmol, 27.1% yield): ¹H NMR (400 MHz, CDCl₃) δ 8.28 (s, 1H), 7.37 (d, J=8.4 Hz, 2H), 6.88 (d, J=8.6 Hz, 2H), 6.13 (s, 1H), 5.30 (s, 2H), 4.00 (q, J=6.8 Hz, 2H), 3.80 (s, 3H), 1.40 (t, J=6.9 Hz, 3H), 1.32 (s, 12H); ES-LCMS m/z 386.2 (M+H).

Step 2: 2-Chloro-4-methylpyrimidin-5-amine

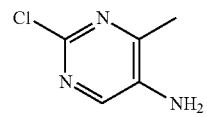

To a solution of 2,4-dichloro-6-methyl-5-nitropyrimidine (20 g, 96 mmol) and NH₄Cl (51.4 g, 962 mmol) in MeOH (600 mL) stirred under N₂ at 20° C. was added zinc (62.9 g, 962 mmol) in one charge. The reaction mixture was stirred at 70° C. for 50 hr. The mixture was filtered, and the filtrate was concentrated in vacuo and the residue was purified by silica column chromatography (DCM/MeOH=30:1). All fractions found to contain product by TLC (EA/EA=1=1:1, R𝑓 0.6) were combined and concentrated to yield a light yellow solid of 2-chloro-4-methylpyrimidin-5-amine (1.8 g, 12.54 mmol, 13.04% yield): ¹H NMR (400 MHz, CD₃OD-d₄) δ 7.92 (s, 1H), 2.33 (s, 3H); ES-LCMS m/z 144.1 (M+1).

Step 3: 2-Chloro-5-isocyanato-4-methylpyrimidine

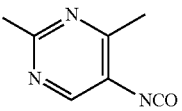

To a solution of 2-chloro-4-methylpyrimidin-5-amine (250 mg, 1.741 mmol) in THF (8 mL) stirred under N₂ at 20° C. was added triphosgene (181 mg, 0.609 mmol) in one charge. The reaction mixture was stirred at 60° C. for 30 min. ES-LCMS m/z 202.1 (M+32).

Step 4: 1-(4-Acetyl-3-(trifluoromethyl)phenyl)-3-(2-chloro-4-methylpyrimidin-5-yl)urea

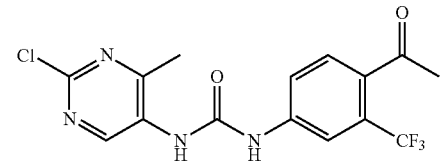 [SMILES: CC(=O)c1ccc(NC(=O)Nc2cnc(Cl)nc2C)cc1C(F)(F)F]

To a solution of 1-(4-amino-2-(trifluoromethyl)phenyl)ethanone dihydrochloride (300 mg, 1.087 mmol), DMAP (398 mg, 3.26 mmol) and Et₃N (7.57 μL, 0.054 mmol) in THF (6 mL) stirred under N₂ at 40° C. was added 2-chloro-5-isocyanato-4-methylpyrimidine (240 mg, 1.413 mmol) in one charge. The reaction mixture was stirred at 40° C. for 1 hr. Then the solution was concentrated and the residue was purified by preparative TLC (PE/EA=1:1, R𝑓 0.2) to yield a light yellow solid of 1-(4-acetyl-3-(trifluoromethyl)phenyl)-

3-(2-chloro-4-methylpyrimidin-5-yl)urea (30 mg, 0.080 mmol, 7.41% yield): $^1$H NMR (400 MHz, CD$_3$OD-d$_4$) δ 9.05 (s, 1H), 7.97 (s, 1H), 7.79-7.69 (m, 2H), 2.56 (s, 3H), 2.51 (s, 3H); ES-LCMS m/z 373.1 (M+H).

Step 5: 1-(4-Acetyl-3-(trifluoromethyl)phenyl)-3-(2-(4-ethoxy-6-((4-methoxybenzyl)oxy)pyridin-3-yl)-4-methylpyrimidin-5-yl)urea

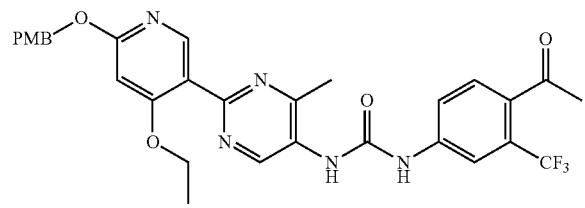

To a solution of (4-ethoxy-6-((4-methoxybenzyl)oxy)pyridin-3-yl)boronic acid (73.2 mg, 0.241 mmol), 1-(4-acetyl-3-(trifluoromethyl)phenyl)-3-(2-chloro-4-methylpyrimidin-5-yl)urea (90 mg, 0.241 mmol) and Cs$_2$CO$_3$ (197 mg, 0.604 mmol) in 1,4-dioxane (3 mL) and water (1.000 mL) stirred under N$_2$ at 20° C. was added PdCl$_2$(PPh$_3$)$_2$ (8.47 mg, 0.012 mmol) in one charge. The reaction vessel was sealed and heated in CEM Discover using initial normal to 110° C. for 20 min. After cooling the reaction solution was concentrated and distributed between EA and water. The combined organic extract was washed with brine, dried over MgSO$_4$, filtered and concentrated. The residue was purified by preparative TLC (DCM/MeOH=10:1, R$_f$=0.6) to yield a brown solid of 1-(4-acetyl-3-(trifluoromethyl)phenyl)-3-(2-(4-ethoxy-6-((4-methoxybenzyl)oxy)pyridin-3-yl)-4-methylpyrimidin-5-yl)urea (30 mg, 0.050 mmol, 20.86% yield): $^1$H NMR (400 MHz, CDCl$_3$) δ 9.12 (s, 1H), 8.45 (s, 1H), 8.21 (br. s., 1H), 7.77 (d, J=8.5 Hz, 1H), 7.66 (s, 1H), 7.50 (d, J=8.5 Hz, 1H), 7.38 (d, J=8.5 Hz, 2H), 7.30 (br. s., 1H), 6.89 (d, J=8.5 Hz, 2H), 6.32 (s, 1H), 5.33 (s, 2H), 4.10 (q, J=6.9 Hz, 2H), 3.81 (s, 3H), 2.59 (s, 3H), 2.50 (s, 3H), 1.37 (t, J=7.0 Hz, 3H); ES-LCMS m/z 596.1 (M+H).

Step 6: 1-(2-(4-Ethoxy-6-oxo-1,6-dihydropyridin-3-yl)-4-methylpyrimidin-5-yl)-3-(4-(2-hydroxypropan-2-yl)-3-(trifluoromethyl)phenyl)urea

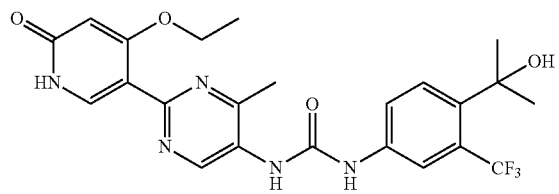 [SMILES: CCOc1cc(=O)[nH]cc1-c1ncc(NC(=O)Nc2ccc(C(C)(C)O)c(C(F)(F)F)c2)c(C)n1]

To a solution of 1-(4-acetyl-3-(trifluoromethyl)phenyl)-3-(2-(4-ethoxy-6-((4-methoxybenzyl)oxy)pyridin-3-yl)-4-methylpyrimidin-5-yl)urea (50 mg, 0.084 mmol) in DCM (10 mL) stirred under N$_2$ at 20° C. was added MeMgBr (0.168 mL, 0.504 mmol) in one charge. The reaction mixture was stirred at 20° C. for 1 hr. To the solution was added saturated NH$_4$Cl solution. The mixture was concentrated. The residue was purified by preparative TLC (DCM/MeOH=10:1, R$_f$=0.4) to yield a light yellow solid of the unpure product. Which was purified by preparative HPLC (MeCN/H$_2$O as eluants, acidic condition) to yield a white solid of 1-(2-(4-ethoxy-6-oxo-1,6-dihydropyridin-3-yl)-4-methylpyrimidin-5-yl)-3-(4-(2-hydroxypropan-2-yl)-3-(trifluoromethyl)phenyl)urea (4.18 mg, 8.28 μmol, 9.87% yield). TLC (DCM/MeOH=10:1, R$_f$=0.4): $^1$H NMR (400 MHz, CD$_3$OD-d$_4$) δ 9.16 (s, 1H), 7.88 (s, 1H), 7.77 (s, 1H), 7.66 (s, 2H), 5.99 (s, 1H), 4.11 (q, J=7.0 Hz, 2H), 2.55 (s, 3H), 1.61 (s, 6H), 1.36 (t, J=6.9 Hz, 3H); ES-LCMS m/z 492. (M+1).

EXAMPLE 52

1-(2-(4-Ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea

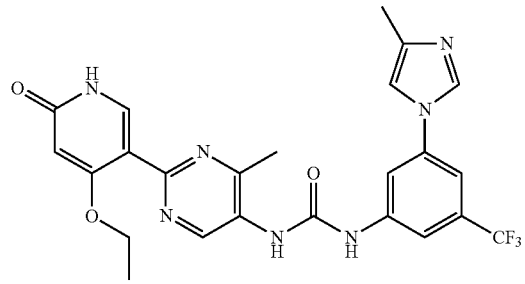 [SMILES: CCOc1cc(=O)[nH]cc1-c1ncc(NC(=O)Nc2cc(-n3cnc(C)c3)cc(C(F)(F)F)c2)c(C)n1]

Step 1: 1-(2-(4-Ethoxy-6-((4-methoxybenzyl)oxy)pyridin-3-yl)-4-methylpyrimidin-5-yl)-3-(3-(4-methyl-1H-imidazol-1-yl)-5-(trifluoromethyl)phenyl)urea

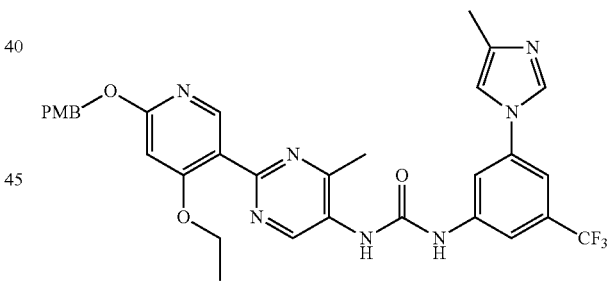

To a solution of 2-(4-ethoxy-6-((4-methoxybenzyl)oxy)pyridin-3-yl)-4-methylpyrimidine-5-carboxylic acid (0.2 g, 0.506 mmol) in 1,4-dioxane (3 mL) stirred under N$_2$ at 20° C. was added Et$_3$N (0.106 mL, 0.759 mmol) and DPPA (0.167 g, 0.607 mmol) in one charge. The reaction mixture was stirred at rt for 30 mins. To the mixture, a solution of 3-(4-methyl-1H-imidazol-1-yl)-5-(trifluoromethyl)aniline (0.122 g, 0.506 mmol) in 1 mL of 1,4-dioxane was added. The reaction solution was heated to 100° C. with stirring for 3 hr. The solution was concentrated in vacuo and the residue was purified by preparative TLC (DCM/MeOH=10:1, R$_f$=0.5) to yield a off white solid of 1-(2-(4-ethoxy-6-((4-methoxybenzyl)oxy)pyridin-3-yl)-4-methylpyrimidin-5-yl)-3-(3-(4-methyl-1H-imidazol-1-yl)-5-(trifluoromethyl)phenyl)urea (60 mg, 0.095 mmol, 18.7% yield): $^1$H NMR (400 MHz, CD$_3$OD) δ 9.18 (s, 1H), 9.15 (s, 1H), 8.39 (s, 1H), 8.25 (s, 1H), 8.04 (s, 1H), 7.81 (s, 1H), 7.54 (s, 1H), 7.25-7.23 (m, 2H), 6.87-6.85 (m, 2H), 6.48 (s, 1H), 5.31 (s, 2H), 4.13-4.10 (m, 2H), 3.79 (s, 3H), 2.82 (s, 3H), 2.59 (s, 3H), 1.40-1.36 (m, 3H); ES-LCMS m/z 634.2 (M+H).

Step 2: 1-(2-(4-Ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea

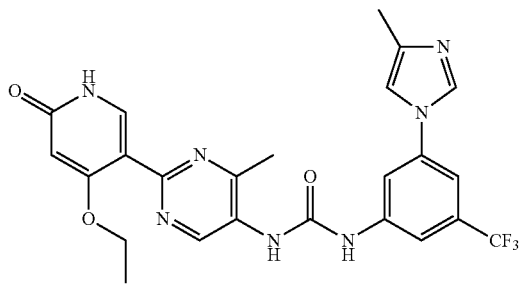 [SMILES: CCOc1cc(=O)[nH]cc1-c1ncc(NC(=O)Nc2cc(-n3cnc(C)c3)cc(C(F)(F)F)c2)c(C)n1]

To a solution of 1-(2-(4-ethoxy-6-((4-methoxybenzyl)oxy)pyridin-3-yl)-4-methylpyrimidin-5-yl)-3-(3-(4-methyl-1H-imidazol-1-yl)-5-(trifluoromethyl)phenyl)urea (70 mg, 0.110 mmol) in DCM (5 mL) stirred under N₂ at 20° C. was added HCl in MeOH (0.5 mL, 2.000 mmol) in one charge. The reaction mixture was stirred at 20° C. for 1 hr. Then the solution was concentrated. The residue was purified by preparative HPLC (Instrument: DC/Column: ASB C18 150*25 mm/Mobile phase A: Water+0.1% HCl/Mobile phase B: MeCN/Flowrate: 25 mL/min/Gradient Profile Description: 32-62(B %)) to yield a off white solid of 1-(2-(4-ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea dihydrochloride (17.58 mg, 0.030 mmol, 27.0% yield). TLC (DCM/MeOH=5:1, $R_f$=0.4): ¹H NMR (400 MHz, CD₃OD) δ 9.49 (s, 1H), 9.47-9.44 (m, 1H), 8.41 (s, 1H), 8.18 (s, 1H), 8.06 (s, 1H), 7.88 (s, 1H), 7.75 (s, 1H), 6.18 (s, 1H), 4.35 (d, J=7.2 Hz, 2H), 2.79 (s, 3H), 2.45 (s, 3H), 1.48 (t, J=6.9 Hz, 3H); ES-LCMS m/z 514.2 (M+H).

EXAMPLE 53

1-(2-(5-Ethoxy-6-oxo-1,6-dihydropyridin-3-yl)-4,6-dimethylpyrimidin-5-yl)-3-(3-(4-methyl-1H-imidazol-1-yl)-5-(trifluoromethyl)phenyl)urea

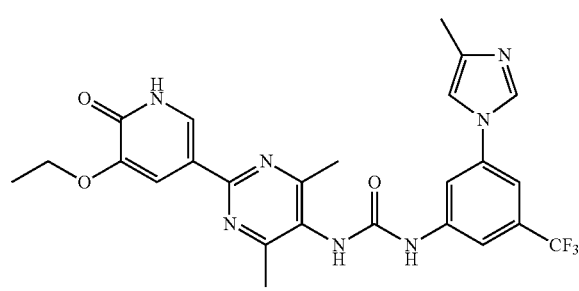 [SMILES: CCOc1cc(-c2nc(C)c(NC(=O)Nc3cc(-n4cnc(C)c4)cc(C(F)(F)F)c3)c(C)n2)c[nH]c1=O]

Step 1: Ethyl 4,6-dimethyl-2-oxo-1,2,5,6-tetrahydropyrimidine-5-carboxylate

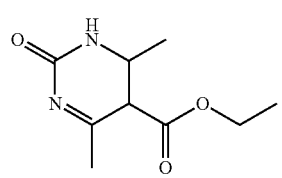

A mixture of ethyl 3-oxobutanoate (16.27 g, 125 mmol), acetaldehyde (5.51 g, 125 mmol), urea (7.51 g, 125 mmol), and glacial AcOH (1 mL, 17.47 mmol) in EtOH (35 mL) was heated to 90° C. overnight in a 350 mL pressure flask. The mixture was diluted with water. The precipitate was collected by filtration, washed with water and air-dried to afford a white solid of ethyl 4,6-dimethyl-2-oxo-1,2,3,4-tetrahydropyrimidine-5-carboxylate (12 g, 60.5 mmol, 48.4% yield): ¹H NMR (400 MHz, DMSO-d₆) δ 8.95 (br. s., 1H), 7.18 (br. s., 1H), 4.13-3.95 (m, 3H), 2.12 (s, 3H), 1.16 (t, J=7.0 Hz, 3H), 1.06 (d, J=6.4 Hz, 3H); LCMS m/z 199.0 (M+H).

Step 2: Ethyl 4,6-dimethyl-2-oxo-1,2-dihydropyrimidine-5-carboxylate

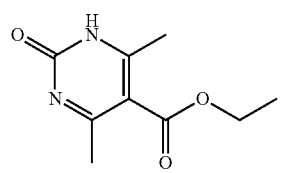

To nitric acid (12 mL, 17.66 mmol) stirred under N₂ at 0° C. was added ethyl 4,6-dimethyl-2-oxo-1,2,3,4-tetrahydropyrimidine-5-carboxylate (3.5 g, 17.66 mmol) portionwise. The reaction mixture was stirred at 0° C. for 10 min. The reaction solution was poured into 60 g of ice water, then extracted with EA. The combined organic extract was washed with brine, dried over Na₂SO₄, filtered and concentrated. The resulting ethyl 4,6-dimethyl-2-oxo-1,2-dihydropyrimidine-5-carboxylate (2.6 g, 13.25 mmol, 75% yield). TLC (PE/EA=5:1, $R_f$=0.6): ¹H NMR (400 MHz, CDCl₃) δ 13.71-13.48 (m, 1H), 4.36 (q, J=7.1 Hz, 2H), 2.56 (s, 6H), 1.38 (t, J=7.1 Hz, 3H); ES-LCMS m/z 197.1 (M+H).

Step 3: Ethyl 2-chloro-4,6-dimethylpyrimidine-5-carboxylate

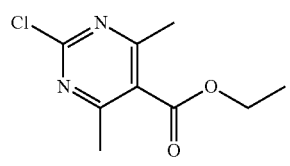

To a solution of POCl₃ (10.42 mL, 122 mmol) and DIEA (33 mL, 189 mmol) stirred under N₂ at 20° C. was added ethyl 4,6-dimethyl-2-oxo-1,2-dihydropyrimidine-5-carboxylate (2.4 g, 12.23 mmol) slowly. The reaction mixture was stirred at 80° C. for 2 hr. Then the solution was concentrated and distributed between EA and saturated NaHCO₃ solution. The combined organic extract was washed with brine, dried over Na₂SO₄, filtered and concentrated. The residue was purified by silica column chromatography (PE/EA=10:1). All fractions found to contain product by TLC (PE/EA=10:1, R$_f$=0.7) were combined and concentrated to yield yellow oil of ethyl 2-chloro-4,6-dimethylpyrimidine-5-carboxylate (1.6 g, 7.45 mmol, 60.9% yield): ¹H NMR (400 MHz, CDCl₃) δ 4.43 (q, J=6.8 Hz, 2H), 2.54 (s, 6H), 1.40 (t, J=7.1 Hz, 3H); ES-LCMS m/z 215.1 (M+H).

Step 4: Ethyl 2-(5-ethoxy-6-((4-methoxybenzyl)oxy)pyridin-3-yl)-4,6-dimethylpyrimidine-5-carboxylate

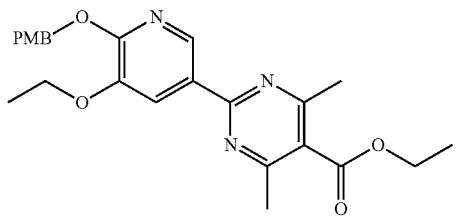

To a solution of 3-ethoxy-2-((4-methoxybenzyl)oxy)-5-(4,4,5,5-tetramethyl-1,3,2-dioxaborolan-2-yl)pyridine (2.51 g, 6.52 mmol), ethyl 2-chloro-4,6-dimethylpyrimidine-5-carboxylate (1.4 g, 6.52 mmol) and Cs₂CO₃ (4.25 g, 13.04 mmol) in 1,4-dioxane (15 mL) and water (5.00 mL) stirred under N₂ at 20° C. was added PdCl₂(dppf) (0.477 g, 0.652 mmol) in one charge. The reaction vessel was heated in 110° C. for 2 hr. Then the solution was concentrated and distributed between EA and water. The combined organic extract was washed with brine, dried over MgSO₄, filtered and concentrated. The residue was purified by silica column chromatography (PE/EA=10:1, 5:1). All fractions found to contain product by TLC (PE/EA=2:1, R$_f$0.5) were combined and concentrated to yield a light yellow solid of ethyl 2-(5-ethoxy-6-((4-methoxybenzyl)oxy)pyridin-3-yl)-4,6-dimethylpyrimidine-5-carboxylate (1.7 g, 3.89 mmol, 59.6% yield): ¹H NMR (400 MHz, CDCl₃) δ 8.86-8.82 (m, 1H), 8.08-8.04 (m, 1H), 7.48-7.42 (m, 2H), 6.87 (d, J=8.6 Hz, 2H), 5.49 (s, 2H), 4.43 (s, 2H), 4.23-4.15 (m, 2H), 3.79 (s, 3H), 2.58 (s, 6H), 1.52-1.45 (m, 3H), 1.41 (t, J=7.1 Hz, 3H); LCMS m/z 438.2 (M+H).

Step 5: 2-(5-Ethoxy-6-oxo-1,6-dihydropyridin-3-yl)-4,6-dimethylpyrimidine-5-carboxylic acid

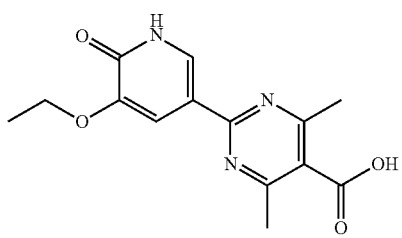 [SMILES: CCOc1cc(-c2nc(C)c(C(=O)O)c(C)n2)c[nH]c1=O]

To a solution of ethyl 2-(5-ethoxy-6-((4-methoxybenzyl)oxy)pyridin-3-yl)-4,6-dimethylpyrimidine-5-carboxylate (500 mg, 1.143 mmol) in THF (5 mL) stirred under N₂ at 20° C. was added NaOH (2.5 mL, 6.25 mmol) in one charge. The reaction mixture was stirred at 100° C. for 12 hr. Then the solution was concentrated and neutralized with con. HCl to pH=7.0 with stirring. Then filtered, and the filtrate cake was washed with water (10 mL). The filtrate cake was dried in vacuo to give a off white solid of 2-(5-ethoxy-6-oxo-1,6-dihydropyridin-3-yl)-4,6-dimethylpyrimidine-5-carboxylic acid (300 mg, 1.037 mmol, 91% yield). TLC (DCM/MeOH=10:1, R$_f$ 0.4): ¹H NMR (400 MHz, CD₃OD) δ 8.16 (d, J=2.0 Hz, 1H), 7.87 (d, J=2.0 Hz, 1H), 4.18-4.12 (m, 2H), 2.59-2.56 (m, 6H), 1.47 (t, J=6.9 Hz, 3H); LCMS m/z 290.2 (M+H).

Step 6: 1-(2-(5-Ethoxy-6-oxo-1,6-dihydropyridin-3-yl)-4,6-dimethylpyrimidin-5-yl)-3-(3-(4-methyl-1H-imidazol-1-yl)-5-(trifluoromethyl)phenyl)urea

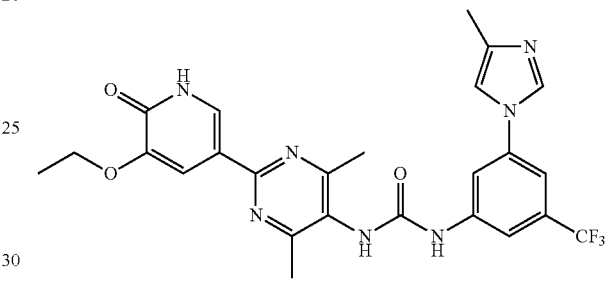

To a solution of 2-(5-ethoxy-6-oxo-1,6-dihydropyridin-3-yl)-4,6-dimethylpyrimidine-5-carboxylic acid (150 mg, 0.519 mmol), 3-(4-methyl-1H-imidazol-1-yl)-5-(trifluoromethyl)aniline (125 mg, 0.519 mmol) and Et₃N (79 mg, 0.778 mmol) in 1,4-dioxane (5 mL) stirred under N₂ at 20° C. was added DPPA (171 mg, 0.622 mmol) in one charge. The reaction mixture was heated to 80° C. for 1 hr. Then the solution was concentrated. The residue was purified by preparative HPLC (Instrument: DC/Column: ASB C18 150*25 mm/Mobile phase A: Water+0.1% HCl/Mobile phase B: MeCN/Flowrate: 25 mL/min/Gradient Profile Description: 15-55(B %)) to yield a off white solid of 1-(2-(5-ethoxy-6-oxo-1,6-dihydropyridin-3-yl)-4,6-dimethylpyrimidin-5-yl)-3-(3-(4-methyl-1H-imidazol-1-yl)-5-(trifluoromethyl)phenyl)urea dihydrochloride (11.53 mg, 3.67%). TLC (DCM/MeOH=5:1, R$_f$=0.4): ¹H NMR (400 MHz, CD₃OD) δ 9.44-9.40 (m, 1H), 8.27-8.23 (m, 1H), 8.20 (s, 1H), 7.92 (s, 2H), 7.84 (s, 1H), 7.69 (s, 1H), 4.17 (d, J=6.8 Hz, 2H), 2.57 (s, 6H), 2.44 (s, 3H), 1.48 (t, J=6.9 Hz, 3H); ES-LCMS m/z 528.2 (M+H).

EXAMPLE 54

1-(4-Chloro-3-(trifluoromethyl)phenyl)-3-(2-(4-ethoxy-6-oxo-1,6-dihydropyridin-3-yl)-4-methylpyrimidin-5-yl)urea

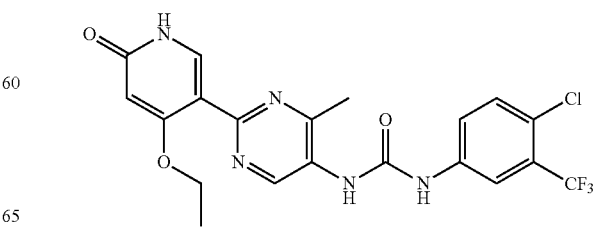

Step 1: 1-(4-Chloro-3-(trifluoromethyl)phenyl)-3-(2-(4-ethoxy-6-((4-methoxybenzyl)oxy)pyridin-3-yl)-4-methylpyrimidin-5-yl)urea

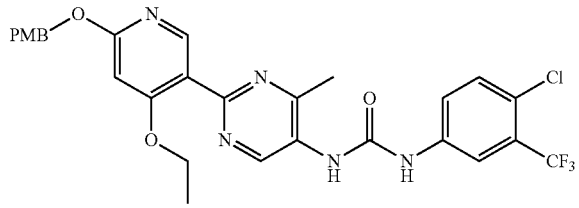

To a solution of 2-(4-ethoxy-6-((4-methoxybenzyl)oxy)pyridin-3-yl)-4-methylpyrimidine-5-carboxylic acid (200 mg, 0.506 mmol) in 1,4-Dioxane (5 mL) stirred under $N_2$ at 20° C. was added $Et_3N$ (0.106 mL, 0.759 mmol) and DPPA (167 mg, 0.607 mmol) in one charge. The reaction mixture was stirred at rt for 30 mins. To the mixture, a solution of 4-chloro-3-(trifluoromethyl)aniline (79 mg, 0.405 mmol) in 1 mL of 1,4-dioxane was added. The reaction solution was heated to 100° C. with stirring for 3 hr. The solution was concentrated in vacuo and the residue was purified by preparative TLC (DCM/MeOH=20:1, $R_f$=0.5) to yield a off white solid of 1-(4-chloro-3-(trifluoromethyl)phenyl)-3-(2-(4-ethoxy-6-((4-methoxybenzyl)oxy)pyridin-3-yl)-4-methylpyrimidin-5-yl)urea (25 mg, 0.043 mmol, 8.41% yield): $^1$H NMR (400 MHz,$CD_3OD$) δ 9.18 (s, 1H), 8.27 (s, 1H), 8.00 (s, 1H), 7.92 (br. s., 1H), 7.85 (s, 1H), 7.39-7.26 (m, 2H), 6.92-6.90 (m, 2H), 6.48 (s, 1H), 5.30 (s, 2H), 4.17-4.15 (m, 2H), 3.79 (s, 3H), 2.58 (s, 3H), 1.42-1.39 (m, 3H); ES-LCMS m/z 588.1 (M+H).

Step 2: 1-(4-Chloro-3-(trifluoromethyl)phenyl)-3-(2-(4-ethoxy-6-oxo-1,6-dihydropyridin-3-yl)-4-methylpyrimidin-5-yl)urea

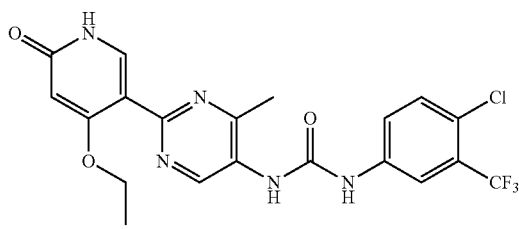 [SMILES: CCOc1cc(=O)[nH]cc1-c1ncc(NC(=O)Nc2ccc(Cl)c(C(F)(F)F)c2)c(C)n1]

To a solution of 1-(4-chloro-3-(trifluoromethyl)phenyl)-3-(2-(4-ethoxy-6-((4-methoxybenzyl)oxy)pyridin-3-yl)-4-methylpyrimidin-5-yl)urea (25 mg, 0.043 mmol) in DCM (2 mL) stirred under $N_2$ at 20° C. was added HCl in MeOH (0.5 mL, 2.000 mmol) in one charge. The reaction mixture was stirred at 20° C. for 1 hr. Then the solution was concentrated. The residue was purified by preparative HPLC (Instrument: DC/Column: ASB C18 150*25 mm/Mobile phase A: Water+ 0.1% HCl/Mobile phase B: MeCN/Flowrate: 25 mL/min/ Gradient Profile Description: 33-63(B%)) to give a off white solid of 1-(4-chloro-3-(trifluoromethyl)phenyl)-3-(2-(4-ethoxy-6-oxo-1,6-dihydropyridin-3-yl)-4-methylpyrimidin-5-yl)urea hydrochloride (6.15 mg, 0.012 mmol, 28.5% yield). TLC (DCM/MeOH=5:1, $R_f$=0.4): $^1$H NMR (400 MHz, $CD_3OD$) δ 9.50 (s, 1H), 8.39 (s, 1H), 8.07 (d, J=2.2 Hz, 1H), 7.68-7.62 (m, 1H), 7.55 (d, J=8.6 Hz, 1H), 6.15 (s, 1H), 4.34 (q, J=6.8 Hz, 2H), 2.75 (s, 3H), 1.47 (t, J=6.9 Hz, 3H); ES-LCMS m/z 468 (M+H).

EXAMPLE 55

1-(4-((Dimethylamino)methyl)-3-(trifluoromethyl)phenyl)-3-(2-(4-ethoxy-6-oxo-1,6-dihydropyridin-3-yl)-4-methylpyrimidin-5-yl)urea

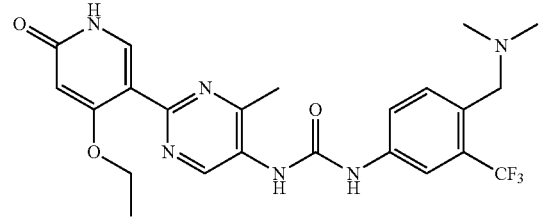 [SMILES: CCOc1cc(=O)[nH]cc1-c1ncc(NC(=O)Nc2ccc(CN(C)C)c(C(F)(F)F)c2)c(C)n1]

Step 1: (6-(Benzyloxy)-4-ethoxypyridin-3-yl)boronic acid

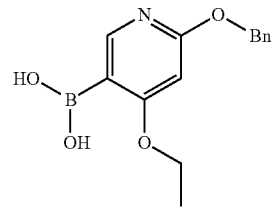 [SMILES: CCOc1cc(OCc2ccccc2)ncc1B(O)O]

To a solution of 2-(benzyloxy)-4-ethoxy-5-iodopyridine (500 mg, 1.408 mmol) in THF (12 mL) stirred at a $N_2$ atomsphere at −70° C. was added n-BuLi (0.619 mL, 1.549 mmol) portionwise during 1 min. The reaction mixture was stirred at −70° C. for 1 hr. Then to the solution was added 2-isopropoxy-4,4,5,5-tetramethyl-1,3,2-dioxaborolane (288 mg, 1.549 mmol) in THF (1 mL) slowly at −70° C. with stirring. The solution was stirred at −70° C. for 1 hr. To the mixture was added saturated $NH_4Cl$ solution. Then the solution was concentrated and distributed between EA and water. The combined organic extract was washed with brine, dried over $Na_2SO_4$, filtered and concentrated. The resulting (6-(benzyloxy)-4-ethoxypyridin-3-yl)boronic acid (300 mg, 1.099 mmol, 78% yield). TLC (PE/EA=2:1, $R_f$=0.4): $^1$H NMR (400 MHz, $CDCl_3$) δ 8.21 (br. s., 1H), 7.46-7.22 (m, 5H), 6.15 (br. s., 1H), 5.26 (br. s., 2H), 4.02 (d, J=6.8 Hz, 2H), 1.41 (t, J=6.7 Hz, 3H); ES-LCMS m/z 274.1 (M+1).

Step 2: 2-Chloro-4-methylpyrimidin-5-amine

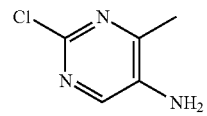

To a solution of 2,4-dichloro-6-methyl-5-nitropyrimidine (20 g, 96 mmol) and 20 (51.4 g, 962 mmol) in MeOH (600 mL) stirred at a N₂ atomsphere at 20° C. was added zinc (62.9 g, 962 mmol) in one charge. The reaction mixture was stirred at 70° C. for 50 hr. The mixture was filtered, and the filtrate was concentrated in vacuo and the residue was purified by silica column chromatography (DCM/MeOH=30:1). All fractions found to contain product by TLC (EA/EA=1=1:1, R$_f$ 0.6) were combined and concentrated to yield a light yellow solid of 2-chloro-4-methylpyrimidin-5-amine (1.8 g, 12.54 mmol, 13.04% yield): ¹H NMR (400 MHz, CD₃OD) δ 7.92 (s, 1H), 2.33 (s, 3H); ES-LCMS m/z 144.1 (M+H).

Step 3: 2-Chloro-5-isocyanato-4-methylpyrimidine

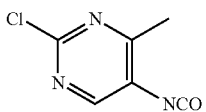

To a solution of 2-chloro-4-methylpyrimidin-5-amine (250 mg, 1.741 mmol) in THF (8 mL) stirred at a N₂ atomsphere at 20° C. was added triphosgene (181 mg, 0.609 mmol) in one charge. The reaction mixture was stirred at 60° C. for 30 min. ES-LCMS m/z 202.1 (M+32).

Step 4: 1-(2-Chloro-4-methylpyrimidin-5-yl)-3-(4-((dimethylamino)methyl)-3-(trifluoromethyl)phenyl)urea

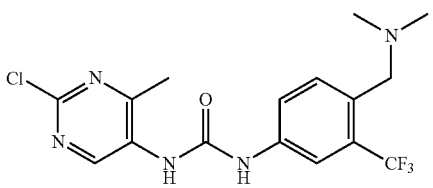 [SMILES: Cc1nc(Cl)ncc1NC(=O)Nc1ccc(CN(C)C)c(C(F)(F)F)c1]

To a solution of 4-((dimethylamino)methyl)-3-(trifluoromethyl)aniline dihydrochloride (200 mg, 0.687 mmol), DMAP (252 mg, 2.061 mmol) and Et₃N (4.79 μL, 0.034 mmol) in THF (6 mL) stirred at a N₂ atomsphere at 40° C. was added 2-chloro-5-isocyanato-4-methylpyrimidine (175 mg, 1.030 mmol) in one charge. The reaction mixture was stirred at 40° C. for 1 hr. Then the solution was concentrated and the residue was purified by preparative TLC (PE/EA=1:1, R$_f$ 0.2) to yield a light yellow solid of 1-(2-chloro-4-methylpyrimidin-5-yl)-3-(4-((dimethylamino)methyl)-3-(trifluoromethyl)phenyl)urea (210 mg, 0.542 mmol, 79% yield): ¹H NMR (400 MHz, CD₃OD) δ 9.05 (s, 1H), 8.08 (s, 1H), 7.83-7.78 (m, 1H), 7.71 (d, J=8.4 Hz, 1H), 4.31 (br. s., 2H), 2.83-2.77 (m, 6H), 2.53 (s, 3H); ES-LCMS m/z 388.1 (M+H).

Step 5: 1-(2-(6-(Benzyloxy)-4-ethoxypyridin-3-yl)-4-methylpyrimidin-5-yl)-3-(4-((dimethylamino)methyl)-3-(trifluoromethyl)phenyl)urea

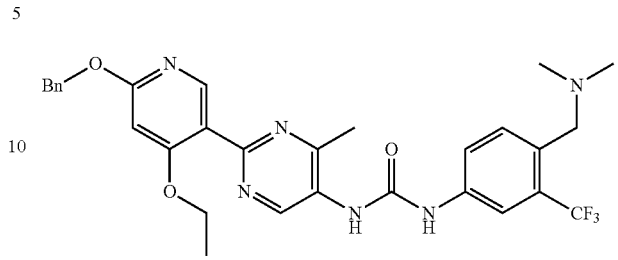

To a solution of (6-(benzyloxy)-4-ethoxypyridin-3-yl)boronic acid (127 mg, 0.464 mmol), 1-(2-chloro-4-methylpyrimidin-5-yl)-3-(4-((dimethylamino)methyl)-3-(trifluoromethyl)phenyl)urea (150 mg, 0.387 mmol) and Cs₂CO₃ (315 mg, 0.967 mmol) in 1,4-dioxane (9 mL) and water (3.00 mL) stirred at a N₂ atomsphere at 20° C. was added PdCl₂(PPh₃)₂ (13.58 mg, 0.019 mmol) in one charge. The reaction vessel was sealed and heated in CEM Discover using initial normal to 110° C. for 20 min. After cooling the reaction solution was concentrated and distributed between EA and water. The combined organic extract was washed with brine, dried over MgSO₄, filtered and concentrated. The residue was purified by silica column chromatography (PE/EA=1:1). All fractions found to contain product by TLC (PE/EA=1:1, R$_f$ 0.3) were combined and concentrated to yield a brown solid of 1-(2-(6-(benzyloxy)-4-ethoxypyridin-3-yl)-4-methylpyrimidin-5-yl)-3-(4-((dimethylamino)methyl)-3-(trifluoromethyl)phenyl)urea (30 mg, 0.052 mmol, 13.36% yield): ¹H NMR (400 MHz, CDCl₃) δ 10.11 (br. s., 1H), 9.31 (s, 1H), 8.62 (br. s., 1H), 8.45 (s, 1H), 8.15 (d, J=8.4 Hz, 1H), 7.46 (d, J=7.5 Hz, 2H), 7.41-7.34 (m, 2H), 7.32 (d, J=7.3 Hz, 1H), 6.33 (s, 1H), 5.41 (s, 2H), 4.30 (s, 2H), 4.09 (q, J=7.1 Hz, 2H), 2.81 (s, 6H), 2.72 (s, 3H), 1.37 (t, J=6.9 Hz, 3H); ES-LCMS m/z 581.0 (M+H).

Step 6: 1-(4-((Dimethylamino)methyl)-3-(trifluoromethyl)phenyl)-3-(2-(4-ethoxy-6-oxo-1,6-dihydropyridin-3-yl)-4-methylpyrimidin-5-yl)urea

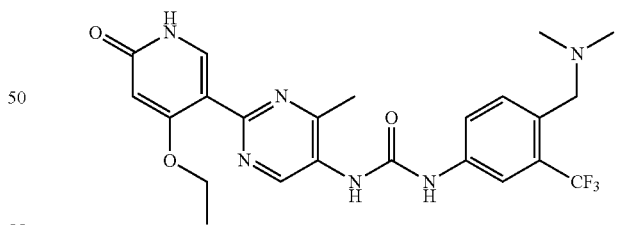

To a solution of 1-(2-(6-(benzyloxy)-4-ethoxypyridin-3-yl)-4-methylpyrimidin-5-yl)-3-(4-((dimethylamino)methyl)-3-(trifluoromethyl)phenyl)urea (30 mg, 0.052 mmol) in MeOH (10 mL) stirred at a N₂ atomsphere at 20° C. was added Pd/C (3 mg, 10% in water) in one charge. The reaction mixture was stirred at 20° C. for 12 hr. The mixture was filtered, and the filtrate was concentrated in vacuo and the residue was purified by preparative HPLC (MeCN/H₂O as eluants, acidic condition) to yield a light yellow solid of 1-(4-((dimethylamino)methyl)-3-(trifluoromethyl)phenyl)-3-(2-(4-ethoxy-6-oxo-1,6-dihydropyridin-3-yl)-4-methylpyrimidin-5-yl)urea dihydrochloride (10.86 mg, 0.019 mmol, 36.5% yield). TLC (DCM/MeOH=10:1, $R_f$ 0.3): $^1$H NMR (400 MHz, CD$_3$OD) δ 9.49 (s, 1H), 8.38 (s, 1H), 8.17 (d, J=2.0 Hz, 1H), 7.88-7.84 (m, 1H), 7.73 (d, J=8.4 Hz, 1H), 6.16 (s, 1H), 4.47 (s, 2H), 4.34 (q, J=6.9 Hz, 2H), 2.93 (s, 6H), 2.76 (s, 3H), 1.47 (t, J=7.1 Hz, 3H); ES-LCMS m/z 491.1 (M+H).

EXAMPLE 56

1-(2-(5-Ethoxy-6-oxo-1,6-dihydropyridin-3-yl)-4-ethylpyrimidin-5-yl)-3-(3-(4-methyl-1H-imidazol-1-yl)-5-(trifluoromethyl)phenyl)urea

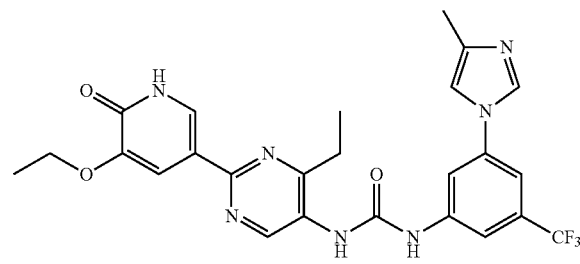 [SMILES: CCOc1cc(-c2ncc(NC(=O)Nc3cc(-n4cnc(C)c4)cc(C(F)(F)F)c3)c(CC)n2)c[nH]c1=O]

Step 1: Ethyl 6-ethyl-2-oxo-1,2-dihydropyrimidine-5-carboxylate

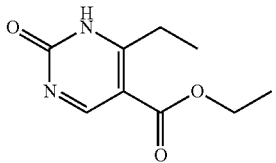

A solution of urea (7.5 g, 125 mmol), ethyl 3-oxopentanoate (19.80 g, 137 mmol) in triethoxymethane (20.36 g, 137 mmol) was stirred for 28 h while distilling off EtOH at 80° C. under N$_2$ atmosphere. Then the mixture was cooled to 20° C. and EtOH (50 mL) was added, NaOEt (12.75 g, 187 mmol) in EtOH (50 mL) was added to above mixture and the mixture was stirred for 2 h at 80° C., the mixture was cooled to 20° C., followed by addition of water (100 mL), AcOH (10 mL) was added at 20° C.-30° C., then the mixture was filtered, the solid was washed with water (150 mL), dried to give ethyl 6-ethyl-2-oxo-1,2-dihydropyrimidine-5-carboxylate (12 g, 61.2 mmol, 49.0% yield). $^1$H NMR (400 MHz, DMSO-d$_6$) δ 8.67 (s, 1H), 4.20 (q, J=7.1 Hz, 2H), 2.87 (q, J=7.3 Hz, 2H), 1.25 (t, J=7.1 Hz, 3H), 1.12 (t, J=7.5 Hz, 3H); LCMS m/z 197.0 (M+H).

Step 2: Ethyl 2-chloro-4-ethylpyrimidine-5-carboxylate

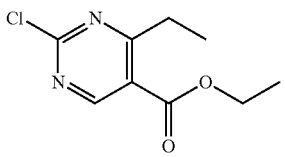

Ethyl 4-ethyl-2-oxo-1,2-dihydropyrimidine-5-carboxylate (2.4 g, 12.23 mmol) was dissolved in POCl$_3$ (28.1 g, 183 mmol) at rt. The reaction mixture was heated to 80° C. for 2 h. The solution was concentrated in vacuo and the residue was purified by silica column chromatography (PE/EA=10:1). All fractions found to contain product by TLC (PE/EA=10:1, $R_f$=0.6) were combined and concentrated to yield a light yellow oil of ethyl 2-chloro-4-ethylpyrimidine-5-carboxylate (0.7 g, 3.26 mmol, 26.7% yield): $^1$H NMR (400 MHz, CDCl$_3$) δ 8.98 (s, 1H), 4.48-4.38 (m, 2H), 3.19-3.13 (m, 2H), 1.42-1.38 (m, 3H), 1.32-1.28 (m, 3H).

Step 3: Ethyl 2-(5-ethoxy-6-((4-methoxybenzyl)oxy)pyridin-3-yl)-4-ethylpyrimidine-5-carboxylate

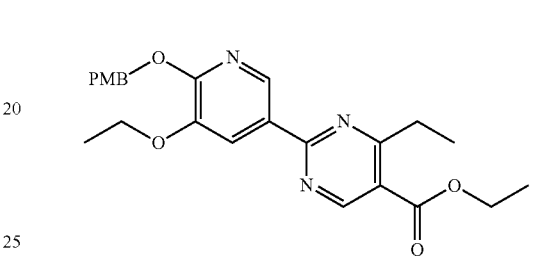

To a solution of 3-ethoxy-2-((4-methoxybenzyl)oxy)-5-(4,4,5,5-tetramethyl-1,3,2-dioxaborolan-2-yl)pyridine (0.897 g, 2.329 mmol), ethyl 2-chloro-4-ethylpyrimidine-5-carboxylate (0.5 g, 2.329 mmol) and Cs$_2$CO$_3$ (1.518 g, 4.66 mmol) in 1,4-dioxane (9 mL) and water (3.00 mL) stirred under N$_2$ at 20° C. was added PdCl$_2$(dppf) (0.170 g, 0.233 mmol) in one charge. The reaction vessel was heated in 110° C. for 2 h. Then the solution was concentrated and distributed between EA and water. The combined organic extract was washed with brine, dried over MgSO$_4$, filtered and concentrated. The residue was purified by silica column chromatography (PE/EA=10:1, 5:1). All fractions found to contain product by TLC (PE/EA=2:1, $R_f$ 0.5) were combined and concentrated to yield a light yellow solid of ethyl 2-(5-ethoxy-6-((4-methoxybenzyl)oxy)pyridin-3-yl)-4-ethylpyrimidine-5-carboxylate (0.7 g, 1.600 mmol, 68.7% yield): $^1$H NMR (400 MHz, CDCl$_3$) δ 9.12 (s, 1H), 8.92 (s, 1H), 8.11 (s, 1H), 7.45 (d, J=8.1 Hz, 2H), 6.88 (d, J=8.1 Hz, 3H), 5.50 (s, 2H), 4.40 (d, J=7.1 Hz, 2H), 4.20 (d, J=7.1 Hz, 2H), 3.79 (s, 3H), 3.20-3.18 (m, 2H), 1.48 (t, J=6.8 Hz, 3H), 1.41 (t, J=7.1 Hz, 3H), 1.36 (t, J=7.5 Hz, 3H); LCMS m/z 438.2 (M+H).

Step 4: 2-(5-Ethoxy-6-((4-methoxybenzyl)oxy)pyridin-3-yl)-4-ethylpyrimidine-5-carboxylic acid

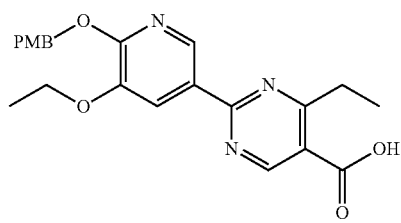

To a solution of ethyl 2-(5-ethoxy-6-((4-methoxybenzyl)oxy)pyridin-3-yl)-4-ethylpyrimidine-5-carboxylate (0.7 g, 1.600 mmol) in MeOH (5 mL) stirred under N$_2$ at 20° C. was added NaOH (5 mL, 12.50 mmol) in one charge. The reaction mixture was stirred at 80° C. for 12 h. Then the solution was concentrated and neutralized with con. HCl to pH=7.0 with stirring. Then filtered, and the filtrate cake was washed with water (10 mL). The filtrate cake was dried in vacuo to give a off white solid of 2-(5-ethoxy-6-((4-methoxybenzyl)oxy)pyridin-3-yl)-4-ethylpyrimidine-5-carboxylic acid (0.5 g, 1.221 mmol, 76% yield). TLC (DCM/MeOH=10:1, $R_f$ 0.4): $^1$H NMR (400 MHz, CD$_3$OD) δ 8.8-8.77 (m, 1H), 8.76-8.72 (m, 1H), 8.14 (d, J=1.7 Hz, 1H), 7.41 (d, J=8.6 Hz, 2H), 6.91 (d, J=8.6 Hz, 2H), 5.39 (s, 2H), 4.17-4.13 (m, 2H), 3.78 (s, 3H), 3.16-3.11 (m, 2H), 1.43 (t, J=7.0 Hz, 3H), 1.34 (t, J=7.6 Hz, 3H); LCMS m/z 410.1 (M+H).

Step 5: 1-(2-(5-Ethoxy-6-((4-methoxybenzyl)oxy)pyridin-3-yl)-4-ethylpyrimidin-5-yl)-3-(3-(4-methyl-1H-imidazol-1-yl)-5-(trifluoromethyl)phenyl)urea

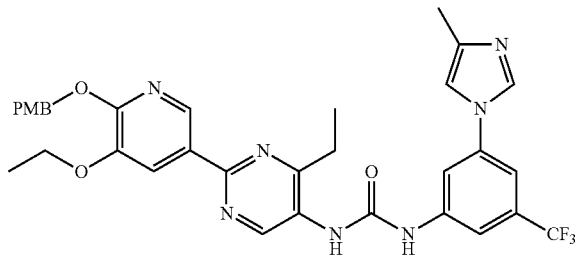

To a solution of 2-(5-ethoxy-6-((4-methoxybenzyl)oxy)pyridin-3-yl)-4-ethylpyrimidine-5-carboxylic acid (150 mg, 0.366 mmol), 3-(4-methyl-1H-imidazol-1-yl)-5-(trifluoromethyl)aniline (88 mg, 0.366 mmol) and Et$_3$N (55.6 mg, 0.550 mmol) in 1,4-dioxane (10 mL) stirred under N$_2$ at 20° C. was added DPPA (121 mg, 0.440 mmol) in one charge. The reaction mixture was stirred at 80° C. for 2 h. Then the solution was concentrated. The residue was purified by preparative TLC (DCM/MeOH=10:1, $R_f$=0.5) to yield a off white solid of 1-(2-(5-ethoxy-6-((4-methoxybenzyl)oxy)pyridin-3-yl)-4-ethylpyrimidin-5-yl)-3-(3-(4-methyl-1H-imidazol-1-yl)-5-(trifluoromethyl)phenyl)urea (50 mg, 0.077 mmol, 21.07% yield). TLC (DCM/MeOH=10:1, $R_f$=0.4): $^1$H NMR (400 MHz, CD$_3$OD) δ 9.07 (s, 1H), 8.74-8.72 (m, 1H), 8.12 (d, J=9.3 Hz, 2H), 7.98 (br. s., 1H), 7.77-7.75 (m, 1H), 7.50 (br. s., 1H), 7.41 (d, J=8.6 Hz, 2H), 7.35 (s, 1H), 6.92 (d, J=8.8 Hz, 2H), 5.40 (s, 2H), 4.17 (d, J=7.1 Hz, 2H), 3.79 (s, 3H), 2.91 (d, J=7.5 Hz, 2H), 2.26 (s, 3H), 1.42 (td, J=7.3, 14.6 Hz, 6H); ES-LCMS m/z 648.3 (M+H).

Step 6: 1-(2-(5-Ethoxy-6-oxo-1,6-dihydropyridin-3-yl)-4-ethylpyrimidin-5-yl)-3-(3-(4-methyl-1H-imidazol-1-yl)-5-(trifluoromethyl)phenyl)urea

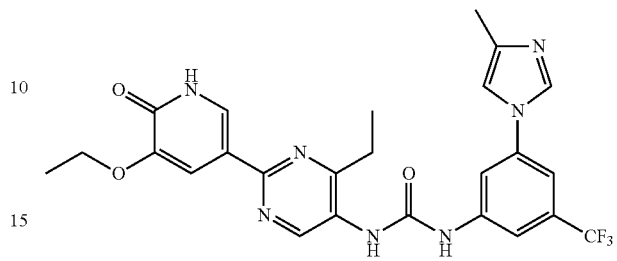

To a solution of 1-(2-(5-ethoxy-6-((4-methoxybenzyl)oxy)pyridin-3-yl)-4-ethylpyrimidin-5-yl)-3-(3-(4-methyl-1H-imidazol-1-yl)-5-(trifluoromethyl)phenyl)urea (50 mg, 0.077 mmol) in DCM (5 mL) stirred under N$_2$ at 20° C. was added HCl in MeOH (1 mL, 4.00 mmol) in one charge. The reaction mixture was stirred at 20° C. for 1 h. Then the solution was concentrated. The residue was purified by preparative HPLC (Instrument: DC/Column: ASB C18 150*25 mm/Mobile phase A: Water+0.1% HCl/Mobile phase B: MeCN/Flowrate: 25 mL/min/Gradient Profile Description: 25-55(B %)) to yield a off white solid of 1-(2-(5-ethoxy-6-oxo-1,6-dihydropyridin-3-yl)-4-ethylpyrimidin-5-yl)-3-(3-(4-methyl-1H-imidazol-1-yl)-5-(trifluoromethyl)phenyl)urea dihydrochloride (10.25 mg, 0.017 mmol, 21.67% yield). TLC (DCM/MeOH=5:1, $R_f$=0.4): $^1$H NMR (400 MHz, DMSO-d$_6$) δ 11.95-11.87 (m, 1H), 10.44 (br. s., 1H), 9.56 (br. s., 1H), 8.98 (d, J=3.4 Hz, 1H), 8.10-7.87 (m, 4H), 7.74 (br. s., 1H), 7.59 (s, 1H), 5.73 (s, 1H), 4.03-3.98 (m, 2H), 2.85-2.80 (m, 2H), 2.32 (s, 3H), 1.34 (t, J=6.8 Hz, 3H), 1.25 (t, J=7.5 Hz, 3H); ES-LCMS m/z 528.2 (M+H).

EXAMPLE 57

1-(2-(5-Ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea

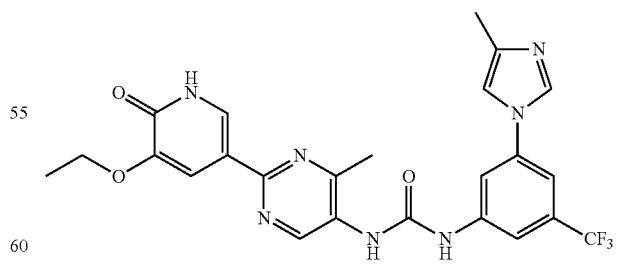

Step 1: 1-(2-(5-Ethoxy-6-((4-methoxybenzyl)oxy) pyridin-3-yl)-4-methylpyrimidin-5-yl)-3-(3-(4-methyl-1H-imidazol-1-yl)-5-(trifluoromethyl)phenyl)urea

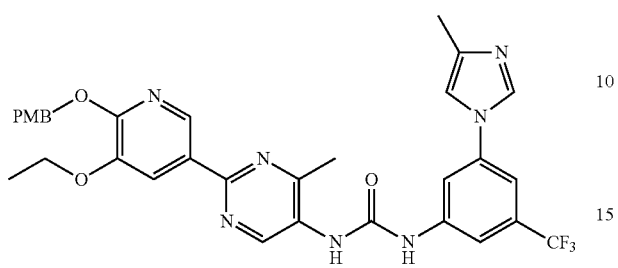

To a solution of 2-(5-ethoxy-6-((4-methoxybenzyl)oxy) pyridin-3-yl)-4-methylpyrimidine-5-carboxylic acid (0.2 g, 0.506 mmol) in 1,4-dioxane (4 mL) stirred at a $N_2$ atmosphere at 20° C. was added $Et_3N$ (0.106 mL, 0.759 mmol) and DPPA (0.167 g, 0.607 mmol) in one charge. The reaction mixture was stirred for 15 mins. To the mixture, a solution of 3-(4-methyl-1H-imidazol-1-yl)-5-(trifluoromethyl)aniline (0.122 g, 0.506 mmol) in 1 mL of 1,4-dioxane was added, and heated to 100° C. for 2 hr. The solvent was removed on a rotational evaporator. The residue was purified by preparative TLC (DCM:MeOH=10:1, $R_f$=0.5) to yield a off white solid of 1-(2-(5-ethoxy-6-((4-methoxybenzyl)oxy) pyridin-3-yl)-4-methylpyrimidin-5-yl)-3-(3-(4-methyl-1H-imidazol-1-yl)-5-(trifluoromethyl)phenyl)urea (70 mg, 0.110 mmol, 21.84% yield): $^1$H NMR (400 MHz, $CD_3OD$) δ 9.10 (s, 1H), 8.66 (s, 1H), 8.22 (s, 1H), 8.07 (s, 1H), 7.98 (s, 1H), 7.78 (s, 1H), 7.50 (s, 1H), 7.39 (d, J=4.2 Hz, 3H), 6.90 (d, J=8.6 Hz, 2H), 5.37 (s, 2H), 4.19-4.13 (m, 2H), 3.78 (s, 3H), 2.59 (s, 3H), 2.29 (s, 3H), 1.43 (t, J=6.9 Hz, 3H); LCMS m/z 634.2 (M+H).

Step 2: 1-(2-(5-Ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea

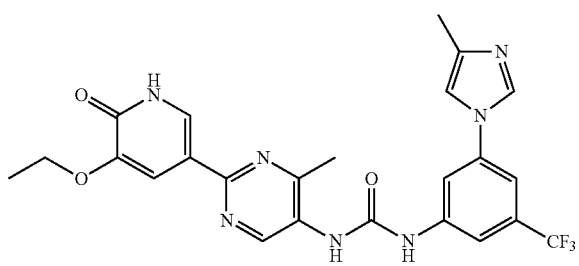 [SMILES: CCOc1cc(-c2ncc(NC(=O)Nc3cc(-n4cnc(C)c4)cc(C(F)(F)F)c3)c(C)n2)c[nH]c1=O]

To a solution of 1-(2-(5-ethoxy-6-((4-methoxybenzyl) oxy)pyridin-3-yl)-4-methylpyrimidin-5-yl)-3-(3-(4-methyl-1H-imidazol-1-yl)-5-(trifluoromethyl)phenyl)urea (70 mg, 0.110 mmol) in DCM (5 mL) stirred at a $N_2$ atmosphere at 20° C. was added HCl in MeOH (0.5 mL, 2.000 mmol) in one charge. The reaction mixture was stirred at 20° C. for 1 hr. Then the solution was concentrated. The residue was purified by preparative HPLC (Instrument: DC; Column: Gemini: C18 150*25 mm*10 ul; Mobile phase A: Water+ 0.1% HCl/Mobile phase B: MeCN/Flowrate: 25 mL/min/Run time: 15 min/Gradient Profile Description: 18-48(B %)) to yield a off white solid of 1-(2-(5-ethoxy-6-oxo-1,6-dihydropyridin-3-yl)-4-methylpyrimidin-5-yl)-3-(3-(4-methyl-1H-imidazol-1-yl)-5-(trifluoromethyl)phenyl)urea dihydrochloride (39.06 mg, 0.065 mmol, 58.5% yield). TLC (DCM/MeOH=10:1, $R_f$=0.4): $^1$H NMR (400 MHz, DMSO-$d_6$) δ 10.95 (br. s., 1H), 9.64 (s, 1H), 9.27 (s, 1H), 9.05 (s, 1H), 8.07 (s, 1H), 8.02 (s, 1H), 7.96 (br. s., 1H), 7.89 (s, 1H), 7.74 (s, 1H), 7.56 (s, 1H), 4.02-3.97 (m, 2H), 2.52 (s, 3H), 2.33 (s, 3H), 1.33 (t, J=6.8 Hz, 3H); ES-LCMS m/z 514.1 (M+H).

EXAMPLE 58

1-(4-((Dimethylamino)methyl)-3-(trifluoromethyl) phenyl)-3-(2-(5-ethoxy-6-oxo-1,6-dihydropyridin-3-yl)-4-methylpyrimidin-5-yl)urea

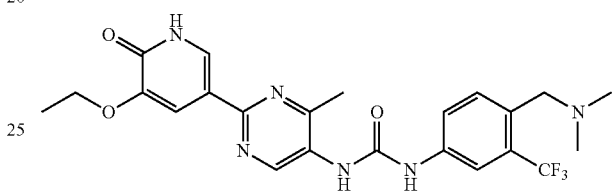

Step 1: 1-(4-((Dimethylamino)methyl)-3-(trifluoromethyl)phenyl)-3-(2-(5-ethoxy-6-((4-methoxybenzyl)oxy)pyridin-3-yl)-4-methylpyrimidin-5-yl)urea

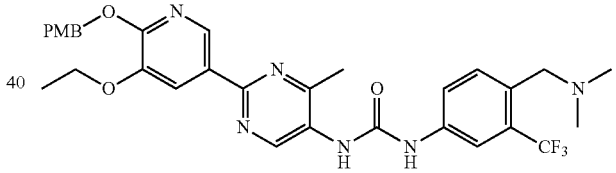

To a solution of 2-(5-ethoxy-6-((4-methoxybenzyl)oxy) pyridin-3-yl)-4-methylpyrimidine-5-carboxylic acid (0.2 g, 0.506 mmol) in 1,4-dioxane (5 mL) stirred at a $N_2$ atmosphere at 20° C. was added $Et_3N$ (0.106 mL, 0.759 mmol) and DPPA (0.167 g, 0.607 mmol) in one charge. The reaction mixture was stirred at rt for 30 mins. To the mixture, a solution of 4-((dimethylamino)methyl)-3-(trifluoromethyl) aniline (0.088 g, 0.405 mmol) in 1 mL of 1,4-dioxane was added, and heated to 100° C. for 3 h. The solvent was removed and the residue was purified by preparative TLC (DCM/MeOH=10:1, $R_f$=0.4) to yield a light yellow solid of 1-(4-((dimethylamino)methyl)-3-(trifluoromethyl)phenyl)-3-(2-(5-ethoxy-6-((4-methoxybenzyl)oxy)pyridin-3-yl)-4-methylpyrimidin-5-yl)urea (110 mg, 0.180 mmol, 35.6% yield). $^1$H NMR (400 MHz, $CD_3OD$) δ 8.67 (d, J=1.8 Hz, 1H), 8.08 (d, J=1.8 Hz, 1H), 7.97 (s, 1H), 7.67 (d, J=8.8 Hz, 1H), 7.40 (d, J=8.6 Hz, 2H), 7.24 (d, J=7.2 Hz, 2H), 6.91 (d, J=8.6 Hz, 2H), 5.38 (s, 2H), 4.16 (q, J=7.1 Hz, 2H), 4.08 (br. s, 2H), 3.78 (s, 3H), 2.57 (s, 3H), 2.44 (s, 6H), 1.29 (t, J=7.3 Hz, 3H); ES-LCMS m/z 611.1 (M+H).

Step 2: 1-(4-((Dimethylamino)methyl)-3-(trifluoromethyl)phenyl)-3-(2-(5-ethoxy-6-oxo-1,6-dihydropyridin-3-yl)-4-methylpyrimidin-5-yl)urea

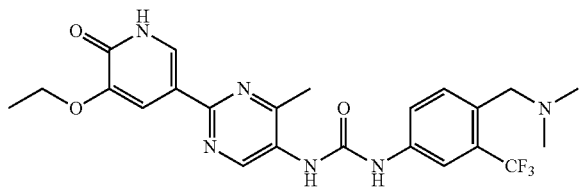 [SMILES: CCOc1cc(-c2ncc(NC(=O)Nc3ccc(CN(C)C)c(C(F)(F)F)c3)c(C)n2)c[nH]c1=O]

To a solution of 1-(4-((dimethylamino)methyl)-3-(trifluoromethyl)phenyl)-3-(2-(5-ethoxy-6-((4-methoxybenzyl)oxy)pyridin-3-yl)-4-methylpyrimidin-5-yl)urea (110 mg, 0.180 mmol) in DCM (2 mL) stirred at a $N_2$ atmosphere at 20° C. was added HCl in MeOH (0.5 mL, 2.000 mmol) in one charge. The reaction mixture was stirred at 20° C. for 1 hr. Then the solution was concentrated. The residue was purified by preparative HPLC (Column: ASB C18 150*25 mm/Mobile phase A: Water+0.1% HCl/Mobile phase B: MeCN/Flowrate: 25 mL/min/Run time: 15 min/Gradient Profile Description: 15-45(B %)) to give a yellow solid of 1-(4-((dimethylamino)methyl)-3-(trifluoromethyl)phenyl)-3-(2-(5-ethoxy-6-oxo-1,6-dihydropyridin-3-yl)-4-methylpyrimidin-5-yl)urea dihydrochloride (21.34 mg, 0.037 mmol, 20.5% yield). TLC (DCM/MeOH=5:1, $R_f$=0.4): $^1$H NMR (400 MHz, CD$_3$OD) δ 9.12 (s, 1H), 8.12 (dd, J=2.1, 5.4 Hz, 2H), 7.90-7.83 (m, 2H), 7.70 (d, J=8.6 Hz, 1H), 4.46 (s, 2H), 4.18-4.15 (m, 2H), 2.93 (s, 6H), 2.61 (s, 3H), 1.48 (t, J=6.9 Hz, 3H); ES-LCMS m/z 491.2 (M+H).

EXAMPLE 59

1-(4-((Dimethylamino)methyl)-3-(trifluoromethyl)phenyl)-3-(2-(5-ethoxy-6-oxo-1,6-dihydropyridin-3-yl)-4,6-dimethylpyrimidin-5-yl)urea

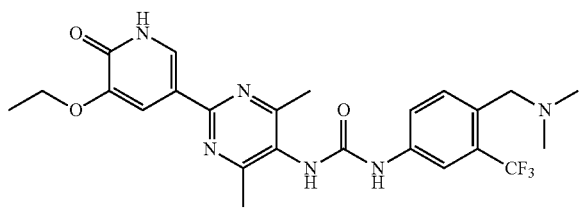 [SMILES: CCOc1cc(-c2nc(C)c(NC(=O)Nc3ccc(CN(C)C)c(C(F)(F)F)c3)c(C)n2)c[nH]c1=O]

Step 1: Ethyl 4,6-dimethyl-2-oxo-1,2,5,6-tetrahydropyrimidine-5-carboxylate

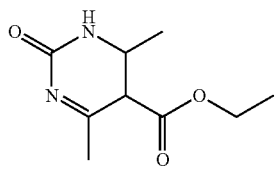

A mixture of ethyl 3-oxobutanoate (16.27 g, 125 mmol), acetaldehyde (5.51 g, 125 mmol), urea (7.51 g, 125 mmol), and glacial AcOH (1 mL, 17.47 mmol) in EtOH (35 mL) was heated to 90° C. overnight in a 350 mL pressure flask. The mixture was diluted with water. The precipitate was collected by filtration, washed with water and air-dried to afford a white solid of ethyl 4,6-dimethyl-2-oxo-1,2,3,4-tetrahydropyrimidine-5-carboxylate (12 g, 60.5 mmol, 48.4% yield): $^1$H NMR (400 MHz, DMSO-d$_6$) δ 8.95 (br. s., 1H), 7.18 (br. s., 1H), 4.13-3.95 (m, 3H), 2.12 (s, 3H), 1.16 (t, J=7.0 Hz, 3H), 1.06 (d, J=6.4 Hz, 3H); LCMS m/z 202.1 (M+H).

Step 2: Ethyl 4,6-dimethyl-2-oxo-1,2-dihydropyrimidine-5-carboxylate

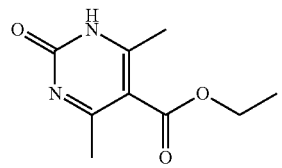

To nitric acid (12 mL, 17.66 mmol) stirred under $N_2$ at 0° C. was added ethyl 4,6-dimethyl-2-oxo-1,2,3,4-tetrahydropyrimidine-5-carboxylate (3.5 g, 17.66 mmol) portionwise. The reaction mixture was stirred at 0° C. for 10 min. The reaction solution was poured into 60 g of ice water, then extracted with EA. The combined organic extract was washed with brine, dried over Na$_2$SO$_4$, filtered and concentrated. The resulting ethyl 4,6-dimethyl-2-oxo-1,2-dihydropyrimidine-5-carboxylate (2.6 g, 13.25 mmol, 75% yield). TLC (PE/EA=5:1, $R_f$=0.6): $^1$H NMR (400 MHz, CDCl$_3$) δ 13.71-13.48 (m, 1H), 4.36 (q, J=7.1 Hz, 2H), 2.56 (s, 6H), 1.38 (t, J=7.1 Hz, 3H); ES-LCMS m/z 197.1 (M+H).

Step 3: Ethyl 2-chloro-4,6-dimethylpyrimidine-5-carboxylate

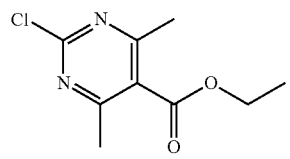

To a solution of POCl$_3$ (10.42 mL, 122 mmol) and DIEA (33 mL, 189 mmol) stirred under $N_2$ at 20° C. was added ethyl 4,6-dimethyl-2-oxo-1,2-dihydropyrimidine-5-carboxylate (2.4 g, 12.23 mmol) slowly. The reaction mixture was stirred at 80° C. for 2 hr. Then the solution was concentrated and distributed between EA and saturated NaHCO$_3$ solution. The combined organic extract was washed with brine, dried over Na$_2$SO$_4$, filtered and concentrated. The residue was purified by silica column chromatography (PE/EA=10:1). All fractions found to contain product by TLC (PE/EA=10:1, $R_f$=0.7) were combined and concentrated to yield yellow oil of ethyl 2-chloro-4,6-dimethylpyrimidine-5-carboxylate (1.6 g, 7.45 mmol, 60.9% yield): $^1$H NMR (400 MHz, CDCl$_3$) δ 4.43 (q, J=6.8 Hz, 2H), 2.54 (s, 6H), 1.40 (t, J=7.1 Hz, 3H); ES-LCMS m/z 215.2 (M+H).

Step 4: Ethyl 2-(5-ethoxy-6-((4-methoxybenzyl)oxy)pyridin-3-yl)-4,6-dimethylpyrimidine-5-carboxylate

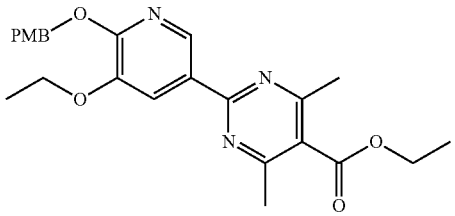

To a solution of 3-ethoxy-2-((4-methoxybenzyl)oxy)-5-(4,4,5,5-tetramethyl-1,3,2-dioxaborolan-2-yl)pyridine (2.51 g, 6.52 mmol), ethyl 2-chloro-4,6-dimethylpyrimidine-5-carboxylate (1.4 g, 6.52 mmol) and Cs$_2$CO$_3$ (4.25 g, 13.04 mmol) in 1,4-dioxane (15 mL) and water (5.00 mL) stirred under N$_2$ at 20° C. was added PdCl$_2$(dppf) (0.477 g, 0.652 mmol) in one charge. The reaction vessel was heated in 110° C. for 2 hr. Then the solution was concentrated and distributed between EA and water. The combined organic extract was washed with brine, dried over MgSO$_4$, filtered and concentrated. The residue was purified by silica column chromatography (PE/EA=10:1, 5:1). All fractions found to contain product by TLC (PE/EA=2:1, R$_f$ 0.5) were combined and concentrated to yield a light yellow solid of ethyl 2-(5-ethoxy-6-((4-methoxybenzyl)oxy)pyridin-3-yl)-4,6-dimethylpyrimidine-5-carboxylate (1.7 g, 3.89 mmol, 59.6% yield): $^1$H NMR (400 MHz, CDCl$_3$) δ 8.86-8.82 (m, 1H), 8.08-8.04 (m, 1H), 7.48-7.42 (m, 2H), 6.87 (d, J=8.6 Hz, 2H), 5.49 (s, 4.43 (s, 2H), 4.23-4.15 (m, 2H), 3.79 (s, 3H), 2.58 (s, 6H), 1.52-1.45 (m, 3H), 1.41 (t, J=7.2 Hz, 3H); LCMS m/z 438.2 (M+H).

Step 5: 2-(5-Ethoxy-6-oxo-1,6-dihydropyridin-3-yl)-4,6-dimethylpyrimidine-5-carboxylic acid

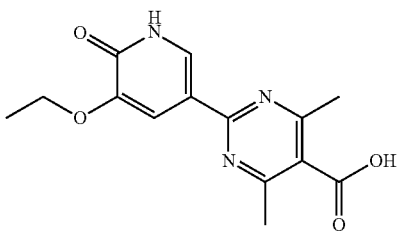 [SMILES: CCOc1cc(-c2nc(C)c(C(=O)O)c(C)n2)c[nH]c1=O]

To a solution of ethyl 2-(5-ethoxy-6-((4-methoxybenzyl)oxy)pyridin-3-yl)-4,6-dimethylpyrimidine-5-carboxylate (500 mg, 1.143 mmol) in THF (5 mL) stirred under N$_2$ at 20° C. was added NaOH (2.5 mL, 6.25 mmol) in one charge. The reaction mixture was stirred at 100° C. for 12 hr. Then the solution was concentrated and neutralized with con. HCl to pH=7.0 with stirring. Then filtered, and the filtrate cake was washed with water (10 mL). The filtrate cake was dried in vacuo to give a off white solid of 2-(5-ethoxy-6-oxo-1,6-dihydropyridin-3-yl)-4,6-dimethylpyrimidine-5-carboxylic acid (300 mg, 1.037 mmol, 91.0% yield). TLC (DCM/MeOH=10:1, R$_f$ 0.4): $^1$H NMR (400 MHz, CD$_3$OD) δ 8.16 (d, J=2.0 Hz, 1H), 7.87 (d, J=2.0 Hz, 1H), 4.18-4.12 (m, 2H), 2.59-2.56 (m, 6H), 1.47 (t, J=6.9 Hz, 3H); LCMS m/z 290.1 (M+H).

Step 6: 1-(4-((Dimethylamino)methyl)-3-(trifluoromethyl)phenyl)-3-(2-(5-ethoxy-6-oxo-1,6-dihydropyridin-3-yl)-4,6-dimethylpyrimidin-5-yl)urea

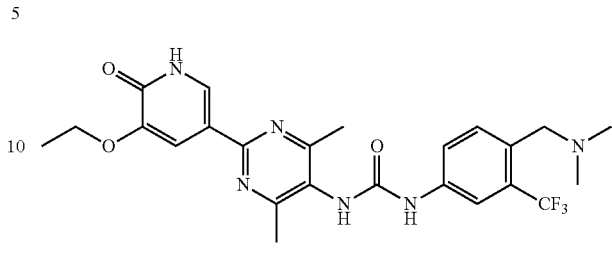

To a solution of 2-(5-ethoxy-6-oxo-1,6-dihydropyridin-3-yl)-4,6-dimethylpyrimidine-5-carboxylic acid (150 mg, 0.519 mmol), 4-((dimethylamino)methyl)-3-(trifluoromethyl)aniline (113 mg, 0.519 mmol) and Et$_3$N (79 mg, 0.778 mmol) in 1,4-dioxane (8 mL) stirred under N$_2$ at 20° C. was added DPPA (171 mg, 0.622 mmol) in one charge. The reaction mixture was heated to 80° C. for 2 hr. Then the solution was concentrated. The residue was purified by preparative HPLC (Instrument: DC/Column: ASB C18 150*25 mm/Mobile phase A: Water+0.1% HCl/Mobile phase B: MeCN/Flowrate: 25 mL/min/Gradient Profile Description: 15-55(B %)) to yield a yellow solid 1-(4-((dimethylamino)methyl)-3-(trifluoromethyl)phenyl)-3-(2-(5-ethoxy-6-oxo-1,6-dihydropyridin-3-yl)-4,6-dimethylpyrimidin-5-yl)urea dihydrochloride (14.17 mg, 0.024 mmol, 4.72% yield). TLC (DCM/MeOH=5:1, R$_f$ 0.4): $^1$H NMR (400 MHz, CD$_3$OD) δ 8.23 (d, J=2.2 Hz, 1H), 8.10 (d, J=2.0 Hz, 1H), 7.92 (d, J=2.0 Hz, 1H), 7.87 (dd, J=2.0, 8.4 Hz, 1H), 7.71 (d, J=8.4 Hz, 1H), 4.46 (s, 2H), 4.18 (q, J=7.2 Hz, 2H), 2.92 (s, 6H), 2.59 (s, 6H), 1.48 (t, J=7.0 Hz, 3H); ES-LCMS m/z 505.3 (M+H).

EXAMPLE 60

1-(4-Chloro-3-(trifluoromethyl)phenyl)-3-(2-(5-ethoxy-6-oxo-1,6-dihydropyridin-3-yl)-4-methylpyrimidin-5-yl)urea

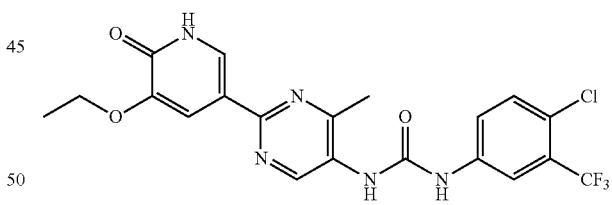

Step 1: 1-(4-Chloro-3-(trifluoromethyl)phenyl)-3-(2-(5-ethoxy-6-((4-methoxybenzyl)oxy)pyridin-3-yl)-4-methylpyrimidin-5-yl)urea

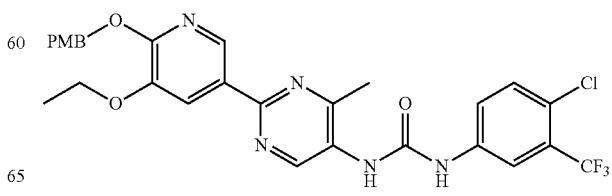

233

To a solution of 2-(5-ethoxy-6-((4-methoxybenzyl)oxy)pyridin-3-yl)-4-methylpyrimidine-5-carboxylic acid (100 mg, 0.253 mmol) in 1,4-dioxane (5 mL) stirred under N₂ at 20° C. was added Et₃N (0.053 mL, 0.379 mmol) and DPPA (84 mg, 0.303 mmol) in one charge. The reaction mixture was stirred at rt for 30 mins. To the mixture, a solution of 4-chloro-3-(trifluoromethyl)aniline (39.6 mg, 0.202 mmol) in 1 mL of 1,4-dioxane (1 mL) was added. The reaction solution was heated to 100° C. with stirring for 3 h. The solution was concentrated in vacuo and the residue was purified by preparative TLC (PE/EA=5:1, R$_f$=0.6) to yield a off white solid of 1-(4-chloro-3-(trifluoromethyl)phenyl)-3-(2-(5-ethoxy-6-((4-methoxybenzyl)oxy)pyridin-3-yl)-4-methylpyrimidin-5-yl)urea (70 mg, 0.088 mmol, 34.8% yield). $^1$H NMR (400 MHz, CD₃OD) δ 8.68 (s, 1H), 8.49 (s, 1H), 8.09 (s, 1H), 8.01-7.98 (m, 1H), 7.65 (s, 1H), 7.51-7.48 (m, 1H), 7.41-7.38 (m, 2H), 6.92-6.89 (m, 2H), 5.39 (s, 2H), 4.16-4.13 (m, 2H), 3.78 (s, 3H), 2.57 (s, 3H), 1.44-1.41 (m, 3H); ES-LCMS m/z 588.0 (M+H).

Step 2: 1-(4-Chloro-3-(trifluoromethyl)phenyl)-3-(2-(5-ethoxy-6-oxo-1,6-dihydropyridin-3-yl)-4-methyl-pyrimidin-5-yl)urea

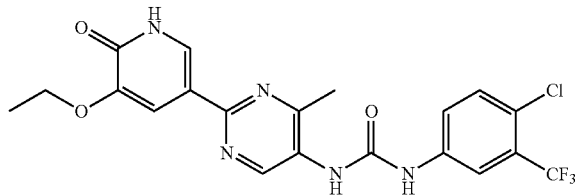 [SMILES: CCOc1cc(-c2ncc(NC(=O)Nc3ccc(Cl)c(C(F)(F)F)c3)c(C)n2)c[nH]c1=O]

To a solution of 1-(4-chloro-3-(trifluoromethyl)phenyl)-3-(2-(5-ethoxy-6-((4-methoxybenzyl)oxy)pyridin-3-yl)-4-methylpyrimidin-5-yl)urea (70 mg, 0.088 mmol) in DCM (2 mL) stirred under N₂ at 20° C. was added HCl in MeOH (0.5 mL, 2.000 mmol) in one charge. The reaction mixture was stirred at 20° C. for 1 hr. Then the solution was concentrated. The residue was purified by preparative HPLC (Column: ASB C18 150*25 mm/Mobile phase A: Water+0.1% HCl)/Mobile phase B: MeCN/Flowrate: 25 mL/min/Run time: 15 min/Gradient Profile Description: 40-70(B %)) to give a yellow solid of 1-(4-chloro-3-(trifluoromethyl)phenyl)-3-(2-(5-ethoxy-6-oxo-1,6-dihydropyridin-3-yl)-4-methylpyrimidin-5-yl)urea hydrochloride (35.11 mg, 0.069 mmol, 78% yield). TLC (DCM/MeOH=5:1, R$_f$=0.4). $^1$H NMR (400 MHz, CD₃OD) δ 9.11 (s, 1H), 8.11 (d, J=2.2 Hz, 1H), 8.03 (d, J=2.4 Hz, 1H), 7.86 (d, J=2.0 Hz, 1H), 7.64 (dd, J=2.4, 8.8 Hz, 1H), 7.52 (d, J=8.8 Hz, 1H), 4.16 (q, J=7.0 Hz, 2H), 2.59 (s, 3H), 1.48 (t, J=7.1 Hz, 3H); ES-LCMS m/z 467.9 (M+H).

EXAMPLE 61

2-(4-(3-(2-(4-Ethoxy-6-oxo-1,6-dihydropyridin-3-yl)-4-methylpyrimidin-5-yl)ureido)-2-(trifluoromethyl)phenyl)-2-methylpropanamide

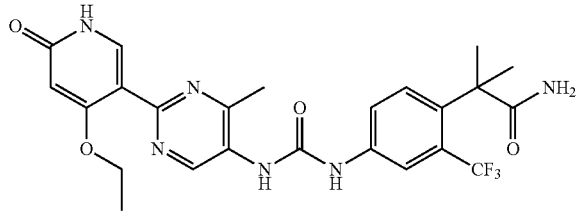 [SMILES: CCOc1cc(=O)[nH]cc1-c1ncc(NC(=O)Nc2ccc(C(C)(C)C(N)=O)c(C(F)(F)F)c2)c(C)n1]

234

Step 1: 2-(4-(3-(2-(4-Ethoxy-6-((4-methoxybenzyl)oxy)pyridin-3-yl)-4-methylpyrimidin-5-yl)ureido)-2-(trifluoromethyl)phenyl)-2-methylpropanamide

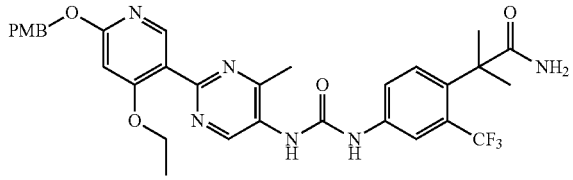

To a solution of 2-(4-ethoxy-6-((4-methoxybenzyl)oxy)pyridin-3-yl)-4-methylpyrimidine-5-carboxylic acid (0.2 g, 0.506 mmol) in dioxane (5 mL) stirred under N₂ at 20° C. was added Et₃N (0.106 mL, 0.759 mmol) and DPPA (0.167 g, 0.607 mmol) in one charge. The reaction mixture was stirred at rt for 30 mins. To the mixture, a solution of 2-(4-amino-2-(trifluoromethyl)phenyl)-2-methylpropanamide (0.125 g, 0.506 mmol) in 1 mL of 1,4-dioxane was added. The reaction solution was heated to 100° C. with stirring for 3 hr. The solution was concentrated in vacuo and the residue was purified by preparative TLC (DCM/MeOH=10:1, R$_f$=0.5) to yield a light yellow solid of 2-(4-(3-(2-(4-ethoxy-6-((4-methoxybenzyl)oxy)pyridin-3-yl)-4-methylpyrimidin-5-yl)ureido)-2-(trifluoromethyl)phenyl)-2-methylpropanamide (25 mg, 0.039 mmol, 7.74% yield): $^1$H NMR (400 MHz, CD₃OD) δ 9.17 (s, 1H), 8.27 (s, 1H), 7.93-7.92 (m, 1H), 7.77 (s, 1H), 7.66 (s, 1H), 7.40-7.37 (m, 2H), 6.93-6.90 (m, 2H), 6.48 (s, 1H), 5.31 (s, 2H), 4.14-4.12 (m, 2H), 3.77 (s, 3H), 2.56 (s, 3H), 1.61 (s, 6H), 1.37-1.35 (m, 3H); ES-LCMS m/z 639.2 (M+H).

Step 2: 2-(4-(3-(2-(4-Ethoxy-6-oxo-1,6-dihydropyridin-3-yl)-4-methylpyrimidin-5-yl)ureido)-2-(trifluoromethyl)phenyl)-2-methylpropanamide

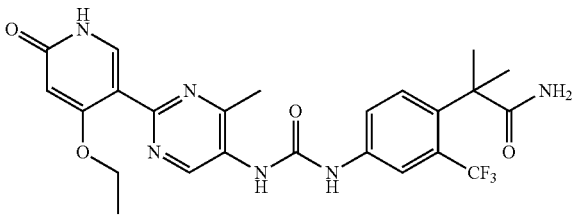 [SMILES: CCOc1cc(=O)[nH]cc1-c1ncc(NC(=O)Nc2ccc(C(C)(C)C(N)=O)c(C(F)(F)F)c2)c(C)n1]

To a solution of 2-(4-(3-(2-(4-ethoxy-6-((4-methoxybenzyl)oxy)pyridin-3-yl)-4-methylpyrimidin-5-yl)ureido)-2-(trifluoromethyl)phenyl)-2-methylpropanamide (25 mg, 0.039 mmol) in DCM (3 mL) stirred under N₂ at 20° C. was added HCl in MeOH (0.5 mL, 2.000 mmol) in one charge. The reaction mixture was stirred at 20° C. for 1 hr. Then the solution was concentrated. The residue was purified by preparative HPLC (Instrument: DC/Column: ASB C18 150*25 mm/Mobile phase A: Water+0.1% HCl/Mobile phase B: MeCN/Flowrate: 25 mL/min/Gradient Profile Description: 20-50(B %)) to yield a off white solid of 2-(4-(3-(2-(4-ethoxy-6-oxo-1,6-dihydropyridin-3-yl)-4-methylpyrimidin-5-yl)ureido)-2-(trifluoromethyl)phenyl)-2-methylpropanamide hydrochloride (9.34 mg, 0.017 mmol, 43.0% yield). TLC (DCM/MeOH=5:1, R$_f$=0.4): $^1$H NMR (400 MHz, CD₃OD) δ 9.53 (s, 1H), 8.40 (s, 1H), 7.98 (s, 1H), 7.68 (s, 2H), 6.15 (s, 1H), 4.35 (q, J=6.9 Hz, 2H), 2.76 (s, 3H), 1.62 (s, 6H), 1.48 (t, J=7.1 Hz, 3H)ES-LCMS m/z 519.1 (M+H).

EXAMPLE 62

1-(5'-Ethoxy-4-methyl-6'-oxo-1',6'-dihydro-[3,3'-bipyridin]-6-yl)-3-(4-((3-methyloxetan-3-yl)oxy)-3-(trifluoromethyl)phenyl)urea

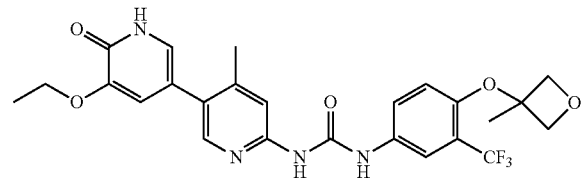 [SMILES: CCOc1cc(-c2cnc(NC(=O)Nc3ccc(OC4(C)COC4)c(C(F)(F)F)c3)cc2C)c[nH]c1=O]

Step 1: 5-Bromo-2-isocyanato-4-methylpyridine

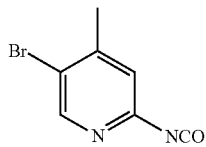

To a solution of 5-bromo-4-methylpyridin-2-amine (500 mg, 2.67 mmol) in THF (6 mL) stirred under N₂ at 20° C. was added triphosgene (278 mg, 0.936 mmol) in one charge. The reaction mixture was stirred at 60° C. for 2 hr.

Step 2: 1-(5-Bromo-4-methylpyridin-2-yl)-3-(4-((3-methyloxetan-3-yl)oxy)-3-(trifluoromethyl)phenyl)urea

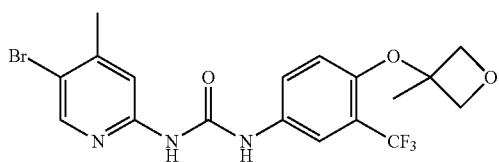 [SMILES: Cc1cc(NC(=O)Nc2ccc(OC3(C)COC3)c(C(F)(F)F)c2)ncc1Br]

To a solution of 4-((3-methyloxetan-3-yl)oxy)-3-(trifluoromethyl)aniline (453 mg, 1.831 mmol), DMAP (11.18 mg, 0.092 mmol) and Et₃N (0.765 mL, 5.49 mmol) in THF (8 mL) stirred under N₂ at 40° C. was added 5-bromo-2-isocyanato-4-methylpyridine (500 mg, 1.831 mmol) in one charge. The reaction mixture was stirred at 40° C. for 1 hr. The solution was concentrated in vacuo and the residue was purified by preparative HPLC (MeCN/H₂O as eluants, acidic condition) to yield a yellow solid of 1-(5-bromo-4-methylpyridin-2-yl)-3-(4-((3-methyloxetan-3-yl)oxy)-3-(trifluoromethyl)phenyl)urea (500 mg, 0.880 mmol, 48.1% yield): ¹H NMR (400 MHz, DMSO-d₆) δ 9.92 (s, 1H), 9.38 (s, 1H), 8.32 (s, 1H), 7.91 (d, J=2.8 Hz, 1H), 7.62 (s, 1H), 7.52-7.49 (m, 1H), 6.70 (d, J=8.8 Hz, 1H), 4.73 (d, J=6.8 Hz, 2H), 4.58 (d, J=7.2 Hz, 2H), 2.31 (s, 3H), 1.63 (s, 3H); ES-LCMS m/z (M+H) 459.8, 461.9.

Step 3: 1-(5'-Ethoxy-6'-((4-methoxybenzyl)oxy)-4-methyl-[3,3'-bipyridin]-6-yl)-3-(4-((3-methyloxetan-3-yl)oxy)-3-(trifluoromethyl)phenyl)urea

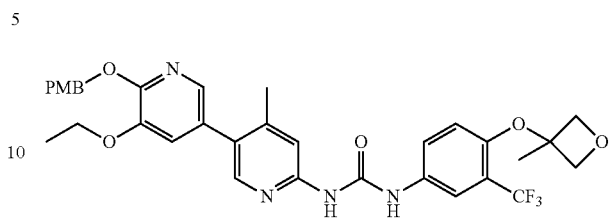

To a solution of 3-ethoxy-2-((4-methoxybenzyl)oxy)-5-(4,4,5,5-tetramethyl-1,3,2-dioxaborolan-2-yl)pyridine (126 mg, 0.326 mmol), 1-(5-bromo-4-methylpyridin-2-yl)-3-(4-((3-methyloxetan-3-yl)oxy)-3-(trifluoromethyl)phenyl)urea (150 mg, 0.326 mmol) and Cs₂CO₃ (265 mg, 0.815 mmol) in DMF (12 mL) and water (4.00 mL) stirred under N₂ at 20° C. was added PdCl₂(dppf) (11.92 mg, 0.016 mmol) in one charge. The reaction vessel was sealed and heated in CEM Discover using initial 100 W to 130° C. for 30 min. After cooling the reaction was concentrated in vacuo and the residue was purified by TLC (DCM:MeOH=10:1, R_f=0.7) to yield a off white solid of 1-(5'-ethoxy-6'-((4-methoxybenzyl)oxy)-4-methyl-[3,3'-bipyridin]-6-yl)-3-(4-((3-methyloxetan-3-yl)oxy)-3-(trifluoromethyl)phenyl)urea (70 mg, 0.068 mmol, 20.85% yield): ¹H NMR (400 MHz, CDCl₃) δ 8.13 (br, 1H), 8.02 (s, 1H), 7.79 (d, J=2.0 Hz, 1H), 7.52-7.59 (m, 2H), 7.41-7.39 (m, 2H), 6.92 (d, J=2.0 Hz, 1H), 6.86-6.84 (m, 2H), 6.68 (s, 1H), 6.38 (d, J=9.2 Hz, 1H), 5.39 (s, 2H), 4.92 (d, J=6.8 Hz, 2H), 4.52 (d, J=7.2 Hz, 2H), 4.06-4.01 (m, 2H), 3.42 (s, 3H), 2.22 (s, 3H), 1.68 (s, 3H), 1.39 (t, J=7.0 Hz, 3H); ES-LCMS m/z 639.2 (M+H).

Step 4: 1-(5'-Ethoxy-4-methyl-6'-oxo-1',6'-dihydro-[3,3'-bipyridin]-6-yl)-3-(4-((3-methyloxetan-3-yl)oxy)-3-(trifluoromethyl)phenyl)urea

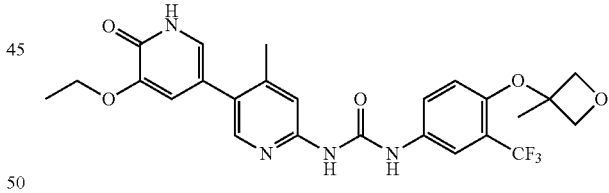

To compound 1-(5'-ethoxy-6'-((4-methoxybenzyl)oxy)-4-methyl-[3,3'-bipyridin]-6-yl)-3-(4-((3-methyloxetan-3-yl)oxy)-3-(trifluoromethyl)phenyl)urea (70 mg, 0.110 mmol) was added TFA in DCM (3 mL, 4.46 mmol) at rt. The reaction mixture was stirred at 20° C. for 1 hr. Then the solution was concentrated and distributed between EA and saturated NaHCO₃ solution. The combined organic extract was washed with brine, dried over MgSO₄, filtered and concentrated. The residue was purified by preparative HPLC (MeCN/H₂O as eluants, basic condition) to yield a white solid of 1-(5'-ethoxy-4-methyl-6'-oxo-1',6'-dihydro-[3,3'-bipyridin]-6-yl)-3-(4-((3-methyloxetan-3-y0oxy)-3-(trifluoromethyl)phenyl)urea (26 mg, 0.049 mmol, 44.8% yield). TLC (DCM/MeOH=10:1, R_f 0.3): ¹H NMR (400 MHz, CDCl₃) δ 8.07 (s, 1H), 7.75-7.70 (m, 3H), 6.95 (s, 1H), 6.70-6.67 (m, 2H), 6.44 (d, J=8.8 Hz, 1H), 4.98 (d, J=6.8 Hz, 2H), 4.58 (d, J=6.8 Hz, 2H), 4.09-4.04 (m, 2H), 2.30 (s, 3H), 1.74 (s, 3H), 1.53 (t, J=7.2 Hz, 3H); ES-LCMS m/z 519.2 (M+H).

EXAMPLE 63

2-(4-(3-(2-(5-Ethoxy-6-oxo-1,6-dihydropyridin-3-yl)-4-methylpyrimidin-5-yl)ureido)-2-(trifluoromethyl)phenyl)-2-methylpropanamide

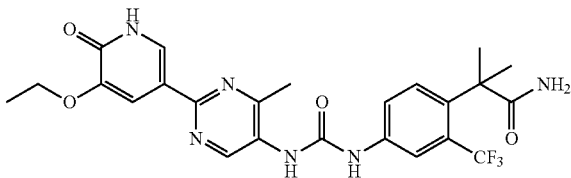 [SMILES: CCOc1cc(-c2ncc(NC(=O)Nc3ccc(C(C)(C)C(N)=O)c(C(F)(F)F)c3)c(C)n2)c[nH]c1=O]

Step 1: 2-(4-(3-(2-(5-Ethoxy-6-((4-methoxybenzyl)oxy)pyridin-3-yl)-4-methylpyrimidin-5-yl)ureido)-2-(trifluoromethyl)phenyl)-2-methylpropanamide

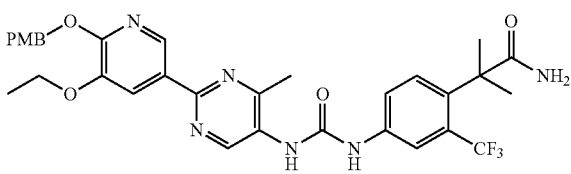

To a solution of 2-(5-ethoxy-6-((4-methoxybenzyl)oxy)pyridin-3-yl)-4-methylpyrimidine-5-carboxylic acid (0.2 g, 0.506 mmol) in 1,4-dioxane (4 mL) stirred under a $N_2$ atmosphere at 20° C. was added $Et_3N$ (0.106 mL, 0.759 mmol) and DPPA (0.167 g, 0.607 mmol) in one charge. The reaction mixture was stirred for 15 mins. To the mixture, a solution of 2-(4-amino-2-(trifluoromethyl)phenyl)-2-methylpropanamide (0.125 g, 0.506 mmol) in 1 mL of 1,4-dioxane was added, and heated to 100° C. for 2 hr. The solvent was removed on a rotational evaporator. The residue was purified by preparative TLC (DCM:MeOH=10:1, $R_f$=0.5) to yield a yellow solid of 2-(4-(3-(2-(5-ethoxy-6-((4-methoxybenzyl)oxy)pyridin-3-yl)-4-methylpyrimidin-5-yl)ureido)-2-(trifluoromethyl)phenyl)-2-methylpropanamide (0.15 g, 0.235 mmol, 46.4% yield): $^1$H NMR (400 MHz, $CD_3OD$) δ 9.05 (s, 1H) 8.63 (s, 1H), 8.00 (s, 1H), 7.63 (s, 1H), 7.58-7.53 (m, 2H), 7.42-7.40 (m, 2H), 6.94-6.92 (m, 2H), 5.38 (s, 2H), 4.15-4.11 (m, 2H), 3.78 (s, 3H), 2.50 (s, 3H), 1.47 (s, 6H), 1.35-1.33 (m, 3H); LCMS m/z: 639.8 (M+H).

Step 2: 2-(4-(3-(2-(5-Ethoxy-6-oxo-1,6-dihydropyridin-3-yl)-4-methylpyrimidin-5-yl)ureido)-2-(trifluoromethyl)phenyl)-2-methylpropanamide

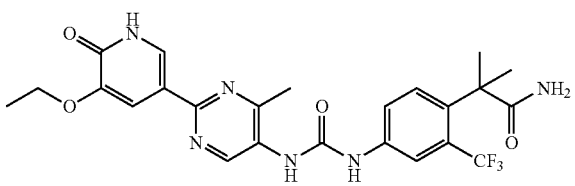 [SMILES: CCOc1cc(-c2ncc(NC(=O)Nc3ccc(C(C)(C)C(N)=O)c(C(F)(F)F)c3)c(C)n2)c[nH]c1=O]

To a solution of 2-(4-(3-(2-(5-ethoxy-6-((4-methoxybenzyl)oxy)pyridin-3-yl)-4-methylpyrimidin-5-yl)ureido)-2-(trifluoromethyl)phenyl)-2-methylpropanamide (150 mg, 0.235 mmol) in DCM (5 mL) stirred at a $N_2$ atmosphere at 20° C. was added HCl in MeOH (0.5 mL, 2.000 mmol) in one charge. The reaction mixture was stirred at 20° C. for 1 hr. Then the solution was concentrated. The residue was purified by preparative HPLC (Instrument: DC/Column: ASB C18 150*25 mm/Mobile phase A: Water+0.1% HCl/Mobile phase B: MeCN/Flowrate: 25 mL/min/Gradient Profile Description: 17-47(B %)) to yield a off white solid of 2-(4-(3-(2-(5-ethoxy-6-oxo-1,6-dihydropyridin-3-yl)-4-methylpyrimidin-5-yl)ureido)-2-(trifluoromethyl)phenyl)-2-methylpropanamide hydrochloride (69.57 mg, 0.121 mmol, 51.6% yield). TLC (DCM/MeOH=5:1, $R_f$=0.4): $^1$H NMR (400 MHz, $CD_3OD$) δ 9.26 (s, 1H), 8.19 (d, J=2.0 Hz, 1H), 7.95 (s, 1H), 7.88 (d, J=2.0 Hz, 1H), 7.67 (s, 2H), 4.19 (q, J=6.9 Hz, 2H), 2.66 (s, 3H), 1.62 (s, 6H), 1.50 (t, J=6.9 Hz, 3H); ES-LCMS m/z 519.1 (M+H).

EXAMPLE 64

1-(4-(5-Ethoxy-6-oxo-1,6-dihydropyridin-3-yl)-2-fluorophenyl)-3-(4-(3-hydroxy-2,2-dimethylpropyl)-3-(trifluoromethyl)phenyl)urea

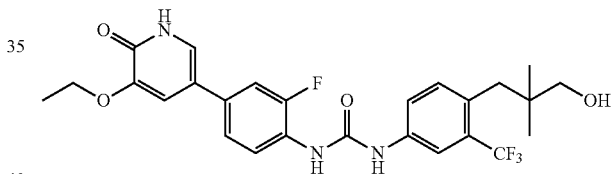

Step 1: 2-(3-Fluoro-4-isocyanatophenyl)-4,4,5,5-tetramethyl-1,3,2-dioxaborolane

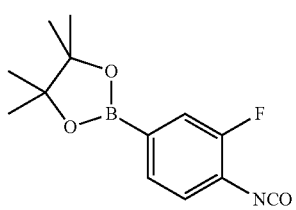

A mixture of 2-fluoro-4-(4,4,5,5-tetramethyl-1,3,2-dioxaborolan-2-yl)aniline (450 mg, 1.898 mmol) in THF (10 mL) was added triphosgene (225 mg, 0.759 mmol). The mixture was stirred at 60° C. for 1 hr. LCMS showed the reaction was finished. The mixture was concentrated to give 2-(3-fluoro-4-isocyanatophenyl)-4,4,5,5-tetramethyl-1,3,2-dioxaborolane (478 mg, 1.733 mmol, 91% yield).

Step 2: Ethyl 3-(4-(3-(2-fluoro-4-(4,4,5,5-tetramethyl-1,3,2-dioxaborolan-2-yl)phenyl)ureido)-2-(trifluoromethyl)phenyl)-2,2-dimethylpropanoate

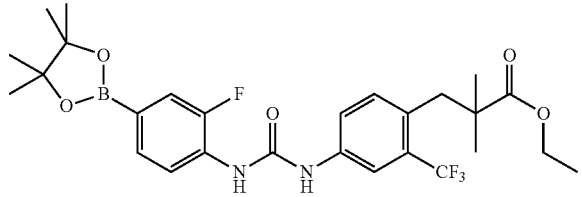 [SMILES: CCOC(=O)C(C)(C)Cc1ccc(NC(=O)Nc2ccc(B3OC(C)(C)C(C)(C)O3)cc2F)cc1C(F)(F)F]

To a mixture of 2-(3-fluoro-4-isocyanatophenyl)-4,4,5,5-tetramethyl-1,3,2-dioxaborolane (415 mg, 1.578 mmol) in THF (20 mL) was added Et$_3$N (0.440 mL, 3.16 mmol) and ethyl 3-(4-amino-2-(trifluoromethyl)phenyl)-2,2-dimethylpropanoate (456 mg, 1.578 mmol). The mixture was stirred at 60° C. for 12 hrs. LCMS showed the reaction was finished. The mixture was concentrated in vacuo and the residue was purified by column (PE/EA=3:1, R$_f$ 0.2) to give ethyl 3-(4-(3-(2-fluoro-4-(4,4,5,5-tetramethyl-1,3,2-dioxaborolan-2-yl)phenyl)ureido)-2-(trifluoromethyl)phenyl)-2,2-dimethylpropanoate (857 mg, 1.341 mmol, 85% yield). $^1$H NMR (400 MHz, CDCl$_3$) 8.18 (d, J=8.0 Hz, 1H), 7.67 (d, J=2.0 Hz, 1H), 7.54 (d, J=4.4 Hz, 1H), 7.48-7.45 (m, 1H), 7.20 (d, J=2.8 Hz, 1H), 7.12 (d, J=8.8 Hz, 1H), 4.22-4.16 (m, 2H), 3.08 (s, 2H),1.32 (s, 12H), 1.29-1.25 (m, 3H); 1.23 (s, 6H), ES-LCMS m/z 553.1 (M+H).

Step 3: 3-(4-(3-(4-(5-Ethoxy-6-((4-methoxybenzyl)oxy)pyridin-3-yl)-2-fluorophenyl)ureido)-2-(trifluoromethyl)phenyl)-2,2-dimethylpropanoate

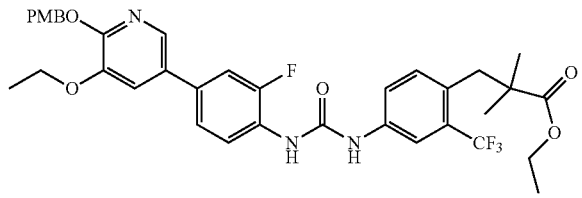

To a mixture of ethyl 3-(4-(3-(2-fluoro-4-(4,4,5,5-tetramethyl-1,3,2-dioxaborolan-2-yl)phenyl)ureido)-2-(trifluoromethyl)phenyl)-2,2-dimethylpropanoate (150 mg, 0.272 mmol) in 1,4-dioxane (3 mL) and water (1 mL) was added 5-bromo-3-ethoxy-2-((4-methoxybenzyl)oxy)pyridine (100 mg, 0.296 mmol), PdCl$_2$(dppf) (19.87 mg, 0.027 mmol)and Cs$_2$CO$_3$ (177 mg, 0.543 mmol) under N$_2$. The mixture was stirred at 110° C. under microwave irradiation for 30 min. LCMS showed the reaction was finished. The mixture was filtered, and the filtrate was concentrated in vacuo and the residue was purified by TLC to obtain ethyl 3-(4-(3-(4-(5-ethoxy-6-((4-methoxybenzyl)oxy)pyridin-3-yl)-2-fluorophenyl)ureido)-2-(trifluoromethyl)phenyl)-2,2-dimethylpropanoate (104 mg, 0.133 mmol, 49.1% yield). $^1$H NMR (400 MHz, CDCl$_3$) 8.11-8.05 (m, 1H), 7.85 (d, J=6.4 Hz, 2H), 7.65-7.60 (m, 1H), 7.37-7.34 (m, 4H), 7.17(d, J=8.4 Hz, 2H), 6.88-6.85 (m, 2H), 5.46 (s, 2H), 4.15-4.09 (m, 4H), 3.76 (s, 3H), 3.05 (s, 2H), 1.40-1.39 (m, 3H), 1.38-1.37 (m, 3H), 1.25 (s, 6H); ES-LCMS m/z 564.2 (M-PMB+H).

Step 4: 1-(4-(5-Ethoxy-6-((4-methoxybenzyl)oxy)pyridin-3-yl)-2-fluorophenyl)-3-(4-(3-hydroxy-2,2-dimethylpropyl)-3-(trifluoromethyl)phenyl)urea

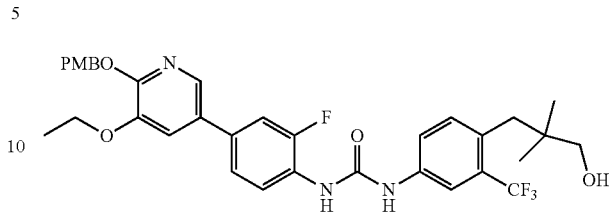

To a mixture of ethyl 3-(4-(3-(4-(5-ethoxy-6-((4-methoxybenzyl)oxy)pyridin-3-yl)-2-fluorophenyl)ureido)-2-(trifluoromethyl)phenyl)-2,2-dimethylpropanoate (80 mg, 0.117 mmol) in THF (10 mL) was added LAH (4.44 mg, 0.117 mmol) under N$_2$. The mixture was stirred at 20° C. under H$_2$ for 1 hr. LCMS showed the reaction was finished. The mixture was concentrated in vacuo and the residue was purified by TLC (PE/EA=2:1, R$_f$ 0.2) to give 1-(4-(5-ethoxy-6-((4-methoxybenzyl)oxy)pyridin-3-yl)-2-fluorophenyl)-3-(4-(3-hydroxy-2,2-dimethylpropyl)-3-(trifluoromethyl)phenyl)urea (30 mg, 0.042 mmol, 35.8% yield). $^1$H NMR (400 MHz, CDCl$_3$) 8.11-8.07 (m, 1H), 7.80 (d, J=2.0 Hz, 1H), 7.56 (d, J=7.6 Hz, 2H), 7.37-7.32 (m, 3H), 7.18-7.14 (m, 2H), 7.11-7.10 (m, 1H), 6.99-6.77 (m, 2H), 5.36 (s, 2H), 4.07-4.02 (m, 2H), 3.70 (s, 3H), 3.66 (d, J=8.0 Hz, 2H), 3.00 (s, 2H), 1.38-1.34 (m, 3H), 1.22 (s, 6H); ES-LCMS m/z 522.0 (M-PMB+H).

Step 5: 1-(4-(5-Ethoxy-6-oxo-1,6-dihydropyridin-3-yl)-2-fluorophenyl)-3-(4-(3-hydroxy-2,2-dimethylpropyl)-3-(trifluoromethyl)phenyl)urea

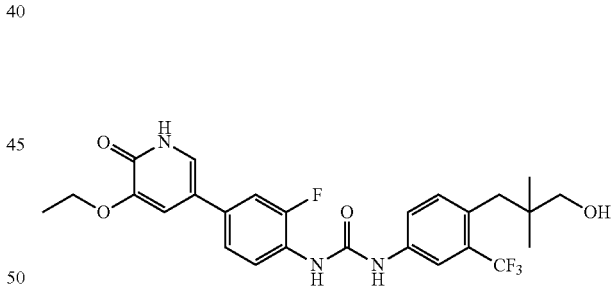

To a mixture of 1-(4-(5-ethoxy-6-((4-methoxybenzyl)oxy)pyridin-3-yl)-2-fluorophenyl)-3-(4-(3-hydroxy-2,2-dimethylpropyl)-3-(trifluoromethyl)phenyl)urea (30 mg, 0.047 mmol) in MeOH (5 mL) was added Pd/C (4.98 mg, 0.047 mmol) under N$_2$. The mixture was stirred at 20° C. under H$_2$ for 1 hr. LCMS showed the reaction was finished. The mixture was concentrated in vacuo and the residue was purified by preparative HPLC to give 1-(4-(5-ethoxy-6-oxo-1,6-dihydropyridin-3-yl)-2-fluorophenyl)-3-(4-(3-hydroxy-2,2-dimethylpropyl)-3-(trifluoromethyl)phenyl)urea (2.79 mg, 5.26 µmol, 11.24% yield): $^1$H NMR (400 MHz, CD$_3$OD) 8.15-8.13 (m, 1H), 7.84 (d, J=2.0 Hz, 1H), 7.54 (d, J=2.4 Hz, 1H), 7.39-7.35 (m, 3H), 7.32-7.25 (m, 2H), 4.14 (d, J=7.2 Hz, 2H), 3.34 (s, 2H), 2.76 (s, 2H), 1.48 (d, J=6.8 Hz, 3H), 0.84 (s, 6H); ES-LCMS m/z 522.2 (M+H).

EXAMPLE 65

1-(4-((4-Ethylpiperazin-1-yl)methyl)-3-(trifluoromethyl)phenyl)-3-(4-(6-oxo-1,6-dihydropyridin-3-yl)phenyl)urea

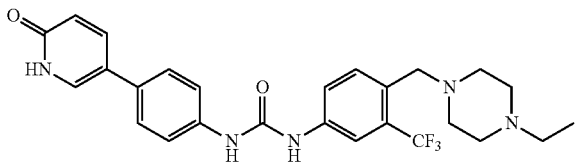 [SMILES: CCN1CCN(Cc2ccc(NC(=O)Nc3ccc(-c4ccc(=O)[nH]c4)cc3)cc2C(F)(F)F)CC1]

Step 1: 4-((1-Methyl-1H-pyrazol-4-yl)methyl)-3-(trifluoromethyl)aniline

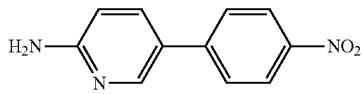

A mixture of 5-bromopyridin-2-amine (2 g, 11.56 mmol), (4-nitrophenyl)boronic acid (1.930 g, 11.56 mmol), PdCl$_2$(dppf) (0.423 g, 0.578 mmol), Cs$_2$CO$_3$ (7.53 g, 23.12 mmol) in 1,4-dioxane (30 mL) and water (5 mL) was heated to 100° C. for 1 hr at microwave. Then the mixture was concentrated to give the residue which was extracted with DCM (20 mL×2), dried over Na$_2$SO$_4$, concentrated to give the residue which was purified by via column chromatography to give 5-(4-nitrophenyl)pyridin-2-amine (1 g, 4.65 mmol, 40.2% yield); ES-LCMS m/z 216.1 (M+1).

Step 2: 5-(4-Nitrophenyl)pyridin-2(1H)-one

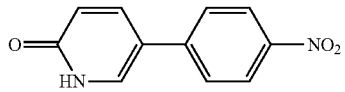

To a mixture of 5-(4-nitrophenyl)pyridin-2-amine (1 g, 4.65 mmol) in H$_2$SO$_4$ (33.2 mL, 3.5 M, 116 mmol) was added NaNO$_2$ (20.10 mL, 2 M, 40.2 mmol) at 0° C. After the mixture was stirred for 2 hrs later, the mixture was pour into ice water and extracted with DCM (200 mL×2), dried over Na$_2$SO$_4$, concentrated to give 5-(4-nitrophenyl)pyridin-2 (1H)-one (800 mg, 3.70 mmol, 80% yield): $^1$H NMR (400 MHz, CD$_3$OD) δ 8.30-8.27 (dd, J=8.8, 2.8 Hz, 2H), 8.02 (dd, J=9.2, 2.8 Hz, 1H), 7.89 (m, 1H), 7.80-7.77 (m, 2H), 6.68-6.65 (m, 1H); ES-LCMS m/z 217.1 (M+H).

Step 3: 1-(2-Fluoro-4-(4,4,5,5-tetramethyl-1,3,2-dioxaborolan-2-yl)phenyl)-3-(4(1-methyl-1H-pyrazol-4-yl)methyl)-3-(trifluoromethyl)phenyl)urea

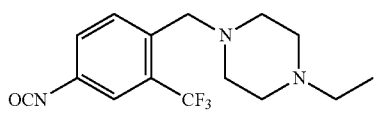

To a mixture of 4-((4-ethylpiperazin-1-yl)methyl)-3-(trifluoromethyl)aniline (80 mg, 0.278 mmol) in THF (10 mL) was added triphosgene (27.3 mg, 0.092 mmol), then mixture was heated to 70° C. for 30 min, the mixture was concentrated to give 1-ethyl-4-(4-isocyanato-2-(trifluoromethyl)benzyl)piperazine (84 mg, 0.268 mmol, 96% yield).

Step 4: 5-(4-Aminophenyl)pyridin-2(1H)-one

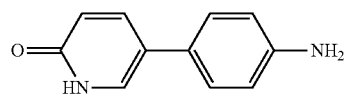

A mixture of 5-(4-nitrophenyl)pyridin-2(1H)-one (800 mg, 3.70 mmol), nickel (21.72 mg, 0.370 mmol) in MeOH (20 mL) was stirred overnight at 20 psi under H$_2$ atmosphere. Then the mixture was filtered and the filtrate was concentrated to give 5-(4-aminophenyl)pyridin-2(1H)-one (400 mg, 2.148 mmol, 58.1% yield): $^1$H NMR (400 MHz, CD$_3$OD) δ 7.88-7.85 (dd, J=8.8, 2.8 Hz, 1H), 7.58-7.57 (d, J=2.8 Hz, 1H), 7.25 (d, J=8.4 Hz, 1H), 6.79-6.77 (d, J=2.0 Hz, 1H), 6.62-6.59 (d, J=10.2 Hz, 1H); ES-LCMS m/z 187.1 (M+H).

Step 5: 1-(4-((4-Ethylpiperazin-1-yl)methyl)-3-(trifluoromethyl)phenyl)-3-(4-(6-oxo-1,6-dihydropyridin-3-yl)phenyl)urea

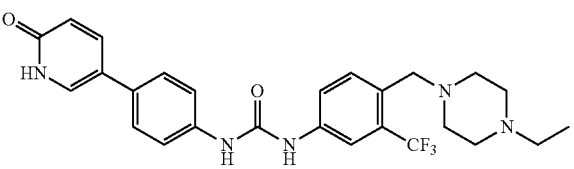 [SMILES: CCN1CCN(Cc2ccc(NC(=O)Nc3ccc(-c4ccc(=O)[nH]c4)cc3)cc2C(F)(F)F)CC1]

A mixture of 5-(4-aminophenyl)pyridin-2-ol (50 mg, 0.269 mmol), 5-(4-aminophenyl)pyridin-2-ol (50 mg, 0.269 mmol), Et$_3$N (0.075 mL, 0.537 mmol) in THF (10 mL) was stirred for overnight. Then the mixture was concentrated to give the residue which was purified by preparative HPLC to give 1-(4-((4-ethylpiperazin-1-yl)methyl)-3-(trifluoromethyl)phenyl)-3-(4-(6-oxo-1,6-dihydropyridin-3-yl)phenyl)urea dihydrochloride (119.55 mg, 0.209 mmol, 78% yield): $^1$H NMR (400 MHz, CD$_3$OD) δ 8.60 (dd, J=9.2, 2.4 Hz, 1H), 8.41-8.40 (d, J=2.0 Hz, 1H), 8.17-8.16 (d, J=2.0 Hz, 1H), 8.05-8.03 (m, 1H), 7.85-7.83 (m, 1H), 7.66 (s, 4H), 7.32-7.29 (m, 1H), 4.64 (m, 2H), 3.88-3.70 (m, 8H), 3.40-3.34 (m, 2H), 1.43 (t, J=7.20 Hz, 3H); ES-LCMS m/z 500.1 (M+H).

EXAMPLE 66

1-(2-(5-Ethoxy-6-oxo-1,6-dihydropyridin-3-yl)-4-methylpyrimidin-5-yl)-3-(4-(1-(hydroxymethyl)cyclopropyl)-3-(trifluoromethyl)phenyl)urea hydrochloride

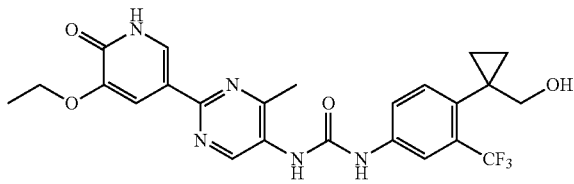 [SMILES: CCOc1cc(-c2ncc(NC(=O)Nc3ccc(C4(CO)CC4)c(C(F)(F)F)c3)c(C)n2)c[nH]c1=O]

Step 1: 1-(2-(Trifluoromethyl)phenyl)cyclopropanecarbonitrile

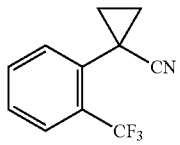

A solution of 2-(2-(trifluoromethyl)phenyl)acetonitrile (7 g, 37.8 mmol), N-benzyl-N,N-diethylethanaminium chloride (0.172 g, 0.756 mmol), 1-bromo-2-chloroethane (8.13 g, 56.7 mmol) was heated to 50° C. Then NaOH (9.07 g, 227 mmol) in water (10 mL) was added to above mixture portion wise at 50° C., the resulting mixture was stirred at this temperature for 16 h. The mixture was cooled to 25° C., pour into 150 mL of water, extracted with DCM (150 mL×2). The combined organic layer was washed with brine (100 mL), dried over anhydrous Na$_2$SO$_4$, filtered and concentrated under reduced pressure to afford 1-(2-(trifluoromethyl)phenyl)cyclopropanecarbonitrile (8 g, 36.0 mmol, 95% yield): $^1$H NMR (400 MHz, MeOD-d4) δ 7.76 (d, J=7.7 Hz, 1H), 7.66 (q, J=7.7 Hz, 2H), 7.60-7.54 (m, 1H), 1.77-1.73 (m, 2H), 1.52-1.47 (m, 2H); ES-LCMS m/z 212 (M+1).

Step 2: 1-(4-Nitro-2-(trifluoromethyl)phenyl)cyclopropanecarbonitrile

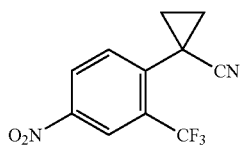 [SMILES: N#CC1(c2ccc([N+](=O)[O-])cc2C(F)(F)F)CC1]

To a solution of 1-(2-(trifluoromethyl)phenyl)cyclopropanecarbonitrile (8.5 g, 40.2 mmol) in H$_2$SO$_4$ (40 mL) was added potassium nitroperoxous acid (4.07 g, 40.2 mmol) portion wise at 0° C., the resulting mixture was stirred at this temperature for 20 min. The mixture was pour into 100 mL of ice/water, extracted with DCM (100 mL×2). The combined organic layer was washed with brine (50 mL), dried over anhydrous Na$_2$SO$_4$, filtered and concentrated under reduced pressure to afford 1-(4-nitro-2-(trifluoromethyl) phenyl)cyclopropanecarbonitrile (9 g, 26.0 mmol, 64.6% yield): $^1$H NMR (400 MHz, MeOD-d4) δ 8.57 (d, J=2.2 Hz, 1H), 8.49 (dd, J=2.3, 8.5 Hz, 1H), 7.99 (d, J=8.6 Hz, 1H), 1.89-1.82 (m, 2H), 1.63-1.57 (m, 2H).

Step 3: 1-(4-Nitro-2-(trifluoromethyl)phenyl)cyclopropanecarbaldehyde

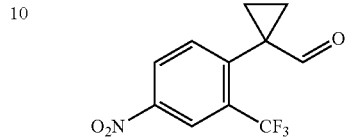

To a solution of 1-(4-nitro-2-(trifluoromethyl)phenyl)cyclopropanecarbonitrile (8 g, 31.2 mmol) in DCM (100 mL) was added DIBAl—H portionwise at −78° C., the resulting mixture was stirred at this temperature for 2 h. The mixture was pour into 50 mL of 2N HCl solution, extracted with DCM (150 mL×2). The combined organic layer was washed with brine (50 mL), dried over anhydrous Na$_2$SO$_4$, filtered and concentrated under reduced pressure to afford 1-(4-nitro-2-(trifluoromethyl)phenyl)cyclopropanecarbaldehyde (8 g, 24.69 mmol, 79% yield): $^1$H NMR (400 MHz, MeOD-d4) δ 8.85 (s, 1H), 8.54 (d, J=2.2 Hz, 1H), 8.45 (dd, J=2.3, 8.5 Hz, 1H), 7.77 (d, J=8.6 Hz, 1H), 1.84-1.77 (m, 2H), 1.65-1.56 (m, 2H); ES-LCMS m/z 202 (M+1).

Step 4: 1-(4-Amino-2-(trifluoromethyl)phenyl)cyclopropanecarbaldehyde

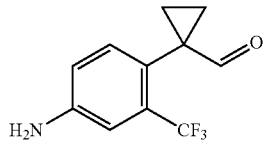 [SMILES: O=CC1(c2ccc([N+](=O)[O-])cc2C(F)(F)F)CC1]

A mixture of 1-(4-nitro-2-(trifluoromethyl)phenyl)cyclopropanecarbaldehyde (8 g, 30.9 mmol), Pd/C (3.28 g, 30.9 mmol) in MeOH (100 mL) was stirred for 2 h under H$_2$ atmosphere at 25° C. Then the mixture was filtered and the filtrate was concentrated was purified by silica column chromatography (20% EA:80% PE, 80 g silica column). All fractions found to contain product by TLC (EA:PE=1:2, R$_f$=0.5) were combined and concentrated to yield light yellow oil of 1-(4-amino-2-(trifluoromethyl)phenyl)cyclopropanecarbaldehyde (3.5 g, 12.22 mmol, 39.6% yield): $^1$H NMR (400 MHz, MeOD-d4) δ 9.01 (s, 1H), 7.14 (d, J=8.4 Hz, 1H), 7.02-6.96 (m, 1H), 6.82 (dd, J=2.1, 8.3 Hz, 1H), 1.58 (br. s., 2H), 1.38 (d, J=2.9 Hz, 2H); ES-LCMS m/z 230 (M+1).

Step 5: (1-(4-Amino-2-(trifluoromethyl)phenyl)cyclopropyl)methanol

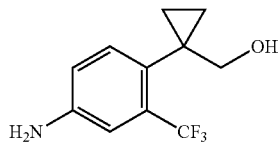 [SMILES: Nc1ccc(C2(CO)CC2)c(C(F)(F)F)c1]

To a solution of 1-(4-amino-2-(trifluoromethyl)phenyl) cyclopropanecarbaldehyde (4 g, 17.45 mmol) in MeOH (50 mL) was added NaBH₄ (1.321 g, 34.9 mmol) portion wise at 25° C., the resulting mixture was stirred at this temperature for 2 h. The mixture was concentrated, 20 mL of water was added, extracted with DCM (50 mL×2). The combined organic layer was washed with brine (50 mL), dried over anhydrous Na₂SO₄, filtered and concentrated under reduced pressure to afford (1-(4-amino-2-(trifluoromethyl)phenyl) cyclopropyl)methanol (3.1 g, 12.07 mmol, 69.1% yield): ¹H NMR (400 MHz, MeOD-d4) δ 7.29 (d, J=8.4 Hz, 1H), 6.93 (d, J=2.4 Hz, 1H), 6.79 (dd, J=2.2, 8.4 Hz, 1H), 3.49 (br. s., 2H), 0.90-0.83 (m, 2H), 0.80-0.73 (m, 2H); ES-LCMS m/z 232 (M+1).

Step 6: 4-(1-(((tert-Butyldimethylsilyl)oxy)methyl) cyclopropyl)-3-(trifluoromethyl)aniline

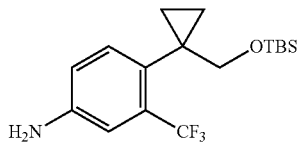 [SMILES: CC(C)(C)[Si](C)(C)OCC1(c2ccc(N)cc2C(F)(F)F)CC1]

To a solution of (1-(4-amino-2-(trifluoromethyl)phenyl) cyclopropyl)methanol (2.1 g, 9.08 mmol), 1H-imidazole (1.546 g, 22.71 mmol) in DCM (30 mL) was added TBSCl (1.506 g, 9.99 mmol) at 25° C., the resulting mixture was stirred at this temperature for 2 h. The mixture was pour into 50 mL of water, extracted with DCM (50 mL×2). The combined organic layer was washed with brine (50 mL), dried over anhydrous Na₂SO₄, filtered and concentrated under reduced pressure to afford the residue which was purified by silica column chromatography (20% EA:80% PE, 24 g silica column). All fractions found to contain product by TLC (EA:PE=1:2, R$_f$=0.5) were combined and concentrated to yield light yellow oil of 4-(1-(((tert-butyldimethylsilyl)oxy)methyl)cyclopropyl)-3-(trifluoromethyl)aniline (2.5 g, 6.51 mmol, 71.7% yield): ¹H NMR (400 MHz, MeOD-d4) δ 7.41 (d, J=8.4 Hz, 1H), 7.07 (d, J=2.2 Hz, 1H), 6.93 (dd, J=2.2, 8.4 Hz, 1H), 3.72 (br. s., 2H), 1.02-0.99 (m, 2H), 0.96 (s, 9H), 0.89 (s, 2H), 0.00 (s, 6H); ES-LCMS m/z 346 (M+1).

Step 7: 1-(4-(1-(((tert-Butyldimethylsilyl)oxy) methyl)cyclopropyl)-3-(trifluoromethyl)phenyl)-3-(2-(5-ethoxy-6-((4-methoxybenzyl)oxy)pyridin-3-yl)-4-methylpyrimidin-5-yl)urea

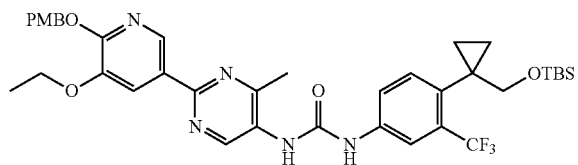

To a solution of 2-(5-ethoxy-6-((4-methoxybenzyl)oxy) pyridin-3-yl)-4-methylpyrimidine-5-carboxylic acid (100 mg, 0.253 mmol), Et₃N (0.053 mL, 0.379 mmol) in 1,4-dioxane (10 mL) was added DPPA (77 mg, 0.278 mmol) portionwise at 25° C., the resulting mixture was stirred at this temperature for 20 min. 4-(1-(((tert-butyldimethylsilyl) oxy)methyl)cyclopropyl)-3-(trifluoromethyl)aniline (96 mg, 0.278 mmol) was added to above mixture and heated to 100° C. for 2 h. The mixture was pour into 20 mL of water, extracted with DCM (50 mL×2). The organic phase was washed with brine, dried over Na₂SO₄, filtered and concentrated. The residue was purified by preparative TLC (DCM: MeOH=20:1, R$_f$=0.5) yield a white solid of 1-(4-(1-(((tert-butyldimethylsilyl)oxy)methyl)cyclopropyl)-3-(trifluoromethyl)phenyl)-3-(2-(5-ethoxy-6-((4-methoxybenzyl)oxy)pyridin-3-yl)-4-methylpyrimidin-5-yl) urea (50.0 mg, 0.047 mmol, 18.8% yield): ¹H NMR (400 MHz, MeOD-d4) δ 9.16 (s, 1H), 8.19 (d, J=2.0 Hz, 1H), 7.99 (d, J=2.0 Hz, 2H), 7.68-7.64 (m, 1H), 7.54 (d, J=8.6 Hz, 1H), 7.38 (d, J=8.6 Hz, 2H), 7.00 (d, J=8.6 Hz, 2H), 4.30-4.24 (m, 2H), 3.91-3.88 (m, 3H), 3.75 (br. s., 2H), 2.68 (s, 3H), 1.61 (t, J=7.1 Hz, 3H), 0.95 (s, 9H), 0.00 (s, 6H); ES-LCMS m/z 738 (M+1).

Step 8: 1-(2-(5-Ethoxy-6-oxo-1,6-dihydropyridin-3-yl)-4-methylpyrimidin-5-yl)-3-(4-(1-(hydroxymethyl)cyclopropyl)-3-(trifluoromethyl)phenyl)urea hydrochloride

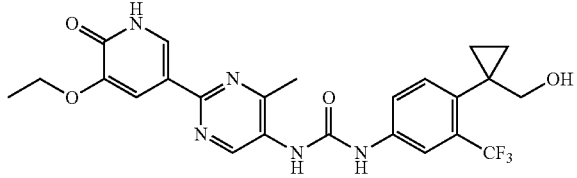 [SMILES: CCOc1cc(-c2ncc(NC(=O)Nc3ccc(C4(CO)CC4)c(C(F)(F)F)c3)c(C)n2)c[nH]c1=O]

A solution of 1-(4-(1-(((tert-butyldimethylsilyl)oxy) methyl)cyclopropyl)-3-(trifluoromethyl)phenyl)-3-(2-(5-ethoxy-6-((4-methoxybenzyl)oxy)pyridin-3-yl)-4-methylpyrimidin-5-yl)urea (50 mg, 0.068 mmol) in TFA in DCM (20%, 10 mL) was stirred for 30 min. Then the solution was concentrated, the residue was purified by preparative HPLC (Instrument: DC/Column:Gemini C18 150*25 mm*10 ul/Mobile phase A: Water (Water+0.1% HCl)/Mobile phase B: MeCN/Gradient: 30-60(B %)/Flowrate: 25 mL/min/Run time: 15 min) to yield a white solid of 1-(2-(5-ethoxy-6-oxo-1,6-dihydropyridin-3-yl)-4-methylpyrimidin-5-yl)-3-(4-(1-(hydroxymethyl)cyclopropyl)-3-(trifluoromethyl)phenyl)urea hydrochloride (6.71 mg, 0.012 mmol, 18.2% yield): ¹H NMR (400 MHz, MeOD-d4) δ 9.09 (s, 1H), 8.10 (d, J=2.0 Hz, 1H), 7.86 (d, J=2.2 Hz, 2H), 7.60-7.52 (m, 2H), 4.16 (q, J=6.9 Hz, 2H), 3.54 (br. s., 2H), 2.58 (s, 3H), 1.48 (t, J=6.9 Hz, 3H), 0.94 (s, 2H), 0.87 (br. s., 2H); ES-LCMS m/z 504.1 (M+H).

EXAMPLE 67

1-(2-(4-Ethoxy-6-oxo-1,6-dihydropyridin-3-yl)-4-methylpyrimidin-5-yl)-3-(3-(5-methyl-1,3,4-oxadiazol-2-yl)-5-(trifluoromethyl)phenyl)urea

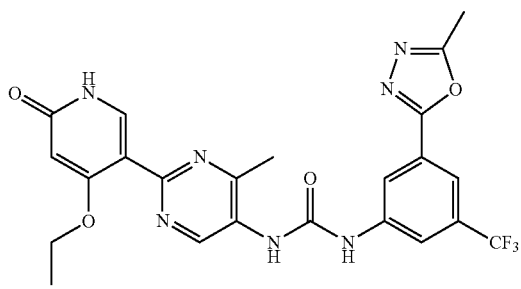 [SMILES: CCOc1cc(=O)[nH]cc1-c1ncc(NC(=O)Nc2cc(-c3nnc(C)o3)cc(C(F)(F)F)c2)c(C)n1]

Step 1: 1-(2-(4-Ethoxy-6-((4-methoxybenzyl)oxy)pyridin-3-yl)-4-methylpyrimidin-5-yl)-3-(3-(5-methyl-1,3,4-oxadiazol-2-yl)-5-(trifluoromethyl)phenyl)urea

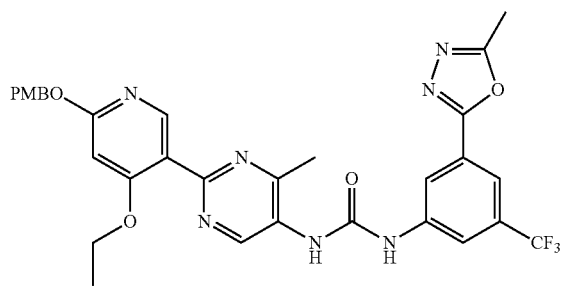

To a solution of 2-(4-ethoxy-6-((4-methoxybenzyl)oxy)pyridin-3-yl)-4-methylpyrimidine-5-carboxylic acid (100 mg, 0.253 mmol), Et$_3$N (0.053 mL, 0.379 mmol) in 1,4-dioxane (10 mL) was added DPPA (77 mg, 0.278 mmol) portionwise at 25° C., the resulting mixture was stirred at this temperature for 20 min 3-(5-methyl-1,3,4-oxadiazol-2-yl)-5-(trifluoromethyl)aniline (67.7 mg, 0.278 mmol) was added to above mixture and heated to 100° C. for 2 h. The mixture was pour into 20 mL of water, extracted with DCM (50 mL×2). The organic extract was washed with brine, dried over Na$_2$SO$_4$, filtered and concentrated. The residue was purified by preparative TLC (DCM:MeOH=20:1, R$_f$=0.5) yield a white solid of 1-(2-(4-ethoxy-6-((4-methoxybenzyl)oxy)pyridin-3-yl)-4-methylpyrimidin-5-yl)-3-(3-(5-methyl-1,3,4-oxadiazol-2-yl)-5-(trifluoromethyl)phenyl)urea (20 mg, 0.031 mmol, 12.4% yield): $^1$H NMR (400 MHz, MeOD-d4) δ 9.17 (s, 1H), 8.39 (s, 1H), 7.94-7.91 (m, 1H), 7.79 (s, 1H), 7.55 (s, 1H), 7.26 (s, 2H), 6.88 (s, 2H), 5.97-5.94 (m, 1H), 5.29 (d, J=12.7 Hz, 2H), 4.07 (d, J=6.8 Hz, 3H), 3.76 (s, 3H), 2.64 (s, 3H), 2.38 (s, 3H), 1.37-1.33 (m, 3H); ES-LCMS m/z 738 (M+1).

Step 2: 1-(2-(4-Ethoxy-6-oxo-1,6-dihydropyridin-3-yl)-4-methylpyrimidin-5-yl)-3-(3-(5-methyl-1,3,4-oxadiazol-2-yl)-5-(trifluoromethyl)phenyl)urea

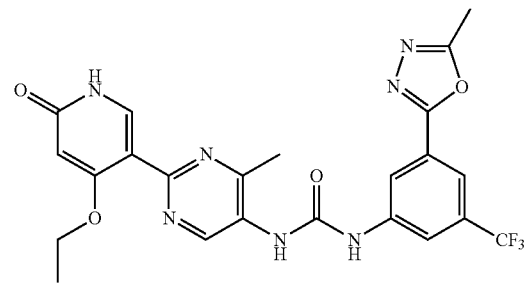 [SMILES: CCOc1cc(=O)[nH]cc1-c1ncc(NC(=O)Nc2cc(-c3nnc(C)o3)cc(C(F)(F)F)c2)c(C)n1]

A mixture of 1-(2-(4-ethoxy-6-((4-methoxybenzyl)oxy)pyridin-3-yl)-4-methylpyrimidin-5-yl)-3-(3-(5-methyl-1,3,4-oxadiazol-2-yl)-5-(trifluoromethyl)phenyl)urea (25 mg, 0.039 mmol), Pd/C (4.19 mg, 0.039 mmol) in MeOH (10 mL) was stirred for 2 h under H$_2$ balloon atmosphere at 25° C. Then the mixture was filtered and the filtrate was concentrated to give the residue which was purified by preparative HPLC (Instrument: Gilson 215/Column: Gemini C18 10 u 150*25 mm/Mobile phase A: Water (0.01 mol/L (NH$_4$)HCO$_3$)/Mobile phase B: MeCN (neutral)/Gradient: 20-50(B %)/Flowrate: 25 mL/min) to yield 1-(2-(4-ethoxy-6-oxo-1,6-dihydropyridin-3-yl)-4-methylpyrimidin-5-yl)-3-(3-(5-methyl-1,3,4-oxadiazol-2-yl)-5-(trifluoromethyl)phenyl)urea (4.08 mg, 7.64 µmol, 19.4% yield): $^1$H NMR (400 MHz, DMSO-d$_6$) δ 11.44-11.33 (m, 1H), 9.85 (s, 1H), 8.93 (s, 1H), 8.53 (s, 1H), 8.36 (s, 1H), 8.04 (s, 1H), 7.78 (s, 1H), 7.64 (s, 1H), 5.76 (s, 1H), 4.01 (q, J=6.8 Hz, 2H), 2.58 (s, 3H), 2.44 (s, 3H), 1.25 (t, J=7.0 Hz, 3H); ES-LCMS m/z 515.8 (M+H).

EXAMPLE 68

1-(3-(tert-Butyl)-1-phenyl-1H-pyrazol-5-yl)-3-(4-(6-oxo-1,6-dihydropyridin-3-yl)phenyl)urea

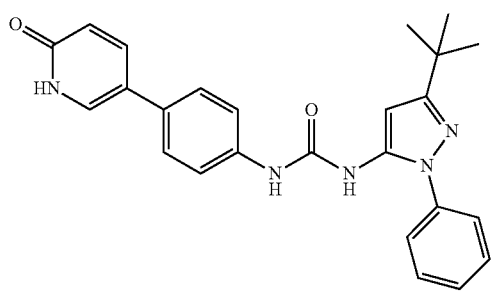 [SMILES: CC(C)(C)c1cc(NC(=O)Nc2ccc(-c3ccc(=O)[nH]c3)cc2)n(-c2ccccc2)n1]

Step 1: 3-(4-Isocyanato-2-(trifluoromethyl)phenoxy)-3-methyloxetane

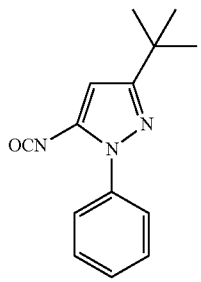

To a mixture of 3-(tert-butyl)-1-phenyl-1H-pyrazol-5-amine (100 mg, 0.464 mmol), NaHCO₃ (195 mg, 2.322 mmol) in DCM (10 mL) and H₂O (10 mL) was added triphosgene (45.5 mg, 0.153 mmol) at 0° C. After the mixture was stirred for 30 min, the mixture was extracted with DCM (20 mL×2), dried over Na₂SO₄, concentrated to give 3-(tert-butyl)-5-isocyanato-1-phenyl-1H-pyrazole (40 mg, 0.166 mmol, 35.7% yield).

Step 2: 1-(3-(tert-Butyl)-1-phenyl-1H-pyrazol-5-yl)-3-(4-(6-oxo-1,6-dihydropyridin-3-yl)phenyl)urea

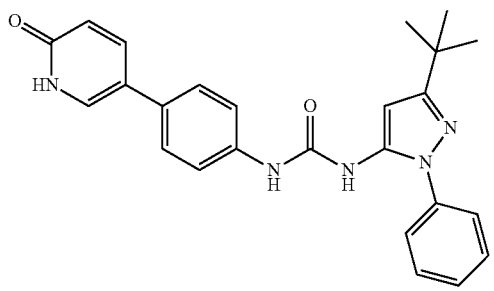 [SMILES: CC(C)(C)c1cc(NC(=O)Nc2ccc(-c3ccc(=O)[nH]c3)cc2)n(-c2ccccc2)n1]

To a mixture of 5-(4-aminophenyl)pyridin-2(1H)-one (30.9 mg, 0.166 mmol) and 3-(tert-butyl)-5-isocyanato-1-phenyl-1H-pyrazole (40 mg, 0.166 mmol) in THF (15 mL) was added Et₃N (0.046 mL, 0.332 mmol). Then mixture was heated to 60° C. for 60 min. Then the mixture was concentrated to give the residue which was purified by preparative HPLC to give 1-(3-(tert-butyl)-1-phenyl-1H-pyrazol-5-yl)-3-(4-(6-oxo-1,6-dihydropyridin-3-yl)phenyl)urea (15.87 mg, 0.037 mmol, 22.4% yield): ¹H NMR (400 MHz, CD₃OD) δ 8.31-8.28 (dd, J=9.20, 2.80 Hz, 1H), 8.08-8.07 (d, J=2.80 Hz, 1H), 7.75-7.73 (m, 3H), 7.70-7.68 (m, 2H), 7.57 (m, 4H), 7.02-7.00 (m, 1H), 6.90 (s, 1H), 1.45 (s, 9H);.ES-LCMS m/z 428.2 (M+H).

EXAMPLE 69

1-(4-(5-Ethoxy-6-oxo-1,6-dihydropyridin-3-yl)-2-fluorophenyl)-3-(4-((4-ethylpiperazin-1-yl)methyl)-3-(trifluoromethyl)phenyl)urea

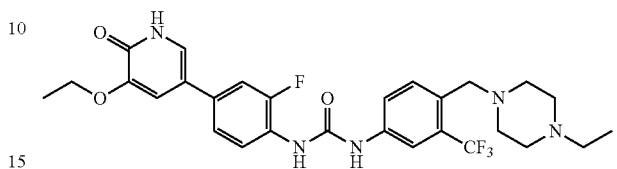

Step 1: 1-(4-((4-Ethylpiperazin-1-yl)methyl)-3-(trifluoromethyl)phenyl)-3-(2-fluoro-4-(4,4,5,5-tetramethyl-1,3,2-dioxaborolan-2-yl)phenyl)urea

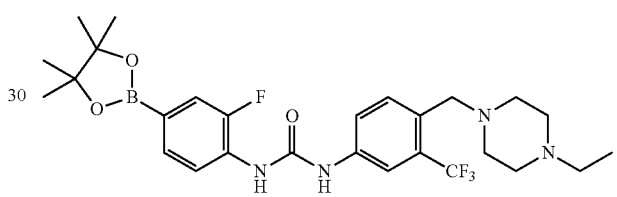

To a solution of 2-fluoro-4-(4,4,5,5-tetramethyl-1,3,2-dioxaborolan-2-yl)aniline (500 mg, 2.109 mmol) in THF (50 mL) was added triphosgene (219 mg, 0.738 mmol). The resulting miature was stirred at 70° C. After 30 min, LCMS analysis showed the starting material was disappeared. The solvent was removed in vacuo to give 2-(3-fluoro-4-isocyanatophenyl)-4,4,5,5-tetramethyl-1,3,2-dioxaborolane (520 mg, 1.977 mmol, 94% yield). To a solution of4-((4-ethylpiperazin-1-yl)methyl)-3-(trifluoromethyl)aniline (568 mg, 1.977 mmol), Et₃N (0.827 mL, 5.93 mmol) and DMAP (24.15 mg, 0.198 mmol) in THF (50 mL) was added a solution of 2-(3-fluoro-4-isoeyanatophenyl)-4,4,5,5-tetramethyl-1,3,2-dioxaborolane (520 mg, 1.977 mmol) at 70° C. The resulting mixture was stirred at 70° C. After LCMS analysis showed the starting material was disappeared. The solvent was removed in vacuo. The residue was dissolved in DCM (100 mL) and washed with H₂O (30 mL) and brine (30 mL). The organic layer was dried over Na₂SO₄, filtered and concentrated. The residue was purified by column chromatography (DCM/MeOH=20/1) to yiled 1-(4-((4-ethylpiperazin-1-yl)methyl)-3-(trifluoromethyl)phenyl)-3-(2-fluoro-4-(4,4,5,5-tetramethyl-1,3,2-dioxaborolan-2-yl)phenyl)urea (0.67 g, 0.851 mmol, 43.0% yield): ¹H NMR (400 MHz, CD₃OD) δ 8.17-8.14 (m, 1H), 7.86 (s, 1H), 7.69-7.67 (m, 1H), 7.60 (d, J=8.4 Hz, 1H), 7.49 (d, J=8.0 Hz, 1H), 7.41 (d, J=11.2 Hz, 1H), 4.59 (s, 2H), 3.60 (s, 2H), 2.52-2.47 (m, 8H), 1.33 (s, 12H), 1.10 (t, J=7.2 Hz, 3H); ES-LCMS m/z m/z 551.2 (M+H).

Step 2: 1-(4-(5-Ethoxy-6-((4-methoxybenzyl)oxy) pyridin-3-yl)-2-fluorophenyl)-3-(4-((4-ethylpiperazin-1-yl)methyl)-3-(trifluoromethyl)phenyl)urea

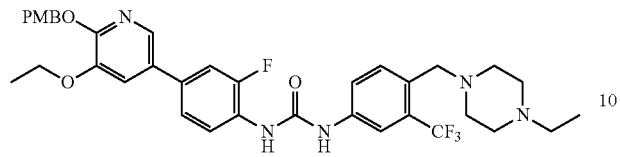

A solution of 1-(4-((4-ethylpiperazin-1-yl)methyl)-3-(trifluoromethyl)phenyl)-3-(2-fluoro-4-(4,4,5,5-tetramethyl-1,3,2-dioxaborolan-2-yl)phenyl)urea (0.67 g, 1.217 mmol), 5-bromo-3-ethoxy-2-((4-methoxybenzyl)oxy)pyridine (0.412 g, 1.217 mmol), PdCl$_2$(dppf)-DCM adduct (0.099 g, 0.122 mmol) and Cs$_2$CO$_3$ (0.793 g, 2.435 mmol) in 1,4-dioxane (12 mL) and water (4 mL) was stirred at 110° C. overnight under a N$_2$ atmosphere. After LCMS analysis showed the starting material was disappeared. The solvent was removed in vacuo. The residue was dissolved in EA (120 mL) and washed with H$_2$O (40 mL) and brine (40 mL). The organic layer was dried over Na$_2$SO$_4$, filtered and concentrated. The residue was purified by silica column chromatography (DCM/MeOH=30/1 to 20/1). All fractions found to contain product by TLC (DCM/MeOH=10/1) were combined and concentrated to yield a brown solid of 1-(4-(5-ethoxy-6-((4-methoxybenzyl)oxy)pyridin-3-yl)-2-fluorophenyl)-3-(4-((4-ethylpiperazin-1-yl)methyl)-3-(trifluoromethyl)phenyl)urea (0.53 g, 0.638 mmol, 52.4% yield): $^1$H NMR (400 MHz, CD$_3$OD) δ 8.17 (m, 1H), 7.91-7.89 (m, 2H), 7.68 (d, J=8.4 Hz, 1H), 7.61 (m, 1H), 7.44-7.38 (m, 5H), 6.90 (d, J=8.8 Hz, 1H), 5.35 (s, 2H), 4.17-4.11 (s, 2H), 3.70 (s, 3H), 3.67-3.65 (m, 2H), 2.53-2.44 (m, 8H), 1.41 (t, J=7.0 Hz, 3H), 1.12-1.08 (m, 3H); ES-LCMS m/z 682.2 (M+H).

Step 3: 1-(4-(5-Ethoxy-6-oxo-1,6-dihydropyridin-3-yl)-2-fluorophenyl)-3-(4-((4-ethylpiperazin-1-yl)methyl)-3-(trifluoromethyl)phenyl)urea

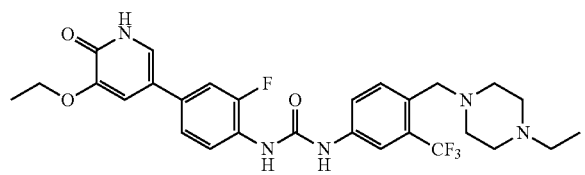 [SMILES: CCOc1cc(-c2ccc(NC(=O)Nc3ccc(CN4CCN(CC)CC4)c(C(F)(F)F)c3)c(F)c2)c[nH]c1=O]

A solution of 1-(4-(5-ethoxy-6-((4-methoxybenzyl)oxy)pyridin-3-yl)-2-fluorophenyl)-3-(4-((4-ethylpiperazin-1-yl)methyl)-3-(trifluoromethyl)phenyl)urea (0.53 g, 0.777 mmol) in HCl in MeOH (10 mL) was stirred at 25° C. After LCMS analysis showed the starting material was disappeared. The solvent was removed in vacuo and the residue was purified by preparative HPLC to yield a yellow solid of 1-(4-(5-ethoxy-6-oxo-1,6-dihydropyridin-3-yl)-2-fluorophenyl)-3-(4-((4-ethylpiperazin-1-yl)methyl)-3-(trifluoromethyl)phenyl)urea dihydrochloride (293.81 mg, 0.459 mmol, 59.0% yield): $^1$H NMR (400 MHz, CD$_3$OD) δ 8.18 (t, J=8.4 Hz, 1H), 8.02 (s, 1H), 7.82 (m, 1H), 7.73 (m, 1H), 7.49-7.41 (m, 4H), 4.24-4.18 (m, 4H), 3.76-3.25 (m, 8H), 3.12 (m, 2H), 1.49 (t, J=7.0 Hz, 3H), 1.37 (t, J=7.2 Hz, 3H); ES-LCMS m/z 562.1 (M+H).

EXAMPLE 70

1-(4-(1-Amino-2-methylpropan-2-yl)-3-(trifluoromethyl)phenyl)-3-(2-(5-ethoxy-6-oxo-1,6-dihydropyridin-3-yl)-4-methylpyrimidin-5-yl)urea dihydrochloride

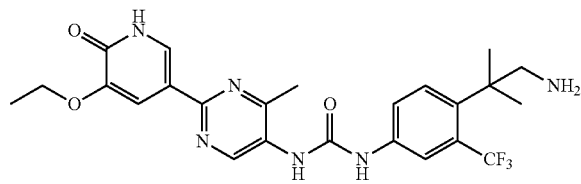 [SMILES: CCOc1cc(-c2ncc(NC(=O)Nc3ccc(C(C)(C)CN)c(C(F)(F)F)c3)c(C)n2)c[nH]c1=O]

Step 1: tert-Butyl (2-(4-amino-2-(trifluoromethyl)phenyl)-2-methylpropyl)carbamate

To a suspension of 2-(4-amino-2-(trifluoromethyl)phenyl)-2-methylpropanenitrile (2 g, 8.76 mmol) in MeOH (20 mL) was added Boc$_2$O (2.238 mL, 9.64 mmol) and Raney Ni (0.514 g, 8.76 mmol, 50% in H$_2$O). The mixture was hydrogenated under H$_2$ atmosphere (15 Psi) at 28° C. for 16 h. Then the solution was filtered, concentrated and distributed between EA and saturated NaHCO$_3$ solution. The combined organic extract was washed with brine, dried over MgSO$_4$, filtered and concentrated. The residue was purified by silica column chromatography (PE/EA=5:1, Silica gel=3 g). All fractions found to contain product by TLC (PE/EA=5:1, R$_f$=0.5) were combined and concentrated to yield a light yellow solid of tert-butyl (2-(4-amino-2-(trifluoromethyl)phenyl)-2-methylpropyl)carbamate (2.1 g, 6.09 mmol, 69.5% yield): $^1$H NMR (400 MHz, CDCl$_3$) δ 7.35-7.33 (d, J=8.4 Hz, 1H), 7.06 (d, J=2.8 Hz, 1H), 6.79-6.77 (d, J=8.4 Hz, 1H), 3.78 (br. s., 2H), 3.43-3.42 (d, J=6.4 Hz, 2H), 1.40 (s, 15H); ES-LCMS m/z 355.1 (M+23H).

Step 2: tert-Butyl (2-(4-(3-(2-(5-ethoxy-6-((4-methoxybenzyl)oxy)pyridin-3-yl)-4-methylpyrimidin-5-yl)ureido)-2-(trifluoromethyl)phenyl)-2-methylpropyl)carbamate

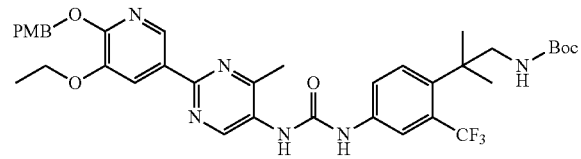

To a solution of 2-(5-ethoxy-6-((4-methoxybenzyl)oxy) pyridin-3-yl)-4-methylpyrimidine-5-carboxylic acid (300 mg, 0.759 mmol) and tert-butyl (2-(4-amino-2-(trifluoromethyl)phenyl)-2-methylpropyl)carbamate (252 mg, 0.759 mmol) in 1,4-Dioxane (10 mL) was added Et$_3$N (0.317 mL, 2.276 mmol) and DPPA (313 mg, 1.138 mmol). The mixture was stirred at 70° C. for 12 h. Then the solution was concentrated and distributed between EA and saturated NaHCO$_3$ solution. The combined organic extract was washed with brine, dried over MgSO$_4$, filtered and concentrated. The residue was purified by preparative TLC (PE/EA=1:1, R$_f$=0.5) to yield a light yellow solid of tert-butyl (2-(4-(3-(2-(5-ethoxy-6-((4-methoxybenzyl)oxy)pyridin-3-yl)-4-methylpyrimidin-5-yl)ureido)-2-(trifluoromethyl)phenyl)-2-methylpropyl)carbamate (125 mg, 0.138 mmol, 18.19% yield): $^1$H NMR (400 MHz, CD$_3$OD) δ 9.12 (s, 1H), 8.67 (s, 1H), 8.10-8.06 (m, 1H), 7.91 (s, 1H), 7.64-7.58 (m, 2H), 7.42-7.40 (d, J=8.4 Hz, 2H), 6.93-6.91 (d, J=8.4 Hz, 2H), 5.38 (s, 2H), 4.19-4.14 (q, J=7.2 Hz, 2H),), 3.79 (s, 3H), 3.37 (s., 2H), 2.57 (m, 3H), 1.52-1.26 (m, 18H); ES-LCMS m/z 725.2 (M+H).

Step 3: 1-(4-(1-Amino-2-methylpropan-2-yl)-3-(trifluoromethyl)phenyl)-3-(2-(5-ethoxy-6-oxo-1,6-dihydropyridin-3-yl)-4-methylpyrimidin-5-yl)urea dihydrochloride

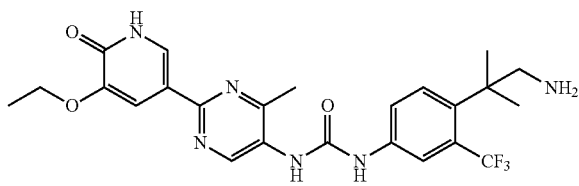 [SMILES: CCOc1cc(-c2ncc(NC(=O)Nc3ccc(C(C)(C)CN)c(C(F)(F)F)c3)c(C)n2)c[nH]c1=O]

To a suspension of tert-butyl (2-(4-(3-(2-(5-ethoxy-6-((4-methoxybenzyl)oxy)pyridin-3-yl)-4-methylpyrimidin-5-yl)ureido)-2-(trifluoromethyl)phenyl)-2-methylpropyl)carbamate (125 mg, 0.172 mmol) in DCM (5 mL) was added TFA (6.64 mL, 8.62 mmol) (10% in DCM). The mixture was stirred at 25° C. for 2 h. Then the solution was concentrated and distributed between EA and saturated NaHCO$_3$ solution. The combined organic extract was washed with brine, dried over MgSO$_4$, filtered and concentrated. The residue was purified by preparative HPLC (Instrument: DC/Column: ASB C18 150*25 mm/Mobile phase A: Water+0.1% HCl/ Mobile phase B: MeCN/Flowrate: 25 mL/min/Gradient Profile Description: 12-42(B %)) to yield a light yellow solid of 1-(4-(1-amino-2-methylpropan-2-yl)-3-(trifluoromethyl)phenyl)-3-(2-(5-ethoxy-6-oxo-1,6-dihydropyridin-3-yl)-4-methylpyrimidin-5-yl)urea dihydrochloride (70.82 mg, 0.122 mmol, 70.6% yield). TLC (DCM/MeOH=10:1, R$_f$=0.4): $^1$H NMR (400 MHz, CD$_3$OD) δ 9.16 (s, 1H), 8.15-8.14 (d, J=2.0 Hz, 1H), 8.05 (s, 1H), 7.87 (d, J=2.0 Hz, 1H), 7.77-7.75 (m, 1H), 7.69-7.67 (m, 1H), 4.20-4.15 (q, J=7.2 Hz, 2H), 3.33 (s, 2H), 2.63 (s, 3H), 1.58 (s, 6H), 1.52-1.48 (t, J=7.2 Hz, 3H); ES-LCMS m/z 505.2 (M+H).

EXAMPLE 71

1-(2-(5-Ethoxy-6-oxo-1,6-dihydropyridin-3-yl)-4-methylpyrimidin-5-yl)-3-(4-(2-hydroxypropan-2-yl)-3-(trifluoromethyl)phenyl)urea

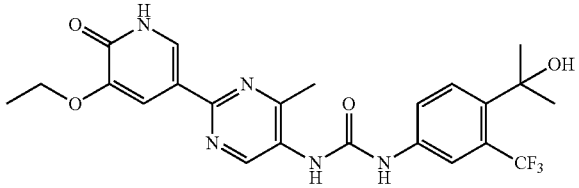 [SMILES: CCOc1cc(-c2ncc(NC(=O)Nc3ccc(C(C)(C)O)c(C(F)(F)F)c3)c(C)n2)c[nH]c1=O]

Step 1: 2-Chloro-5-isocyanato-4-methylpyrimidine

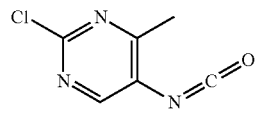

To a suspension of 2-chloro-4-methylpyrimidin-5-amine (150 mg, 1.045 mmol) in THF (10 mL) was added triphosgene (140 mg, 0.470 mmol). The mixture was stirred at 60° C. for 1 h. The mixture was cooled to rt. Then the solution was concentrated. The resulting 2-chloro-5-isocyanato-4-methylpyrimidine (170 mg, 1.003 mmol, 96% yield). TLC (PE/EA=5:1, R$_f$=0.5); ES-LCMS m/z 202.0 (M+MeOH+H).

Step 2: 1-(4-Acetyl-3-(trifluoromethyl)phenyl)-3-(2-chloro-4-methylpyrimidin-5-yl)urea

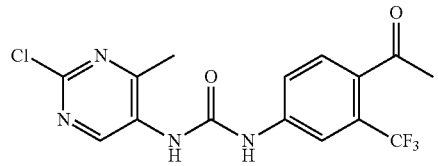 [SMILES: CC(=O)c1ccc(NC(=O)Nc2cnc(Cl)nc2C)cc1C(F)(F)F]

A suspension of 1-(4-amino-2-(trifluoromethyl)phenyl)ethanone (213 mg, 1.048 mmol) in THF (5 mL) was added to a solution of 2-chloro-5-isocyanato-4-methylpyrimidine (178 mg, 1.048 mmol) in THF (5 mL). Et$_3$N (0.365 mL, 2.62 mmol) and DMAP (12.81 mg, 0.105 mmol) was added and the mixture was at 60° C. for 10 h. The mixture was cooled to rt. Then the solution was concentrated and distributed between EA and saturated NaHCO$_3$ solution. The combined organic extract was washed with brine, dried over MgSO$_4$, filtered and concentrated. The residue was purified by preparative TLC (PE/EA=5:1, R$_f$=0.6) to yield a light yellow solid of 1-(4-acetyl-3-(trifluoromethyl)phenyl)-3-(2-chloro-4-methylpyrimidin-5-yl)urea (110 mg, 0.295 mmol, 28.1% yield): $^1$H NMR (400 MHz, CD$_3$OD) δ 9.06-9.05 (d, J=6.0 Hz, 1H), 7.98 (s, 1H), 7.79-7.72 (m, 2H), 2.68 (s, 3H), 2.47 (s, 3H); ES-LCMS m/z 373.0 (M+H).

Step 3: 1-(4-Acetyl-3-(trifluoromethyl)phenyl)-3-(2-(5-ethoxy-6-((4-methoxybenzyl)oxy)pyridin-3-yl)-4-methylpyrimidin-5-yl)urea

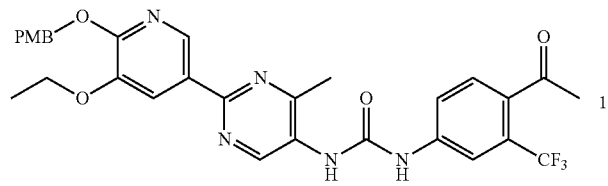

To a solution of 1-(4-acetyl-3-(trifluoromethyl)phenyl)-3-(2-chloro-4-methylpyrimidin-5-yl)urea (110 mg, 0.295 mmol) in DMF (2.4 mL) and Water (0.800 mL) was added 3-ethoxy-2-((4-methoxybenzyl)oxy)-5-(4,4,5,5-tetramethyl-1,3,2-dioxaborolan-2-yl)pyridine (114 mg, 0.295 mmol). $Cs_2CO_3$ (240 mg, 0.738 mmol) and $PdCl_2(PPh_3)_2$ (20.71 mg, 0.030 mmol) was added and the mixture was at 110° C. for 15 min under microwave. The mixture was cooled to rt. Then the solution was concentrated and distributed between EA and saturated $NaHCO_3$ solution. The combined organic extract was washed with brine, dried over $MgSO_4$, filtered and concentrated. The residue was purified by preparative TLC (DCM/MeOH=10:1, $R_f$=0.5) to yield a light yellow solid of 1-(4-acetyl-3-(trifluoromethyl)phenyl)-3-(2-(5-ethoxy-6-((4-methoxybenzyl)oxy)pyridin-3-yl)-4-methylpyrimidin-5-yl)urea (120 mg, 0.201 mmol, 68.3% yield): $^1$H NMR (400 MHz, $CD_3OD$) δ 9.10 (s, 1H), 8.66 (d, J=1.6 Hz, 1H), 8.07 (s, 1H), 7.98-7.96 (d, J=8.4 Hz, 1H), 7.74-7.62 (m, 3H), 7.41-7.39 (d, J=8.4 Hz, 1H), 6.91-6.89 (d, J=8.4 Hz, 2H), 5.37 (s, 2H), 4.18-4.13 (q, J=6.8 Hz, 2H), 3.78 (s, 3H), 2.59-2.55 (m, 6H), 1.45-1.41 (t, J=6.8 Hz, 3H); ES-LCMS m/z 596.1 (M+H).

Step 4: 1-(2-(5-Ethoxy-6-((4-methoxybenzyl)oxy)pyridin-3-yl)-4-methylpyrimidin-5-yl)-3-(4-(2-hydroxypropan-2-yl)-3-(trifluoromethyl)phenyl)urea

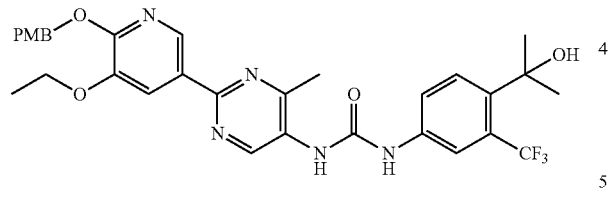

To a solution of 1-(4-acetyl-3-(trifluoromethyl)phenyl)-3-(2-(5-ethoxy-6-((4-methoxybenzyl)oxy)pyridin-3-yl)-4-methylpyrimidin-5-yl)urea (120 mg, 0.201 mmol) in THF (10 mL) was added MeMgBr (3.36 mL, 10.07 mmol) at 0° C. The mixture was at 0° C. for 2 h. Then the solution was quenched with saturated aqueous $NH_4Cl$, concentrated and distributed between EA and saturated $NaHCO_3$ solution. The combined organic extract was washed with brine, dried over $MgSO_4$, filtered and concentrated. The residue was purified by preparative TLC (PE/EA=5:1, $R_f$=0.6) to yield a light yellow solid of 1-(2-(5-ethoxy-6-((4-methoxybenzyl)oxy)pyridin-3-yl)-4-methylpyrimidin-5-yl)-3-(4-(2-hydroxypropan-2-yl)-3-(trifluoromethyl)phenyl)urea (21 mg, 0.029 mmol, 14.48% yield): $^1$H NMR (400 MHz, $CD_3OD$) δ 9.09 (s, 1H), 8.66 (s, 1H), 8.08-8.07 (d, J=2.0 Hz, 1H), 7.88 (s, 1H), 7.65 (s, 2H), 7.41-7.39 (d, J=8.8 Hz, 2H), 6.92-6.89 (d, J=8.8 Hz, 2H), 5.38 (s, 2H), 4.18-4.13 (q, J=6.8 Hz, 2H), 3.78 (s, 3H), 2.57 (s, 3H), 1.59 (s 6H), 1.45-1.41 (m, J=6.8 Hz, 3H); ES-LCMS m/z 612.2 (M+H).

Step 5: 1-(2-(5-Ethoxy-6-oxo-1,6-dihydropyridin-3-yl)-4-methylpyrimidin-5-yl)-3-(4-(2-hydroxypropan-2-yl)-3-(trifluoromethyl)phenyl)urea

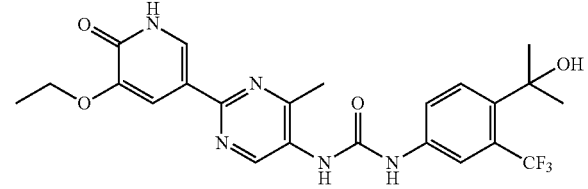 [SMILES: CCOc1cc(-c2ncc(NC(=O)Nc3ccc(C(C)(C)O)c(C(F)(F)F)c3)c(C)n2)c[nH]c1=O]

To a suspension of 1-(2-(5-ethoxy-6-((4-methoxybenzyl)oxy)pyridin-3-yl)-4-methylpyrimidin-5-yl)-3-(4-(2-hydroxypropan-2-yl)-3-(trifluoromethyl)phenyl)urea (21 mg, 0.034 mmol) in MeOH (10 mL) was added Pd/C (3.65 mg, 0.034 mmol, 10%). The mixture was hydrogenated under $H_2$ atmosphere (15 Psi) at 26° C. for 2 h. Then the solution was filtered and concentrated. The residue was purified by preparative HPLC ($MeCN/H_2O$ as eluants, acidic condition) to yield a white solid of 1-(2-(5-ethoxy-6-oxo-1,6-dihydropyridin-3-yl)-4-methylpyrimidin-5-yl)-3-(4-(2-hydroxypropan-2-yl)-3-(trifluoromethyl)phenyl)urea (9.63 mg, 0.020 mmol, 57.1% yield). TLC (DCM/MeOH=10:1, $R_f$=0.4): $^1$H NMR (400 MHz, DMSO-$d_6$) δ 9.42 (br. s., 1H), 8.98 (s, 1H), 8.42 (br. s., 1H), 7.90-7.88 (dd, J=2.0, 8.4 Hz, 2H), 7.62-7.57 (m, 3H), 5.01 (s, 1H), 4.03-3.98 (q, J=6.8 Hz, 2H), 2.45 (s, 3H), 1.49 (s, 6H), 1.35-1.32 (t, J=6.8 Hz, 3H); ES-LCMS m/z 492.1 (M+H).

EXAMPLE 72

1-(3-(1H-1,2,4-Triazol-1-yl)-5-(trifluoromethyl)phenyl)-3-(4-(5-ethoxy-6-oxo-1,6-dihydropyridin-3-yl)-2-fluorophenyl)urea hydrochloride

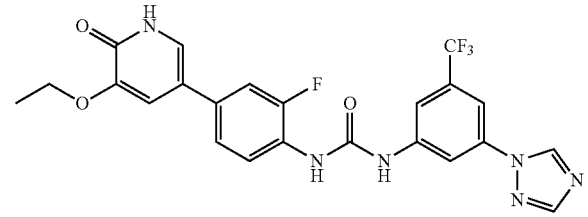 [SMILES: CCOc1cc(-c2ccc(NC(=O)Nc3cc(-n4cncn4)cc(C(F)(F)F)c3)c(F)c2)c[nH]c1=O]

Step 1: 2-Fluoro-4-(4,4,5,5-tetramethyl-1,3,2-dioxaborolan-2-yl)aniline

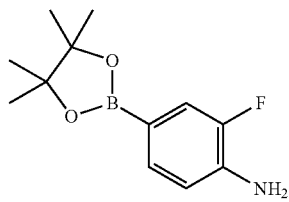 [SMILES: CC1(C)OB(c2ccc(N)c(F)c2)OC1(C)C]

To a solution of 4-bromo-2-fluoroaniline (40 g, 211 mmol), 4,4,4',4',5,5,5',5'-octamethyl-2,2'-bi(1,3,2-dioxaborolane) (64.1 g, 253 mmol) and KOAc (41.3 g, 421 mmol) in 1,4-dioxane (500 mL) stirred under N₂ at 20° C. was added PdCl₂(dppf) (7.70 g, 10.53 mmol) in one charge. The reaction mixture was stirred at 100° C. for 3 h. The solution was concentrated in vacuo to give 2-fluoro-4-(4,4,5,5-tetramethyl-1,3,2-dioxaborolan-2-yl)aniline (44 g, 158 mmol, 74.9% yield): ¹H NMR (400 MHz, CDCl₃) δ 7.46-7.40 (m, 2H), 6.75-6.71 (m, 1H), 1.30 (s, J=3.6 Hz, 12H); ES-LCMS m/z 238.1 (M+H).

Step 2: 4-(5-Ethoxy-6-((4-methoxybenzyl)oxy)pyridin-3-yl)-2-fluoroaniline

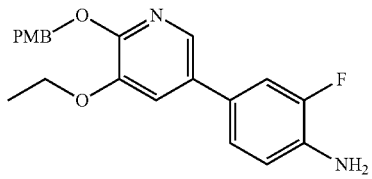

To a mixture of 5-bromo-3-ethoxy-2-((4-methoxybenzyl)oxy)pyridine (5 g, 14.78 mmol) in 1,4-dioxane (30 mL) and water (10.0 mL) was added 5-bromo-3-ethoxy-2-((4-methoxybenzyl)oxy)pyridine (5 g, 14.78 mmol), Cs₂CO₃ (9.63 g, 29.6 mmol) and PdCl₂(dppf) (1.082 g, 1.478 mmol). The mixture was stirred under N₂ at 110° C. for 16 h. Then the reaction residue was filtered and the filtrate was concentrated, which was purified by silica column chromatography (PE/EA=8/1). All fractions found to contain product by TLC (PE/EA=8/1, R_f 0.6) were combined and concentrated to yield a white solid of 4-(5-ethoxy-6-((4-methoxybenzyl)oxy)pyridin-3-yl)-2-fluoroaniline (4 g, 9.77 mmol, 66.1% yield): ¹H NMR (400 MHz, CD₃OD) δ 7.83 (d, J=2.0 Hz, 1H), 7.40-7.37 (m, 2H), 7.34 (d, J=2.0 Hz, 1H), 7.24-7.20 (m, 1H), 7.17-7.14 (m, 1H), 6.92-6.89 (m, 3H), 5.33 (s, 2H), 4.15-4.09 (m, 2H), 3.78 (s, 3H), 1.40 (t, J=7.2 Hz, 3H); ES-LCMS m/z 369.1 (M+H).

Step 3: 3-Ethoxy-5-(3-fluoro-4-isocyanatophenyl)-2-((4-methoxybenzyl)oxy)pyridine

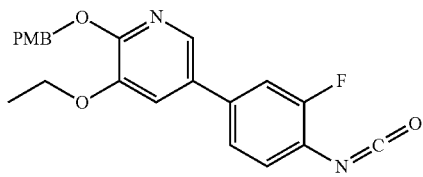

A suspension of 4-(5-ethoxy-6-((4-methoxybenzyl)oxy)pyridin-3-yl)-2-fluoroaniline (193.76 mg, 0.526 mmol) in THF (10 mL) was added to a solution of triphosgene (70.2 mg, 0.237 mmol) in THF (10 mL). The mixture was at 60° C. for 5 min. The mixture was cooled to rt. Then the solution was concentrated. The resulting 3-ethoxy-5-(3-fluoro-4-isocyanatophenyl)-2-((4-methoxybenzyl)oxy)pyridine (195 mg, 0.494 mmol, 94% yield). TLC (PE/EA=5/1, R_f 0.5): ES-LCMS m/z 307.0 (M-87H).

Step 4: 1-(3-Nitro-5-(trifluoromethyl)phenyl)-1H-1,2,4-triazole

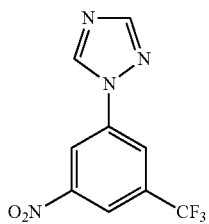 [SMILES: O=[N+]([O-])c1cc(-n2cncn2)cc(C(F)(F)F)c1]

To a solution of 1-fluoro-3-nitro-5-(trifluoromethyl)benzene (1 g, 4.78 mmol) in DMF (15 mL) was added 1H-1,2,4-triazole (0.396 g, 5.74 mmol). Cs₂CO₃ (3.12 g, 9.56 mmol) was added and the mixture was at 80° C. for 8 h. The mixture was cooled to rt. Then the solution was concentrated and distributed between EA and saturated NaHCO₃ solution. The combined organic extract was washed with brine, dried over MgSO₄, filtered and concentrated. The residue was purified by silica column chromatography (PE/EA=5/1). All fractions found to contain product by TLC (PE/EA=1/1, R_f=0.5) were combined and concentrated to yield a light yellow solid of 1-(3-nitro-5-(trifluoromethyl)phenyl)-1H-1,2,4-triazole (690 mg, 2.67 mmol, 55.9% yield): ¹H NMR (400 MHz, CD₃OD) δ 9.43 (s, 1H), 9.01 (s, 1H), 8.65 (s, 1H), 8.55 (s, 1H), 8.26 (s, 1H); ES-LCMS m/z 259.0 (M+H).

Step 5: 3-(1H-1,2,4-Triazol-1-yl)-5-(trifluoromethyl)aniline

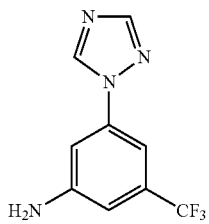

To a suspension of 1-(3-nitro-5-(trifluoromethyl)phenyl)-1H-1,2,4-triazole (690 mg, 2.67 mmol) in MeOH (10 mL) was added Pd/C (284 mg, 2.67 mmol, 10%). The mixture was hydrogenated under H₂ atmosphere (15 Psi) at 26° C. for 2 h. Then the solution was filtered and concentrated. The resulting 3-(1H-1,2,4-triazol-1-yl)-5-(trifluoromethyl)aniline (571 mg, 2.502 mmol, 94% yield) as a white solid. TLC (PE/EA=1/1, R_f=0.3): ¹H NMR (400 MHz, CD₃OD) δ 9.06 (s, 1H), 8.13 (s, 1H), 7.26 (s, 2H), 6.93 (s, 1H); ES-LCMS m/z 229.1 (M+H).

Step 6: 1-(3-(1H-1,2,4-Triazol-1-yl)-5-(trifluoromethyl)phenyl)-3-(4-(5-ethoxy-6-((4-methoxybenzyl)oxy)pyridin-3-yl)-2-fluorophenyl)urea

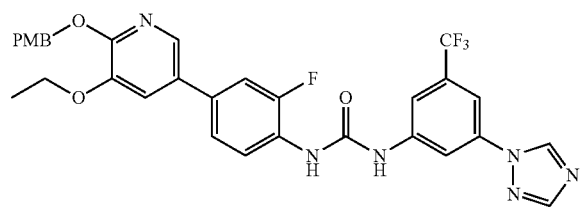

To a suspension of 3-(1H-1,2,4-triazol-1-yl)-5-(trifluoromethyl)aniline (100 mg, 0.438 mmol) in THF (10 mL) was added 3-ethoxy-5-(3-fluoro-4-isocyanatophenyl)-2-((4-methoxybenzyl)oxy)pyridine (208 mg, 0.526 mmol). Et$_3$N (0.153 mL, 1.096 mmol) and DMAP (5.35 mg, 0.044 mmol) was added and the mixture was at 60° C. for 10 h. The mixture was cooled to rt. Then the solution was concentrated and distributed between EA and saturated NaHCO$_3$ solution. The combined organic extract was washed with brine, dried over MgSO$_4$, filtered and concentrated. The residue was purified by preparative TLC (DCM/MeOH=20/1, R$_f$=0.4) to yield a light yellow solid of 1-(3-(1H-1,2,4-triazol-1-yl)-5-(trifluoromethyl)phenyl)-3-(4-(5-ethoxy-6-((4-methoxybenzyl)oxy)pyridin-3-yl)-2-fluorophenyl)urea (102 mg, 0.164 mmol, 37.4% yield): ES-LCMS m/z 623.1 (M+H).

Step 7: 1-(3-(1H-1,2,4-Triazol-1-yl)-5-(trifluoromethyl)phenyl)-3-(4-(5-ethoxy-6-oxo-1,6-dihydropyridin-3-yl)-2-fluorophenyl)urea hydrochloride

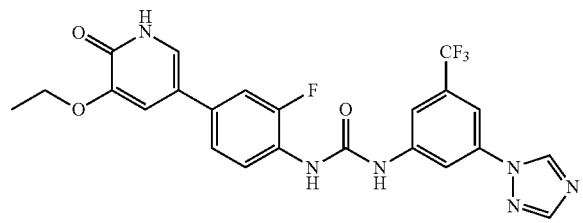 [SMILES: CCOc1cc(-c2ccc(NC(=O)Nc3cc(-n4cncn4)cc(C(F)(F)F)c3)c(F)c2)c[nH]c1=O]

To a suspension of 1-(3-(1H-1,2,4-triazol-1-yl)-5-(trifluoromethyl)phenyl)-3-(4-(5-ethoxy-6-((4-methoxybenzyl)oxy)pyridin-3-yl)-2-fluorophenyl)urea (30 mg, 0.048 mmol) in MeOH (10 mL) was added Pd/C (10.26 mg, 0.096 mmol, 10%). The mixture was hydrogenated under H$_2$ atmosphere (15 Psi) at 26° C. for 3 h. Then the solution was filtered and concentrated. The residue was purified by preparative HPLC (MeCN/H$_2$O as eluants, acidic condition) to yield an off white solid of 1-(3-(1H-1,2,4-triazol-1-yl)-5-(trifluoromethyl)phenyl)-3-(4-(5-ethoxy-6-oxo-1,6-dihydropyridin-3-yl)-2-fluorophenyl)urea hydrochloride (16.88 mg, 0.031 mmol, 65.0% yield). TLC (DCM/MeOH=10/1, R$_f$=0.4): $^1$H NMR (400 MHz, DMSO-d$_6$) δ 10.11 (s, 1H), 9.45 (s, 1H), 8.92 (s, 1H), 8.30 (s, 1H), 8.22 (s, 1H), 8.12-8.07 (t, J=8.6 Hz, 1H), 7.92-7.88 (d, J=7.8 Hz, 1H), 7.59-7.55 (dd, J=12.8, 2.0 Hz, 1H), 7.42-7.40 (dd, J=8.8, 2.0 Hz, 1H), 7.33-7.32 (d, J=2.4 Hz, 1H), 7.15-7.14 (d, J=2.4 Hz, 1H), 4.09-4.04 (q, J=6.8 Hz, 2H), 1.36-1.33 (t, J=6.8 Hz, 3H); ES-LCMS m/z 503.0 (M+H).

EXAMPLE 73

1-(4-(1-(Dimethylamino)-2-methylpropan-2-yl)-3-(trifluoromethyl)phenyl)-3-(2-(5-ethoxy-6-oxo-1,6-dihydropyridin-3-yl)-4-methylpyrimidin-5-yl)urea dihydrochloride

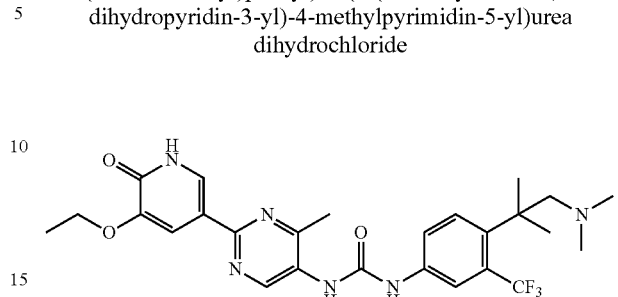

Step 1: tert-Butyl (4-(2-cyanopropan-2-yl)-3-(trifluoromethyl)phenyl)carbamate

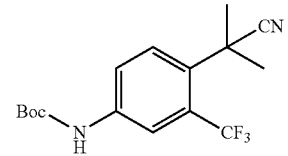 [SMILES: CC(C)(C)OC(=O)Nc1ccc(C(C)(C)C#N)c(C(F)(F)F)c1]

To a suspension of 2-(4-amino-2-(trifluoromethyl)phenyl)-2-methylpropanenitrile (2 g, 8.76 mmol) in EtOH (20 mL) was added Boc$_2$O (3.05 mL, 13.15 mmol). The mixture was stirred at 28° C. for 16 h. Then the solution was concentrated and distributed between EA and saturated NaHCO$_3$ solution. The combined organic extract was washed with brine, dried over MgSO$_4$, filtered and concentrated. The residue was purified by silica column chromatography (PE/EA=5:1, Silica gel=3 g). All fractions found to contain product by TLC (PE/EA=5:1, R$_f$=0.6) were combined and concentrated to yield a light yellow solid of tert-butyl (4-(2-cyanopropan-2-yl)-3-(trifluoromethyl)phenyl)carbamate (2.8 g, 6.40 mmol, 73.0% yield): $^1$H NMR (400 MHz, CDCl$_3$) δ 7.76 (s, 1H), 7.62 (s, 2H), 1.85 (s, 6H), 1.53 (s, 9H); ES-LCMS m/z 329.1 (M+H).

Step 2: tert-Butyl (4-(1-amino-2-methylpropan-2-yl)-3-(trifluoromethyl)phenyl)carbamate

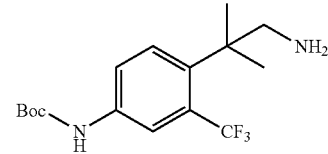 [SMILES: CC(C)(C)OC(=O)Nc1ccc(C(C)(C)CN)c(C(F)(F)F)c1]

To a suspension of tert-butyl (4-(2-cyanopropan-2-yl)-3-(trifluoromethyl)phenyl)carbamate (3.18 g, 9.69 mmol) in MeOH (20 mL) was added Raney Ni (1.137 g, 19.37 mmol, 50% in H$_2$O) and NH$_4$OH (10 mL). The mixture was hydrogenated under H$_2$ atmosphere at 40 psi at 28° C. for 12 h. Then the solution was filtered and concentrated to yield the residue. The resulting tert-butyl (4-(1-amino-2-methylpropan-2-yl)-3-(trifluoromethyl)phenyl)carbamate (1.5 g, 4.39 mmol, 45.3% yield). TLC (PE/EA=1:1, $R_f$=0.5): $^1$H NMR (400 MHz, CD$_3$OD) δ 7.92 (s, 1H), 7.67-7.65 (d, J=8.4 Hz, 1H), 7.60-7.58 (d, J=8.8 Hz, 1H), 3.17 (s, 2H), 1.57-1.43 (m, 15H); ES-LCMS m/z 333.1 (M+H).

Step 3: tert-Butyl (4-(1-(dimethylamino)-2-methylpropan-2-yl)-3-(trifluoromethyl)phenyl)carbamate

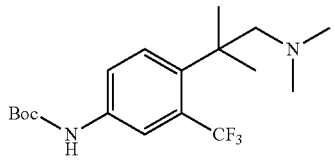 [SMILES: CN(C)CC(C)(C)c1ccc(NC(=O)OC(C)(C)C)cc1C(F)(F)F]

To a suspension of tert-butyl (4-(1-amino-2-methylpropan-2-yl)-3-(trifluoromethyl)phenyl)carbamate (1.5 g, 4.51 mmol) in MeOH (15 mL) was added NaBH(OAc)$_3$ (4.78 g, 22.57 mmol) and formaldehyde (0.249 mL, 9.03 mmol). The mixture was stirred at 28° C. for 5 h. Then the solution was concentrated and distributed between EA and saturated NaHCO$_3$ solution. The combined organic extract was washed with brine, dried over MgSO$_4$, filtered and concentrated. The residue was purified by silica column chromatography (PE/EA=1:1, Silica gel=2 g). All fractions found to contain product by TLC (PE/EA=1:1, $R_f$=0.5) were combined and concentrated to yield a light yellow solid of tert-butyl (4-(1-(dimethylamino)-2-methylpropan-2-yl)-3-(trifluoromethyl)phenyl)carbamate (1.48 g, 2.93 mmol, 64.9% yield): $^1$H NMR (400 MHz, CDCl$_3$) δ 7.77 (s, 1H), 7.61-7.59 (d, J=8.8 Hz, 1H), 7.50-7.48 (d, J=8.0 Hz, 1H), 6.66 (s, 1H), 2.75 (s, 2H), 2.17 (s, 6H), 1.53-1.51 (m, 15H); ES-LCMS m/z 361.2 (M+H).

Step 4: 4-(1-(Dimethylamino)-2-methylpropan-2-yl)-3-(trifluoromethyl)aniline

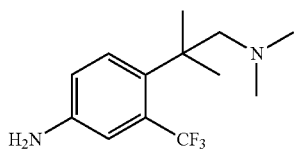

TFA (0.633 mL, 8.21 mmol, 10% TFA in DCM, 10 mL) was added to a solution of tert-butyl (4-(1-(dimethylamino)-2-methylpropan-2-yl)-3-(trifluoromethyl)phenyl)carbamate (1.48 g, 4.11 mmol) in DCM (15 mL). The mixture was at 28° C. for 4 h. Then the solution was concentrated to give the residue. The rersidue was purified by silica column chromatography (PE/EA=1:1, Silica gel=2 g). All fractions found to contain product by TLC (PE/EA=1:1, $R_f$=0.4) were combined and concentrated to yield a light yellow solid of 4-(1-(dimethylamino)-2-methylpropan-2-yl)-3-(trifluoromethyl)aniline (700 mg, 2.313 mmol, 56.3% yield): $^1$H NMR (400 MHz, CDCl$_3$) δ 7.44-7.42 (d, J=8.8 Hz, 1H), 7.04 (s, 1H), 6.77 (dd, J=2.4, 8.8 Hz, 1H), 2.49 (s, 2H), 2.07 (s, 6H), 1.43 (s, 6H); ES-LCMS m/z 261.1 (M+H).

Step 5: 1-(4-(1-(Dimethylamino)-2-methylpropan-2-yl)-3-(trifluoromethyl)phenyl)-3-(2-(5-ethoxy-6-((4-methoxybenzyl)oxy)pyridin-3-yl)-4-methylpyrimidin-5-yl)urea

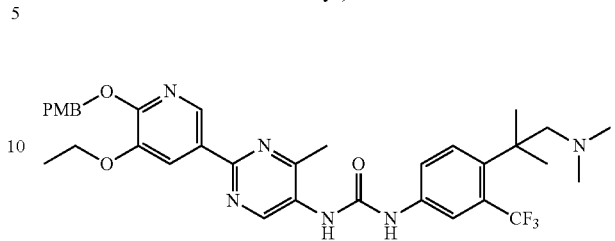

To a solution of 2-(5-ethoxy-6-((4-methoxybenzyl)oxy)pyridin-3-yl)-4-methylpyrimidine-5-carboxylic acid (300 mg, 0.759 mmol) and 4-(1-(dimethylamino)-2-methylpropan-2-yl)-3-(trifluoromethyl)aniline (197 mg, 0.759 mmol) in 1,4-dioxane (10 mL) was added Et$_3$N (0.317 mL, 2.276 mmol) and DPPA (313 mg, 1.138 mmol). The mixture was stirred at 70° C. for 12 h. Then the solution was concentrated and distributed between EA and saturated NaHCO$_3$ solution. The combined organic extract was washed with brine, dried over MgSO$_4$, filtered and concentrated. The residue was purified by preparative TLC (DCM/MeOH=10:1, $R_f$=0.5) to yield a light yellow solid of 1-(4-(1-(dimethylamino)-2-methylpropan-2-yl)-3-(trifluoromethyl)phenyl)-3-(2-(5-ethoxy-6-((4-methoxybenzyl)oxy)pyridin-3-yl)-4-methylpyrimidin-5-yl)urea (150 mg, 0.129 mmol, 16.96% yield): $^1$H NMR (400 MHz, CD$_3$OD) δ 8.69 (s, 1H), 7.38-7.35 (m, 2H), 7.27-7.19 (m, 3H), 7.07-7.03 (t, J=7.2 Hz, 2H), 6.93-6.91 (d, J=8.4 Hz, 2H), 5.39 (s, 2H), 4.20-4.14 (q, J=7.2 Hz, 2H), 3.78 (s, 3H), 2.67-2.57 (m, 11H), 1.64 (s, 6H), 1.46-1.43 (t, J=7.2 Hz, 3H); ES-LCMS m/z 653.1 (M+H).

Step 6: 1-(4-(1-(Dimethylamino)-2-methylpropan-2-yl)-3-(trifluoromethyl)phenyl)-3-(2-(5-ethoxy-6-oxo-1,6-dihydropyridin-3-yl)-4-methylpyrimidin-5-yl)urea dihydrochloride

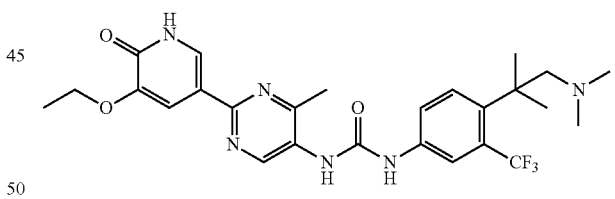

To a suspension of 1-(4-(1-(dimethylamino)-2-methylpropan-2-yl)-3-(trifluoromethyl)phenyl)-3-(2-(5-ethoxy-6-((4-methoxybenzyl)oxy)pyridin-3-yl)-4-methylpyrimidin-5-yl)urea (150 mg, 0.230 mmol) in MeOH (10 mL) was added Pd/C (24.46 mg, 0.230 mmol, 10%). The mixture was hydrogenated under H$_2$ atmosphere (15 Psi) at 26° C. for 6 h. Then the solution was filtered and concentrated to yield the residue. The residue was purified by preparative HPLC (Instrument: DC/Column: ASB C18 150*25 mm/Mobile phase A: Water+0.1% HCl/Mobile phase B: MeCN/Flowrate: 25 mL/min/Gradient Profile Description: 15-45(B %)) to yield a yellow solid of 1-(4-(1-(dimethylamino)-2-methylpropan-2-yl)-3-(trifluoromethyl)phenyl)-3-(2-(5-ethoxy-6-oxo-1,6-dihydropyridin-3-yl)-4-methylpyrimidin-5-yl)urea dihydrochloride (52.74 mg, 0.086 mmol, 37.6% yield). TLC (DCM/MeOH=10:1, $R_f$=0.4): $^1$H NMR (400 MHz, CD$_3$OD) δ 9.22 (s, 1H), 8.18 (d, J=2.0 Hz, 1H), 8.12-8.11 (d, J=2.0 Hz, 1H), 7.89 (s, 1H), 7.79-7.74 (m, 2H), 4.22-4.16 (q, J=6.8 Hz, 2H), 3.61 (s, 2H), 2.72 (s, 6H), 2.66 (s, 3H), 1.66 (s, 6H), 1.52-1.48 (t, J=6.8 Hz, 3H); ES-LCMS m/z 533.3 (M+H).

EXAMPLE 74

1-(3-(2-(Dimethylamino)ethoxy)-5-(trifluoromethyl)phenyl)-3-(2-(5-ethoxy-6-oxo-1,6-dihydropyridin-3-yl)-4-methylpyrimidin-5-yl)urea dihydrochloride

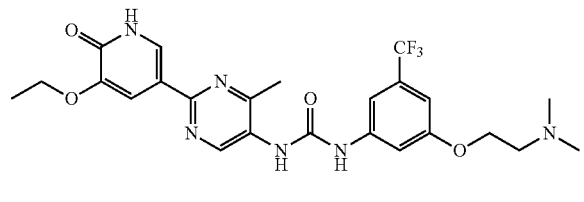 [SMILES: CCOc1cc(-c2ncc(NC(=O)Nc3cc(OCCN(C)C)cc(C(F)(F)F)c3)c(C)n2)c[nH]c1=O]

Step 1: N,N-Dimethyl-2-(3-nitro-5-(trifluoromethyl)phenoxy)ethanamine

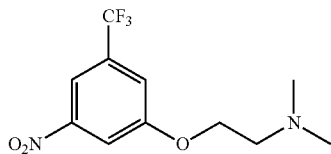

To a suspension of 1-fluoro-3-nitro-5-(trifluoromethyl)benzene (2 g, 9.56 mmol) in DMF (10 mL) was added 2-(dimethylamino)ethanol (2.56 g, 28.7 mmol) and K$_2$CO$_3$ (2.64 g, 19.13 mmol). The mixture was stirred at 80° C. for 8 h. The mixture was cooled to rt. Then the solution was concentrated and distributed between EA and saturated NaHCO$_3$ solution. The combined organic extract was washed with brine, dried over MgSO$_4$, filtered and concentrated. The residue was purified by silica column chromatography (10% EA:90% PE, 3 g silica column). All fractions found to contain product by TLC (PE/EA=5:1, R$_f$=0.5) to yield a light yellow solid of N,N-dimethyl-2-(3-nitro-5-(trifluoromethyl)phenoxy)ethanamine (1.35 g, 4.85 mmol, 50.7% yield): $^1$H NMR (400 MHz, CDCl$_3$) δ 8.08 (s, 1H), 7.94 (s, 1H), 7.51 (s, 1H), 4.20-4.17 (t, J=5.6 Hz, 2H), 2.81-2.78 (t, J=5.6 Hz, 2H), 2.36 (s, 6H); ES-LCMS m/z 279.1 (M+H).

Step 2: 3-(2-(Dimethylamino)ethoxy)-5-(trifluoromethyl)aniline

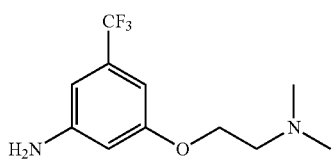 [SMILES: CN(C)CCOc1cc([N+](=O)[O-])cc(C(F)(F)F)c1]

To a suspension of N,N-dimethyl-2-(3-nitro-5-(trifluoromethyl)phenoxy)ethanamine (900 mg, 3.23 mmol) in MeOH (10 mL) was added Pd/C (172 mg, 0.162 mmol) (10%). The mixture was hydrogenated under H$_2$ atmosphere (15 Psi) at 26° C. for 3 h. Then the solution was filtered and concentrated. The resulting 3-(2-(dimethylamino)ethoxy)-5-(trifluoromethyl)aniline (600 mg, 2.417 mmol, 74.7% yield). TLC (PE/EA=1:1, R$_f$=0.4): $^1$H NMR (400 MHz, CDCl$_3$) δ 6.58-6.51 (m, 2H), 6.38 (s, 1H), 4.06-4.03 (t, J=5.6 Hz, 2H), 3.83 (br. s., 2H), 2.73-2.70 (t, J=5.6 Hz, 2H), 2.34 (s, 6H); ES-LCMS m/z 249.1 (M+H).

Step 3: 1-(3-(2-(Dimethylamino)ethoxy)-5-(trifluoromethyl)phenyl)-3-(2-(5-ethoxy-6-((4-methoxybenzyl)oxy)pyridin-3-yl)-4-methylpyrimidin-5-yl)urea

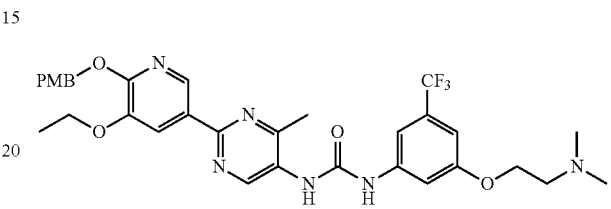

To a solution of 2-(5-ethoxy-6-((4-methoxybenzyl)oxy)pyridin-3-yl)-4-methylpyrimidine-5-carboxylic acid (200 mg, 0.506 mmol) and 3-(2-(dimethylamino)ethoxy)-5-(trifluoromethyl)aniline (126 mg, 0.506 mmol) in 1,4-dioxane (10 mL) was added Et$_3$N (0.211 mL, 1.517 mmol) and DPPA (209 mg, 0.759 mmol). The mixture was stirred at 70° C. for 12 h. Then the solution was concentrated and distributed between EA and saturated NaHCO$_3$ solution. The combined organic extract was washed with brine, dried over MgSO$_4$, filtered and concentrated. The residue was purified by preparative TLC (PE/EA=1:1, R$_f$=0.5) to yield a light yellow solid of 1-(3-(2-(dimethylamino)ethoxy)-5-(trifluoromethyl)phenyl)-3-(2-(5-ethoxy-6-((4-methoxybenzyl)oxy)pyridin-3-yl)-4-methylpyrimidin-5-yl)urea (150 mg, 0.234 mmol, 46.3% yield): $^1$H NMR (400 MHz, CD$_3$OD) δ 9.12 (s, 1H), 8.67 (d, J=1.8 Hz, 1H), 8.08-8.07 (d, J=1.8 Hz, 1H), 7.53 (s, 1H), 7.47-7.35 (m, 3H), 6.93-6.91 (d, J=8.8 Hz, 3H), 5.39 (s, 2H), 4.30-4.28 (t, J=5.2 Hz, 2H), 4.19-4.14 (q, J=6.8 Hz, 2H), 3.80 (s, 3H), 3.23-3.20 (m, 2H), 2.69 (s, 6H), 2.59 (s, 3H), 1.31 (t, J=7.2 Hz, 3H); ES-LCMS m/z 641.3 (M+H).

Step 4: 1-(3-(2-(Dimethylamino)ethoxy)-5-(trifluoromethyl)phenyl)-3-(2-(5-ethoxy-6-oxo-1,6-dihydropyridin-3-yl)-4-methylpyrimidin-5-yl)urea dihydrochloride

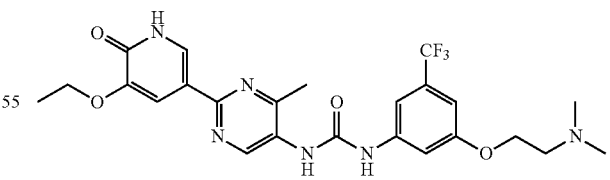

To a suspension of 1-(3-(2-(dimethylamino)ethoxy)-5-(trifluoromethyl)phenyl)-3-(2-(5-ethoxy-6-((4-methoxybenzyl)oxy)pyridin-3-yl)-4-methylpyrimidin-5-yl)urea (100 mg, 0.156 mmol) in MeOH (10 mL) was added Pd/C (16.61 mg, 0.156 mmol, 10%). The mixture was hydrogenated under H$_2$ atmosphere (15 Psi) at 25° C. for 3 h. Then the solution was filtered and concentrated to give the residue. The residue was purified by preparative HPLC (Instrument:

DC/Column: ASB C18 150*25 mm/Mobile phase A: Water+ 0.1% HCl/Mobile phase B: MeCN/Flowrate: 25 mL/min/ Gradient Profile Description: 23-53(B %)) to yield a yellow solid of 1-(3-(2-(dimethylamino)ethoxy)-5-(trifluoromethyl)phenyl)-3-(2-(5-ethoxy-6-oxo-1,6-dihydropyridin-3-yl)-4-methylpyrimidin-5-yl)urea dihydrochloride (25.02 mg, 0.042 mmol, 26.9% yield). TLC (DCM/MeOH=10:1, R$_f$=0.4): $^1$H NMR (400 MHz, CD$_3$OD) δ 9.26 (s, 1H), 8.18 (d, J=2.0 Hz, 1H), 7.87 (d, J=2.0 Hz, 1H), 7.49-7.47 (d, J=9.7 Hz, 2H), 6.99 (s, 1H), 4.48-4.40 (m, 2H), 4.21-4.16 (q, J=6.8 Hz, 2H), 3.71-3.59 (m, 2H), 3.02 (s, 6H), 2.69 (s, 3H), 1.51-1.48 (t, J=6.8 Hz, 3H); ES-LCMS m/z 521.2 (M+H).

The following examples were prepared according to analogous procedure to those described above:

| Example | Structure | NMR | LCMS |
|---|---|---|---|
| 75 | 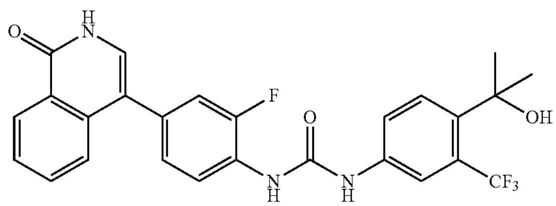 [SMILES: CC(C)(O)c1ccc(NC(=O)Nc2ccc(-c3c[nH]c(=O)c4ccccc34)cc2F)cc1C(F)(F)F] | $^1$H NMR (400 MHz, CDCl$_3$) δ 8.49 (s, 1H), 8.36 (s, 1H), 8.29-8.27 (m, 1H), 8.08-8.06 (m, 2H), 7.86 (s, 1H), 7.67-7.65 (m, 1H), 7.57-7.53 (m, 1H), 7.42-7.40 (m, 1H), 4.26 (s, 3H), 3.99 (s, 2H), 3.63-3.60 (m, 2H), 3.29 (s, 3H), 3.30-3.15 (m, 8H), 1.38 (t, J = 7.2 Hz, 3H); | ES-LCMS m/z 500.0 (M + H) |
| 76 | 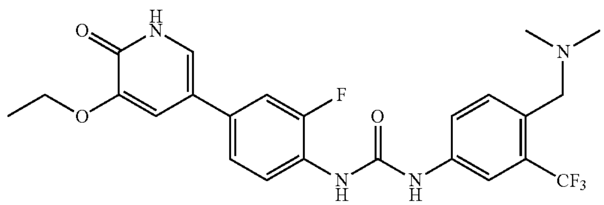 [SMILES: CCOc1cc(-c2ccc(NC(=O)Nc3ccc(CN(C)C)c(C(F)(F)F)c3)c(F)c2)c[nH]c1=O] | $^1$H NMR (400 MHz, DMSO-d$_6$) δ 9.356 (s, 1H), 8.64 (s, 1H), 8.14 (t, J = 8.8 Hz, 1H), 7.97 (s, 1H), 7.65 (d, J = 8.8 Hz, 1H), 7.58-7.55 (m, 2H), 7.41 (dd, J = 2.0 Hz and 8.8 Hz, 1H), 7.31 (d, J = 2.0 Hz, 1H), 7.14 (d, J = 2.0 Hz, 1H), 4.08 (q, J = 6.8 Hz, 2H), 3.46 (s, 2H), 2.17 (s.6H), 1.36 (t, J = 6.8 Hz, 3H) | ES-LCMS m/z 493.1 (M + H) |
| 77 | 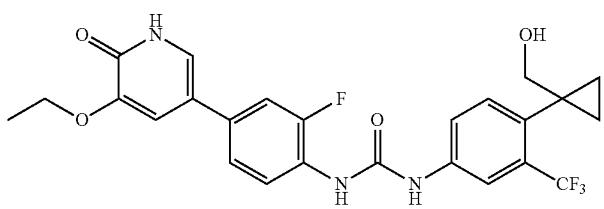 [SMILES: CCOc1cc(-c2ccc(NC(=O)Nc3ccc(C4(CO)CC4)c(C(F)(F)F)c3)c(F)c2)c[nH]c1=O] | $^1$H NMR (400 MHz, CD$_3$OD) δ 8.18 (t, J = 8.4 Hz, 1H), 7.87 (s, 1H), 7.55 (s, 2H), 7.35-7.45 (m, 4H), 4.18 (q, J = 7.0 Hz, 2H), 3.55 (br. s., 2H), 1.48 (t, J = 7.0 Hz, 3H), 0.84-0.97 (m, 4H); | ES-LCMS m/z 506.0 (M + H) |
| 78 | 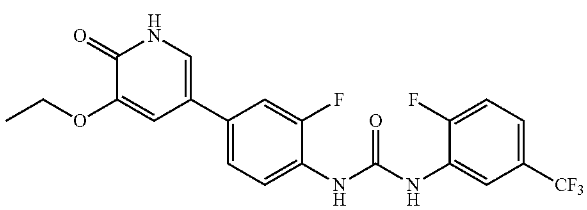 [SMILES: CCOc1cc(-c2ccc(NC(=O)Nc3cc(C(F)(F)F)ccc3F)c(F)c2)c[nH]c1=O] | $^1$H NMR (400 MHz, CD$_3$OD) 8.62 (d, J = 7.6 Hz, 1H), 8.22 (t, J = 8.4 Hz, 1H), 7.41-7.31 (m, 5H), 7.30-7.26 (m, 1H), 4.14 (d, J = 7.2 Hz, 2H), 1.46 (t, J = 7.2 Hz, 3H); | ES-LCMS m/z 454.0 (M + H) |
| 79 | 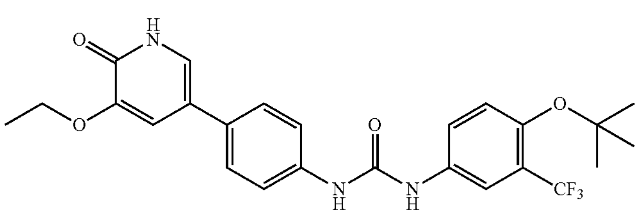 [SMILES: CCOc1cc(-c2ccc(NC(=O)Nc3ccc(OC(C)(C)C)c(C(F)(F)F)c3)cc2)c[nH]c1=O] | $^1$H NMR (400 MHz, CD$_3$OD) δ 7.72 (d, J = 2.8 Hz, 1H), 7.52-7.50 (m, 5H), 7.34-7.31 (m, 2H), 7.26 (d, J = 9.2 Hz, 1H), 4.18-4.13 (m, 2H), 1.48-1.42 (m, 3H), 1.41 (s, 9H); | ES-LCMS m/z 490.1 (M + H) |
| 80 | 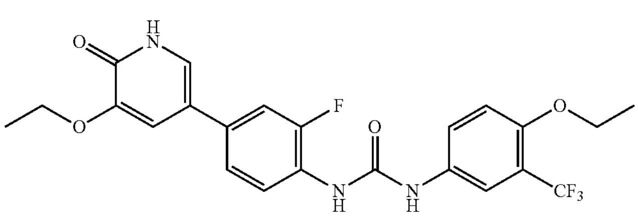 [SMILES: CCOc1ccc(NC(=O)Nc2ccc(-c3c[nH]c(=O)c(OCC)c3)cc2F)cc1C(F)(F)F] | $^1$H NMR (400 MHz, CD$_3$OD) δ 8.12 (t, J = 8.40 Hz, 1H), 7.72 (d, J = 2.80 Hz, 1H), 7.54-7.53 (d, J = 2.80 Hz, 1H), 7.38-7.31 (m, 2H), 7.25-7.20 (m, 2H), 7.12-7.09 (d, J = 2.80 Hz, 2H), 4.13-4.08 (m, 4H), 1.45 (d, J = 7.00 Hz, 3H), 1.39 (d, J = 7.00 Hz, 3H); | ES-LCMS m/z 480 (M + H) |

| Example | Structure | NMR | LCMS |
|---|---|---|---|
| 81 | 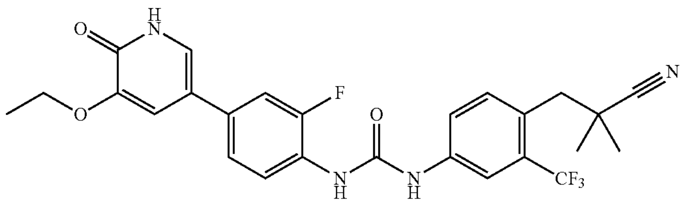 [SMILES: CCOc1cc(-c2ccc(NC(=O)Nc3ccc(CC(C)(C)C#N)c(C(F)(F)F)c3)c(F)c2)c[nH]c1=O] | ¹H NMR (400 MHz, CDCl₃ + CD₃OD) δ: 8.15 (d, J = 8.4 Hz, 1H), 7.92 (d, J = 2.0 Hz, 1H), 7.66-7.60 (m, 2H), 7.32-7.27 (m, 2H), 7.21 (d, J = 2.4 Hz, 1H), 7.14 (d, J = 2.0 Hz, 1H), 4.11 (q, J = 6.8 Hz, 2H), 3.01 (s, 2H), 1.46 (t, J = 6.8 Hz, 3H), 1.37 (s, 6H); | ES-LCMS m/z 517.1 (M + H) |
| 82 | 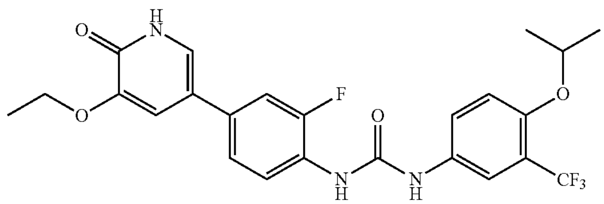 [SMILES: CCOc1cc(-c2ccc(NC(=O)Nc3ccc(OC(C)C)c(C(F)(F)F)c3)c(F)c2)c[nH]c1=O] | ¹H NMR (400 MHz, CD₃OD) δ 8.15 (t, J = 8.6 Hz, 1H), 7.71 (d, J = 2.8 Hz, 1H), 7.55-7.52 (m, 1H), 7.40-7.26 (m, 4H), 7.14 (d, J = 9.2 Hz, 1H), 4.72-4.64 (m, 1H), 4.16-4.11 (m, 2H), 1.46 (t, J = 7.0 Hz, 3H), 1.32 (d, J = 6.0 Hz, 6H); | ES-LCMS m/z 494.1 (M + H) |
| 83 | 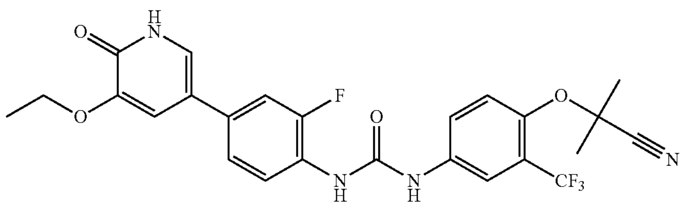 [SMILES: CCOc1cc(-c2ccc(NC(=O)Nc3ccc(OC(C)(C)C#N)c(C(F)(F)F)c3)c(F)c2)c[nH]c1=O] | ¹H NMR (400 MHz, CD₃OD) δ: 8.14 (t, J = 8.4 Hz, 1H), 7.89 (d, J = 2.4 Hz, 1H), 7.65-7.59 (m, 2H), 7.38 (dd, J = 2.4, 12.8 Hz, 1H), 7.35-7.32 (m, 1H), 7.27 (d, J = 2.4 Hz, 1H), 7.23 (d, J = 2.0 Hz, 1H), 4.13 (q, J = 7.2 Hz, 2H), 1.75 (s, 6H), 1.46 (t, J = 7.2 Hz, 3H); | ES-LCMS m/z 519.1 (M + H) |
| 84 | 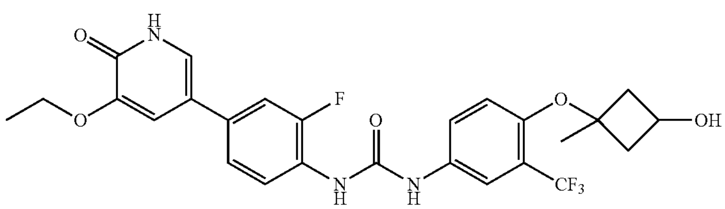 [SMILES: CCOc1cc(-c2ccc(NC(=O)Nc3ccc(OC4(C)CC(O)C4)c(C(F)(F)F)c3)c(F)c2)c[nH]c1=O] | ¹H NMR (400 MHz, CD₃OD) δ: 8.12 (t, J = 8.4 Hz, 1H), 7.85 (s, 1H), 7.74 (d, J = 2.4 Hz, 1H), 7.50 (dd, J = 2.8, 8.8 Hz, 1H), 7.39-7.31 (m, 2H), 7.28 (d, J = 2.0 Hz, 1H), 6.93 (d, J = 9.2 Hz, 1H), 4.17-4.12 (m, 2H), 4.07-3.99 (m, 1H), 2.69-2.65 (m, 2H), 2.34-2.29 (m, 2H), 1.49-1.48 (m, 6H); | ES-LCMS m/z 536.2 (M + H) |
| 85 | 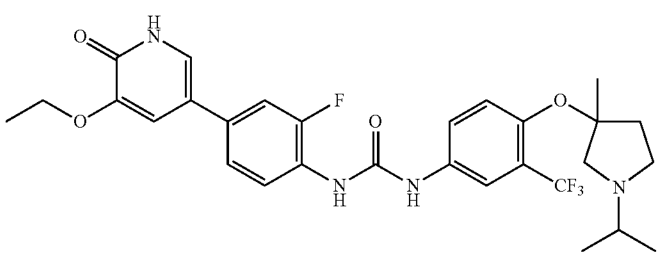 [SMILES: CCOc1cc(-c2ccc(NC(=O)Nc3ccc(OC4(C)CCN(C(C)C)C4)c(C(F)(F)F)c3)c(F)c2)c[nH]c1=O] | ¹H NMR (400 MHz, CD₃OD) δ 8.15 (t, J = 8.60 Hz, 1H), 7.81-7.80 (m, 1H), 7.64-7.61 (dd, J = 9.20, 2.80 Hz, 1H), 7.43 (m, 1H), 7.40-7.35 (m, 3H), 7.30-7.24 (m, 1H), 4.19-4.14 (m, 2H), 3.84-3.73 (m, 2H), 3.50-3.46 (m, 2H), 3.34 (m, 1H), 2.79-2.61 (m, 1H), 2.45-2.14 (m, 1H), 1.61-1.51 (m, 3H), 1.50-1.37 (m, 9H); | ES-LCMS m/z 577.1 (M + H) |
| 86 | 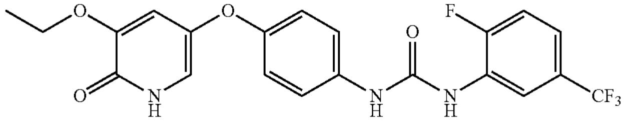 [SMILES: CCOc1cc(Oc2ccc(NC(=O)Nc3cc(C(F)(F)F)ccc3F)cc2)c[nH]c1=O] | ¹H NMR (400 MHz, DMSO-d₆) δ 9.09 (s, 1H), 8.80 (s, 1H), 8.58-8.57 (m, 1H), 7.49-7.33 (m, 4H), 6.92-6.90 (m, 2H), 6.67 (s, 1H), 6.66 (s, 1H), 3.89-3.84 (m, 2H), 1.26 (t, J = 6.8 Hz, 3H); | ES-LCMS m/z 452.1 (M + H) |
| 87 | 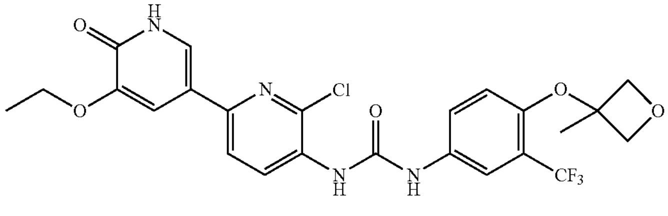 [SMILES: CCOc1cc(-c2ccc(NC(=O)Nc3ccc(OC4(C)COC4)c(C(F)(F)F)c3)c(Cl)n2)c[nH]c1=O] | ¹H NMR (400 MHz, CD₃OD) δ: 8.57 (d, J = 8.4 Hz, 1H), 7.81 (d, J = 2.4 Hz, 1H), 7.71-7.69 (m, 2H), 7.56-7.53 (m, 2H), 6.63 (d, J = 9.2 Hz, 1H), 4.89-4.88 (m, 2H), 4.62 (d, J = 7.2 Hz, 2H), 4.13 (q, J = 6.8 Hz, 2H), 1.72 (s, 3H), 1.47 (t, J = 6.8 Hz, 3H); | ES-LCMS m/z 538.9 (M + H) |

-continued

| Example | Structure | NMR | LCMS |
|---|---|---|---|
| 88 | 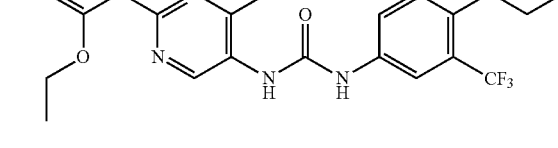 | ¹H NMR (400 MHz, MeOD-d4) δ 9.55 (s, 1H), 8.43 (s, 1H), 7.93 (s, 1H), 7.58 (s, 2H), 6.15 (s, 1H), 4.36 (q, J = 6.9 Hz, 2H), 3.54 (br. s., 2H), 2.76 (s, 3H), 1.48 (t, J = 7.1 Hz, 3H), 0.99-0.84 (m, 4H); | ES-LCMS m/z 504.2 (M + H) |
| 89 | 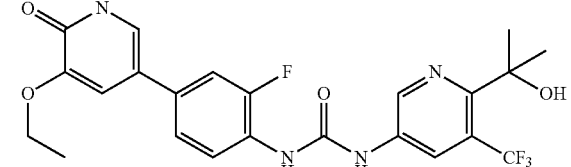 | ¹H NMR (400 MHz, CD₃OD) δ 8.72 (d, J = 2.4 Hz, 1H), 8.40 (d, J = 2.4 Hz, 1H), 8.15 (t, J = 8.4 Hz, 1H), 7.42-7.31 (m, 2H), 7.26 (d, J = 2.4 Hz, 1H), 7.22 (d, J = 2.4 Hz, 1H), 4.12 (m, 2H), 1.59 (s, 6H), 1.46 (t, J = 6.8 Hz, 3H); | ES-LCMS m/z 495.1 (M + H) |
| 90 | 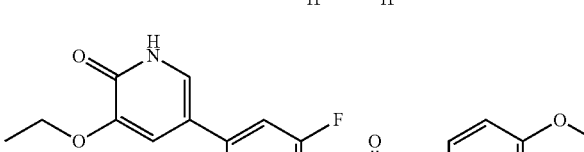 | ¹H NMR (400 MHz, CD₃OD) 7.74 (d, J = 2.4 Hz, 1H), 7.53-7.51 (s, 1H), 7.33 (d, J = 2.0 Hz, 1H), 7.27 (d, J = 9.2 Hz, 2H), 7.21 (d, J = 2.4 Hz, 1H), 6.60 (d, J = 9.2 Hz, 1H), 4.89 (d, J = 6.8 Hz, 2H), 4.62 (d, J = 7.6 Hz, 2H), 4.10 (t, J = 7.2 Hz, 2H), 1.71 (s, 3H), 1.45 (t, J = 7.2 Hz, 3H); | ES-LCMS m/z 540.1 (M + H) |
| 91 | 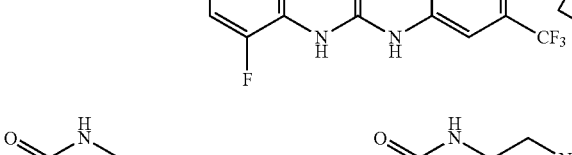 | ¹H NMR (400 MHz, CD₃OD) δ 9.08 (s, 1H), 8.15 (s, 1H), 8.10 (s, 2H), 7.90 (s, 1H), 7.84 (s, 1H), 4.18 (q, J = 7.2 Hz, 2H), 3.58 (t, J = 6.8 Hz, 2H), 2.63 (t, J = 6.8 Hz, 2H), 2.59 (s, 3H), 2.36 (s, 6H), 1.51 (t, J = 7.2 Hz, 3H); | ES-LCMS m/z 548.2 (M + H) |
| 92 | 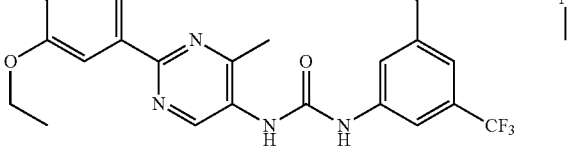 | ¹H NMR (400 MHz, CD₃OD) δ 8.32 (d, J = 2.4 Hz, 1H), 8.18 (d, J = 2.8 Hz, 1H), 8.12 (t, J = 8.4 Hz, 1H), 7.40 (d, J = 2.0 Hz, 1H), 7.37 (d, J = 2.0 Hz, 1H), 7.33 (d, J = 8.8 Hz, 1H), 7.26 (dd, J = 8.4, 2.4 Hz, 1H), 5.40-5.34 (m, 1H), 4.16-4.10 (m, 2H), 1.46 (t, J = 6.8 Hz, 3H), 1.34 (d, J = 6.4 Hz, 6H); | ES-LCMS m/z 495.1 (M + H) |
| 93 | 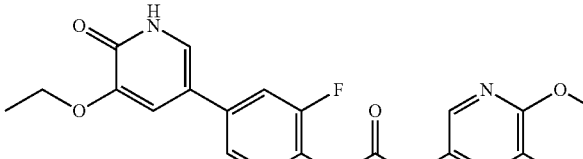 | ¹H NMR (400 MHz, DMSO-d₆) δ 11.77 (s, 1H), 9.17 (s, 1H), 8.54 (d, J = 2.0 Hz, 1H), 8.09 (t, J = 8.6 Hz, 1H), 7.73 (d, J = 2.4 Hz, 1H), 7.52 (dd, J = 12.8, 2.0 Hz, 1H), 7.35 (d, J = 8.8 Hz, 2H), 7.27 (m, 1H), 7.20-6.93 (m, 1H), 6.58 (d, J = 9.2 Hz, 1H), 4.73 (d, J = 6.8 Hz, 2H), 4.54 (d, J = 6.8 Hz, 2H), 4.05-4.00 (m, 2H), 1.61 (s, 3H), 1.31 (t, J = 7.0 Hz, 3H); | ES-LCMS m/z 504.2 (M + H) |
| 94 | 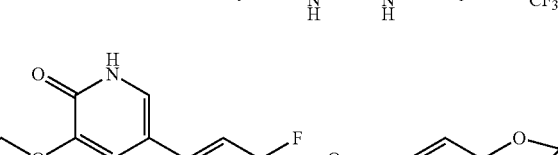 | ¹H NMR (400 MHz, MeOD) δ: 8.10 (d, J = 7.2 Hz, 1H), 7.79 (s, 1H), 7.53 (d, J = 8.0 Hz, 1H), 7.32-7.26 (m, 2H), 7.18-7.17 (m, 1H), 7.04-6.91 (m, 1H), 6.63-6.61 (m, 1H), 4.90 (s, 2H), 4.62 (d, J = 8.0 6.8 Hz, 2H), 1.72 (s, 3H); | ES-LCMS m/z 494.1 (M + 1) |

| Example | Structure | NMR | LCMS |
|---|---|---|---|
| 95 | 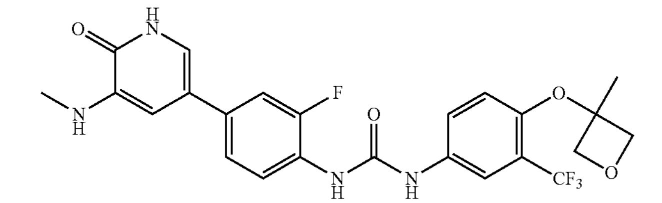 [SMILES: CNc1cc(-c2ccc(NC(=O)Nc3ccc(OC4(C)COC4)c(C(F)(F)F)c3)c(F)c2)c[nH]c1=O] | ¹H NMR (400 MHz, CD₃OD) δ 8.15 (t, J = 8.6 Hz, 1H), 7.82 (d, J = 2.8 Hz, 1H), 7.55-7.53 (m, 1H), 7.35-7.30 (m, 2H), 7.28-7.23 (m, 1H), 7.09-7.01 (m, 1H), 6.65 (d, J = 9.2 Hz, 1H), 4.89 (m, 2H), 4.62 (d, J = 7.2 Hz, 2H), 2.88 (s, 3H), 1.75 (s, 3H); | ES-LCMS m/z 507.1 (M + H) |
| 96 | 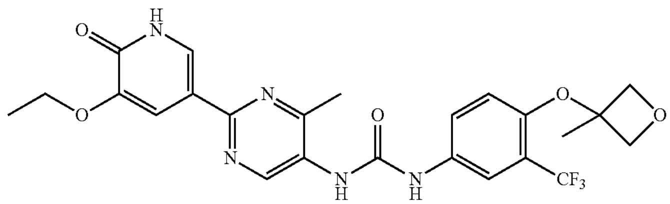 [SMILES: CCOc1cc(-c2ncc(NC(=O)Nc3ccc(OC4(C)COC4)c(C(F)(F)F)c3)c(C)n2)c[nH]c1=O] | ¹H NMR (400 MHz, CD₃OD) δ 9.00 (s, 1H), 8.05 (d, J = 2.0 Hz, 1H), 7.85 (d, J = 2.0 Hz, 1H), 7.78 (d, J = 2.4 Hz, 1H), 7.56 (dd, J = 2.4, 9.0 Hz, 1H), 6.63 (d, J = 8.8 Hz, 1H), 4.89 (d, J = 6.6 Hz, 2H), 4.63 (d, J = 7.2 Hz, 2H), 4.14 (q, J = 7.0 Hz, 2H), 2.54 (s, 3H), 1.72 (s, 3H), 1.47 (t, J = 7.0 Hz, 3H); | ES-LCMS m/z 520.1 (M + H) |
| 97 | 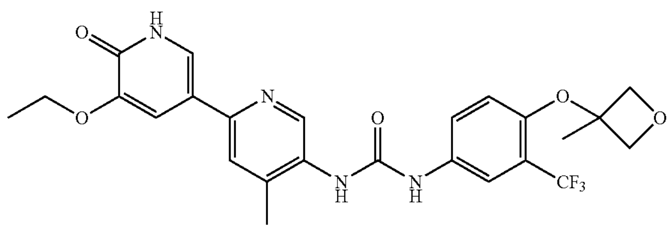 [SMILES: CCOc1cc(-c2cc(C)c(NC(=O)Nc3ccc(OC4(C)COC4)c(C(F)(F)F)c3)cn2)c[nH]c1=O] | ¹H NMR (400 MHz, CD₃OD) δ 8.83 (s, 1H), 7.78 (d, J = 2.4 Hz, 1H), 7.64-7.63 (m, 2H), 7.57-7.54 (m, 2H), 6.63 (d, J = 8.8 Hz, 1H), 4.92-4.90 (m, 2H), 4.63 (d, J = 7.2 Hz, 2H), 4.15-4.14 (m, 2H), 2.38 (s, 3H), 1.72 (s, 3H), 1.49 (t, J = 7.2 Hz, 3H); | ES-LCMS m/z 519.2 (M + H) |
| 98 | 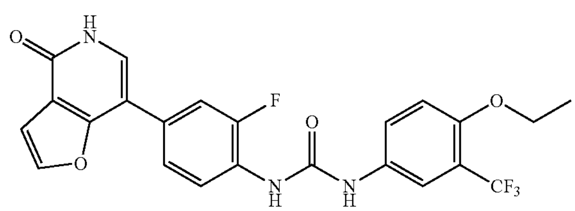 [SMILES: CCOc1ccc(NC(=O)Nc2ccc(-c3c[nH]c(=O)c4ccoc34)cc2F)cc1C(F)(F)F] | ¹H NMR (400 MHz, CD₃OD) δ 8.23 (t, J = 8.8 Hz, 1H), 7.88 (d, J = 2.0 Hz, 1H), 7.76 (d, J = 2.8 Hz, 1H), 7.64-7.55 (m, 4H), 7.15 (d, J = 9.2 Hz, 1H), 7.09 (d, J = 2.4 Hz, 1H), 4.17-4.12 (m, 2H), 1.43 (t, J = 6.8 Hz, 3H); | ES-LCMS m/z 476.1 (M + H) |
| 99 | 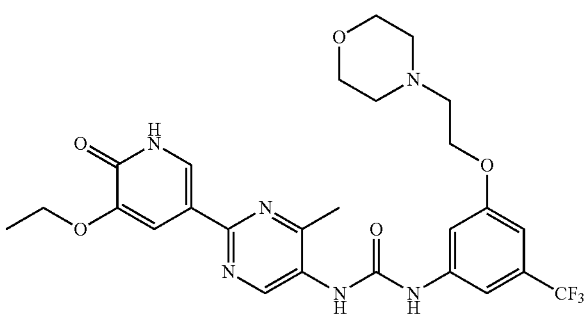 [SMILES: CCOc1cc(-c2ncc(NC(=O)Nc3cc(OCCN4CCOCC4)cc(C(F)(F)F)c3)c(C)n2)c[nH]c1=O] | ¹H NMR (400 MHz, DMSO-d₆) δ: 11.89 (s, 1H), 10.65 (s, 1H), 10.46 (s, 1H), 9.05-9.01 (m, 2H), 7.88 (s, 1H), 7.57 (s, 1H), 7.48-7.42 (m, 2H), 6.93 (s, 1H), 4.44 (s, 2H), 4.03-3.94 (m, 5H), 3.57-3.48 (m, 5H), 3.20-3.18 (m, 2H), 2.51 (s, 3H), 1.33 (t, J = 7.2 Hz, 3H); | ES-LCMS m/z: 563.3 (M + H) |
| 100 | 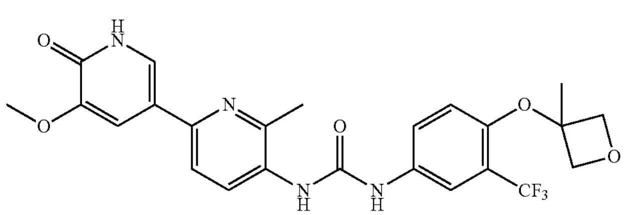 [SMILES: COc1cc(-c2ccc(NC(=O)Nc3ccc(OC4(C)COC4)c(C(F)(F)F)c3)c(C)n2)c[nH]c1=O] | ¹H NMR (400 MHz, CD₃OD) δ 8.84-8.86 (d, J = 8.80 Hz, 1H), 7.95-7.93 (d, J = 8.80 Hz, 1H), 7.83 (d, J = 2.80 Hz, 1H), 7.72-7.71 (d, J = 2.00 Hz, 1H), 7.55 (t, J = 4.20 Hz, 1H), 7.43 (d, J = 2.40 Hz, 1H), 6.65-6.63 (d, J = 8.80 Hz, 1H), 7.69-7.67 (m, 2H), 7.58-7.56 (m, 1H), 6.67-6.64 (d, J = 8.80 Hz, 1H), 4.90-4.89 (d, J = 4.40 Hz, 2H), 4.64-4.62 (d, J = 7.20 Hz, 2H), 3.93 (s, 3H), 2.74 (s, 3H), 2.64 (s, 3H), 1.72 (s, 3H); | ES-LCMS m/z 505 (M + H) |

-continued

| Example | Structure | NMR | LCMS |
|---|---|---|---|
| 101 | 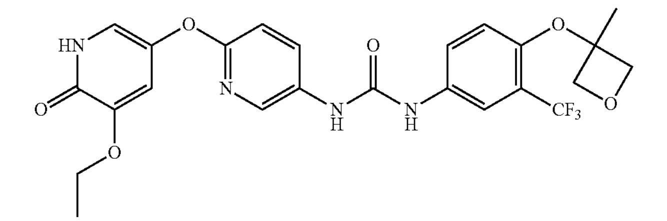 [SMILES: CCOc1cc(Oc2ccc(NC(=O)Nc3ccc(OC4(C)COC4)c(C(F)(F)F)c3)cn2)c[nH]c1=O] | $^1$H NMR (400 MHz, CD$_3$OD) δ 8.14 (d, J = 2.8 Hz, 1H), 7.95 (dd, J = 8.8, 2.8 Hz, 1H), 7.74 (d, J = 2.8 Hz, 1H), 7.52 (dd, J = 9.2, 2.8 Hz, 1H), 6.98 (s, 1H), 6.96-6.95 (m, 1H), 6.87 (d, J = 2.8 Hz, 1H), 6.60 (d, J = 8.8 Hz, 1H), 4.87 (m, 2H), 4.61 (d, J = 7.2 Hz, 2H), 4.01-3.96 (m, 2H), 1.71 (s, 3H), 1.41 (t, J = 7.0 Hz, 3H); | ES-LCMS m/z 521.0 (M + H) |
| 102 | 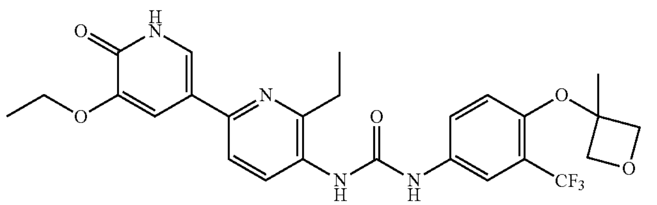 [SMILES: CCOc1cc(-c2ccc(NC(=O)Nc3ccc(OC4(C)COC4)c(C(F)(F)F)c3)c(CC)n2)c[nH]c1=O] | $^1$H NMR (400 MHz, MeOD-d$_4$) δ 8.12-8.10 (t, J = 8.4 Hz, 1H), 7.78 (d, J = 2.4 Hz, 1H), 7.68 (d, J = 2.0 Hz, 1H), 7.64 (d, J = 2.4 Hz, 1H), 7.56-7.51 (m, 2H), 6.62-6.60 (m, 1H), 4.89-4.88 (d, J = 5.2 Hz, 1H), 4.63-4.61 (d, J = 7.2 Hz, 2H), 4.15 (q, J = 7.0 Hz, 2H), 2.87 (q, J = 7.6 Hz, 2H), 1.71 (s., 3H), 1.46 (t, J = 7.0 Hz, 3H), 1.33 (t, J = 7.4 Hz, 3H); | ES-LCMS m/z 533.1 (M + H) |
| 103 | 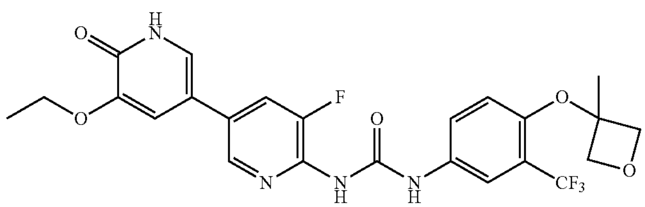 [SMILES: CCOc1cc(-c2cnc(NC(=O)Nc3ccc(OC4(C)COC4)c(C(F)(F)F)c3)c(F)c2)c[nH]c1=O] | $^1$H NMR (400 MHz, CD$_3$OD) δ 8.39 (d, J = 2.00 Hz, 1H), 7.91-7.87 (m, 2H), 7.69-7.67 (d, J = 8.80 Hz, 1H), 7.35-7.34 (d, J = 2.40 Hz, 1H), 7.24-7.23 (d, J = 2.40 Hz, 1H), 6.66-6.63 (d, J = 8.80 Hz, 1H), 4.85 (m, 2H), 4.64-4.62 (m, 2H), 4.13-4.11 (m, 2H), 1.73 (s, 3H), 1.46 (t, J = 7.00 Hz, 3H); | ES-LCMS m/z 523.1 (M + H) |
| 104 | 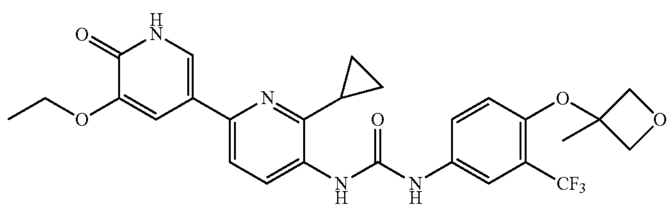 [SMILES: CCOc1cc(-c2ccc(NC(=O)Nc3ccc(OC4(C)COC4)c(C(F)(F)F)c3)c(C3CC3)n2)c[nH]c1=O] | $^1$H NMR (400 MHz, CD$_3$OD) δ 846 (d, J = 8.4 Hz, 1H), 7.82 (d, J = 2.4 Hz, 1H), 7.68 (m, 2H), 7.58-7.52 (m, 2H), 6.63 (d, J = 8.8 Hz, 1H), 4.90 (s, 1H), 4.83 (s, 1H), 4.62 (d, J = 6.8 Hz, 1H), 4.14 (q, J = 6.8 Hz, 2H), 1.72 (s, 3H), 1.47 (t, J = 6.8 Hz, 3H), 1.16-1.29 (m, 4 H); | ES-LCMS m/z 545.2 (M + H) |
| 105 | 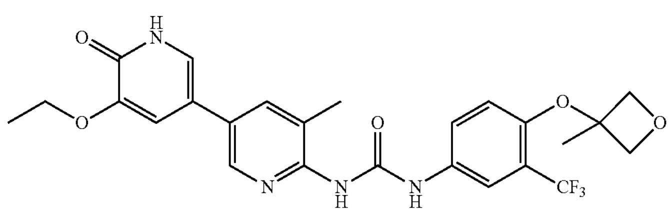 [SMILES: CCOc1cc(-c2cnc(NC(=O)Nc3ccc(OC4(C)COC4)c(C(F)(F)F)c3)c(C)c2)c[nH]c1=O] | $^1$H NMR (400 MHz, CD$_3$OD) δ 8.41 (s, 1H), 7.90 (s, 1H), 7.83 (s, 1H), 7.68 (d, J = 9.2 Hz, 1H), 7.30 (d, J = 2.0 Hz, 1H), 7.24 (d, J = 2.4 Hz, 1H), 6.66 (d, J = 8.8 Hz, 1H), 4.75 (d, J = 6.4 Hz, 2H), 4.64 (d, J = 7.2 Hz, 2H), 4.13-4.12 (m, 2H), 2.36 (s, 3H), 1.73 (s, 3H), 1.46 (t, J = 7.0 Hz, 3H); | ES-LCMS m/z 519.1 (M + H) |
| 106 | 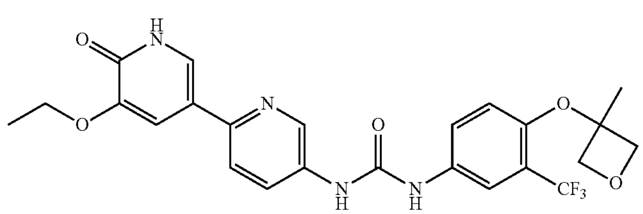 [SMILES: CCOc1cc(-c2ccc(NC(=O)Nc3ccc(OC4(C)COC4)c(C(F)(F)F)c3)cn2)c[nH]c1=O] | $^1$H NMR (400 MHz, CD$_3$OD) 8.60 (d, J = 2.8 Hz, 1H), 8.03-8.00 (m, 1H), 7.77 (d, J = 2.4 Hz, 1H), 7.67 (d, J = 8.8 Hz, 1H), 7.60 (d, J = 2.4 Hz, 1H), 7.56 (d, J = 2.0 Hz, 2H), 6.61 (d, J = 8.8 Hz, 1H), 4.89 (d, J = 6.8 Hz, 2H), 4.62 (d, J = 7.2 Hz, 2H), 4.13 (d, J = 7.2 Hz, 2H), 1.71 (s, 3H), 1.46 (t, J = 7.2 Hz, 3H); | ES-LCMS m/z 505.1 (M + H) |
| 107 | 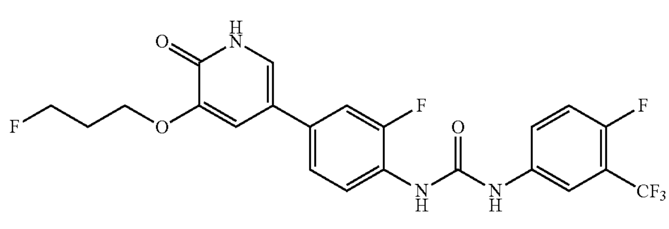 [SMILES: O=C(Nc1ccc(F)c(C(F)(F)F)c1)Nc1ccc(-c2c[nH]c(=O)c(OCCCF)c2)cc1F] | $^1$H NMR (400 MHz, CD$_3$OD) 8.13 (d, J = 8.4 Hz, 1H), 7.90 (dd, J = 2.8, 6.4 Hz, 1H), 7.40-7.37 (m, 1H), 7.34-7.32 (m, 2H), 7.28-7.26 (m, 3H), 4.72 (t, J = 6.0 Hz, 1H), 4.60 (t, J = 5.6 Hz, 1H), 4.17 (t, J = 6.0 Hz, 2H), 2.25-2.18 (m, 2H); | ES-LCMS m/z 486.1 (M + H) |

| Example | Structure | NMR | LCMS |
|---|---|---|---|
| 108 | 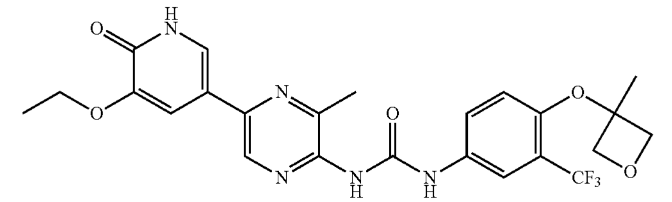 [SMILES: CCOc1cc(-c2cnc(NC(=O)Nc3ccc(OC4(C)COC4)c(C(F)(F)F)c3)c(C)n2)c[nH]c1=O] | $^1$H NMR (400 MHz, CD$_3$OD) δ 8.60 (s, 1H), 7.91 (s, 1H), 7.76 (s, 1H), 7.72 (m, 1H), 7.61 (m, 1H), 6.69-6.67 (m, 1H), 4.87 (m, 2H), 4.67 (m, 2H), 4.18-4.17 (m, 2H), 2.64 (s, 3H), 1.76 (s, 3H), 1.52 (d, J = 7.00 Hz, 3H); | ES-LCMS m/z 520.1 (M + H) |
| 109 | 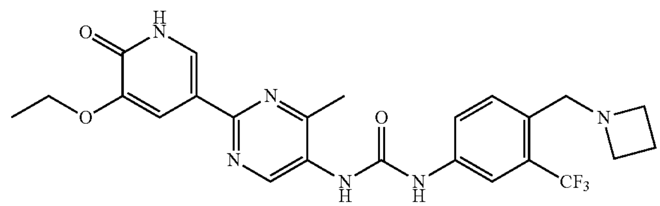 [SMILES: CCOc1cc(-c2ncc(NC(=O)Nc3ccc(CN4CCC4)c(C(F)(F)F)c3)c(C)n2)c[nH]c1=O] | $^1$H NMR (400 MHz, CD$_3$OD) δ 9.06 (s, 1H), 8.09 (d, J = 2.0 Hz, 1H), 7.94 (s, 1H), 7.89 (d, J = 1.5 Hz, 1H), 7.66 (d, J = 8.5 Hz, 1H), 7.55 (d, J = 8.5 Hz, 1H), 4.17 (q, J = 7.0 Hz, 2H), 3.78 (s, 2H), 3.40-3.35 (m, 4H), 2.58 (s, 3H), 2.20-2.12 (m, 2H), 1.51 (t, J = 7.0 Hz, 3H); | ES-LCMS m/z 503.2 (M + H) |
| 110 | 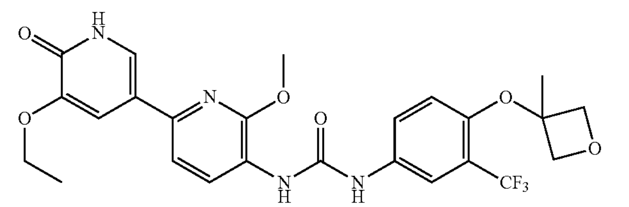 [SMILES: CCOc1cc(-c2ccc(NC(=O)Nc3ccc(OC4(C)COC4)c(C(F)(F)F)c3)c(OC)n2)c[nH]c1=O] | $^1$H NMR (400 MHz, CD$_3$OD) δ 8.39 (d, J = 8.4 Hz, 1H), 7.79 (d, J = 2.8 Hz, 1H), 7.70 (s, 1H), 7.60 (d, J = 2.0 Hz, 1H), 7.54-7.51 (m, 1H), 7.30 (d, J = 8.0 Hz, 1H), 6.61 (d, J = 8.8 Hz, 1H), 4.89 (d, J = 6.4 Hz, 2H), 4.62 (d, J = 7.2 Hz, 2H), 4.15-4.10 (m, 2H), 4.09 (s, 3H), 1.72 (s, 3H), 1.47 (t, J = 6.8 Hz, 3H); | ES-LCMS m/z 535.0 (M + H) |
| 111 | 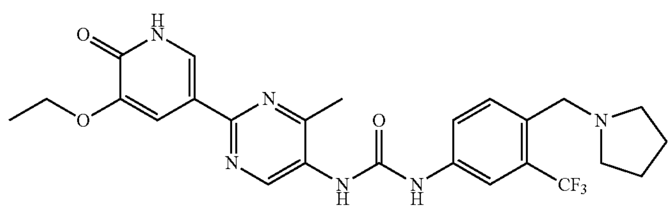 [SMILES: CCOc1cc(-c2ncc(NC(=O)Nc3ccc(CN4CCCC4)c(C(F)(F)F)c3)c(C)n2)c[nH]c1=O] | $^1$H NMR (400 MHz, MeOD-d$_4$): δ 9.05 (s, 1H), 8.07 (d, J = 2.0 Hz, 1H), 7.91 (s, 1H), 7.87 (d, J = 1.6 Hz, 1H), 7.70-7.62 (m, 2H), 4.18-4.13 (m, 2H), 3.78 (s, 2H), 2.60 (br. s., 4H), 2.56 (s, 3H), 1.83 (br. s., 4H), 1.49 (t, J = 7.0 Hz, 3H); | ES-LCMS m/z 517.2 (M + H) |
| 112 | 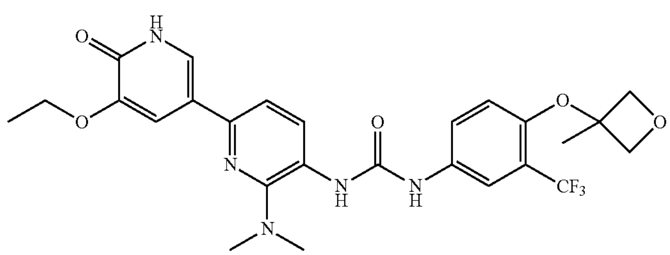 [SMILES: CCOc1cc(-c2ccc(NC(=O)Nc3ccc(OC4(C)COC4)c(C(F)(F)F)c3)c(N(C)C)n2)c[nH]c1=O] | $^1$H NMR (400 MHz, CD$_3$OD) δ: 8.26 (d, J = 8.4 Hz, 1H), 7.79 (d, J = 2.8 Hz, 1H), 7.68 (d, J = 2.0 Hz, 1H), 7.62 (d, J = 2.0 Hz, 1H), 7.54 (dd, J = 2.8, 8.8 Hz, 1H), 7.36 (d, J = 8.4 Hz, 1H), 6.61 (d, J = 9.2 Hz, 1H), 4.89-4.88 (m, 2H), 4.62 (d, J = 7.2 Hz, 2H), 4.13 (q, J = 6.8 Hz, 2H), 3.82 (s, 6H), 1.71 (s, 3H), 1.46 (t, J = 6.8 Hz, 3H); | ES-LCMS m/z 548.2 (M + H) |
| 113 | 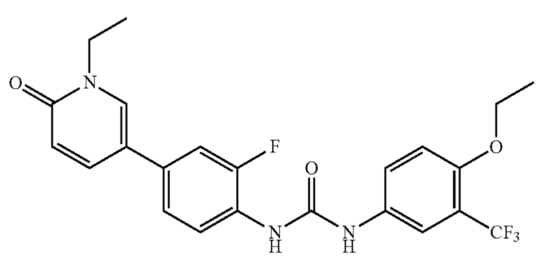 [SMILES: CCOc1ccc(NC(=O)Nc2ccc(-c3ccc(=O)n(CC)c3)cc2F)cc1C(F)(F)F] | $^1$H NMR (400 MHz, CD$_3$OD) δ 8.12 (t, J = 8.4 Hz, 1H), 8.02 (s, 1H), 7.87 (d, J = 6.8 Hz, 1H), 733 (s, 1H), 7.54 (d, J = 8.4 Hz, 1H), 7.39 (d, J = 12.4 Hz, 1H), 7.32 (d, J = 9.2 Hz, 1H), 7.10 (d, J = 9.2 Hz, 1H), 6.65 (d, J = 9.2 Hz, 1H), 4.11 (m, 4H), 1.39 (m, 6H), | ES-LCMS m/z 464.0 (M + H) |
| 114 | 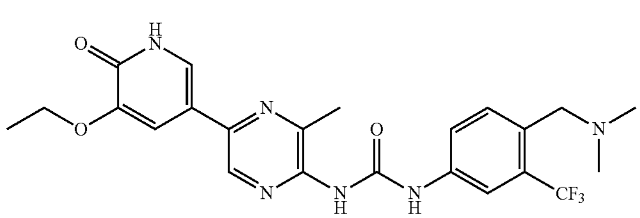 [SMILES: CCOc1cc(-c2cnc(NC(=O)Nc3ccc(CN(C)C)c(C(F)(F)F)c3)c(C)n2)c[nH]c1=O] | $^1$H NMR (400 MHz, CD$_3$OD) δ 8.65 (s, 1H), 8.22 (s, 1H), 8.03 (d, J = 8.4 Hz, 1H), 7.84 (s, 1H), 7.77 (d, J = 8.0 Hz, 1H), 7.68 (s, 1H), 4.51 (s, 2H), 4.20 (q, J = 7.0 Hz, 2H), 2.97 (s, 6H), 2.66 (s, 3H), 1.52 (t, J = 7.0 Hz, 3H); | ES-LCMS m/z 491.0 (M + H) |

| Example | Structure | NMR | LCMS |
|---|---|---|---|
| 115 | 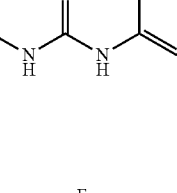 | $^1$H NMR (400 MHz, CD$_3$OD) δ 8.40 (d, J = 8.0 Hz, 1H), 7.79 (d, J = 2.4 Hz, 1H), 7.66 (s, 1H), 7.57-7.52 (m, 2H), 7.26 (d, J = 8.4 Hz, 1H), 6.61 (d, J = 9.2 Hz, 1H), 4.89 (d, J = 6.0 Hz, 2H), 4.62 (d, J = 6.8 Hz, 2H), 4.56 (s, 1H), 4.15-4.10 (m, 2H), 1.71 (s, 3H), 1.46 (t, J = 8.8 Hz, 9H); | ES-LCMS m/z 563.2 (M + H) |
| 116 | 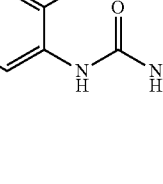 | $^1$H NMR (400 MHz, CD$_3$OD) δ 8.20-8.16 (t, J = 8.4 Hz, 1H), 7.87 (s, 1H), 7.76-7.73 (d, J = 8.8 Hz, 1H), 7.62-7.61 (d, J = 2.4 Hz, 1H), 7.44-7.37 (m, 3H), 7.36-7.35 (dd, J = 2.4, 0.8 Hz, 1H), 5.17-5.15 (m, 1H), 4.21-4.16 (q, J = 7.2 Hz, 2H), 1.49-1.45 (t, J = 7.2 Hz, 3H), 1.41-1.39 (d, J = 6.4 Hz, 3H); | ES-LCMS m/z 480.0 (M + H) |
| 117 | 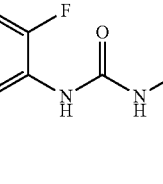 | $^1$H NMR (400 MHz, CD$_3$OD) δ 8.14 (t, J = 8.8 Hz, 1H), 7.82 (d, J = 2.8 Hz, 1H), 7.64 (dd, J = 2.0, 9.2 Hz, 1H), 7.43-7.39 (m, 1H), 7.35-7.31 (m, 3H), 6.93-6.84 (m, 1H), 4.66-4.57 (m, 2H), 4.39-4.30 (m, 2H), 4.18-4.13 (m, 2H), 3.03 (s, 3H), 1.71 (s, 3H), 1.47 (t, J = 6.8 Hz, 3H); | ES-LCMS m/z 535.2 (M + H) |
| 118 | 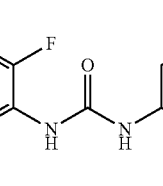 | $^1$H NMR (400 MHz, CD$_3$OD) δ 8.16 (t, J = 8.8 Hz, 1H), 7.78 (d, J = 2.8 Hz, 1H), 7.54 (dd, J = 2.8, 9.2 Hz, 1H), 7.42-7.34 (m, 3H), 7.29 (d, J = 2.4 Hz, 1H), 7.25 (d, J = 2.0 Hz, 1H), 4.18-4.13 (m, 2H), 3.65 (s, 2H), 1.47 (t, J = 6.8 Hz, 3H), 1.38 (s, 6H); | ES-LCMS m/z 524.2 (M + H) |
| 119 | 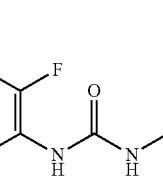 | $^1$H NMR (400 MHz, CD$_3$OD) δ: 7.98-7.94 (m, 1H), 7.80 (d, J = 2.8 Hz, 1H), 7.56-7.53 (m, 2H), 7.13 (d, J = 1.6 Hz, 1H), 6.63 (d, J = 9.2 Hz, 1H), 4.91-4.90 (m, 2H), 4.63 (d, J = 7.2 Hz, 2H), 4.10 (q, J = 6.8 Hz, 2H), 1.73 (s, 3H), 1.45 (t, J = 7.2 Hz, 3H); | ES-LCMS m/z 540.1 (M + H) |
| 120 | 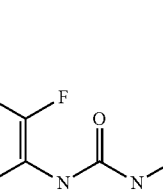 | $^1$H NMR (400 MHz, CD$_3$OD) δ 8.16 (t, J = 8.49 Hz, 1 H), 7.92 (d, J = 2.21 Hz, 1 H), 7.57-7.67 (m, 2 H), 7.27-7.42 (m, 4 H), 4.15 (q, J = 6.84 Hz, 2H), 3.70 (s, 2 H), 1.46 (t, J = 6.95 Hz, 3 H), 1.41 (s, 6 H); | ES-LCMS m/z 508 (M + H). |
| 121 | 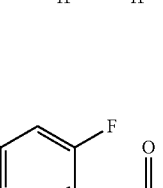 | $^1$H NMR (400 MHz, CD$_3$OD) 8.14-8.10 (m, 1H), 7.71 (d, J = 2.8 Hz, 1H), 7.54 (d, J = 6.4 Hz, 1H), 7.41-7.32 (m, 4H), 7.14 (d, J = 8.8 Hz, 1H), 4.72-4.68 (m, 2H), 4.60 (t, J = 5.6 Hz, 1H), 4.20 (t, J = 6.0 Hz, 2H), 2.27-2.19 (m, 2H), 1.32 (d, J = 6.0 Hz, 6H); | ES-LCMS m/z 526.2 (M + H) |

| Example | Structure | NMR | LCMS |
|---|---|---|---|
| 122 | 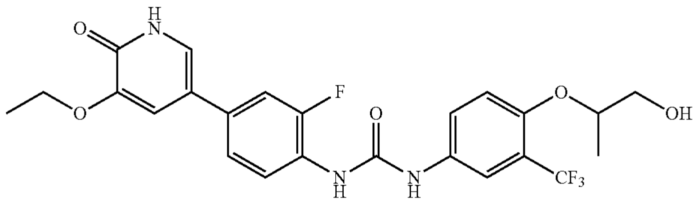 [SMILES: CCOc1cc(-c2ccc(NC(=O)Nc3ccc(OC(C)CO)c(C(F)(F)F)c3)c(F)c2)c[nH]c1=O] | ¹H NMR (400 MHz, MeOH-d4) δ 8.16 (t, J = 8.49 Hz, 1 H), 7.74 (d, J = 2.65 Hz, 1 H), 7.55 (dd, J = 9.04, 2.43 Hz, 1 H), 7.27-7.46 (m, 4 H), 7.22 (d, J = 9.04 Hz, 1 H), 4.56 (dd, J = 11.47, 5.95 Hz, 1 H), 4.18 (q, J = 6.84 Hz, 2 H), 3.73 (dd, J = 11.69, 6.17 Hz, 1 H), 3.61 (dd, J = 11.47, 4.85 Hz, 1 H), 1.48 (t, J = 6.95 Hz, 3 H), 1.27 (d, J = 6.17 Hz, 3 H); | ES-LCMS m/z 510 (M + H) |
| 123 | 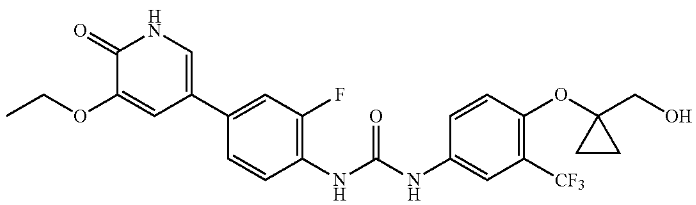 [SMILES: CCOc1cc(-c2ccc(NC(=O)Nc3ccc(OC4(CO)CC4)c(C(F)(F)F)c3)c(F)c2)c[nH]c1=O] | ¹H NMR (400 MHz, MeOD-d4) δ 8.13 (t, J = 8.8 Hz, 1H), 7.71 (t, J = 2.4 Hz, 1H), 7.52-7.51 (m, 1H), 7.44-7.40 (m, 2H), 7.37-7.31 (m, 3H), 4.15 (q, J = 7.2 Hz, 2H), 3.83 (s., 3H), 1.46 (t, J = 7.0 Hz, 3H), 0.97-0.93 (m, 4H); | ES-LCMS m/z 522.1 (M + H) |
| 124 | 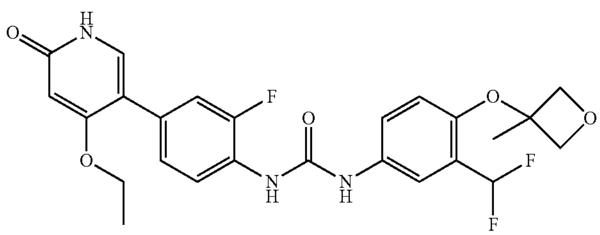 [SMILES: CCOc1cc(=O)[nH]cc1-c1ccc(NC(=O)Nc2ccc(OC3(C)COC3)c(C(F)F)c2)c(F)c1] | ¹H NMR (400 MHz, CD₃OD) δ 8.08 (t, J = 8.4 Hz, 1H), 7.66 (d, J = 2.8 Hz, 1H), 7.48 (dd, J = 2.4, 8.8 Hz, 1H), 7.35 (s, 1H), 7.25 (dd, J = 2.4, 8.8 Hz, 1H), 7.18-7.16 (m, 1H), 6.94 (t, J = 55.6 Hz, 1H), 6.55 (d, J = 9.2 Hz, 1H), 5.95 (s, 1H), 4.89 (d, J = 3.6 Hz, 2H), 4.62 (d, J = 7.6 Hz, 2H), 4.13-4.10 (m, 2H), 4.53 (s, 2H), 1.71 (s, 3H), 1.38 (t, J = 6.8 Hz, 3H); | ES-LCMS m/z 504.2 (M + H) |
| 125 | 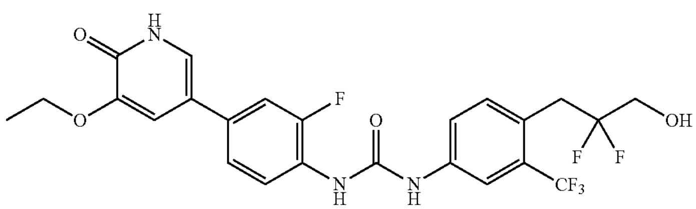 [SMILES: CCOc1cc(-c2ccc(NC(=O)Nc3ccc(CC(F)(F)CO)c(C(F)(F)F)c3)c(F)c2)c[nH]c1=O] | ¹H NMR (400 MHz, CD₃OD) δ 8.17 (t, J = 8.6 Hz, 1H), 7.92 (d, J = 2.0 Hz, 1H), 7.64-7.57 (m, 1H), 7.50 (d, J = 8.6 Hz, 1H), 7.41 (dd, J = 1.8, 12.3 Hz, 1H), 7.38-7.22 (m, 3H), 4.16 (d, J = 6.8 Hz, 2H), 3.68 (t, J = 12.8 Hz, 2H), 3.44 (s, 2H), 1.47 (t, J = 7.0 Hz, 3H); | ES-LCMS m/z 530.1 (M + H) |
| 126 | 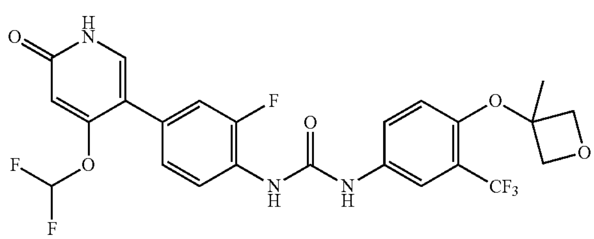 [SMILES: CC1(Oc2ccc(NC(=O)Nc3ccc(-c4c[nH]c(=O)cc4OC(F)F)cc3F)cc2C(F)(F)F)COC1] | ¹H NMR (400 MHz, CD₃OD) δ 8.14 (t, J = 8.4 Hz, 1H), 7.79 (s, 1H), 7.51-7.45 (m, 2H), 7.28-6.90 (m, 3H), 6.62 (d, J = 8.8 Hz, 1H), 6.19 (s, 1H), 4.90-4.62 (m, 4H), 1.72 (s, 3H); | ES-LCMS m/z 544.1 (M + H) |
| 127 | 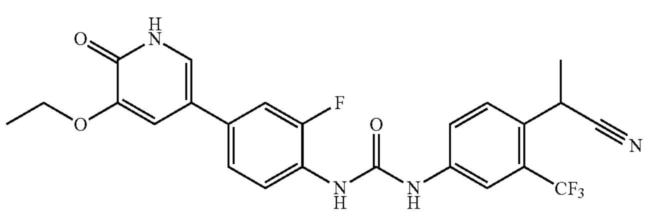 [SMILES: CCOc1cc(-c2ccc(NC(=O)Nc3ccc(C(C)C#N)c(C(F)(F)F)c3)c(F)c2)c[nH]c1=O] | ¹H NMR (400 MHz, CD₃OD) δ 8.18 (t, J = 8.4 Hz, 1H), 8.03 (s, 1H), 7.75 (d, J = 1.6 Hz, 2H), 7.43-7.35 (m, 2H), 7.30-7.24 (m, 2H), 4.36-4.31 (m, 1H), 4.18-4.13 (m, 2H), 1.66 (d, J = 7.2 Hz, 3H), 1.49 (t, J = 7.2 Hz, 3H); | ES-LCMS m/z 489.2 (M + H) |
| 128 | 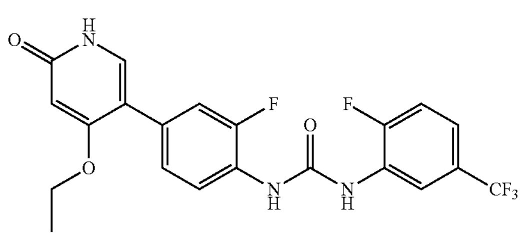 [SMILES: CCOc1cc(=O)[nH]cc1-c1ccc(NC(=O)Nc2cc(C(F)(F)F)ccc2F)c(F)c1] | ¹H NMR (400 MHz, DMSO-d₆) δ 8.63 (d, J = 7.6 Hz, 1H), 8.23 (t, J = 8.4 Hz, 1H), 7.67 (s, 1H), 7.37-7.22 (m, 3H), 7.25 (d, J = 8.8 Hz, 1H), 6.27 (s, 1H), 4.21 (m, 2H), 1.42 (t, J = 6.8 Hz, 3H); | ES-LCMS m/z 454.1 (M + H) |

| Example | Structure | NMR | LCMS |
|---|---|---|---|
| 129 | 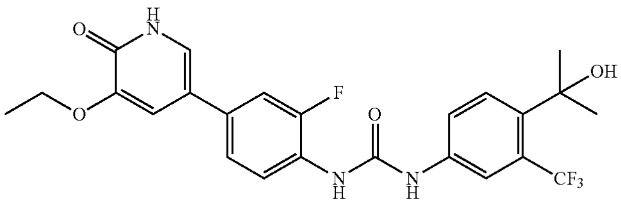 [SMILES: CCOc1cc(-c2ccc(NC(=O)Nc3ccc(C(C)(C)O)c(C(F)(F)F)c3)c(F)c2)c[nH]c1=O] | ¹H NMR (400 MHz, CD₃OD) δ 8.16-8.12 (m, 1H), 7.88 (s, 1H), 7.64-7.63 (m, 2H), 7.39-7.34 (m, 2H), 7.26 (s, 1H), 7.21 (d, J = 2.4 Hz, 1H), 4.13-4.09 (q, J = 7.0 Hz, 2H), 1.61 (s, 6H), 1.47-1.44 (t, J = 7.0 Hz, 3H); | ES-LCMS m/z 494.1 (M + H) |
| 130 | 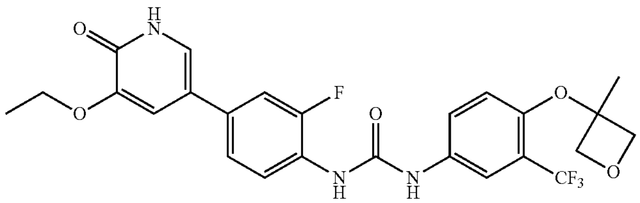 [SMILES: CCOc1cc(-c2ccc(NC(=O)Nc3ccc(OC4(C)COC4)c(C(F)(F)F)c3)c(F)c2)c[nH]c1=O] | ¹H NMR (400 MHz, CD₃OD) δ 8.14 (t, J = 8.4 Hz, 1H), 7.79 (d, J = 2.8 Hz, 1H), 7.53 (dd, J = 2.4, 8.8 Hz, 1H), 7.40-7.27 (m, 4H), 6.62 (d, J = 8.8 Hz, 1H), 4.89 (d, J = 6.8 Hz, 2H), 4.63 (d, J = 7.2 Hz, 2H), 4.16-4.11 (m, 2H), 1.72 (s, 3H), 1.46 (t, J = 7.2 Hz, 3H); | ES-LCMS m/z 522.1 (M + H) |
| 131 | 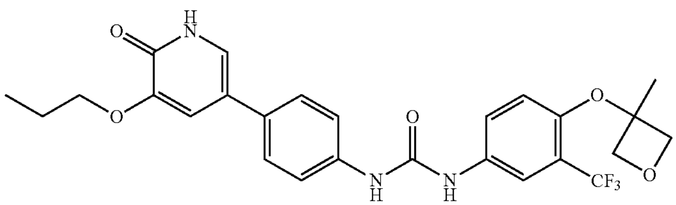 [SMILES: CCCOc1cc(-c2ccc(NC(=O)Nc3ccc(OC4(C)COC4)c(C(F)(F)F)c3)cc2)c[nH]c1=O] | ¹H NMR (400 MHz, CD₃OD) 7.77 (d, J = 2.8 Hz, 1H), 7.51-7.50 (m, 5H), 7.37 (d, J = 2.0 Hz, 1H), 7.34 (d, J = 2.0 Hz, 1H), 6.62 (d, J = 9.2 Hz, 1H), 4.89 (d, J = 7.6 Hz, 2H), 4.62 (d, J = 7.2 Hz, 2H), 4.06 (t, J = 6.8 Hz, 2H), 1.89-1.87 (m, 2H), 1.71 (s, 3H), 1.07 (t, J = 7.6 Hz, 3H); | ES-LCMS m/z 518.2 (M + H) |
| 132 | 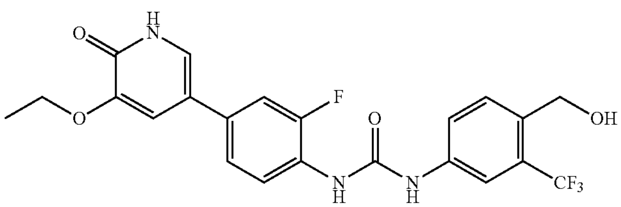 [SMILES: CCOc1cc(-c2ccc(NC(=O)Nc3ccc(CO)c(C(F)(F)F)c3)c(F)c2)c[nH]c1=O] | ¹H NMR (400 MHz, CD₃OD) δ 8.17-8.12 (t, J = 8.4 Hz, 1H), 7.89 (s, 1H), 7.65-7.62 (m, 2H), 7.39-7.34 (m, 2H), 7.26-7.25 (d, J = 2.4 Hz, 1H), 7.21-7.20 (d, J = 2.4 Hz, 1H), 4.72 (s, 2H), 4.12-4.10 (q, J = 7.2 Hz, 2H), 1.47-1.44 (t, J = 7.2 Hz, 3H); | ES-LCMS m/z 466.0 (M + H) |
| 133 | 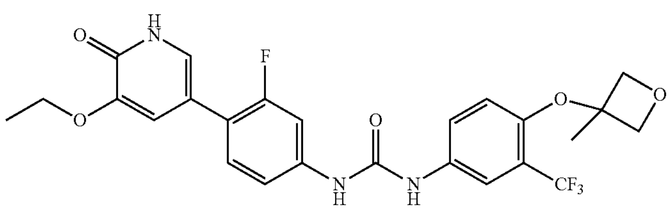 [SMILES: CCOc1cc(-c2ccc(NC(=O)Nc3ccc(OC4(C)COC4)c(C(F)(F)F)c3)cc2F)c[nH]c1=O] | ¹H NMR (400 MHz, CD₃OD) δ 7.75 (d, J = 2.4 Hz, 1H), 7.56-7.54 (m, 1H), 7.51 (dd, J = 13.6, 2.4 Hz,, 1H), 7.38 (t, J = 8.6 Hz, 1H), 7.19-7.17 (m, 2H), 7.13 (s, 1H), 6.61 (d, J = 9.2 Hz, 1H), 4.86 (m, 2H), 4.62 (d, J = 7.2 Hz, 2H), 4.10-4.05 (m, 2H), 1.72 (s, 3H), 1.45 (t, J = 6.8 Hz, 3H); | ES-LCMS m/z 522.1 (M + H) |
| 134 | 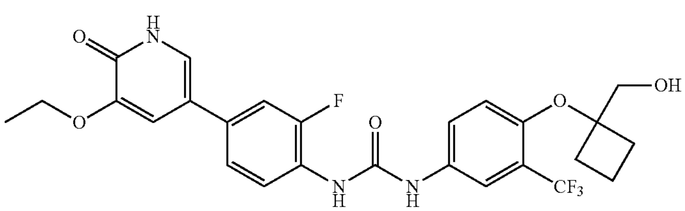 [SMILES: CCOc1cc(-c2ccc(NC(=O)Nc3ccc(OC4(CO)CCC4)c(C(F)(F)F)c3)c(F)c2)c[nH]c1=O] | ¹H NMR (400 MHz, CD₃OD) δ 8.13 (t, J = 8.4 Hz, 1H), 7.73 (d, J = 2.8 Hz, 1H), 7.46 (dd, J = 9.0, 2.6 Hz, 1H), 7.40-7.27 (m, 4H), 7.03 (d, J = 9.2 Hz, 1H), 4.16-4.11 (m, 2H), 3.86 (d, J = 6.8 Hz, 2H), 2.30-2.28 (m, 4H), 1.82-1.63 (m, 2H), 1.46 (t, J = 7.0 Hz, 3H); | ES-LCMS m/z 536.2 (M + H) |
| 135 | 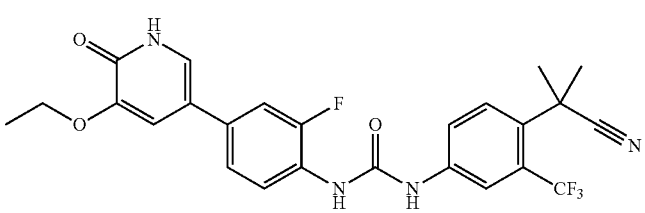 [SMILES: CCOc1cc(-c2ccc(NC(=O)Nc3ccc(C(C)(C)C#N)c(C(F)(F)F)c3)c(F)c2)c[nH]c1=O] | ¹H NMR (400 MHz, CD₃OD) δ 8.21 (t, J = 8.4 Hz, 1H), 8.04 (d, J = 2.4 Hz, 1H), 7.77-7.71 (m, 2H) 7.46-7.37 (m, 4H), 4.22-4.17 (m, 2H), 1.88 (s, 6H), 1.51 (t, J = 6.8 Hz, 3H); | ES-LCMS m/z 503.1 (M + H) |

| Example | NMR | LCMS |
|---|---|---|
| 136 | ¹H NMR (400 MHz, CD₃OD) δ 8.18 (t, J = 8.8 Hz, 1H), 7.83 (d, J = 2.8 Hz, 1H), 7.57 (dd, J = 2.8 Hz, 8.4 Hz, 1H), 7.43-7.42 (m, 1H), 7.40-7.37 (m, 3H), 6.65 (d, J = 9.2 Hz, 1H), 4.92 (d, J = 6.4 Hz, 2H), 4.83-4.77 (m, 1H), 4.66 (d, J = 7.2 Hz, 2H), 1.75 (s, 3H), 1.41 (d, J = 6.4 Hz, 6H); | ES-LCMS m/z 536.1 (M + H) |
| 137 | ¹H NMR (400 MHz, CD₃OD) δ 8.21 (dd, J = 9.20, 2.40 Hz, 1H), 7.97-7.96 (m, 1H), 7.83-7.78 (m, 2H), 7.53 (dd, J = 8.40, 2.80 Hz, 1H), 7.43 (d, J = 2.40 Hz, 1H), 7.40 (dd, J = 8.40, 2.00 Hz, 1H), 6.91-6.89 (m, 1H), 4.86 (m, 2H), 4.62 (d, J = 7.60 Hz, 2H), 2.35 (s, 3H), 1.71 (s, 3H); | ES-LCMS m/z 474.1 (M + H) |
| 138 | ¹H NMR (400 MHz, CD₃OD) 8.15 (d, J = 8.4 Hz, 1H), 7.79 (d, J = 2.8 Hz, 1H), 7.38 (d, J = 3.2 Hz, 1H), 7.37-7.35 (m, 4H), 6.62 (d, J = 9.2 Hz, 1H), 4.89 (d, J = 6.4 Hz, 2H), 4.62 (d, J = 7.2 Hz, 2H), 4.06 (d, J = 6.8 Hz, 2H), 1.88-1.87 (m, 2H), 1.71 (s, 3H), 1.07 (t, J = 7.2 Hz, 3H); | ES-LCMS m/z 536.1 (M + H) |
| 139 | ¹H NMR (400 MHz, CD₃OD) δ 8.16 (t, J = 8.4 Hz, 1H), 7.80 (d, J = 2.8 Hz, 1H), 7.61 (dd, J = 2.8, 9.2 Hz, 1H), 7.42-7.34 (m, 2H), 7.29 (d, J = 2.4 Hz, 1H), 7.25 (d, J = 2.4 Hz, 1H), 7.16 (d, J = 9.2 Hz, 1H), 4.18-4.13 (m, 2H), 4.09 (s, 1H), 4.06 (s, 1H), 1.51 (t, J = 6.8 Hz, 3H), 1.47 (s, 6H); | ES-LCMS m/z 526.2 (M + H) |
| 140 | ¹H NMR (400 MHz, CD₃OD) 7.77 (d, J = 2.8 Hz, 1H), 7.54-7.53 (m, 5H), 7.47 (d, J = 2.4 Hz, 1H), 7.42 (d, J = 2.4 Hz, 1H), 6.62 (d, J = 9.2 Hz, 1H), 4.88 (s, 2H), 4.63 (d, J = 7.6 Hz, 2H), 4.20 (d, J = 6.8 Hz, 2H), 1.71 (s, 3H), 1.47 (t, J = 7.2 Hz, 3H); | ES-LCMS m/z 504.2 (M + H) |
| 141 | ¹H NMR (400 MHz, CD₃OD) δ 8.42-8.41 (d, J = 1.98 Hz, 1H), 8.23-8.21 (t, J = 4.2 Hz, 1H), 7.46-7.36 (m, 4H), 7.13 (s, 1H), 6.93-6.91 (d, J = 8.4 Hz, 1H), 4.23-4.17 (q, J = 6.8 Hz, 2H), 1.49-1.46 (t, J = 6.8 Hz, 3H); | ES-LCMS m/z 452.1 (M + H) |
| 142 | ¹H NMR (400 MHz, MeOD) 8.17 (t, J = 8.4 Hz, 1H), 7.90 (d, J = 2.4 Hz, 1H), 7.61 (d, J = 2.4 Hz, 1H), 7.59-7.33 (m, 4H), 7.22 (d, J = 7.6 Hz, 1H), 4.68 (d, J = 6.0 Hz, 2H), 4.30 (d, J = 6.0 Hz, 2H), 4.17 (q, J = 6.8 Hz, 2H), 3.03 (s, 2H), 1.47 (t, J = 6.0 Hz, 3H), 1.35 (s, 3H); | ES-LCMS m/z 520.2 (M + H) |

| Example | Structure | NMR | LCMS |
|---|---|---|---|
| 143 | 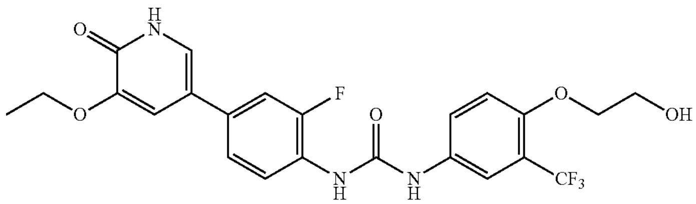 [SMILES: CCOc1cc(-c2ccc(NC(=O)Nc3ccc(OCCO)c(C(F)(F)F)c3)c(F)c2)c[nH]c1=O] | ¹H NMR (400 MHz, CD₃OD) δ 8.16 (t, J = 8.6 Hz, 1H), 7.78 (d, J = 2.4 Hz, 1H), 7.61-7.58 (m, 1H), 7.42-7.34 (m, 2H), 7.28 (d, J = 2.4 Hz, 1H), 7.24 (d, J = 2.0 Hz, 1H), 7.19 (d, J = 8.8 Hz, 1H), 4.18-4.13 (m, 4H), 3.91 (t, J = 5.0 Hz, 2H), 1.49 (t, J = 7.0 Hz, 3H); | ES-LCMS m/z 496.1 (M + H) |
| 144 | 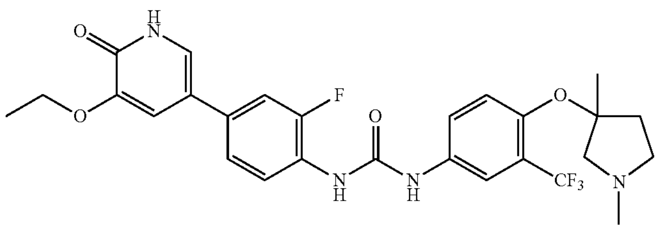 [SMILES: CCOc1cc(-c2ccc(NC(=O)Nc3ccc(OC4(C)CCN(C)C4)c(C(F)(F)F)c3)c(F)c2)c[nH]c1=O] | ¹H NMR (400 MHz, CD₃OD) δ 8.19 (t, J = 8.80 Hz, 1H), 7.84-7.82 (m, 1H), 7.62-7.60 (d, J = 8.80 Hz, 1H), 7.53-7.52 (m, 2H), 7.47-7.44 (d, J = 2.40 Hz, 1H), 7.38 (m, 1H), 7.28-7.23 (m, 1H), 4.25-4.20 (m, 2H), 4.17-3.89 (m, 2H), 3.66-3.36 (m, 2H), 2.81-2.79 (m, 3H), 2.69-2.48 (m, 1H), 2.55-2.28 (m, 1H), 1.60-1.53 (m, 3H), 1.49 (t, J = 7.00 Hz, 3H); | ES-LCMS m/z 549.3 (M + H) |
| 145 | 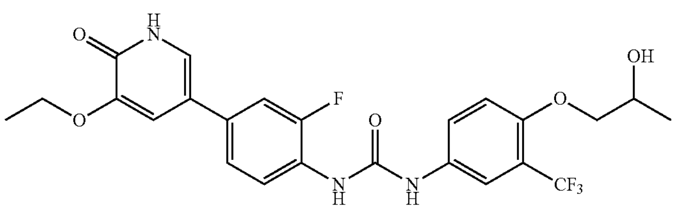 [SMILES: CCOc1cc(-c2ccc(NC(=O)Nc3ccc(OCC(C)O)c(C(F)(F)F)c3)c(F)c2)c[nH]c1=O] | ¹H NMR (400 MHz, CD₃OD) δ 8.18 (t, J = 8.4 Hz, 1 H), 7.76 (d, J = 2.4 Hz, 1H), 7.59-7.50 (m, 3H), 7.47-7.36 (m, 2H) 7.14 (d, J = 8.8 Hz, 1H), 4.25-4.20 (m, 2 H), 4.11-4.06 (m, 1H), 4.00 (dd, J = 5.6, 9.2 Hz, 1H), 3.87 (dd, J = 5.6, 9.2 Hz, 1H), 1.48 (t, J = 6.8 Hz, 3H), 1.28 (d, J = 6.4 Hz, 3H); | ES-LCMS m/z 510.1 (M + H) |
| 146 | 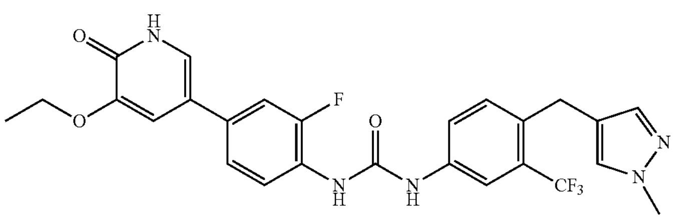 [SMILES: CCOc1cc(-c2ccc(NC(=O)Nc3ccc(Cc4cnn(C)c4)c(C(F)(F)F)c3)c(F)c2)c[nH]c1=O] | ¹H NMR (400 MHz, CD₃OD) δ 8.17 (t, J = 6.8 Hz, 1H), 7.90 (d, J = 2.4 Hz, 1H), 7.61-7.57 (m, 3H), 7.44-7.34 (m, 5H), 4.17 (q, J = 7.20 Hz, 2H), 3.98 (s, 2H), 3.92 (s, 3H), 1.47 (t, J = 7.00 Hz, 3H); | ES-LCMS m/z 530.1 (M + H) |
| 147 | 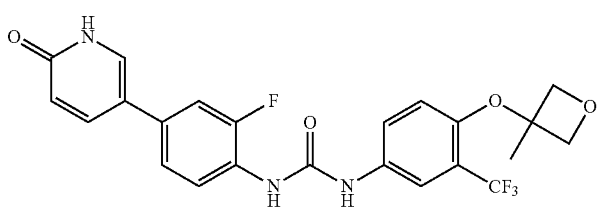 [SMILES: CC1(Oc2ccc(NC(=O)Nc3ccc(-c4ccc(=O)[nH]c4)cc3F)cc2C(F)(F)F)COC1] | ¹H NMR (400 MHz, CD₃OD) δ: 8.18 (t, J = 8.4 Hz, 1H), 8.10 (d, J = 8.0 Hz, 1H), 7.89 (s, 1H), 7.79 (d, J = 2.8 Hz, 1H), 7.52 (dd, J = 2.8, 8.8 Hz, 1H), 7.42-7.33 (m, 2H), 6.79 (d, J = 8.8 Hz, 1H), 6.61 (d, J = 8.8 Hz, 1H), 4.89 (s, 2H), 4.62 (d, J = 7.2 Hz, 2H), 1.71 (s, 3H); | ES-LCMS m/z 478.1 (M + H) |
| 148 | 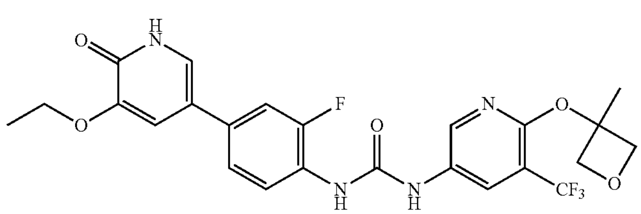 [SMILES: CCOc1cc(-c2ccc(NC(=O)Nc3cnc(OC4(C)COC4)c(C(F)(F)F)c3)c(F)c2)c[nH]c1=O] | ¹H NMR (400 MHz, CD₃OD) 8.26-8.19 (m, 2H), 8.10-8.02 (m, 1H), 7.39-7.35 (m, 2H), 7.25 (d, J = 2.4 Hz, 1H), 7.21 (d, J = 2.4 Hz, 1H), 4.89 (d, J = 7.6 Hz, 2H), 4.61 (d, J = 7.6 Hz, 2H), 4.13 (d, J = 7.2 Hz, 2H), 1.80 (s, 3H), 1.45 (t, J = 6.8 Hz, 3H); | ES-LCMS m/z 523.2 (M + H) |
| 149 | 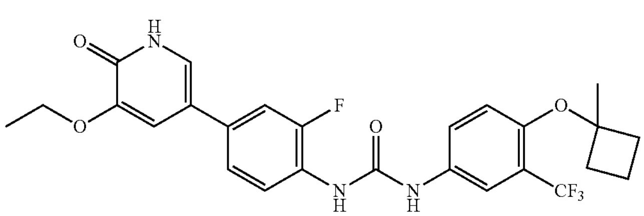 [SMILES: CCOc1cc(-c2ccc(NC(=O)Nc3ccc(OC4(C)CCC4)c(C(F)(F)F)c3)c(F)c2)c[nH]c1=O] | ¹H NMR (400 MHz, CD₃OD) δ 8.14 (t, J = 8.60 Hz, 1H), 7.72-7.71 (d, J = 2.80 Hz, 1H), 7.48 (dd, J = 9.20, 2.80 Hz, 1H), 7.41-7.37 (m, 1H), 7.34-7.32 (m, 3H), 6.91-6.89 (d, J = 9.20 Hz, 1H), 4.18-4.12 (m, 2H), 2.45-2.40 (m, 2H), 2.22-2.17 (m, 1H), 1.84-1.72 (m, 2H), 1.53 (s, 3H), 1.46 (t, J = 7.00 Hz, 3H); | ES-LCMS m/z 520.2 (M + H) |

| Example | Structure | NMR | LCMS |
|---|---|---|---|
| 150 | 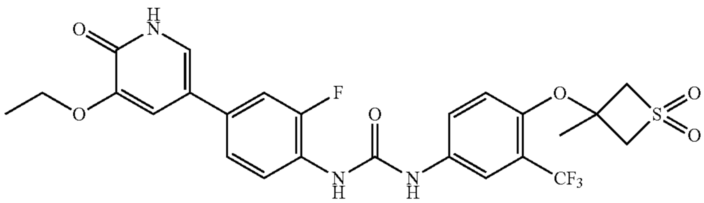 [SMILES: CCOc1cc(-c2ccc(NC(=O)Nc3ccc(OC4(C)CS(=O)(=O)C4)c(C(F)(F)F)c3)c(F)c2)c[nH]c1=O] | ¹H NMR (400 MHz, CD₃OD) δ: 8.17 (d, J = 8.8 Hz, 1H), 7.86 (d, J = 2.0 Hz, 1H), 7.62 (d, J = 6.4 Hz, 1H), 7.43-7.36 (m, 4H), 7.03 (d, J = 8.8 Hz, 1H), 4.61 (d, J = 16 Hz, 2H), 4.47 (d, J = 14.8 Hz, 2H), 4.18 (m, J = 6.0 Hz, 2H), 1.87 (s, 3H), 1.49 (t, J = 6.8 Hz, 3H); | ES-LCMS m/z 570.1 (M + H) |
| 151 | 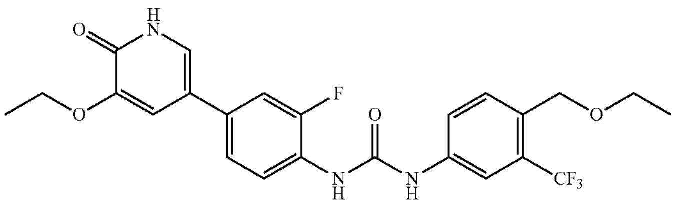 [SMILES: CCOCc1ccc(NC(=O)Nc2ccc(-c3c[nH]c(=O)c(OCC)c3)cc2F)cc1C(F)(F)F] | ¹H NMR (400 MHz, CD₃OD) 8.15 (t, J = 8.49 Hz, 1H), 7.91 (s, 1H), 7.60 (br. s., 2H), 7.29-7.42 (m, 2H), 7.25 (d, J = 2.21 Hz, 1H), 7.21 (d, J = 1.98 Hz, 1H), 4.60 (s, 2H), 4.12 (q, J = 6.98 Hz, 2H), 3.57 (q, J = 7.06 Hz, 2H), 1.45 (t, J = 7.06 Hz, 3H), 1.23 (t, J = 7.06 Hz, 3H); | ES-LCMS m/z 494.2 (M + H) |
| 152 | 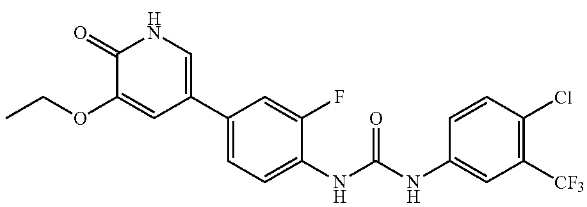 [SMILES: CCOc1cc(-c2ccc(NC(=O)Nc3ccc(Cl)c(C(F)(F)F)c3)c(F)c2)c[nH]c1=O] | ¹H NMR (400 MHz, CD₃OD) δ 8.18 (t, J = 8.4 Hz, 1H), 8.02 (d, J = 2.8 Hz, 1H), 7.62-7.60 (m, 1H), 7.51 (d, J = 8.4 Hz, 1H), 7.41-7.28 (m, 4H), 4.17-4.12 (m, 2H), 1.48 (t, J = 7.0 Hz, 3H); | ES-LCMS m/z 470.0 (M + H) |
| 153 | 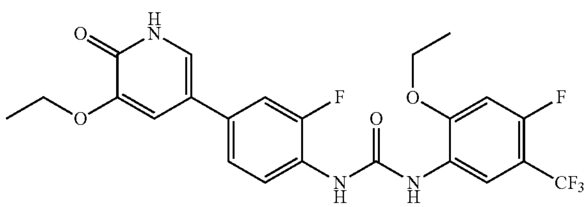 [SMILES: CCOc1cc(F)c(C(F)(F)F)cc1NC(=O)Nc1ccc(-c2c[nH]c(=O)c(OCC)c2)cc1F] | ¹H NMR (DMSO-d₆, 400 MHz) δ 11.83 (br. s., 1H), 9.46 (br. s., 1H), 8.80-8.87 (m, 1H), 8.49 (d, J = 8.0 Hz, 1H), 8.08-8.18 (m, 1H), 7.57 (dd, J = 13.1, 2.0 Hz, 1H), 7.39 (d, J = 8.5 Hz, 1H), 7.23-7.34 (m, 2H), 7.14 (d, J = 2.3 Hz, 1H), 4.26 (q, J = 7.0 Hz, 2H), 4.06 (q, J = 7.0 Hz, 2H), 1.44 (t, J = 6.9 Hz, 3H), 1.34 ppm (t, J = 7.0 Hz, 3H) | ES-LCMS m/z 498.3 (M + H) |
| 154 | 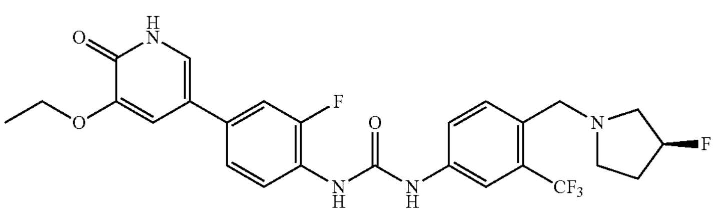 [SMILES: CCOc1cc(-c2ccc(NC(=O)Nc3ccc(CN4CC[C@H](F)C4)c(C(F)(F)F)c3)c(F)c2)c[nH]c1=O] | ¹H NMR (400 MHz, CD₃OD) δ 8.21 (t, J = 8.6 Hz, 1H), 8.13 (s, 1H), 7.87-7.78 (m, 2H), 7.49-7.41 (m, 4H), 5.57-5.44 (m, 1H), 4.66-4.63 (m, 2H), 4.25-4.20 (m, 2H), 3.89-3.50 (m, 4H), 2.68-2.36 (m, 2H), 1.51 (t, J = 7.0 Hz, 3H); | ES-LCMS m/z 537.2 (M + H) |
| 155 | 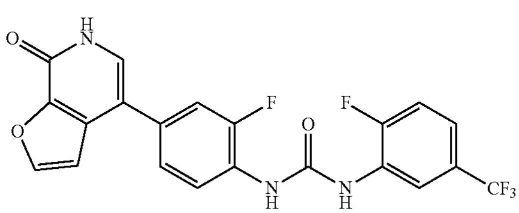 [SMILES: O=C(Nc1ccc(-c2c[nH]c(=O)c3occc23)cc1F)Nc1cc(C(F)(F)F)ccc1F] | ¹H NMR (400 MHz, CD₃OD) δ 8.64-8.62 (d, J = 7.6 Hz, 1H), 8.31-8.27 (m, 1H), 8.15 (s, 1H), 7.40-7.34 (m, 5H), 7.03 (s, 1H) | ES-LCMS m/z 449.9 (M + H) |
| 156 | 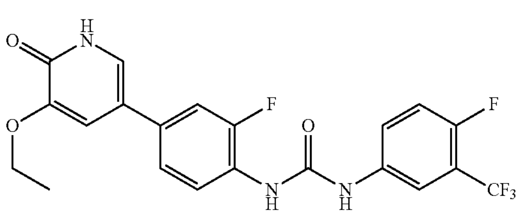 [SMILES: CCOc1cc(-c2ccc(NC(=O)Nc3ccc(F)c(C(F)(F)F)c3)c(F)c2)c[nH]c1=O] | ¹H NMR (400 MHz, DMSO-d₆) δ 11.78 (s, 1H), 9.39 (s, 1H), 8.65 (s, 1H), 8.06 (t, J = 8.4 Hz, 1H), 7.99 (dd, J = 2.4, 6.4 Hz, 1H),, 7.62-7.51 (m, 2 H), 7.46-7.35 (m, 2H), 7.28 (s., 1H), 7.11 (d, J = 2.0 Hz, 1H), 4.06-4.00 (m, 2H), 1.32 (t, J = 6.8 Hz, 3H); | ES-LCMS m/z 454.1 (M + H) |

| Example | Structure | NMR | LCMS |
|---|---|---|---|
| 157 | 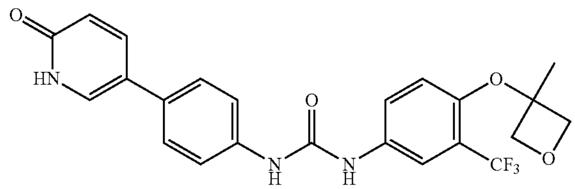 [SMILES: CC1(Oc2ccc(NC(=O)Nc3ccc(-c4ccc(=O)[nH]c4)cc3)cc2C(F)(F)F)COC1] | ¹H NMR (400 MHz, CD₃OD) δ 8.21-8.18 (m, 1H), 7.95 (d, J = 2.4 Hz, 1H), 7.77 (d, J = 2.4 Hz, 1H), 7.54-7.53 (m, 5H), 6.89 (d, J = 9.2 Hz, 1H), 6.62 (d, J = 9.2 Hz, 1H), 4.89-4.86 (m, 2H), 4.62 (d, J = 7.2 Hz, 2H), 1.72 (s, 3H); | ES-LCMS m/z 460.1 (M + H) |
| 158 | 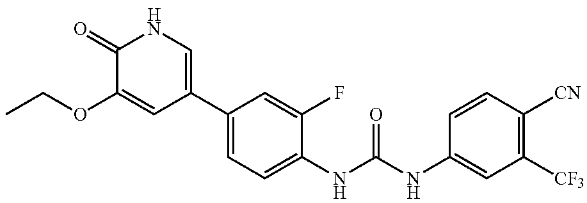 [SMILES: CCOc1cc(-c2ccc(NC(=O)Nc3ccc(C#N)c(C(F)(F)F)c3)c(F)c2)c[nH]c1=O] | ¹H NMR (400 MHz, DMSO-d₆ and CD₃OD) δ 9.85-9.84 (m, 1H), 8.82 (s, 1H), 8.18 (s, 1H), 8.06-8.00 (m, 2H), 7.72 (d, J = 9.6 Hz, 1H), 7.55 (d, J = 12.8 Hz, 1H), 7.39 (d, J = 9.6 Hz, 1H), 7.29 (s, 1H), 7.11 (s, 1H), 4.01 (m, 2H), 1.32 (t, J = 7.0 Hz, 3H); | ES-LCMS m/z 461.0 (M + H) |
| 159 | 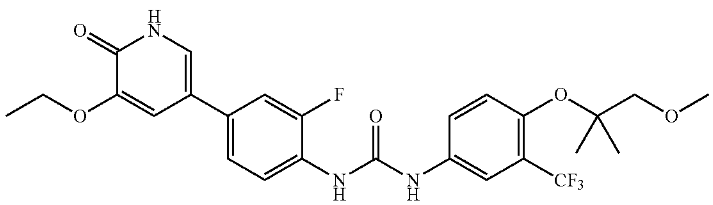 [SMILES: CCOc1cc(-c2ccc(NC(=O)Nc3ccc(OC(C)(C)COC)c(C(F)(F)F)c3)c(F)c2)c[nH]c1=O] | ¹H NMR (400 MHz, CD₃OD) δ 8.15-8.11 (t, J = 8.4 Hz, 1H), 7.76-7.75 (d, J = 5.2 Hz, 1H), 7.57-7.54 (dd, J = 9.2 Hz, J = 2.8 Hz, 1H), 7.40-7.31 (m, 3H), 7.30-7.29 (d, J = 2.4 Hz, 1H), 7.27-7.26 (d, J = 2.0 Hz, 1H), 7.13-7.11 (d, J = 8.8 Hz, 1H), 4.16-4.11 (q, J = 7.2 Hz, 2H), 3.91 (s, 2H), 3.29 (s, 3H), 1.47-1.44 (t, J = 7.2 Hz, 3H), 1.30 (s, 6H); | ES-LCMS m/z 538.2 (M + H) |
| 160 | 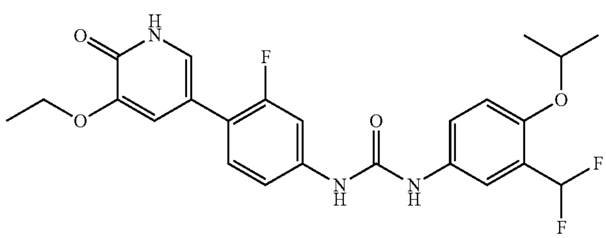 [SMILES: CCOc1cc(-c2ccc(NC(=O)Nc3ccc(OC(C)C)c(C(F)F)c3)cc2F)c[nH]c1=O] | ¹H NMR (400 MHz, CD₃OD) δ 7.57 (d, J = 2.40 Hz, 1H), 7.52 (d, J = 2.00 Hz, 1H), 7.49-7.48 (d, J = 2.00 Hz, 1H), 7.39-7.35 (t, J = 8.80 Hz, 2H), 7.06 (d, J = 2.00 Hz, H), 6.92 (t, J = 50.00 Hz, 1H), 4.65-4.59 (m, 1H), 4.11-4.06 (m, 2H), 1.44 (t, J = 7.00 Hz, 3H), 1.32-1.31 (d, J = 6.00 Hz, 6H); | ES-LCMS m/z 476 (M + H) |
| 161 | 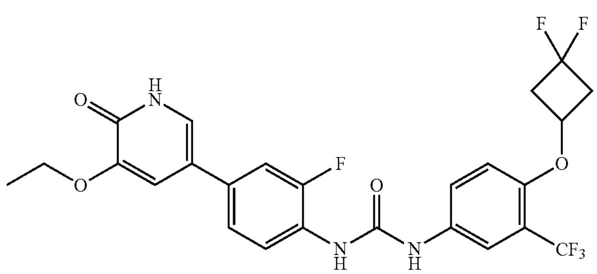 [SMILES: CCOc1cc(-c2ccc(NC(=O)Nc3ccc(OC4CC(F)(F)C4)c(C(F)(F)F)c3)c(F)c2)c[nH]c1=O] | ¹H NMR (400 MHz, CD₃OD) δ 8.15 (t, J = 8.8 Hz, 1H), 7.81 (d, J = 2.4 Hz, 1H), 7.60-7.62 (d, J = 6.4 Hz, 1H), 7.34-7.42 (m, 2H), 7.28 (d, J = 2 Hz, 1H), 7.24 (d, J = 2 Hz, 1H), 7.03 (d, J = 9.2 Hz, 1H), 4.15 (q, J = 6.8 Hz, 2H), 3.10-3.20 (m, 2H), 2.67-2.79 (m, 2H), 1.49 (t, J = 6.8 Hz, 3H) | ES-LCMS m/z: 542.2 (M + H) |
| 162 | 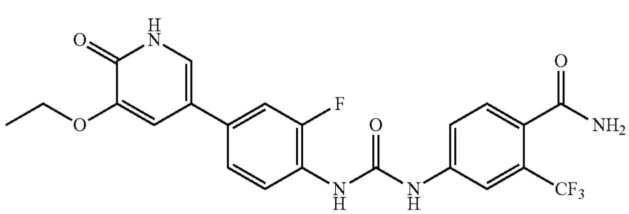 [SMILES: CCOc1cc(-c2ccc(NC(=O)Nc3ccc(C(N)=O)c(C(F)(F)F)c3)c(F)c2)c[nH]c1=O] | ¹H NMR (400 MHz, CD₃OD) δ 8.16 (t, J = 8.20 Hz, 1H), 7.97 (d, J = 2.00 Hz, 1H), 7.69-7.66 (m, 1H), 7.52-7.50 (d, J = 8.40 Hz, 1H), 7.39-7.33 (m, 1H), 7.30 (d, J = 2.00 Hz, 3H), 4.15-4.14 (d, J = 6.80 Hz, 2H), 1.46 (t, J = 7.00 Hz, 3H); | ES-LCMS m/z 479 (M + H) |
| 163 | 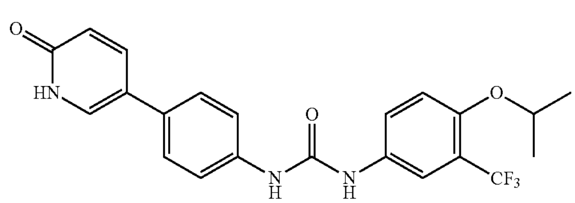 [SMILES: CC(C)Oc1ccc(NC(=O)Nc2ccc(-c3ccc(=O)[nH]c3)cc2)cc1C(F)(F)F] | ¹H NMR (400 MHz, CD₃OD) δ 8.24 (dd, J = 9.60, 2.80 Hz, 1H), 8.00-7.99 (m, 1H), 7.69 (d, J = 1.20 Hz, 1H), 7.54-7.51 (m, 4H), 7.12 (d, J = 8.80 Hz, 1H), 6.94 (dd, J = 9.20, 0.40 Hz, 1H), 1.31 (d, J = 3.00, 6H); | ES-LCMS m/z 432 (M + H) |

| Example | Structure | NMR | LCMS |
|---|---|---|---|
| 164 | 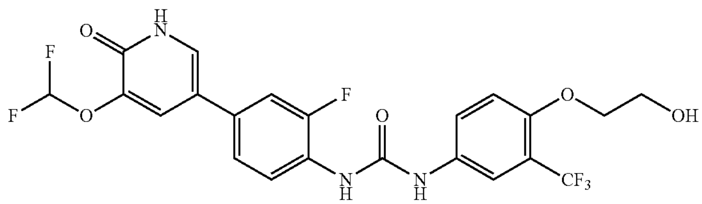 [SMILES: O=C(Nc1ccc(OCCO)c(C(F)(F)F)c1)Nc1ccc(-c2c[nH]c(=O)c(OC(F)F)c2)cc1F] | ¹H NMR (400 MHz, CD₃OD) 8.11 (d, J = 7.2 Hz, 1H), 7.73 (d, J = 2.4 Hz, 2H), 7.62 (d, J = 2.8 Hz, 1H), 7.58 (d, J = 8.4 Hz, 1H), 7.37 (d, J = 2.0 Hz, 1H), 7.32 (d, J = 6.8 Hz, 1H), 7.20-7.16 (m, 1H), 6.83 (s, 1H), 4.13 (t, J = 5.2 Hz, 2H), 3.88 (t, J = 5.2 Hz, 2H); | ES-LCMS m/z 518.0 (M + H) |
| 165 | 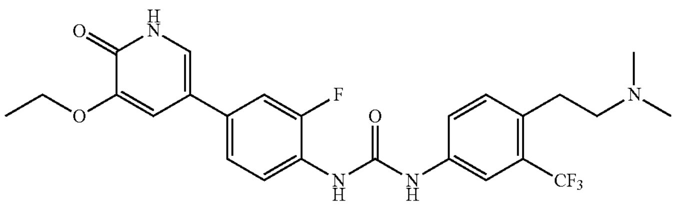 [SMILES: CCOc1cc(-c2ccc(NC(=O)Nc3ccc(CCN(C)C)c(C(F)(F)F)c3)c(F)c2)c[nH]c1=O] | ¹H NMR (400 MHz, CD₃OD) δ 8.18-8.14 (t, J = 8.4 Hz, 1H), 7.95-7.94 (d, J = 2.0 Hz, 1H), 7.65-7.64 (d, J = 2.4 Hz, 1H), 7.48-7.35 (m, 5H), 4.20-4.15 (q, J = 6.8 Hz, 2H), 3.34-3.32 (t, J = 3.2 Hz, 2H), 3.19-3.17 (m, 2H), 2.97 (s, 6H), 1.48-1.45 (t, J = 6.8 Hz, 3H); | ES-LCMS m/z 507.0 (M + H) |
| 166 | 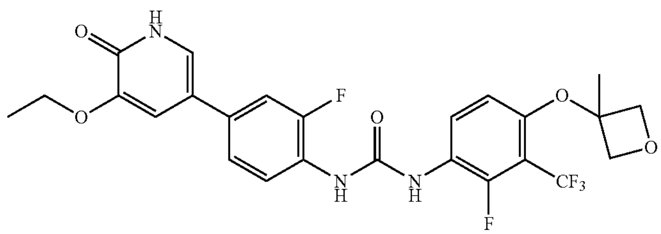 [SMILES: CCOc1cc(-c2ccc(NC(=O)Nc3ccc(OC4(C)COC4)c(C(F)(F)F)c3F)c(F)c2)c[nH]c1=O] | ¹H NMR (400 MHz, DMSO-d₆) δ 11.80 (s, 1H), 9.01-8.97 (m, 2H), 8.23-8.11 (m, 2H), 7.59 (dd, J = 2.0 Hz, 13.2 Hz, 1H), 7.41-7.39 (m, 1H), 7.31 (s, 1H,), 7.14 (d, J = 2.0 Hz, 1H), 6.60 (d, J = 9.2 Hz, 1H), 4.76 (d, J = 7.2 Hz, 2H), 4.62 (d, J = 6.8 Hz, 2H), 4.06-4.05 (m, 2H), 1.68 (s, 3H), 1.36 (t, J = 7.0 Hz, 3H); | ES-LCMS m/z 540.1 (M + H) |
| 167 | 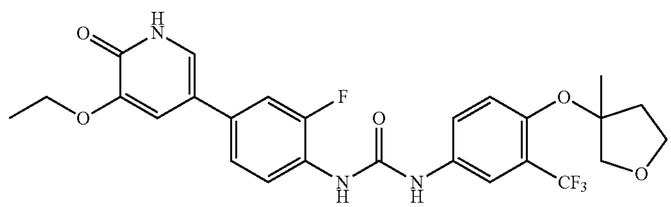 [SMILES: CCOc1cc(-c2ccc(NC(=O)Nc3ccc(OC4(C)CCOC4)c(C(F)(F)F)c3)c(F)c2)c[nH]c1=O] | ¹H NMR (400 MHz, MeOD-d4) δ 8.26-8.24 (t, J = 7.2 Hz, 1H), 7.77 (d, J = 2.8 Hz, 1H), 7.52 (m, 1H), 7.25-7.23 (m, 2H), 7.19-7.14 (m, 3H), 4.14-4.11 (m, 3H), 3.99-3.97 (m, 1H), 3.91-3.90 (m, 1H), 3.76-3.74 (m, 1H), 2.49-2.44 (m, 2H), 2.13-2.10 (m., 1H), 1.56 (s, 3H), 1.46 (t, J = 7.0 Hz, 3H); | ES-LCMS m/z 536.2 (M + H) |
| 168 | 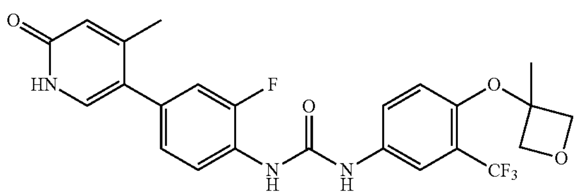 [SMILES: Cc1cc(=O)[nH]cc1-c1ccc(NC(=O)Nc2ccc(OC3(C)COC3)c(C(F)(F)F)c2)c(F)c1] | ¹H NMR (400 MHz, CD₃OD) δ 8.17 (dd, J = 2.4 Hz and 7.6 Hz, 1H), 7.85 (d, J = 2.4 Hz, 1H), 7.80 (s, 1H), 7.54 (dd, J = 2.4 Hz and 8.6 Hz, 1H), 7.31-7.26 (m, 1H), 7.06-7.02 (m, 1H), 6.93 (s, 1H), 6.66 (d, J = 8.9 Hz, 1H), 4.92-4.90 (m, 2H), 4.66 (d, J = 7.2 Hz, 2H), 2.38 (s, 3H), 1.74 (s, 3H) | ES-LCMS m/z 492.2 (M + H) |
| 169 | 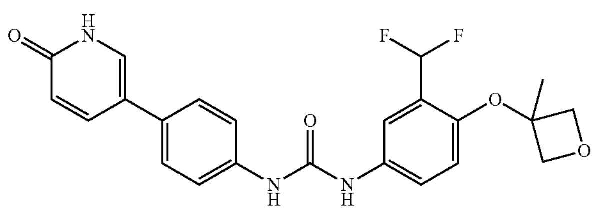 [SMILES: CC1(Oc2ccc(NC(=O)Nc3ccc(-c4ccc(=O)[nH]c4)cc3)cc2C(F)F)COC1] | ¹H NMR (400 MHz, CD₃OD) δ: 8.34 (d, J = 8.8 Hz, 1H), 8.12 (s, 1H), 7.70 (s, 1H), 7.69-7.49 (m, 5H), 7.06 (d, J = 8.8 Hz, 1H), 6.97 (t, J = 15.2 Hz, 1H), 6.56 (d, J = 8.8 Hz, 1H), 4.94-4.93 (m, 2H), 4.65 (d, J = 6.8 Hz, 2H), 1.74 (s, 3H); | ES-LCMS m/z 442.1 (M + H) |
| 170 | 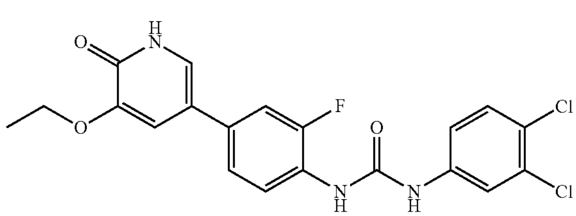 [SMILES: CCOc1cc(-c2ccc(NC(=O)Nc3ccc(Cl)c(Cl)c3)c(F)c2)c[nH]c1=O] | ¹H NMR (400 MHz, DMSO) δ 11.77 (s, 1H), 9.45 (s, 1H), 8.70 (s, 1H), 8.05 (d, J = 8.4 Hz, 1 H), 7.86 (d, J = 2.4 Hz, 1H), 7.54-7.49 (m, 2H), 7.37 (d, J = 8.4 Hz, 1H), 7.30-7.25 (m, 2H), 7.11 (s, 1H), 4.05-3.99 (m, 2 H), 1.31 (t, J = 6.8 Hz, 3H); | ES-LCMS m/z 436.0 (M + H) |

EXAMPLE 171

1-(2-(5-Ethoxy-6-oxo-1,6-dihydropyridin-3-yl)-4-methylpyrimidin-5-yl)-3-(2-fluoro-4-((4-(2-hydroxyethyl)piperazin-1-yl)methyl)-5-(trifluoromethyl)phenyl)urea

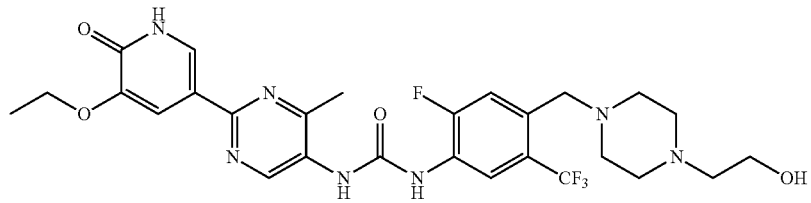 [SMILES: CCOc1cc(-c2ncc(NC(=O)Nc3cc(C(F)(F)F)c(CN4CCN(CCO)CC4)cc3F)c(C)n2)c[nH]c1=O]

Step 1: 2-(4-(4-(3-(2-(5-Ethoxy-6-((4-methoxybenzyl)oxy)pyridin-3-yl)-4-methylpyrimidin-5-yl)ureido)-5-fluoro-2-(trifluoromethyl)benzyl)piperazin-1-yl)ethyl acetate

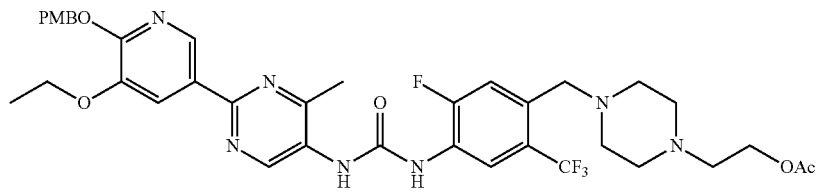

To a mixture of 2-(5-ethoxy-6-((4-methoxybenzyl)oxy)pyridin-3-yl)-4-methylpyrimidine-5-carboxylic acid (0.4 g, 0.910 mmol) in toluene (50 mL) was added triethylamine (0.184 g, 1.821 mmol), DPPA (0.376 g, 1.366 mmol) and 2-(4-(4-amino-5-fluoro-2-(trifluoromethyl)benzyl)piperazin-1-yl)ethyl acetate (0.473 g, 0.910 mmol). The mixture was stirred at 120° C. for 12 hr. LCMS showed the reaction was finished. The mixture was concentrated to give crude product, which was purified by column (DCM/MeOH=15:1, $R_f$=0.4) to give 2-(4-(4-(3-(2-(5-ethoxy-6-((4-methoxybenzyl)oxy)pyridin-3-yl)-4-methylpyrimidin-5-yl)ureido)-5-fluoro-2-(trifluoromethyl)benzyl)piperazin-1-yl)ethyl acetate (340 mg, 0.292 mmol, 32.1% yield) as a brown solid: $^1$H NMR (METHANOL-$d_4$, 400 MHz) δ 8.66 (s, 1H), 8.35 (d, J=7.5 Hz, 1H), 7.58 (d, J=11.9 Hz, 1H), 7.40 (d, J=7.5 Hz, 4H), 6.90 (d, J=8.8 Hz, 2H), 5.43 (s, 2H), 4.16-4.24 (m, 4H), 3.78 (s, 3H), 3.61 (s, 2H), 2.50-2.61 (m, 10H), 2.17 (s, 3H), 2.04 (s, 3H), 1.40-1.47 (m, 3H); ES-LCMS m/z 756.2 (M+H).

Step 2: 1-(2-(5-Ethoxy-6-((4-methoxybenzyl)oxy)pyridine-3-yl)-4-methyl pyrimidin-5-yl)-3-(2-fluoro-4-((4-(2-hydroxyethyl)piperazin-1-yl)methyl)-5-(trifluoromethyl)phenyl)urea

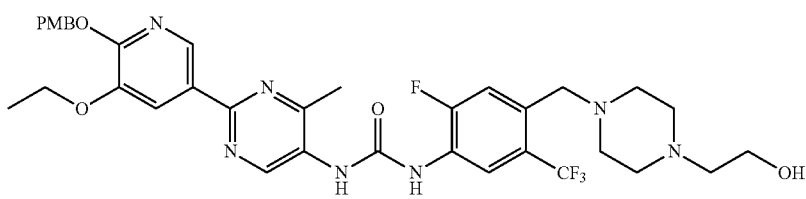

To a mixture of 2-(4-(4-(3-(2-(5-ethoxy-6-((4-methoxybenzyl)oxy)pyridin-3-yl)-4-methylpyrimidin-5-yl)ureido)-5-fluoro-2-(trifluoromethyl)benzyl)piperazin-1-yl)ethyl acetate (340 mg, 0.292 mmol) in MeOH (10 mL) was added NaOH (35.1 mg, 0.877 mmol) in water (5 mL). The mixture was stirred at 20° C. for 2 hr. LCMS showed the reaction was finished. The mixture was extract with EtOAc (20 mL×3). The organic layer was washed with brine. and concentrated to give crude product, which was purified by preparative TLC (DCM:MeOH=10:1, R$_f$=0.4) to give 1-(2-(5-ethoxy-6-((4-methoxybenzyl)oxy)pyridine-3-yl)-4-methylpyrimidin-5-yl)-3-(2-fluoro-4-((4-(2-hydroxyethyl)piperazin-1-yl)methyl)-5-(trifluoromethyl)phenyl)urea (120 mg, 0.101 mmol, 34.5% yield) as a brown solid: $^1$H NMR (400 MHz, CHLOROFORM-d) δ 9.04 (s, 1H), 8.56 (d, J=7.5 Hz, 2H), 7.48 (d, J=11.9 Hz, 2H), 7.30 (br. s., 2H), 6.81 (d, J=8.4 Hz, 2H), 5.41 (s, 2H), 4.13 (d, J=6.6 Hz, 2H), 3.73 (s, 3H), 3.62 (d, J=5.3 Hz, 4H), 2.67-2.61 (m, 10H), 2.17 (s, 3H), 1.41 (m, 3H); ES-LCMS m/z 714.3 (M+H).

Step 3: 1-(2-(5-Ethoxy-6-oxo-1,6-dihydropyridin-3-yl)-4-methylpyrimidin-5-yl)-3-(2-fluoro-4-((4-(2-hydroxyethyl)piperazin-1-yl)methyl)-5-(trifluoromethyl)phenyl)urea

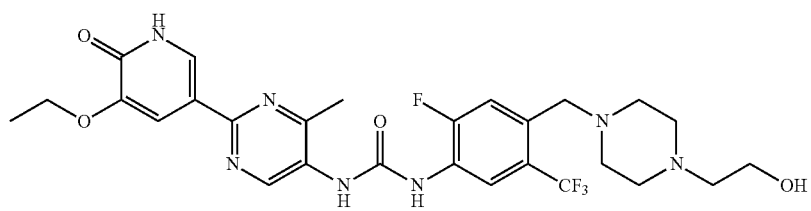 [SMILES: CCOc1cc(-c2ncc(NC(=O)Nc3cc(C(F)(F)F)c(CN4CCN(CCO)CC4)cc3F)c(C)n2)c[nH]c1=O]

To a mixture of 1-(2-(5-ethoxy-6-((4-methoxybenzyl)oxy)pyridin-3-yl)-4-methylpyrimidin-5-yl)-3-(2-fluoro-4-((4-(2-hydroxyethyl)piperazin-1-yl)methyl)-5-(trifluoromethyl)phenyl)urea (120 mg, 0.101 mmol) in dichloromethane (DCM) (5 mL) was added hydrogen chloride, methanol (solvate) (0.252 mL, 1.009 mmol). The mixture was stirred at 20° C. for 1 hr. LCMS showed the reaction was finished. The mixture was concentrated to give crude product, which was purified by preparative HPLC (Column: ASB C18 150*25 mm; Mobile phase A: Water+ 0.1% HCl; Mobile phase B: MeCN; Flowrate: 25 mL/min; Gradient Profile Description: 17-37 (B %)) to give 1-(2-(5-ethoxy-6-oxo-1,6-dihydropyridin-3-yl)-4-methylpyrimidin-5-yl)-3-(2-fluoro-4-((4-(2-hydroxyethyl)piperazin-1-yl)methyl)-5-(trifluoromethyl)phenyl)urea trihydrochloride (18.5 mg, 0.025 mmol, 24.91% yield) as a yellow solid: $^1$H NMR (400 MHz, METHANOL-d$_4$) δ 9.37 (s, 1H), 8.81 (d, J=7.5 Hz, 1H), 8.24 (s, 1H), 7.93 (br. s., 2H), 4.38 (br. s., 2H), 4.21 (d, J=7.1 Hz, 2H), 3.94-3.90 (m, 2H), 3.40 (d, J=4.4 Hz, 10H), 2.70 (s, 3H), 1.51 (t, J=6.8 Hz, 3H); ES-LCMS m/z 594.4 (M+H).

EXAMPLE 172

1-(4-((4-Ethylpiperazin-1-yl)methyl)-2-fluoro-5-(trifluoromethyl)phenyl)-3-(2-(5-(2-hydroxyethoxy)-6-oxo-1,6-dihydropyridin-3-yl)-4-methylpyrimidin-5-yl)urea

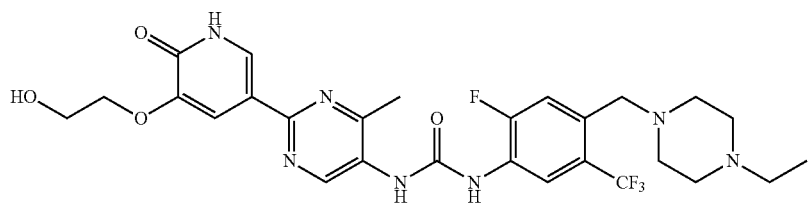 [SMILES: CCN1CCN(Cc2cc(F)c(NC(=O)Nc3cnc(-c4c[nH]c(=O)c(OCCO)c4)nc3C)cc2C(F)(F)F)CC1]

Step 1: 1-(2-(5-(2-(Benzyloxy)ethoxy)-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea

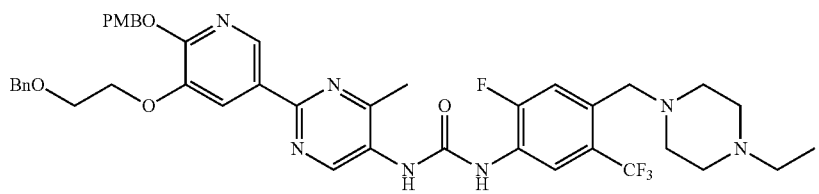

To a mixture of 2-(5-(2-(benzyloxy)ethoxy)-6-((4-methoxybenzyl)oxy)pyridin-3-yl)-4-methylpyrimidine-5- carboxylic acid (0.25 g, 0.449 mmol) in toluene (50 mL) was added triethylamine (0.091 g, 0.897 mmol), DPPA (0.185 g, 0.673 mmol) and 4-((4-ethylpiperazin-1-yl)methyl)-2-fluoro-5-(trifluoromethyl)aniline (0.152 g, 0.449 mmol) at 20° C. The mixture was stirred at 120° C. for 3 hrs. The mixture was concentrated to give crude product, which was purified by column chromatography (DCM/MeOH=20:1, $R_f$=0.4) to give 1-(2-(5-(2-(benzyloxy)ethoxy)-6-((4-methoxybenzyl)oxy)pyridine-3-yl)-4-methylpyrimidin-5-yl)-3-(4-((4-ethylpiperazin-1-yl)methyl)-2-fluoro-5-(trifluoromethyl)phenyl)urea (205 mg, 0.226 mmol, 50.3% yield) as a brown solid: $^1$H NMR (400 MHz, METHANOL-$d_4$) δ 9.21 (s, 1H), 8.63 (d, J=7.9 Hz, 1H), 8.15 (d, J=1.8 Hz, 1H), 7.42 (d, J=8.4 Hz, 2H), 7.25 (d, J=7.5 Hz, 7H), 6.89 (d, J=8.4 Hz, 2H), 5.40 (s, 2H), 4.62 (s, 2H), 4.34-4.27 (m, 2H), 3.90-3.86 (m, 2H), 3.78 (s, 3H), 3.71 (s, 2H), 3.20-3.07 (m, 10H), 2.58 (s, 3H), 1.35-1.32 (m, 3H); ES-LCMS m/z 804.2 (M+H).

Step 2: 1-(4-((4-Ethylpiperazin-1-yl)methyl)-2-fluoro-5-(trifluoromethyl)phenyl)-3-(2-(5-(2-hydroxyethoxy)-6-oxo-1,6-dihydropyridin-3-yl)-4-methylpyrimidin-5-yl)urea

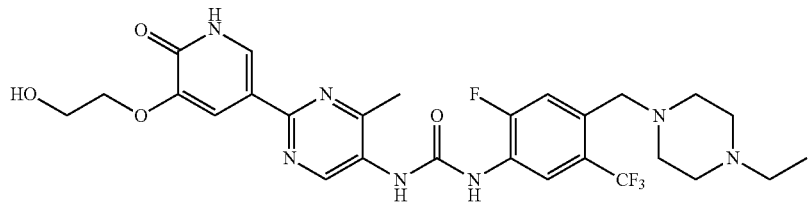 [SMILES: CCN1CCN(Cc2cc(F)c(NC(=O)Nc3cnc(-c4c[nH]c(=O)c(OCCO)c4)nc3C)cc2C(F)(F)F)CC1]

A mixture of 1-(2-(5-(2-(benzyloxy)ethoxy)-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea (100 mg, 0.110 mmol) in hydrogen chloride, $H_2O$ (1428 μl, 11.01 mmol) was stirred at 80° C. for 1 hr. The mixture was concentrated to give crude product, which was purified by preparative HPLC (Column: ASB C18 150*25 mm; Mobile phase A: Water+0.1% HCl; Mobile phase B: MeCN; Flowrate: 25 mL/min; Gradient Profile Description: 15-45 (B %)) to give 1-(4-((4-ethylpiperazin-1-yl)methyl)-2-fluoro-5-(trifluoromethyl)phenyl)-3-2-(5-(2-hydroxyethoxy)-6-oxo-1,6-dihydropyridin-3-yl)-4-methylpyrimidin-5-yl)urea trihydrochloride (24.87 mg, 0.035 mmol, 32.1% yield) as a yellow solid. $^1$H NMR (400 MHz, METHANOL-$d_4$) δ 9.25 (s, 1H), 8.69 (d, J=7.9 Hz, 1H), 8.16 (d, J=2.2 Hz, 1H), 7.90 (d, J=2.2 Hz, 1H), 7.74 (d, J=11.9 Hz, 1H), 4.13 (d, J=4.4 Hz, 2H), 4.08-4.01 (m, 2H), 3.94 (br. s., 2H), 3.66 (br. s., 2H), 3.48-3.33 (m, 4H), 3.28-3.18 (m, 2H), 3.01-2.77 (m, 2H), 2.62 (s, 3H), 1.38 (t, J=7.3 Hz, 3H); ES-LCMS m/z 594.3 (M+H).

EXAMPLE 173

1-(2-Fluoro-4-((4-(2-hydroxyethyl)piperazin-1-yl)methyl)-5-(trifluoromethyl)phenyl)-3-(2-(5-(2-hydroxyethoxy)-6-oxo-1,6-dihydropyridin-3-yl)-4-methylpyrimidin-5-yl)urea

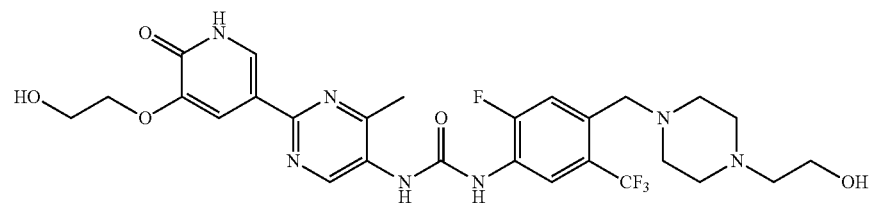 [SMILES: Cc1nc(-c2c[nH]c(=O)c(OCCO)c2)ncc1NC(=O)Nc1cc(C(F)(F)F)c(CN2CCN(CCO)CC2)cc1F]

Step 1: 2-(4-(4-(3-(2-(5-(2-(Benzyloxy)ethoxy)-6-((4-methoxybenzyl)oxy)pyridine-3-yl)-4-methylpyrimidin-5-yl)ureido)-5-fluoro-2-(trifluoromethyl)benzyl)piperazin-1-yl)ethyl acetate

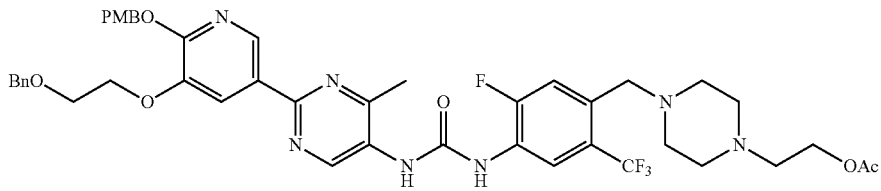

To a mixture of 2-(5-(2-(benzyloxy)ethoxy)-6-((4-methoxybenzyl)oxy)pyridine-3-yl)-4-methylpyrimidine-5-carboxylic acid (0.5 g, 0.897 mmol) in toluene (50 mL) was added triethylamine (0.182 g, 1.795 mmol), DPPA (0.370 g, 1.346 mmol) and 2-(4-(4-amino-5-fluoro-2-(trifluoromethyl)benzyl)piperazin-1-yl)ethyl acetate (0.435 g, 0.897 mmol). The mixture was stirred at 120° C. for 12 hr. The mixture was concentrated to give crude product, which was purified by column (DCM/MeOH=15:1, $R_f$=0.4) to give 2-(4-(4-(3-(2-(5-(2-(benzyloxy)ethoxy)-6-((4-methoxybenzyl)oxy)pyridine-3-yl)-4-methylpyrimidin-5-yl)ureido)-5-fluoro-2-(trifluoromethyl)benzyl)piperazin-1-yl)ethyl acetate (420 mg, 0.341 mmol, 38.0% yield) as a brown solid: $^1$H NMR (400 MHz, METHANOL-$d_4$) δ 8.70 (d, J=1.8 Hz, 1H), 8.36 (d, J=7.5 Hz, 1H), 8.13 (s, 1H), 7.59 (d, J=11.9 Hz, 1H), 7.41 (d, J=8.4 Hz, 2H), 7.25-7.15 (m, 6H), 6.87 (d, J=8.4 Hz, 2H), 5.39 (s, 2H), 4.61 (s, 2H), 4.31-4.24 (m, 4H), 3.87 (br. s., 2H), 3.77 (s, 3H), 3.64 (s, 2H), 2.87-2.74 (m, 6H), 2.61-2.57 (m, 4H), 2.18 (s, 3H), 2.05 (s, 3H); ES-LCMS m/z 862.2 (M+H).

Step 2: 1-(2-(5-(2-(Benzyloxy)ethoxy)-6-((4-methoxybenzyl)oxy)pyridine-3-yl)-4-methylpyrimidin-5-yl)-3-(2-fluoro-4-((4-(2-hydroxyethyl)piperazin-1-yl)methyl)-5-(trifluoromethyl)phenyl)urea

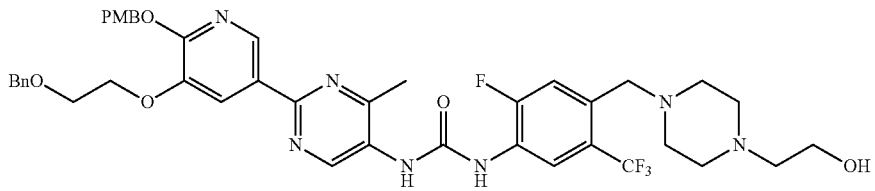

To a mixture of 2-(4-(4-(3-(2-(5-(2-(benzyloxy)ethoxy)-6-((4-methoxybenzyl)oxy)pyridine-3-yl)-4-methylpyrimidin-5-yl)ureido)-5-fluoro-2-(trifluoromethyl)benzyl)piperazin-1-yl)ethyl acetate (420 mg, 0.341 mmol) in MeOH (10 mL) was added NaOH (40.9 mg, 1.023 mmol) in water (5 mL). The mixture was stirred at 20° C. for 2 hrs. LCMS showed the reaction was finished. The mixture was extracted with EtOAc (20 mL×3). The organic layer was washed with brine and concentrated to give crude product, which was purified by TLC (DCM:MeOH=10:1, $R_f$=0.4) to give 1-(2-(5-(2-(benzyloxy)ethoxy)-6-((4-methoxybenzyl)oxy)pyridin-3-yl)-4-methylpyrimidin-5-yl)-3-(2-fluoro-4-((4-(2-hydroxyethyl)piperazin-1-yl)methyl)-5-(trifluoromethyl)phenyl)urea (110 mg, 0.087 mmol, 25.6% yield) as a brown solid: $^1$H NMR (400 MHz, CHLOROFORM-d) δ 9.02 (s, 1H), 8.68 (s, 1H), 8.56 (d, J=7.5 Hz, 2H), 8.28 (br. s., 1H), 8.01 (s, 1H), 7.50 (d, J=11.9 Hz, 2H), 7.33-7.22 (m, 4H), 6.79 (d, J=8.4 Hz, 2H), 5.39 (s, 2H), 4.57 (s, 2H), 4.24 (br. s., 2H), 3.82 (br. s., 2H), 3.73 (s, 3H), 3.57 (t, J=5.1 Hz, 4H), 2.51-2.34 (m, 10H), 2.17 (s, 3H); ES-LCMS m/z 820.2 (M+H).

Step 3: 1-(2-Fluoro-4-((4-(2-hydroxyethyl)piperazin-1-yl)methyl)-5-(trifluoromethyl)phenyl)-3-(2-(5-(2-hydroxyethoxy)-6-oxo-1,6-dihydropyridin-3-yl)-4-methylpyrimidin-5-yl)urea

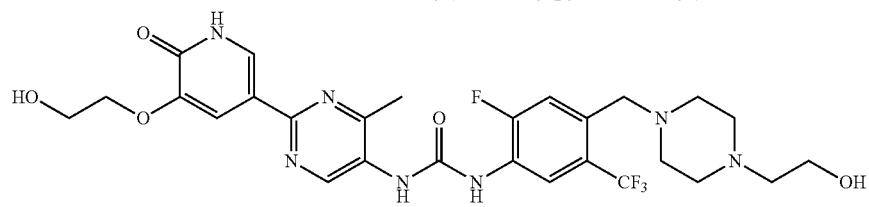 [SMILES: Cc1nc(-c2c[nH]c(=O)c(OCCO)c2)ncc1NC(=O)Nc1cc(C(F)(F)F)c(CN2CCN(CCO)CC2)cc1F]

A mixture of 1-(2-(5-(2-(benzyloxy)ethoxy)-6-((4-methoxybenzyl)oxy)pyridin-3-yl)-4-methylpyrimidin-5-yl)-3-(2-fluoro-4-((4-(2-hydroxyethyl)piperazin-1-yl)methyl)-5-(trifluoromethyl)phenyl)urea (110 mg, 0.087 mmol) in hydrogen chloride solution (1.5 mL, 18%) was stirred at 80° C. for 1 hr. LCMS showed the reaction was finished. The mixture was concentrated to give crude product, which was purified by preparative HPLC (Column: ASB C18 150*25 mm; Mobile phase A: Water+0.1% HCl; Mobile phase B: MeCN; Flowrate: 25mL/min; Gradient Profile Description: 10-40 (B %)) to give 1-(2-fluoro-4-((4-(2-hydroxyethyl)piperazin-1-yl)methyl)-5-(trifluoromethyl)phenyl)-3-(2-(5-(2-hydroxyethoxy)-6-oxo-1,6-dihydropyridin-3-yl)-4-methylpyrimidin-5-yl)urea trihydrochloride (32.5 mg, 0.045 mmol, 51.8% yield) as a yellow solid: $^1$H NMR (400 MHz, METHANOL-$d_4$) δ 9.31 (s, 1H), 8.79-8.74 (m, 1H), 8.22-8.19 (m, 1H), 7.92 (d, J=1.8 Hz, 1H), 7.89-7.84 (m, 1H), 4.33-4.27 (m, 2H), 4.14 (d, J=4.0 Hz, 2H), 3.98-3.92 (m, 4H), 3.67-3.34 (m, 10H), 2.66 (s, 3H); ES-LCMS m/z 610.3 (M+H).

EXAMPLE 174

N-(2-(dimethylamino)ethyl)-3-(3-(2-(5-ethoxy-6-oxo-1,6-dihydropyridin-3-yl)-4-methylpyrimidin-5-yl)ureido)-5-(trifluoromethyl)benzenesulfonamide

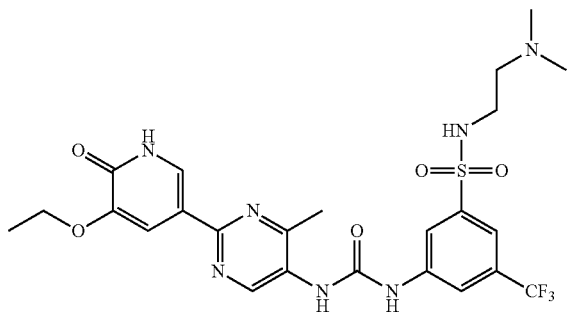 [SMILES: CCOc1cc(-c2ncc(NC(=O)Nc3cc(C(F)(F)F)cc(S(=O)(=O)NCCN(C)C)c3)c(C)n2)c[nH]c1=O]

Step 1: N-(2-(dimethylamino)ethyl)-3-(3-(2-(5-ethoxy-6-((4-methoxybenzyl)oxy)pyridin-3-yl)-4-methylpyrimidin-5-yl)ureido)-5-(trifluoromethyl)benzenesulfonamide

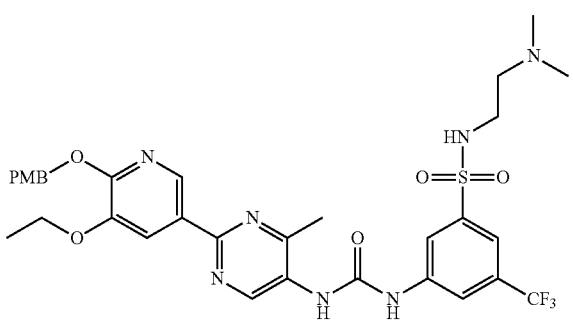

A solution of 2-(5-ethoxy-6-((4-methoxybenzyl)oxy)pyridin-3-yl)-4-methylpyrimidine-5-carboxylic acid (1016 mg, 2.57 mmol), 3-amino-N-(2-(dimethylamino)ethyl)-5-(trifluoromethyl)-benzenesulfonamide (800 mg, 2.57 mmol) and Et$_3$N (0.716 mL, 5.14 mmol) in 1,4-dioxane (15 mL) was added diphenyl phosphorazidate (0.701 mL, 3.08 mmol) in portions. Then the mixture was stirred under N$_2$ atmosphere and heated at 80-90° C. to reflux for 2 hrs. LCMS analysis showed the starting material disappeared. The solvent was removed in vacuo and the residue was dissolved in DCM (60 mL) and washed with H$_2$O (20 mL) and brine (20 mL). The organic layer was dried over Na$_2$SO$_4$, filtered and concentrated to give the crude product, which was purified by silica column chromatography (DCM/MeOH=20:1 to 10:1). All fractions found to contain product by TLC (DCM/MeOH=10:1, R$_f$=0.5) were combined and concentrated to give crude material. The crude product was purified further by preparative HPLC: (Instrument: Gilson 215/Column: Gemini C18 10 u 150*25mm/Mobile phase A: water with 0.01 mol/l NH3H2O/Mobile phase B: MeCN/Flowrate: 25 mL/min/Gradient Profile Description: 60-90 (B %)) to afford pure product of N-(2-(dimethylamino)ethyl)-3-(3-(2-(5-ethoxy-6-((4-methoxybenzyl)oxy)pyridin-3-yl)-4-methylpyrimidin-5-yl)ureido)-5-(trifluoromethyl)benzenesulfonamide (170 mg, 0.205 mmol, 8.0% yield) as a white solid: $^1$H NMR (400 MHz, CD$_3$OD) δ 9.10 (s, 1H), 8.70 (d, J=2.0 Hz, 1H), 8.26 (s, 1H), 8.12-8.06 (m, 2H), 7.76 (s, 1H), 7.42 (d, J=9.0 Hz, 2H), 6.92 (d, J=8.6 Hz, 2H), 5.40 (s, 2H), 4.18 (q, J=7.0 Hz, 2H), 3.80 (s, 3H), 3.04 (t, J=6.8 Hz, 2H), 2.60 (s, 3H), 2.44 (t, J=6.8 Hz, 2H), 2.21 (s, 6H), 1.45 (t, J=7.0 Hz, 3H); ES-LCMS m/z: 584.2 (M-PMB+H), 704.2 (M+H).

Step 2: N-(2-(dimethylamino)ethyl)-3-(3-(2-(5-ethoxy-6-oxo-1,6-dihydropyridin-3-yl)-4-methylpyrimidin-5-yl)ureido)-5-(trifluoromethyl)benzenesulfonamide

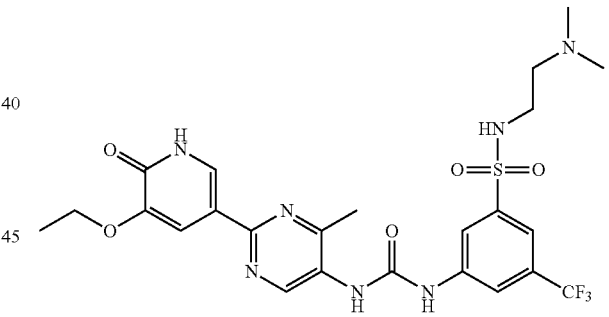

To a solution of N-(2-(dimethylamino)ethyl)-3-(3-(2-(5-ethoxy-6-((4-methoxybenzyl)oxy)pyridin-3-yl)-4-methylpyrimidin-5-yl)ureido)-5-(trifluoromethyl)benzenesulfonamide (170 mg, 0.242 mmol) in DCM (10 mL) was added 2,2,2-trifluoroacetic acid (1 mL, 0.242 mmol). Then the mixture was stirred at 25° C. for 30 minutes. The reaction mixture was concentrated to dryness. Then the crude material was purified by preparative HPLC (Instrument: AA/Column: Gemini C18 10 u 150*25mm/Mobile phase A: Water+0.1% HCl/Mobile phase B: MeCN/Flowrate: 25 mL/min/Gradient Profile Description: 5-35 (B %)) to afford pure product of N-(2-(dimethylamino)ethyl)-3-(3-(2-(5-ethoxy-6-oxo-1,6-dihydropyridin-3-yl)-4-methylpyrimidin-5-yl)ureido)-5-(trifluoromethyl)benzenesulfonamide hydrochloride (98 mg, 0.158 mmol, 65.4% yield) as a yellow solid: $^1$H NMR (400 MHz, DMSO) δ 11.94 (br. s., 1H), 10.68 (s, 1H), 9.77 (br. s., 1H), 9.06 (s, 1H), 9.02 (s, 1H), 8.34 (br. s., 1H), 8.25 (s, 1H), 8.13 (s, 1H), 7.92 (s, 1H), 7.71 (s, 1H), 7.60 (d, J=2.0 Hz, 1H), 4.03 (q, J=6.8 Hz, 2H), 3.15 (br. s., 3H), 2.78 (d, J=4.8 Hz, 4H), 2.53 (s, 6H), 1.36 (t, J=7.0 Hz, 3H); ES-LCMS m/z : 584.2 (M+H).

EXAMPE 175

1-(4-(1-Aminoethyl)-3-(trifluoromethyl)phenyl)-3-(2-(5-ethoxy-6-oxo-1,6-dihydropyridin-3-yl)-4-methylpyrimidin-5-yl)urea

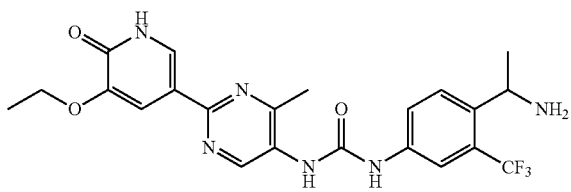 [SMILES: CCOc1cc(-c2ncc(NC(=O)Nc3ccc(C(C)N)c(C(F)(F)F)c3)c(C)n2)c[nH]c1=O]

Step 1: Tert-butyl (1-(4-(3-(2-(5-ethoxy-6-((4-methoxybenzyl)oxy)pyridin-3-yl)-4-methyl-pyrimidin-5-yl)ureido)-2-(trifluoromethyl)phenyl)ethyl) carbamate

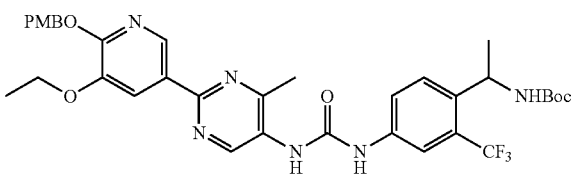

To a mixture of 2-(5-ethoxy-6-((4-methoxybenzyl)oxy) pyridin-3-yl)-4-methylpyrimidine-5-carboxylic acid (100 mg, 0.253 mmol) in 1,4-dioxane (15 mL) was added Et₃N (0.053 mL, 0.379 mmol), diphenyl phosphorazidate (84 mg, 0.303 mmol), tert-butyl (1-(4-amino-2-(trifluoromethyl) phenyl)ethyl)carbamate (92 mg, 0.303 mmol) and DMAP (3.09 mg, 0.025 mmol). The mixture was stirred at 80° C. for 3 hrs and then was concentrated and purified by preparative TLC (DCM/MeOH=20:1, R$_f$=0.6) to yield a yellow solid of tert-butyl (1-(4-(3-(2-(5-ethoxy-6-((4-methoxybenzyl)oxy) pyridin-3-yl)-4-methylpyrimidin-5-yl)ureido)-2-(trifluoromethyl)phenyl)ethyl)carbamate (60 mg, 0.073 mmol, 28.9% yield): ¹H NMR (400 MHz, CD₃OD) δ 9.13 (s, 1H), 8.71 (d, J=2.0 Hz, 1H), 8.12 (d, J=1.6 Hz, 1H), 7.84 (s., 1H), 7.70 (s., 1H), 7.61 (d, J=8.4 Hz, 1H), 7.44 (d, J=8.4 Hz, 2H), 6.94 (d, J=8.4 Hz, 2H), 5.42 (s, 2H), 5.08-5.01 (m, 1H), 4.20 (q, J=7.2 Hz, 2H), 3.82 (s, 3H), 2.61 (s, 3H), 1.47 (t, J=6.8 Hz, 3H), 1.43 (s, 9H), 1.38 (d, J=7.2 Hz, 3H); ES-LCMS m/z 697.1 (M+H).

Step 2: 1-(4-(1-Aminoethyl)-3-(trifluoromethyl) phenyl)-3-(2-(5-ethoxy-6-oxo-1,6-dihydropyridin-3-yl)-4-methylpyrimidin-5-yl)urea

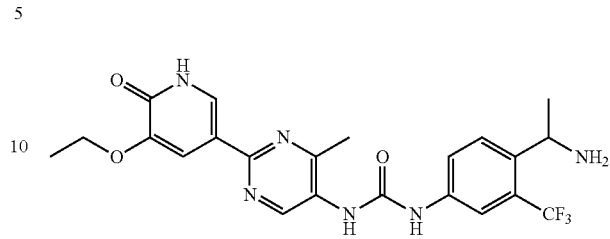

To a solution of tert-butyl (1-(4-(3-(2-(5-ethoxy-6-((4-methoxybenzyl)oxy)-pyridin-3-yl)-4-methylpyrimidin-5-yl) ureido)-2-(trifluoromethyl)phenyl)ethyl)carbamate (60 mg, 0.086 mmol) in DCM (10 mL) was added TFA (1 mL, 12.98 mmol). The mixture was stirred at 25° C. for 2 hrs. The reaction mixture was concentrated and purified by preparative HPLC (Column: ASB C18 150*25 mm; Moble phase A: Water+0.1% HCl; Mobile phase B: MeCN; Flowrate: 25 mL/min; Gradient Profile Description: 10-40(B %)) to yield a yellow solid of 1-(4-(1-aminoethyl)-3-(trifluoromethyl) phenyl)-3-(2-(5-ethoxy-6-oxo-1,6-dihydropyridin-3-yl)-4-methylpyrimidin-5-yl)urea dihydrochloride (19.4 mg, 0.035 mmol, 41.0% yield): ¹H NMR (400 MHz, CD₃OD) δ 9.22 (s, 1H), 8.18 (d, J=2.0 Hz, 1H), 8.08 (d, J=2.0 Hz, 1H), 7.92-7.84 (m, 2H), 7.76 (d, J=8.4 Hz, 1H), 4.74 (q, J=6.8 Hz, 1H), 4.20 (q, J=7.2 Hz, 2H), 2.68 (s, 3H), 1.68 (d, J=7.2 Hz, 3H), 1.52 (t, J=7.2 Hz, 3H); ES-LCMS m/z 477.0 (M+H). TLC (DCM/MeOH=8:1, R$_f$=0.2).

EXAMPLE 176

1-(4-(1-(Dimethylamino)ethyl)-3-(trifluoromethyl) phenyl)-3-(2-(5-ethoxy-6-oxo-1,6-dihydropyridin-3-yl)-4-methylpyrimidin-5-yl)urea

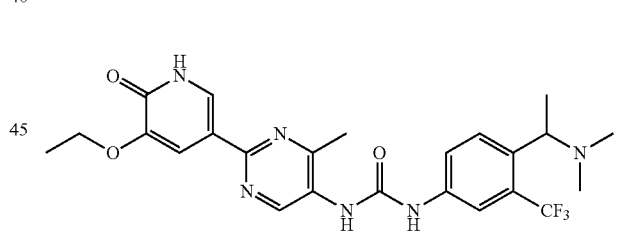

Step 1: 1-(4-(1-(Dimethylamino)ethyl)-3-(trifluoromethyl)phenyl)-3-(2-(5-ethoxy-6-oxo-1,6-dihydropyridin-3-yl)-4-methylpyrimidin-5-yl)urea

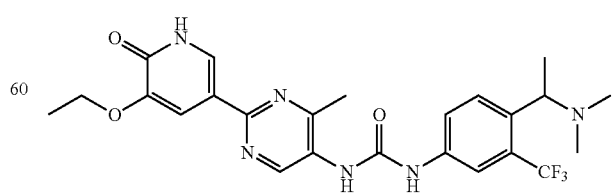

To a solution of 1-(4-(1-aminoethyl)-3-(trifluoromethyl) phenyl)-3-(2-(5-ethoxy-6-oxo-1,6-dihydropyridin-3-yl)-4- methylpyrimidin-5-yl)urea (40 mg, 0.084 mmol) was added formic acid (5 mL, 130 mmol) and formaldehyde (7 mL, 94 mmol). The mixture was brought to ambient temperature and heated to 70° C. The reaction mixture was refluxed for 3 hours. Then the mixture was concentrated and made alkaline by addition of excess of 50% solution of NaOH. The mixture was concentrated and purified by preparative HPLC (Instrument: Gilson GX281; Column: Gemini 150*25 mm*5 um; Mobile phase A: Water (0.05% ammonia solution); Mobile phase B: Acetonitrile; Gradient: 30-60 (B %); Flowrate: 25 mL/min; Run time: 10 min) to yield a white solid of 1-(4-(1-(dimethylamino)ethyl)-3-(trifluoromethyl)phenyl)-3-(2-(5-ethoxy-6-oxo-1,6-dihydropyridin-3-yl)-4-methylpyrimidin-5-yl)urea (19.81 mg, 0.039 mmol, 45.9% yield) without further purification. TLC (DCM/MeOH=10:1, $R_f$=0.2): $^1$H NMR (400 MHz, CD$_3$OD) δ 9.02 (s, 1H), 8.05 (d, J=2.4 Hz, 1H), 7.90 (d, J=2.0 Hz, 1H), 7.84 (d, J=2.0 Hz, 1H), 7.71-7.68 (m, 1H), 7.65-7.61 (m, 1H), 4.13 (q, J=6.8 Hz, 2H), 3.51-3.45 (m, 1H), 2.54 (s, 3H), 2.21 (s, 6H), 1.47 (t, J=7.2 Hz, 3H), 1.32 (d, J=6.4 Hz, 3H); ES-LCMS m/z 505.1 (M+H).

EXAMPLE 177

1-(2-(5-Ethoxy-6-oxo-1,6-dihydropyridin-3-yl)-4-methylpyrimidin-5-yl)-3-(4-(2-(pyrrolidin-1-yl)ethyl)-3-(trifluoromethyl)phenyl)urea

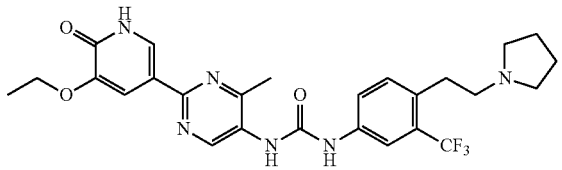 [SMILES: CCOc1cc(-c2ncc(NC(=O)Nc3ccc(CCN4CCCC4)c(C(F)(F)F)c3)c(C)n2)c[nH]c1=O]

Step 1: 1-(2-(5-Ethoxy-6-((4-methoxybenzyl)oxy)pyridin-3-yl)-4-methylpyrimidin-5-yl)-3-(4-(2-(pyrrolidin-1-yl)ethyl)-3-(trifluoromethyl)phenyl)urea

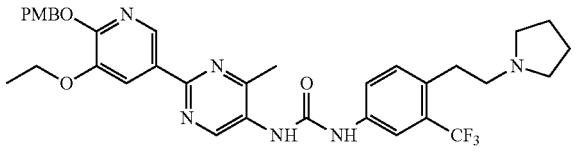

To a solution of 2-(5-ethoxy-6-((4-methoxybenzyl)oxy)pyridine-3-yl)-4-methylpyrimidine-5-carboxylic acid (800 mg, 2.023 mmol), 4-(2-(pyrrolidin-1-yl)ethyl)-3-(trifluoromethyl)aniline (575 mg, 2.226 mmol) and Et$_3$N (0.846 mL, 6.07 mmol) in 1,4-dioxane (15 mL) was added diphenyl phosphorazidate (835 mg, 3.03 mmol) in one portion. Then the mixture was stirred under N$_2$ atmosphere and heated at 100° C. for 3 hours. LCMS analysis showed the starting material disappeared. The solvent was removed in vacuo. The residue was dissolved in DCM (60 mL) and washed with H$_2$O (20 mL) and brine (20 mL). The organic layer was dried over Na$_2$SO$_4$, filtered and concentrated to give crude material which was purified by silica column chromatography (DCM/MeOH=20:1 to 5:1) to yield a crude product 1-(2-(5-ethoxy-6-((4-methoxybenzyl)oxy)pyridin-3-yl)-4-methylpyrimidin-5-yl)-3-(4-(2-(pyrrolidin-1-yl)ethyl)-3-(trifluoromethyl)phenyl)urea (300 mg, 0.300 mmol, 14.8% yield) as a deep yellow solid: $^1$H NMR (400 MHz, CD$_3$OD) δ 9.02 (s, 1H), 8.06 (d, J=2.0 Hz, 1H), 7.93 (d, J=2.0 Hz, 1H), 7.84 (d, J=2.0 Hz, 1H), 7.66 (d, J=8.6 Hz, 1H), 7.43 (d, J=8.6 Hz, 1H), 7.26 (d, J=7.0 Hz, 2H), 7.21-7.19 (m, 2H), 4.14 (q, J=7.0 Hz, 2H), 3.71 (br. s., 2H), 3.42-3.36 (m, 4H), 3.31 (br. s., 3H), 3.21-3.11 (m, 4H), 2.53 (s, 3H), 2.17 (br. s., 2H), 2.08-1.98 (m, 2H), 1.48 (t, J=6.8 Hz, 3H); ES-LCMS: m/z 531.3 (M-PMB+H), 651.3 (M+H).

Step 2: 1-(2-(5-Ethoxy-6-oxo-1,6-dihydropyridin-3-yl)-4-methylpyrimidin-5-yl)-3-(4-(2-(pyrrolidin-1-yl)ethyl)-3-(trifluoromethyl)phenyl)urea

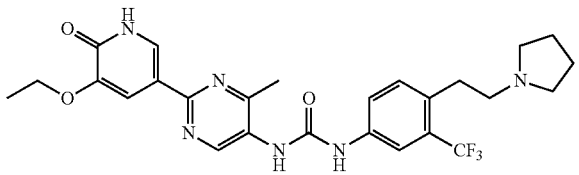 [SMILES: CCOc1cc(-c2ncc(NC(=O)Nc3ccc(CCN4CCCC4)c(C(F)(F)F)c3)c(C)n2)c[nH]c1=O]

To a solution of 1-(2-(5-ethoxy-6-((4-methoxybenzyl)oxy)pyridin-3-yl)-4-methylpyrimidin-5-yl)-3-(4-(2-(pyrrolidin-1-yl)ethyl)-3-(trifluoromethyl)phenyl)urea (300 mg, 0.461 mmol) in dichloromethane (18 mL) was added TFA (2 mL, 26.0 mmol) in dropwise. The mixture was stirred at 20° C. for 1 hour. LCMS analysis showed the starting material disappeared. The solvent was removed in vacuo. Then the residue was purified by preparative HPLC: (Instrument: Gilson 215/Column: Gemini C18 10 u150*25 mm/Mobile phase A: Water (0.01 mol/L NH$_3$H$_2$O)/Mobile phase B: MeCN/Flowrate: 25 mL/min/Gradient Profile Description: 36-76 (B %)) to afford pure product 1-(2-(5-ethoxy-6-oxo-1,6-dihydropyridin-3-yl)-4-methylpyrimidin-5-yl)-3-(4-(2-(pyrrolidin-1-yl)ethyl)-3-(trifluoromethyl)phenyl)urea (35.6 mg, 0.067 mmol, 14.5% yield) as an off white solid: $^1$H NMR (400 MHz, CD$_3$OD) δ 9.05 (s, 1H), 8.08 (d, J=2.0 Hz, 1H), 7.90-7.84 (m, 2H), 7.62 (d, J=10.0 Hz, 1H), 7.40 (d, J=8.4 Hz, 1H), 4.18-4.13 (m, 2H), 3.02-2.95 (m, 2H), 2.73 (d, J=9.0 Hz, 2H), 2.67 (br. s., 4H), 2.56 (s, 3H), 1.87 (br. s., 4H), 1.49 (t, J=7.0 Hz, 3H); ES-LCMS: m/z 530.4.

EXAMPLE 178

1-(3-(2-(dimethylamino)ethoxy)-5-(trifluoromethyl)phenyl)-3-(2-(5-ethoxy-6-oxo-1,6-dihydropyridin-3-yl)pyrimidin-5-yl)urea dihydrochloride

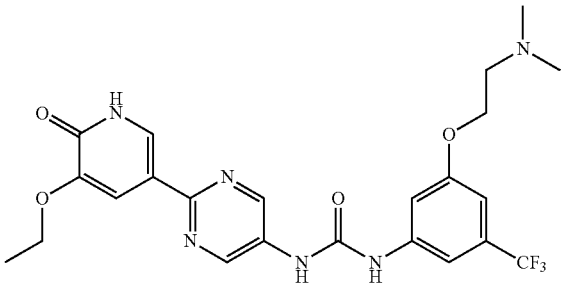 [SMILES: CCOc1cc(-c2ncc(NC(=O)Nc3cc(OCCN(C)C)cc(C(F)(F)F)c3)cn2)c[nH]c1=O]

Step 1: 2-Chloropyrimidin-5-amine

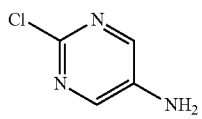

To a solution of 2-chloro-5-nitropyrimidine (5 g, 31.3 mmol) and zinc (20.49 g, 313 mmol) in Methanol (150 mL) was added ammonium chloride (16.77 g, 313 mmol) at 0° C. The resulting mixture was stirred at 25° C. for 16 hrs. LCMS analysis showed the starting material disappeared. The mixture was filtered. The filtrate was concentrated to give the crude product, which was purified by column chromatography (PE/EA=3/1 to 1/1). All fractions found to contain product by TLC (PE/EA=1/1, $R_f$=0.5) were combined and concentrated to yield a yellow solid of 2-chloropyrimidin-5-amine (1 g, 7.72 mmol, 24.63% yield): $^1$H NMR (400 MHz, METHANOL-$d_4$) δ 8.04 (s, 2H); ES-LCMS m/z 130.1 (M+H).

Step 2: 1-(2-Chloropyrimidin-5-yl)-3-(3-(2-(dimethylamino)ethoxy)-5-(trifluoromethyl)-phenyl)urea

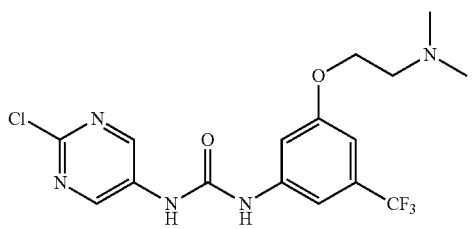 [SMILES: CN(C)CCOc1cc(NC(=O)Nc2cnc(Cl)nc2)cc(C(F)(F)F)c1]

To a solution of 2-chloropyrimidin-5-amine (100 mg, 0.772 mmol) in THF (15 mL) was added triphosgene (80 mg, 0.270 mmol). The resulting mixture was stirred at 60° C. for 0.5 hr. LCMS analysis showed the starting material disappeared. The solvent was removed in vacuo to yield a yellow oil of 2-chloro-5-isocyanatopyrimidine (120 mg, 0.744 mmol, 96% yield). To a solution of 3-(2-(dimethylamino)ethoxy)-5-(trifluoromethyl)aniline (192 mg, 0.771 mmol) and Et$_3$N (0.323 mL, 2.314 mmol) in THF (15 mL) was added a solution of 2-chloro-5-isocyanatopyrimidine (120 mg, 0.771 mmol) in THF (15 mL) at 60° C. The resulting mixture was stirred at 60° C. for 1 hr. The solvent was removed in vacuo. The residue was distributed between DCM (30 mL) and H$_2$O (20 mL), extracted with DCM (30 mL×2). The organic layer was washed with brine (20 mL), dried over Na$_2$SO$_4$, filtered and concentrated to yield a yellow solid of 1-(2-chloropyrimidin-5-yl)-3-(3-(2-(dimethylamino)ethoxy)-5-(trifluoromethyl)phenyl)urea (300 mg, 0.743 mmol, 96% yield): $^1$H NMR (400 MHz, METHANOL-$d_4$) δ 8.86 (s, 2H), 8.04 (s, 1H), 7.42 (s, 1H), 6.90 (s, 1H), 4.17 (t, J=5.3 Hz, 2H), 4.08 (t, J=5.4 Hz, 2H), 2.38 (s, 6H); ES-LCMS m/z 404.2 (M+H).

Step 3: 1-(3-(2-(Dimethylamino)ethoxy)-5-(trifluoromethyl)phenyl)-3-(2-(5-ethoxy-6-((4-methoxybenzyl)oxy)pyridin-3-yl)pyrimidin-5-yl)urea

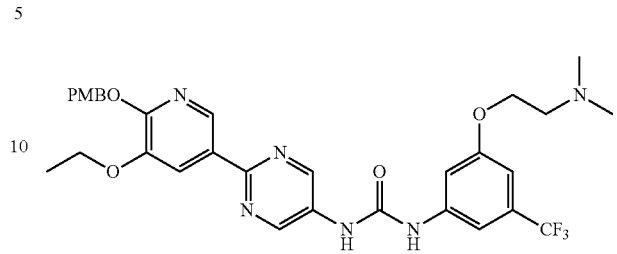

A solution of 1-(2-chloropyrimidin-5-yl)-3-(3-(2-(dimethylamino)ethoxy)-5-(trifluoromethyl)phenyl)urea (150 mg, 0.371 mmol), 3-ethoxy-2-((4-methoxybenzyl)oxy)-5-(4,4,5,5-tetramethyl-1,3,2-dioxaborolan-2-yl)pyridine (143 mg, 0.371 mmol), PdCl$_2$(dppf) (27.2 mg, 0.037 mmol) and Cs$_2$CO$_3$ (242 mg, 0.743 mmol) in 1,4-dioxane (18 mL) and water (6 mL) was stirred at 110° C. for 1 hr under a N$_2$ atmosphere. LCMS analysis showed the starting material disappeared. The organic layer was separated and concentrated to give the crude product, which was purified by preparative TLC (DCM/MeOH=10/1, $R_f$=0.2) to yield a yellow solid of 1-(3-(2-(dimethylamino)ethoxy)-5-(trifluoromethyl)phenyl)-3-(2-(5-ethoxy-6-((4-methoxybenzyl)oxy)pyridin-3-yl)pyrimidin-5-yl)urea (60 mg, 0.091 mmol, 24.5% yield): $^1$H NMR (400 MHz, METHANOL-$d_4$) δ8.98 (s, 2H), 8.67 (d, J=1.8 Hz, 1H), 8.08 (s, 1H), 7.60 (br. s., 1H), 7.41 (d, J=8.6 Hz, 2H), 7.34 (brs, 1H), 6.96 (br s, 1H), 6.92 (d, J=8.8 Hz, 2H), 5.40 (s, 2H), 4.37-4.30 (m, 2H), 4.27-4.21 (m, 3H), 4.17 (q, J=7.0 Hz, 2H), 3.79 (s, 3H), 2.77 (s, 6H), 1.45 (t, J=6.9 Hz, 3H); ES-LCMS m/z 627.3 (M+H), 507.2 (M+H-PMB).

Step 4: 1-(3-(2-(dimethylamino)ethoxy)-5-(trifluoromethyl)phenyl)-3-(2-(5-ethoxy-6-oxo-1,6-dihydropyridin-3-yl)pyrimidin-5-yl)urea dihydrochloride

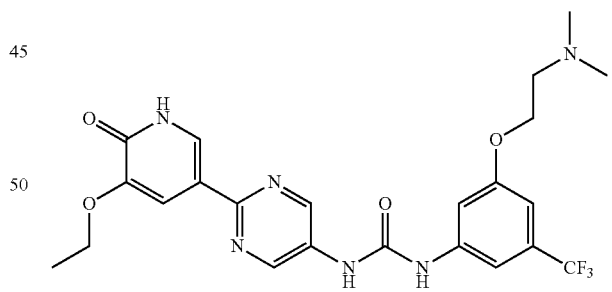

A solution of 1-(3-(2-(dimethylamino)ethoxy)-5-(trifluoromethyl)phenyl)-3-(2-(5-ethoxy-6-((4-methoxybenzyl)oxy)pyridin-3-yl)pyrimidin-5-yl)urea (60 mg, 0.096 mmol) in 2,2,2-trifluoroacetic acid, dichloromethane (solvate) (5 mL, 3.72 mmol) was stirred at 25° C. for 0.5 hr. LCMS analysis showed the starting material disappeared. The solvent was removed in vacuo. The crude product was purified by preparative HPLC (Instrument: DG/Column: Phenomenex Synergi C18 150*30 mm*4 um/Mobile phase A: Water+0.1% HCl/Mobile phase B: MeCN/Flowrate: 25 mL/min/Gradient Profile Description: 18-48 (B %)) to yield a yellow solid of 1-(3-(2-(dimethylamino)ethoxy)-5-(trifluoromethyl)phenyl)-3-(2-(5-ethoxy-6-oxo-1,6-dihydropyridin-3-yl)pyrimidin-5-yl)urea dihydrochloride (20 mg, 0.035 mmol, 36.1% yield): $^1$H NMR (400 MHz, METHANOL-d$_4$) δ8.96 (s, 2H), 8.11 (s, 1H), 7.92 (d, J=2.0 Hz, 1H), 7.65 (s, 1H), 7.35 (s, 1H), 7.00 (s, 1H), 4.45-4.41 (m, 2H), 4.20-4.15 (m, 2H), 3.66-3.62 (m, 2H), 3.00 (s, 6H), 1.49 (t, J=6.9 Hz, 3H); ES-LCMS m/z 507.3 (M+H).

EXAMPLE 179

1-(4-((Dimethylamino)methyl)-3-(trifluoromethyl)phenyl)-3-(2-(5-ethoxy-6-oxo-1,6-dihydropyridin-3-yl)pyrimidin-5-yl)urea

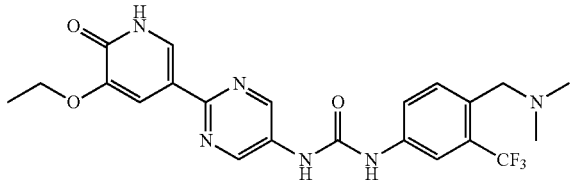 [SMILES: CCOc1cc(-c2ncc(NC(=O)Nc3ccc(CN(C)C)c(C(F)(F)F)c3)cn2)c[nH]c1=O]

Step 1: 1-(2-Chloropyrimidin-5-yl)-3-(4-((dimethylamino)methyl)-3-(trifluoromethyl)-phenyl)-urea

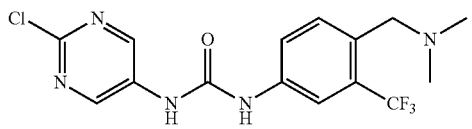 [SMILES: CN(C)Cc1ccc(NC(=O)Nc2cnc(Cl)nc2)cc1C(F)(F)F]

To a solution of 2-chloropyrimidin-5-amine (200 mg, 1.544 mmol) in THF (10 mL) was added triphosgene (151 mg, 0.509 mmol). The mixture was stirred at 60° C. for 0.5 h. The mixture was concentrated to give the crude product as a yellow solid (240 mg), which used for next step: ES-LCMS m/z 188.0 (M+MeOH). To a solution of 4-((dimethylamino)methyl)-3-(trifluoromethyl)aniline (337 mg, 1.543 mmol), triethylamine (156 mg, 1.543 mmol) in THF (10 mL) was added 2-chloro-5-isocyanatopyrimidine (240 mg, 1.543 mmol). The mixture was stirred at 60° C. for 0.5 hr. The mixture was concentrated to give the crude product, which was purified by preparative HPLC (Column Phenomenex Synergi C18 250*21.2 mm*4 um Condition 0.05% HCl-ACN Begin B 13 End B 43 Gradient Time (min) 10 100% B Hold Time (min) 3 FlowRate (ml/min) 25) to afford the product 1-(2-chloropyrimidin-5-yl)-3-(4-((dimethylamino)methyl)-3-(trifluoromethyl)phenyl)urea dihydrochloride (90 mg, 0.199 mmol, 12.88% yield) as a yellow solid: $^1$HNMR (400 MHz, METHANOL-d$_4$) δ8.87 (s, 2H), 8.06 (s, 1H), 7.91 (d, J=10.58 Hz, 1H), 7.68 (d, J=8.60 Hz, 1H), 4.46 (s, 2H), 2.93 (s, 6H); ES-LCMS m/z: 374.1 (M+H)

Step 2: 1-(4-((Dimethylamino)methyl)-3-(trifluoromethyl)phenyl)-3-(2-(5-ethoxy-6-((4-methoxybenzyl)oxy)pyridin-3-yl)pyrimidin-5-yl)urea

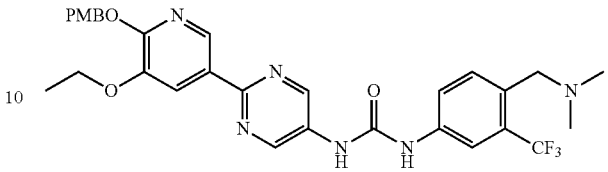

The mixture of 1-(2-chloropyrimidin-5-yl)-3-(4-((dimethylamino)methyl)-3-(trifluoromethyl)-phenyl)urea (50 mg, 0.134 mmol), 3-ethoxy-2-((4-methoxybenzyl)oxy)-5-(4,4,5,5-tetramethyl-1,3,2-dioxaborolan-2-yl)pyridine (51.5 mg, 0.134 mmol), Cs$_2$CO$_3$ (43.6 mg, 0.134 mmol), PdCl$_2$(dppf) (9.79 mg, 0.013 mmol) in 1,4-dioxane (3 mL) water (1 mL) was stirred at 110° C. for 0.5 hr in microwave. The mixture was filtered and concentrated to give the crude product. After purification by preparative TLC (DCM/MeOH=10:1, R$_f$=0.4), the product of 1-(4-((dimethylamino)methyl)-3-(trifluoromethyl)phenyl)-3-(2-(5-ethoxy-6-((4-methoxybenzyl)oxy)pyridin-3-yl)pyrimidin-5-yl)urea (75 mg, 0.094 mmol, 70.5% yield) was obtained as a yellow solid: $^1$H NMR (400 MHz, METHANOL-d$_4$) δ8.98 (s, 2H), 8.66 (d, J=1.98 Hz, 1H), 8.08 (d, J=1.98 Hz, 1H), 7.97 (s, 1H), 7.64-7.75 (m, 2H), 7.41 (d, J=8.60 Hz, 2H), 6.92 (d, J=8.60 Hz, 2H), 5.39 (s, 2H), 4.17 (q, J=6.98 Hz, 2H), 3.79 (s, 3H), 2.66 (brs, 2H), 2.41 (s, 6H), 1.44 (t, J=6.95 Hz, 3H); ES-LCMS m/z: 597.2 (M+H)

Step 3: 1-(4-((Dimethylamino)methyl)-3-(trifluoromethyl)phenyl)-3-(2-(5-ethoxy-6-oxo-1,6-dihydropyridin-3-yl)pyrimidin-5-yl)urea

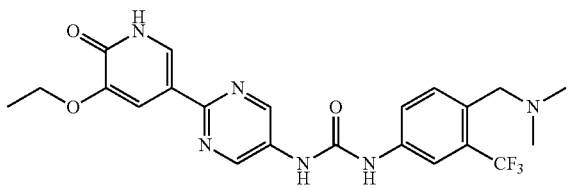 [SMILES: CCOc1cc(-c2ncc(NC(=O)Nc3ccc(CN(C)C)c(C(F)(F)F)c3)cn2)c[nH]c1=O]

To a solution of 1-(4-((dimethylamino)methyl)-3-(trifluoromethyl)phenyl)-3-(2-(5-ethoxy-6-((4-methoxybenzyl)oxy)pyridin-3-yl)pyrimidin-5-yl)urea (75 mg, 0.094 mmol) in DCM (5 mL) was added TFA (0.145 mL, 1.886 mmol). The mixture was stirred at 22° C. for 0.5 hr. The mixture was concentrated to give the crude product, which was purified by preparative HPLC (Column Phenomenex Gemini 150*25 mm*10 um Condition 0.05% HCl-ACN Begin B 14 End B 44 Gradient Time (min) 12.2 100% B Hold Time (min) 2.5 FlowRate (ml/min) 22) to afford the product of 1-(4-((dimethylamino)methyl)-3-(trifluoromethyl)phenyl)-3-(2-(5-ethoxy-6-oxo-1,6-dihydropyridin-3-yl)pyrimidin-5-yl)urea dihydrochloride (17.06 mg, 0.029 mmol, 31.3% yield) as yellow solid: $^1$H NMR (400 MHz, METHANOL-d$_4$) δ8.93 (s, 2H) 8.07 (m, 2H) 7.86 (m, 2H) 7.69 (d, J=8.31 Hz, 1H) 4.45 (s, 2H) 4.14 (q, J=6.85 Hz, 2H) 2.92 (s, 6H) 1.47 (t, J=6.85 Hz, 3H); ES-LCMS m/z 477.2 (M+H)

EXAMPLE 180

1-(2-(4-Ethoxy-6-oxo-1,6-dihydropyridin-3-yl)pyrimidin-5-yl)-3-(5-(1,1,1-trifluoro-2-methylpropan-2-yl)isoxazol-3-yl)urea hydrochloride

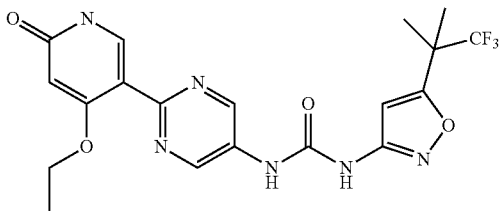 [SMILES: CCOc1cc(=O)[nH]cc1-c1ncc(NC(=O)Nc2cc(C(C)(C)C(F)(F)F)on2)cn1]

Step 1: 1-(2-(4-Ethoxy-6-((4-methoxybenzyl)oxy)pyridin-3-yl)pyrimidin-5-yl)-3-(5-(1,1,1-trifluoro-2-methylpropan-2-yl)isoxazol-3-yl)urea

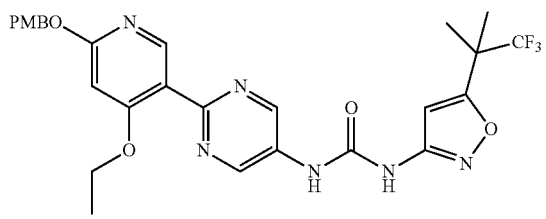

To a solution of 2-(4-ethoxy-6-((4-methoxybenzyl)oxy)pyridin-3-yl)pyrimidine-5-carboxylic acid (300 mg, 0.787 mmol) in toluene (10 mL) was added 5-(1,1,1-trifluoro-2-methylpropan-2-yl)isoxazol-3-amine (153 mg, 0.787 mmol), diphenyl phosphorazidate (325 mg, 1.180 mmol) and Et$_3$N (0.219 mL, 1.573 mmol). The mixture was stirred at 120° C. for 2 hrs. The mixture was concentrated to give the crude product, which was purified by preparative TLC (DCM/MeOH=10:1, R$_f$=0.4) to afford the yellow product 1-(2-(4-ethoxy-6-((4-methoxybenzyl)oxy)pyridin-3-yl)pyrimidin-5-yl)-3-(5-(1,1,1-trifluoro-2-methylpropan-2-yl)isoxazol-3-yl)urea (50 mg, 0.053 mmol, 6.7% yield): $^1$H NMR (400 MHz, METHANOL-d$_4$) δ9.04 (s, 2 H) 8.31 (s, 1 H) 7.26 (d, J=7.28 Hz, 2 H) 7.19-7.22 (m, 2 H) 6.85 (s, 1 H) 6.48-6.52 (m, 1 H) 5.32 (s, 2 H) 4.12-4.18 (m, 2 H) 3.81 (s, 3 H) 1.61 (s, 6 H) 1.36-1.39 (m, 3 H); ES-LCMS m/z 573.2 (M+H).

Step 2: 1-(2-(4-Ethoxy-6-oxo-1,6-dihydropyridin-3-yl)pyrimidin-5-yl)-3-(5-(1,1,1-trifluoro-2-methylpropan-2-yl)isoxazol-3-yl)urea hydrochloride

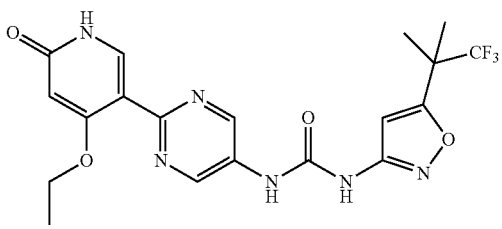 [SMILES: CCOc1cc(=O)[nH]cc1-c1ncc(NC(=O)Nc2cc(C(C)(C)C(F)(F)F)on2)cn1]

To a solution of 1-(2-(4-ethoxy-6-((4-methoxybenzyl)oxy)pyridine-3-yl)pyrimidin-5-yl)-3-(5-(1,1,1-trifluoro-2-methylpropan-2-yl)isoxazol-3-yl)urea (50 mg, 0.087 mmol) in DCM (5 mL) was added TFA (0.067 mL, 0.873 mmol). The mixture was stirred at 15° C. for 1 hr. After inspection by LCMS, the material was consumed. The mixture was concentrated to give the crude product, which was purified by preparative HPLC (Column Gemini 150*25 5 u Condition 0.05% HCl-ACN Begin B 14 End B 44 Gradient Time (min) 100% B Hold Time (min) Flow Rate (ml/min) 25) to give the product of 1-(2-(4-ethoxy-6-oxo-1,6-dihydropyridin-3-yl)pyrimidin-5-yl)-3-(5-(1,1,1-trifluoro-2-methylpropan-2-yl)isoxazol-3-yl)urea hydrochloride (10.38 mg, 0.021 mmol, 24.3% yield) as a yellow solid: $^1$H NMR (400 MHz, METHANOL-d$_4$) δ9.14(s, 2H), 8.17(s, 1H), 6.84(s, 1H), 6.22(s, 1H), 4.28(q, 2H, J=7.6 Hz), 1.61(s, 6H), 1.45(t, J=7.6 Hz, 3H); ES-LCMS m/z 453.1 (M+H).

EXAMPLE 181

1-(2-(5-Ethoxy-6-oxo-1,6-dihydropyridin-3-yl)pyrimidin-5-yl)-3-(5-(1,1,1-trifluoro-2-methylpropan-2-yl)isoxazol-3-yl)urea hydrochloride

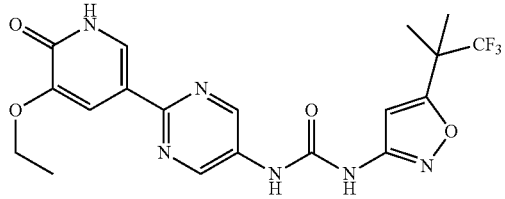 [SMILES: CCOc1cc(-c2ncc(NC(=O)Nc3cc(C(C)(C)C(F)(F)F)on3)cn2)c[nH]c1=O]

Step 1: 1-(2-(5-Ethoxy-6-((4-methoxybenzyl)oxy)pyridin-3-yl)pyrimidin-5-yl)-3-(5-(1,1,1-trifluoro-2-methylpropan-2-yl)isoxazol-3-yl)urea

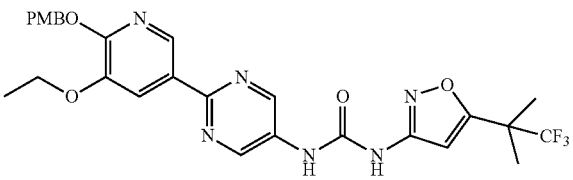

To a solution of 2-(5-ethoxy-6-((4-methoxybenzyl)oxy)pyridin-3-yl)pyrimidine-5-carboxylic acid (300 mg, 0.787 mmol) in 1,4-dioxane (10 mL) was added diphenyl phosphorazidate (260 mg, 0.944 mmol) at 23° C. The mixture was stirred for 10 mines Et$_3$N (0.164 mL, 1.180 mmol) was added to the above mixture. To the mixture was added 5-(1,1,1-trifluoro-2-methylpropan-2-yl)isoxazol-3-amine (153 mg, 0.787 mmol). The mixture was stirred at 23° C. for 10 min, then at 100° C. for 1 h. The mixture was concentrated to give the crude product, which was purified by preparative TLC (DCM/MeOH=10:1, R$_f$=0.3) to afford the crude product of 1-(2-(5-ethoxy-6-((4-methoxybenzyl)-oxy)pyridin-3-yl)pyrimidin-5-yl)-3-(5-(1,1,1-trifluoro-2-methylpropan-2-yl)isoxazol-3-yl)urea (100 mg, 60% purity, 0.087 mmol, 13.4% yield): ES-LCMS m/z 573.0 (M+H).

Step 2: 1-(2-(5-Ethoxy-6-oxo-1,6-dihydropyridin-3-yl)pyrimidin-5-yl)-3-(5-(1,1,1-trifluoro-2-methylpropan-2-yl)isoxazol-3-yl)urea hydrochloride

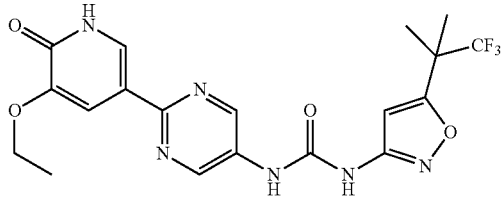 [SMILES: CCOc1cc(-c2ncc(NC(=O)Nc3cc(C(C)(C)C(F)(F)F)on3)cn2)c[nH]c1=O]

To a solution of 1-(2-(5-ethoxy-6-((4-methoxybenzyl)oxy)pyridin-3-yl)pyrimidin-5-yl)-3-(5-(1,1,1-trifluoro-2-methylpropan-2-yl)isoxazol-3-yl)urea (100 mg, 60%, 0.105 mmol) in DCM (5 mL) was added TFA (2 mL, 10% in DCM). The mixture was stirred at 23° C. for 0.5 h. The mixture was concentrated to give the crude product, which was purified by preparative HPLC (Gilson GX281 Column: Gemini 150*25 mm*5 um Mobile phase A: water with 0.1% HCl Mobile phase B: MeCN Column temperature: 40° C. Gradient: 30-60% B 10 min Flow rate: 25 mL/min). The product of 1-(2-(5-ethoxy-6-oxo-1,6-dihydropyridin-3-yl)pyrimidin-5-yl)-3-(5-(1,1,1-trifluoro-2-methylpropan-2-yl)isoxazol-3-yl)urea hydrochloride 7.71 mg, 0.015 mmol, 14.3% yield) was obtained as a yellow solid: $^1$H NMR (400 MHz, DMSO-$d_6$) δ8.83 (s, 2H) 7.94 (d, J=1.98 Hz, 1H) 7.71 (d, J=2 Hz, 1H) 6.76 (s, 1H) 4.03 (q, J=7.2Hz, 2H) 1.49 (s, 6H) 1.36 (t, J=7.2 Hz, 3H); ES-LCMS m/z 453.0(M+H)

EXAMPLE 182

1-(4-((4-Ethylpiperazin-1-yl)methyl)-2-fluoro-5-(trifluoromethyl)phenyl)-3-(2-(4-(2-methoxyethoxy)-6-oxo-1,6-dihydropyridin-3-yl)-4-methylpyrimidin-5-yl)urea

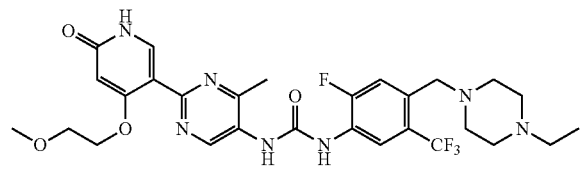 [SMILES: CCN1CCN(Cc2cc(F)c(NC(=O)Nc3cnc(-c4c[nH]c(=O)cc4OCCOC)nc3C)cc2C(F)(F)F)CC1]

Step 1: 1-(4-((4-ethylpiperazin-1-yl)methyl)-2-fluoro-5-(trifluoromethyl)phenyl)-3-(2-(6-((4-methoxybenzyl)oxy)-4-(2-methoxyethoxy)pyridin-3-yl)-4-methylpyrimidin-5-yl)urea

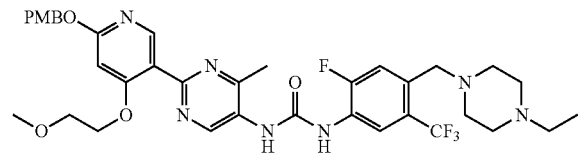

To a mixture of 4-((4-ethylpiperazin-1-yl)methyl)-2-fluoro-5-(trifluoromethyl)aniline (79 mg, 0.259 mmol), Et$_3$N (0.098 mL, 0.705 mmol), 2-(6-((4-methoxybenzyl)oxy)-4-(2-methoxyethoxy)pyridin-3-yl)-4-methylpyrimidine-5-carboxylic acid (100 mg, 0.235 mmol) in toluene (40 mL) was added diphenyl phosphorazidate (97 mg, 0.353 mmol) at 25° C. The mixture was stirred at 120° C. for 2 hrs. The reaction was quenched by water (20 mL). The mixture was extracted with DCM (20 ml×3), the organic extract was washed with brine (20 mL), dried over Na$_2$SO$_4$, filtered and concentrated to give crude product of 1-(4-((4-ethylpiperazin-1-yl)methyl)-2-fluoro-5-(trifluoromethyl)phenyl)-3-(2-(6-((4-methoxybenzyl)oxy)-4-(2-methoxyethoxy)pyridin-3-yl)-4-methylpyrimidin-5-yl)urea (100 mg, 0.110 mmol, 46.8% yield) as a yellow solid: $^1$H NMR (400 MHz, CD$_3$OD) 9.32-9.25 (m, 1H), 8.60 (d, J=7.5 Hz, 1H), 8.31-8.23 (m, 1H), 7.61 (d, J=12.3 Hz, 1H), 7.39 (d, J=8.4 Hz, 2H), 6.94-6.88 (m, 2H), 6.53-6.49 (m, 1H), 5.32 (s, 2H), 4.24-4.17 (m, 2H), 3.79 (s, 2H), 3.73-3.70 (m, 2H), 3.63 (s, 2H), 3.53 (s, 3H), 3.33 (s, 3H), 2.59 (s, 3H), 2.56-2.42 (m, 8H), 1.13-1.08 (m, 3H); ES-LCMS m/z 698.3 (M+H).

Step 2: 1-(4-((4-Ethylpiperazin-1-yl)methyl)-2-fluoro-5-(trifluoromethyl)phenyl)-3-(2-(4-(2-methoxyethoxy)-6-oxo-1,6-dihydropyridin-3-yl)-4-methylpyrimidin-5-yl)urea

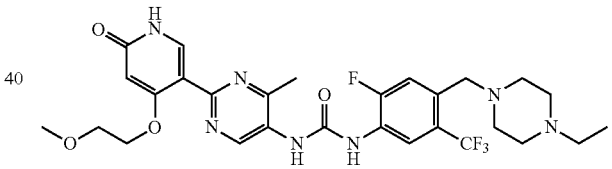

To a solution of 1-(4-((4-ethylpiperazin-1-yl)methyl)-2-fluoro-5-(trifluoromethyl)phenyl)-3-(2-(6-((4-methoxybenzyl)oxy)-4-(2-methoxyethoxy)pyridin-3-yl)-4-methylpyrimidin-5-yl)urea (100 mg, 0.117 mmol) in DCM (10 mL) was added 2,2,2-trifluoroacetic acid (66.6 mg, 0.584 mmol), the mixture was stirred at 25° C. for 20 min. The solvent was removed in vacuo and purified by preparative HPLC (Column: Gemini 150*25 5 u; Mobile phase: 10 mM NH4HCO3-ACN; Gradient: B from 20 to 50in 25 min; Flow rate: 25 mL/min; Wavelength: 220/254 nm.) and was lyophilized to provide 1-(4-((4-ethylpiperazin-1-yl)methyl)-2-fluoro-5-(trifluoromethyl)phenyl)-3-(2-(4-(2-methoxyethoxy)-6-oxo-1,6-dihydropyridin-3-yl)-4-methylpyrimidin-5-yl)urea (19.22 mg, 0.032 mmol, 27.1% yield) as a white solid: $^1$H NMR (400 MHz, METHANOL-d4) 9.25 (s, 1H), 8.60 (d, J=7.5 Hz, 1H), 7.80 (s, 1H), 7.61 (d, J=12.3 Hz, 1H), 6.03 (s, 1H), 4.24-4.16 (m, 2H), 3.78-3.70 (m, 2H), 3.64 (s, 2H), 3.34 (s, 3H), 2.56 (s, 13H), 1.13 (t, J=7.3 Hz, 3H); ES-LCMS (m/z) (M+H)=608.2.

EXAMPLE 183

1-(2-(5-Ethoxy-6-oxo-1,6-dihydropyridin-3-yl)pyrimidin-5-yl)-3-(4-((4-ethylpiperazin-1-yl)methyl)-2-fluoro-5-(trifluoromethyl)phenyl)urea trihydrochloride

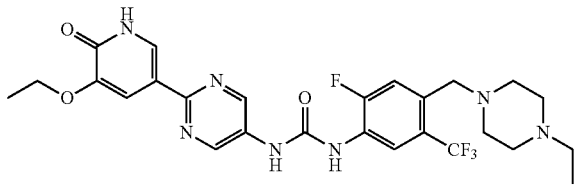 [SMILES: CCOc1cc(-c2ncc(NC(=O)Nc3cc(C(F)(F)F)c(CN4CCN(CC)CC4)cc3F)cn2)c[nH]c1=O]

Step 1: 1-(2-chloropyrimidin-5-yl)-3-(4-((4-ethylpiperazin-1-yl)methyl)-2-fluoro-5-(trifluoromethyl)phenyl)urea

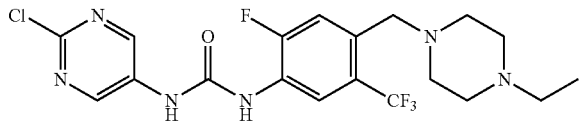 [SMILES: CCN1CCN(Cc2cc(F)c(NC(=O)Nc3cnc(Cl)nc3)cc2C(F)(F)F)CC1]

To a solution of 2-chloropyrimidin-5-amine (100 mg, 0.772 mmol) in THF (15 mL) was added triphosgene (80 mg, 0.270 mmol). The resulting mixture was stirred at 60° C. for 0.5 hr. LCMS analysis showed the starting material disappeared. The solvent was removed in vacuo to yield a yellow oil of 2-chloro-5-isocyanatopyrimidine (120 mg, 95% yield). To a solution of 4-((4-ethylpiperazin-1-yl)methyl)-2-fluoro-5-(trifluoromethyl)aniline (236 mg, 0.771 mmol) and Et₃N (0.323 mL, 2.314 mmol) in THF (15 mL) was added a solution of 2-chloro-5-isocyanatopyrimidine (120 mg, 0.771 mmol) in THF (15 mL) at 60° C. The resulting mixture was stirred at 60° C. for 1 hr. The solvent was removed in vacuo. The residue was distributed between DCM (30 mL) and H₂O (20 mL), extracted with DCM (30 mL×2). The organic layer was washed with brine (20 mL), dried over Na₂SO₄, filtered and concentrated to give the crude product, which was purified by preparative TLC (DCM/MeOH=10/1, R$_f$=0.4) to yield a brown solid of 1-(2-chloropyrimidin-5-yl)-3-(4-((4-ethylpiperazin-1-yl)methyl)-2-fluoro-5-(trifluoromethyl)phenyl)urea (60 mg, 0.111 mmol, 14.34% yield): ¹H NMR (400 MHz, METHANOL-d₄) δ8.89 (s, 2H), 8.81 (s, 2H), 3.76 (s, 2H), 2.92-2.60 (m, 10H), 1.22 (t, J=7.4 Hz, 3H); ES-LCMS m/z 461.2 (M+H).

Step 2: 1-(2-(5-ethoxy-6-((4-methoxybenzyl)oxy)pyridin-3-yl)pyrimidin-5-yl)-3-(4-((4-ethylpiperazin-1-yl)methyl)-2-fluoro-5-(trifluoromethyl)phenyl)urea

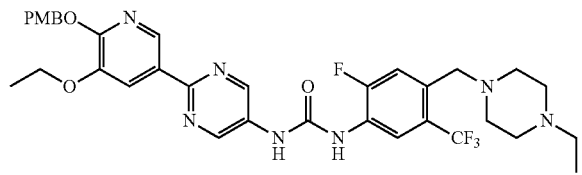

A solution of 1-(2-chloropyrimidin-5-yl)-3-(4-((4-ethylpiperazin-1-yl)methyl)-2-fluoro-5-(trifluoromethyl)phenyl)urea (59.8 mg, 0.130 mmol), 3-ethoxy-2-((4-methoxybenzyl)oxy)-5-(4,4,5,5-tetramethyl-1,3,2-dioxaborolan-2-yl)pyridine (50 mg, 0.130 mmol), PdCl₂(dppf) (9.50 mg, 0.013 mmol) and Cs₂CO₃ (85 mg, 0.260 mmol) in 1,4-dioxane (18 mL) and water (6 mL) was stirred at 110° C. for 1 hr under a N₂ atmosphere. LCMS analysis showed the starting material disappeared. The organic layer was separated and concentrated to give the crude product, which was purified by preparative TLC (DCM/MeOH=10/1, R$_f$=0.2) to yield a yellow solid of 1-(2-(5-ethoxy-6-((4-methoxybenzyl)oxy)pyridin-3-yl)pyrimidin-5-yl)-3-(4-((4-ethylpiperazin-1-yl)methyl)-2-fluoro-5-(trifluoromethyl)phenyl)urea (60 mg, 0.070 mmol, 54.1% yield): ¹H NMR (400 MHz, METHANOL-d₄) δ8.97 (s, 2H), 8.58 (d, J=7.6 Hz, 1H), 8.09-8.07 (m, 1H), 7.62 (d, J=12.0 Hz, 2H), 7.41 (d, J=8.8 Hz, 2H), 6.92 (d, J=8.4 Hz, 2H), 5.39 (s, 2H), 4.17 (d, J=6.8 Hz, 2H), 3.79 (s, 3H), 3.69-3.65 (m, 4H), 3.59 (s, 2H), 3.57-3.53 (m, 4H), 2.61 (br. s., 2H), 1.47-1.43 (m, 3H), 1.28 (m, 3H); ES-LCMS m/z 684.3 (M+H), 564.2 (M+H-PMB).

Step 3: 1-(2-(5-ethoxy-6-oxo-1,6-dihydropyridin-3-yl)pyrimidin-5-yl)-3-(4-((4-ethylpiperazin-1-yl)methyl)-2-fluoro-5-(trifluoromethyl)phenyl)urea trihydrochloride

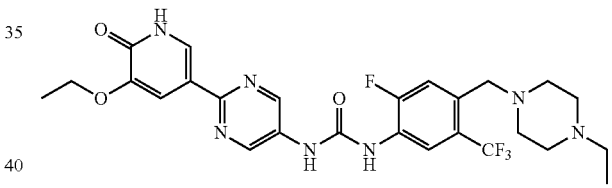

A solution of 1-(2-(5-ethoxy-6-((4-methoxybenzyl)oxy)pyridin-3-yl)pyrimidin-5-yl)-3-(4-((4-ethylpiperazin-1-yl)methyl)-2-fluoro-5-(trifluoromethyl)phenyl)urea (50 mg, 0.073 mmol) in 2,2,2-trifluoroacetic acid (10% in DCM) (2 mL, 1.488 mmol) was stirred at 25° C. for 0.5 hr. LCMS analysis showed the starting material disappeared. The solvent was removed in vacuo. The crude product was purified by preparative HPLC (Instrument: DB/Column: Gemini 150*25 5 u/Mobile phase A: Water+0.1% HCl/Mobile phase B: MeCN/Flowrate: 25 mL/min/Gradient Profile Description: 9-39 (B %)) to yield a yellow solid of 1-(2-(5-ethoxy-6-oxo-1,6-dihydropyridin-3-yl)pyrimidin-5-yl)-3-(4-((4-ethylpiperazin-1-yl)methyl)-2-fluoro-5-(trifluoromethyl)phenyl)urea trihydrochloride (5 mg, 7.43 μmol, 10.2% yield): ¹H NMR (400 MHz, METHANOL-d₄) δ 8.94 (s, 2H), 8.61 (d, J=7.2 Hz, 1H), 8.07 (s, 1H), 7.87 (d, J=2.0 Hz, 1H), 7.67 (s, 1H), 4.16 (m, 2H), 3.80 (br. s., 2H), 3.69-3.65 (m, 2H), 3.56 (d, J=4.8 Hz, 2H), 3.25-3.20 (m, 2H), 3.13 (br. s., 2H), 2.55 (br. s., 2H), 1.49 (t, J=7.0 Hz, 3H), 1.36 (t, J=7.2 Hz, 3H); ES-LCMS m/z 564.2 (M+H).

EXAMPLE 184

1-(2-Fluoro-4-((4-methylpiperazin-1-yl)methyl)-5-(trifluoromethyl)-phenyl)-3-(2-(5-(2-methoxyethoxy)-6-oxo-1,6-dihydropyridin-3-yl)-4-methylpyrimidin-5-yl)urea trihydrochloride

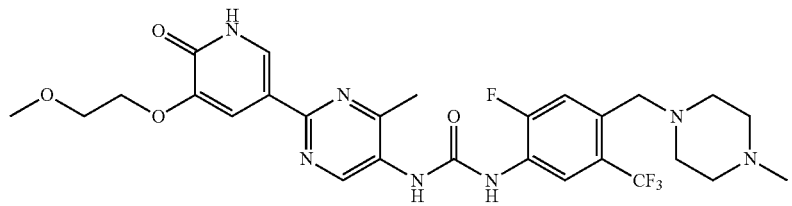

Step 1: 1-(2-Fluoro-4-((4-methylpiperazin-1-yl)methyl)-5-(trifluoromethyl)phenyl)-3-(2-(6-((4-methoxybenzyl)oxy)-5-(2-methoxyethoxy)pyridin-3-yl)-4-methylpyrimidin-5-yl)urea

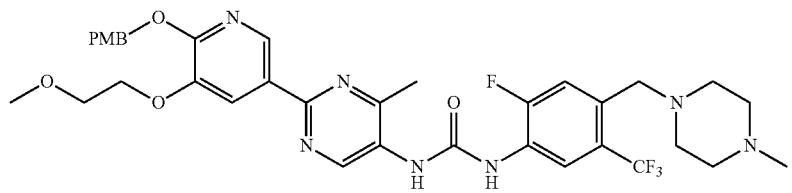

A solution of 2-(6-((4-methoxybenzyl)oxy)-5-(2-methoxyethoxy)pyridin-3-yl)-4-methylpyrimidine-5-carboxylic acid (100 mg, 0.235 mmol), 2-fluoro-4-((4-methylpiperazin-1-yl)methyl)-5-(trifluoromethyl)aniline (68.5 mg, 0.235 mmol), diphenyl phosphorazidate (78 mg, 0.282 mmol) and Et$_3$N (0.066 mL, 0.470 mmol) in toluene (5 mL) was stirred at 120° C. for 2 hours under a N$_2$ atmosphere. The solvent was removed in vacuo. The mixture was purified by preparative TLC (DCM/MeOH=15/1, R$_f$=0.3) to yield a yellow solid of 1-(2-fluoro-4-((4-methylpiperazin-1-yl)methyl)-5-(trifluoromethyl)phenyl)-3-(2-(6-((4-methoxybenzyl)oxy)-5-(2-methoxyethoxy)pyridin-3-yl)-4-methylpyrimidin-5-yl)urea (53.3 mg, 0.049 mmol, 21% yield): $^1$H NMR (400 MHz, METHANOL-d$_4$) 9.20 (s, 1H), 8.69 (d, J=2.0 Hz, 1H), 8.61 (d, J=7.6 Hz, 1H), 8.12 (d, J=1.6 Hz, 1H), 7.58 (d, J=12.0 Hz, 1H), 7.40 (d, J=8.8 Hz, 2H), 6.90 (d, J=8.4 Hz, 2H), 5.39 (s, 2H), 4.24-4.22 (m, 2H), 3.82-3.76 (m, 7H), 3.69 (s, 2H), 3.41 (s, 3H), 3.26 (m, 2H), 3.11 (m, 4H), 2.76 (s, 3H), 2.58 (s, 3H); ES-LCMS m/z: 714.2 (M+H).

Step 2: 1-(2-Fluoro-4-((4-methylpiperazin-1-yl)methyl)-5-(trifluoromethyl)phenyl)-3-(2-(5-(2-methoxyethoxy)-6-oxo-1,6-dihydropyridin-3-yl)-4-methylpyrimidin-5-yl)urea trihydrochloride

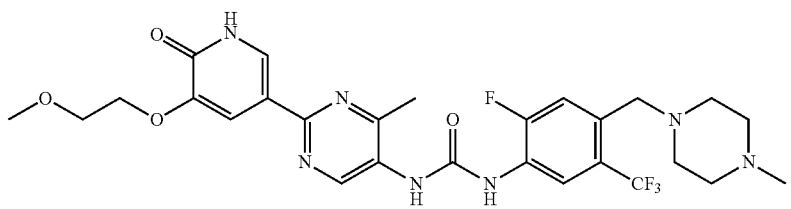

A solution of 1-(2-fluoro-4-((4-methylpiperazin-1-yl)methyl)-5-(trifluoromethyl)phenyl)-3-(2-(6-((4-methoxybenzyl)oxy)-5-(2-methoxyethoxy)pyridin-3-yl)-4-methylpyrimidin-5-yl)urea (80 mg, 0.112 mmol) in TFA (10% in DCM) (5 mL) was stirred at 25° C. for 0.5 hr. LCMS analysis showed the starting material disappeared. The solvent was removed in vacuo. The residue was purified by preparative HPLC (Column: Phenomenex Synergi C18 250*21.2 mm*4 um/Mobile phase A: Water+0.1% HCl/Mobile phase B: MeCN/Flowrate: 25 mL/min/Gradient Profile Description: 15-45 (B %)). After lyophilization, a yellow solid of 1-(2-fluoro-4-((4-methylpiperazin-1-yl)methyl)-5-(trifluoromethyl)phenyl)-3-(2-(5-(2-methoxyethoxy)-6-oxo-1,6-dihydropyridin-3-yl)-4-methylpyrimidin-5-yl)urea trihydrochloride (50 mg, 0.070 mmol, 62.5% yield) was obtained: $^1$H NMR (400 MHz, METHANOL-d4) d=9.25 (s, 1H), 8.68 (d, J=8.0 Hz, 1H), 8.18 (s, 1H), 7.98 (s, 1H), 7.69 (d, J=12.0 Hz, 1H), 4.26 (d, J=4.5 Hz, 2H), 3.94-3.82 (m, 4H), 3.63-3.40 (m, 7H), 3.15 (br. s., 2H), 2.96 (s, 3H), 2.68 (s, 2H), 2.63 (s, 3H); ES-LCMS m/z 594.2 (M+H).

EXAMPLE 185

1-(4-(2-Amino-2-methylpropyl)-3-(trifluoromethyl)phenyl)-3-(2-(5-ethoxy-6-oxo-1,6-dihydropyridin-3-yl)-4-methylpyrimidin-5-yl)urea

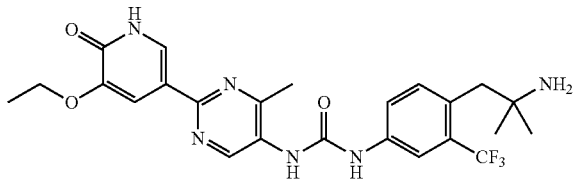 [SMILES: CCOc1cc(-c2ncc(NC(=O)Nc3ccc(CC(C)(C)N)c(C(F)(F)F)c3)c(C)n2)c[nH]c1=O]

Step 1: Tert-butyl(1-(4-(3-(2-(5-ethoxy-6-oxo-1,6-dihydropyridin-3-yl)-4-methyl-pyrimidin-5-yl)ureido)-2-(trifluoromethyl)phenyl)-2-methylpropan-2-yl)carbamate

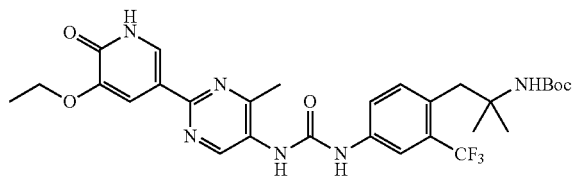 [SMILES: CCOc1cc(-c2ncc(NC(=O)Nc3ccc(CC(C)(C)NC(=O)OC(C)(C)C)c(C(F)(F)F)c3)c(C)n2)c[nH]c1=O]

To a suspension of 2-(5-ethoxy-6-((4-methoxybenzyl)oxy)pyridin-3-yl)-4-methylpyrimidine-5-carboxylic acid (500 mg, 1.265 mmol) in toluene (25 mL) was added tert-butyl (1-(4-amino-2-(trifluoromethyl)phenyl)-2-methylpropan-2-yl)carbamate (647 mg, 1.265 mmol), Et$_3$N (0.264 mL, 1.897 mmol) and diphenyl phosphorazidate (522 mg, 1.897 mmol). The mixture was stirred at 130° C. for 12 hrs. Then the solution was concentrated and distributed between ethyl acetate (15 mL) and water (10 mL). The organic extract was washed with brine (10 mL), dried over Na$_2$SO$_4$, filtered and concentrated. The crude material was purified by preparative TLC (DCM/MeOH=10:1, R$_f$=0.4) to yield a yellow solid of tert-butyl (1-(4-(3-(2-(5-ethoxy-6-oxo-1,6-dihydropyridin-3-yl)-4-methylpyrimidin-5-yl)ureido)-2-(trifluoromethyl)phenyl)-2-methylpropan-2-yl)carbamate (124 mg, 0.152 mmol, 12.0% yield): ES-LCMS m/z 605.4 (M+H).

Step 2: 1-(4-(2-Amino-2-methylpropyl)-3-(trifluoromethyl)phenyl)-3-(2-(5-ethoxy-6-oxo-1,6-dihydropyridin-3-yl)-4-methylpyrimidin-5-yl)urea

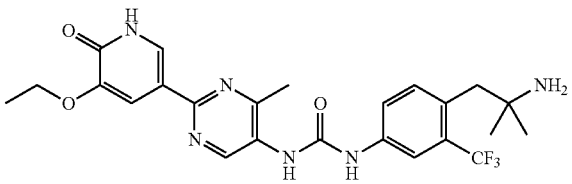 [SMILES: CCOc1cc(-c2ncc(NC(=O)Nc3ccc(CC(C)(C)N)c(C(F)(F)F)c3)c(C)n2)c[nH]c1=O]

A solution of tert-butyl(1-(4-(3-(2-(5-ethoxy-6-oxo-1,6-dihydropyridin-3-yl)-4-methylpyrimidin-5-yl)ureido)-2-(trifluoromethyl)phenyl)-2-methylpropan-2-yl)carbamate (124 mg, 0.152 mmol) in HCl in EtOAc (10 mL, 4 N) was stirred at 16° C. for 5 hrs. Then the solution was concentrated. The crude material was purified by preparative HPLC (Instrument: DB/Column: Gemini 150*25 mm*5 um/Mobile phase A: Water (0.05% ammonia solution)/Mobile phase B: Acetonitrile/Gradient: 25-55(B %)/Flowrate: 25 mL/min/Run time: 10 min) to yield 1-(4-(2-amino-2-methylpropyl)-3-(trifluoromethyl)phenyl)-3-(2-(5-ethoxy-6-oxo-1,6-dihydropyridin-3-yl)-4-methylpyrimidin-5-yl)urea (31.8 mg, 0.063 mmol, 41.5% yield). TLC (DCM/MeOH=10:1, R$_f$=0.2): $^1$H NMR (400 MHz, CD$_3$OD) δ 9.06 (s, 1H), 8.09 (d, J=2.0 Hz, 1H), 7.90 (dd, J=2.0, 15.1 Hz, 2H), 7.65 (d, J=7.0 Hz, 1H), 7.49 (d, J=8.5 Hz, 1H), 4.17 (q, J=6.9 Hz, 2H), 2.94 (s, 2H), 2.58 (s, 3H), 1.51 (t, J=7.0 Hz, 3H); 1.16 (s, 6H); ES-LCMS m/z 505.2 (M+H).

EXAMPLE 186

1-(4-(2-Amino-2-methylpropyl)-3-(trifluoromethyl)phenyl)-3-(2-(4-ethoxy-6-oxo-1,6-dihydropyridin-3-yl)-4-methylpyrimidin-5-yl)urea

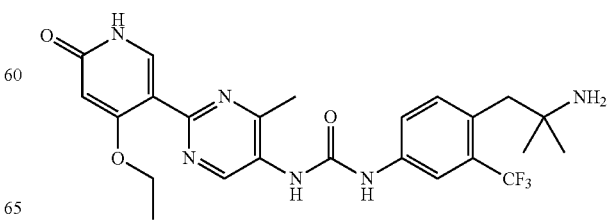

Step 1: Tert-butyl(1-(4-(3-(2-(4-ethoxy-6-((4-methoxybenzyl)oxy)pyridin-3-yl)-4-methyl-pyrimidin-5-yl)ureido)-2-(trifluoromethyl)phenyl)-2-methylpropan-2-yl)carbamate

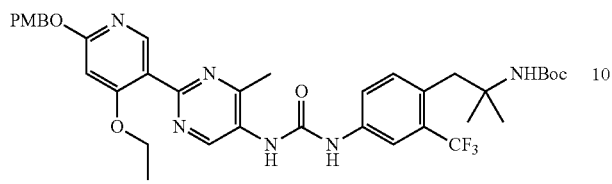

To a suspension of 2-(4-ethoxy-6-((4-methoxybenzyl)oxy)pyridin-3-yl)-4-methylpyrimidine-5-carboxylic acid (500 mg, 1.265 mmol) in toluene (15 mL) was added tert-butyl (1-(4-amino-2-(trifluoromethyl)phenyl)-2-methylpropan-2-yl)carbamate (647 mg, 1.265 mmol), Et$_3$N (0.264 mL, 1.897 mmol) and diphenyl phosphorazidate (522 mg, 1.897 mmol). The mixture was stirred at 120° C. for 12 hrs. Then the solution was concentrated and distributed between ethyl acetate (20 mL) and water (10 mL). The organic extract was washed with brine (10 mL), dried over Na$_2$SO$_4$, filtered and concentrated. The crude material was purified by preparative TLC (DCM/MeOH=10:1, R$_f$=0.7) to yield a yellow solid of tert-butyl (1-(4-(3-(2-(4-ethoxy-6-((4-methoxybenzyl)oxy)pyridin-3-yl)-4-methyl pyrimidin-5-yl)ureido)-2-(trifluoromethyl)phenyl)-2-methylpropan-2-yl)carbamate (300 mg, 0.372 mmol, 29.4% yield): $^1$H NMR (400 MHz, CD$_3$OD) δ 9.40-9.05 (m, 1H), 8.29 (s, 1H), 7.47-7.22 (m, 5H), 6.94 (d, J=8.5 Hz, 2H), 6.50 (s, 1H), 5.33 (s, 2H), 4.16 (q, J=7.0 Hz, 2H), 3.84-3.80 (m, 3H), 3.24-3.16 (m, 2H), 2.66-2.54 (m, 3H), 1.52 (s, 9H), 1.42-1.35 (m, 3H), 1.24-1.20 (m, 6H); ES-LCMS m/z 725.4 (M+H).

Step 2: 1-(4-(2-Amino-2-methylpropyl)-3-(trifluoromethyl)phenyl)-3-(2-(4-ethoxy-6-oxo-1,6-dihydropyridin-3-yl)-4-methylpyrimidin-5-yl)urea

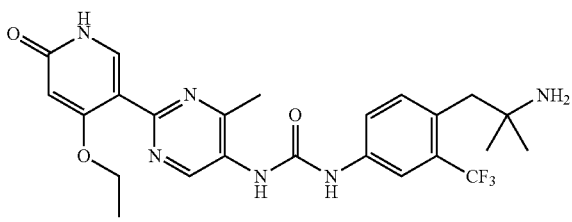 [SMILES: CCOc1cc(=O)[nH]cc1-c1ncc(NC(=O)Nc2ccc(CC(C)(C)N)c(C(F)(F)F)c2)c(C)n1]

A solution of tert-butyl 1-(4-(3-(2-(4-ethoxy-6-((4-methoxybenzyl)oxy)pyridin-3-yl)-4-methylpyrimidin-5-yl)ureido)-2-(trifluoromethyl)phenyl)-2-methylpropan-2-yl)carbamate (300 mg, 0.372 mmol) in HCl in EtOAc (10 mL, 4 N, 40.0 mmol) was stirred at 18° C. for 10 hrs. Then the solution was concentrated. The crude material was purified by preparative HPLC (Instrument: DB/Column: Gemini 150*25 mm*5 um/Mobile phase A: water (0.05% ammonia solution)/Mobile phase B: Acetonitrile/Gradient: 23-53 (B %)/Flowrate: 25 mL/min/Run time: 10 min) to yield a white solid of 1-(4-(2-amino-2-methylpropyl)-3-(trifluoromethyl) phenyl)-3-(2-(4-ethoxy-6-oxo-1,6-dihydropyridin-3-yl)-4-methylpyrimidin-5-yl)urea (56.88 mg, 0.111 mmol, 29.8% yield). TLC (DCM/MeOH=10:1, R$_f$=0.1): $^1$H NMR (400 MHz, CD$_3$OD) δ 9.17 (s, 1H), 7.90 (d, J=2.2 Hz, 1H), 7.78 (s, 1H), 7.69-7.60 (m, 1H), 7.47 (d, J=8.4 Hz, 1H), 6.00 (s, 1H), 4.12 (q, J=6.8 Hz, 2H), 2.93 (s, 2H), 2.57 (s, 3H), 1.37 (t, J=7.1 Hz, 3H), 1.14 (s, 6H); ES-LCMS m/z 505.1 (M+H).

EXAMPLE 187

N-(2-(dimethylamino)ethyl)-3-(3-(2-(4-(2-methoxyethoxy)-6-oxo-1,6-dihydropyridin-3-yl)-4-methylpyrimidin-5-yl)ureido)-5-(trifluoromethyl)benzamide

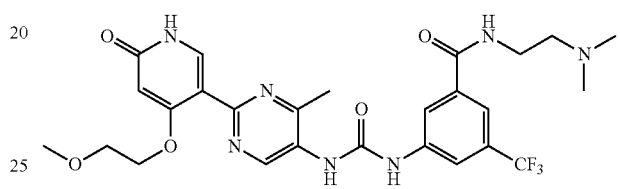

Step 1: N-(2-(dimethylamino)ethyl)-3-(3-(2-(6-((4-methoxybenzyl)oxy)-4-(2-methoxyethoxy)pyridin-3-yl)-4-methylpyrimidin-5-yl)ureido)-5-(trifluoromethyl)benzamide

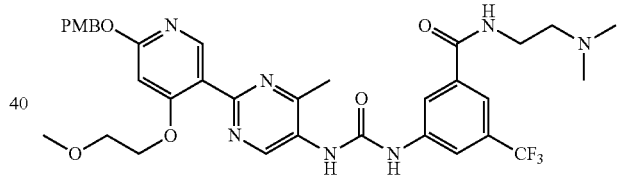

To a mixture of 3-amino-N-(2-(dimethylamino)ethyl)-5-(trifluoromethyl)benzamide (100 mg, 0.349 mmol), Et$_3$N (0.133 mL, 0.952 mmol), 2-(6-((4-methoxybenzyl)oxy)-4-(2-methoxy ethoxy)pyridin-3-yl)-4-methylpyrimidine-5-carboxylic acid (150 mg, 0.317 mmol) in toluene (40 mL) was added diphenyl phosphorazidate (131 mg, 0.476 mmol) at 25° C. The mixture was stirred at 120° C. for 2 hrs. Solvent was removed in vacuo to give a residue, which was extracted with DCM (20 mL×2). The organic extract was washed with brine (20 mL), dried over Na$_2$SO$_4$, filtered and concentrated to give crude product N-(2-(dimethylamino) ethyl)-3-(3-(2-(6-((4-methoxybenzyl)oxy)-4-(2-methoxyethoxy)pyridin-3-yl)-4-methylpyrimidin-5-yl)ureido)-5-(trifluoromethyl)benzamide (150 mg, 0.129 mmol, 40.7% yield) as a yellow solid: $^1$H NMR (400 MHz, CD$_3$OD) 9.40 (s, 1H), 8.27-8.18 (m, 3H), 7.83 (br. s., 1H), 7.49 (br. s., 1H), 7.33 (br. s., 1H), 6.88 (d, J=8.8 Hz, 2H), 6.13 (s, 1H), 4.37-4.34 (m, 2H), 3.78-3.75 (m, 3H), 3.74-3.69 (m, 4H), 3.42-3.38 (m, 3H), 3.18-3.13 (m, 4H), 2.88 (s, 3H), 1.27 (t, J=7.3 Hz, 6H); ES-LCMS (m/z) (M+H)=698.4.

Step 2: N-(2-(dimethylamino)ethyl)-3-(3-(2-(4-(2-methoxyethoxy)-6-oxo-1,6-dihydropyridin-3-yl)-4-methylpyrimidin-5-yl)ureido)-5-(trifluoromethyl)benzamide

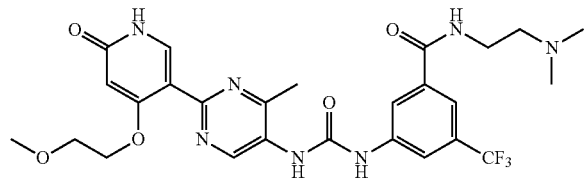

To a solution of N-(2-(dimethylamino)ethyl)-3-(3-(2-(64 (4-methoxybenzyl)oxy)-4-(2-methoxyethoxy)pyridin-3-yl)-4-methylpyrimidin-5-yl)ureido)-5-(trifluoromethyl)benzamide (150 mg, 0.129 mmol) in dichloromethane (10 mL) was added 2,2,2-trifluoroacetic acid (73.5 mg, 0.645 mmol). The mixture was stirred at 25° C. for 20 min. Solvent was removed in vacuo and purified by preparative HPLC (Column: Gemini 150*25 5 u; Mobile phase: water (0.05% ammonia hydroxide v/v)-ACN; Gradient: B from 14 to 44 in 10 min; Flow rate: 25 mL/min; Wavelength: 220/254 nm) and was lyophilized to provide N-(2-(dimethylamino)ethyl)-3-(3-(2-(4-(2-methoxyethoxy)-6-oxo-1,6-dihydropyridin-3-yl)-4-methylpyrimidin-5-yl)ureido)-5-(trifluoromethyl)benzamide (45.4 mg, 0.079 mmol, 60.9% yield) as a white solid: $^1$H NMR (400 MHz, CD$_3$OD) 9.17 (s, 1H), 8.10 (d, J=13.2 Hz, 2H), 7.81 (s, 2H), 6.04 (s, 1H), 4.21-4.18 (m, 2H), 3.75-3.72 (m, 2H), 3.55 (t, J=6.6 Hz, 2H), 3.34 (s, 3H), 2.61 (t, J=6.6 Hz, 2H), 2.57 (s, 3H), 2.34 (s, 6H); ES-LCMS (m/z) (M+H)=578.4.

EXAMPLE 188

1-(4-((Dimethylamino)methyl)-2-fluoro-5-(trifluoromethyl)phenyl)-3-(2-(5-ethoxy-6-oxo-1,6-dihydropyridin-3-yl)pyrimidin-5-yl)urea dihydrochloride

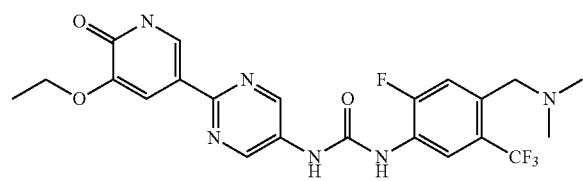 [SMILES: CCOc1cc(-c2ncc(NC(=O)Nc3cc(C(F)(F)F)c(CN(C)C)cc3F)cn2)c[nH]c1=O]

Step 1: 1-(2-Chloropyrimidin-5-yl)-3-(4-((dimethylamino)methyl)-2-fluoro-5-(trifluoromethyl)phenyl)urea

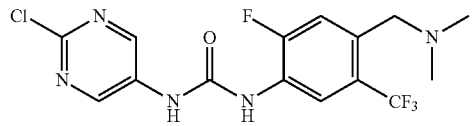 [SMILES: CN(C)Cc1cc(F)c(NC(=O)Nc2cnc(Cl)nc2)cc1C(F)(F)F]

To a solution of 2-chloropyrimidin-5-amine (150 mg, 1.158 mmol) in THF (20 mL) was added bis(trichloromethyl)carbonate (0.082 mL, 0.405 mmol). The resulting mixture was stirred at 65° C. for 0.5 hr. LCMS analysis showed the starting material disappeared. The solvent was removed in vacuo to give a yellow solid of 2-chloro-5-isocyanatopyrimidine (180 mg, 1.104 mmol, 95% yield). To a solution of 4-((dimethylamino)methyl)-2-fluoro-5-(trifluoromethyl)aniline (273 mg, 1.157 mmol) and Et$_3$N (0.484 mL, 3.47 mmol) in THF (20 mL) was added a solution of 2-chloro-5-isocyanatopyrimidine (180 mg, 1.157 mmol) in THF (20 mL) at 60° C. The resulting mixture was stirred at 60° C. for 1 hr. The solvent was removed in vacuo to give a yellow solid of 1-(2-chloropyrimidin-5-yl)-3-(4-((dimethylamino)methyl)-2-fluoro-5-(trifluoromethyl)phenyl)urea (380 mg, 0.165 mmol, 14.2% yield): $^1$H NMR (400 MHz, METHANOL-d$_4$) d=8.85 (s, 2H), 7.61 (dd, J=4.9, 9.0 Hz, 1H), 7.33-7.28 (m, 1H), 3.70 (s, 2H), 2.30-2.28 (m, 6H); ES-LCMS m/z 392.1 (M+H).

Step 2: 1-(4-((Dimethylamino)methyl)-2-fluoro-5-(trifluoromethyl)phenyl)-3-(2-(5-ethoxy-6-((4-methoxybenzyl)oxy)pyridin-3-yl)pyrimidin-5-yl)urea

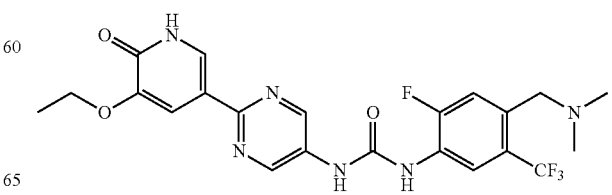

A solution of 1-(2-chloropyrimidin-5-yl)-3-(4-((dimethylamino)methyl)-2-fluoro-5-(trifluoromethyl)phenyl)urea (380 mg, 0.165 mmol), 3-ethoxy-2-((4-methoxybenzyl)oxy)-5-(4,4,5,5-tetramethyl-1,3,2-dioxaborolan-2-yl)pyridine (63.5 mg, 0.165 mmol), PdCl$_2$(dppf) (12.07 mg, 0.016 mmol) and Cs$_2$CO$_3$ (107 mg, 0.330 mmol) in 1,4-Dioxane (15 mL) and Water (5 mL) was stirred at 110° C. for 1 hr under a N$_2$ atmosphere. LCMS analysis showed the starting material disappeared. The water layer was separated. The organic layer was concentrated to give the crude product, which was purified by preparative TLC (DCM/MeOH=15/1, R$_f$=0.3) to yield a brown solid of 1-(4-((dimethylamino)methyl)-2-fluoro-5-(trifluoromethyl)phenyl)-3-(2-(5-ethoxy-6-((4-methoxybenzyl)oxy)pyridin-3-yl)pyrimidin-5-yl)urea (60 mg, 0.078 mmol, 47.4% yield): $^1$H NMR (400 MHz, DMSO-d$_6$) d=8.98 (d, J=6.6 Hz, 2H), 8.65-8.61 (m, 1H), 8.50 (d, J=7.7 Hz, 1H), 8.01 (br. s., 1H), 7.56 (d, J=12.3 Hz, 1H), 7.40 (d, J=8.6 Hz, 2H), 6.93 (d, J=8.4 Hz, 2H), 5.35 (s, 2H), 4.13 (q, J=7.1 Hz, 2H), 3.74 (s, 2H), 3.47 (s,3H), 3.28 (s, 6H), 1.34 (t, J=6.7 Hz, 3H); ES-LCMS m/z 495.2 (M+H-PMB).

Step 3: 1-(4-((Dimethylamino)methyl)-2-fluoro-5-(trifluoromethyl)phenyl)-3-(2-(5-ethoxy-6-oxo-1,6-dihydropyridin-3-yl)pyrimidin-5-yl)urea dihydrochloride A solution of 1-(4-((dimethylamino)methyl)-2-fluoro-5-(trifluoromethyl)phenyl)-3-(2-(5-ethoxy-6-((4-methoxybenzyl)oxy)pyridin-3-yl)pyrimidin-5-yl)urea (50 mg, 0.081 mmol) in 2,2,2-trifluoroacetic acid (10% in Dichloromethane) (2 mL, 1.488 mmol) was stirred at 25° C. for 0.5 hr. LCMS analysis showed the starting material disappeared. The solvent was removed in vacuo. The crude product was purified by preparative HPLC (Column: Phenomenex Synergi C18 250*21.2 mm*4 um/Mobile phase A: Water+ 0.05% HCl/Mobile phase B: MeCN/Flowrate: 25 mL/min/ Gradient Profile Description: 22-52 (B %)) to yield a yellow solid of 1-(4-((dimethylamino)methyl)-2-fluoro-5-(trifluoromethyl)phenyl)-3-(2-(5-ethoxy-6-oxo-1,6-dihydropyridin-3-yl)pyrimidin-5-yl)urea dihydrochloride (15 mg, 0.026 mmol, 31.6% yield): $^1$H NMR (400 MHz, METHANOL-d$_4$) δ9.02 (s, 2H), 8.92 (d, J=7.2 Hz, 1H), 8.11 (d, J=1.2 Hz, 1H), 7.86-7.82 (m, 2H), 4.53 (s, 2H), 4.22-4.17 (m, 2H), 2.97 (s, 6H), 1.53 (t, J=6.6 Hz, 3H); ES-LCMS m/z 495.3 (M+H).

EXAMPLE 189

N-(2-(Dimethylamino)ethyl)-3-(3-(2-(5-ethoxy-6-oxo-1,6-dihydropyridin-3-yl)-pyrimidin-5-yl)ureido)-5-(trifluoromethyl)benzamide

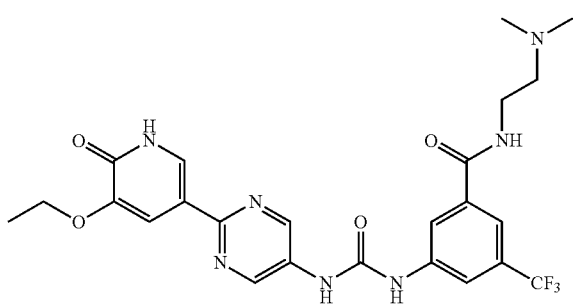 [SMILES: CCOc1cc(-c2ncc(NC(=O)Nc3cc(C(=O)NCCN(C)C)cc(C(F)(F)F)c3)cn2)c[nH]c1=O]

Step 1: 3-(3-(2-chloropyrimidin-5-yl)ureido)-N-(2-(dimethylamino)ethyl)-5-(trifluoromethyl)benzamide

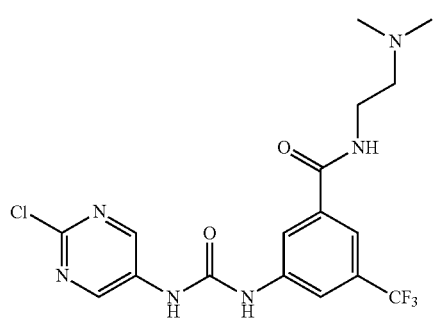 [SMILES: CN(C)CCNC(=O)c1cc(NC(=O)Nc2cnc(Cl)nc2)cc(C(F)(F)F)c1]

To a solution of 2-chloro-5-isocyanatopyrimidine (240 mg, 0.984 mmol) and Et$_3$N (0.206 mL, 1.477 mmol) in THF (10 mL) was added 3-amino-N-(2-(dimethylamino)ethyl)-5-(trifluoromethyl)benzamide (271 mg, 0.984 mmol). The mixture was stirred at 60° C. for 0.5 h. The mixture was concentrated to give the crude product, which was purified by preparative HPLC (Column Phenomenex Gemini 150*25 mm*10 um Condition 0.225% FA-ACN Begin B 15 End B 45 Gradient Time (min) 12.2 100% B Hold Time (min) 2.5 Flow Rate (ml/min) 22) to give the product of 3-(3-(2-chloropyrimidin-5-yl)ureido)-N-(2-(dimethylamino)ethyl)-5-(trifluoromethyl)benzamide (200 mg, 0.413 mmol, 42.0% yield) as yellow solid: $^1$H NMR (400 MHz, METHANOL-d$_4$): δ 8.88 (s, 2 H) 8.26 (s, 1 H) 8.02 (s, 1 H) 7.82 (s, 1 H) 3.74 (t, j=5.77 Hz, 2 H) 3.27 (br. s., 2 H) 2.90 (s, 6 H); ES-LCMS m/z: 431.1 (M+H).

Step 2: N-(2-(dimethylamino)ethyl)-3-(3-(2-(5-ethoxy-6-((4-methoxybenzyl)oxy)-pyridin-3-yl)pyrimidin-5-yl)ureido)-5-(trifluoromethyl)benzamide

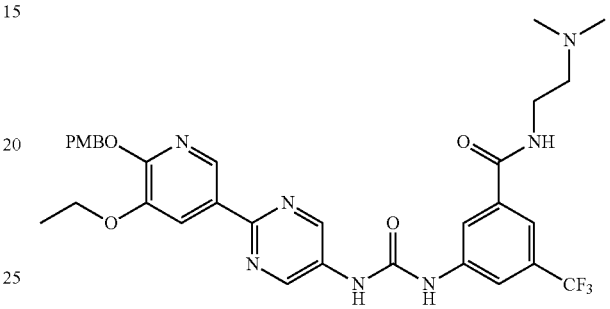

To a mixture of 3-(3-(2-chloropyrimidin-5-yl)ureido)-N-(2-(dimethylamino)ethyl)-5-(trifluoromethyl)benzamide (100 mg, 0.232 mmol), 3-ethoxy-2-((4-methoxybenzyl)oxy)-5-(4,4,5,5-tetramethyl-1,3,2-dioxaborolan-2-yl)pyridine (89 mg, 0.232 mmol), Cs$_2$CO$_3$ (76 mg, 0.232 mmol) in 1,4-dioxane (6 mL)/water (2.00 mL) was added PdCl$_2$(dppf) (170 mg, 0.232 mmol) under nitrogen atmosphere. The mixture was stirred at 110° C. for 0.5 h in the microwave and then was concentrated to give the crude product, which was purified by preparative TLC (DCM/MeOH=10:1, R$_f$=0.2) to give the product N-(2-(dimethylamino)ethyl)-3-(3-(2-(5-ethoxy-6-((4-methoxybenzyl)oxy)pyridin-3-yl)pyrimidin-5-yl)ureido)-5-(trifluoromethyl)benzamide (60 mg, 0.079 mmol, 33.9% yield) as yellow solid: $^1$H NMR (400 MHz, METHANOL-d$_4$) δ8.99 (s, 2 H) 8.65 (s, 1 H) 8.21 (br. s., 1 H) 8.08 (d, J12.96 Hz, 2 H) 7.82 (s, 1 H) 7.41 (d, J=8.56 Hz, 1 H) 6.91 (d, J=8.56 Hz, 2 H) 5.38 (s, 2 H) 4.16 (q, j=7.01 Hz, 2 H) 3.79 (s, 3 H) 3.73 (br. s., 2 H) 3.19 (br. s., 2 H) 2.81 (s, 6 H) 1.44 (t, J=6.85 Hz, 3 H); ES-LCMS m/z: 654.2 (M+H).

Step 3: N-(2-(dimethylamino)ethyl)-3-(3-(2-(5-ethoxy-6-oxo-1,6-dihydropyridin-3-yl)-pyrimidin-5-yl)ureido)-5-(trifluoromethyl)benzamide

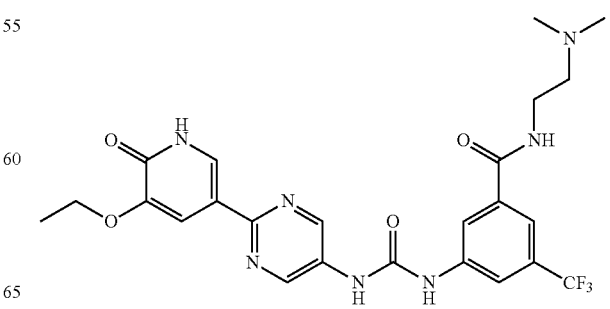

To a solution of N-(2-(dimethylamino)ethyl)-3-(3-(2-(5-ethoxy-6-((4-methoxybenzyl)-oxy)pyridin-3-yl)pyrimidin-5-yl)ureido)-5-(trifluoromethyl)benzamide (60 mg, 0.092 mmol) in DCM (5 mL) was added TFA (0.141 mL, 1.836 mmol). The mixture was stirred at 25° C. for 1 hr. The mixture was concentrated to give the crude product, which was purified by preparative HPLC (Column Phenomenex Synergi C18 250*21.2 mm*4 um Condition 0.05% HCl-ACN Begin B 15 End B 45 Gradient Time (min): 10 100% B Hold Time (min) 3 FlowRate (ml/min) 25) to afford the product N-(2-(dimethylamino)ethyl)-3-(3-(2-(5-ethoxy-6-oxo-1,6-dihydropyridin-3-yl)pyrimidin-5-yl)ureido)-5-(trifluoromethyl)benzamide dihydrochloride (7.77 mg, 0.013 mmol, 14.0% yield) as a yellow solid: $^1$H NMR (400 MHz, DMSO-d$_6$): δ11.93 (brs, 1H), 9.83 (s, 1H), 9.54 (s, 1H), 8.91 (s, 2H), 8.18 (s, 1H), 8.12 (s, 1H), 7.90 (brs., 1H), 7.85 (s, 1H), 7.58 (d, J=2.01 Hz, 1H), 4.03 (q, J=7.19 Hz, 2H), 3.63 (d, J=5.52 Hz, 2H), 3.27 (brs, 2H), 2.84 (s, 6H), 1.36 (t, J=6.90 Hz, 3H); ES-LCMS m/z 534.1 (M+H).

EXAMPLE 190

1-(4-((Dimethylamino)methyl)-2-fluoro-5-(trifluoromethyl)phenyl)-3-(2-(5-ethoxy-6-oxo-1,6-dihydropyridin-3-yl)-4-methylpyrimidin-5-yl)urea dihydrochloride

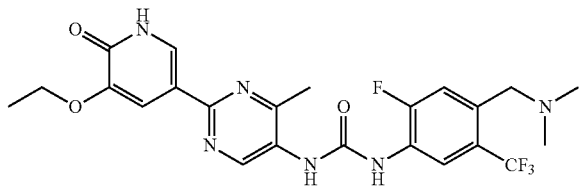 [SMILES: CCOc1cc(-c2ncc(NC(=O)Nc3cc(C(F)(F)F)c(CN(C)C)cc3F)c(C)n2)c[nH]c1=O]

Step 1: 1-(4-((Dimethylamino)methyl)-2-fluoro-5-(trifluoromethyl)phenyl)-3-(2-(5-ethoxy-6-((4-methoxybenzyl)oxy)pyridin-3-yl)-4-methylpyrimidin-5-yl)urea

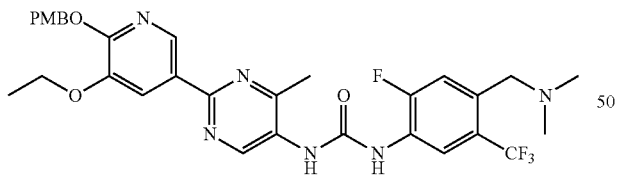

To a solution of 2-(5-ethoxy-6-((4-methoxybenzyl)oxy)pyridin-3-yl)-4-methylpyrimidine-5-carboxylic acid (200 mg, 0.506 mmol), diphenyl phosphorazidate (209 mg, 0.759 mmol) and Et$_3$N (0.106 mL, 0.759 mmol) in 1,4-dioxane (20 mL) was added diphenyl phosphorazidate (209 mg, 0.759 mmol) under a N$_2$ atmosphere. The resulting mixture was stirred at 70° C. for 18 hrs. LCMS analysis showed the starting material disappeared. The solvent was removed in vacuo. The residue was purified by preparative TLC (DCM/MeOH=10/1, R$_f$=0.3) to yield a yellow solid of 1-(4-((dimethylamino)methyl)-2-fluoro-5-(trifluoromethyl)phenyl)-3-(2-(5-ethoxy-6-((4-methoxybenzyl)oxy)pyridin-3-yl)-4-methylpyrimidin-5-yl)urea (100 mg, 0.151 mmol, 29.9% yield): $^1$H NMR (400 MHz, CD$_3$OD) δ8.68 (br. s., 1H), 8.09 (br. s., 1H), 7.41 (d, J=8.8 Hz, 2H), 7.30 (s, 1H), 7.04 (br. s., 2H), 6.92 (d, J=8.8 Hz, 2H), 5.39 (s, 2H), 4.17 (d, J=6.8 Hz, 2H), 3.83-3.74 (m, 5H), 2.59 (s, 3H), 2.31 (s, 6H), 1.44 (t, J=6.9 Hz, 3H); ES-LCMS m/z: 629.2 (M+H); 509.1 (M+H-PMB).

Step 2: 2-(4-(4-Ethoxy-6-oxo-1,6-dihydropyridin-3-yl)-2-fluorophenyl)-N-(3-(1-methylpyrrolidin-3-yl)-5-(trifluoromethyl)phenyl)acetamide

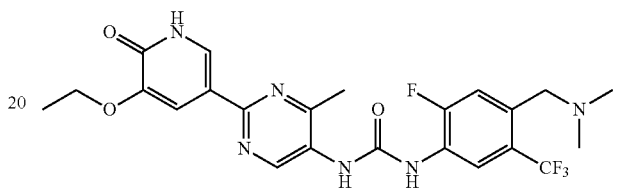

A solution of 1-(4-((dimethylamino)methyl)-2-fluoro-5-(trifluoromethyl)phenyl)-3-(2-(5-ethoxy-6-((4-methoxybenzyl)oxy)pyridin-3-yl)-4-methylpyrimidin-5-yl)urea (100 mg, 0.159 mmol) in 2,2,2-trifluoroacetic acid, dichloromethane (solvate) (3 mL, 10%) was stirred at 25° C. for 0.5 hr. LCMS analysis showed the starting material disappeared. The solvent was removed in vacuo. The crude product was purified by preparative HPLC (Column: Gemini 150*25 mm*5 um/Mobile phase A: Water+0.1% HCl/Mobile phase B: MeCN/Flowrate: 25 mL/min/Gradient Profile Description: 5-35 (B %)) to yield a yellow solid of 1-(4-((dimethylamino)methyl)-2-fluoro-5-(trifluoromethyl)phenyl)-3-(2-(5-ethoxy-6-oxo-1,6-dihydropyridin-3-yl)-4-methylpyrimidin-5-yl)urea dihydrochloride (40 mg, 0.069 mmol, 43.2% yield): $^1$H NMR (400 MHz, CD$_3$OD) δ 9.22-9.17 (m, 1H), 8.92 (d, J=7.6 Hz, 1H), 8.12 (d, J=1.5 Hz, 1H), 7.90 (d, J=2.0 Hz, 1H), 7.68 (d, J=11.5 Hz, 1H), 4.51 (s, 2H), 4.21-4.15 (m, 2H), 2.97 (s, 6H), 2.61 (s, 3H), 1.51 (t, J=7.0 Hz, 3H); ES-LCMS m/z: 509.1 (M+H).

EXAMPLE 191

1-(2-(4-Ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea trihydrochloride

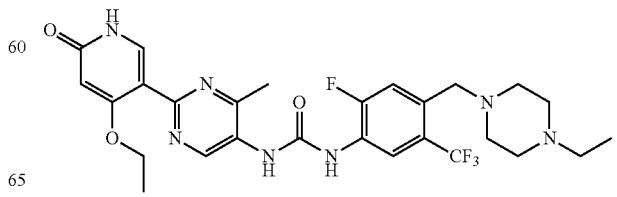

Step 1: 1-(2-(4-Ethoxy-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea

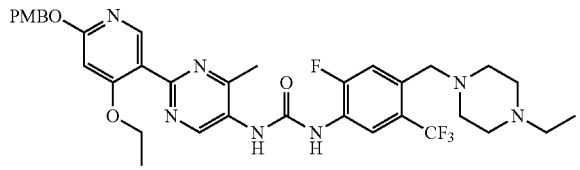

To a mixture of 2-(4-ethoxy-6-((4-methoxybenzyl)oxy)pyridin-3-yl)-4-methylpyrimidine-5-carboxylic acid (200 mg, 0.455 mmol) in toluene (30 mL) was added triethylamine (92 mg, 0.910 mmol), DPPA (188 mg, 0.683 mmol) and 4-((4-ethylpiperazin-1-yl)methyl)-2-fluoro-5-(trifluoromethyl)aniline (164 mg, 0.455 mmol). The mixture was stirred at 120° C. for 12 hours. The solvent was removed in vacuo. The residue was purified by column chromatography (DCM/MeOH=10/1, $R_f$=0.4) to yield an off-white solid of 1-(2-(4-ethoxy-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea (200 mg, 0.172 mmol, 37.8% yield): $^1$H NMR (400 MHz, METHANOL-$d_4$) δ9.25 (s, 1H), 8.67-8.61 (m, 2H), 8.27 (s, 1H), 7.60 (dd, J=5.7, 12.3 Hz, 2H), 7.46-7.37 (m, 2H), 7.34 (br. s., 1H), 4.94 (br. s., 2H), 4.62 (br. s., 2H), 4.17-4.11 (m, 2H), 3.70 (br. s., 3H), 3.20-3.00 (m, 8H), 2.65-2.53 (m, 5H), 1.40-1.35 (m, 3H), 1.31-1.28 (m, 3H); ES-LCMS m/z 698.2 (M+H).

Step 2: 1-(2-(4-Ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea trihydrochloride

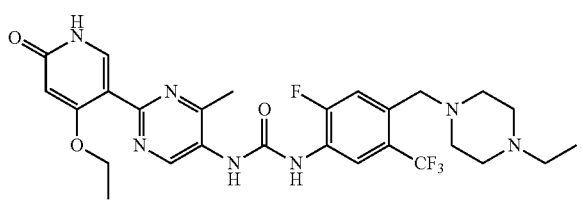 [SMILES: CCOc1cc(=O)[nH]cc1-c1ncc(NC(=O)Nc2cc(C(F)(F)F)c(CN3CCN(CC)CC3)cc2F)c(C)n1]

To a solution of 1-(2-(4-ethoxy-6-((4-methoxybenzyl)oxy)pyridin-3-yl)-4-methylpyrimidin-5-yl)-3-(4-((4-ethylpiperazin-1-yl)methyl)-2-fluoro-5-(trifluoromethyl)phenyl)urea (200 mg, 0.263 mmol) in dichloromethane (3 mL) was added TFA (10% in DCM, 2 mL, 2.60 mmol). The mixture was stirred at 25° C. for 1 hour. The solvent was removed in vacuo. The residue was purified by preparative HPLC (Instrument: AA/Column: Phenomenex Synergi C18 250*21.2 mm*4 um/Mobile phase A: 0.05% HCl/Mobile phase B: MeCN/Flowrate: 25 ml/min/Run time: 10 min/Gradient Profile Description: 14-44 (B %)) and dried by lyophilization to yield an off white solid of 1-(2-(4-ethoxy-6-oxo-1,6-dihydropyridin-3-yl)-4-methylpyrimidin-5-yl)-3-(4-((4-ethylpiperazin-1-yl)methyl)-2-fluoro-5-(trifluoromethyl)phenyl)urea trihydrochloride (70.1 mg, 0.098 mmol, 37.2% yield): $^1$H NMR (400 MHz, METHANOL-$d_4$) δ9.64 (s, 1H), 8.79 (d, J=7.5 Hz, 1H), 8.55 (s, 1H), 7.89 (d, J=11.9 Hz, 1H), 6.22 (s, 1H), 4.41 (q, J=6.9 Hz, 2H), 4.19 (brs, 2H), 3.70 (brs, 4H), 3.42 (dd, J=2.4, 6.8 Hz, 2H), 3.20-2.97 (m, J=15.0 Hz, 4H), 2.82 (s, 3H), 1.51 (t, J=6.8 Hz, 3H), 1.38 (t, J=7.1 Hz, 3H); ES-LCMS m/z 578.2 (M+H).

EXAMPLE 192

Crystalline anhydrous free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A free base anhydrate)

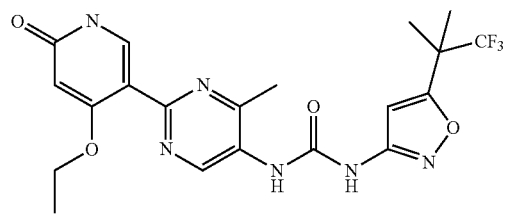 [SMILES: CCOc1cc(=O)[nH]cc1-c1ncc(NC(=O)Nc2cc(C(C)(C)C(F)(F)F)on2)c(C)n1]

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (493.5 mg) in 12.5 mL of acetone was stirred overnight while cycling the temperature between 40° C. and 5° C. Seeds of Compound A free base anhydrate were added at 5° C. The solids were isolated by vacuum filtration and dried overnight in a vacuum oven at 40° C. to give the title compound as a crystalline solid. Compound A free base anhydrate was physically stable when exposed to 75% RH for five days.

Seed Preparation:

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in acetone was stirred for 3 days while cycling the temperature between 40° C. and 5° C. The solids were isolated by vacuum filtration and dried to give the title compound as a crystalline solid.

The X-ray powder diffraction (XRPD) pattern of Compound A free base anhydrate is shown in FIG. 1 and a summary of the diffraction angles and d-spacings is given in Table I below. The XRPD analysis was conducted on a PANanalytical X'Pert Pro Diffractometer on Si zero-background wafers. The acquisition conditions included: Cu $K_α$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE I

| Diff. Angle [°2θ] | d-spacing [Å] |
| --- | --- |
| 2.2002 | 40.15547 |
| 4.8974 | 18.04439 |
| 5.4534 | 16.20567 |
| 5.7331 | 15.41569 |
| 11.7654 | 7.52194 |
| 11.9049 | 7.43406 |
| 12.8119 | 6.90976 |
| 12.8788 | 6.87403 |
| 13.0574 | 6.78042 |
| 14.3385 | 6.17733 |

TABLE I-continued

| Diff. Angle [°2θ] | d-spacing [Å] |
| --- | --- |
| 16.1093 | 5.50207 |
| 16.6104 | 5.33721 |
| 17.1409 | 5.1732 |
| 17.2394 | 5.14387 |
| 21.1927 | 4.18895 |
| 21.2755 | 4.17282 |
| 21.9468 | 4.04669 |
| 22.0164 | 4.03404 |
| 22.6845 | 3.91673 |
| 22.8172 | 3.89425 |
| 23.1382 | 3.84094 |
| 25.3332 | 3.5129 |
| 25.4056 | 3.51175 |

Figure 2:
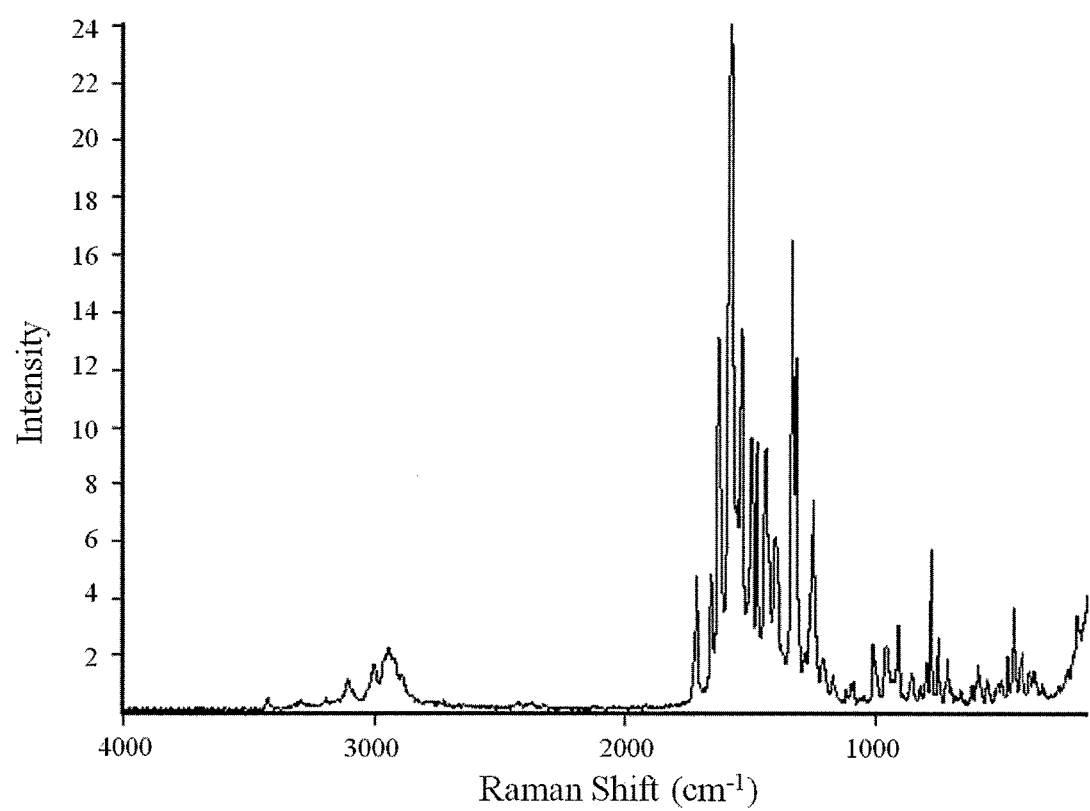
FIG. 2 shows a Raman spectrum of hydrate 1 of Compound A free base anhydrate.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A free base anhydrate is shown in FIG. 2 with major peaks observed at 187.4, 360.1, 409.4, 441.9, 466.5, 585.1, 707.5, 742.7, 772.7, 790.0, 850.8, 904.4, 950.3, 1005.2, 1247.3, 1313.6, 1329.7, 1396.8, 1435.0, 1468.6, 1491.7, 1530.2, 1576.5, 1622.9, 1653.0, 1710.0, 2939.9 cm$^{-1}$.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 3. The experiments were conducted using a heating rate of 15° C./min in a crimped aluminum pan. The DSC thermogram of Compound A free base anhydrate exhibited a sharp endotherm with an onset temperature of 251.95° C., a peak temperature about 256.30° C., and enthalpy of 214.7 J/g. A person skilled in the art would recognize that the onset temperature, peak temperature, and enthalpy of the endotherm may vary depending on the experimental conditions.

The thermogravimetric analysis (TGA) thermogram of the title compound was recorded on a TA Instruments Q500 Thermogravimetric Analyzer and is shown in FIG. 4. The experiments were conducted with 40 mL/min N$_2$ flow and a heating rate of 15° C./min in an aluminum pan. The TGA thermogram of Compound A free base anhydrate exhibited negligible weight loss in the temperature range of 25° C. to 150° C. and a thermal decomposition onset temperature of 243.34° C.

EXAMPLE 193

First crystalline hydrate of the free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A free base hydrate 1)

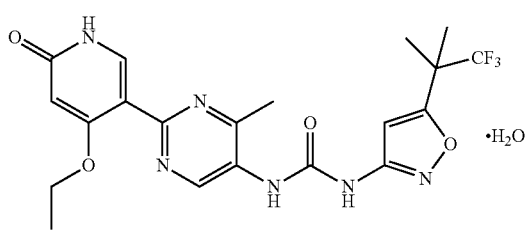

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in water was stirred for 3 days while cycling the temperature between 40° C. and 5° C. The solids were isolated by vacuum filtration, air dried for 1 h, and then dried overnight in a vacuum oven at 40° C. to give the title compound as a crystalline solid.

Figure 5:
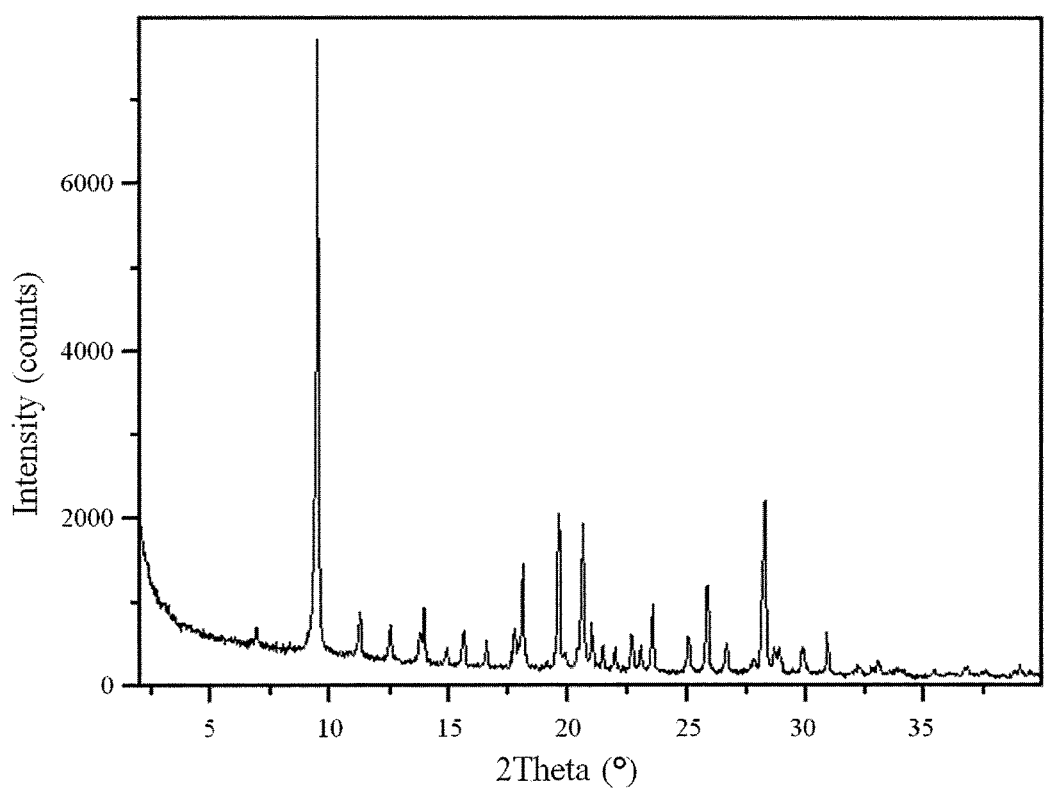
FIG. 5 shows an X-ray powder diffraction pattern of Compound A free base hydrate 1.

The X-ray powder diffraction (XRPD) pattern of Compound A free base hydrate 1 is shown in FIG. 5 and a summary of the diffraction angles and d-spacings is given in Table II below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE II

| Diff. Angle [°2θ] | d-spacing [Å] |
| --- | --- |
| 6.9748 | 12.67381 |
| 9.525 | 9.28552 |
| 11.2921 | 7.83608 |
| 13.8118 | 6.41172 |
| 13.9878 | 6.33141 |
| 14.9163 | 5.93935 |
| 15.641 | 5.66574 |
| 16.5918 | 5.34315 |
| 17.7915 | 4.98547 |
| 17.9704 | 4.93624 |
| 18.138 | 4.89099 |
| 19.6655 | 4.51439 |
| 19.9037 | 4.45722 |
| 20.4514 | 4.33908 |
| 20.6671 | 4.29427 |
| 21.0489 | 4.21722 |
| 21.2526 | 4.17726 |
| 21.4997 | 4.12982 |
| 22.0174 | 4.03387 |
| 22.7117 | 3.9121 |
| 23.0855 | 3.84959 |
| 23.5817 | 3.7697 |
| 25.0939 | 3.54585 |
| 25.8729 | 3.44082 |
| 26.6761 | 3.33903 |
| 27.8509 | 3.20079 |
| 28.1874 | 3.16334 |
| 28.2831 | 3.15285 |
| 28.7022 | 3.10776 |
| 28.9044 | 3.08648 |
| 29.8904 | 2.98687 |
| 29.9607 | 2.98743 |
| 30.9426 | 2.88765 |
| 31.0264 | 2.88721 |
| 33.0866 | 2.70527 |

Figure 6:
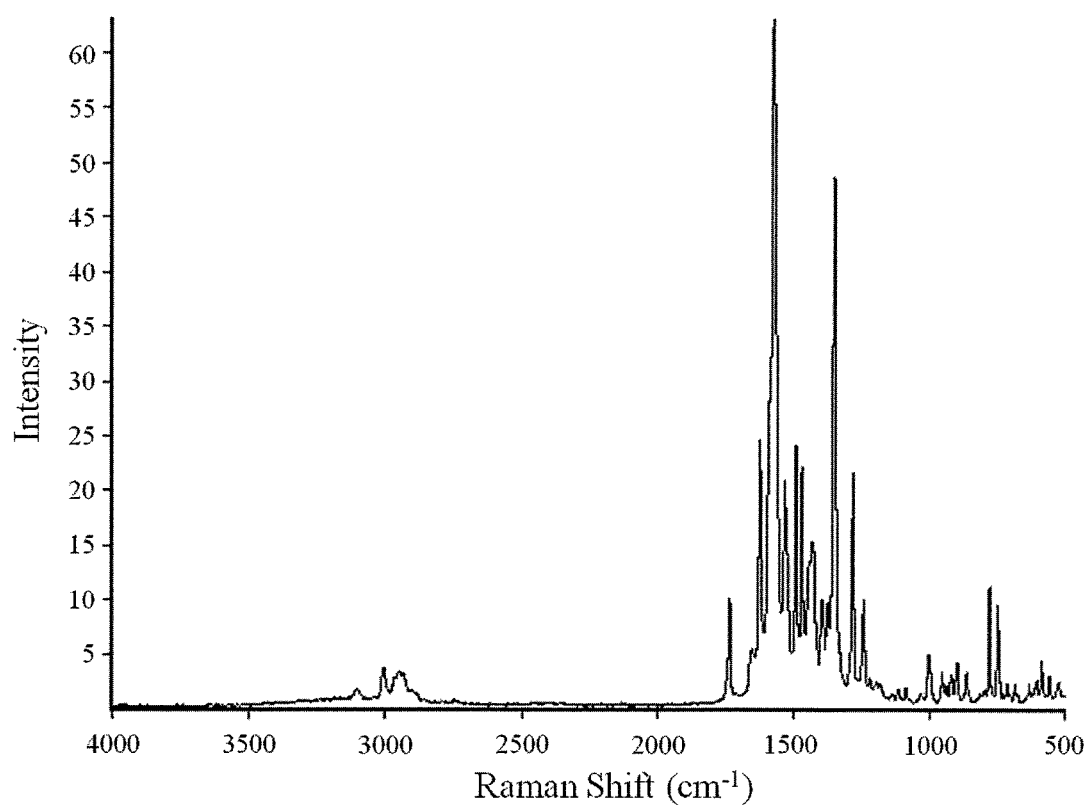
FIG. 6 shows a Raman spectrum of Compound A free base hydrate 1.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A free base hydrate 1 is shown in FIG. 6 with major peaks observed at 582.9, 744.4, 776.1, 859.7, 896.0, 999.8, 1239.7, 1278.0, 1345.9, 1372.5, 1392.1, 1428.9, 1468.0, 1488.3, 1529.6, 1572.1, 1621.2, 1732.7, 3000.4 cm$^{-1}$.

Figure 7:
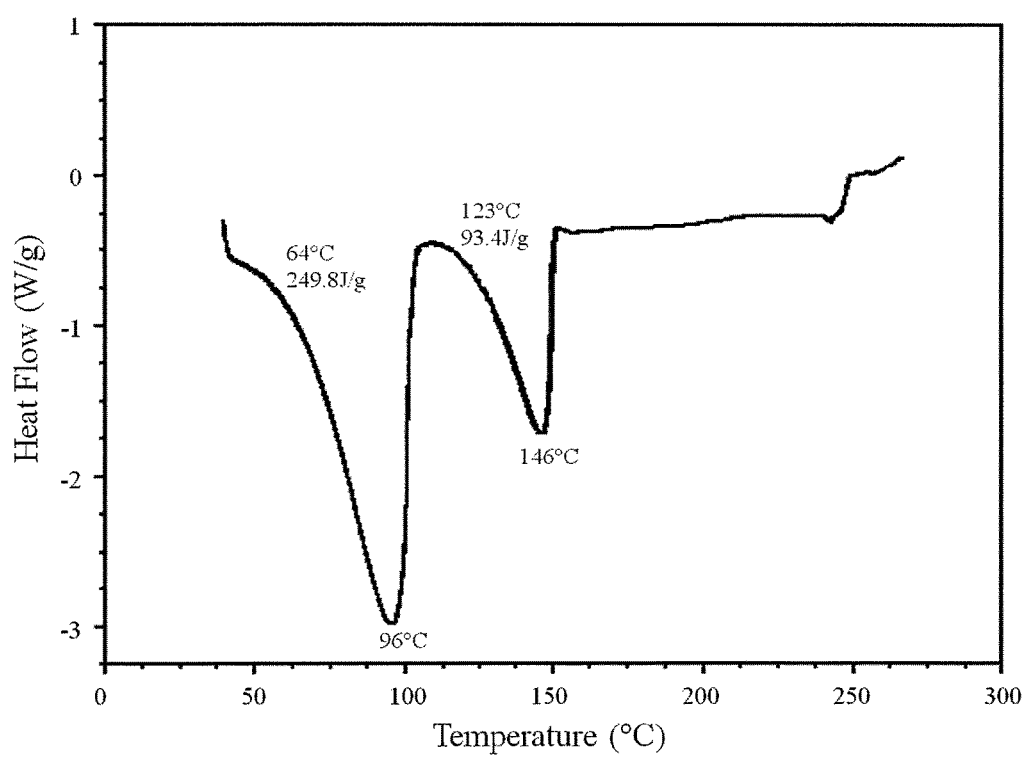
FIG. 7 shows a differential scanning calorimetry trace of Compound A free base hydrate 1.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 7. The experiments were conducted using a heating rate of 15° C./min in a crimped aluminum pan. The DSC thermogram of Compound A free base hydrate 1 exhibited a first endotherm with an onset temperature of about 64° C., a peak temperature about 96° C., and enthalpy of 249.8 J/g, followed by a second endotherm with an onset temperature of about 123° C., a peak temperature about 146° C., and enthalpy of 93.4 J/g. A person skilled in the art would recognize that the onset temperature, peak temperature, and enthalpy of the endotherm may vary depending on the experimental conditions.

Figure 8:
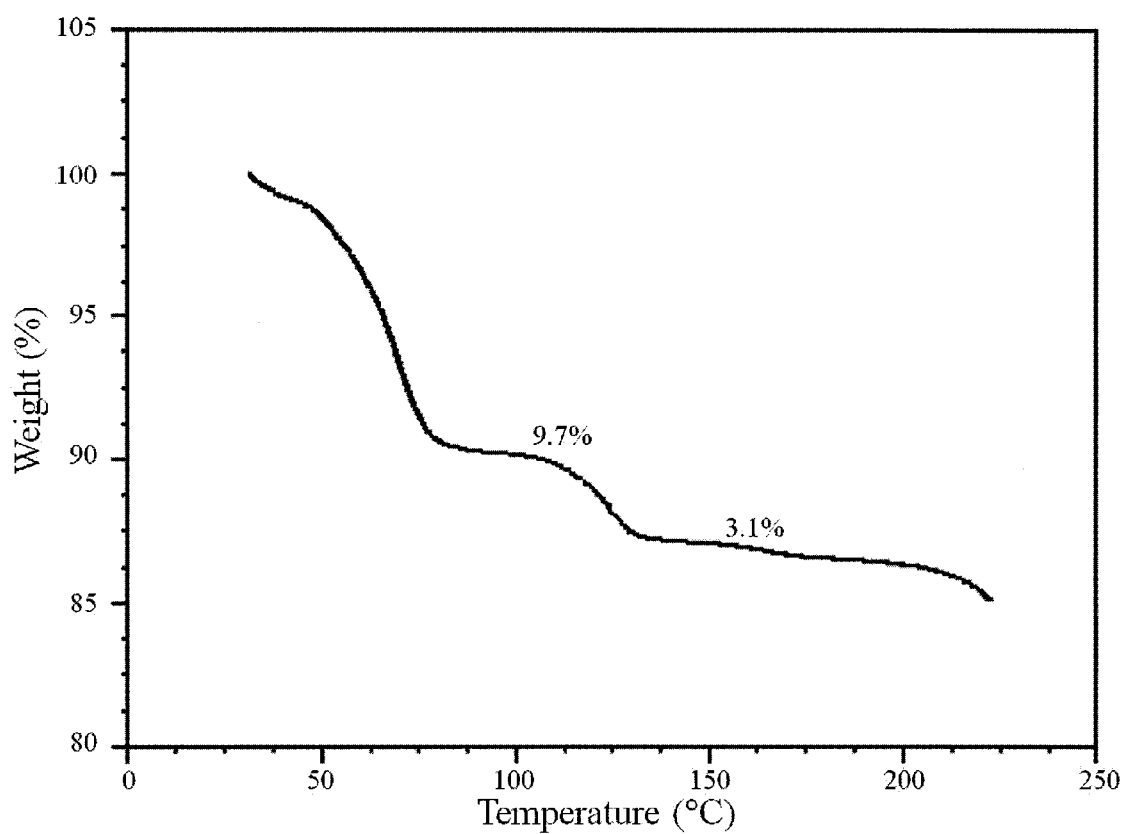
FIG. 8 shows a thermogravimetric analysis trace of Compound A free base hydrate 1.

The thermogravimetric analysis (TGA) thermogram of the title compound was recorded on a TA Instruments Q500 Thermogravimetric Analyzer and is shown in FIG. 8. The experiments were conducted with 40 mL/min $N_2$ flow and a heating rate of 15° C./min in an aluminum pan. The TGA thermogram of Compound A free base hydrate 1 exhibited two steps of weight loss events observed prior to the final thermal decomposition. The first weight loss event takes place in the temperature range of 30° C. to 100° C. with a weight loss of about 9.7%. The second weight loss event takes place in the temperature range of 100° C. to 150° C. with a weight loss of about 3.1%.

EXAMPLE 194

Second crystalline hydrate of the free base of 1-(2-(4-Ethoxy-6-oxo-1,6-dihydropyridin-3-yl)-4-methyl-pyrimidin-5-yl)-3-(5-(1,1,1-trifluoro-2-methylpropan-2-yl)isoxazol-3-yl)urea (Compound A free base hydrate 2)

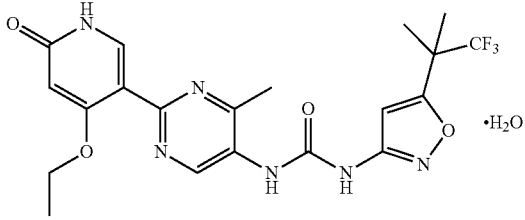

·$H_2O$

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in ethanol was stirred for 3 days while cycling the temperature between 40° C. and 5° C. The solids were isolated by vacuum filtration, air dried for 1 h, and then dried overnight in a vacuum oven at 40° C. to give the title compound as a crystalline solid.

Figure 9:
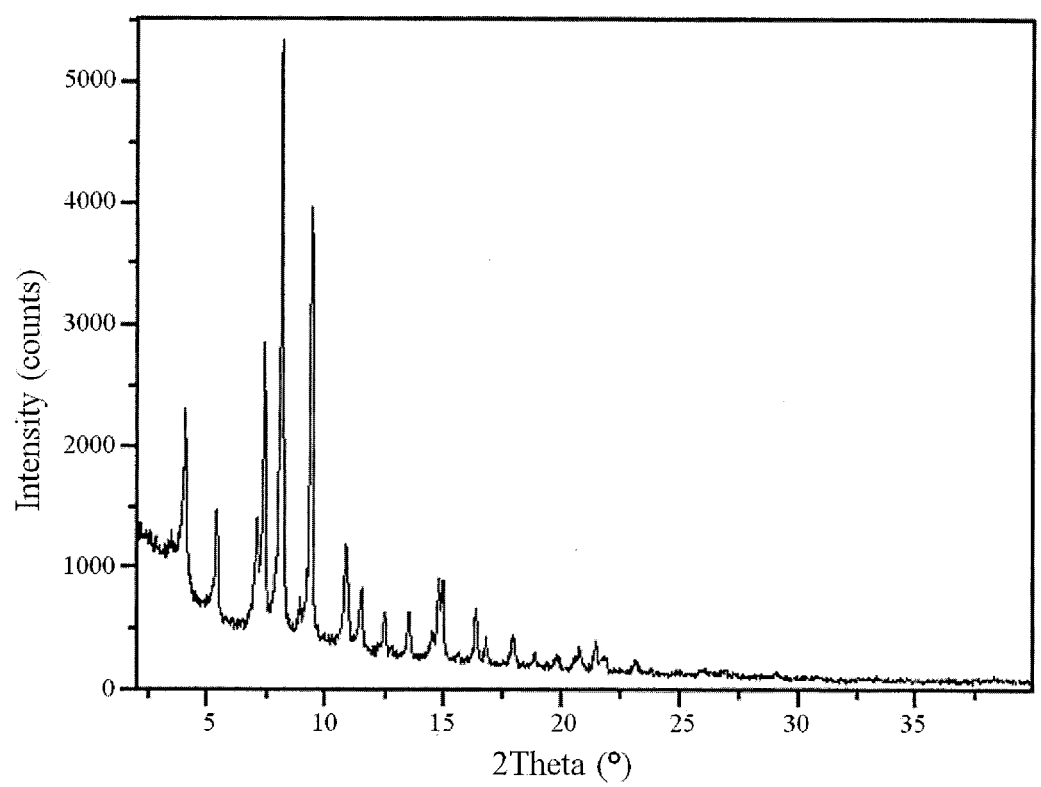
FIG. 9 shows an X-ray powder diffraction pattern of Compound A free base hydrate 2.

The X-ray powder diffraction (XRPD) pattern of Compound A free base hydrate 2 is shown in FIG. 9 and a summary of the diffraction angles and d-spacings is given in Table III below. The XRPD analysis was conducted on a PANanalytical X'Pert Pro Diffractometer on Si zero-background wafers. The acquisition conditions included: Cu $K_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE III

| Diff. Angle [°2θ] | d-spacing [Å] |
|---|---|
| 3.3674 | 26.23886 |
| 3.5146 | 25.14004 |
| 4.0838 | 21.63708 |
| 5.4154 | 16.31934 |
| 6.8354 | 12.93207 |
| 7.0961 | 12.4575 |
| 7.4458 | 11.87319 |
| 8.1748 | 10.81592 |
| 8.9271 | 9.90602 |
| 9.4362 | 9.37273 |
| 10.8771 | 8.1341 |
| 10.9718 | 8.06415 |
| 11.5221 | 7.6802 |
| 12.5191 | 7.07069 |
| 13.5447 | 6.53751 |
| 14.5457 | 6.0898 |
| 14.8113 | 5.98119 |
| 14.9639 | 5.92055 |
| 16.3869 | 5.4095 |
| 16.6982 | 5.30934 |
| 16.8225 | 5.27037 |
| 17.9586 | 4.93945 |
| 20.7756 | 4.27208 |
| 21.466 | 4.13623 |

Figure 10:
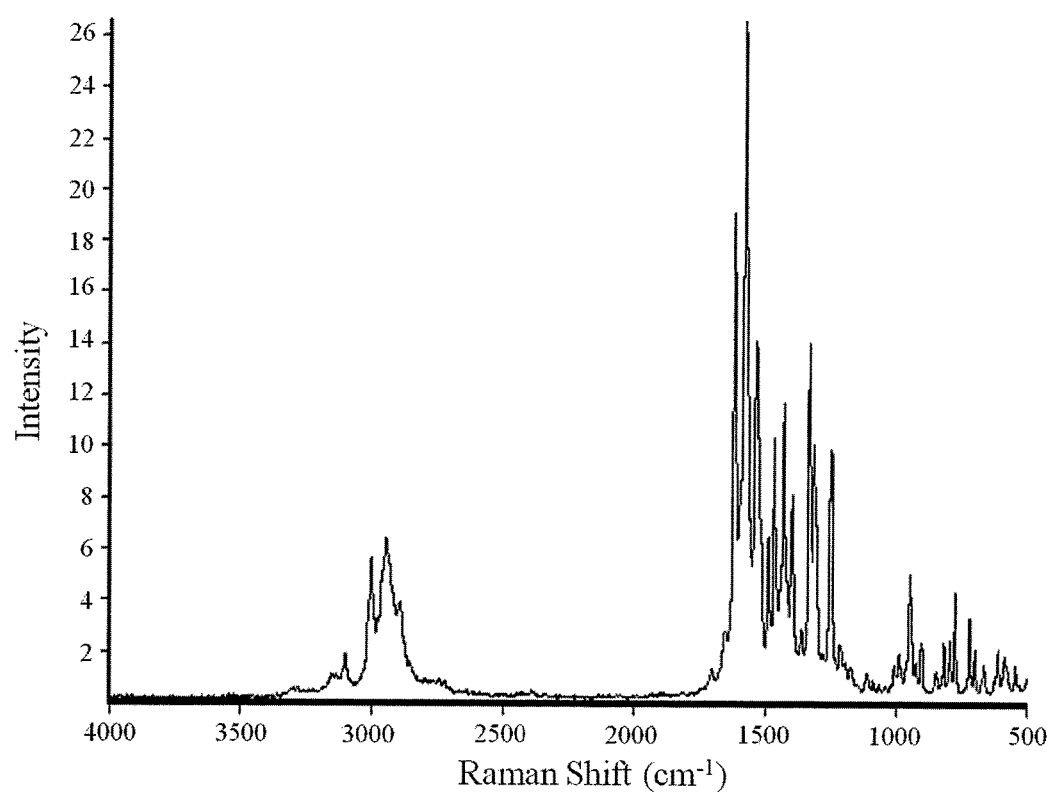
FIG. 10 shows a Raman spectrum of Compound A free base hydrate 2.

The Raman spectrum of the title compound was recorded on a Nicolet NXR 9650 FT-Raman Spectrometer, at 4 $cm^{-1}$ resolution with excitation from a Nd:YVO4 laser (λ=1064 nm). The Raman spectrum of Compound A free base hydrate 2 is shown in FIG. 10 with major peaks observed at 541.0, 579.9, 609.4, 664.3, 696.7, 719.2, 773.7, 792.4, 817.3, 901.9, 945.5, 987.5, 1211.1, 1246.6, 1312.2, 1331.9, 1362.2, 1398.1, 1428.5, 1465.5, 1487.2, 1535.5, 1579.1, 1617.4, 2943.7, 2998.9, 3096.1 $cm^{-1}$.

Figure 11:
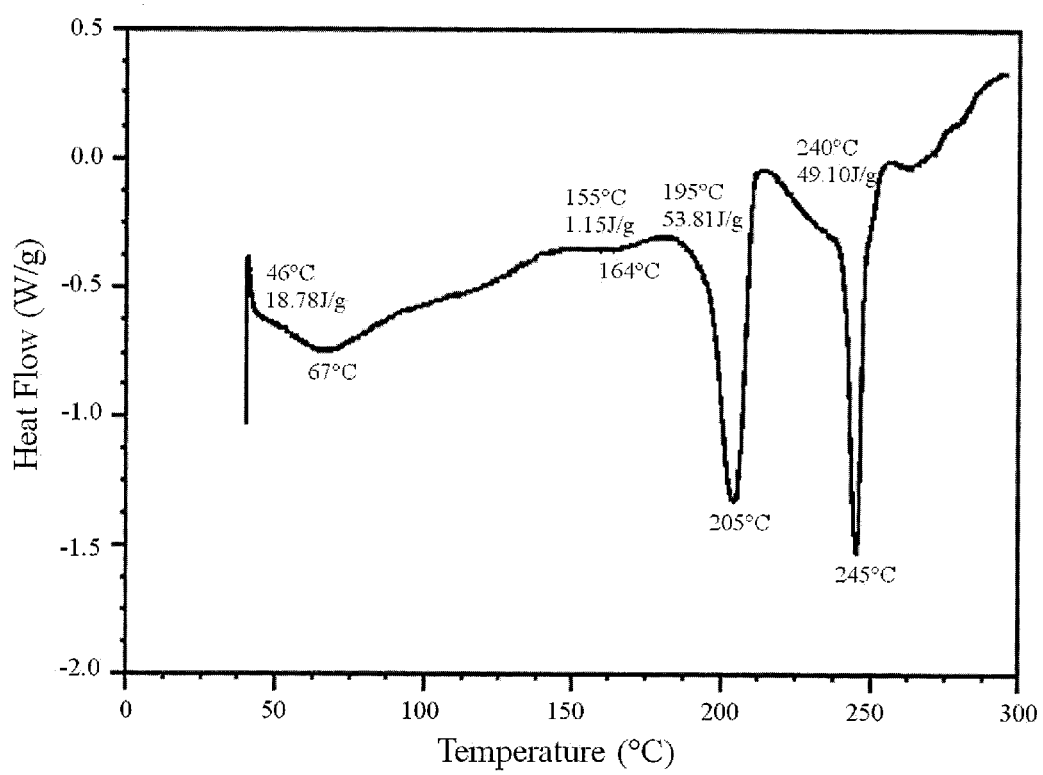
FIG. 11 shows a differential scanning calorimetry trace of Compound A free base hydrate 2.

The differential scanning calorimetry (DSC) thermogram of the title compound was recorded on a TA Instruments Q100 Differential Scanning calorimeter equipped with an autosampler and a refrigerated cooling system under 40 mL/min $N_2$ purge and is shown in FIG. 11. The experiments were conducted using a heating rate of 15° C./min in a crimped aluminum pan. The DSC thermogram of Compound A free base hydrate 2 exhibited a first endotherm with an onset temperature of about 46° C., a peak temperature about 67° C., and enthalpy of 18.78 J/g, followed by a second endotherm with an onset temperature of about 155° C., a peak temperature about 164° C., and enthalpy of 1.15 J/g, followed by a third endotherm with an onset temperature of about 195° C., a peak temperature about 205° C., and enthalpy of 53.81 J/g, followed by a fourth endotherm with an onset temperature of about 240° C., a peak temperature about 245° C., and enthalpy of 49.10 J/g. A person skilled in the art would recognize that the onset temperature, peak temperature, and enthalpy of the endotherm may vary depending on the experimental conditions.

Figure 12:
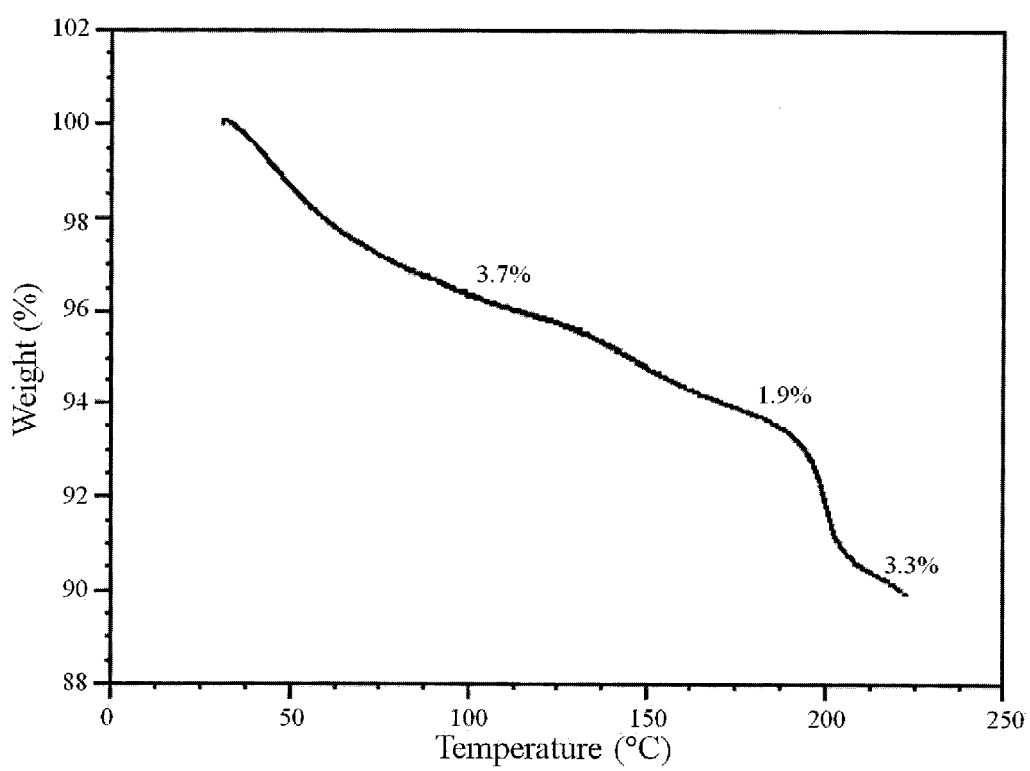
FIG. 12 shows a thermogravimetric analysis trace of Compound A free base hydrate 2.

The thermogravimetric analysis (TGA) thermogram of the title compound was recorded on a TA Instruments Q500 Thermogravimetric Analyzer and is shown in FIG. 12. The experiments were conducted with 40 mL/min $N_2$ flow and a heating rate of 15° C./min in an aluminum pan. The TGA thermogram of Compound A free base hydrate 2 exhibited multiple weight loss events observed prior to the final thermal decomposition. The first weight loss event takes place in the temperature range of 25° C. to 100° C. with a weight loss of about 3.7%. The second weight loss event takes place in the temperature range of 130° C. to 175° C. with a weight loss of about 1.9%. The final weight loss event takes place in the temperature range of 175° C. to 210° C.

with a weight loss of about 3.3%. Thermal decomposition was not observed below 225° C.

EXAMPLE 195

Third crystalline hydrate of the free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A free base hydrate 3)

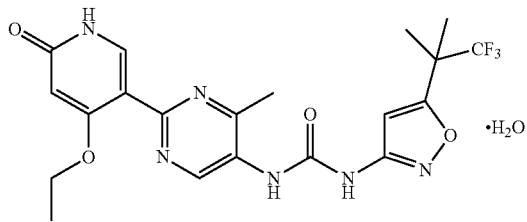

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in 9:1 acetone:water was stirred for 3 days while cycling the temperature between 40° C. and 5° C. The solids were isolated by vacuum filtration, air dried for 1 h, and then dried overnight in a vacuum oven at 40° C. to give the title compound as a crystalline solid.

Figure 13:
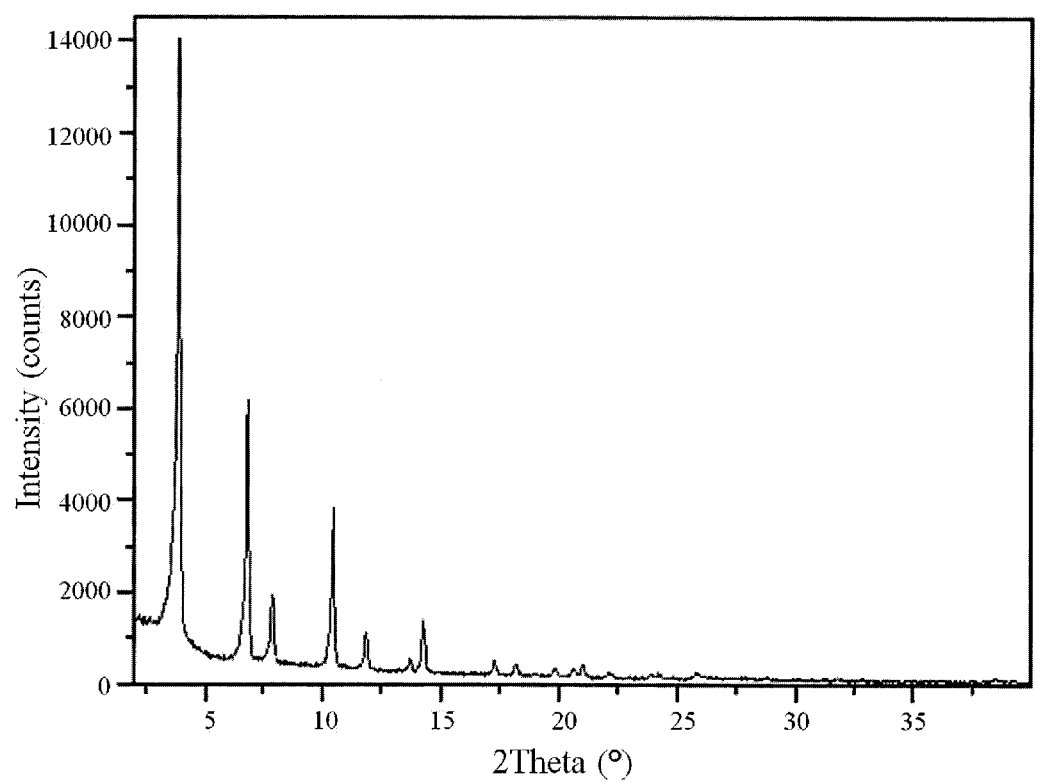
FIG. 13 shows an X-ray powder diffraction pattern of Compound A free base hydrate 3.

The X-ray powder diffraction (XRPD) pattern of Compound A free base hydrate 3 is shown in FIG. 13 and a summary of the diffraction angles and d-spacings is given in Table IV below. The XRPD analysis was conducted on a PANanalytical X'Pert Pro Diffractometer on Si zero-background wafers. The acquisition conditions included: Cu $K_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE IV

| Diff. Angle [°2θ] | d-spacing [Å] |
| --- | --- |
| 2.2624 | 39.05161 |
| 2.4655 | 35.83471 |
| 2.8761 | 30.71939 |
| 3.0614 | 28.86087 |
| 3.9161 | 22.56305 |
| 4.2514 | 20.7847 |
| 6.8171 | 12.96661 |
| 7.878 | 11.22267 |
| 10.4403 | 8.47346 |
| 11.8539 | 7.46597 |
| 13.6955 | 6.4659 |
| 14.2661 | 6.20851 |
| 17.2638 | 5.13238 |
| 17.3244 | 5.1273 |
| 18.1874 | 4.87377 |
| 19.8682 | 4.46511 |
| 20.6353 | 4.30083 |
| 20.9611 | 4.23469 |
| 21.0409 | 4.21883 |

Figure 14:
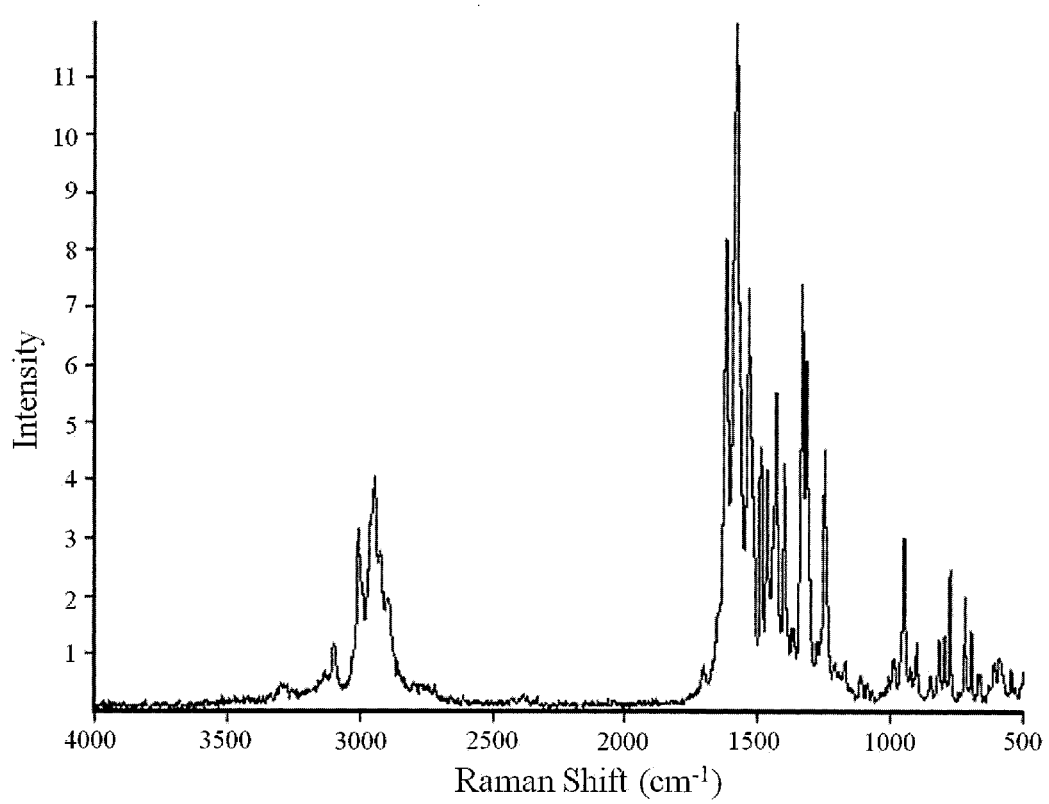
FIG. 14 shows a Raman spectrum of Compound A free base hydrate 3.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A free base hydrate 3 is shown in FIG. 14 with major peaks observed at 542.9, 587.4, 671.6, 696.4, 719.1, 775.4, 794.7, 817.6, 900.8, 949.6, 988.4, 1246.5, 1316.2, 1333.2, 1361.8, 1399.2, 1430.4, 1463.4, 1486.2, 1534.7, 1580.2, 1616.9, 2942.3, 3001.5, 3094.6 cm$^{-1}$.

Figure 15:
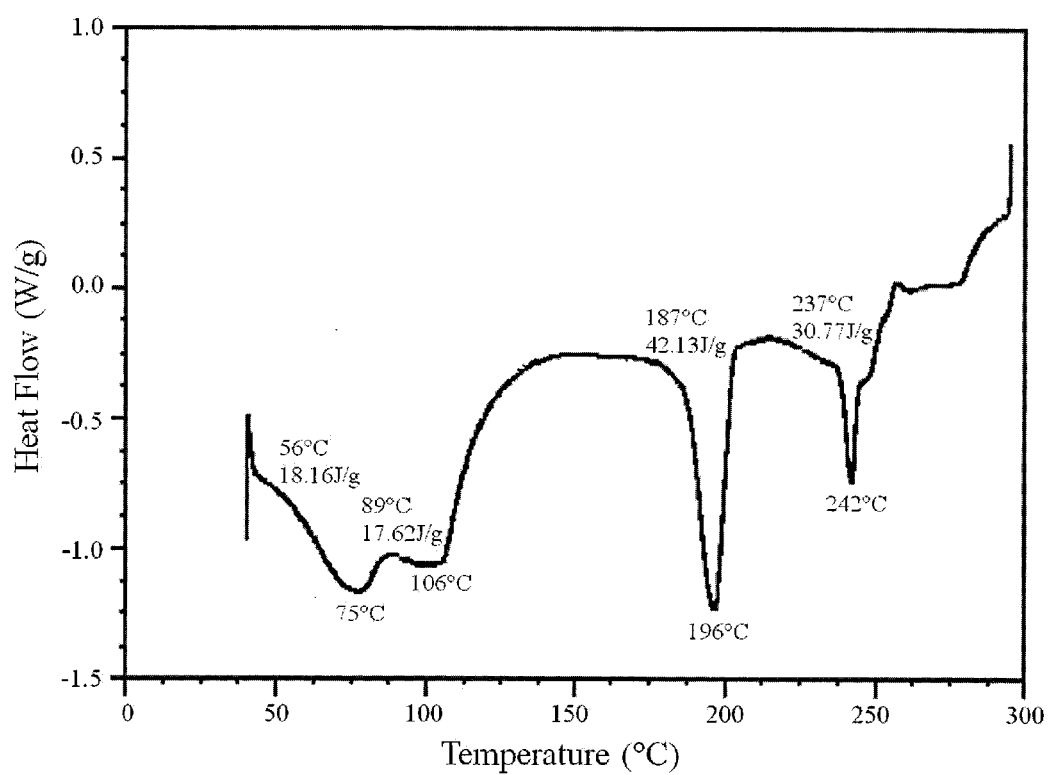
FIG. 15 shows a differential scanning calorimetry trace of Compound A free base hydrate 3.

The differential scanning calorimetry (DSC) thermogram of the title compound was recorded on a TA Instruments Q100 Differential Scanning calorimeter equipped with an autosampler and a refrigerated cooling system under 40 mL/min $N_2$ purge and is shown in FIG. 15. The experiments were conducted using a heating rate of 15° C./min in a crimped aluminum pan. The DSC thermogram of Compound A free base hydrate 3 exhibited a first endotherm with an onset temperature of about 56° C., a peak temperature about 75° C., and enthalpy of 18.16 J/g, followed by a second endotherm with an onset temperature of about 89° C., a peak temperature about 106° C., and enthalpy of 17.62 J/g, followed by a third endotherm with an onset temperature of about 187° C., a peak temperature about 196° C., and enthalpy of 42.13 J/g, followed by a fourth endotherm with an onset temperature of about 237° C., a peak temperature about 242° C., and enthalpy of 30.77 J/g. A person skilled in the art would recognize that the onset temperature, peak temperature, and enthalpy of the endotherm may vary depending on the experimental conditions.

Figure 16:
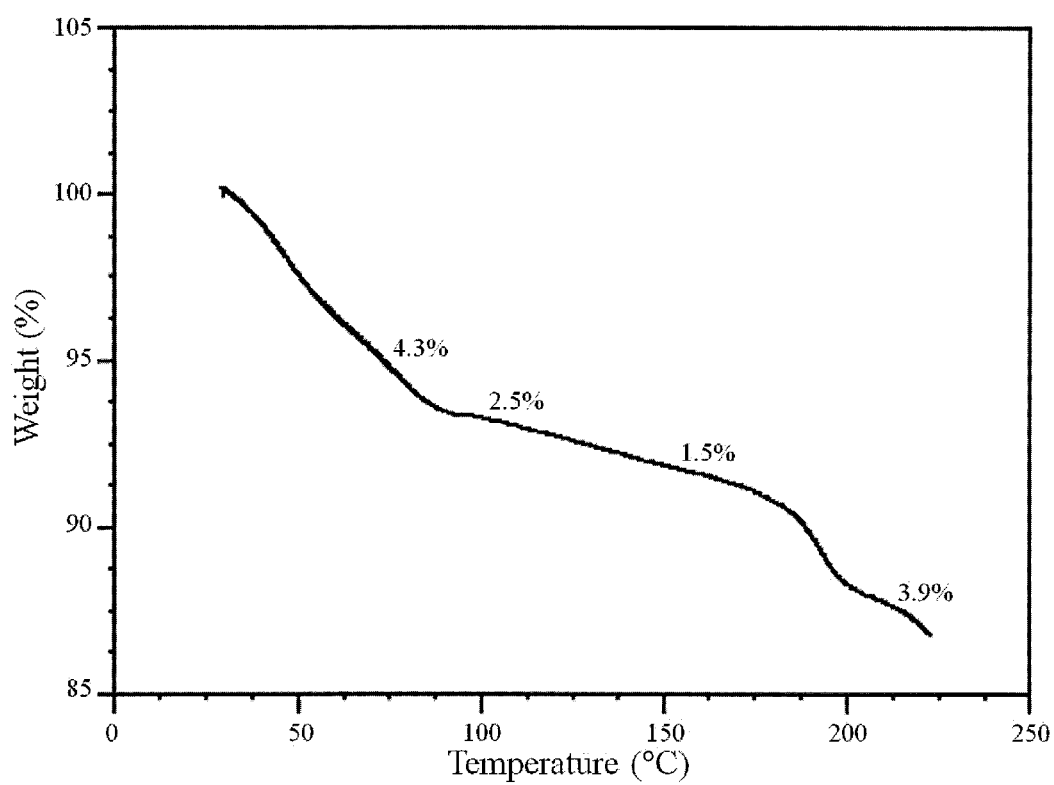
FIG. 16 shows a thermogravimetric analysis trace of Compound A free base hydrate 3.

The thermogravimetric analysis (TGA) thermogram of the title compound was recorded on a TA Instruments Q500 Thermogravimetric Analyzer and is shown in FIG. 16. The experiments were conducted with 40 mL/min $N_2$ flow and a heating rate of 15° C./min in an aluminum pan. The TGA thermogram of Compound A free base hydrate 3 exhibited multiple weight loss events observed prior to the final thermal decomposition. The first weight loss event takes place in the temperature range of 25° C. to 63° C. with a weight loss of about 4.3%. The second weight loss event takes place in the temperature range of 63° C. to 100° C. with a weight loss of about 2.5%. The third weight loss event takes place in the temperature range of 100° C. to 150° C. with a weight loss of about 1.5%. The final weight loss event takes place in the temperature range of 150° C. to 210° C. with a weight loss of about 3.9%. Thermal decomposition was not observed below 225° C.

EXAMPLE 196

Fourth crystalline hydrate of the free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A free base hydrate 4)

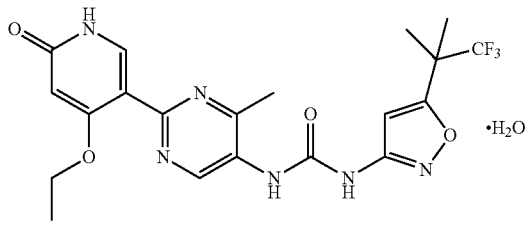

A suspension of 1-(2-(4-ethoxy-6-oxo-1,6-dihydropyridin-3-yl)-4-methylpyrimidin-5-yl)-3-(5-(1,1,1-trifluoro-2- methylpropan-2-yl)isoxazol-3-yl)urea in 2-methoxyethanol was stirred for 3 days while cycling the temperature between 40° C. and 5° C. The solids were isolated by vacuum filtration, air dried for 1 h, and then dried overnight in a vacuum oven at 40° C. to give the title compound as a crystalline solid.

Figure 17:
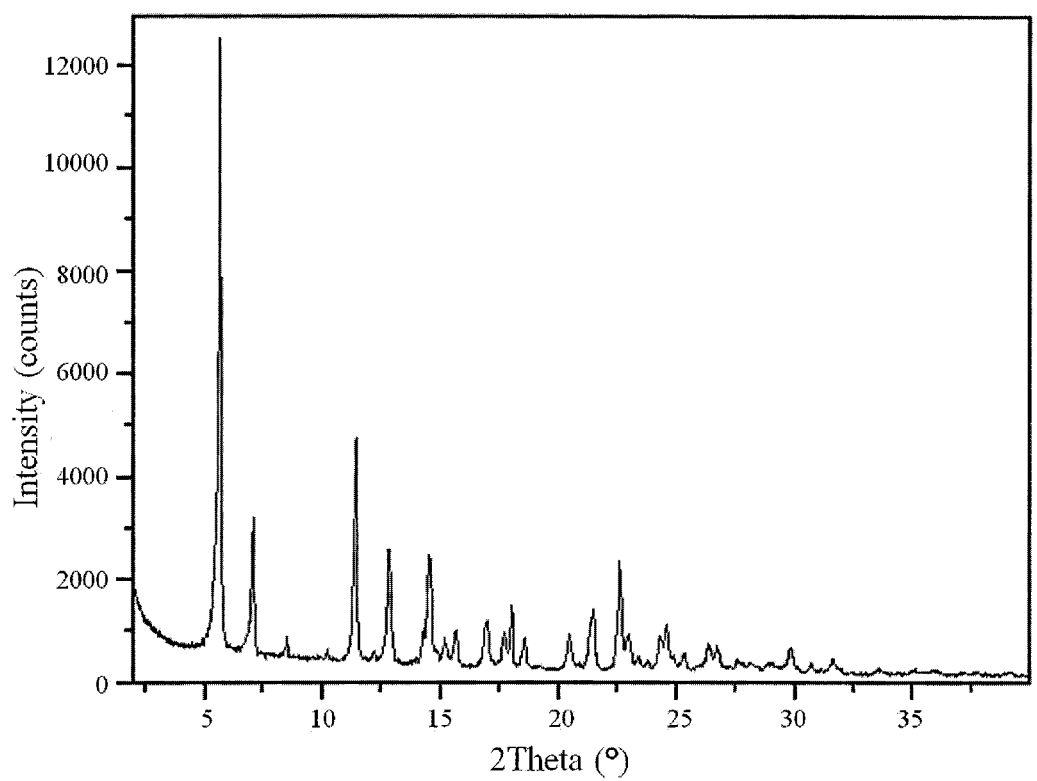
FIG. 17 shows an X-ray powder diffraction pattern of Compound A free base hydrate 4.

The X-ray powder diffraction (XRPD) pattern of Compound A free base hydrate 4 is shown in FIG. 17 and a summary of the diffraction angles and d-spacings is given in Table V below. The XRPD analysis was conducted on a PANanalytical X'Pert Pro Diffractometer on Si zero-background wafers. The acquisition conditions included: Cu $K_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE V

| Diff. Angle [°2θ] | d-spacing [Å] |
|---|---|
| 2.2321 | 39.57999 |
| 2.3446 | 37.68216 |
| 4.9817 | 17.73906 |
| 5.6944 | 15.52037 |
| 6.8184 | 12.96427 |
| 7.1087 | 12.43542 |
| 8.5054 | 10.3962 |
| 10.246 | 8.63367 |
| 11.4263 | 7.74435 |
| 12.1951 | 7.25784 |
| 12.8575 | 6.88533 |
| 14.2792 | 6.20288 |
| 14.5602 | 6.08378 |
| 14.8712 | 5.95725 |
| 15.2123 | 5.82441 |
| 15.6538 | 5.66113 |
| 16.9524 | 5.23029 |
| 17.0723 | 5.19383 |
| 17.7203 | 5.00533 |
| 18.021 | 4.92248 |
| 18.5746 | 4.777 |
| 20.4891 | 4.33476 |
| 20.8009 | 4.27048 |
| 20.9261 | 4.2417 |
| 21.0259 | 4.22528 |
| 21.3267 | 4.16638 |
| 21.4898 | 4.13511 |
| 22.6284 | 3.92956 |
| 23.0094 | 3.86535 |
| 23.4305 | 3.79682 |
| 24.3449 | 3.65625 |
| 24.6076 | 3.6178 |
| 24.8855 | 3.57507 |
| 24.9703 | 3.56607 |
| 25.3548 | 3.51286 |
| 26.3055 | 3.38522 |
| 26.4121 | 3.37179 |
| 26.4876 | 3.37071 |
| 26.7372 | 3.33153 |
| 26.8104 | 3.33086 |
| 27.5974 | 3.22962 |
| 29.6834 | 3.00723 |
| 29.8045 | 2.99528 |
| 29.8651 | 2.98935 |
| 31.605 | 2.82863 |
| 31.7234 | 2.82535 |

Figure 18:
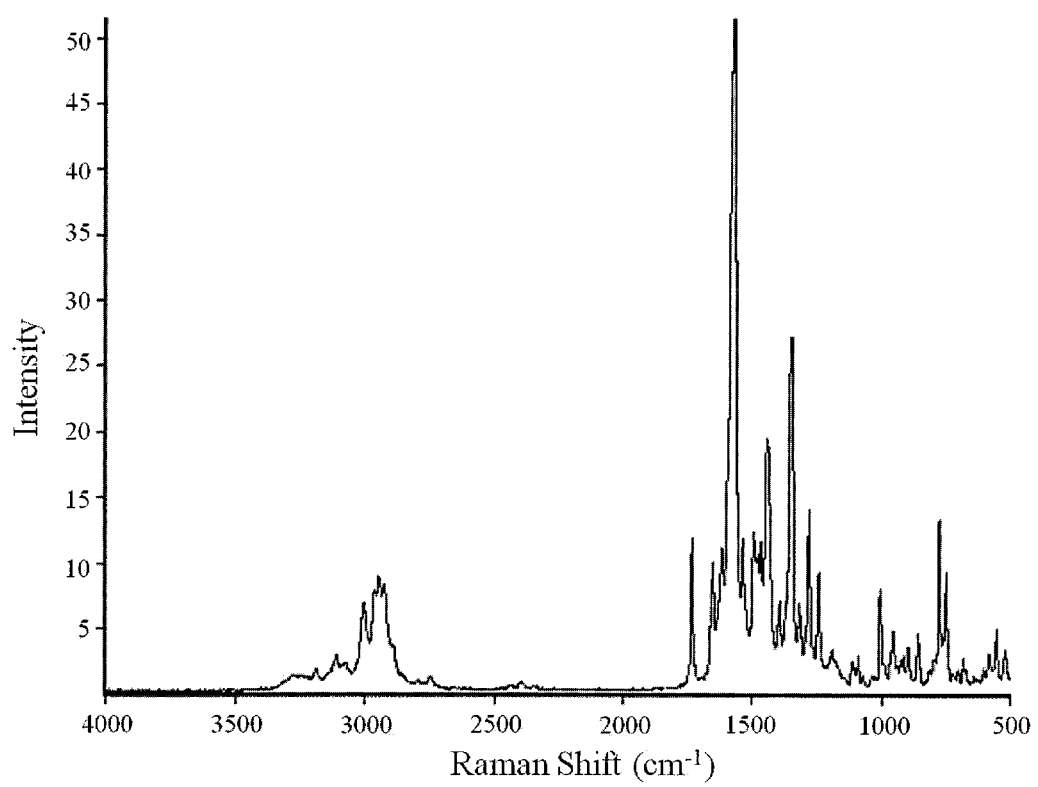
FIG. 18 shows a Raman spectrum of Compound A free base hydrate 4.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A free base hydrate 4 is shown in FIG. 18 with major peaks observed at 550.9, 680.5, 747.5, 776.0, 856.6, 894.3, 954.6, 1002.6, 1088.1, 1240.5, 1277.7, 1314.5, 1343.9, 1390.6, 1439.9, 1463.3, 1491.7, 1532.6, 1569.5, 1613.3, 1650.6, 1729.1, 2940.4, 2998.1 cm$^{-1}$.

Figure 19:
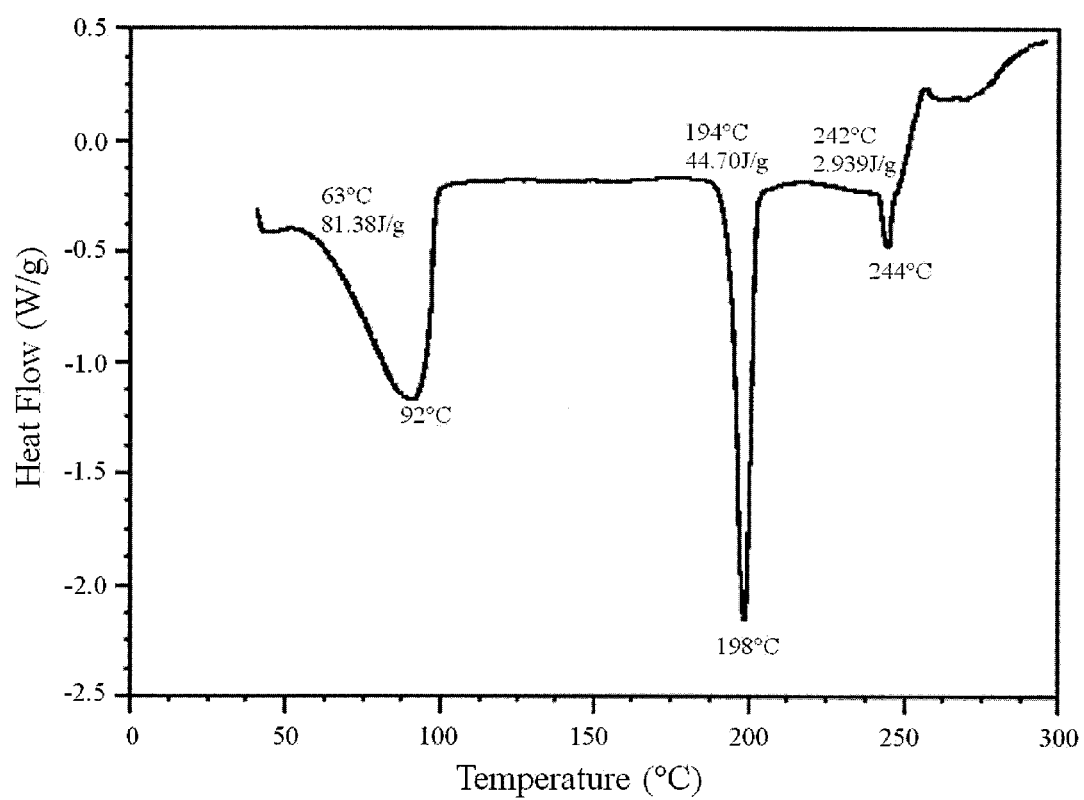
FIG. 19 shows a differential scanning calorimetry trace of Compound A free base hydrate 4.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 19. The experiments were conducted using a heating rate of 15° C./min in a crimped aluminum pan. The DSC thermogram of Compound A free base hydrate 4 exhibited a first endotherm with an onset temperature of about 63° C., a peak temperature about 92° C., and enthalpy of 81.38 J/g, followed by a second endotherm with an onset temperature of about 194° C., a peak temperature about 198° C., and enthalpy of 44.70 J/g, followed by a third endotherm with an onset temperature of about 242° C., a peak temperature about 244° C., and enthalpy of 2.939 J/g. A person skilled in the art would recognize that the onset temperature, peak temperature, and enthalpy of the endotherm may vary depending on the experimental conditions.

Figure 20:
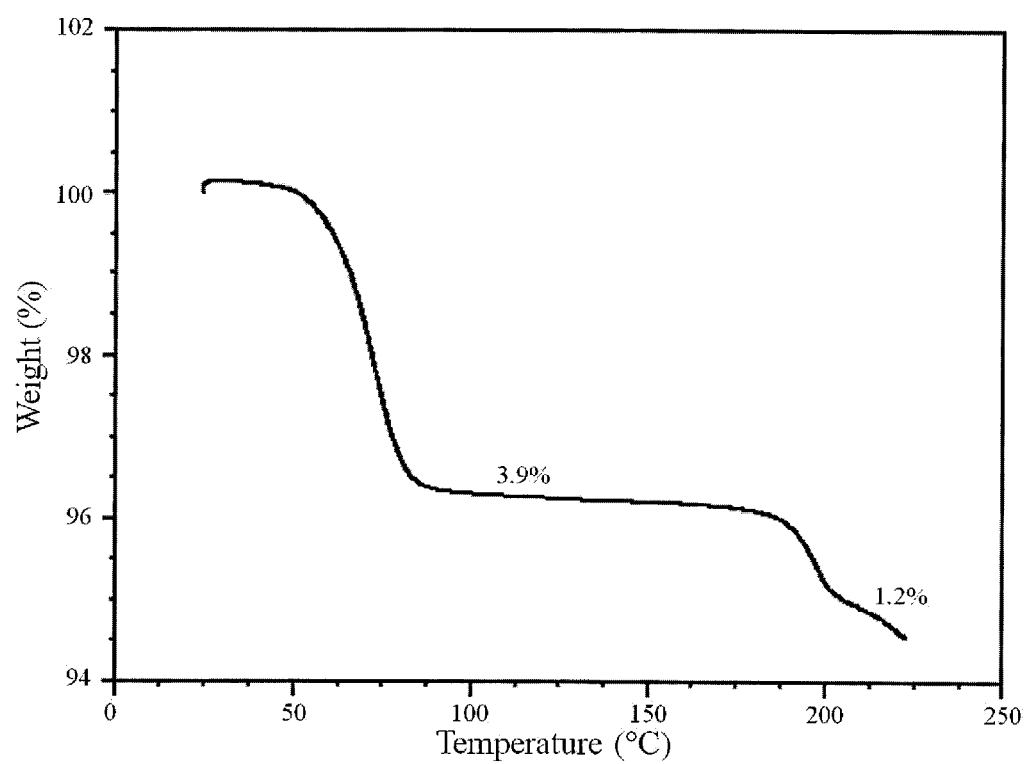
FIG. 20 shows a thermogravimetric analysis trace of Compound A free base hydrate 4.

The thermogravimetric analysis (TGA) thermogram of the title compound was recorded on a TA Instruments Q500 Thermogravimetric Analyzer and is shown in FIG. 20. The experiments were conducted with 40 mL/min N$_2$ flow and a heating rate of 15° C./min in an aluminum pan. The TGA thermogram of Compound A free base hydrate 4 exhibited multiple weight loss events observed prior to the final thermal decomposition. The first weight loss event takes place in the temperature range of 25° C. to 110° C. with a weight loss of about 3.9%. The second weight loss event takes place in the temperature range of 155° C. to 210° C. with a weight loss of about 1.2%. Thermal decomposition was not observed below 225° C.

EXAMPLE 197

Fifth crystalline hydrate of the free base of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A free base hydrate 5)

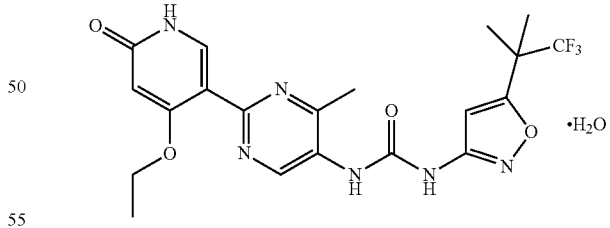

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in 19:1 acetone:water was stirred for 3 days while cycling the temperature between 40° C. and 5° C. The solids were isolated by vacuum filtration, air dried for 1 h, and then dried overnight in a vacuum oven at 40° C. to give the title compound as a crystalline solid.

Figure 21:
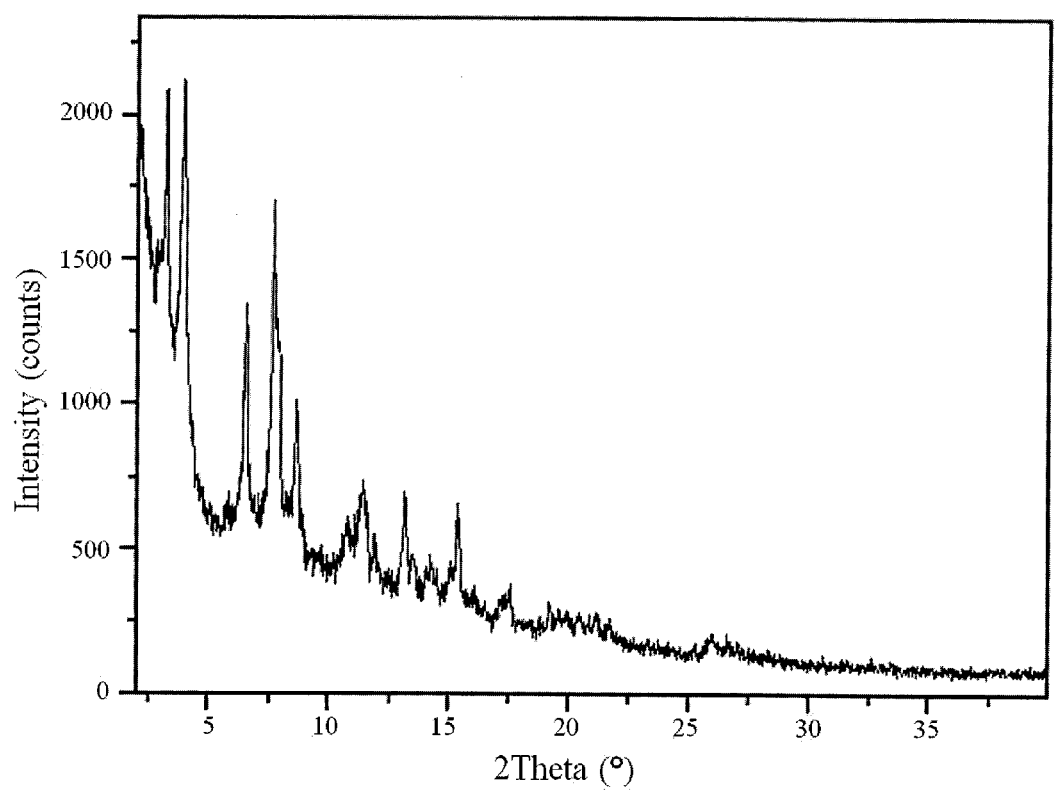
FIG. 21 shows an X-ray powder diffraction pattern of Compound A free base hydrate 5.

The X-ray powder diffraction (XRPD) pattern of Compound A free base hydrate 5 is shown in FIG. 21 and a summary of the diffraction angles and d-spacings is given in Table VI below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE VI

| Diff. Angle [°2θ] | d-spacing [Å] |
|---|---|
| 2.2139 | 39.90616 |
| 2.9893 | 29.55637 |
| 3.236 | 27.30406 |
| 3.6224 | 24.3923 |
| 3.7924 | 23.29924 |
| 3.9534 | 22.35029 |
| 4.1324 | 21.38297 |
| 6.579 | 13.43542 |
| 6.8983 | 12.81425 |
| 7.0705 | 12.50247 |
| 7.4474 | 11.87067 |
| 7.7039 | 11.47587 |
| 7.9458 | 11.12712 |
| 8.2294 | 10.74432 |
| 8.6592 | 10.2119 |
| 10.8082 | 8.18583 |
| 11.0854 | 7.98177 |
| 11.3234 | 7.81454 |
| 11.4512 | 7.72755 |
| 11.581 | 7.64127 |
| 13.0744 | 6.77164 |
| 13.1945 | 6.71024 |
| 15.1009 | 5.86714 |
| 15.298 | 5.79197 |
| 15.397 | 5.75495 |

Figure 22:
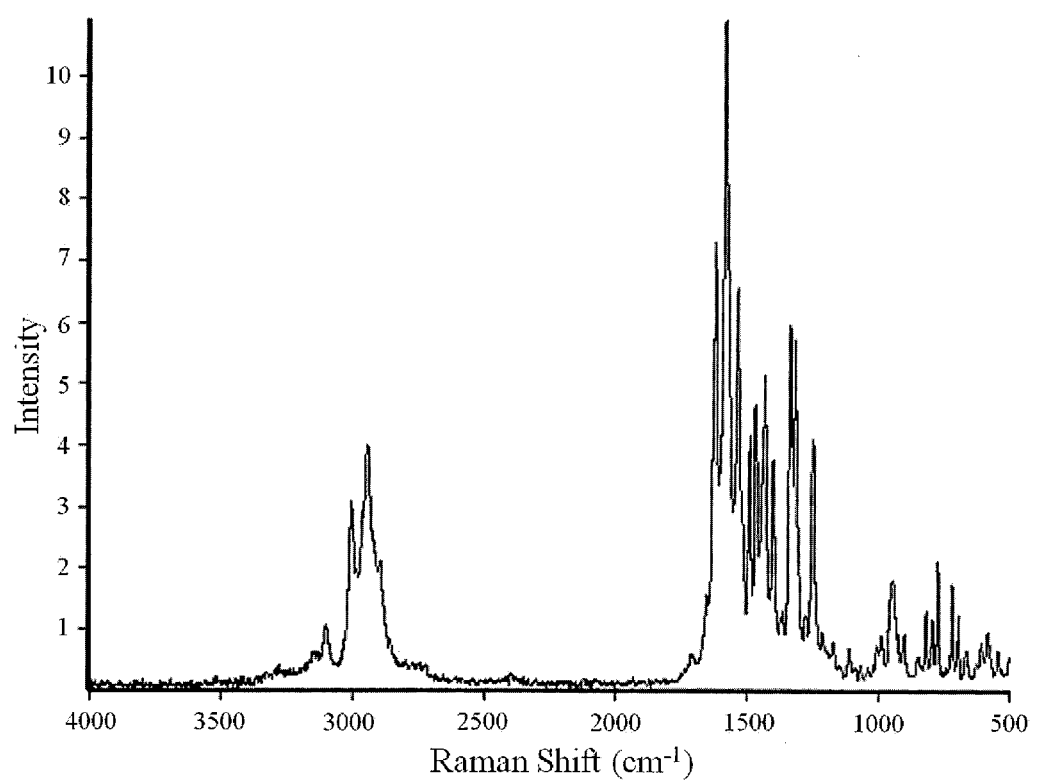
FIG. 22 shows a Raman spectrum of Compound A free base hydrate 5.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A free base hydrate 5 is shown in FIG. 22 with major peaks observed at 542.9, 581.1, 664.4, 696.3, 719.5, 774.8, 793.9, 817.9, 898.4, 944.0, 988.9, 1109.8, 1247.0, 1315.3, 1332.8, 1399.4, 1429.9, 1464.5, 1486.7, 1533.4, 1580.3, 1617.5, 2938.9, 2998.5, 3098.4 cm$^{-1}$.

Figure 23:
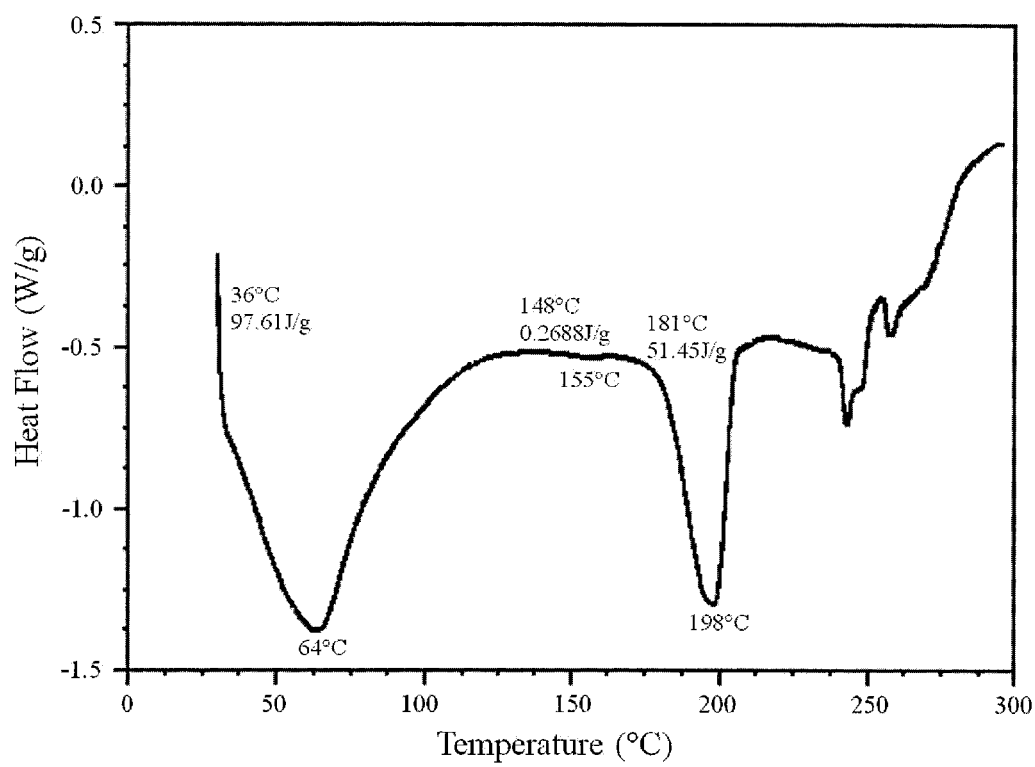
FIG. 23 shows a differential scanning calorimetry trace of Compound A free base hydrate 5.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 23. The experiments were conducted using a heating rate of 15° C./min in a crimped aluminum pan. The DSC thermogram of Compound A free base hydrate 5 exhibited a first endotherm with an onset temperature of about 36° C., a peak temperature about 64° C., and enthalpy of 97.61 J/g, followed by a second endotherm with an onset temperature of about 148° C., a peak temperature about 155° C., and enthalpy of 0.2688 J/g, followed by a third endotherm with an onset temperature of about 181° C., a peak temperature about 198° C., and enthalpy of 51.45 J/g. A person skilled in the art would recognize that the onset temperature, peak temperature, and enthalpy of the endotherm may vary depending on the experimental conditions.

Figure 24:
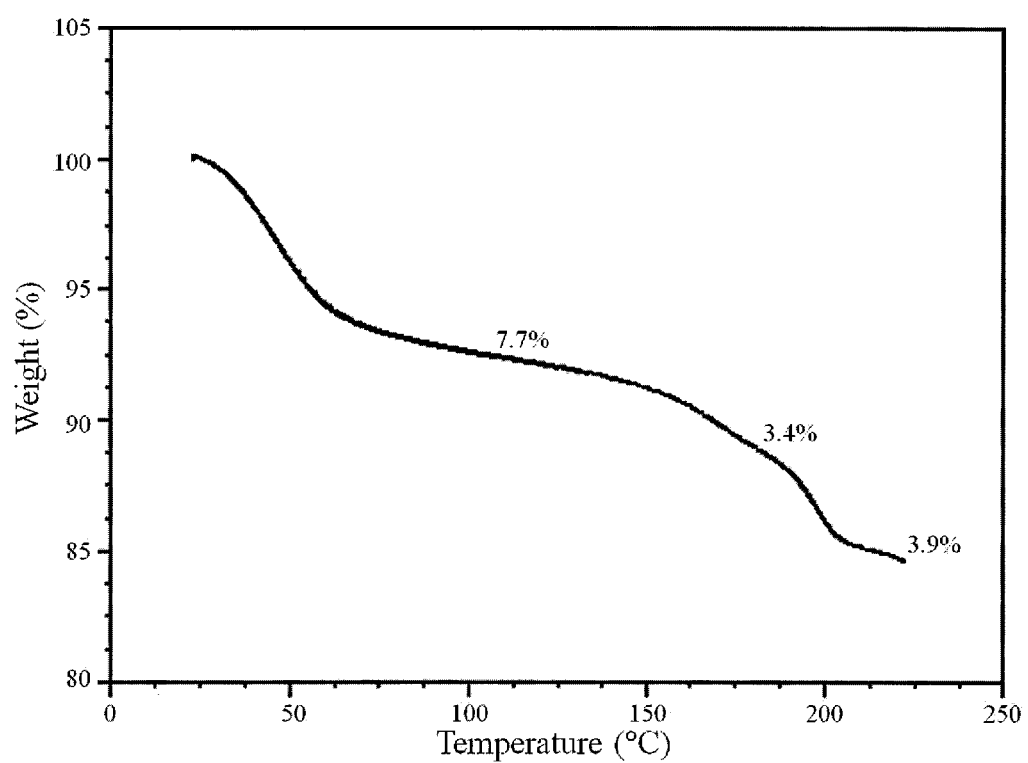
FIG. 24 shows a thermogravimetric analysis trace of Compound A free base hydrate 5.

The thermogravimetric analysis (TGA) thermogram of the title compound was recorded on a TA Instruments Q500 Thermogravimetric Analyzer and is shown in FIG. 24. The experiments were conducted with 40 mL/min N$_2$ flow and a heating rate of 15° C./min in an aluminum pan. The TGA thermogram of Compound A free base hydrate 5 exhibited multiple weight loss events observed prior to the final thermal decomposition. The first weight loss event takes place in the temperature range of 25° C. to 105° C. with a weight loss of about 7.7%. The second weight loss event takes place in the temperature range of 105° C. to 175° C. with a weight loss of about 3.4%. The final weight loss event takes place in the temperature range of 175° C. to 225° C. with a weight loss of about 3.9%. Thermal decomposition was not observed below 225° C.

EXAMPLE 198

Crystalline anhydrous hydrochloric acid salt of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A hydrochloride anhydrate)

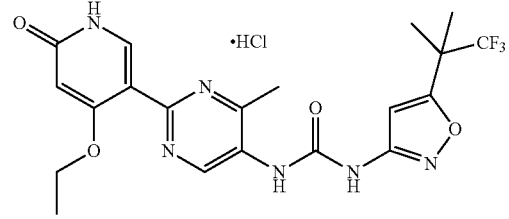 [SMILES: CCOc1cc(=O)[nH]cc1-c1ncc(NC(=O)Nc2cc(C(C)(C)C(F)(F)F)on2)c(C)n1 ; Cl]

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in acetone was heated to 40° C. One equivalent of 3M aqueous hydrochloric acid was added and the slurry was stirred for 2 days while cycling the temperature between 40° C. and 5° C. in one hour blocks, followed by equilibration at room temperature for 4 h. The solids were filtered, air-dried, and washed with acetone to give the title compound as a crystalline solid. Ion chromatography analysis indicated 1:1 acid:free base stoichiometry.

Figure 25:
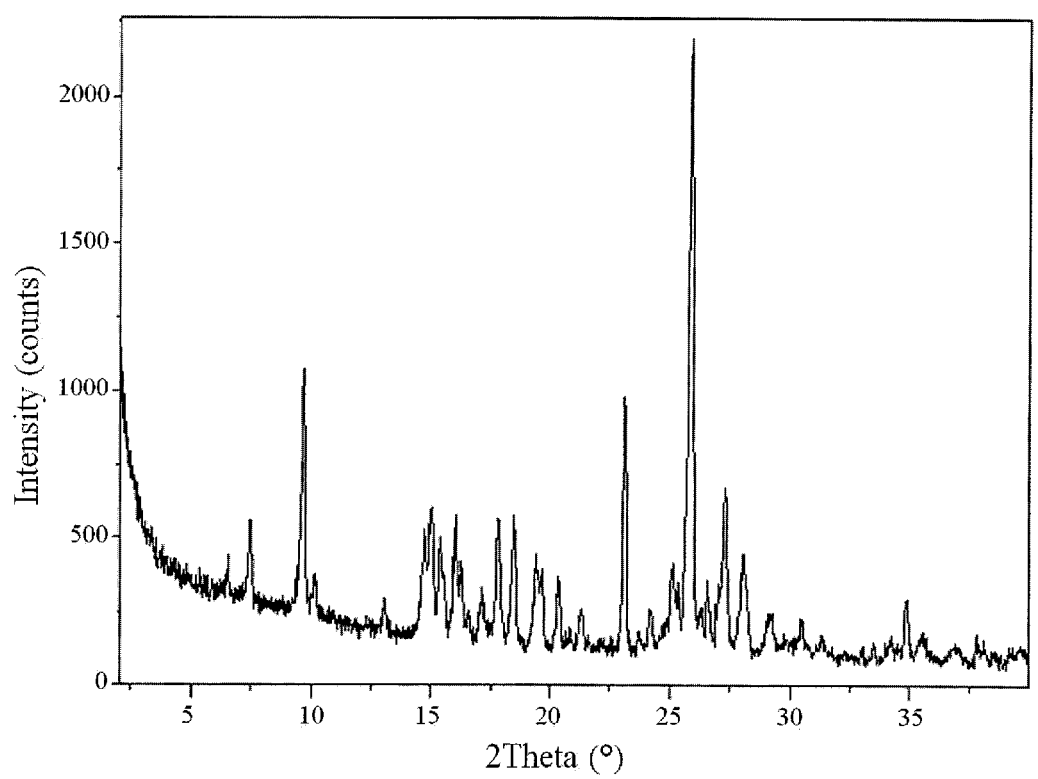
FIG. 25 shows an X-ray powder diffraction pattern of Compound A hydrochloride anhydrate.

The X-ray powder diffraction (XRPD) pattern of Compound A hydrochloride anhydrate is shown in FIG. 25 and a summary of the diffraction angles and d-spacings is given in Table VII below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE VII

| Diff. Angle [°2θ] | d-spacing [Å] |
|---|---|
| 7.4431 | 11.87738 |
| 9.6794 | 9.13773 |
| 14.6085 | 6.05877 |
| 14.7259 | 6.01073 |
| 14.9405 | 5.92487 |
| 15.041 | 5.88548 |
| 15.3713 | 5.75977 |

TABLE VII-continued

| Diff. Angle [°2θ] | d-spacing [Å] |
|---|---|
| 15.5848 | 5.68134 |
| 16.0312 | 5.52414 |
| 16.2562 | 5.44818 |
| 17.1352 | 5.17062 |
| 17.7713 | 4.98696 |
| 17.8528 | 4.96437 |
| 18.4689 | 4.80013 |
| 19.3906 | 4.57398 |
| 19.6152 | 4.52212 |
| 20.3513 | 4.36019 |
| 23.1104 | 3.8455 |
| 25.102 | 3.54473 |
| 25.3262 | 3.51385 |
| 25.5881 | 3.47848 |
| 25.8589 | 3.44266 |
| 26.5603 | 3.35331 |
| 27.0276 | 3.29639 |
| 27.2162 | 3.27398 |
| 27.2957 | 3.26462 |
| 27.9834 | 3.18594 |
| 28.072 | 3.17608 |
| 28.2141 | 3.16041 |
| 34.8469 | 2.57254 |

Figure 26:
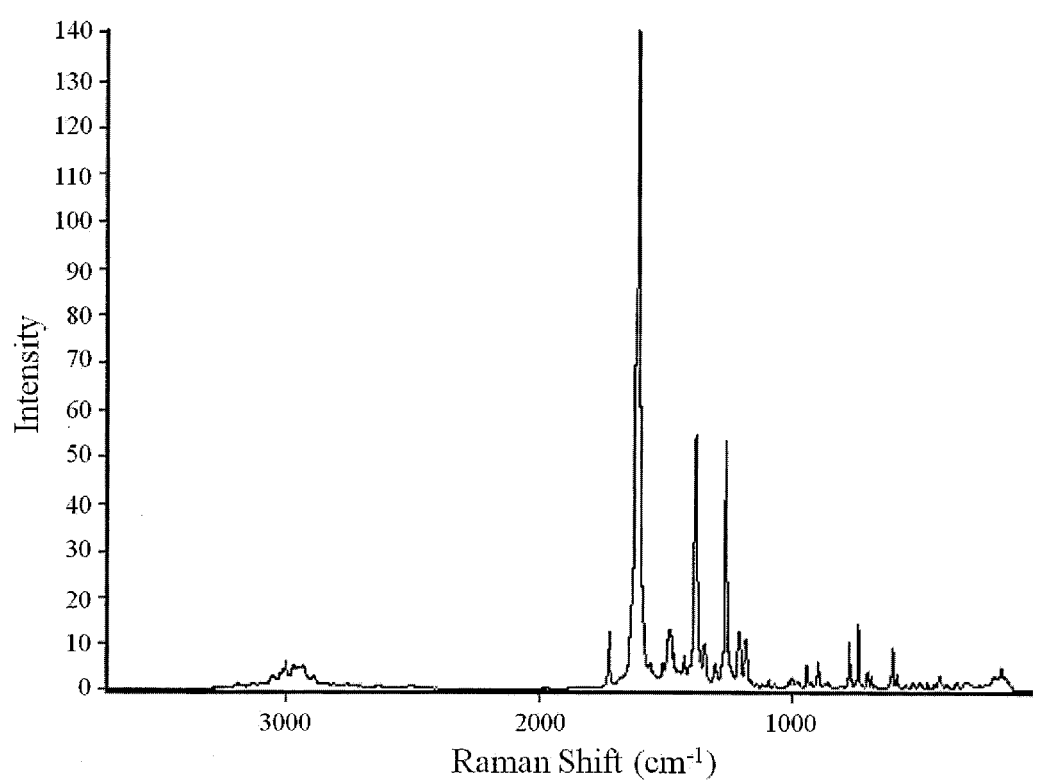
FIG. 26 shows a Raman spectrum of Compound A hydrochloride anhydrate.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A hydrochloride anhydrate is shown in FIG. 26 with major peaks observed at 589.0, 734.4, 768.5, 893.3, 1177.3, 1203.0, 1257.1, 1374.9, 1475.7, 1602.0, 1715.5, 2993.2 cm$^{-1}$.

Figure 27:
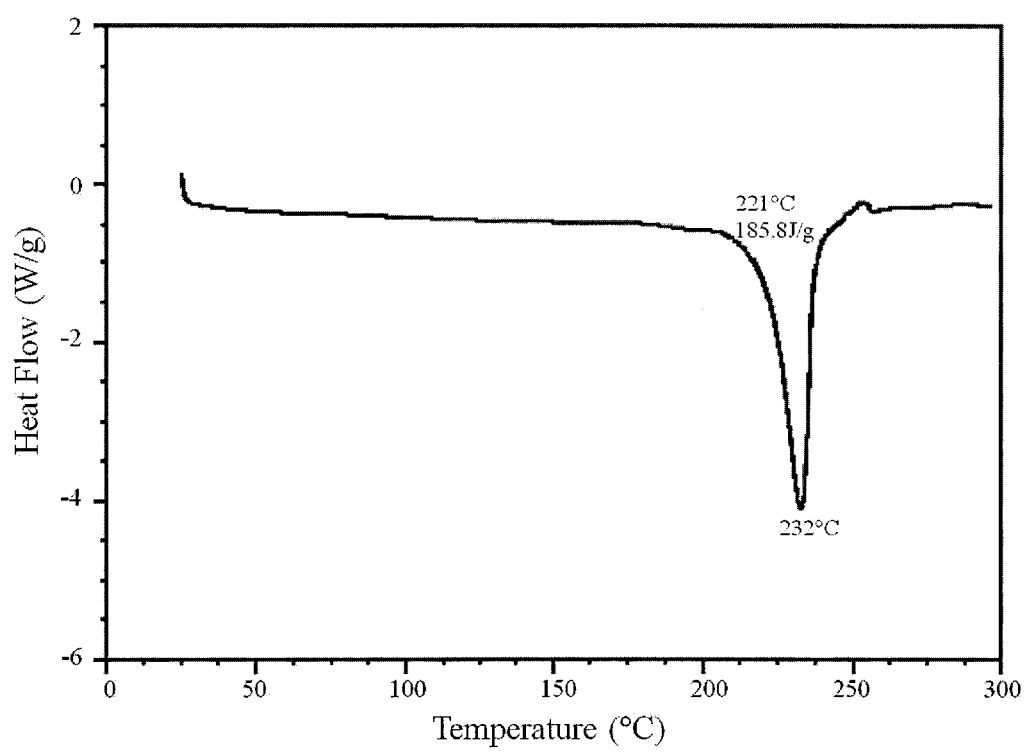
FIG. 27 shows a differential scanning calorimetry trace of Compound A hydrochloride anhydrate.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 27. The experiments were conducted using a heating rate of 15° C./min in a crimped aluminum pan. The DSC thermogram of Compound A hydrochloride anhydrate exhibited a sharp endotherm with an onset temperature of about 221° C., a peak temperature about 232° C., and enthalpy of 185.8 J/g. A person skilled in the art would recognize that the onset temperature, peak temperature, and enthalpy of the endotherm may vary depending on the experimental conditions.

Figure 28:
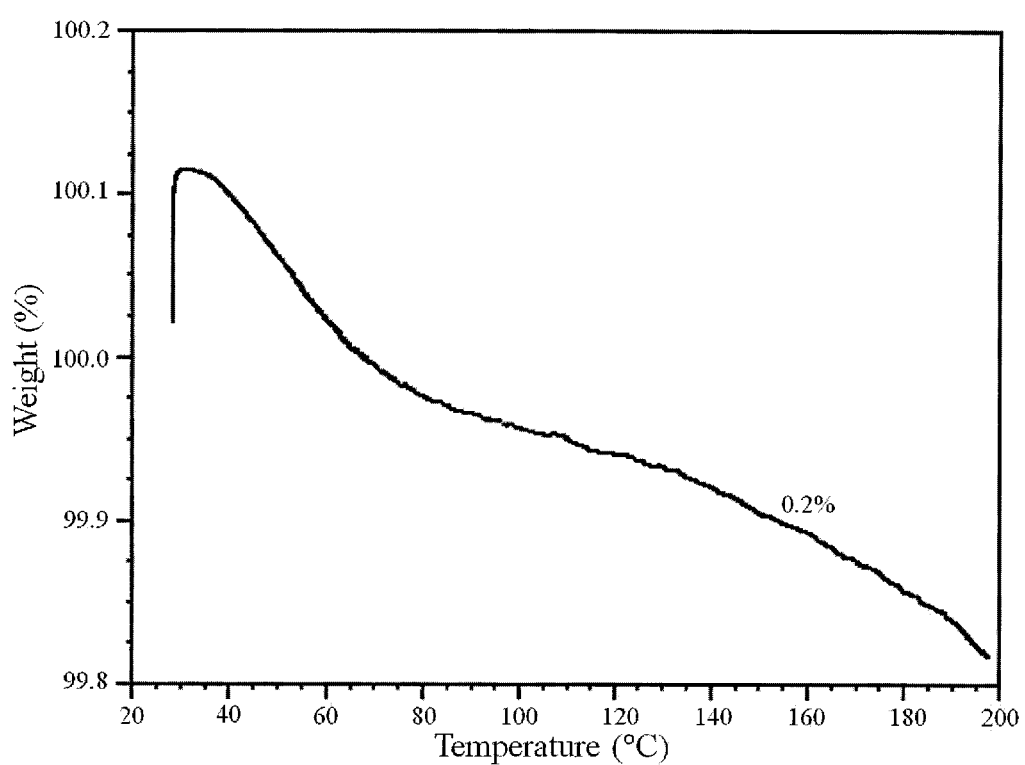
FIG. 28 shows a thermogravimetric analysis trace of Compound A hydrochloride anhydrate.

The thermogravimetric analysis (TGA) thermogram of the title compound was recorded on a TA Instruments Q500 Thermogravimetric Analyzer and is shown in FIG. 28. The experiments were conducted with 40 mL/min N$_2$ flow and a heating rate of 15° C./min in an aluminum pan. The TGA thermogram of Compound A hydrochloride anhydrate exhibited a minor weight loss event in the temperature range of 25° C. to 150° C. with a weight loss of about 0.2%. Thermal decomposition was not observed below 200° C.

EXAMPLE 199

Crystalline hydrate of the hydrochloric acid salt of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A hydrochloride hydrate)

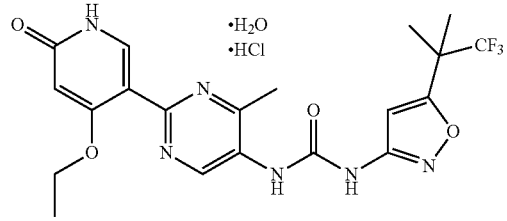 [SMILES: CCOc1cc(=O)[nH]cc1-c1ncc(NC(=O)Nc2cc(C(C)(C)C(F)(F)F)on2)c(C)n1 ; "·H2O·HCl"]

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in acetonitrile was heated to 40° C. One equivalent of 3M aqueous hydrochloric acid was added and the slurry was stirred overnight while cycling the temperature between 40° C. and 5° C. in one hour blocks, followed by equilibration at room temperature for 1 h. The solids were filtered, air-dried, and washed with acetonitrile to give the title compound as a crystalline solid.

Figure 29:
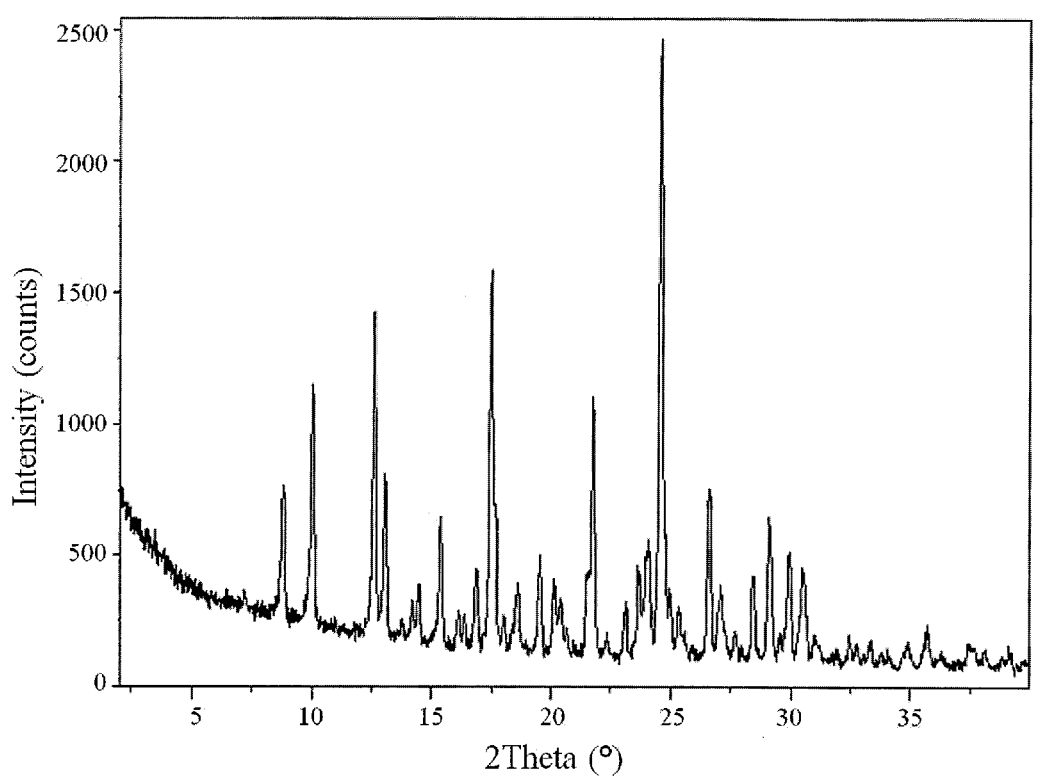
FIG. 29 shows an X-ray powder diffraction pattern of Compound A hydrochloride hydrate.

The X-ray powder diffraction (XRPD) pattern of Compound A hydrochloride hydrate is shown in FIG. 29 and a summary of the diffraction angles and d-spacings is given in Table VIII below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE VIII

| Diff. Angle [°2θ] | d-spacing [Å] |
|---|---|
| 8.6684 | 10.2011 |
| 8.8312 | 10.01337 |
| 10.0419 | 8.80872 |
| 12.6021 | 7.02431 |
| 13.058 | 6.78006 |
| 14.405 | 6.14899 |
| 14.4771 | 6.11851 |
| 15.363 | 5.76763 |
| 16.864 | 5.2575 |
| 17.483 | 5.07273 |
| 17.6738 | 5.01839 |
| 18.5936 | 4.76821 |
| 19.4603 | 4.55776 |
| 19.5214 | 4.54363 |
| 20.0793 | 4.41863 |
| 20.1454 | 4.40429 |
| 20.3921 | 4.35155 |
| 20.4549 | 4.34912 |
| 20.9397 | 4.23898 |
| 21.1515 | 4.19701 |
| 21.5292 | 4.12422 |
| 21.7438 | 4.084 |
| 23.1368 | 3.84117 |
| 23.6519 | 3.75867 |

343

TABLE VIII-continued

| Diff. Angle [°2θ] | d-spacing [Å] |
|---|---|
| 23.6994 | 3.76057 |
| 23.9391 | 3.71422 |
| 24.0691 | 3.69446 |
| 24.5836 | 3.61829 |
| 24.9893 | 3.56046 |
| 25.3396 | 3.51203 |
| 26.6195 | 3.34599 |
| 26.9866 | 3.3013 |
| 27.0934 | 3.28854 |
| 28.4387 | 3.13595 |
| 28.8674 | 3.09035 |
| 29.1149 | 3.06464 |
| 29.1904 | 3.06448 |
| 29.9485 | 2.98121 |
| 30.4503 | 2.93321 |
| 30.5391 | 2.92489 |
| 30.6032 | 2.92616 |

Figure 30:
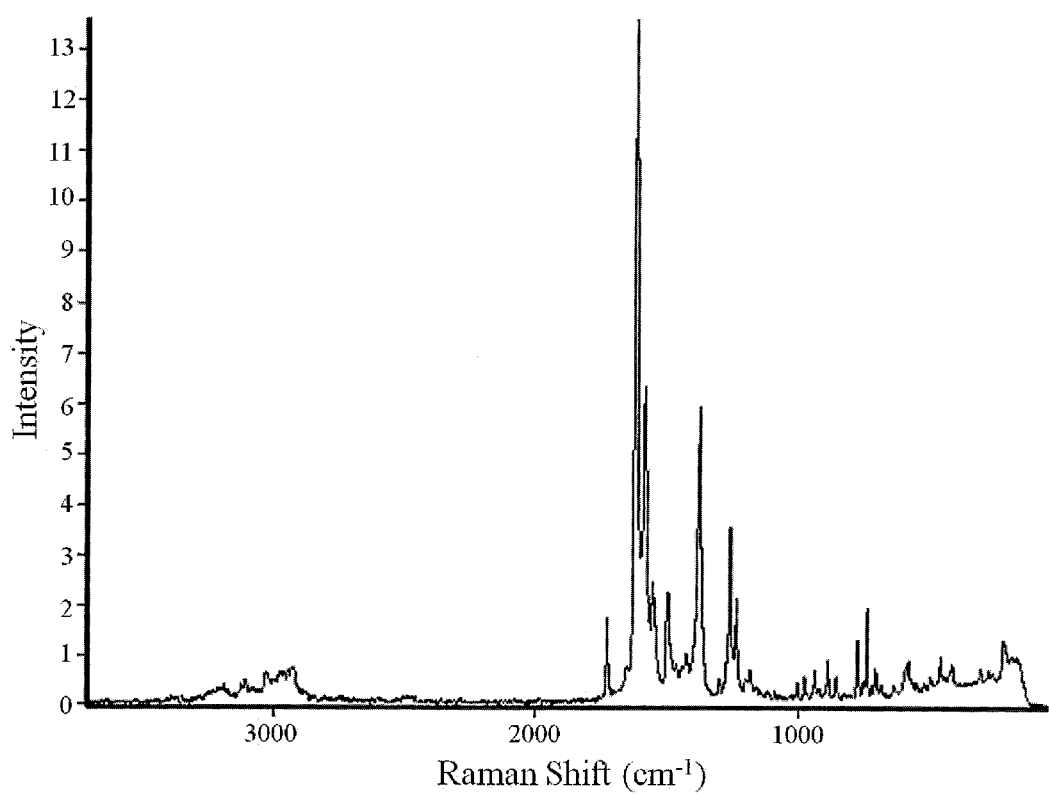
FIG. 30 shows a Raman spectrum of Compound A hydrochloride hydrate.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A hydrochloride hydrate is shown in FIG. 30 with major peaks observed at 213.1, 456.7, 575.1, 704.6, 735.5, 770.1, 885.3, 934.8, 1232.5, 1256.0, 1369.8, 1493.3, 1548.5, 1578.9, 1612.9, 1722.2, 2918.2 cm$^{-1}$.

Figure 31:
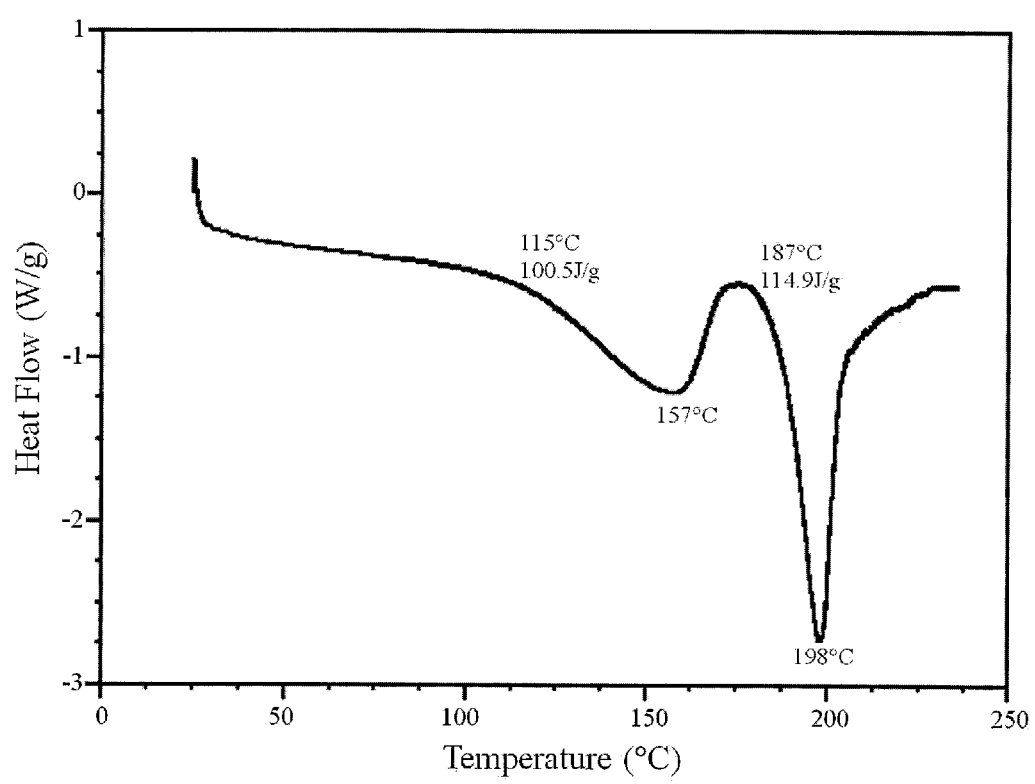
FIG. 31 shows a differential scanning calorimetry trace of Compound A hydrochloride hydrate.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 31. The experiments were conducted using a heating rate of 15° C./min in a crimped aluminum pan. The DSC thermogram of Compound A hydrochloride hydrate exhibited a first endotherm with an onset temperature of about 115° C., a peak temperature about 157° C., and enthalpy of 100.5 J/g, followed by a second endotherm with an onset temperature of about 187° C., a peak temperature about 198° C., and enthalpy of 114.9 J/g. A person skilled in the art would recognize that the onset temperature, peak temperature, and enthalpy of the endotherm may vary depending on the experimental conditions.

Figure 32:
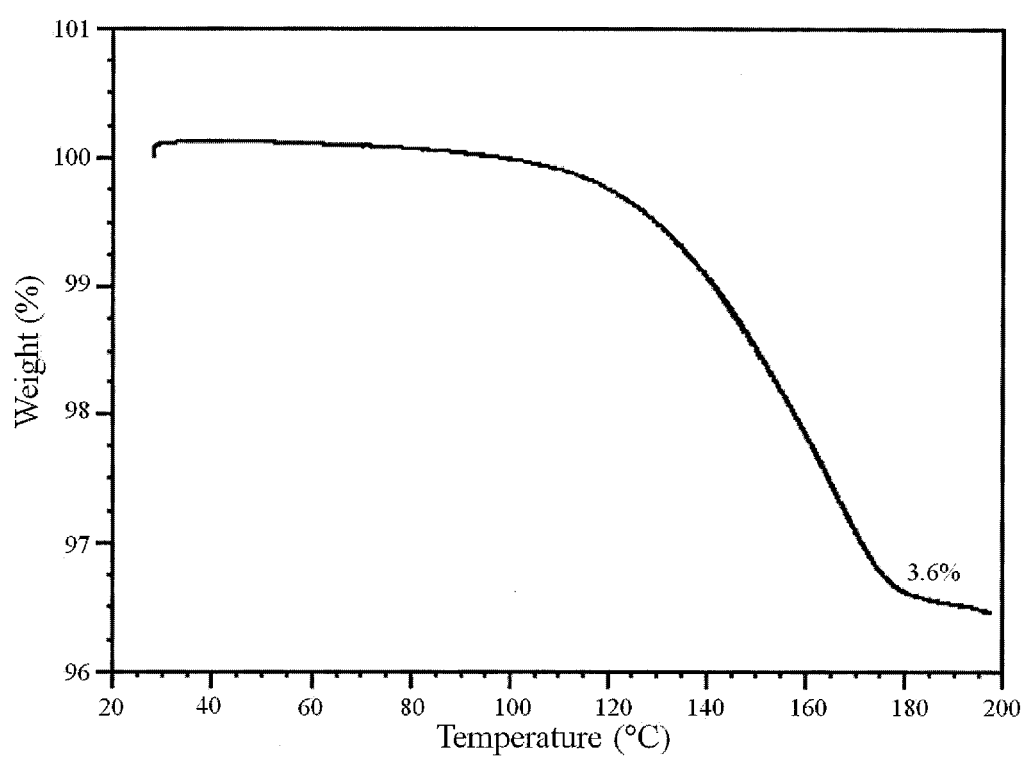
FIG. 32 shows a thermogravimetric analysis trace of Compound A hydrochloride hydrate.

The thermogravimetric analysis (TGA) thermogram of the title compound was recorded on a TA Instruments Q500 Thermogravimetric Analyzer and is shown in FIG. 32. The experiments were conducted with 40 mL/min N$_2$ flow and a heating rate of 15° C./min in an aluminum pan. The TGA thermogram of Compound A hydrochloride hydrate exhibited a weight loss event in the temperature range of 25° C. to 180° C. with a weight loss of about 3.6%. Thermal decomposition was not observed below 200° C.

344

EXAMPLE 200

Crystalline ethanesulfonic acid salt of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A esylate)

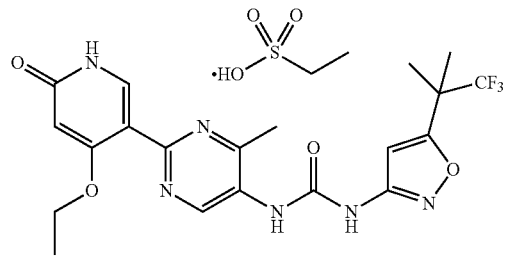

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in acetonitrile was heated to 40° C. One equivalent of 3M aqueous ethanesulfonic acid was added and the slurry was stirred overnight while cycling the temperature between 40° C. and 5° C. in one hour blocks, followed by equilibration at room temperature for 1 h. The solids were filtered, air-dried, and washed with acetonitrile to give the title compound as a crystalline solid. $^1$H NMR analysis indicated 1:1 acid:free base stoichiometry.

Figure 33:
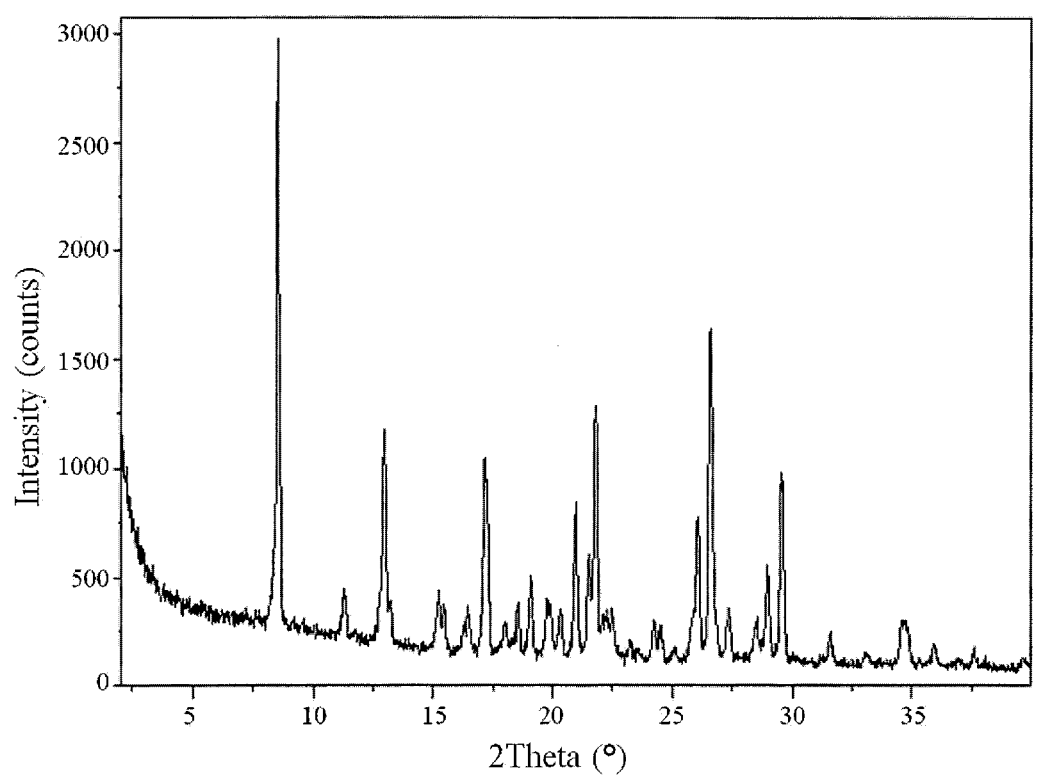
FIG. 33 shows an X-ray powder diffraction pattern of Compound A esylate.

The X-ray powder diffraction (XRPD) pattern of Compound A esylate is shown in FIG. 33 and a summary of the diffraction angles and d-spacings is given in Table IX below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE IX

| Diff. Angle [°2θ] | d-spacing [Å] |
|---|---|
| 8.5394 | 10.35491 |
| 8.6428 | 10.23126 |
| 11.3062 | 7.82635 |
| 12.7495 | 6.94345 |
| 12.964 | 6.82902 |
| 13.1974 | 6.70878 |
| 15.1654 | 5.84235 |
| 15.2444 | 5.81223 |
| 15.4498 | 5.73542 |
| 16.4543 | 5.38303 |
| 17.1632 | 5.16223 |
| 17.2575 | 5.13426 |
| 18.548 | 4.77984 |
| 19.7459 | 4.49249 |
| 20.3296 | 4.36478 |
| 20.968 | 4.23332 |
| 21.5163 | 4.12667 |
| 21.8003 | 4.07355 |
| 22.081 | 4.02239 |
| 22.2781 | 3.98724 |
| 22.4806 | 3.95179 |
| 24.2258 | 3.67091 |

TABLE IX-continued

| Diff. Angle [°2θ] | d-spacing [Å] |
|---|---|
| 25.7987 | 3.45055 |
| 26.0615 | 3.41636 |
| 26.594 | 3.34915 |
| 27.2642 | 3.26832 |
| 27.361 | 3.25697 |
| 28.4262 | 3.13731 |
| 28.528 | 3.12634 |
| 28.9678 | 3.07987 |
| 29.048 | 3.07918 |
| 29.5627 | 3.01923 |
| 34.5329 | 2.59521 |
| 34.8089 | 2.57526 |

Figure 34:
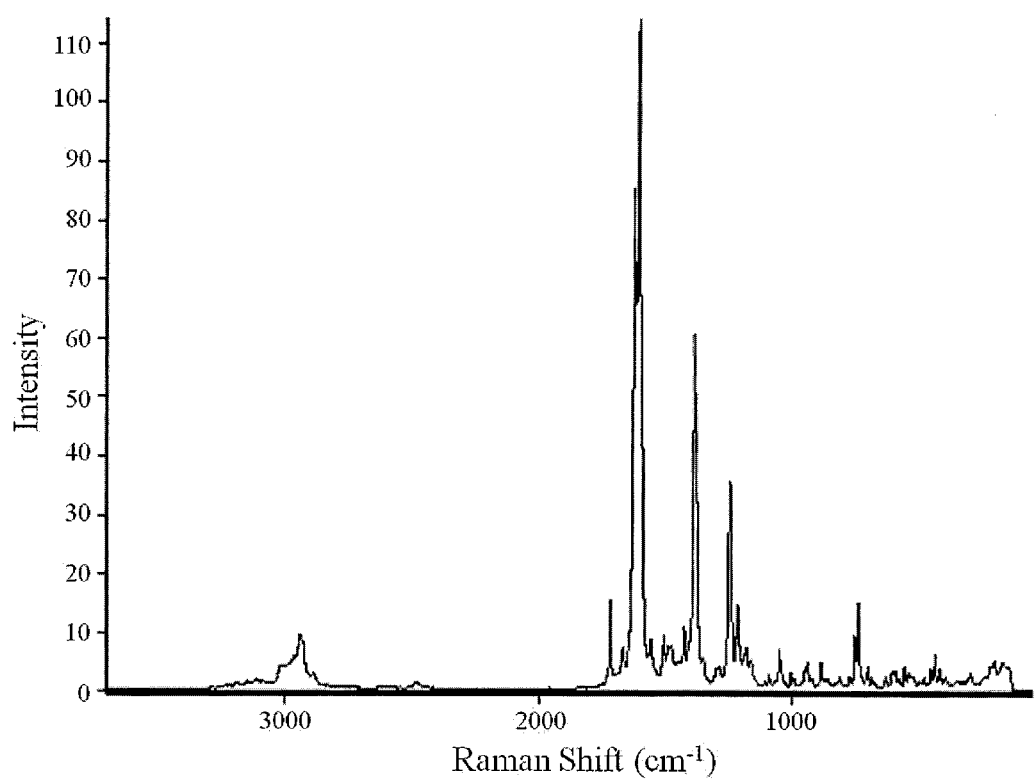
FIG. 34 shows a Raman spectrum of Compound A esylate.

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of Compound A esylate is shown in FIG. 34 with major peaks observed at 195.0, 432.2, 734.5, 749.7, 882.2, 1046.1, 1211.4, 1240.4, 1380.1, 1422.3, 1502.1, 1600.0, 1617.0, 1713.9, 2937.7 cm$^{-1}$.

Figure 35:
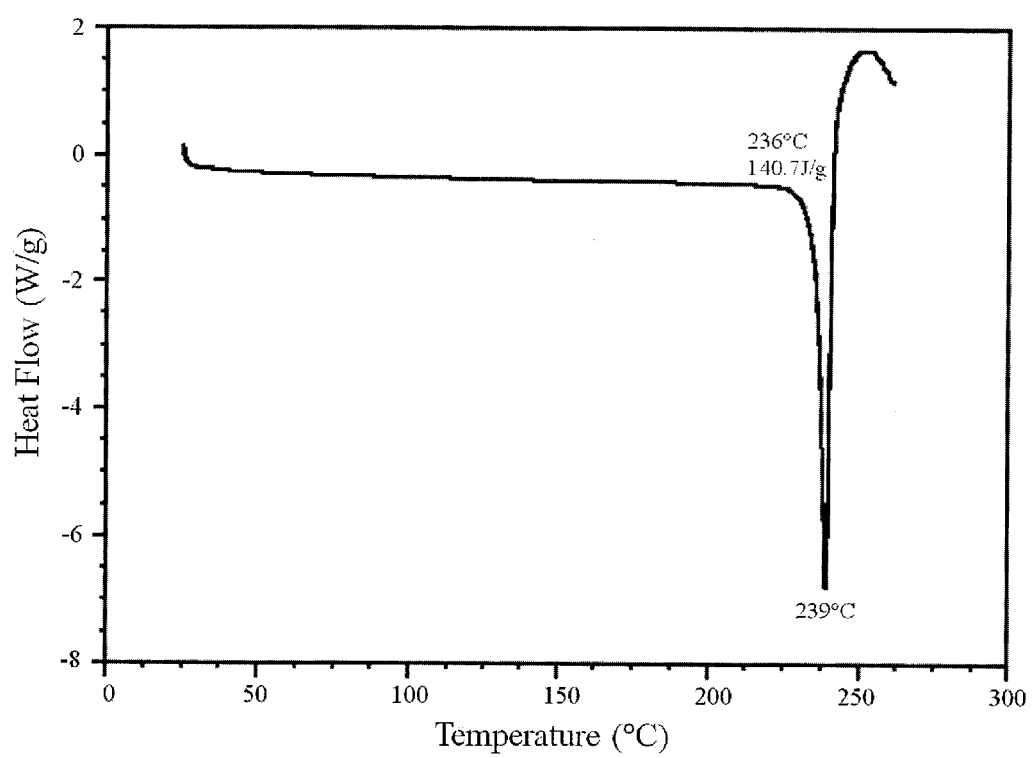
FIG. 35 shows a differential scanning calorimetry trace of Compound A esylate.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 35. The experiments were conducted using a heating rate of 15° C./min in a crimped aluminum pan. The DSC thermogram of Compound A esylate exhibited a sharp endotherm with an onset temperature of about 236° C., a peak temperature about 239° C., and enthalpy of 140.7 J/g. A person skilled in the art would recognize that the onset temperature, peak temperature, and enthalpy of the endotherm may vary depending on the experimental conditions.

Figure 36:
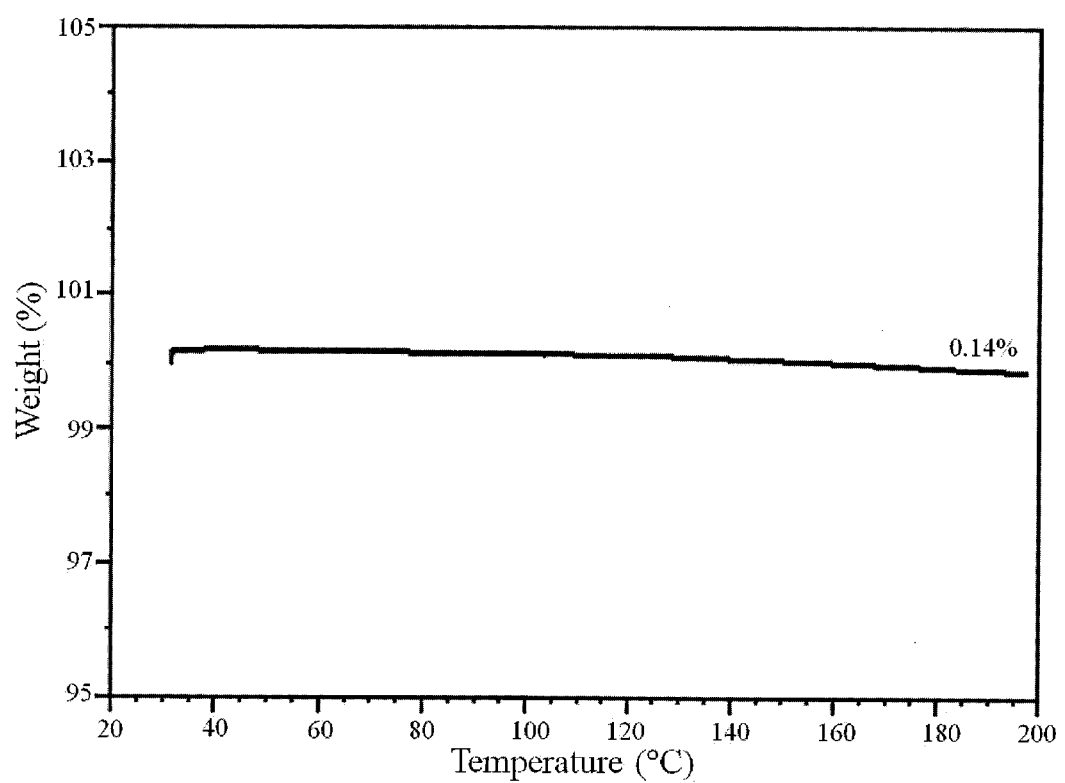
FIG. 36 shows a thermogravimetric analysis trace of Compound A esylate.

The thermogravimetric analysis (TGA) thermogram of the title compound was recorded on a TA Instruments Q500 Thermogravimetric Analyzer and is shown in FIG. 36. The experiments were conducted with 40 mL/min N$_2$ flow and a heating rate of 15° C./min in an aluminum pan. The TGA thermogram of Compound A esylate exhibited a minor weight loss event in the temperature range of 25° C. to 180° C. with a weight loss of about 0.14%. Thermal decomposition was not observed below 200° C.

EXAMPLE 201

Crystalline sulfuric acid salt of 1-(2-(4-Ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea (Compound A sulfate)

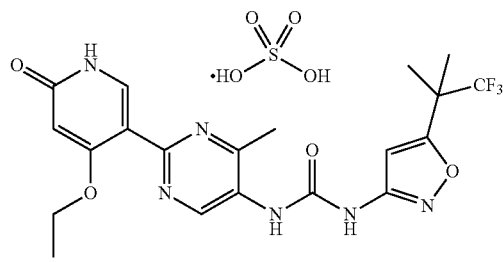

A suspension of 1-(2-(4-ethoxy-6-oxo-1,6-dihydropyridin-3-yl)-4-methylpyrimidin-5-yl)-3-(5-(1,1,1-trifluoro-2-methylpropan-2-yl)isoxazol-3-yl)urea in acetonitrile was heated to 40° C. One equivalent of 2.5M aqueous sulfuric acid was added and the slurry was stirred overnight while cycling the temperature between 40° C. and 5° C. in one hour blocks, followed by equilibration at room temperature for 1 h. The solids were filtered, air-dried, and washed with acetonitrile to give the title compound as a crystalline solid. Ion chromatography analysis indicated 1:1 acid:free base stoichiometry.

Figure 37:
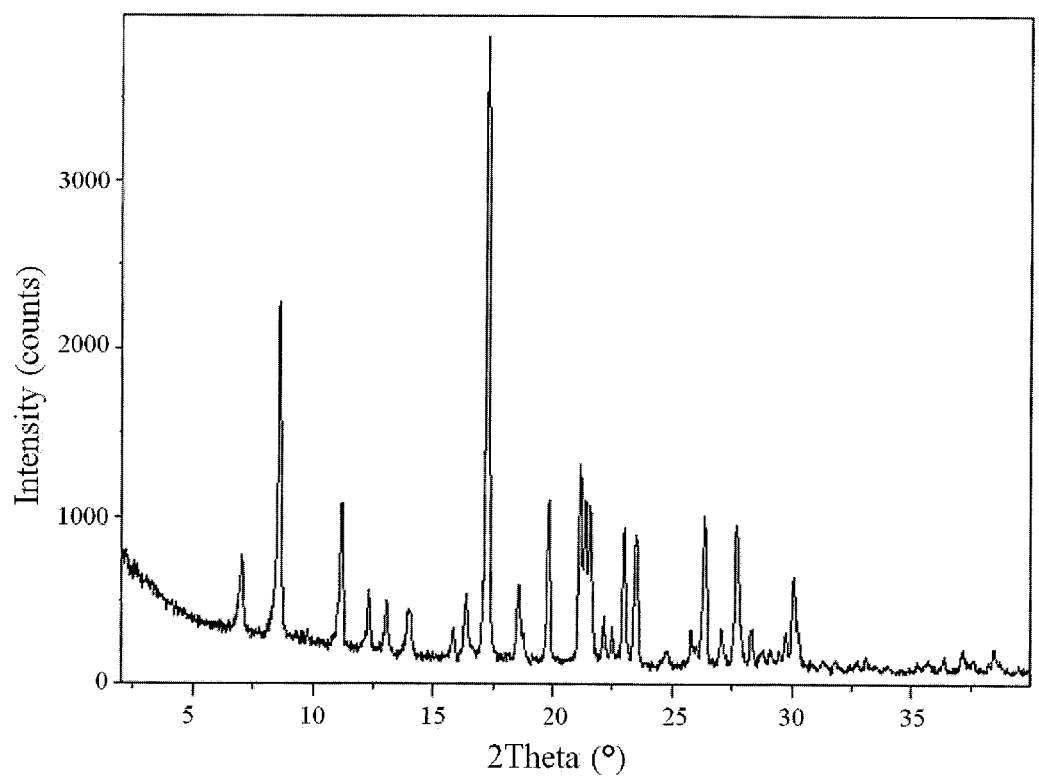
FIG. 37 shows an X-ray powder diffraction pattern of Compound A sulfate.

The X-ray powder diffraction (XRPD) pattern of Compound A sulfate is shown in FIG. 37 and a summary of the diffraction angles and d-spacings is given in Table X below. The XRPD analysis was conducted on a PANanalytical X'Pert Pro Diffractometer on Si zero-background wafers. The acquisition conditions included: Cu K$_\alpha$ radiation, generator tension: 45 kV, generator current: 40 mA, step size: 0.02° 2θ, X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit.

TABLE X

| Diff. Angle [°2θ] | d-spacing [Å] |
|---|---|
| 7.0328 | 12.56942 |
| 8.6064 | 10.27449 |
| 11.1879 | 7.90883 |
| 12.3105 | 7.19007 |
| 12.3774 | 7.15136 |
| 13.058 | 6.78011 |
| 13.9541 | 6.34663 |
| 14.0734 | 6.29308 |
| 15.8244 | 5.6005 |
| 16.3618 | 5.41324 |
| 16.4404 | 5.40094 |
| 17.2476 | 5.13718 |
| 18.5525 | 4.77868 |
| 18.7478 | 4.72934 |
| 19.8162 | 4.47671 |
| 21.1428 | 4.19871 |
| 21.3524 | 4.15797 |
| 21.55 | 4.12029 |
| 22.1262 | 4.01427 |
| 22.4768 | 3.95244 |
| 22.9749 | 3.86787 |
| 23.475 | 3.78658 |
| 25.7967 | 3.45082 |
| 25.9988 | 3.42445 |
| 26.3608 | 3.37824 |
| 27.05 | 3.29371 |
| 27.6839 | 3.21972 |
| 28.3016 | 3.15083 |
| 29.7546 | 3.00019 |
| 30.0597 | 2.97043 |
| 30.2444 | 2.95272 |

Figure 38:
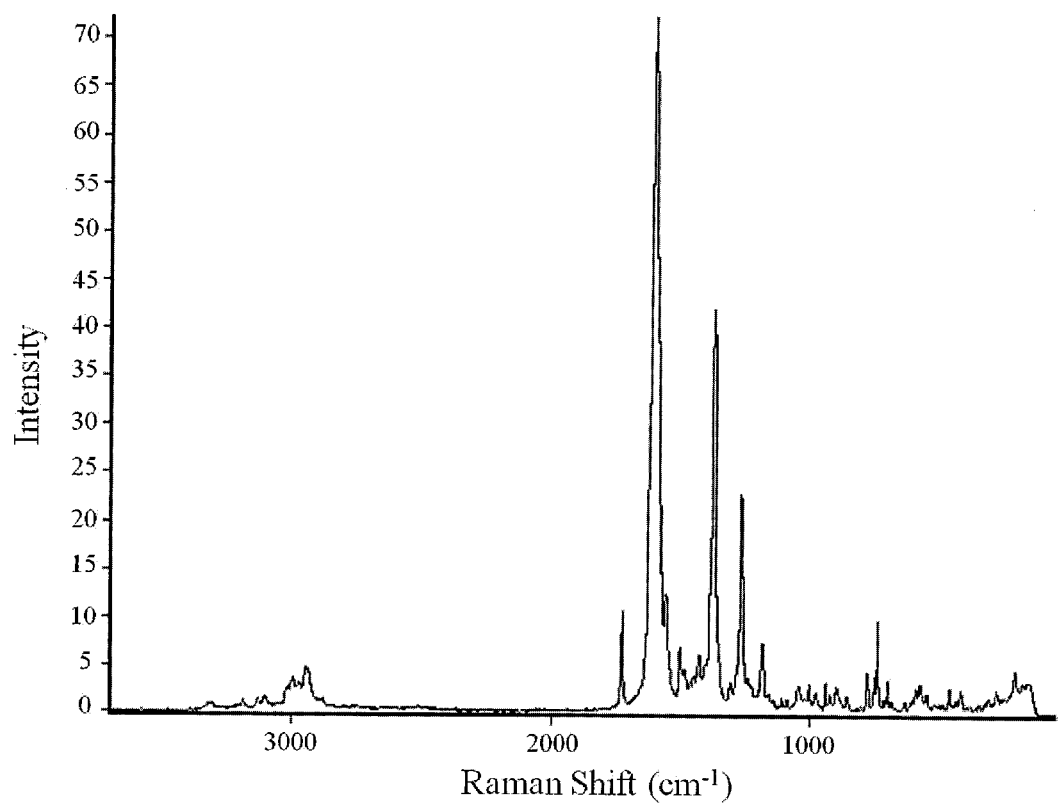
FIG. 38 shows a Raman spectrum of Compound A sulfate.

The Raman spectrum of the title compound was recorded on a Nicolet NXR 9650 FT-Raman Spectrometer, at 4 cm$^{-1}$ resolution with excitation from a Nd:YV04 laser (λ=1064 nm). The Raman spectrum of Compound A sulfate is shown in FIG. 38 with major peaks observed at 202.1, 572.0, 697.9, 737.5, 777.3, 937.1, 1181.1, 1264.9, 1370.0, 1499.4, 1554.8, 1602.3, 1723.7, 2942.8 cm$^{-1}$.

Figure 39:
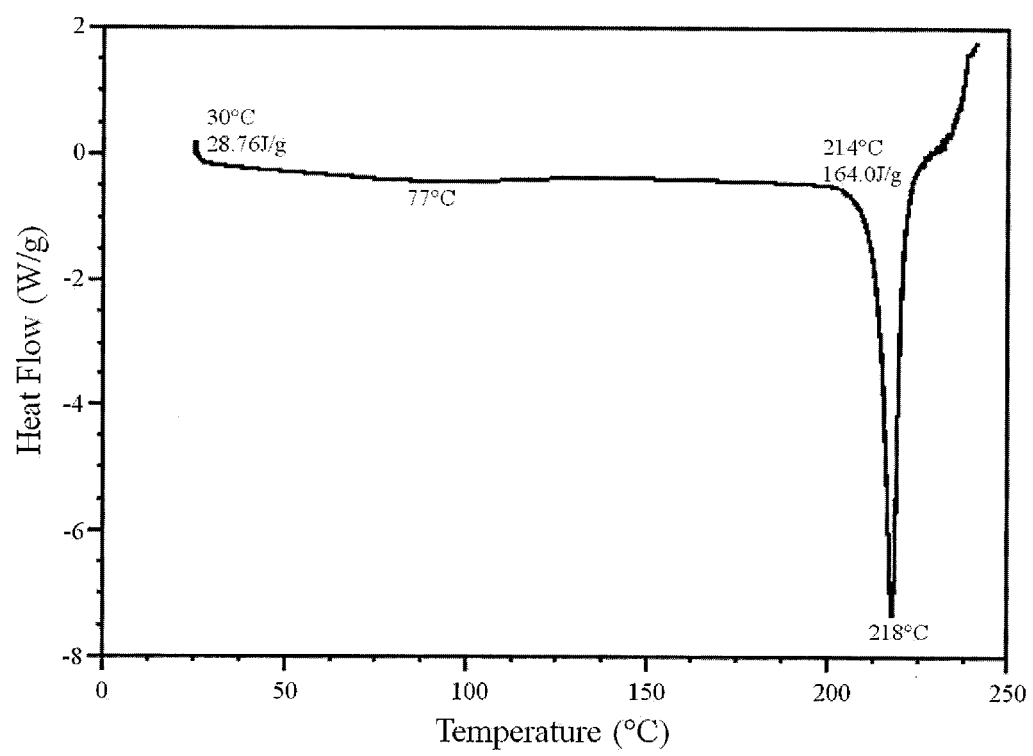
FIG. 39 shows a differential scanning calorimetry trace of Compound A sulfate.

The differential scanning calorimetry (DSC) thermogram of the title compound was recorded on a TA Instruments Q100 Differential Scanning calorimeter equipped with an autosampler and a refrigerated cooling system under 40 mL/min N$_2$ purge and is shown in FIG. 39. The experiments were conducted using a heating rate of 15° C./min in a crimped aluminum pan. The DSC thermogram of Compound A sulfate exhibited a first endotherm with an onset temperature of about 30° C., a peak temperature about 77° C., and enthalpy of 28.76 J/g, followed by a second endotherm with an onset temperature of about 214° C., a peak temperature about 218° C., and enthalpy of 164.0 J/g. A person skilled in the art would recognize that the onset temperature, peak temperature, and enthalpy of the endotherm may vary depending on the experimental conditions.

Figure 40:
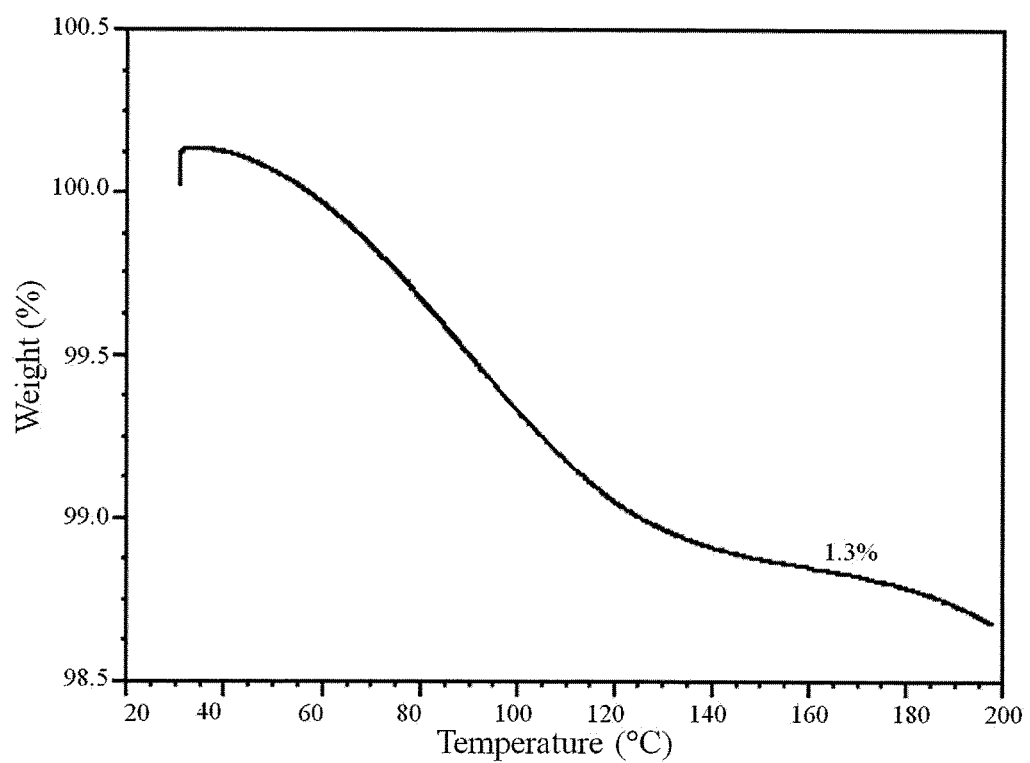
FIG. 40 shows a thermogravimetric analysis trace of Compound A sulfate.

The thermogravimetric analysis (TGA) thermogram of the title compound was recorded on a TA Instruments Q500 Thermogravimetric Analyzer and is shown in FIG. 40. The experiments were conducted with 40 mL/min $N_2$ flow and a heating rate of 15° C./min in an aluminum pan. The TGA thermogram of Compound A sulfate exhibited a weight loss event in the temperature range of 30° C. to 160° C. with a weight loss of about 1.3%. Thermal decomposition was not observed below 200° C.

Biological Assays
RET Kinase Enzymatic Assay

Human RET kinase cytoplasmic domain (amino acids 658-1114 of accession number NP_000314.1) was expressed as an N-terminal GST-fusion protein using a baculovirus expression system. GST-RET was purified using glutathione sepharose chromatography. The RET kinase enzymatic assay was performed in a total volume of 10 uL with increasing concentrations of RET kinase inhibitor as a singlet in a 384 well format as follows: RET inhibitor compound plates are prepared by adding 100 nL of RET inhibitor at different concentrations to a 384-well plate. 5 µL/well of a 2× enzyme mix (50 mM HEPES (4-(2-hydroxyethyl)-1-piperazineethanesulfonic acid); 1 mM CHAPS (3-[(3-cholamidopropyl)dimethylammonio]-1-propanesulfonate); 0.1 mg/mL BSA (bovine serum albumin); 1 mM DTT (dithiothreitol); 0.2 nM RET kinase) was added to the 384-well plate and incubated for 30 minutes at 23° C. 5 µL/well of a 2× substrate mix (50 mM HEPES; 1 mM CHAPS; 0.1 mg/mL BSA; 20 µM adenosine triphosphate; 20 mM $MgCl_2$ and 1 µM biotinylated peptide substrate) was added and incubated for 1 hour at 23° C. 10 µL/well of 2× stop/detection mix (50 mM HEPES; 0.1% BSA; 800 mM Potassium Fluoride; 50 mM EDTA (Ethylenediaminetetraacetic acid); 200× dilution of Europium Cryptate labeled anti-phosphotyrosine antibody; 62.5 nM Streptavidin-XL665) incubated for 1 hour at 23° C. and read on a Homogenous Time-Resolved Fluorescence reader. $IC_{50}$s were fitted using GraphPad Prism to a sigmoidal dose response.

Biological Data

Exemplified compounds of the present invention were tested in the RET assay described above and were found to be inhibitors of RET with $IC_{50}$<10 µM. Data for specific examples tested in the human RET kinase enzymatic assay are listed below in Table 1 as follows: +=10 µM>$IC_{50}$>500 nM; ++=500 nM≥$IC_{50}$>100 nM; +++=$IC_{50}$≤100 nM.

TABLE 1

| Example # | RET $IC_{50}$ |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |
| 72 | +++ |
| 73 | +++ |
| 74 | +++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | +++ |
| 86 | +++ |
| 87 | +++ |

TABLE 1-continued

| Example # | RET IC$_{50}$ |
|---|---|
| 88 | +++ |
| 89 | +++ |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | ++ |
| 112 | ++ |
| 113 | ++ |
| 114 | ++ |
| 115 | + |
| 116 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | +++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |
| 156 | +++ |
| 157 | +++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |
| 173 | +++ |
| 174 | +++ |
| 175 | +++ |
| 176 | +++ |
| 177 | +++ |
| 178 | +++ |
| 179 | +++ |
| 180 | +++ |
| 181 | +++ |
| 182 | +++ |
| 183 | +++ |
| 184 | +++ |
| 185 | +++ |
| 186 | +++ |
| 187 | +++ |
| 188 | +++ |
| 189 | +++ |
| 190 | +++ |
| 191 | +++ |

RET Kinase Cell-Based Mechanistic Assay

The potency of the compounds of the invention can be tested for their ability to inhibit constitutive RET kinase phosphorylation in a cell-based assay. TT cells (ATCC CRL-1803), a medullary thyroid cancer cell line with constitutively activated RET kinase, are maintained in 150 cm$^2$ dishes in F12 Kaighn's medium, 10% fetal bovine serum, 1× Glutamax, 1× non-essential amino acids, 1× Pen/Strep antibiotics at 37° C. in 5% carbon dioxide. 1.0E5 TT cells/well are plated in a 96-well cell culture plate and allowed to adhere overnight. TT cells are treated with different concentrations of RET inhibitor compounds for 2 h at 37° C. in 5% carbon dioxide, washed with ice cold PBS (phosphate buffered saline) and lysed by adding 200 µL of 25 mM Tris HCl pH 7.5; 2 mM EDTA; 150 mM NaCl; 1% sodium deoxycholate; 1% Triton X-100; 50 mM sodium beta glycerophosphate; 1 mM sodium orthovanadate; 1× phosphatase inhibitor cocktail #2 (Sigma #P5726); 1× phosphatase inhibitor cocktail #3 (Sigma #P0044) and 1× complete mini EDTA free protease inhibitor cocktail (Roche #4693159001), incubation at −80° C. for 10 minutes and thawed on ice. 100 µL of TT cell lysate is added to a 96-well plate overnight at 4° C. that had been coated overnight at 4° C. with 1:1,000 dilution of a rabbit anti-RET antibody (Cell Signaling #7032) blocked with 1× PBS; 0.05% Tween-20; 1% bovine serum albumin. Plates are washed 4× with 200 µL of 1× PBS; 0.05% Tween-20 and then 100 µL of a 1:1,000 dilution of an anti-phosphotyrosine detection antibody (Cell Signaling #7034) is added and incubated for 1 hour at 37° C. Plates are washed 4× with 200 µL of 1× PBS; 0.05% Tween-20 and then 100 µL of a 1:1,000 dilution of an anti-mouse immunoglobulin horse radish peroxidase conjugate antibody (Cell Signaling #7034) is added and incubated for 30 minutes at 37° C. Plates are washed 4× with 200 µL of 1× PBS; 0.05% Tween-20, 100 µL of TMB (3,3',5,5"-tetramethylbenzidine) substrate (Cell Signaling #7004) is added, incubated for 10 minutes at 37° C., 100 µL of Stop solution (Cell Signaling #7002) is added and absorbance read on a spectrophotometer at 450 nm. IC$_{50}$s are fitted using GraphPad Prism to a sigmoidal dose response.

RET Kinase Cell-Based Proliferation Assay

The potency of the compounds of the invention can be tested for their ability to inhibit cell proliferation and cell viability. TT cells (ATCC CRL-1803), a medullary thyroid cancer cell line with constitutively activated RET kinase, are maintained in 150 cm² dishes in F12 Kaighn's medium, 10% fetal bovine serum, 1× Glutamax, 1× non-essential amino acids, 1× Pen/Strep antibiotics at 37° C. in 5% carbon dioxide. 6.0E3 TT cells/well in 50 µL of media are added to a 96-well cell culture plate and allowed to adhere overnight. 50 µL of serially diluted RET inhibitor compounds are added to 96-well plate containing cultured TT cells and incubated at at 37° C. in 5% carbon dioxide for eight days. 50 µL of CellTiter-Glo (Promega #G-7573) is added, contents mixed for 1 minute on shaker followed by 10 minutes in the dark at 23° C. and the luminescence read by EnVision (PerkinElmer). $IC_{50}$s are fitted using GraphPad Prism to a sigmoidal dose response.

In vivo Colonic Hypersensitivity Model

The efficacy of RET kinase inhibitor compounds can be evaluated in an in vivo model of colonic hypersensitivity (Hoffman, J. M., et al., Gastroenterology, 2012, 142:844-854).

What is claimed is:

1. A compound according to Formula (XIX), or a pharmaceutically acceptable salt thereof:

(XIX)

wherein:
$A^1$ is CH, $A^2$ is O, and $A^3$ is N; or $A^1$ is CH, $A^2$ is N, and $A^3$ is O; or $A^1$ is CH, $A^2$ is N, and $A^3$ is $NR^{15}$;
$Z^1$, $Z^2$, $Z^3$, and $Z^4$ are each independently N, CH, or $CR^6$, wherein 0, 1, or 2 of $Z^1$, $Z^2$, $Z^3$, and $Z^4$ are N and 0, 1, or 2 of $Z^1$, $Z^2$, $Z^3$, and $Z^4$ are $CR^6$;
$R^2$ is hydrogen, ($C_1$-$C_4$)alkyl, or ($C_1$-$C_4$)alkoxy;
$R^3$ is hydrogen, hydroxyl, ($C_1$-$C_4$)alkoxy, or ($C_3$-$C_6$) cycloalkoxy;
$R^5$ is hydrogen, hydroxyl, ($C_1$-$C_4$)alkoxy, or ($C_3$-$C_6$) cycloalkoxy;
each $R^6$ is independently selected from the group consisting of fluorine, chlorine, methyl, ethyl, difluoromethyl, cyclopropyl, methoxy, isopropoxy, and dimethylamino-;
$R^{14}$ is ($C_1$-$C_4$)alkyl or halo($C_1$-$C_4$)alkyl; and
$R^{15}$ is hydrogen, methyl, ethyl, or phenyl.

2. The compound or pharmaceutically acceptable salt according to claim 1, wherein $A^1$ is CH, $A^2$ is O, and $A^3$ is N.

3. The compound or pharmaceutically acceptable salt according to claim 1, wherein two of $Z^1$, $Z^2$, $Z^3$, and $Z^4$ are N and the other two are each independently CH or $CR^6$.

4. The compound or pharmaceutically acceptable salt according to claim 1, wherein $R^2$ is hydrogen.

5. The compound or pharmaceutically acceptable salt according to claim 1, wherein $R^3$ is hydrogen or ($C_1$-$C_4$) alkoxy.

6. The compound or pharmaceutically acceptable salt according to claim 1, wherein $R^5$ is hydrogen or ($C_1$-$C_4$) alkoxy.

7. The compound or pharmaceutically acceptable salt according to claim 1, wherein:
$A^1$ is CH, $A^2$ is O, and $A^3$ is N;
two of $Z^1$, $Z^2$, $Z^3$, and $Z^4$ are N and the other two are each independently CH or $CR^6$;
$R^2$ is hydrogen;
$R^3$ is hydrogen or ($C_1$-$C_4$)alkoxy;
$R^5$ is hydrogen or ($C_1$-$C_4$)alkoxy;
each $R^6$ is independently selected from the group consisting of fluorine, chlorine, methyl, ethyl, difluoromethyl, cyclopropyl, methoxy, isopropoxy, and dimethylamino-; and
$R^{14}$ is ($C_1$-$C_4$)alkyl or halo($C_1$-$C_4$)alkyl.

8. The compound according to claim 1 which is:

or a pharmaceutically acceptable salt thereof.

9. The compound according to claim 1 which is:

10. The compound according to claim 9 in crystalline form.

11. The compound according to claim 10, wherein the crystalline form is characterized by an X-ray powder diffraction (XRPD) pattern comprising at least three diffraction angles, when measured using Cu $K_\alpha$ radiation, selected from a group consisting of about 2.2, 4.9, 5.5, 5.7, 11.8, 11.9, 12.8, 12.9, 13.1, 14.3, 16.1, 16.6, 17.1, 17.2, 21.2, 21.3, 21.9, 22.0, 22.7, 22.8, 23.1, 25.3, and 25.4 degrees 2θ.

12. The compound according to claim 10, wherein the crystalline form is characterized by an X-ray powder diffraction (XRPD) pattern comprising diffraction angles, when measured using Cu $K_\alpha$ radiation, of about 5.7, 11.9, 12.9, 14.3, 16.1, and 23.1 degrees 2θ.

13. A pharmaceutical composition comprising the compound or pharmaceutically acceptable salt according to claim 1 and a pharmaceutically acceptable excipient.

14. A pharmaceutical composition comprising the compound or pharmaceutically acceptable salt according to claim 8 and a pharmaceutically acceptable excipient.

15. A pharmaceutical composition comprising the compound according to claim 9 and a pharmaceutically acceptable excipient.

16. A pharmaceutical composition comprising the compound according to claim 12 and a pharmaceutically acceptable excipient.

17. A method of treating irritable bowel syndrome comprising administering to a human in need thereof an effective amount of the compound or pharmaceutically acceptable salt according to claim 1.

18. A method of treating irritable bowel syndrome comprising administering to a human in need thereof an effective amount of the compound or pharmaceutically acceptable salt according to claim 8.

19. A method of treating irritable bowel syndrome comprising administering to a human in need thereof an effective amount of the compound according to claim 9.

20. A method of treating irritable bowel syndrome comprising administering to a human in need thereof an effective amount of the compound according to claim 12.

* * * * *